United States Patent
Ellermann et al.

(10) Patent No.: US 11,427,553 B2
(45) Date of Patent: Aug. 30, 2022

(54) DIHYDROOXADIAZINONES

(71) Applicants: Bayer Aktiengesellschaft, Leverkusen (DE); Bayer Pharma Aktiengesellschaft, Berlin (DE); The Broad Institute, Inc., Cambridge, MA (US); Dana-Farber Cancer Institute, Inc., Boston, MA (US)

(72) Inventors: Manuel Ellermann, Berlin (DE); Stefan Nikolaus Gradl, Berlin (DE); Charlotte Christine Kopitz, Falkensee (DE); Martin Lange, Berlin (DE); Adrian Tersteegen, Wuppertal (DE); Philip Lienau, Berlin (DE); Christa Hegele-Hartung, Mülheim an der Ruhr (DE); Detlev Sülzle, Berlin (DE); Timothy A. Lewis, Cambridge, MA (US); Heidi Greulich, Cambridge, MA (US); Xiaoyun Wu, Cambridge, MA (US); Matthew Meyerson, Boston, MA (US); Alex Burgin, Cambridge, MA (US)

(73) Assignees: Bayer Aktiengesellschaft, Leverkusen (DE); Bayer Pharma Aktiengesellschaft, Berlin (DE); The Broad Institute, Inc., Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/635,504

(22) PCT Filed: Aug. 2, 2018

(86) PCT No.: PCT/EP2018/071039
§ 371 (c)(1),
(2) Date: Jan. 30, 2020

(87) PCT Pub. No.: WO2019/025562
PCT Pub. Date: Feb. 7, 2019

(65) Prior Publication Data
US 2020/0369633 A1    Nov. 26, 2020

Related U.S. Application Data

(60) Provisional application No. 62/541,627, filed on Aug. 4, 2017.

(51) Int. Cl.
| | |
|---|---|
| *C07D 273/04* | (2006.01) |
| *C07D 413/10* | (2006.01) |
| *C07D 413/12* | (2006.01) |
| *C07D 417/10* | (2006.01) |
| *C07D 471/04* | (2006.01) |
| *C07D 491/107* | (2006.01) |
| *C07D 495/10* | (2006.01) |

(52) U.S. Cl.
CPC ......... *C07D 273/04* (2013.01); *C07D 413/10* (2013.01); *C07D 413/12* (2013.01); *C07D 417/10* (2013.01); *C07D 471/04* (2013.01); *C07D 491/107* (2013.01); *C07D 495/10* (2013.01)

(58) Field of Classification Search
CPC .................................................... C07D 273/04
USPC ...................................................... 514/210.2
See application file for complete search history.

(56) References Cited

U.S. PATENT DOCUMENTS

| | | | |
|---|---|---|---|
| 4,052,395 | A | 10/1977 | Jojima et al. |
| 4,158,094 | A | 6/1979 | Niznik |
| 4,334,030 | A | 6/1982 | Kochanowski |
| 4,423,045 | A | 12/1983 | Brown et al. |
| 4,493,835 | A | 1/1985 | Hargreaves et al. |

(Continued)

FOREIGN PATENT DOCUMENTS

| | | |
|---|---|---|
| DE | 19929787 A1 | 1/2001 |
| EP | 0052442 A1 | 5/1982 |

(Continued)

OTHER PUBLICATIONS

King, Med. Chem: Principle and Practice (1994) pp. 206-208.*

(Continued)

*Primary Examiner* — Taofiq A Solola
(74) *Attorney, Agent, or Firm* — Melissa Hunter-Ensor; Scott Goncher; Greenberg Traurig, LLP

(57) ABSTRACT

The present invention provides dihydrooxydiazinone compounds of general formula (I): in which $R^1$, $R^2$, $R^3$, and $R^4$, are as defined herein, methods of preparing said compounds, intermediate compounds useful for preparing said compounds, pharmaceutical compositions and combinations comprising said compounds and the use of said compounds for manufacturing pharmaceutical compositions for the treatment or prophylaxis of diseases, in particular of hyperproliferative diseases, as a sole agent or in combination with other active ingredients.

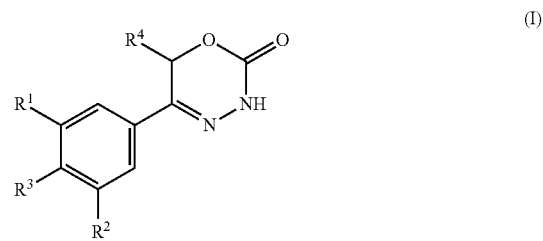

(I)

11 Claims, No Drawings

(56) References Cited

U.S. PATENT DOCUMENTS

| | | | |
|---|---|---|---|
| 4,495,185 | A | 1/1985 | Brown et al. |
| 4,503,054 | A | 3/1985 | Brown et al. |
| 4,584,298 | A | 4/1986 | Brown et al. |
| 4,616,015 | A | 10/1986 | Teraji et al. |
| 4,624,951 | A | 11/1986 | Goschke |
| 4,629,789 | A | 12/1986 | Gainer et al. |
| 4,694,005 | A | 9/1987 | Brown et al. |
| 4,906,628 | A | 3/1990 | Coates |
| 4,933,336 | A | 6/1990 | Martin et al. |
| 5,552,409 | A | 9/1996 | Michelotti et al. |
| 2020/0247783 | A1 | 8/2020 | Ellermann et al. |

FOREIGN PATENT DOCUMENTS

| | | |
|---|---|---|
| EP | 0059688 A1 | 9/1982 |
| EP | 0080296 A1 | 6/1983 |
| EP | 0086301 A1 | 8/1983 |
| EP | 0122494 A2 | 10/1984 |
| EP | 0122627 A2 | 10/1984 |
| EP | 0123254 A1 | 10/1984 |
| EP | 0175363 A2 | 3/1986 |
| EP | 0220044 A2 | 4/1987 |
| EP | 0478195 A1 | 4/1992 |
| EP | 2253625 A1 | 11/2010 |
| EP | 2281822 A1 | 2/2011 |
| JP | H07291968 A | 11/1995 |
| WO | 1994001412 A1 | 1/1994 |
| WO | 2002072103 A1 | 9/2002 |
| WO | 2008108602 A1 | 9/2008 |
| WO | 2009114993 A1 | 9/2009 |
| WO | 2010121022 A1 | 10/2010 |
| WO | 2011138427 A2 | 11/2011 |
| WO | 2012161812 A1 | 11/2012 |
| WO | 2014164704 A2 | 10/2014 |
| WO | 2017027854 A1 | 2/2017 |
| WO | 2017134231 A1 | 8/2017 |
| WO | 2020157194 A1 | 8/2020 |

OTHER PUBLICATIONS

Maurice et al., "Advances in targeting cyclic nucleotide phosphodiesterases," Nature Reviews Drug Discovery, 2014; vol. 13, issue 4, pp. 290-314.

Movsesian et al., "Phosphodiesterase Inhibition in Heart Failure," Phosphodiesterases as Drug Targets, Handbook of Experimental Pharmacology, 2011; vol. 204, pp. 237-249.

International Search Report and Written Opinion in corresponding PCT Patent Application No. PCT/EP2018/071039, dated Oct. 16, 2018 (10 pages).

Forest et al., "A novel class of cardiotonic agents: synthesis and biological evaluation of 5-substituted 3,6-dihydrothiadiazin-2-ones with cyclic AMP phosphodiesterase inhibiting and myofibrillar calcium sensitizing properties," Journal of Medicinal Chemistry, 1992, vol. 35, No. 1, pp. 163-172.

Goeschke et al., "6-(4-Morpholino-phenyl)-4,5-dihydro-2H-pyridazine-3-ones: potent platelet aggregation inhibitors and antithrombotics," European Journal of Medicinal Chemistry, Oct. 1991, vol. 26, No. 7, pp. 715-721.

Hurd et al., "On Acylhydrazones and 1,2,3-Thiadiazoles," Journal of the American Chemical Society, 1955, vol. 77, No. 20, pp. 5359-5364.

James, Christopher W., "Anagrelide-Induced Cardiomyopathy," Pharmacotherapy, 2012, vol. 20, No. 10, pp. 1224-1227.

Packer et al., "Effect of Oral Milrinone on Mortality in Severe Chronic Heart Failure," The New England Journal of Medicine, Nov. 21, 1991, vol. 325, pp. 1468-1475.

Page II et al., "Drugs That May Cause or Exacerbate Heart Failure," Circulation, 2016, vol. 134, No. 6, pp. e32-e69.

Rosenblum et al., "Synthesis of Dihydrooxadiazinones and Study of Geometrical Isomerism in α-Ketol Carbethoxyhydrazones," Journal of the American Chemical Society, 1963, vol. 85, No. 23, pp. 3874-3878.

Rosenblum et al., "The Chemistry of 1,3,4-Oxadiazin-2-ones. Preparation and Thermal Stability," Journal of the American Chemical Society, 1965, 87, No. 24, pp. 5716-5719.

Rosenblum et al., "Thermal Decomposition of 2,3-Dihydro-5,6-Diphenyl-1,3,-4,6-Oxadiazin-2-one," The Society of Chemical Industry, Dec. 15, 1956, pp. 1480-1481.

Savai et al., "Targeting cancer with phosphodiesterase inhibitors," Expert Opinion on Investigational Drugs, 2010, vol. 19, No. 1, pp. 117-131.

Steck et al., "Pyridazines. VI. Some 6-Substituted 3(2H)pyridazinones," Journal of Heterocyclic Chemistry, Oct. 1974, vol. 11, No. 5, pp. 755-761.

* cited by examiner

DIHYDROOXADIAZINONES

CROSS-REFERENCE TO RELATED APPLICATIONS

This application is the U.S. national phase application, pursuant to 35 U.S.C. § 371, of PCT International Application Serial No.: PCT/EP2018/071039, filed Aug. 2, 2018, which claims the benefit of and priority to U.S. Provisional Application No. 62/541,627, filed Aug. 4, 2017, the entire contents of each of which are incorporated herein by reference.

The present invention provides dihydrooxadiazinone compounds of general formula (I) as described and defined herein, methods of preparing said compounds, pharmaceutical compositions and the use of said compounds for the treatment or prophylaxis of diseases, in particular of hyperproliferative diseases.

BACKGROUND

Cancer kills over 550,000 people in the United States and over 8 million people world-wide each year. New agents, including small molecules, molecules that impact tissue-specific growth requirements, and immunomodulatory agents, have been shown to benefit a subset of patients whose cancers have unique genomic mutations or other characteristics. Unfortunately, many cancer patients are still left without effective therapeutic options.

One approach to identify new anti-cancer agents is phenotypic screening to discover novel small molecules displaying strong selectivity between cancer cell lines, followed by predictive chemogenomics to identify the cell features associated with drug response. In the 1990s, Weinstein and colleagues demonstrated that the cytotoxic profile of a compound can be used to identify cellular characteristics, such as gene-expression profiles and DNA copy number, which correlate with drug sensitivity. The ability to identify the features of cancer cell lines that mediate their response to small molecules has strongly increased in recent years with automated high-throughput chemosensitivity testing of large panels of cell lines coupled with comprehensive genomic and phenotypic characterization of the cell lines. Phenotypic observations of small molecule sensitivity can be linked to expression patterns or somatic alterations, as in the case of trastuzumab-sensitive HER2-amplified breast cancer or erlotinib-sensitive EGFR-mutant lung cancer.

Phenotypic screening identified some of the compounds known in the literature to be PDE3 inhibitors to be useful for the treatment of certain cancers. Co-expression of PDE3A and/or PDE3B and Schlafen 12 (SLFN12) polynucleotides or polypeptides are typically required for cells to be sensitive. PDE3A/B inhibitors which cause drug sensitivity have been found to stabilze the formation of a complex between PDE3A or PDE3B and SLFN12. PDE3A/B inhibitors which do not cause cell sensitivity typically do not stabilize the PDE3A- or PDE3B-SLFN12 complex.

Several PDE-3 inhibitors such as milrinone, cilostazol, and levosimendan have been approved for clinical treatment of cardiovascular indications or thrombocythemia (anagrelide), but not for cancer indication. The most recent quality review of PDE inhibitors (Nature Reviews Drug Discovery 13, 290-314, (2014)) barely mentions cancer. From WO 2014/164704, WO2017/027854, and WO2017/134231 some PDE3 inhibitors are known.

Especially the cardiac mode of action mediated unwanted effects of PDE-3 inhibitors (Movsesian &Kukreja, S. H. Francis et al. (eds.), Phosphodiesterases as Drug Targets, Handbook of Experimental Pharmacology 204, 2011; p 237ff) may limit their therapeutic use when PDE3-inhibiting agents are used on a short- or/and long term basis, e.g. in cancer patients and a suitable therapeutic window is needed.

Some dihydrooxydiazinones are known, however, the state of the art does not describe the dihydrooxadiazinone compounds of general formula (I) of the present invention as described and defined herein.

SUMMARY

It has now been found, and this constitutes at least in part one basis of the present invention, that the compounds of the present invention have surprising and advantageous properties.

In particular, the compounds of the present invention have surprisingly been found to inhibit tumor cell proliferation with $IC_{50}$ values of <100 nM in e.g. HeLa cells. Additionally, the compounds require higher concentrations for PDE3A and/or PDE3B inhibition where $IC_{50}$ values for enzymatic PDE3A and/or PDE3B inhibition may be >2.5 times higher than $IC_{50}$ values for tumor cell proliferation. Without wishing to be bound by theory, this distinction in inhibitory properties may be associated with PDE3A-SLFN12 complex induction and/or improved pharmacokinetic parameters in vitro or in vivo and/or improved physicochemical properties and/or improved safety pharmacological properties. With these advantageous properties, the compounds described herein may therefore be used for the treatment or prophylaxis of hyperproliferative diseases, such as cancer diseases.

The present invention provides compounds of general formula (I) which modulate formation of a PDE3A- and/or PDE3B-SLFN12 complex, methods for their preparation, pharmaceutical composition and the use thereof and methods of treatment or prophylaxis of diseases, in particular of hyperproliferative diseases more particularly of cancer diseases. These and other features of the present teachings are set forth herein.

In accordance with a first aspect, the present invention provides compounds of general formula (I):

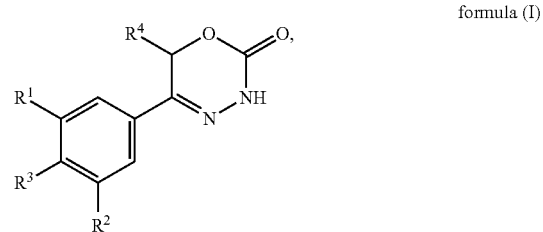

formula (I)

where $R^1$ is selected from a hydrogen atom, a halogen atom, a cyano group, a $C_1$-$C_3$-alkyl group, a $C_1$-$C_3$-haloalkyl group, and a $C_1$-$C_3$-haloalkoxy group;

$R^2$ is selected from a hydrogen atom and a halogen atom;

$R^3$ is selected from, a $C_1$-$C_6$-alkyl group which is optionally substituted with one or two substituents and each substituent is independently selected from a hydroxy group, a $C_1$-$C_4$-alkoxy group, and a 3- to 7-membered heterocycloalkyl group, a $C_2$-$C_6$-alkenyl group which is optionally substituted with an $C_1$-$C_4$-alkoxy group, a $C_3$-$C_9$-cycloalkyl group, which is optionally substituted with a hydroxy group, a $C_5$-$C_9$-cycloalkenyl group, which is optionally substituted with a hydroxy group a 3- to 9-membered heterocycloalkyl group, comprising one, two or three heteroatoms which are independently selected from —O—, —S—, —S(O)—, S(O)$_2$, and —NR$^9$—, and said heterocycloalkyl group optionally further comprising a bridging group selected from —O—, —NR$^9$—, —CH$_2$—, —CH$_2$—CH$_2$—, —O—CH$_2$—, —CH$_2$—O—, —NR$^9$—CH$_2$—, and —CH$_2$—NR$^9$—;

and said heterocycloalkyl group is optionally substituted with one, two or three substituents and each substituent is independently selected from a halogen atom;

a oxo(═O) group;

a cyano group;

a hydroxy group;

a $C_1$-$C_3$-alkyl group which is optionally further substituted with a hydroxy group;

a $C_1$-$C_3$-haloalkyl group;

a $C_1$-$C_3$-alkoxy group;

a $C_1$-$C_3$-haloalkoxy group;

a C(O)NR$^5$R$^6$ group and a NR$^5$R$^6$ group, a 5- to 9-membered heterocycloalkyl group which is partially unsaturated and optionally substituted with one, two or three substituents and each substituent is independently selected from an oxo group (═O), a $C_1$-$C_3$-alkyl group, a —C(O)R$^5$R$^6$ group and a halogen atom, an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a NR$^5$R$^6$ group, a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a NR$^5$R$^6$ group, with the proviso that said monocyclic heteroaryl group is not a pyridin-4-yl group;

and a NR$^7$R$^8$ group;

R$^4$ is selected from a hydrogen atom, and a $C_1$-$C_3$-alkyl group;

R$^5$/R$^6$ is independently selected from a hydrogen atom, a $C_1$-$C_6$-alkyl group, a —$C_1$-$C_5$-alkylene-O—$C_1$-$C_5$-alkyl group, a —$C_1$-$C_5$-alkylene-S—$C_1$-$C_5$-alkyl group, $C_3$-$C_6$-cycloalkyl group, and a $C_3$-$C_5$-heterocycloalkyl group;

R$^7$/R$^8$ are independently selected from a hydrogen atom, with the proviso that R$^7$═R$^8$═hydrogen is excluded, a $C_1$-$C_6$-alkyl group, which is optionally substituted with one, two, three or four substituents and said substituent is independently selected from a halogen atom, a cyano group, a hydroxy group, a C(O)NR$^5$R$^6$ group, a NR$^5$R$^6$ group, a $C_1$-$C_3$-alkoxy group, a $C_3$-$C_7$-cycloalkyl group which is optionally substituted with one or two substitutents and said substituents are independently selected from a C1-$C_3$-alkyl group, a oxo (═O) group, a hydroxy group, and a $C_1$-$C_3$-hydroxyalkyl group;

a 3- to 7-membered heterocycloalkyl group which itself is optionally substituted with a $C_1$-$C_3$-alkyl group or an oxo (═O) group a heteroaryl group, which itself is optionally substituted with a $C_1$-$C_3$-alkyl group;

a —$C_1$-$C_5$-alkylene-O—$C_1$-$C_5$-alkyl group, a —$C_1$-$C_5$-alkylene-S—$C_1$-$C_5$-alkyl group, a —$C_1$-$C_5$-alkylene-NR$^5$—$C_1$-$C_5$-alkyl group, a $C_3$-$C_6$-cycloalkyl group which is optionally substituted with a hydroxy group, and a 3- to 6-membered heterocycloalkyl group which is optionally substituted with one or two substituents, said substituent independently selected from $C_1$-$C_3$-alkyl group and a hydroxy group, R$^9$ is a hydrogen atom or a $C_1$-$C_3$-alkyl group or a bond;

or a stereoisomer, a tautomer, an N-oxide, a hydrate, a solvate, or a salt thereof, or a mixture of same.

The compounds are suitable for the treatment of a patient having a cancer that is sensitive to treatment with a phosphodiesterase 3A/B (PDE3A/B) modulator by detecting co-expression of PDE3A and/or PDE3B and Schlafen 12 (SLFN12) and/or SLFN12L mRNA, polynucleotides or polypeptides and/or a lack of decrease in expression of CREB3L1 mRNA, polynucleotides or polypeptides in a cancer cell derived from such patients.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

Structures drawn include all permissible rotations about bonds.

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, in particular 1, or 2.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

As used herein, an oxo substituent represents an oxygen atom, which is bound to a carbon atom or to a sulfur atom via a double bond.

The term "ring substituent" means a substituent attached to an aromatic or nonaromatic ring which replaces an available hydrogen atom on the ring.

Should a composite substituent be composed of more than one parts, e.g. ($C_1$-$C_4$-alkyl)-O—($C_1$-$C_4$-alkyl)-, a hyphen at the beginning or at the end of such a composite substituent indicates the point of attachment of said composite substituent to the rest of the molecule. Should the composite substituent be substituted said substitutent may be bound at any suitable carbon atom of the composite substitutent.

Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen atom" means a fluorine, chlorine, bromine or iodine atom, particularly a fluorine, chlorine or bromine atom.

The term "$C_1$-$C_6$-alkyl" means a linear or branched, saturated, monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group.

The term "alkylene" derives from the term "alkyl" as being a bivalent constituent named by addition of "ene" to the term "alkyl" e.g. "methyl" becomes "methylene" meaning a "—$CH_2$—" constituent whereby the open bonds of branched constituents are located at the respective ends of the longest chain.

The term "$C_1$-$C_6$-haloalkyl" means a linear or branched, saturated, monovalent hydrocarbon group in which the term "$C_1$-$C_6$-alkyl" is as defined supra, and in which one or more of the hydrogen atoms are replaced, identically or differently, with a halogen atom. Particularly, said halogen atom is a fluorine atom. Said $C_1$-$C_6$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl, more particularly trifluoromethyl or trifluoromethyl.

The term "$C_1$-$C_6$-alkoxy" means a linear or branched, saturated, monovalent group of formula ($C_1$-$C_6$-alkyl)-O—, in which the term "$C_1$-$C_6$-alkyl" is as defined supra, e.g. a methoxy, ethoxy, n-propoxy, isopropoxy, n-butoxy, sec-butoxy, isobutoxy, tert-butoxy, pentyloxy, isopentyloxy or n-hexyloxy group, or an isomer thereof.

The term "$C_1$-$C_6$-haloalkoxy" means a linear or branched, saturated, monovalent $C_1$-$C_6$-alkoxy group, as defined supra, in which one or more of the hydrogen atoms is replaced, identically or differently, with a halogen atom. Particularly, said halogen atom is a fluorine atom. Said $C_1$-$C_6$-haloalkoxy group is, for example, fluoromethoxy, difluoromethoxy, trifluoromethoxy, 2,2,2-trifluoroethoxy or pentafluoroethoxy.

The term "$C_2$-$C_6$-alkenyl" means a linear or branched, monovalent hydrocarbon group, which contains one or two double bonds, and which has 2, 3, 4, 5 or 6 carbon atoms, particularly 2 or 4 carbon atoms ("$C_2$-$C_4$-alkenyl"), it being understood that in the case in which said alkenyl group contains more than one double bond, then it is possible for said double bonds to be isolated from, or conjugated with, each other. Said alkenyl group is, for example, an ethenyl (or "vinyl"), prop-2-en-1-yl (or "allyl"), prop-1-en-1-yl, but-3-enyl, but-2-enyl, but-1-enyl, pent-4-enyl, pent-3-enyl, pent-2-enyl, pent-1-enyl, hex-5-enyl, hex-4-enyl, hex-3-enyl, hex-2-enyl, hex-1-enyl, prop-1-en-2-yl (or "isopropenyl"), 2-methylprop-2-enyl, 1-methylprop-2-enyl, 2-methylprop-1-enyl, 1-methylprop-1-enyl, 3-methylbut-3-enyl, 2-methylbut-3-enyl, 1-methylbut-3-enyl, 3-methylbut-2-enyl, 2-methylbut-2-enyl, 1-methylbut-2-enyl, 3-methylbut-1-enyl, 2-methylbut-1-enyl, 1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, 3-methylpent-3-enyl, 2-methylpent-3-enyl, 1-methylpent-3-enyl, 4-methylpent-2-enyl, 3-methylpent-2-enyl, 2-methylpent-2-enyl, 1-methylpent-2-enyl, 4-methylpent-1-enyl, 3-methylpent-1-enyl, 2-methylpent-1-enyl, 1-methylpent-1-enyl, 3-ethylbut-3-enyl, 2-ethylbut-3-enyl, 1-ethylbut-3-enyl, 3-ethylbut-2-enyl, 2-ethylbut-2-enyl, 1-ethylbut-2-enyl, 3-ethylbut-1-enyl, 2-ethylbut-1-enyl, 1-ethylbut-1-enyl, 2-propylprop-2-enyl, 1-propylprop-2-enyl, 2-isopropylprop-2-enyl, 1-isopropylprop-2-enyl, 2-propylprop-1-enyl, 1-propylprop-1-enyl, 2-isopropylprop-1-enyl, 1-isopropylprop-1-enyl, 3,3-dimethylprop-1-enyl, 1-(1,1-dimethylethyl)ethenyl, buta-1,3-dienyl, penta-1,4-dienyl or hexa-1,5-dienyl group. Particularly, said group is vinyl or allyl, propenyl-, isopropenyl-, butenyl-, or isobutenyl group.

The term "$C_2$-$C_6$-alkynyl" means a linear or branched, monovalent hydrocarbon group which contains one triple bond, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl (or "propargyl"), but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl or 3,3-dimethylbut-1-ynyl group. Particularly, said alkynyl group is ethynyl, prop-1-ynyl or prop-2-ynyl.

The term "$C_3$-$C_9$-cycloalkyl" means a saturated, monovalent, mono- or bicyclic hydrocarbon ring which contains 3, 4, 5, 6, 7 or 8 carbon atoms. Said $C_3$-$C_8$-cycloalkyl group is for example, a monocyclic hydrocarbon ring, e.g. a cyclopropyl, cyclobutyl, cyclopentyl, cyclohexyl, cycloheptyl or cyclooctyl group, it also includes fused-, bridged- and spiro-cycloalkyl ring systems as e.g. a bicyclic hydrocarbon ring, e.g. a bicyclo[4.2.0]octyl, bicyclo[2.2.1]heptyl or octahydropentalenyl as well as spirocycoalkyl systems as defined below.

The term "spirocycloalkyl" means a saturated, monovalent bicyclic hydrocarbon group in which the two rings share one common ring carbon atom, and wherein said bicyclic hydrocarbon group contains 5, 6, 7, 8, or 9 carbon atoms, it being possible for said spirocycloalkyl group to be attached to the rest of the molecule via any one of the carbon atoms except the spiro carbon atom. Said spirocycloalkyl group is, for example, spiro[2.2]pentyl, spiro[2.3]hexyl, spiro[2.4] heptyl, spiro[2.5]octyl, spiro[2.6]nonyl, spiro[3.3]heptyl, spiro[3.4]octyl, spiro[3.5]nonyl, spiro[3.6]decyl, spiro[4.4] nonyl, spiro[4.5]decyl, spiro[4.6]undecyl or spiro[5.5]undecyl.

The term "$C_5$-$C_6$-cycloalkenyl" means a resulting a cyclopentenyl group, a cyclohexenyl group, a cyclopentadienyl group a cyclohexadienyl group The term "$C_4$-$C_9$-cycloalkenyl" means a monovalent, mono- or bicyclic hydrocarbon ring which contains 4, 5, 6, 7, 8 or 9 carbon atoms and one double bond. Particularly, said ring contains 4, 5 or 6 carbon atoms ("$C_4$-$C_6$-cycloalkenyl"). Said $C_4$-$C_8$-cycloalkenyl group is for example, a monocyclic hydrocarbon ring, e.g. a cyclobutenyl, cyclopentenyl, cyclohexenyl, cycloheptenyl or cyclooctenyl group, or a bridged ring system also a bicyclic hydrocarbon ring, e.g. a bicyclo[2.2.1]hept-2-enyl or bicyclo[2.2.2]oct-2-enyl, bicyclo[3.1.0]hex-2-enyl.

The terms "3- to 9-membered heterocycloalkyl" and "3- to 6-membered heterocycloalkyl" mean a saturated heterocycle with 3, 4, 5, 6, 7, 8 or 9 ring atoms respectively, 3, 4, 5 or 6 ring atoms in total, which contains one or two identical or different ring heteroatoms selected from the series N, O, and S, said heterocycloalkyl group being attached to the rest of the molecule via any one of the carbon atoms or heteroatoms. It also includes bicyclic ring systems which are either fused- or bridged- or spiro-systems as defined below. It also includes compounds of formula (I) having potentially a $NR^7R^8$ group where the N-atom belongs to a ring which is being formed by connection of $R^7$ and $R^8$ forming a non-aromatic ring including the N-atom to which they are connected. The term "heterocycloalkane", as used herein, refers to a compound consisting of a heterocycloalkyl group as defined herein, and a hydrogen atom to which said heterocycloalkyl group is bonded with its one valency.

Said heterocycloalkyl group, without being limited thereto, can be a 3- or 4-membered ring, such as azacyclopropyl, oxacyclopropyl, azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, or a fused system like azabicyclo[3.1.0]hexan-3-yl for example.

Particularly, "4- to 6-membered heterocycloalkyl" means a 4- to 6-membered heterocycloalkyl as defined supra containing one ring nitrogen atom or an oxygen atom or a sulfur atom and if it contains a nitrogen atom it may optionally contains one further ring heteroatom from the series: N, O, S. More particularly, "5- or 6-membered heterocycloalkyl" means a monocyclic, saturated heterocycle with 5 or 6 ring atoms in total, containing one ring nitrogen atom and optionally one further ring heteroatom from the series: N, O. Said heterocycloalkyl group is being attached to the rest of the molecule via any carbon atom or where applicable via any nitrogen atom. Both of them may include bicyclic ring systems as mentioned above.

The term a "partially unsaturated 3- to 9-membered heterocycloalkyl" means a monocyclic, unsaturated, non-aromatic heterocycle with 5, 6, 7, 8 or 9 ring atoms in total, which contains one or two double bonds and one or two identical or different ring heteroatoms from the series: N, O, S it being possible for said partially unsaturated heterocycloalkyl group to be attached to the rest of the molecule via any one of the carbon atoms or, if present, a nitrogen atom. The term "partially unsaturated heterocycloalkane", as used herein, refers to a compound consisting of a partially unsaturated heterocycloalkyl group as defined herein, and a hydrogen atom to which said partially unsaturated heterocycloalkyl group is bonded with its one valency.

Said partially unsaturated heterocycloalkyl group is, for example, 4H-pyranyl, 2H-pyranyl, 3,6-dihydro-2H-pyran-4-yl, 5,6-dihydro-2H-pyran-3-yl, tetrahydropyridinyl, e.g. 1,2,3,6-tetrahydropyridin-4-yl, dihydropyridinyl, e.g. 1,6-dihydropyridinyl, 6-oxo-1,6-dihydropyridin-3-yl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl or 4H-[1,4]thiazinyl.

The term "fused heterocycloalkyl" means a bicyclic, saturated heterocycle with 6, 7, 8, or 9 ring atoms in total, or respectively 5, 6 or 7 ring atoms in total, in which the two rings share two adjacent ring atoms, which "fused heterocycloalkyl" contains one or two identical or different ring heteroatoms from the series: N, O, S; it being possible for said fused heterocycloalkyl group to be attached to the rest of the molecule via any one of the carbon atoms or, if present, a nitrogen atom.

Said fused heterocycloalkyl group is, for example, 3-azabicyclo[3.1.0]hexan-3-yl, 3-azabicyclo[3.2.0]heptan-3-yl, azabicyclo[3.3.0]octyl, azabicyclo[4.3.0]nonyl, diazabicyclo[4.3.0]nonyl, oxazabicyclo[4.3.0]nonyl, or thiazabicyclo[4.3.0]nonyl.

The term "bridged heterocycloalkyl" means a bicyclic, saturated heterocycle with 7, 8 or 9 ring atoms in total, or respectively 7 ring atoms in total, in which the two rings share two common ring atoms which are not adjacent, which "bridged heterocycloalkyl" contains one or two identical or different ring heteroatoms from the series: N, O, S; it being possible for said bridged heterocycloalkyl group to be attached to the rest of the molecule via any one of the carbon atoms or, if present, a nitrogen atom. Said bridged heterocycloalkyl group is, for example, azabicyclo[2.2.1]heptyl, oxazabicyclo[2.2.1]heptyl, thiazabicyclo[2.2.1]heptyl, diazabicyclo[2.2.1]heptyl, azabicyclo[2.2.2]octyl, diazabicyclo[2.2.2]octyl, oxazabicyclo[2.2.2]octyl, thiazabicyclo[2.2.2]octyl, azabicyclo[3.2.1]octyl, diazabicyclo[3.2.1]octyl, oxazabicyclo[3.2.1]octyl, thiazabicyclo[3.2.1]octyl, azabicyclo[3.3.1]nonyl, diazabicyclo[3.3.1]nonyl, oxazabicyclo[3.3.1]nonyl, thiazabicyclo[3.3.1]nonyl, azabicyclo[4.2.1]nonyl, diazabicyclo[4.2.1]nonyl, oxazabicyclo[4.2.1]nonyl, thiazabicyclo[4.2.1]nonyl.

The term "heterospirocycloalkyl" means a bicyclic, saturated heterocycle with 6, 7, 8, or 9 ring atoms in total, in which the two rings share one common ring carbon atom, which "heterospirocycloalkyl" contains one or two identical or different ring heteroatoms from the series: N, O, S; it being possible for said heterospirocycloalkyl group to be attached to the rest of the molecule via any one of the carbon atoms, except the spiro carbon atom, or, if present, a nitrogen atom. Said heterospirocycloalkyl group is, for example, azaspiro[2.3]hexyl, azaspiro[3.3]heptyl, oxaazaspiro[3.3]heptyl, thiaazaspiro[3.3]heptyl, 2lambda<sup>6</sup>-thia-6-azaspiro[3.3]heptane-2,2-dione, oxaspiro[3.3]heptyl, oxazaspiro[5.3]nonyl, oxazaspiro[4.3]octyl, diazaspiro[3.3]heptyl, thiazaspiro[3.3]heptyl, thiazaspiro[4.3]octyl, or one of the further homologous scaffolds such as spiro[3.4]-, spiro[4.4]-, spiro[2.4]-, spiro[2.5]-, spiro[2.6]-, spiro[3.5]-, spiro[3.6]-, spiro[4.5]- and spiro[4.6]-.

The term "aryl" refers to an aromatic monocyclic, bicyclic (2 fused rings), tricyclic (3 fused rings), or polycyclic (two or more fused rings) hydrocarbon ring system having 6 to 20 (e.g. 6 to 10 ring carbon atoms). Nonlimiting examples of aryl groups include phenyl, or napthyl (e.g., 1-napthyl, 2-napthyl, etc.).

The term "heteroaryl" means a monovalent, monocyclic or bicyclic aromatic ring having 5, 6, 8, 9 or 10, ring atoms (a "5- to 10-membered heteroaryl" group), particularly 5, 6, 9 or 10 ring atoms, which contains at least one ring heteroatom and optionally one, two or three further ring heteroatoms from the series: N, O and/or S, and which is bound via a ring carbon atom or a heteroatom to the rest of the molecule. The term "heteroarene", as used herein, refers to a compound consisting of a heteroaryl group as defined herein, and a hydrogen atom to which said heteroaryl group is bonded with its one valency.

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl; or a tricyclic heteroaryl group, such as, for example, carbazolyl, acridinyl or phenazinyl; or a 9-membered heteroaryl group, such as, for example, benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, such as, for example, quinolinyl, quinazolinyl, isoquinolinyl, cinnolinyl, phthalazinyl, quinoxalinyl or pteridinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

Particularly the heteroaryl group is a 2H-pyrrol-1-yl group, a 1H-pyrrazol-4-yl group, a 1H-pyrrazol-5-yl group, which is optionally substituted with one or two methyl groups, a 1,2-thiazol-4-yl group, a 1,3-thiazol-5-yl group, a pyridin-3-yl, a pyridin-4-yl and a pyridin 5-yl group each group being optionally substituted with one or two substitutents and each substituent is independently selected from a halogen atom, a methyl group, a trifuoromethyl group, a methoxy group and a $NH_2$ group, a 1H-indol-6-yl group, a 1H-indazol-6-yl group, and a 1H-benzimidazol-6-yl group, each group being optionally substituted with one or two substitutents and each substituent is independently selected from a halogen atom, a methyl group, a trifuoromethyl group, a methoxy group and a $NH_2$ group.

Particularly, the heteroaryl group is a:
2H-pyrrol-1-yl group, which is optionally substituted with one or two substitutents and each substituent is independently selected from a hydrogen atom, a cyano group and a methyl group,
a 1H-pyrrazol-4-yl group, which is optionally substituted with one or two methyl groups,
a 1H-pyrrazol-5-yl group, which is optionally substituted with one or two methyl groups,
a 1,2-thiazol-4-yl group which is optionally substituted with one or two methyl groups,
a 1,3-thiazol-5-yl group which is optionally substituted with one or two methyl groups,
a pyridin-3-yl, and a pyridin 5-yl group each group being optionally substituted with one or two substitutents and each substituent is independently selected from a halogen atom, a methyl group, a trifuoromethyl group, a methoxy group and a $NH_2$ group,
a 1H-indol-6-yl group, a 1H-indazol-6-yl group, and a 1H-benzimidazol-6-yl group.

More particularly the heteroaryl group is a pyridinyl group which is optionally substituted with an amino group, or a pyrazolyl group which is optionally substituted with a difluoromethyl group or a trifluoromethyl group.

Even more particularly the heteroaryl group is
a 4-pyridinyl group which is substituted with a amino group, or
a 1H-pyrazol-4-yl or a 1H-pyrazol-1-yl group which are optionally substituted with a difluoromethyl group or a trifluoromethyl group The term "$C_1$-$C_6$", as used in the present text, e.g. in the context of the definition of "$C_1$-$C_6$-alkyl", "$C_1$-$C_6$-haloalkyl", "$C_1$-$C_6$-alkoxy" or "$C_1$-$C_6$-haloalkoxy" means an alkyl group having a finite number of carbon atoms of 1 to 6, i.e. 1, 2, 3, 4, 5 or 6 carbon atoms.

Further, as used herein, the term "$C_3$-$C_8$", as used in the present text, e.g. in the context of the definition of "$C_3$-$C_8$-cycloalkyl", means a cycloalkyl group having a finite number of carbon atoms of 3 to 8, i.e. 3, 4, 5, 6, 7 or 8 carbon atoms.

When a range of values is given, said range encompasses each value and sub-range within said range.

For example:
"$C_1$-$C_6$" encompasses $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;
"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;
"$C_3$-$C_{10}$" encompasses $C_3$, $C_4$, $C_5$, $C_6$, $C_7$, $C_8$, $C_9$, $C_{10}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;
"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;
"$C_3$-$C_8$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;
"$C_4$-$C_8$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;
"$C_4$-$C_7$" encompasses $C_4$, $C_5$, $C_6$, $C_7$, $C_4$-$C_7$, $C_4$-$C_6$, $C_4$-$C_5$, $C_5$-$C_7$, $C_5$-$C_8$ and $C_6$-$C_7$;
"$C_4$-$C_6$" encompasses $C_4$, $C_5$, $C_6$, $C_4$-$C_6$, $C_4$-$C_5$ and $C_5$-$C_6$;
"$C_5$-$C_{10}$" encompasses $C_5$, $C_6$, $C_7$, $C_8$, $C_9$, $C_{10}$, $C_5$-$C_1$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_8$ and $C_9$-$C_{10}$;
"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_8$ and $C_9$-$C_{10}$.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected. In particular embodiments, the analyte is a PDE3A or SLFN12 polypeptide.

By "disease" is meant any condition or disease that damages or interferes with the normal function of a cell, tissue, or organ. Examples of diseases include hyperproliferatiotive disorder, cancer types such as e.g., adenocarcinoma, breast cancer, cervical cancer, liver cancer, lung cancer and melanoma.

By "effective amount" is meant the amount of a compound described herein required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount. In still other embodiments, the PDE3A modulator is a compound of formula (I).

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy.

By "modulator" is meant any agent that binds to a polypeptide and alters a biological function or activity of the polypeptide. A modulator includes, without limitation, agents that reduce or eliminate a biological function or activity of a polypeptide (e.g., an "inhibitor"). For example, a modulator may inhibit a catalytic activity of a polypeptide. A modulator includes, without limitation, agents that increase or decrease binding of a polypeptide to another agent. For example, a modulator may promote binding of a polypeptide to another polypeptide.

Unless specifically stated or obvious from context, as used herein, the term "or" is understood to be inclusive. Unless specifically stated or obvious from context, as used herein, the terms "a", "an", and "the" are understood to be singular or plural.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The term "prodrugs" or "prodrug" designates compounds which themselves can be biologically active or inactive, but are converted (for example metabolically or hydrolytically) into compounds according to the invention during their residence time in the body. Derivatives of the compound 6 and the salts thereof which are converted into compound 6 or a salt thereof in a biological system (bioprecursors or pro-drugs) are covered by the invention. Said biological system may be, for example, a mammalian organism, particularly a human subject. The bioprecursor is, for example, converted into a compound of formula (I) or a salt thereof by metabolic processes.

The term "pharmaceutically acceptable salt(s)" of the compounds of formula (I) include those derived from pharmaceutically acceptable inorganic and organic acids and bases. For example, see S. M. Berge, et al. "Pharmaceutical Salts," J. Pharm. Sci. 1977, 66, 1-19.

As used herein, the term "pharmaceutically acceptable salt" refers to a salt formed by the addition of a pharmaceutically acceptable acid or base to a compound disclosed herein.

As used herein, the phrase "pharmaceutically acceptable" refers to a substance that is acceptable for use in pharmaceutical applications from a toxicological perspective and does not adversely interact with the active ingredient.

Unless specifically stated or obvious from context, as used herein, if a range is provided, the upper and lower limit are always meant to be included. Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "reference" is meant a standard or control condition.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

DETAILED DESCRIPTION

As a first aspect the invention provides compounds of formula (I)

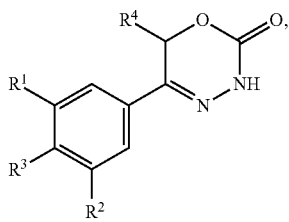

formula (I)

where
R¹ is selected from a hydrogen atom, a halogen atom, a cyano group, a $C_1$-$C_3$-alkyl group, a $C_1$-$C_3$-haloalkyl group, and a $C_1$-$C_3$-haloalkoxy group;
R² is selected from a hydrogen atom and a halogen atom;
R³ is selected from,
  a $C_1$-$C_6$-alkyl group which is optionally substituted with one or two substituents and each substituent is independently selected from a hydroxy group, a $C_1$-$C_4$-alkoxy group, and a 3- to 7-membered heterocycloalkyl group,
  a $C_2$-$C_6$-alkenyl group which is optionally substituted with an $C_1$-$C_4$-alkoxy group,
  a $C_3$-$C_9$-cycloalkyl group, which is optionally substituted with a hydroxy group,
  a $C_5$-$C_9$-cycloalkenyl group, which is optionally substituted with a hydroxy group
  a 3- to 9-membered heterocycloalkyl group, comprising one, two or three heteroatoms
    which are independently selected from —O—, —S—, —S(O)—, S(O)$_2$, and —NR⁹—,
    and said heterocycloalkyl group optionally further comprising a bridging group selected from —O—, —NR⁹—, —CH$_2$—, —CH$_2$—CH$_2$—, —O—CH$_2$—, —CH$_2$—O—, —NR⁹—CH$_2$—, and —CH$_2$—NR⁹—;
    and said heterocycloalkyl group is optionally substituted with one, two or three substituents and each substituent is independently selected from
    a halogen atom;
    a oxo(=O) group;
    a cyano group;
    a hydroxy group;
    a $C_1$-$C_3$-alkyl group which is optionally further substituted with a hydroxy group;
    a $C_1$-$C_3$-haloalkyl group;
    a $C_1$-$C_3$-alkoxy group;
    a $C_1$-$C_3$-haloalkoxy group;
    a C(O)NR⁵R⁶ group and
    a NR⁵R⁶ group,
  a 5- to 9-membered heterocycloalkyl group which is partially unsaturated and optionally substituted with one, two or three substituents and each substituent is independently selected from an oxo group (=O), a $C_1$-$C_3$-alkyl group a —C(O)R⁵R⁶ group and a halogen atom,
  an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a NR⁵R⁶ group,
  a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a NR⁵R⁶ group, with the proviso that said monocyclic heteroaryl group is not a pyridin-4-yl group;
  and a NR⁷R⁸ group;
R⁴ is selected from a hydrogen atom, and a $C_1$-$C_3$-alkyl group;
R⁵/R⁶ is independently selected from a hydrogen atom, a $C_1$-$C_6$-alkyl group, a —$C_1$-$C_5$-alkylene-O—$C_1$-$C_5$-alkyl group, a —$C_1$-$C_5$-alkylene-S—$C_1$-$C_5$-alkyl group, $C_3$-$C_6$-cycloalkyl group, and a $C_3$-$C_5$-heterocycloalkyl group;
R⁷/R⁸ are independently selected from
  a hydrogen atom, with the proviso that R⁷=R⁸=hydrogen is excluded,
  a $C_1$-$C_6$-alkyl group,
  which is optionally substituted with one, two, three or four substituents and said substituent is independently selected from
    a halogen atom, a cyano group, a hydroxy group, a C(O)NR⁵R⁶ group, a NR⁵R⁶ group,
    a $C_1$-$C_3$-alkoxy group,
    a $C_3$-$C_7$-cycloalkyl group which is optionally substituted with one or two substitutents and said substituents are independently selected from a $C_1$-$C_3$-alkyl group, a oxo (=O) group, a hydroxy group, and a $C_1$-$C_3$-hydroxyalkyl group;
    a 3- to 7-membered heterocycloalkyl group which itself is optionally substituted
      with a $C_1$-$C_3$-alkyl group or an oxo (=O) group
    a heteroaryl group, which itself is optionally substituted with a $C_1$-$C_3$-alkyl group;
  a —$C_1$-$C_5$-alkylene-O—$C_1$-$C_5$-alkyl group,
  a —$C_1$-$C_5$-alkylene-S—$C_1$-$C_5$-alkyl group,
  a —$C_1$-$C_5$-alkylene-NR⁵—$C_1$-$C_5$-alkyl group,
  a $C_3$-$C_6$-cycloalkyl group which is optionally substituted with a hydroxy group, and
  a 3- to 6-membered heterocycloalkyl group which is optionally substituted with one or two substituents, said substituent independently selected from $C_1$-$C_3$-alkyl group and a hydroxy group,
R⁹ is a hydrogen atom or a $C_1$-$C_3$-alkyl group or a bond;
or a stereoisomer, a tautomer, an N-oxide, a hydrate, a solvate, or a salt thereof, or a mixture of same.

The invention is further based at least in part on the discovery that the compounds of formula (I) are PDE3A- or PDE3B-SLFN12 complex modulators Accordingly, in a further embodiment the invention further provides methods of selecting a subject as having a cancer that responds to a PDE3A- or PDE3B-SLFN12 complex modulator, especially a compound of formula (I), where the selection method involves detecting co-expression of PDE3A and/or PDE3B and Schlafen 12 (SLFN12) polypeptides or polynucleotides, in a cancer cell derived from such subjects.

In a further embodiment, the invention provides methods of determining that the expression of CREB3L1 or SLFN12 polynucleotide or polypeptide is reduced or is undetectable in a cancer cell that has acquired resistance to a PDE3A- and/or PDE3B-SLFN12 complex modulator in order to prevent ineffective treatment with a compound of formula (I).

Accordingly, the invention provides methods comprising the steps of
- identifying subjects that have a malignancy that is likely to respond to PDE3A- and/or PDE3B-SLF12 complex modulator treatment, especially a treatment with a compound of formula (I), based on the level of PDE3A and/or PDE3B and SLFN12 expression in a subject biological sample comprising a cancer cell
- administering an effective amount of a compound of formula (I).

In particular embodiments, the invention provides methods comprising the steps of
- identifying subjects that have a malignancy that is resistant to PDE3A- and/or PDE3B-SLF12 complex modulator treatment, especially to the treatment of a compound of formula (I), based on a loss or reduction in the level of CREB3L1 or SLFN12 expression relative to a reference and
- subsequently excluding them from an envisaged treatment schedule with a compound of formula (I).

Compound Forms and Salts

It is possible for the compounds of formula (I) to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include $C_{1-6}$ alkyl esters of carboxylic acid groups, which, upon administration to a subject, are capable of providing active compounds.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the present invention and their pharmaceutically acceptable acid addition salts.

Further, another suitably pharmaceutically acceptable salt of a compound of formula (I), which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

In certain embodiments salts are derived from appropriate bases include alkali metal (e.g., sodium), alkaline earth metal (e.g., magnesium), ammonium and N-(alkyl) salts. The present invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxyl groups (e.g., L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x $CF_3OOOH$", "x $Na^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

In addition to salt forms, the present invention provides compounds which are in a prodrug form. Prodrugs of the compounds described herein are those compounds that undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the present invention.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta—etc. solvates or hydrates, respectively, are possible. The present invention includes all such hydrates or solvates.

The present invention also includes various hydrate and solvate forms of the compounds.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention. particularly deuterium-containing compounds of formula (I).

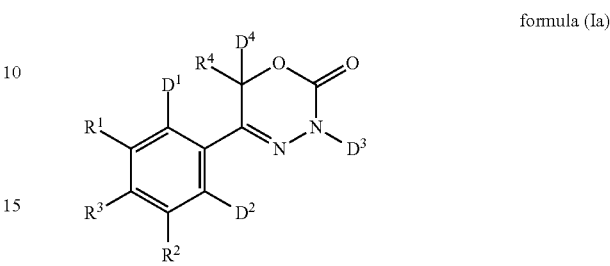

formula (Ia)

Formula (Ia) shows the positions $D^1$, $D^2$, $D^3$ and $D^4$ in which anyone of the hydrogen atoms may be exchanged by a deuterium atom. Additionally in residues $R^1$-$R^4$ if these residues contain a heteroatom-H or carbon-H bond accessible for a chemical reaction such an exchange may be possible. Hydrogen atoms can be replaced by deuterium atoms using methods known to those with ordinary skill in the art to obtain a heteroatom-D or carbon-D bond. Anyone of $R^1$, $R^2$, or $R^4$ themselves can also be deuterium instead of hydrogen.

Thus one aspect of the invention are those compounds wherein independently anyone of $R^1$, $R^2$, or $R^4$ is deuterium and/or anyone of the hydrogen atoms as shown in formula (I) are replaced by a deuterium atom and or anyone of $R^1$, $R^2$, $R^3$, or $R^4$ bears a deuterium atom at a chemically accessible position or any combination of positions being deuterated at the same time.

The term "Isotopic variant" of a compound or a reagent is defined as a compound exhibiting an unnatural proportion of one or more of the isotopes that constitute such a compound. The term "Isotopic variant of the compound of general formula (I)" is defined as a compound of general formula (I) exhibiting an unnatural proportion of one or more of the isotopes that constitute such a compound. The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998. Examples of such isotopes include stable and radioactive isotopes of hydrogen, carbon, nitrogen, oxygen, phosphorus, sulfur, fluorine, chlorine, bromine and iodine, such as $^2H$ (deuterium), $^3H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prophylaxis of the diseases specified herein the isotopic variant(s) of the compounds of general formula (I) may contain deuterium ("deuterium-containing compounds of general formula (I)"). Isotopic variants of the compounds of general formula (I) in which one or more radioactive isotopes, such as 3H or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I)

can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a direct route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites In some aspects, the compounds of formula (I) may be isomers. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this invention The symbol ═══ denotes a bond that can be a single or a double bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

The compounds of the present invention optionally contain one or more asymmetric centres, depending upon the location and nature of the various substituents desired, which are e.g. carbon atoms having four different substituents. It is possible that one or more asymmetric carbon atoms are present in the (R) or (S) configuration, which can result in racemic mixtures in the case of a single asymmetric centre, and in diastereomeric mixtures in the case of multiple asymmetric centres. The term "(±)" is used to designate a racemic mixture where appropriate. In certain instances, it is possible that asymmetry also be present due to restricted rotation about a given bond, for example, the central bond adjoining two substituted aromatic rings of the specified compounds. When a compound is an enantiomer, the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art including chiral high pressure liquid chromatography (HPLC), the formation and crystallization of chiral salts, or prepared by asymmetric syntheses.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Preferred is the stereoisomer which shows the desired effect. For compounds of formula (I) wherein $R^4$=methyl it is discovered that the compounds having said methyl group in the S-configuration do have a significantly better pharmacological effect.

Thus as one aspect of the invention for the configuration of the alkyl group in $R^4$ the invention preferably includes those compounds in which $R^4$=$C_1$-$C_3$-alkyl, more particularly $R^4$=methyl with S-configuration as indicated in formula (Ia)

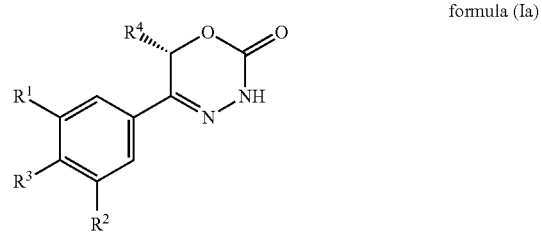

formula (Ia)

Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers. For example, any compound of the present invention which contains an imidazopyridine moiety as a heteroaryl group for example can exist as a 1H tautomer, or a 3H tautomer, or even a mixture in any amount of the two tautomers, namely:

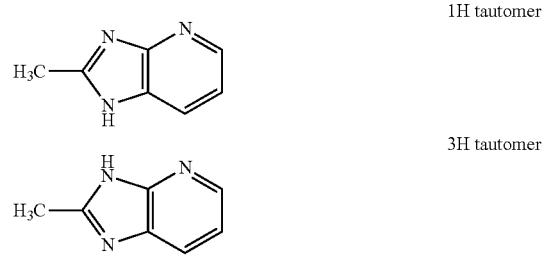

1H tautomer 3H tautomer

The present invention includes all possible tautomers of the compounds of the present invention as single tautomers, or as any mixture of said tautomers, in any ratio.

Further, the compounds of the present invention can potential exist as N-oxides, which are defined in that at least one nitrogen of the compounds of the present invention is oxidised. The present invention includes all such chemically possible N-oxides.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

Thus the present invention includes prodrugs of the compounds of formula (I).

In yet another embodiment the present invention includes stereoisomers, tautomes, an N-oxides, hydrates, solvates, or a salts, or a mixture of same of a compounds of formula (I).

In another embodiment the present invention includes stereoisomers, tautomes, hydrates, solvates, or a salts, or a mixture of same of a compounds of formula (I).

In a further embodiment the present invention includes stereoisomers, tautomes, solvates, or a salts, or a mixture of same of a compounds of formula (I).

In yet a further embodiment the present invention includes stereoisomers, tautomes, solvates, or a salts, or a mixture of same of a compounds of formula (I).

In yet another embodiment the present invention includes stereoisomers, tautomes, or a salts, or a mixture of same of a compounds of formula (I).

Further Aspects and Embodiments

In accordance with an embodiment of the first aspect, the present invention provides compounds of general formula (I):
where
$R^1$ is selected from a hydrogen atom, a halogen atom, a cyano group, a $C_1$-$C_3$-alkyl group, a $C_1$-$C_3$-haloalkyl group, and a $C_1$-$C_3$-haloalkoxy group;
$R^2$ is selected from a hydrogen atom and a halogen atom;
$R^3$ is selected from,
- a $C_1$-$C_6$-alkyl group which is optionally substituted with a substituent which is selected from a hydroxy group, a $C_1$-$C_4$-alkoxy group, and a 3- to 7-membered heterocycloalkyl group,
- a $C_2$-$C_6$-alkenyl group which is optionally substituted with an $C_1$-$C_4$-alkoxy group,
- a $C_3$-$C_7$-cycloalkyl group, which is optionally substituted with a hydroxy group,
- a $C_5$-$C_7$-cycloalkenyl group, which is optionally substituted with a hydroxy group
- a 3- to 7-membered-heterocycloalkyl group, comprising one, or two heteroatoms which
  - are independently selected from —O—, S(O)$_2$, and —NR$^9$—,
  - and said heterocycloalkyl group is optionally substituted with one, or two substituents and each substituent is independently selected from
    - a halogen atom;
    - a cyano group;
    - a hydroxy group;
    - a $C_1$-$C_3$-alkyl group which is optionally further substituted with a hydroxy group;
    - a $C_1$-$C_3$-alkoxy group;
    - a C(O)NR$^5$R$^6$ group and
    - a NR$^5$R$^6$ group;
- a 5- to 7-membered-heterocycloalkyl group, comprising a heteroatom which is selected from —O—, —S— and —NR$^9$—, which is partially unsaturated and optionally substituted with a substituent which is selected from a $C_1$-$C_3$-alkyl group a —C(O)R$^5$R$^6$ group and a halogen atom,
- an aryl group which is optionally substituted with one, two, or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, and a NR$^5$R$^6$ group,
- a mono- or bicyclic heteroaryl group which is optionally substituted with a substituent which is selected from a halogen atom, a $C_1$-$C_3$-alkyl group, a cyano group, a $C_1$—$C_3$-haloalkyl group, a $C_1$-$C_3$-alkoxy group, and a NR$^5$R$^6$ group, with the proviso that said monocyclic heteroaryl group is not a pyridin-4-yl group;
and a NR$^7$R$^8$ group;
$R^4$ is selected from a hydrogen atom, and a $C_1$-$C_3$-alkyl group;

$R^5$/$R^6$ is independently selected from a hydrogen atom and a $C_1$-$C_6$-alkyl group;
$R^7$/$R^8$ are independently selected from
- a hydrogen atom, with the proviso that $R^7$=$R^8$=hydrogen is excluded,
- a $C_1$-$C_6$-alkyl group, which is optionally substituted with one, two, three or four substituents and said substituent is independently selected from
  - a halogen atom, a cyano group, a hydroxy group, a C(O)NR$^5$R$^6$ group, a NR$^5$R$^6$ group,
  - a $C_1$-$C_3$-alkoxy group,
  - a $C_3$-$C_7$-cycloalkyl group which is optionally further substituted with one or two substituents and said substituents are independently selected from a $C_1$-$C_3$-alkyl group, a oxo (=O) group, a hydroxy group, and a $C_1$-$C_3$-hydroxyalkyl group;
  - a 3- to 7-membered heterocycloalkyl group, comprising one, two or three heteroatoms which are independently selected from —O— and —NR$^9$—, which is optionally further substituted with a $C_1$-$C_3$-alkyl group, a heteroaryl group, which is optionally further substituted with a $C_1$-$C_3$-alkyl group
- a $C_3$-$C_7$-cycloalkyl group which is optionally substituted with a hydroxy group, or a $C_1$-$C_3$-alkyl group and
- a 3- to 6-membered heterocycloalkyl group, which is optionally substituted with one or two substituents, said substituent independently selected from $C_1$-$C_3$-alkyl group and a hydroxy group,
$R^9$ is a hydrogen atom or a $C_1$-$C_3$-alkyl group or a bond;
or a stereoisomer, a tautomer, an N-oxide, a hydrate, a solvate, or a salt thereof, or a mixture of same.

In accordance with an embodiment of the first aspect, the present invention provides compounds of general formula (I):
where
$R^1$ is selected from a hydrogen atom, a halogen atom, a $C_1$-$C_3$-alkyl group, a $C_1$-$C_3$-haloalkyl group, and a $C_1$-$C_3$-haloalkoxy group;
$R^2$ is selected from a hydrogen atom and a halogen atom;
$R^3$ is selected from,
- a $C_1$-$C_6$-alkyl group which is optionally substituted with a substituent which is selected from a hydroxy group, a $C_1$-$C_4$-alkoxy group, and a 3- to 7-membered heterocycloalkyl group,
- a $C_2$-$C_6$-alkenyl group which is optionally substituted with an $C_1$-$C_4$-alkoxy group,
- a $C_3$-$C_7$-cycloalkyl group, which is optionally substituted with a hydroxy group,
- a $C_5$-$C_7$-cycloalkenyl group,
- a 3- to 7-membered heterocycloalkyl group, comprising one, or two heteroatoms which are independently selected from —O—, and —NR$^9$—,
  - and said heterocycloalkyl group is optionally substituted with one, or two substituents and each substituent is independently selected from
    - a halogen atom;
    - a cyano group;
    - a hydroxy group;
    - a $C_1$-$C_3$-alkyl group which is optionally further substituted with a hydroxy group;
    - a $C_1$-$C_3$-alkoxy group; and
    - a C(O)NR$^5$R$^6$ group
- a 5- to 7-membered-heterocycloalkyl group, comprising a heteroatom which is selected from —O—, and —NR$^9$—, which is partially unsaturated and optionally substituted with a substituent which is selected from a $C_1$-$C_3$-alkyl group and a halogen atom, an aryl group which is optionally substituted with one, two, or three substituents and each substituent is independently selected from a halogen atom, a hydroxy group, a cyano group, a $C_1$-$C_3$-alkyl group, a $C_1$-$C_3$-haloalkyl group, and a $NR^5R^6$ group, a mono- or bicyclic heteroaryl group which is optionally substituted with a substituent which is selected from a halogen atom, a $C_1$-$C_3$-alkyl group a $C_1$-$C_3$-haloalkyl group, a $C_1$-$C_3$-alkoxy group, and a $NR^5R^6$ group;

and a $NR^7R^8$ group, with the proviso that said monocyclic heteroaryl group is not a pyridin-4-yl group;

$R^4$ is selected from a hydrogen atom, and a $C_1$-$C_3$-alkyl group;

$R^5/R^6$ is independently selected from a hydrogen atom and a $C_1$-$C_6$-alkyl group;

$R^7/R^8$ are independently selected from a hydrogen atom, with the proviso that $R^7$=$R^8$=hydrogen is excluded, a $C_1$-$C_6$-alkyl group, which is optionally substituted with one, two, three or four substituents and said substituent is independently selected from a halogen atom, a cyano group, a hydroxy group, a $NR^5R^6$ group, a $C_1$-$C_3$-alkoxy group, a $C_3$-$C_7$-cycloalkyl group which is optionally further substituted with one or two substituents and said substituents are independently selected from a $C_1$-$C_3$-alkyl group, a oxo (=O) group, a hydroxy group, and a $C_1$-$C_3$-hydroxyalkyl group;

a 3- to 7-membered heterocycloalkyl group, comprising one, two or three heteroatoms which are independently selected from —O— and —$NR^9$—, which is optionally further substituted with a $C_1$-$C_3$-alkyl group, a heteroaryl group, which is optionally further substituted with a $C_1$-$C_3$-alkyl group a $C_3$-$C_7$-cycloalkyl group which is optionally substituted with a hydroxy group, or a $C_1$-$C_3$-alkyl group and a 3- to 6-membered heterocycloalkyl group, which is optionally substituted with one or two substituents, said substituent independently selected from $C_1$-$C_3$-alkyl group and a hydroxy group, $R^9$ is a hydrogen atom or a $C_1$-$C_3$-alkyl group or a bond;

or a stereoisomer, a tautomer, an N-oxide, a hydrate, a solvate, or a salt thereof, or a mixture of same.

In accordance with an embodiment of the first aspect, the present invention provides compounds of general formula (I):

where $R^1$ is selected from a hydrogen atom, a halogen atom, a $C_1$-$C_3$-alkyl group, a $C_1$-$C_3$-haloalkyl group, and a $C_1$-$C_3$-haloalkoxy group;

$R^2$ is selected from a hydrogen atom and a halogen atom;

$R^3$ is selected from, a $C_1$-$C_6$-alkyl group which is optionally substituted with a substituent which is selected from a hydroxy group, a $C_1$-$C_4$-alkoxy group, and a 3- to 7-membered heterocycloalkyl group, a $C_2$-$C_6$-alkenyl group which is optionally substituted with an $C_1$-$C_4$-alkoxy group, a $C_4$-$C_6$-cycloalkyl group, which is optionally substituted with a hydroxy group, a $C_5$-$C_7$-cycloalkenyl group, a 3- to 6-membered heterocycloalkyl group, comprising one, or two heteroatoms which are independently selected from —O—, and —$NR^9$—, and said heterocycloalkyl group is optionally substituted with one, or two substituents and each substituent is independently selected from a halogen atom;

a cyano group;

a hydroxy group a $C_1$-$C_3$-alkyl group which is optionally further substituted with a hydroxy group;

a 5- to 6-membered-heterocycloalkyl group, comprising a heteroatom which is selected from —O—, and —$NR^9$—, which is partially unsaturated and optionally substituted with a substituent which is selected from a $C_1$-$C_3$-alkyl group and a halogen atom, an aryl group which is optionally substituted with one, or two, substituents and each substituent is independently selected from a halogen atom, a hydroxy group, a cyano group, a $C_1$-$C_3$-alkyl group, a $C_1$-$C_3$-haloalkyl group, and a $NR^5R^6$ group, a mono- or bicyclic heteroaryl group which is optionally substituted with a substituent which is selected from a halogen atom, a $C_1$-$C_3$-alkyl group a $C_1$-$C_3$-haloalkyl group, a $C_1$-$C_3$-alkoxy group, and a $NR^5R^6$ group;

and a $NR^7R^8$ group, with the proviso that said monocyclic heteroaryl group is not a pyridin-4-yl group;

$R^4$ is selected from a hydrogen atom, and a $C_1$-$C_3$-alkyl group;

$R^5/R^6$ is independently selected from a hydrogen atom and a $C_1$-$C_6$-alkyl group;

$R^7/R^8$ are independently selected from a hydrogen atom, with the proviso that $R^7$=$R^8$=hydrogen is excluded, a $C_1$-$C_6$-alkyl group, which is optionally substituted with one, two, three or four substituents and said substituent is independently selected from a halogen atom, a hydroxy group, a $C_1$-$C_3$-alkoxy group, a $C_3$-$C_6$-cycloalkyl group which is optionally further substituted with one or two substituents and said substituents are independently selected from a $C_1$-$C_3$-alkyl group and a $C_1$-$C_3$-hydroxyalkyl group;

a 4- to 6-membered heterocycloalkyl group, comprising one, two or three heteroatoms which are independently selected from —O— and —$NR^9$—, which is optionally further substituted with a $C_1$-$C_3$-alkyl group, a heteroaryl group, which is optionally further substituted with a $C_1$-$C_3$-alkyl group;

a $C_3$-$C_6$-cycloalkyl group which is optionally substituted with a hydroxy group, or a $C_1$-$C_3$-alkyl group a 3- to 6-membered heterocycloalkyl group, which is optionally substituted with one or two substituents, said substituent independently selected from $C_1$-$C_3$-alkyl group and a hydroxy group, and $R^9$ is a hydrogen atom or a $C_1$-$C_3$-alkyl group or a bond;

or a stereoisomer, a tautomer, an N-oxide, a hydrate, a solvate, or a salt thereof, or a mixture of same.

In accordance with an embodiment of the first aspect, the present invention provides compounds of general formula (I):

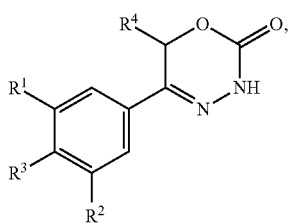

formula (I)

where
R$^1$ is selected from a hydrogen atom, a halogen atom, a cyano group, a C$_1$-C$_3$-alkyl group, a C$_1$-C$_3$-haloalkyl group, and a C$_1$-C$_3$-haloalkoxy group;
R$^2$ is selected from a hydrogen atom and a halogen atom,
R$^3$ is selected from a halogen atom,
  a C$_2$-C$_6$-alkenyl group,
  a C$_3$-C$_6$-cycloalkyl group
  a C$_5$-C$_6$-cycloalkenyl group,
  a C$_3$-C$_7$-heterocycloalkyl group, which is optionally substituted with one, two or three substituents and each substituent is independently selected from a halogen atom and a C$_1$-C$_3$-alkyl group, a hydroxy group, NR$^5$R$^6$ group, a C$_1$-C$_3$-haloalkyl group and a C$_1$-C$_3$-haloalkoxy group,
  a C$_5$-C$_7$-heterocycloalkyl group which is partially unsaturated and optionally substituted with one, two or three substituents and each substituent is independently selected from an oxo group (=O), a C$_1$-C$_3$-alkyl group and a halogen atom,
  an aryl group which is optionally substituted with one, two, three or four substituents and each substituent is independently selected from a halogen atom, a hydroxy group, a cyano group, a C$_1$-C$_3$-alkyl group, a C$_1$-C$_3$-haloalkyl group, a C$_1$-C$_3$-alkoxy group, a C$_1$-C$_3$-haloalkoxy group, and a NR$^5$R$^6$ group,
  a mono- or bicyclic heteroaryl group which is optionally substituted with one, two or three substituents and each substituent is independently selected from a halogen atom, a C$_1$-C$_3$-alkyl group, a cyano group, a C$_1$-C$_3$-haloalkyl group, a C$_1$-C$_3$-alkoxy group, a hydroxy group, and a NR$^5$R$^6$ group;
  and a NR$^7$R$^8$ group,
R$^4$ is selected from a hydrogen atom, and a C$_1$-C$_3$-alkyl group,
R$^5$/R$^6$ is independently selected from a hydrogen atom, a C$_1$-C$_6$-alkyl group, a —C$_1$-C$_5$-alkylene-O—C$_1$-C$_5$-alkyl group, a —C$_1$-C$_5$-alkylene-S—C$_1$-C$_5$-alkyl group, C$_3$-C$_6$-cycloalkyl group, and a C$_3$-C$_5$-heterocycloalkyl group,
R$^7$/R$^8$ is independently selected from a hydrogen atom, and a C$_1$-C$_6$-alkyl group, a —C$_1$—C— alkylene-O—C$_1$-C$_5$-alkyl group, a —C$_1$-C$_5$-alkylene-S—C$_1$-C$_5$-alkyl group, a —C$_1$-C$_5$-alkylene-NR$^5$—C$_1$-C$_5$-alkyl group, a C$_3$-C$_6$-cycloalkyl group, a C$_3$-C$_5$-heterocycloalkyl group,
or R$^7$ and R$^8$ together form a 3-, 4-, 5-, 6- or 7-membered ring optionally containing one or two additional heteroatoms selected from the group consisting of —O—, —S— and —NR$^9$—,
  and which is optionally substituted one, two or three times with a substitutent selected from a halogen atom, a C$_1$-C$_3$-alkyl group, a hydroxy group, a cyano group, an oxo group (=O), and a NR$^5$R$^6$ group, and if R$^7$ and R$^8$ together form a 5-, 6- or 7-membered ring, said ring can optionally contain a bridging group selected from —O—, —NR$^9$—, —CH$_2$—, —CH$_2$—CH$_2$—, —O—CH$_2$—, —NR$^9$—CH$_2$—;
R$^9$ is a hydrogen atom or a C$_1$-C$_3$-alkyl group,
or a stereoisomer, a tautomer, an N-oxide, a hydrate, a solvate, or a salt thereof, or a mixture of same.

In accordance with an embodiment of the first aspect, the present invention provides compounds of general formula (I):
wherein
R$^1$ is selected from a hydrogen atom, a halogen atom, a C$_1$-C$_3$-alkyl group, a C$_1$-C$_3$-haloalkyl group, a C$_1$-C$_3$-haloalkoxy group;
R$^2$ is selected from a hydrogen atom, and a halogen atom,
R$^3$ is selected from a halogen atom,
  a C$_2$-C$_4$-alkenyl group,
  a C$_1$-C$_6$-cycloalkenyl group,
  a C$_3$-C$_6$-heterocycloalkyl group, which is optionally substituted with one or two substituents and each substituent is independently selected from a halogen atom and a C$_1$-C$_3$-alkyl group;
  a C$_5$-C$_6$-heterocycloalkyl group which is partially unsaturated and optionally substituted with one or two substituents and each substituent is independently selected from an oxo group (=O), a C$_1$-C$_3$-alkyl group and a halogen atom;
  an aryl group which is optionally substituted with one, two, or three substituents and each substituent is independently selected from a halogen atom, a hydroxy group, a C$_1$-C$_3$-alkyl group, a C$_1$-C$_3$-haloalkyl group, and a NR$^5$R$^6$ group;
  a mono- or bicyclic heteroaryl group which is optionally substituted with one, two or three substituents and each substituent is independently selected from a halogen atom, a C$_1$-C$_3$-alkyl group, a cyano group, a C$_1$-C$_3$-haloalkyl group, a C$_1$-C$_3$-alkoxy group, and a NR$^5$R$^6$ group;
  and a NR$^7$R$^8$ group;
R$^4$ is selected from a hydrogen atom, and a C$_1$-C$_3$-alkyl group;
R$^5$/R$^6$ is independently selected from a hydrogen atom, a C$_1$-C$_6$-alkyl group, a —C$_1$-C$_3$-alkylene-O—C$_1$-C$_3$-alkyl group, a —C$_1$-C$_3$-alkylene-S—C$_1$-C$_3$-alkyl group, and a C$_3$-C$_5$-heterocycloalkyl group,
R$^7$/R$^8$ is independently selected from a hydrogen atom, and a C$_1$-C$_6$-alkyl group, a —C$_1$-C$_3$-alkylene-O—C$_1$-C$_3$-alkyl group, a —C$_1$-C$_3$-alkylene-S—C$_1$-C$_3$-alkyl group, a —C$_1$-C$_3$-alkylene-NR$^5$—C$_1$-C$_3$-alkyl group, a C$_3$-C$_6$-cycloalkyl group, a C$_3$-C$_5$-heterocycloalkyl group, or R$^7$ and R$^8$ together form a 3-, 4-, 5-, 6- or 7-membered ring optionally containing one or two additional heteroatoms selected from the group consisting of —O—, —S— and —NR$^9$—,
  and which is optionally substituted one, two or three times with a substitutent selected from a halogen atom, a C$_1$-C$_3$-alkyl group, a hydroxy group, a cyano group, an oxo group (=O), and a NR$^5$R$^6$ group,
R$^9$ is a hydrogen atom or a C$_1$-C$_3$-alkyl group,
or a stereoisomer, a tautomer, an N-oxide, a hydrate, a solvate, or a salt thereof, or a mixture of same.

In accordance with a second embodiment of the first aspect, the present invention provides compounds of general formula (I):
wherein
R$^1$ is selected from a halogen atom, a C$_1$-C$_3$-alkyl group and a C$_1$-C$_3$-haloalkyl group;

$R^2$ is selected from a hydrogen atom and a halogen atom,
$R^3$ is selected from a halogen atom,
  a $C_2$-$C_4$-alkenyl group,
  a $C_5$-$C_6$-cycloalkyenyl group,
  a $C_3$-$C_6$-heterocycloalkyl group, which is optionally substituted with one or two substituents and each substituent is independently selected from a halogen atom and a $C_1$-$C_3$-alkyl group;
  a $C_5$-$C_6$-heterocycloalkyl group which is partially unsaturated and optionally substituted with an oxo group (=O);
  an phenyl group which is optionally substituted with one, two or three substituents and each substituent is independently selected from a halogen atom, a hydroxy group, a $C_1$-$C_3$-alkyl group, a $C_1$-$C_3$-haloalkyl group, and a $NR^5R^6$ group;
  a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, and a $NR^5R^6$ group;
  and a $NR^7R^8$ group;
$R^4$ is selected from a hydrogen atom, and a methyl group;
$R^5/R^6$ is independently selected from a hydrogen atom and a $C_1$-$C_3$-alkyl group; and
$R^7/R^8$ is independently selected from a hydrogen atom, a $C_3$-$C_5$-cycloalkyl group, and a $C_1$-$C_6$-alkyl group;
or $R^7$ and $R^8$ together form a 4-, 5-, or 6-membered ring optionally containing one additional oxygen atom,
  and which is optionally substituted one or two times with a substitutent selected from a halogen atom and a $C_1$-$C_3$-alkyl group;
or a stereoisomer, a tautomer, an N-oxide, a hydrate, a solvate, or a salt thereof, or a mixture of same.

In accordance with a third embodiment of the first aspect, the present invention provides compounds of general formula (I):
wherein
$R^1$ is selected from $CF_3$, —$CH_3$, —$OCF_3$ and a fluorine atom,
$R^2$ is selected from a hydrogen atom
$R^3$ is selected from a halogen atom,
  a $C_2$-$C_4$-alkenyl group,
  a $C_5$-$C_6$-cycloalkyenyl group,
  a $C_3$-$C_6$-heterocycloalkyl group, which is optionally substituted with one or two substituents and each substituent is independently selected from a halogen atom and a $C_1$-$C_3$-alkyl group;
  a $C_5$-$C_6$-heterocycloalkyl group which is partially unsaturated and optionally substituted with an oxo group (=O);
  an phenyl group which is optionally substituted with one, two or three substituents and each substituent is independently selected from a halogen atom, a hydroxy group, a $C_1$-$C_3$-alkyl group, a $C_1$-$C_3$-haloalkyl group, and a $NR^5R^6$ group;
  a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, and a $NR^5R^6$ group;
  and a $NR^7R^8$ group;
$R^4$ is selected from a hydrogen atom, and a $C_1$-$C_3$-alkyl group;
$R^5/R^6$ is independently selected from a hydrogen atom and a $C_1$-$C_3$-alkyl group; and
$R^7/R^8$ is independently selected from a hydrogen atom and a $C_1$-$C_6$-alkyl group;
or $R^7$ and $R^8$ together form a 4-, 5-, or 6-membered ring optionally containing one additional oxygen atom,
  and which is optionally substituted one or two times with a substitutent selected from a halogen atom and a $C_1$-$C_3$-alkyl group;
or a stereoisomer, a tautomer, an N-oxide, a hydrate, a solvate, or a salt thereof, or a mixture of same.

In accordance with a fourth embodiment of the first aspect, the present invention provides compounds of general formula (I):
wherein
$R^1$ is selected from $CF_3$, —$CH_3$, —$OCF_3$ and a fluorine atom,
$R^2$ is selected from a hydrogen atom
$R^3$ is selected from
  a halogen atom,
  a prop-1-en-1-yl group which is optionally substituted with a methyl group,
  a piperidin-1-yl group which is optionally substituted with one or two substitutents and each substituent is independently selected from a fluorine atom and a methyl group
  a morpholin-4-yl group which is optionally substituted with one or two methyl groups,
  a pyrrolidin-1-yl group which is optionally substituted with one or two halogen atoms,
  a 1,2,3,6-tetrahydropyridin-4-yl group which is optionally substituted with a methyl group,
  an azitidin-1-yl group,
  a 3,6-dihydro-1H-pyran-4-yl group,
  a 6-oxo-1,6-dihydropyridin-3-yl group which is optionally substituted with one or two substitutents and each substituent is independently selected from a hydrogen atom and a methyl group,
  a cyclopent-1en-1-yl group,
  a phenyl group which is optionally substituted with one, two or three substituents and each substituent is independently selected from a halogen atom, a hydroxy group, a methyl group, an ethyl group, a $CF_3$, $CF_2H$ group, a methoxy group, a $CF_3O$ group, a $NH_2$ group and a $NHCH_3$ group,
  a 2H-pyrrol-1-yl group, which is optionally substituted with one or two substitutents and each substituent is independently selected from a hydrogen atom, a cyano group and a methyl group,
  a 1H-pyrrazol-4-yl group, which is optionally substituted with one or two substitutents and each substituent is independently selected from a methyl group, an ethyl group or a $CF_3$ group,
  a 1H-pyrrazol-5-yl group, which is optionally substituted with a methyl group,
  1,2-oxazol-4-yl which is optionally substituted with one or two methyl groups,
  a 1,2-thiazol-4-yl group which is optionally substituted with a methyl group,
  a 1,3-thiazol-5-yl group which is optionally substituted with a methyl group,
  a pyridin-3-yl, a pyridin-4-yl and a pyridin 5-yl group each group being optionally substituted with one or two substitutents and each substituent is independently selected from a halogen atom, a methyl group, a $CF_3$ group, a methoxy group and a $NH_2$ group, a pyrimidin-5-yl group which is optionally substituted with a methyl group,
a 1H-indol-6-yl group,
a 1H-indazol-6-yl group which is optionally substituted with a methyl group,
a 1H-benzimidazol-6-yl group which is optionally substituted with a methyl group,
a $NH(C_2H)$ group, a $NH(C_3H_7)$ group, a $NH(C_4H_9)$ group, a $NCH_3(C_4H_9)$ group, a $NH(C_5H_{11})$ group, a NH(cyclopentyl) group, a $NCH_3$(cyclopentyl) group;

$R^4$ is selected from a hydrogen atom, and a $C_1$-$C_3$-alkyl group;

or a stereoisomer, a tautomer, an N-oxide, a hydrate, a solvate, or a salt thereof, or a mixture of same.

In accordance with a further embodiment of the first aspect, the present invention provides compounds of general formula (I):

where $R^1$ is selected from a hydrogen atom, a halogen atom, a $C_1$-$C_3$-alkyl group, and a $C_1$-$C_3$-haloalkyl group;

$R^2$ is selected from a hydrogen atom and a halogen atom;

$R^3$ is selected from,
  a $C_1$-$C_6$-alkyl group which is optionally substituted with one or two substituents and each substituent is independently selected from a hydroxy group, a $C_1$-$C_4$-alkoxy group, and a 3- to 7-membered heterocycloalkyl group,
  a $C_2$-$C_6$-alkenyl group which is optionally substituted with an $C_1$-$C_3$-alkoxy group,
  a $C_3$-$C_7$-cycloalkyl group, which is optionally substituted with a hydroxy group,
  a $C_5$-$C_6$-cycloalkenyl group, which is optionally substituted with a hydroxy group
  a 3- to 6-membered heterocycloalkyl group, comprising one, two or three heteroatoms which are independently selected from —O— and —$NR^9$—,
    and said heterocycloalkyl group is optionally substituted with one, two or three substituents and each substituent is independently selected from
    a halogen atom;
    a oxo(=O) group;
    a cyano group;
    a hydroxy group;
    a $C_1$-$C_3$-alkyl group which is optionally substituted with a hydroxy group;
  a 5- to 7-membered heterocycloalkyl group which is partially unsaturated and optionally substituted with one or two substituents and each substituent is independently selected from a $C_1$-$C_3$-alkyl group and a halogen atom,
  an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a $NR^5R^6$ group,
  a mono- or bicyclic heteroaryl group which is optionally substituted with one or two substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^5R^6$ group, with the proviso that said monocyclic heteroaryl group is not a pyridin-4-yl group;
  and a $NR^7R^8$ group;

$R^4$ is selected from a hydrogen atom, and a $C_1$-$C_3$-alkyl group;

$R^5/R^6$ is independently selected from a hydrogen atom and a $C_1$-$C_6$-alkyl group;

$R^7/R^8$ are independently selected from
  a hydrogen atom, with the proviso that $R^7$=$R^8$=hydrogen is excluded,
  a $C_1$-$C_6$-alkyl group,
    which is optionally substituted with one, two, three or four substituents and said substituent is independently selected from
    a halogen atom, a cyano group, and a hydroxy group,
    a $C_1$-$C_3$-alkoxy group,
    a $C_3$-$C_7$-cycloalkyl group which is optionally substituted with one or two substitutents and said substituents are independently selected from a $C_1$-$C_3$-alkyl group, a hydroxy group, and a $C_1$-$C_3$-hydroxyalkyl group;
    a 3- to 7-membered heterocycloalkyl group which itself is optionally substituted with a $C_1$-$C_3$-alkyl group
    a heteroaryl group, which is optionally further substituted with a $C_1$-$C_3$-alkyl group;
  a $C_3$-$C_6$-cycloalkyl group which is optionally substituted with a hydroxy group, and
  a 3- to 6-membered heterocycloalkyl group which is optionally substituted with one or two substituents said substituent independently selected from $C_1$-$C_3$-alkyl group and a hydroxy group, $R^9$ is a hydrogen atom or a $C_1$-$C_3$-alkyl group or a bond;

or a stereoisomer, a tautomer, an N-oxide, a hydrate, a solvate, or a salt thereof, or a mixture of same.

In accordance with a further embodiment of the first aspect, the present invention provides compounds of general formula (I):

where $R^1$ is selected from a hydrogen atom, a halogen atom, a $C_1$-$C_3$-alkyl group, and a $C_1$-$C_3$-haloalkyl group;

$R^2$ is selected from a hydrogen atom and a halogen atom;

$R^3$ is selected from,
  a 3- to 6-membered heterocycloalkyl group, comprising one, or two heteroatoms which are independently selected from —O—, and —$NR^9$—,
    and said heterocycloalkyl group is optionally substituted with one, or two substituents and each substituent is independently selected from
    a halogen atom;
    a hydroxy group
    a $C_1$-$C_3$-alkyl group which is optionally further substituted with a hydroxy group;
  an aryl group which is optionally substituted with one, or two, substituents and each substituent is independently selected from a halogen atom, a hydroxy group, and a $C_1$-$C_3$-haloalkyl group,
  a mono- or bicyclic heteroaryl group which is optionally substituted with a substituent which is selected from a halogen atom, a $C_1$-$C_3$-alkyl group a $C_1$-$C_3$-haloalkyl group and a $NR^5R^6$ group, with the proviso that said monocyclic heteroaryl group is not a pyridin-4-yl group;
  and a $NR^7R^8$ group;

$R^4$ is selected from a hydrogen atom, and a $C_1$-$C_3$-alkyl group;

$R^5/R^6$ is independently selected from a hydrogen atom and a $C_1$-$C_3$-alkyl group;

$R^7/R^8$ are independently selected from
  a hydrogen atom, with the proviso that $R^7$=$R^8$=hydrogen is excluded, a $C_1$-$C_6$-alkyl group, which is optionally substituted with one or two, three or four substituents and said substituent is independently selected from
  a halogen atom, a hydroxy group,
  a $C_1$-$C_3$-alkoxy group,
  a $C_3$-$C_5$-cycloalkyl group which is optionally further substituted with one or two substituents and said substituents are independently selected from a $C_1$-$C_3$-alkyl group and a $C_1$-$C_3$-hydroxyalkyl group;
  a 5- to 6-membered heterocycloalkyl group, comprising one, or two heteroatoms which are independently selected from —O— and —NR$^9$—, which is optionally further substituted with a $C_1$-$C_3$-alkyl group,
  a heteroaryl group, which is optionally further substituted with a $C_1$-$C_3$-alkyl group;
a $C_3$-$C_6$-cycloalkyl group which is optionally substituted with a hydroxy group, or a $C_1$-$C_3$-alkyl group
a 4- to 5-membered heterocycloalkyl group, which is optionally substituted with one or two substituents, said substituent independently selected from $C_1$-$C_3$-alkyl group and a hydroxy group, and
$R^9$ is a hydrogen atom or a $C_1$-$C_3$-alkyl group or a bond;
or a stereoisomer, a tautomer, an N-oxide, a hydrate, a solvate, or a salt thereof, or a mixture of same.

In accordance with yet a further embodiment of the first aspect, the present invention provides compounds of general formula (I):
$R^1$ is selected from $CF_3$ and a fluorine atom;
$R^2$ is a hydrogen atom;
$R^3$ is selected from
  an aryl group which is optionally substituted with a substituent which is selected from a halogen atom and a $C_1$-$C_3$-haloalkyl group,
  a monocyclic heteroaryl group substituted with a substituent which is selected from $C_1$-$C_3$-haloalkyl group and NR$^5$R$^6$ group;
  and a NR$^7$R$^8$ group;
$R^4$ is selected from a hydrogen atom and a methyl group;
$R^5$/$R^6$ is a hydrogen atom or a methyl group;
$R^7$/$R^8$ are independently selected from
  a hydrogen atom, with the proviso that $R^7$=$R^8$=hydrogen is excluded,
  a $C_1$-$C_3$-alkyl group, which is optionally substituted with one two or four substituents and said substituent is independently selected from
    a halogen atom, a hydroxy group, and a methoxy group,
or a stereoisomer, a tautomer, an N-oxide, a hydrate, a solvate, or a salt thereof, or a mixture of same.

In accordance with a further embodiment of the first aspect, the present invention provides compounds of general formula (I):
wherein
$R^1$ is selected from a hydrogen atom, a fluorine atom, a cyano group, a methyl group a $OCF_3$ group, a $CHF_2$ group and a $CF_3$ group,
$R^2$ is selected from a hydrogen atom, or a fluorine atom;
$R^3$ is selected from
a $C_1$-$C_6$-akyl group, which is optionally substituted with a substitutent said substitutent is selected from a 2-hydroxy group, a methoxy group and a morpholino group;
a $C_2$-$C_6$-alkenyl group which is optionally substituted with a methoxy group;
a cyclohexyl group, which is optionally substituted with a hydroxy group;
a $C_5$-$C_7$-cycloalkenyl group;
a 3-6-membered heterocycloalkyl group which is optionally substituted with one or two substitutents said substitutents are independently selected from a fluorine atom, a —C(O)NH2 group, a hydroxy group a methyl group, an ethyl group, a hydroxymethyl group, a cyano group, and a amino group;
a partially unsaturated 5-6-membered heterocycloalkyl group which is optionally substituted with a methyl group;
a phenyl group, which is optionally substituted with one, two or three substitutents said substitutents are independently selected from a methyl group, an ethyl group, a fluorine atom, a chlorine atom, an amino group, a hydroxy group, a methoxy group, a cyano group, a difluoromethyl group, a trifluoromethyl group and a methylamino group;
a 5-membered heteroaryl group, which is optionally substituted with one or two substitutents said substitutents are independently selected from a methyl group, an ethyl group, a trifluoromethyl group, a difluoromethyl group, and a cyano group,
a 6-membered heteroaryl group, which is optionally substituted with one or two substitutents said substitutents are independently selected from a methyl group, a fluorine atom, a chlorine atom, a trifluoromethyl group, a amino group, and a methoxy group,
a bicyclic heteroaryl group which is optionally substituted with a methyl group;
a NR$^7$R$^8$: group,
  where R$^7$R$^8$ are independently selected from a hydrogen atom,
  a $C_1$-$C_6$ alkyl group which is optionally substituted with one or two substitutents said substitutents are independently selected from a amino group, a methoxy group, a ethoxy group, a cyano group, a hydroxy group, a trifluoromethyl group, a cyclopropyl group, a 2,2-dimethylcyclopropyl group, a 1-hydroxycyclobutyl group, a 3-hydroxycyclobutyl group, methyloxetanyl group, an oxolanyl group, an oxanyl group, a methyloxanyl group, a tetrahydrofuranyl group, oxopyrrolidinyl group, a oxopiperidinyl group, a methyl-1H-imidazolyl group, a 1H-pyrazolyl group, 1H-imidazolyl group, a 1-methyl-1H-pyrazolyl group, a pyrazinyl group, a pyridinyl group, a pyrimidinyl group,
a $C_5$-$C_7$-cycloalkyl group, which is optionally substituted with a hydroxy group, a 4-6-membered heterocycloalkyl group which is optionally substituted with a methyl group,
$R^4$ is a hydrogen atom or a methyl group
or a stereoisomer, a tautomer, an N-oxide, a hydrate, a solvate, or a salt thereof, or a mixture of same.

In accordance with a further embodiment of the first aspect, the present invention provides compounds of general formula (I):
wherein
$R^1$ is selected from a hydrogen atom, a fluorine atom, a cyano group, a $CH_3$ group a $OCF_3$ group a $CHF_2$ group and a $CF_3$ group,
$R^2$ is selected from a hydrogen atom (many examples), or a fluorine atom;
$R^3$ is selected from
a methyl group, a propan-2-yl group, a 2-methylpropyl group, a 2-hydroxypropan-2-yl group, a 3,3-dimethylbutyl group, a 3-methoxypropyl group,
a —$CH_2$-(morpholin-4-yl) group,
a prop-1-en-2-yl group, a 2-methylprop-1-en-1-yl group, a 3,3-dimethylbut-1-en-1-yl group, a 3-methoxyprop-1-en-1-yl group,
a 4-hydroxycyclohexyl group, a cyclopent-1-en-1-yl group, a cyclohex-1-en-1-yl group, a bicyclo[2.2.1]hept-2-en-2-yl group a oxan-3-yl group, a 3,3-difluoroazetidin-1-yl group, azetidin-3-carbocxamide, a 2-hydroxyazetidin-1-yl group, a 3-hydroxy-3-methylazetidin-1-yl group, a 2-(hydroxymethyl)azetidin-1-yl group, a 3-cyano-3-methylazetidin-1-yl group, a 2,4-dimethylazetidin-1-yl group, a -2lambda<sup>6</sup>-thia-6-azaspiro[3.3]heptane-2,2-dione group, a 3-hydroxypyrrolidin-1-yl group, a 3,3-difluoropyrrolidin-1-yl group, a 3-azabicyclo[3.1.0]hexan-3-yl group, a 1-amino-3-azabicyclo[3.1.0]hexan-3-yl group, a 4-fluoropiperidin-1-yl group, 4,4-fluoropiperidin-1-yl group, a 4-cyano-piperidin-1-yl group, a 4-fluoro-4-methylpiperidin-1-yl group, a 4-ethyl-4-hydroxypiperidin-1-yl group, a 4-hydroxypiperidin-1-yl group, a 3-hydroxypiperidin-1-yl group, a 3-aminocarbonylpiperidin-1-yl group, a morpholin-4-yl group, a 2-methylmorpholin-4-yl group, a 2,6-dimethylmorpholin-4-yl group, a 4-methylpiperazin-1-yl group, a 2,5-dihydrofuran-3-yl group, a 5,6-dihydro-2H-pyran-3-yl group, a 3,6-dihydro-2H-pyran-4-yl group, a 1,2,3,6-tetrahydropyridin-4-yl group, a 1-methyl-1,2,3,6-tetrahydropyridin-4-yl group, a 6-oxo-1,6-dihydropyridin-3-yl group, a phenyl group, 2-methylphenyl group, 2-ethylphenyl group, a 2-fluorophenyl group, a 2-aminophenyl group, a 2-hydroxyphenyl group, a 2-methoxyphenyl group, a 2,4-dimethylphenyl group, a 2-fluoro-4-methylphenyl group, a 2-fluoro-4-aminophenyl group, a 4-cyano-2-methylphenyl group, a 2-chloro-4-fluorophenyl group, a 2,3-difluorophenyl group, a 2-fluoro-3-aminophenyl group, a 2,5-difluorophenyl group, a 2,6-difluorophenyl group, a 4-fluoro-6-methylphenyl group, a (2-difluoromethyl)phenyl group, a 2-cyanophenyl group, a 2,4-difluorophenyl group, a 3-methylphenyl group, a 3-aminophenyl group, a 3-fluorophenyl group, a 3-hydroxyphenyl group, a 3,4-difluorophenyl group, a 3-amino-4-methlyphenyl group, a 3-amino-4-chlorophenyl group, a 3-amino-4-fluorophenyl group, a 3-fluoro-4-methylphenyl group, a 4-amino-3-fluorophenyl group, a 4-fluoro-3-methylphenyl group, a 4-fluoro-3-hydroxyphenyl group, a 3-hydroxy-4-methylphenyl group, a 4-methylphenyl group, a 4-fluorophenyl group, a 4-chlorophenyl group, a 4-(difluoromethyl)phenyl group, a 4-(trifluoromethyl)phenyl group, a 4-cyanophenyl group, a 4-aminophenyl group, a 4-(methylamino)phenyl group, a 4-hydroxyphenyl group, a 4-methoxyphenyl group, a 3,5-difluorophenyl group, a 2,4,5-trifluorophenyl group, a 2,3,4-trifluorophenyl group, a 3,4,5-trifluorophenyl group, a 3-amino-4,6-difluorophenyl group, a 1H-pyrazol-4-yl group, a 1-methyl-1H-pyrazol-4-yl group, a 1-ethyl-a 3-(trifluoromethyl)-1H-pyrazol-1-yl group, 1H-pyrazol-4-yl group, a 1-(propan-2-yl)-1H-pyrazol-4-yl group, a 1-(difluoromethyl)-1H-pyrazol-4-yl group, a 1-methyl-1H-pyrazol-5-yl group, a 3-methyl-1H-pyrazol-4-yl group, a 1,3-dimethyl-1H-pyrazol-4-yl group, a 3,5-dimethyl-1H-pyrazol-4-yl group, a 1-methyl-3-(trifluoromethyl)-1H-pyrazol-4-yl group, a 3-(trifluoromethyl)-1H-pyrazol-4-yl group, 1-methyl-5-cyano-1H-pyrrol-2-yl group, a 1-ethyl-1H-imidazol-4-yl group, a 4-(trifluoromethyl)-1H-imidazol-1-yl group, a 3,5-dimethyl-1,2-oxazol-4-yl group, a 1,2-thiazol-4-yl group, a 2-methyl-1,3-thiazol-5-yl group, a 5-(trifluoromethyl)thiophen-2-yl group, a 5-cyano-4-methyl-thiophen-2-yl group, a 5-(trifluoromethyl)thiophen-3-yl group, a pyridin-2-yl group, a 5-methyl-pyridin-2-yl group, a 5-chloro-pyridin-2-yl group, a 5-fluoropyridin-2-yl group, a pyridin-3-yl group, a 4-methylpyridin-3-yl group, a 2-methylpyridin-3-yl group, a 6-fluoropyridin-3-yl group, a 6-methylpyridin-3-yl group, a 6-(trifluoromethyl)pyridin-3-yl group, a 6-aminopyridin-3-yl group, a 6-methoxypyridin-3-yl group, a 5-fluoro-6-methylpyridin-3-yl group, a 2-methoxy-6-methylpyridin-3-yl group, a pyridin-4-yl group, a 2-methylpyridin-4-yl group, a 2-methoxypyridin-4-yl group, a 2-aminopyridin-4-yl group, a 3-methylpyridin-4-yl group, a pyrimidin-5-yl group, 2-methylpyrimidin-5-yl group, a 1-benzothiophen-2-yl group, an imidazo[1,2-a]pyridin-6-yl group, a 1-methyl-1H-benzimidazol-6-yl group, a 1-methyl-1H-indazol-6-yl group, a 1H-indazol-6-yl group, a 1H-indol-6-yl group, a 1H-indol-5-yl group, a methylamino group, a ethylamino group, a (propan-2-yl)amino group, a propylamino group, a butylamino group, a tert-butylamino group, a pentylamino group, a ethyl(methyl)amino group, a (butyl)methylamino group, an aminocarbonylmethyl group, a (2-aminoethyl)amino group, a (2-methylpropyl)amino group, a (3-methylbutyl)amino group, a (2-methoxyethyl)amino group, a (2-ethoxyethyl)amino group, a (3-methoxypropyl)amino group, a (3-cyanopropyl)amino group, a (2-hydroxypropyl)amino group, a (2-hydroxy-2-methylpropyl)amino group, a (2-methoxypropyl)amino group, a (2-ethoxypropyl)amino group, a (3,3,3-trifluoro-2-hydroxypropyl)amino group, a (2-methoxy-2-methylpropyl)amino group, a (2-methoxybutyl)amino group, a (3-hydroxybutyl)amino group, a (1-hydroxybutan-2-yl)amino group, a (4-hydroxybutan-2-yl)amino group, a (1-hydroxypentan-2-yl)amino group, a (3-hydroxy-3-methylbutyl)amino group, a (2-hydroxy-3-methoxypropyl)amino group, a (cyclopropylmethyl)amino group, a (1-cyclopropylethyl)amino group, a ((1-hydroxycyclobutyl)methyl]amino group, a (1-hydroxy-4-methylpentan-2-yl)amino group, a (1,3-dihydroxybutan-2-yl)amino group, a (2,2-dimethylcyclopropyl)methyl]amino group, a (dicyclopropylmethyl)amino group, a (3-hydroxycyclobutyl)amino group, a [1-(hydroxymethyl)cyclobutyl]methyl group, a cyclopentylamino group, a (2-hydroxycyclopentyl)amino group, a (cyclopentyl)(methyl)amino group, a (4-hydroxycyclohexyl)amino group, a bicyclo[2.2.1]heptan-2-yl]amino group, an [(3-methyloxetan-3-yl)methyl]amino group, a (oxetan-3-yl)amino group, an (oxolan-3-yl)methyl)amino group, a (tetrahydrofuran-2-ylmethyl)amino group, a (oxan-4-yl)amino group, a ((oxan-4-yl)methyl)amino group, a ((4-methyloxan-4-yl)methyl)amino group, an (3-methyloxetan-3-yl)methyl]amino group, a [(5-oxopyrrolidin-2-yl)methyl]amino group, a [(6-oxopiperidin-3-yl)methyl]amino group, a [(1-methyl-1H-imidazol-2-yl)methyl]amino group, a [2-(1H-pyrazol-1-yl)ethyl]amino group, a [2-(1H-imidazol-5-yl)ethyl]amino group, a (3-(1H-imidazol-1-yl)propyl)amino group, a [(1-methyl-1H-pyrazol-5-yl)methyl]amino group, a [(1H-pyrazol-3-yl)methyl]aminogroup, a [(1-methyl-1H-pyrazol-3-yl)methyl]amino group, a [(1-methyl-1H-pyrazol-4-yl)methyl]amino group, a [(pyrazin-2-yl)methyl]aminogroup, a [(pyridin-3-yl)methyl]amino group, a [(pyrimidin-5-yl)methyl]amino group, a[(pyrimidin-2-yl)methyl]amino group, R$^4$ is a hydrogen atom or a methyl group or a stereoisomer, a tautomer, an N-oxide, a hydrate, a solvate, or a salt thereof, or a mixture of same.

In accordance with a further embodiment of the first aspect, the present invention provides compounds of general formula (I):

wherein
R¹ is selected from $CF_3$, and a fluorine atom,
R² is selected from a hydrogen atom
R³ is selected from
- a halogen atom,
- a prop-1-en-1-yl group which is optionally substituted with a methyl group,
- a piperidin-1-yl group which is optionally substituted with one or two substitutents and each substituent is independently selected from a fluorine atom and a methyl group
- a morpholin-4-yl group which is optionally substituted with one or two methyl groups,
- a pyrrolidin-1-yl group which is optionally substituted with one or two halogen atoms,
- a 1,2,3,6-tetrahydropyridin-4-yl group which is optionally substituted with a methyl group,
- an azitidin-1-yl group,
- a 3,6-dihydro-1H-pyran-4-yl group,
- a 6-oxo-1,6-dihydropyridin-3-yl group which is optionally substituted with one or two substitutents and each substituent is independently selected from a hydrogen atom and a methyl group,
- a cyclopent-1en-1-yl group,
- a phenyl group which is optionally substituted with one, two or three substitutents and each substituent is independently selected from a halogen atom, a hydroxy group, a methyl group, an ethyl group, a $CF_3$, $CF_2H$ group, a methoxy group, a $CF_3O$ group, a $NH_2$ group and a $NHCH_3$ group,
- a 2H-pyrrol-1-yl group, which is optionally substituted with one or two substitutents and each substituent is independently selected from a hydrogen atom, a cyano group and a methyl group,
- a 1H-pyrrazol-4-yl group, which is optionally substituted with one or two substitutents and each substituent is independently selected from a methyl group, an ethyl group or a $CF_3$ group,
- a 1H-pyrrazol-5-yl group, which is optionally substituted with a methyl group,
- 1,2-oxazol-4-yl which is optionally substituted with one or two methyl groups,
- a 1,2-thiazol-4-yl group which is optionally substituted with a methyl group,
- a 1,3-thiazol-5-yl group which is optionally substituted with a methyl group,
- a pyridin-3-yl, a pyridin-4-yl and a pyridin 5-yl group each group being optionally substituted with one or two substitutents and each substituent is independently selected from a halogen atom, a methyl group, a $CF_3$ group, a methoxy group and a $NH_2$ group,
- a pyrimidin-5-yl group which is optionally substituted with a methyl group,
- a 1H-indol-6-yl group,
- a 1H-indazol-6-yl group which is optionally substituted with a methyl group,
- a 1H-benzimidazol-6-yl group which is optionally substituted with a methyl group,
- a $NH(C_2H)$ group, a $NH(C_3H_7)$ group, a $NH(C_4H_9)$ group, a $NCH_3(C_4H_9)$ group, a $NH(C_5H_{11})$ group, a $NH(cyclopentyl)$ group, a $NCH_3(cyclopentyl)$ group;

R⁴ is selected from a hydrogen atom and a methyl group;
or a stereoisomer, a tautomer, an N-oxide, a hydrate, a solvate, or a salt thereof, or a mixture of same.

In accordance with a further embodiment of the first aspect, the present invention provides compounds of general formula (I):

wherein the compound is selected from the group
5-[4-(4,4-difluoropiperidin-1-yl)-3-fluorophenyl]-3,6-dihydro-2H-1,3,4-oxadiazin-2-one,
5-[4-chloro-3-(trifluoromethyl)phenyl]-3,6-dihydro-2H-1,3,4-oxadiazin-2-one,
5-[4'-fluoro-2-(trifluoromethyl)biphenyl-4-yl]-3,6-dihydro-2H-1,3,4-oxadiazin-2-one,
5-[3-fluoro-4-(morpholin-4-yl)phenyl]-3,6-dihydro-2H-1,3,4-oxadiazin-2-one,
5-[3-fluoro-4-(4-fluoro-4-methylpiperidin-1-yl)phenyl]-3,6-dihydro-2H-1,3,4-oxadiazin-2-one,
5-[3-fluoro-4-(4-fluoropiperidin-1-yl)phenyl]-3,6-dihydro-2H-1,3,4-oxadiazin-2-one,
5-(4'-fluoro-2-methylbiphenyl-4-yl)-3,6-dihydro-2H-1,3,4-oxadiazin-2-one,
5-(3',4'-difluoro-2-methylbiphenyl-4-yl)-3,6-dihydro-2H-1,3,4-oxadiazin-2-one,
5-(4'-fluoro-2,2'-dimethylbiphenyl-4-yl)-3,6-dihydro-2H-1,3,4-oxadiazin-2-one,
5-[4-(3,6-dihydro-2H-pyran-4-yl)-3-methylphenyl]-3,6-dihydro-2H-1,3,4-oxadiazin-2-one,
5-[3-methyl-4-(1H-pyrazol-4-yl)phenyl]-3,6-dihydro-2H-1,3,4-oxadiazin-2-one,
5-[3-methyl-4-(6-oxo-1,6-dihydropyridin-3-yl)phenyl]-3,6-dihydro-2H-1,3,4-oxadiazin-2-one,
5-[3-methyl-4-(pyridin-3-yl)phenyl]-3,6-dihydro-2H-1,3,4-oxadiazin-2-one,
5-[3-methyl-4-(pyrimidin-5-yl)phenyl]-3,6-dihydro-2H-1,3,4-oxadiazin-2-one,
5-(3'-fluoro-2-methylbiphenyl-4-yl)-3,6-dihydro-2H-1,3,4-oxadiazin-2-one,
(rac)-6-methyl-5-(3,4,5-trifluorophenyl)-3,6-dihydro-2H-1,3,4-oxadiazin-2-one,
(rac)-5-[3,5-difluoro-4-(morpholin-4-yl)phenyl]-6-methyl-3,6-dihydro-2H-1,3,4-oxadiazin-2-one,
(rac)-5-{3,5-difluoro-4-[(2S)-2-methylmorpholin-4-yl]phenyl}-6-methyl-3,6-dihydro-2H-1,3,4-oxadiazin-2-one,
(rac)-5-(4-bromophenyl)-6-methyl-3,6-dihydro-2H-1,3,4-oxadiazin-2-one
(rac)-6-methyl-5-[4-(morpholin-4-yl)phenyl]-3,6-dihydro-2H-1,3,4-oxadiazin-2-one,
5-[3,5-difluoro-4-(morpholin-4-yl)phenyl]-3,6-dihydro-2H-1,3,4-oxadiazin-2-one,
2-(morpholin-4-yl)-5-(2-oxo-3,6-dihydro-2H-1,3,4-oxadiazin-5-yl)benzonitrile,
3-chloro-2-(morpholin-4-yl)-5-(2-oxo-3,6-dihydro-2H-1,3,4-oxadiazin-5-yl)benzonitrile,
5-{4-[2,6-dimethylmorpholin-4-yl]-3-fluorophenyl}-3,6-dihydro-2H-1,3,4-oxadiazin-2-one,
(6S)-5-(3-Fluoro-4-morpholinophenyl)-6-methyl-3,6-dihydro-2H-1,3,4-oxadiazin-2-one,
(6S)-5-(3,5-Difluoro-4-morpholinophenyl)-6-methyl-3,6-dihydro-2H-1,3,4-oxadiazin-2-one,
5-[4-(3,3-difluoropyrrolidin-1-yl)-3-fluorophenyl]-3,6-dihydro-2H-1,3,4-oxadiazin-2-one,
5-(2-methylbiphenyl-4-yl)-3,6-dihydro-2H-1,3,4-oxadiazin-2-one,
5-[3-methyl-4-(2-methylpyrimidin-5-yl)phenyl]-3,6-dihydro-2H-1,3,4-oxadiazin-2-one,
5-[3-methyl-4-(1-methyl-1H-pyrazol-5-yl)phenyl]-3,6-dihydro-2H-1,3,4-oxadiazin-2-one,
5-(2,4'-difluorobiphenyl-4-yl)-3,6-dihydro-2H-1,3,4-oxadiazin-2-one,
5-[4'-chloro-2-(trifluoromethyl)biphenyl-4-yl]-3,6-dihydro-2H-1,3,4-oxadiazin-2-one,
5-[4-(6-methylpyridin-3-yl)-3-(trifluoromethyl)phenyl]-3,6-dihydro-2H-1,3,4-oxadiazin-2-one, 5-[4-(pyridin-3-yl)-3-(trifluoromethyl)phenyl]-3,6-dihydro-2H-1,3,4-oxadiazin-2-one,
5-[4'-amino-2-(trifluoromethyl)biphenyl-4-yl]-3,6-dihydro-2H-1,3,4-oxadiazin-2-one,
5-[3'-hydroxy-4'-methyl-2-(trifluoromethyl)biphenyl-4-yl]-3,6-dihydro-2H-1,3,4-oxadiazin-2-one,
5-{3-(trifluoromethyl)-4-[6-(trifluoromethyl)pyridin-3-yl]phenyl}-3,6-dihydro-2H-1,3,4-oxadiazin-2-one,
5-[4'-fluoro-3'-hydroxy-2-(trifluoromethyl)biphenyl-4-yl]-3,6-dihydro-2H-1,3,4-oxadiazin-2-one,
5-[5'-amino-2',4'-difluoro-2-(trifluoromethyl)biphenyl-4-yl]-3,6-dihydro-2H-1,3,4-oxadiazin-2-one,
5-[4'-amino-3'-fluoro-2-(trifluoromethyl)biphenyl-4-yl]-3,6-dihydro-2H-1,3,4-oxadiazin-2-one,
5-[4-(6-aminopyridin-3-yl)-3-(trifluoromethyl)phenyl]-3,6-dihydro-2H-1,3,4-oxadiazin-2-one,
5-[3'-amino-4'-chloro-2-(trifluoromethyl)biphenyl-4-yl]-3,6-dihydro-2H-1,3,4-oxadiazin-2-one,
5-[3'-amino-4'-methyl-2-(trifluoromethyl)biphenyl-4-yl]-3,6-dihydro-2H-1,3,4-oxadiazin-2-one,
5-[3'-amino-2'-fluoro-2-(trifluoromethyl)biphenyl-4-yl]-3,6-dihydro-2H-1,3,4-oxadiazin-2-one,
5-[4'-amino-2'-fluoro-2-(trifluoromethyl)biphenyl-4-yl]-3,6-dihydro-2H-1,3,4-oxadiazin-2-one,
5-[4-(1-methyl-1H-pyrazol-4-yl)-3-(trifluoromethyl)phenyl]-3,6-dihydro-2H-1,3,4-oxadiazin-2-one,
5-[4-(3-methyl-1H-pyrazol-4-yl)-3-(trifluoromethyl)phenyl]-3,6-dihydro-2H-1,3,4-oxadiazin-2-one,
5-[4-(1H-indazol-6-yl)-3-(trifluoromethyl)phenyl]-3,6-dihydro-2H-1,3,4-oxadiazin-2-one,
5-[4-(5-fluoro-6-methylpyridin-3-yl)-3-(trifluoromethyl)phenyl]-3,6-dihydro-2H-1,3,4-oxadiazin-2-one,
5-[4-(1,2-thiazol-4-yl)-3-(trifluoromethyl)phenyl]-3,6-dihydro-2H-1,3,4-oxadiazin-2-one,
1-methyl-5-[4-(2-oxo-3,6-dihydro-2H-1,3,4-oxadiazin-5-yl)-2-(trifluoromethyl)phenyl]-1H-pyrrole-2-carbonitrile,
5-[2,4'-bis(trifluoromethyl)biphenyl-4-yl]-3,6-dihydro-2H-1,3,4-oxadiazin-2-one,
5-[4-(1,3-dimethyl-1H-pyrazol-4-yl)-3-(trifluoromethyl)phenyl]-3,6-dihydro-2H-1,3,4-oxadiazin-2-one,
5-[4-(2-methoxy-6-methylpyridin-3-yl)-3-(trifluoromethyl)phenyl]-3,6-dihydro-2H-1,3,4-oxadiazin-2-one,
5-[4-(2-methyl-1,3-thiazol-5-yl)-3-(trifluoromethyl)phenyl]-3,6-dihydro-2H-1,3,4-oxadiazin-2-one,
5-[4'-(methylamino)-2-(trifluoromethyl)biphenyl-4-yl]-3,6-dihydro-2H-1,3,4-oxadiazin-2-one,
5-[3'-amino-4'-fluoro-2-(trifluoromethyl)biphenyl-4-yl]-3,6-dihydro-2H-1,3,4-oxadiazin-2-one,
5-[4-fluoro-3-(trifluoromethyl)phenyl]-3,6-dihydro-2H-1,3,4-oxadiazin-2-one,
5-[3',4',5'-trifluoro-2-(trifluoromethyl)biphenyl-4-yl]-3,6-dihydro-2H-1,3,4-oxadiazin-2-one,
5-[2',5'-difluoro-2-(trifluoromethyl)biphenyl-4-yl]-3,6-dihydro-2H-1,3,4-oxadiazin-2-one,
5-[3'-amino-4'-fluoro-2-(trifluoromethoxy)biphenyl-4-yl]-3,6-dihydro-2H-1,3,4-oxadiazin-2-one,
5-[3',4'-difluoro-2-(trifluoromethyl)biphenyl-4-yl]-3,6-dihydro-2H-1,3,4-oxadiazin-2-one,
5-[4-(1H-indol-6-yl)-3-(trifluoromethyl)phenyl]-3,6-dihydro-2H-1,3,4-oxadiazin-2-one,
5-[4-(2-methylprop-1-en-1-yl)-3-(trifluoromethyl)phenyl]-3,6-dihydro-2H-1,3,4-oxadiazin-2-one,
5-[2',3'-difluoro-2-(trifluoromethyl)biphenyl-4-yl]-3,6-dihydro-2H-1,3,4-oxadiazin-2-one,
5-[4-(morpholin-4-yl)-3-(trifluoromethyl)phenyl]-3,6-dihydro-2H-1,3,4-oxadiazin-2-one,
5-[4-(butylamino)-3-(trifluoromethyl)phenyl]-3,6-dihydro-2H-1,3,4-oxadiazin-2-one,
5-[4-(ethylamino)-3-(trifluoromethyl)phenyl]-3,6-dihydro-2H-1,3,4-oxadiazin-2-one,
5-[4-(1-methyl-1H-pyrazol-4-yl)-3-(trifluoromethoxy)phenyl]-3,6-dihydro-2H-1,3,4-oxadiazin-2-one,
5-[4-(propylamino)-3-(trifluoromethyl)phenyl]-3,6-dihydro-2H-1,3,4-oxadiazin-2-one,
5-[4-(6-methylpyridin-3-yl)-3-(trifluoromethoxy)phenyl]-3,6-dihydro-2H-1,3,4-oxadiazin-2-one,
5-[4'-chloro-2-(trifluoromethoxy) biphenyl-4-yl]-3,6-dihydro-2H-1,3,4-oxadiazin-2-one,
5-[4-(azetidin-1-yl)-3-(trifluoromethyl)phenyl]-3,6-dihydro-2H-1,3,4-oxadiazin-2-one,
5-[4-(1-methyl-1H-benzimidazol-6-yl)-3-(trifluoromethyl)phenyl]-3,6-dihydro-2H-1,3,4-oxadiazin-2-one,
5-[4-(pentylamino)-3-(trifluoromethyl)phenyl]-3,6-dihydro-2H-1,3,4-oxadiazin-2-one,
5-[4-(1-methyl-1H-indazol-6-yl)-3-(trifluoromethyl)phenyl]-3,6-dihydro-2H-1,3,4-oxadiazin-2-one,
5-[4'-fluoro-2-(trifluoromethoxy)biphenyl-4-yl]-3,6-dihydro-2H-1,3,4-oxadiazin-2-one,
5-[3-fluoro-4-(6-fluoropyridin-3-yl)phenyl]-3,6-dihydro-2H-1,3,4-oxadiazin-2-one,
5-[3-fluoro-4-(3-methylpyridin-4-yl)phenyl]-3,6-dihydro-2H-1,3,4-oxadiazin-2-one,
5-[3-fluoro-4-(2-methylpyridin-4-yl)phenyl]-3,6-dihydro-2H-1,3,4-oxadiazin-2-one,
5-(4'-amino-2-fluorobiphenyl-4-yl)-3,6-dihydro-2H-1,3,4-oxadiazin-2-one,
5-(2-fluoro-2'-methylbiphenyl-4-yl)-3,6-dihydro-2H-1,3,4-oxadiazin-2-one,
5-(2'-chloro-2,4'-difluorobiphenyl-4-yl)-3,6-dihydro-2H-1,3,4-oxadiazin-2-one,
5-[4-(cyclopent-1-en-1-yl)-3-fluorophenyl]-3,6-dihydro-2H-1,3,4-oxadiazin-2-one,
5-(2'-ethyl-2-fluorobiphenyl-4-yl)-3,6-dihydro-2H-1,3,4-oxadiazin-2-one,
5-[3-fluoro-4-(6-methoxypyridin-3-yl)phenyl]-3,6-dihydro-2H-1,3,4-oxadiazin-2-one,
5-(2,4'-difluoro-3'-methylbiphenyl-4-yl)-3,6-dihydro-2H-1,3,4-oxadiazin-2-one,
5-(2-fluoro-3'-methylbiphenyl-4-yl)-3,6-dihydro-2H-1,3,4-oxadiazin-2-one,
5-(2-fluoro-4'-methylbiphenyl-4-yl)-3,6-dihydro-2H-1,3,4-oxadiazin-2-one,
5-(2-fluorobiphenyl-4-yl)-3,6-dihydro-2H-1,3,4-oxadiazin-2-one,
5-[4-(2-aminopyridin-4-yl)-3-fluorophenyl]-3,6-dihydro-2H-1,3,4-oxadiazin-2-one,
5-(3'-amino-2-fluorobiphenyl-4-yl)-3,6-dihydro-2H-1,3,4-oxadiazin-2-one,
5-[4'-(difluoromethyl)-2-fluorobiphenyl-4-yl]-3,6-dihydro-2H-1,3,4-oxadiazin-2-one,
5-[3-fluoro-4-(pyridin-4-yl)phenyl]-3,6-dihydro-2H-1,3,4-oxadiazin-2-one,
5-[3-fluoro-4-(2-methylpyrimidin-5-yl)phenyl]-3,6-dihydro-2H-1,3,4-oxadiazin-2-one,
5-[3-fluoro-4-(2-methoxypyridin-4-yl)phenyl]-3,6-dihydro-2H-1,3,4-oxadiazin-2-one,
5-[3-fluoro-4-(2-methylpyridin-3-yl)phenyl]-3,6-dihydro-2H-1,3,4-oxadiazin-2-one,
5-[3-fluoro-4-(6-methylpyridin-3-yl)phenyl]-3,6-dihydro-2H-1,3,4-oxadiazin-2-one,
5-(2,2',4',5'-tetrafluorobiphenyl-4-yl)-3,6-dihydro-2H-1,3,4-oxadiazin-2-one, 5-(2,2',3',4'-tetrafluorobiphenyl-4-yl)-3,6-dihydro-2H-1,3,4-oxadiazin-2-one,
5-(2,2',5'-trifluorobiphenyl-4-yl)-3,6-dihydro-2H-1,3,4-oxadiazin-2-one,
2'-fluoro-4'-(2-oxo-3,6-dihydro-2H-1,3,4-oxadiazin-5-yl)biphenyl-4-carbonitrile,
5-(2'-amino-2-fluorobiphenyl-4-yl)-3,6-dihydro-2H-1,3,4-oxadiazin-2-one,
5-(3'-amino-2-fluoro-4'-methylbiphenyl-4-yl)-3,6-dihydro-2H-1,3,4-oxadiazin-2-one,
5-(2-fluoro-3'-hydroxybiphenyl-4-yl)-3,6-dihydro-2H-1,3,4-oxadiazin-2-one,
5-(2-fluoro-4'-hydroxybiphenyl-4-yl)-3,6-dihydro-2H-1,3,4-oxadiazin-2-one,
5-(2-fluoro-2'-hydroxybiphenyl-4-yl)-3,6-dihydro-2H-1,3,4-oxadiazin-2-one,
5-(2,3',4'-trifluorobiphenyl-4-yl)-3,6-dihydro-2H-1,3,4-oxadiazin-2-one,
5-[3-fluoro-4-(pyridin-3-yl)phenyl]-3,6-dihydro-2H-1,3,4-oxadiazin-2-one,
5-(2,2',3'-trifluorobiphenyl-4-yl)-3,6-dihydro-2H-1,3,4-oxadiazin-2-one,
5-(2,3',5'-trifluorobiphenyl-4-yl)-3,6-dihydro-2H-1,3,4-oxadiazin-2-one,
5-(2,2',4'-trifluorobiphenyl-4-yl)-3,6-dihydro-2H-1,3,4-oxadiazin-2-one,
5-(2-fluoro-2',4'-dimethylbiphenyl-4-yl)-3,6-dihydro-2H-1,3,4-oxadiazin-2-one,
5-(2,3'-difluoro-4'-methylbiphenyl-4-yl)-3,6-dihydro-2H-1,3,4-oxadiazin-2-one,
5-(2,2'-difluorobiphenyl-4-yl)-3,6-dihydro-2H-1,3,4-oxadiazin-2-one,
5-(2,2',6'-trifluorobiphenyl-4-yl)-3,6-dihydro-2H-1,3,4-oxadiazin-2-one,
5-(2-fluoro-2'-methoxybiphenyl-4-yl)-3,6-dihydro-2H-1,3,4-oxadiazin-2-one,
5-(2,3'-difluorobiphenyl-4-yl)-3,6-dihydro-2H-1,3,4-oxadiazin-2-one,
5-[3-fluoro-4-(4-methylpyridin-3-yl)phenyl]-3,6-dihydro-2H-1,3,4-oxadiazin-2-one,
(rac)-5-(3-Fluoro-4-morpholinophenyl)-6-methyl-3,6-dihydro-2H-1,3,4-oxadiazin-2-one,
(6S)-6-methyl-5-[4-(morpholin-4-yl)-3-(trifluoromethyl)phenyl]-3,6-dihydro-2H-1,3,4-oxadiazin-2-one,
(6S)-5-(-[(3-chloro-4-(morpholin-4-yl)-5-(trifluoromethyl)phenyl)-)]-6-methyl-3,6-dihydro-2H-1,3,4-oxadiazin-2-one,
6S)-5-(-[(4-chloro-3-(trifluoromethyl)phenyl)-)]-6-methyl-3,6-dihydro-2H-1,3,4-oxadiazin-2-one,
(6S)-5-(-[(4-fluoro-3-(trifluoromethyl)phenyl)-)]-6-methyl-3,6-dihydro-2H-1,3,4-oxadiazin-2-one,
5-[4-chloro-3-(trifluoromethoxy)phenyl]-3,6-dihydro-2H-1,3,4-oxadiazin-2-one,
5-(4-chloro-3-methylphenyl)-3,6-dihydro-2H-1,3,4-oxadiazin-2-one,
(rac)-6-methyl-5-(4-morpholino-3-(trifluoromethyl)phenyl)-3,6-dihydro-2H-1,3,4-oxadiazin-2-one,
5-{4-[1-methyl-3-(trifluoromethyl)-1H-pyrazol-4-yl]-3-(trifluoromethyl)phenyl}-3,6-dihydro-2H-1,3,4-oxadiazin-2-one,
5-[4-(3,5-dimethyl-1H-pyrazol-4-yl)-3-(trifluoromethyl)phenyl]-3,6-dihydro-2H-1,3,4-oxadiazin-2-one,
5-[4-(3,5-dimethyl-1,2-oxazol-4-yl)-3-(trifluoromethyl)phenyl]-3,6-dihydro-2H-1,3,4-oxadiazin-2-one,
5-{3-(trifluoromethyl)-4-[3-(trifluoromethyl)-1H-pyrazol-4-yl]phenyl}-3,6-dihydro-2H-1,3,4-oxadiazin-2-one,
5-[4-(1-ethyl-1H-pyrazol-4-yl)-3-(trifluoromethyl)phenyl]-3,6-dihydro-2H-1,3,4-oxadiazin-2-one,
5-{4-[cyclopentyl(methyl)amino]-3-(trifluoromethyl)phenyl}-3,6-dihydro-2H-1,3,4-oxadiazin-2-one,
5-[4-(1-methyl-1,2,3,6-tetrahydropyridin-4-yl)-3-(trifluoromethyl)phenyl]-3,6-dihydro-2H-1,3,4-oxadiazin-2-one,
5-{4-[butyl(methyl)amino]-3-(trifluoromethyl)phenyl}-3,6-dihydro-2H-1,3,4-oxadiazin-2-one,
(6S)-5-[4'-fluoro-2-(trifluoromethyl)biphenyl-4-yl]-6-methyl-3,6-dihydro-2H-1,3,4-oxadiazin-2-one,
5-[4-(cyclopentylamino)-3-(trifluoromethyl)phenyl]-3,6-dihydro-2H-1,3,4-oxadiazin-2-one,
5-[4-(cyclopentylamino)-3-(trifluoromethyl)phenyl]-3,6-dihydro-2H-1,3,4-oxadiazin-2-one and
5-[3'-fluoro-2-(trifluoromethyl)biphenyl-4-yl]-3,6-dihydro-2H-1,3,4-oxadiazin-2-one or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is selected from the group
5-[4-(4,4-difluoropiperidin-1-yl)-3-fluorophenyl]-3,6-dihydro-2H-1,3,4-oxadiazin-2-one,
5-[4-chloro-3-(trifluoromethyl)phenyl]-3,6-dihydro-2H-1,3,4-oxadiazin-2-one,
5-[4'-fluoro-2-(trifluoromethyl)biphenyl-4-yl]-3,6-dihydro-2H-1,3,4-oxadiazin-2-one,
5-[3-fluoro-4-(morpholin-4-yl)phenyl]-3,6-dihydro-2H-1,3,4-oxadiazin-2-one,
5-[3-fluoro-4-(4-fluoro-4-methylpiperidin-1-yl)phenyl]-3,6-dihydro-2H-1,3,4-oxadiazin-2-one,
5-[3-fluoro-4-(4-fluoropiperidin-1-yl)phenyl]-3,6-dihydro-2H-1,3,4-oxadiazin-2-one,
5-(4'-fluoro-2-methylbiphenyl-4-yl)-3,6-dihydro-2H-1,3,4-oxadiazin-2-one,
5-(3',4'-difluoro-2-methylbiphenyl-4-yl)-3,6-dihydro-2H-1,3,4-oxadiazin-2-one,
5-(4'-fluoro-2,2'-dimethylbiphenyl-4-yl)-3,6-dihydro-2H-1,3,4-oxadiazin-2-one,
5-[4-(3,6-dihydro-2H-pyran-4-yl)-3-methylphenyl]-3,6-dihydro-2H-1,3,4-oxadiazin-2-one,
5-[3-methyl-4-(1H-pyrazol-4-yl)phenyl]-3,6-dihydro-2H-1,3,4-oxadiazin-2-one,
5-[3-methyl-4-(6-oxo-1,6-dihydropyridin-3-yl)phenyl]-3,6-dihydro-2H-1,3,4-oxadiazin-2-one,
5-[3-methyl-4-(pyridin-3-yl)phenyl]-3,6-dihydro-2H-1,3,4-oxadiazin-2-one,
5-[3-methyl-4-(pyrimidin-5-yl)phenyl]-3,6-dihydro-2H-1,3,4-oxadiazin-2-one,
5-(3'-fluoro-2-methylbiphenyl-4-yl)-3,6-dihydro-2H-1,3,4-oxadiazin-2-one,
(rac)-6-methyl-5-(3,4,5-trifluorophenyl)-3,6-dihydro-2H-1,3,4-oxadiazin-2-one,
(rac)-5-[3,5-difluoro-4-(morpholin-4-yl)phenyl]-6-methyl-3,6-dihydro-2H-1,3,4-oxadiazin-2-one,
(rac)-5-{3,5-difluoro-4-[(2S)-2-methylmorpholin-4-yl]phenyl}-6-methyl-3,6-dihydro-2H-1,3,4-oxadiazin-2-one,
(rac)-6-methyl-5-[4-(morpholin-4-yl)phenyl]-3,6-dihydro-2H-1,3,4-oxadiazin-2-one,
5-[3,5-difluoro-4-(morpholin-4-yl)phenyl]-3,6-dihydro-2H-1,3,4-oxadiazin-2-one,
2-(morpholin-4-yl)-5-(2-oxo-3,6-dihydro-2H-1,3,4-oxadiazin-5-yl)benzonitrile,
3-chloro-2-(morpholin-4-yl)-5-(2-oxo-3,6-dihydro-2H-1,3,4-oxadiazin-5-yl)benzonitrile, 5-{4-[2,6-dimethylmorpholin-4-yl]-3-fluorophenyl}-3,6-dihydro-2H-1,3,4-oxadiazin-2-one,
(6S)-5-(3-Fluoro-4-morpholinophenyl)-6-methyl-3,6-dihydro-2H-1,3,4-oxadiazin-2-one,
(6S)-5-(3,5-Difluoro-4-morpholinophenyl)-6-methyl-3,6-dihydro-2H-1,3,4-oxadiazin-2-one,
5-[4-(3,3-difluoropyrrolidin-1-yl)-3-fluorophenyl]-3,6-dihydro-2H-1,3,4-oxadiazin-2-one,
5-(2-methylbiphenyl-4-yl)-3,6-dihydro-2H-1,3,4-oxadiazin-2-one,
5-[3-methyl-4-(2-methylpyrimidin-5-yl)phenyl]-3,6-dihydro-2H-1,3,4-oxadiazin-2-one,
5-[3-methyl-4-(1-methyl-1H-pyrazol-5-yl)phenyl]-3,6-dihydro-2H-1,3,4-oxadiazin-2-one,
5-(2,4'-difluorobiphenyl-4-yl)-3,6-dihydro-2H-1,3,4-oxadiazin-2-one,
5-[4'-chloro-2-(trifluoromethyl)biphenyl-4-yl]-3,6-dihydro-2H-1,3,4-oxadiazin-2-one,
5-[4-(6-methylpyridin-3-yl)-3-(trifluoromethyl)phenyl]-3,6-dihydro-2H-1,3,4-oxadiazin-2-one,
5-[4-(pyridin-3-yl)-3-(trifluoromethyl)phenyl]-3,6-dihydro-2H-1,3,4-oxadiazin-2-one,
5-[4'-amino-2-(trifluoromethyl)biphenyl-4-yl]-3,6-dihydro-2H-1,3,4-oxadiazin-2-one,
5-[3'-hydroxy-4'-methyl-2-(trifluoromethyl)biphenyl-4-yl]-3,6-dihydro-2H-1,3,4-oxadiazin-2-one,
5-{3-(trifluoromethyl)-4-[6-(trifluoromethyl)pyridin-3-yl]phenyl}-3,6-dihydro-2H-1,3,4-oxadiazin-2-one,
5-[4'-fluoro-3'-hydroxy-2-(trifluoromethyl)biphenyl-4-yl]-3,6-dihydro-2H-1,3,4-oxadiazin-2-one,
5-[5'-amino-2',4'-difluoro-2-(trifluoromethyl)biphenyl-4-yl]-3,6-dihydro-2H-1,3,4-oxadiazin-2-one,
5-[4'-amino-3'-fluoro-2-(trifluoromethyl)biphenyl-4-yl]-3,6-dihydro-2H-1,3,4-oxadiazin-2-one,
5-[4-(6-aminopyridin-3-yl)-3-(trifluoromethyl)phenyl]-3,6-dihydro-2H-1,3,4-oxadiazin-2-one,
5-[3'-amino-4'-chloro-2-(trifluoromethyl)biphenyl-4-yl]-3,6-dihydro-2H-1,3,4-oxadiazin-2-one,
5-[3'-amino-4'-methyl-2-(trifluoromethyl)biphenyl-4-yl]-3,6-dihydro-2H-1,3,4-oxadiazin-2-one,
5-[3'-amino-2'-fluoro-2-(trifluoromethyl)biphenyl-4-yl]-3,6-dihydro-2H-1,3,4-oxadiazin-2-one,
5-[4'-amino-2'-fluoro-2-(trifluoromethyl)biphenyl-4-yl]-3,6-dihydro-2H-1,3,4-oxadiazin-2-one,
5-[4-(1-methyl-1H-pyrazol-4-yl)-3-(trifluoromethyl)phenyl]-3,6-dihydro-2H-1,3,4-oxadiazin-2-one,
5-[4-(3-methyl-1H-pyrazol-4-yl)-3-(trifluoromethyl)phenyl]-3,6-dihydro-2H-1,3,4-oxadiazin-2-one,
5-[4-(1H-indazol-6-yl)-3-(trifluoromethyl)phenyl]-3,6-dihydro-2H-1,3,4-oxadiazin-2-one,
5-[4-(5-fluoro-6-methylpyridin-3-yl)-3-(trifluoromethyl)phenyl]-3,6-dihydro-2H-1,3,4-oxadiazin-2-one,
5-[4-(1,2-thiazol-4-yl)-3-(trifluoromethyl)phenyl]-3,6-dihydro-2H-1,3,4-oxadiazin-2-one,
1-methyl-5-[4-(2-oxo-3,6-dihydro-2H-1,3,4-oxadiazin-5-yl)-2-(trifluoromethyl)phenyl]-1H-pyrrole-2-carbonitrile,
5-[2,4'-bis(trifluoromethyl)biphenyl-4-yl]-3,6-dihydro-2H-1,3,4-oxadiazin-2-one,
5-[4-(1,3-dimethyl-1H-pyrazol-4-yl)-3-(trifluoromethyl)phenyl]-3,6-dihydro-2H-1,3,4-oxadiazin-2-one,
5-[4-(2-methoxy-6-methylpyridin-3-yl)-3-(trifluoromethyl)phenyl]-3,6-dihydro-2H-1,3,4-oxadiazin-2-one,
5-[4-(2-methyl-1,3-thiazol-5-yl)-3-(trifluoromethyl)phenyl]-3,6-dihydro-2H-1,3,4-oxadiazin-2-one,
5-[4'-(methylamino)-2-(trifluoromethyl)biphenyl-4-yl]-3,6-dihydro-2H-1,3,4-oxadiazin-2-one,
5-[3'-amino-4'-fluoro-2-(trifluoromethyl)biphenyl-4-yl]-3,6-dihydro-2H-1,3,4-oxadiazin-2-one,
5-[4-fluoro-3-(trifluoromethyl)phenyl]-3,6-dihydro-2H-1,3,4-oxadiazin-2-one,
5-[3',4',5'-trifluoro-2-(trifluoromethyl)biphenyl-4-yl]-3,6-dihydro-2H-1,3,4-oxadiazin-2-one,
5-[2',5'-difluoro-2-(trifluoromethyl)biphenyl-4-yl]-3,6-dihydro-2H-1,3,4-oxadiazin-2-one,
5-[3'-amino-4'-fluoro-2-(trifluoromethoxy)biphenyl-4-yl]-3,6-dihydro-2H-1,3,4-oxadiazin-2-one,
5-[3',4'-difluoro-2-(trifluoromethyl)biphenyl-4-yl]-3,6-dihydro-2H-1,3,4-oxadiazin-2-one,
5-[4-(1H-indol-6-yl)-3-(trifluoromethyl)phenyl]-3,6-dihydro-2H-1,3,4-oxadiazin-2-one,
5-[4-(2-methylprop-1-en-1-yl)-3-(trifluoromethyl)phenyl]-3,6-dihydro-2H-1,3,4-oxadiazin-2-one,
5-[2',3'-difluoro-2-(trifluoromethyl)biphenyl-4-yl]-3,6-dihydro-2H-1,3,4-oxadiazin-2-one,
5-[4-(morpholin-4-yl)-3-(trifluoromethyl)phenyl]-3,6-dihydro-2H-1,3,4-oxadiazin-2-one,
5-[4-(butylamino)-3-(trifluoromethyl)phenyl]-3,6-dihydro-2H-1,3,4-oxadiazin-2-one,
5-[4-(ethylamino)-3-(trifluoromethyl)phenyl]-3,6-dihydro-2H-1,3,4-oxadiazin-2-one,
5-[4-(1-methyl-1H-pyrazol-4-yl)-3-(trifluoromethoxy)phenyl]-3,6-dihydro-2H-1,3,4-oxadiazin-2-one,
5-[4-(propylamino)-3-(trifluoromethyl)phenyl]-3,6-dihydro-2H-1,3,4-oxadiazin-2-one,
5-[4-(6-methylpyridin-3-yl)-3-(trifluoromethoxy)phenyl]-3,6-dihydro-2H-1,3,4-oxadiazin-2-one,
5-[4'-chloro-2-(trifluoromethoxy)biphenyl-4-yl]-3,6-dihydro-2H-1,3,4-oxadiazin-2-one,
5-[4-(azetidin-1-yl)-3-(trifluoromethyl)phenyl]-3,6-dihydro-2H-1,3,4-oxadiazin-2-one,
5-[4-(1-methyl-1H-benzimidazol-6-yl)-3-(trifluoromethyl)phenyl]-3,6-dihydro-2H-1,3,4-oxadiazin-2-one,
5-[4-(pentylamino)-3-(trifluoromethyl)phenyl]-3,6-dihydro-2H-1,3,4-oxadiazin-2-one,
5-[4-(1-methyl-1H-indazol-6-yl)-3-(trifluoromethyl)phenyl]-3,6-dihydro-2H-1,3,4-oxadiazin-2-one,
5-[4'-fluoro-2-(trifluoromethoxy)biphenyl-4-yl]-3,6-dihydro-2H-1,3,4-oxadiazin-2-one,
5-[3-fluoro-4-(6-fluoropyridin-3-yl)phenyl]-3,6-dihydro-2H-1,3,4-oxadiazin-2-one,
5-[3-fluoro-4-(3-methylpyridin-4-yl)phenyl]-3,6-dihydro-2H-1,3,4-oxadiazin-2-one,
5-[3-fluoro-4-(2-methylpyridin-4-yl)phenyl]-3,6-dihydro-2H-1,3,4-oxadiazin-2-one,
5-(4'-amino-2-fluorobiphenyl-4-yl)-3,6-dihydro-2H-1,3,4-oxadiazin-2-one,
5-(2-fluoro-2'-methylbiphenyl-4-yl)-3,6-dihydro-2H-1,3,4-oxadiazin-2-one,
5-(2'-chloro-2,4'-difluorobiphenyl-4-yl)-3,6-dihydro-2H-1,3,4-oxadiazin-2-one,
5-[4-(cyclopent-1-en-1-yl)-3-fluorophenyl]-3,6-dihydro-2H-1,3,4-oxadiazin-2-one,
5-(2'-ethyl-2-fluorobiphenyl-4-yl)-3,6-dihydro-2H-1,3,4-oxadiazin-2-one,
5-[3-fluoro-4-(6-methoxypyridin-3-yl)phenyl]-3,6-dihydro-2H-1,3,4-oxadiazin-2-one,
5-(2,4'-difluoro-3'-methylbiphenyl-4-yl)-3,6-dihydro-2H-1,3,4-oxadiazin-2-one,
5-(2-fluoro-3'-methylbiphenyl-4-yl)-3,6-dihydro-2H-1,3,4-oxadiazin-2-one,
5-(2-fluoro-4'-methylbiphenyl-4-yl)-3,6-dihydro-2H-1,3,4-oxadiazin-2-one, 5-(2-fluorobiphenyl-4-yl)-3,6-dihydro-2H-1,3,4-oxadiazin-2-one,
5-[4-(2-aminopyridin-4-yl)-3-fluorophenyl]-3,6-dihydro-2H-1,3,4-oxadiazin-2-one,
5-(3'-amino-2-fluorobiphenyl-4-yl)-3,6-dihydro-2H-1,3,4-oxadiazin-2-one,
5-[4'-(difluoromethyl)-2-fluorobiphenyl-4-yl]-3,6-dihydro-2H-1,3,4-oxadiazin-2-one,
5-[3-fluoro-4-(pyridin-4-yl)phenyl]-3,6-dihydro-2H-1,3,4-oxadiazin-2-one,
5-[3-fluoro-4-(2-methylpyrimidin-5-yl)phenyl]-3,6-dihydro-2H-1,3,4-oxadiazin-2-one,
5-[3-fluoro-4-(2-methoxypyridin-4-yl)phenyl]-3,6-dihydro-2H-1,3,4-oxadiazin-2-one,
5-[3-fluoro-4-(2-methylpyridin-3-yl)phenyl]-3,6-dihydro-2H-1,3,4-oxadiazin-2-one,
5-[3-fluoro-4-(6-methylpyridin-3-yl)phenyl]-3,6-dihydro-2H-1,3,4-oxadiazin-2-one,
5-(2,2',4',5'-tetrafluorobiphenyl-4-yl)-3,6-dihydro-2H-1,3,4-oxadiazin-2-one,
5-(2,2',3',4'-tetrafluorobiphenyl-4-yl)-3,6-dihydro-2H-1,3,4-oxadiazin-2-one,
5-(2,2',5'-trifluorobiphenyl-4-yl)-3,6-dihydro-2H-1,3,4-oxadiazin-2-one,
2'-fluoro-4'-(2-oxo-3,6-dihydro-2H-1,3,4-oxadiazin-5-yl)biphenyl-4-carbonitrile,
5-(2'-amino-2-fluorobiphenyl-4-yl)-3,6-dihydro-2H-1,3,4-oxadiazin-2-one,
5-(3'-amino-2-fluoro-4'-methylbiphenyl-4-yl)-3,6-dihydro-2H-1,3,4-oxadiazin-2-one,
5-(2-fluoro-3'-hydroxybiphenyl-4-yl)-3,6-dihydro-2H-1,3,4-oxadiazin-2-one,
5-(2-fluoro-4'-hydroxybiphenyl-4-yl)-3,6-dihydro-2H-1,3,4-oxadiazin-2-one,
5-(2-fluoro-2'-hydroxybiphenyl-4-yl)-3,6-dihydro-2H-1,3,4-oxadiazin-2-one,
5-(2,3',4'-trifluorobiphenyl-4-yl)-3,6-dihydro-2H-1,3,4-oxadiazin-2-one,
5-[3-fluoro-4-(pyridin-3-yl)phenyl]-3,6-dihydro-2H-1,3,4-oxadiazin-2-one,
5-(2,2',3'-trifluorobiphenyl-4-yl)-3,6-dihydro-2H-1,3,4-oxadiazin-2-one,
5-(2,3',5'-trifluorobiphenyl-4-yl)-3,6-dihydro-2H-1,3,4-oxadiazin-2-one,
5-(2,2',4'-trifluorobiphenyl-4-yl)-3,6-dihydro-2H-1,3,4-oxadiazin-2-one,
5-(2-fluoro-2',4'-dimethylbiphenyl-4-yl)-3,6-dihydro-2H-1,3,4-oxadiazin-2-one,
5-(2,3'-difluoro-4'-methylbiphenyl-4-yl)-3,6-dihydro-2H-1,3,4-oxadiazin-2-one,
5-(2,2'-difluorobiphenyl-4-yl)-3,6-dihydro-2H-1,3,4-oxadiazin-2-one,
5-(2,2',6'-trifluorobiphenyl-4-yl)-3,6-dihydro-2H-1,3,4-oxadiazin-2-one,
5-(2-fluoro-2'-methoxybiphenyl-4-yl)-3,6-dihydro-2H-1,3,4-oxadiazin-2-one,
5-(2,3'-difluorobiphenyl-4-yl)-3,6-dihydro-2H-1,3,4-oxadiazin-2-one,
5-[3-fluoro-4-(4-methylpyridin-3-yl)phenyl]-3,6-dihydro-2H-1,3,4-oxadiazin-2-one,
(rac)-5-(3-Fluoro-4-morpholinophenyl)-6-methyl-3,6-dihydro-2H-1,3,4-oxadiazin-2-one,
(6S)-6-methyl-5-[4-(morpholin-4-yl)-3-(trifluoromethyl)phenyl]-3,6-dihydro-2H-1,3,4-oxadiazin-2-one,
(6S)-5-(-[(3-chloro-4-(morpholin-4-yl)-5-(trifluoromethyl)phenyl)-)]-6-methyl-3,6-dihydro-2H-1,3,4-oxadiazin-2-one,
6S)-5-(-[(4-chloro-3-(trifluoromethyl)phenyl)-)]-6-methyl-3,6-dihydro-2H-1,3,4-oxadiazin-2-one,
(6S)-5-(-[(4-fluoro-3-(trifluoromethyl)phenyl)-)]-6-methyl-3,6-dihydro-2H-1,3,4-oxadiazin-2-one,
5-[4-chloro-3-(trifluoromethoxy)phenyl]-3,6-dihydro-2H-1,3,4-oxadiazin-2-one,
5-(4-chloro-3-methylphenyl)-3,6-dihydro-2H-1,3,4-oxadiazin-2-one,
(rac)-6-methyl-5-(4-morpholino-3-(trifluoromethyl)phenyl)-3,6-dihydro-2H-1,3,4-oxadiazin-2-one,
5-{4-[1-methyl-3-(trifluoromethyl)-1H-pyrazol-4-yl]-3-(trifluoromethyl)phenyl}-3,6-dihydro-2H-1,3,4-oxadiazin-2-one,
5-[4-(3,5-dimethyl-1H-pyrazol-4-yl)-3-(trifluoromethyl)phenyl]-3,6-dihydro-2H-1,3,4-oxadiazin-2-one,
5-[4-(3,5-dimethyl-1,2-oxazol-4-yl)-3-(trifluoromethyl)phenyl]-3,6-dihydro-2H-1,3,4-oxadiazin-2-one,
5-{3-(trifluoromethyl)-4-[3-(trifluoromethyl)-1H-pyrazol-4-yl]phenyl}-3,6-dihydro-2H-1,3,4-oxadiazin-2-one,
5-[4-(1-ethyl-1H-pyrazol-4-yl)-3-(trifluoromethyl)phenyl]-3,6-dihydro-2H-1,3,4-oxadiazin-2-one,
5-{4-[cyclopentyl(methyl)amino]-3-(trifluoromethyl)phenyl}-3,6-dihydro-2H-1,3,4-oxadiazin-2-one,
5-[4-(1-methyl-1,2,3,6-tetrahydropyridin-4-yl)-3-(trifluoromethyl)phenyl]-3,6-dihydro-2H-1,3,4-oxadiazin-2-one,
5-{4-[butyl(methyl)amino]-3-(trifluoromethyl)phenyl}-3,6-dihydro-2H-1,3,4-oxadiazin-2-one,
(6S)-5-[4'-fluoro-2-(trifluoromethyl)biphenyl-4-yl]-6-methyl-3,6-dihydro-2H-1,3,4-oxadiazin-2-one,
5-[4-(cyclopentylamino)-3-(trifluoromethyl)phenyl]-3,6-dihydro-2H-1,3,4-oxadiazin-2-one,
5-[4-(cyclopentylamino)-3-(trifluoromethyl)phenyl]-3,6-dihydro-2H-1,3,4-oxadiazin-2-one and
5-[3'-fluoro-2-(trifluoromethyl)biphenyl-4-yl]-3,6-dihydro-2H-1,3,4-oxadiazin-2-one or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is selected from the group
5-[4-methyl-3-(trifluoromethyl)phenyl]-3,6-dihydro-2H-1,3,4-oxadiazin-2-one,
5-{4-[3-methoxyprop-1-en-1-yl]-3-(trifluoromethyl)phenyl}-3,6-dihydro-2H-1,3,4-oxadiazin-2-one,
(rac)-5-[4'-hydroxy-2-(trifluoromethyl)-2',3',4',5'-tetrahydro[1,1'-biphenyl]-4-yl]-3,6-dihydro-2H-1,3,4-oxadiazin-2-one,
5-[4-(5,6-dihydro-2H-pyran-3-yl)-3-(trifluoromethyl)phenyl]-3,6-dihydro-2H-1,3,4-oxadiazin-2-one,
5-[4-(imidazo[1,2-a]pyridin-6-yl)-3-(trifluoromethyl)phenyl]-3,6-dihydro-2H-1,3,4-oxadiazin-2-one,
5-{4-[3,3-dimethylbut-1-en-1-yl]-3-(trifluoromethyl)phenyl}-3,6-dihydro-2H-1,3,4-oxadiazin-2-one,
5-{3-(trifluoromethyl)-4-[5-(trifluoromethyl)thiophen-3-yl]phenyl}-3,6-dihydro-2H-1,3,4-oxadiazin-2-one,
5-{4-[1-(difluoromethyl)-1H-pyrazol-4-yl]-3-(trifluoromethyl)phenyl}-3,6-dihydro-2H-1,3,4-oxadiazin-2-one,
5-[4-(prop-1-en-2-yl)-3-(trifluoromethyl)phenyl]-3,6-dihydro-2H-1,3,4-oxadiazin-2-one,
5-[4-(1-benzothiophen-2-yl)-3-(trifluoromethyl)phenyl]-3,6-dihydro-2H-1,3,4-oxadiazin-2-one,
5-[4-(2,5-dihydrofuran-3-yl)-3-(trifluoromethyl)phenyl]-3,6-dihydro-2H-1,3,4-oxadiazin-2-one,
5-[4-(cyclopent-1-en-1-yl)-3-(trifluoromethyl)phenyl]-3,6-dihydro-2H-1,3,4-oxadiazin-2-one, 5-[4-(1-ethyl-1H-imidazol-4-yl)-3-(trifluoromethyl)phenyl]-3,6-dihydro-2H-1,3,4-oxadiazin-2-one,
3-methyl-5-[4-(2-oxo-3,6-dihydro-2H-1,3,4-oxadiazin-5-yl)-2-(trifluoromethyl)phenyl]thiophene-2-carbonitrile,
5-{4-[1-(propan-2-yl)-1H-pyrazol-4-yl]-3-(trifluoromethyl)phenyl}-3,6-dihydro-2H-1,3,4-oxadiazin-2-one,
(rac)-5-[4-(bicyclo[2.2.1]hept-2-en-2-yl)-3-(trifluoromethyl)phenyl]-3,6-dihydro-2H-1,3,4-oxadiazin-2-one,
5-[2'-fluoro-2-(trifluoromethyl)[1,1'-biphenyl]-4-yl]-3,6-dihydro-2H-1,3,4-oxadiazin-2-one,
5-{3-(Trifluoromethyl)-4-[5-(trifluoromethyl)thiophen-2-yl]phenyl}-3,6-dihydro-2H-1,3,4-oxadiazin-2-one,
5-[4-(5-methylpyridin-2-yl)-3-(trifluoromethyl)phenyl]-3,6-dihydro-2H-1,3,4-oxadiazin-2-one,
5-[4-(5-fluoropyridin-2-yl)-3-(trifluoromethyl)phenyl]-3,6-dihydro-2H-1,3,4-oxadiazin-2-one,
5-[4-(5-chloropyridin-2-yl)-3-(trifluoromethyl)phenyl]-3,6-dihydro-2H-1,3,4-oxadiazin-2-one,
5-[4-(pyridin-2-yl)-3-(trifluoromethyl)phenyl]-3,6-dihydro-2H-1,3,4-oxadiazin-2-one,
5-[2'-(Difluoromethyl)-2-fluoro[1,1'-biphenyl]-4-yl]-3,6-dihydro-2H-1,3,4-oxadiazin-2-one,
5-(2,4'-Difluoro-2'-methyl[1,1'-biphenyl]-4-yl)-3,6-dihydro-2H-1,3,4-oxadiazin-2-one,
2'-fluoro-2-methyl-4'-(2-oxo-3,6-dihydro-2H-1,3,4-oxadiazin-5-yl)[1,1'-biphenyl]-4-carbonitrile,
5-[4-(2-Methylprop-1-en-1-yl)-3-(trifluoromethoxy)phenyl]-3,6-dihydro-2H-1,3,4-oxadiazin-2-one,
(6S)-5-[4-(2-aminopyridin-4-yl)-3-(trifluoromethyl)phenyl]-6-methyl-3,6-dihydro-2H-1,3,4-oxadiazin-2-one,
(6S)-6-methyl-5-[4-(pyridin-4-yl)-3-(trifluoromethyl)phenyl]-3,6-dihydro-2H-1,3,4-oxadiazin-2-one,
(6S)-6-methyl-5-[4-(6-methylpyridin-3-yl)-3-(trifluoromethyl)phenyl]-3,6-dihydro-2H-1,3,4-oxadiazin-2-one,
(6S)-5-[2'-fluoro-4'-methyl-2-(trifluoromethyl)[1,1'-biphenyl]-4-yl]-6-methyl-3,6-dihydro-2H-1,3,4-oxadiazin-2-one,
(6S)-6-methyl-5-[2',4',5'-trifluoro-2-(trifluoromethyl)[1,1'-biphenyl]-4-yl]-3,6-dihydro-2H-1,3,4-oxadiazin-2-one,
(6S)-6-methyl-5-[2',3',4'-trifluoro-2-(trifluoromethyl)[1,1'-biphenyl]-4-yl]-3,6-dihydro-2H-1,3,4-oxadiazin-2-one,
(6S)-5-[2',5'-difluoro-2-(trifluoromethyl)[1,1'-biphenyl]-4-yl]-6-methyl-3,6-dihydro-2H-1,3,4-oxadiazin-2-one,
4'-[(6S)-6-methyl-2-oxo-3,6-dihydro-2H-1,3,4-oxadiazin-5-yl]-2'-(trifluoromethyl)[1,1'-biphenyl]-2-carbonitrile,
(6S)-5-[4-(1H-indol-5-yl)-3-(trifluoromethyl)phenyl]-6-methyl-3,6-dihydro-2H-1,3,4-oxadiazin-2-one,
(6S)-5-[4'-hydroxy-2-(trifluoromethyl)[1,1'-biphenyl]-4-yl]-6-methyl-3,6-dihydro-2H-1,3,4-oxadiazin-2-one,
(6S)-5-[3'-hydroxy-2-(trifluoromethyl)[1,1'-biphenyl]-4-yl]-6-methyl-3,6-dihydro-2H-1,3,4-oxadiazin-2-one,
(6S)-5-[3'-amino-2-(trifluoromethyl)[1,1'-biphenyl]-4-yl]-6-methyl-3,6-dihydro-2H-1,3,4-oxadiazin-2-one,
(6S)-5-[2',4'-difluoro-2-(trifluoromethyl)[1,1'-biphenyl]-4-yl]-6-methyl-3,6-dihydro-2H-1,3,4-oxadiazin-2-one,
(6S)-5-[3'-fluoro-4'-methyl-2-(trifluoromethyl)[1,1'-biphenyl]-4-yl]-6-methyl-3,6-dihydro-2H-1,3,4-oxadiazin-2-one,
(6S)-5-[2'-fluoro-2-(trifluoromethyl)[1,1'-biphenyl]-4-yl]-6-methyl-3,6-dihydro-2H-1,3,4-oxadiazin-2-one,
(6S)-5-[2'-methoxy-2-(trifluoromethyl)[1,1'-biphenyl]-4-yl]-6-methyl-3,6-dihydro-2H-1,3,4-oxadiazin-2-one,
(6S)-5-[3'-fluoro-2-(trifluoromethyl)[1,1'-biphenyl]-4-yl]-6-methyl-3,6-dihydro-2H-1,3,4-oxadiazin-2-one,
(6S)-6-methyl-5-[4-(4-methylpyridin-3-yl)-3-(trifluoromethyl)phenyl]-3,6-dihydro-2H-1,3,4-oxadiazin-2-one,
(6S)-6-methyl-5-[4-(3-methylpyridin-4-yl)-3-(trifluoromethyl)phenyl]-3,6-dihydro-2H-1,3,4-oxadiazin-2-one,
(6S)-6-methyl-5-[4-(2-methylpyridin-4-yl)-3-(trifluoromethyl)phenyl]-3,6-dihydro-2H-1,3,4-oxadiazin-2-one,
(6S)-5-[4-(1H-indol-6-yl)-3-(trifluoromethyl)phenyl]-6-methyl-3,6-dihydro-2H-1,3,4-oxadiazin-2-one,
(6S)-5-[2'-ethyl-2-(trifluoromethyl)[1,1'-biphenyl]-4-yl]-6-methyl-3,6-dihydro-2H-1,3,4-oxadiazin-2-one,
(6S)-5-[4-(6-methoxypyridin-3-yl)-3-(trifluoromethyl)phenyl]-6-methyl-3,6-dihydro-2H-1,3,4-oxadiazin-2-one,
(6S)-5-[4'-methoxy-2-(trifluoromethyl)[1,1'-biphenyl]-4-yl]-6-methyl-3,6-dihydro-2H-1,3,4-oxadiazin-2-one,
(6S)-6-methyl-5-[4'-methyl-2-(trifluoromethyl)[1,1'-biphenyl]-4-yl]-3,6-dihydro-2H-1,3,4-oxadiazin-2-one,
(6S)-5-{4-[1-(difluoromethyl)-1H-pyrazol-4-yl]-3-(trifluoromethyl)-phenyl}-6-methyl-3,6-dihydro-2H-1,3,4-oxadiazin-2-one,
5-{4-[1-(difluoromethyl)-1H-pyrazol-4-yl]-3-(trifluoromethyl)-phenyl}-6-methyl-3,6-dihydro-2H-1,3,4-oxadiazin-2-one,
5-[4'-fluoro-2-(trifluoromethyl)[1,1'-biphenyl]-4-yl]-6-methyl-3,6-dihydro-2H-1,3,4-oxadiazin-2-one,
5-{4-[1-(difluoromethyl)-1H-pyrazol-4-yl]-3-fluoro-5-(trifluoromethyl)phenyl}-3,6-dihydro-2H-1,3,4-oxadiazin-2-one,
5-{3-(difluoromethyl)-4-[1-(difluoromethyl)-1H-pyrazol-4-yl]phenyl}-3,6-dihydro-2H-1,3,4-oxadiazin-2-one,
(6S)-6-methyl-5-{4-[(morpholin-4-yl)methyl]-3-(trifluoromethyl)phenyl}-3,6-dihydro-2H-1,3,4-oxadiazin-2-one,
5-{4-[(morpholin-4-yl)methyl]-3-(trifluoromethyl)phenyl}-3,6-dihydro-2H-1,3,4-oxadiazin-2-one,
5-[2-(difluoromethyl)-4'-fluoro[1,1'-biphenyl]-4-yl]-3,6-dihydro-2H-1,3,4-oxadiazin-2-one,
5-[4'-chloro-2-(difluoromethyl)[1,1'-biphenyl]-4-yl]-3,6-dihydro-2H-1,3,4-oxadiazin-2-one,
5-[3-(difluoromethyl)-4-(6-methylpyridin-3-yl)phenyl]-3,6-dihydro-2H-1,3,4-oxadiazin-2-one,
5-[4-(cyclopent-1-en-1-yl)-3-(difluoromethyl)phenyl]-3,6-dihydro-2H-1,3,4-oxadiazin-2-one,
5-[3-(difluoromethyl)-4-(1H-pyrazol-4-yl)phenyl]-3,6-dihydro-2H-1,3,4-oxadiazin-2-one,
5-[4-(3-Hydroxy-3-methylazetidin-1-yl)-3-(trifluoromethyl)phenyl]-3,6-dihydro-2H-1,3,4-oxadiazin-2-one,
(rac)-5-[4-{[3,3,3-trifluoro-2-hydroxypropyl]amino}-3-(trifluoromethyl)phenyl]-3,6-dihydro-2H-1,3,4-oxadiazin-2-one,
5-{4-[(Oxan-4-yl)amino]-3-(trifluoromethyl)phenyl}-3,6-dihydro-2H-1,3,4-oxadiazin-2-one,
5-[4-{[(cis/trans)-3-hydroxycyclobutyl]amino}-3-(trifluoromethyl)phenyl]-3,6-dihydro-2H-1,3,4-oxadiazin-2-one,
5-{4-[(rac)-2,4-Dimethylazetidin-1-yl]-3-(trifluoromethyl)phenyl}-3,6-dihydro-2H-1,3,4-oxadiazin-2-one,
5-{4-[(cis or trans)-2,4-Dimethylazetidin-1-yl]-3-(trifluoromethyl)phenyl}-3,6-dihydro-2H-1,3,4-oxadiazin-2-one,
5-[4-{[3,3,3-Trifluoro-2(S)-hydroxypropyl]amino}-3-(trifluoromethyl)phenyl]-3,6-dihydro-2H-1,3,4-oxadiazin-2-one,
5-{4-[(2-Hydroxy-2-methylpropyl)amino]-3-(trifluoromethyl)phenyl}-3,6-dihydro-2H-1,3,4-oxadiazin-2-one,
5-{4-[(trans)-4-Hydroxycyclohexyl]amino}-3-(trifluoromethyl)phenyl}-3,6-dihydro-2H-1,3,4-oxadiazin-2-one,
5-{4-[(Cyclopropylmethyl)amino]-3-(trifluoromethyl)phenyl}-3,6-dihydro-2H-1,3,4-oxadiazin-2-one,
5-{4-{[(3-Methyloxetan-3-yl)methyl]amino}-3-(trifluoromethyl)phenyl]-3,6-dihydro-2H-1,3,4-oxadiazin-2-one, -{4-[(3-Methoxypropyl)amino]-3-(trifluoromethyl)phenyl}-3,6-dihydro-2H-1,3,4-oxadiazin-2-one,
5-[4-({[(rac)-Oxolan-2-yl]methyl}amino)-3-(trifluoromethyl)phenyl]-3,6-dihydro-2H-1,3,4-oxadiazin-2-one,
5-[4-{[2(R)-2-Hydroxypropyl]amino}-3-(trifluoromethyl)phenyl]-3,6-dihydro-2H-1,3,4-oxadiazin-2-one,
5-[4-{[(3R)-3-Hydroxybutyl]amino}-3-(trifluoromethyl)phenyl]-3,6-dihydro-2H-1,3,4-oxadiazin-2-one,
5-[4-{[(2S)-2-Hydroxypropyl]amino}-3-(trifluoromethyl)phenyl]-3,6-dihydro-2H-1,3,4-oxadiazin-2-one,
5-[4-{[(1-Hydroxycyclobutyl)methyl]amino}-3-(trifluoromethyl)phenyl]-3,6-dihydro-2H-1,3,4-oxadiazin-2-one,
5-{4-[(3-Methylbutyl)amino]-3-(trifluoromethyl)phenyl}-3,6-dihydro-2H-1,3,4-oxadiazin-2-one,
5-{4-[(2-Methylpropyl)amino]-3-(trifluoromethyl)phenyl}-3,6-dihydro-2H-1,3,4-oxadiazin-2-one,
5-{4-[(2-Methoxyethyl)amino]-3-(trifluoromethyl)phenyl}-3,6-dihydro-2H-1,3,4-oxadiazin-2-one,
5-{4-[Ethyl(methyl)amino]-3-(trifluoromethyl)phenyl}-3,6-dihydro-2H-1,3,4-oxadiazin-2-one,
5-[4-(tert-butylamino)-3-(trifluoromethyl)phenyl]-3,6-dihydro-2H-1,3,4-oxadiazin-2-one,
5-[4-({[(2R)-oxolan-2-yl]methyl}amino)-3-(trifluoromethyl)phenyl]-3,6-dihydro-2H-1,3,4-oxadiazin-2-one,
5-[4-{[(pyrazin-2-yl)methyl]amino}-3-(trifluoromethyl)phenyl]-3,6-dihydro-2H-1,3,4-oxadiazin-2-one,
5-[4-(4-hydroxypiperidin-1-yl)-3-(trifluoromethyl)phenyl]-3,6-dihydro-2H-1,3,4-oxadiazin-2-one,
5-[4-{[(2S)-1-hydroxybutan-2-yl]amino}-3-(trifluoromethyl)phenyl]-3,6-dihydro-2H-1,3,4-oxadiazin-2-one,
5-[4-(3-hydroxypiperidin-1-yl)-3-(trifluoromethyl)phenyl]-3,6-dihydro-2H-1,3,4-oxadiazin-2-one (racemic mixture),
(rac)-1-[4-(2-oxo-3,6-dihydro-2H-1,3,4-oxadiazin-5-yl)-2-(trifluoromethyl)phenyl]piperidine-3-carboxamide,
5-{4-[(3-hydroxy-2,2-dimethylpropyl)amino]-3-(trifluoromethyl)phenyl}-3,6-dihydro-2H-1,3,4-oxadiazin-2-one,
5-[4-(4,4-difluoropiperidin-1-yl)-3-(trifluoromethyl)phenyl]-3,6-dihydro-2H-1,3,4-oxadiazin-2-one,
5-[4-{[(1R,2R,4R)-bicyclo[2.2.1]heptan-2-yl]amino}-3-(trifluoromethyl)phenyl]-3,6-dihydro-2H-1,3,4-oxadiazin-2-one,
5-{4-[(3S)-3-hydroxypyrrolidin-1-yl]-3-(trifluoromethyl)phenyl}-3,6-dihydro-2H-1,3,4-oxadiazin-2-one,
(rac)-5-{4-[(2-hydroxy-3-methoxypropyl)amino]-3-(trifluoromethyl)phenyl}-3,6-dihydro-2H-1,3,4-oxadiazin-2-one,
5-[4-{[(1-methyl-1H-pyrazol-5-yl)methyl]amino}-3-(trifluoromethyl)phenyl]-3,6-dihydro-2H-1,3,4-oxadiazin-2-one,
5-[4-{[(1H-pyrazol-3-yl)methyl]amino}-3-(trifluoromethyl)phenyl]-3,6-dihydro-2H-1,3,4-oxadiazin-2-one,
5-[4-{[2-(1H-pyrazol-1-yl)ethyl]amino}-3-(trifluoromethyl)phenyl]-3,6-dihydro-2H-1,3,4-oxadiazin-2-one,
1-[4-(2-oxo-3,6-dihydro-2H-1,3,4-oxadiazin-5-yl)-2-(trifluoromethyl)phenyl]piperidine-4-carbonitrile,
(rac)-5-{4-[(1-cyclopropylethyl)amino]-3-(trifluoromethyl)phenyl}-3,6-dihydro-2H-1,3,4-oxadiazin-2-one,
(rac)-5-{4-[(2-ethoxypropyl)amino]-3-(trifluoromethyl)phenyl}-3,6-dihydro-2H-1,3,4-oxadiazin-2-one
(rac)-5-{4-[(2-methoxypropyl)amino]-3-(trifluoromethyl)phenyl}-3,6-dihydro-2H-1,3,4-oxadiazin-2-one
5-[4-(3-ethoxyazetidin-1-yl)-3-(trifluoromethyl)phenyl]-3,6-dihydro-2H-1,3,4-oxadiazin-2-one,
5-[4-{[(pyrimidin-2-yl)methyl]amino}-3-(trifluoromethyl)phenyl]-3,6-dihydro-2H-1,3,4-oxadiazin-2-one,
5-[4-{[(oxolan-3-yl)methyl]amino}-3-(trifluoromethyl)phenyl]-3,6-dihydro-2H-1,3,4-oxadiazin-2-one (racemic mixture),
5-[4-{[(2S)-4-hydroxybutan-2-yl]amino}-3-(trifluoromethyl)phenyl]-3,6-dihydro-2H-1,3,4-oxadiazin-2-one,
(rac)-5-[4-{[(6-oxopiperidin-3-yl)methyl]amino}-3-(trifluoromethyl)phenyl]-3,6-dihydro-2H-1,3,4-oxadiazin-2-one,
(rac)-5-[4-{[(2,2-dimethylcyclopropyl)methyl]amino}-3-(trifluoromethyl)phenyl]-3,6-dihydro-2H-1,3,4-oxadiazin-2-one,
5-[4-({[1-(hydroxymethyl)cyclobutyl]methyl}amino)-3-(trifluoromethyl)phenyl]-3,6-dihydro-2H-1,3,4-oxadiazin-2-one,
5-{4-[(2S)-2-(hydroxymethyl)azetidin-1-yl]-3-(trifluoromethyl)phenyl}-3,6-dihydro-2H-1,3,4-oxadiazin-2-one,
3-methyl-1-[4-(2-oxo-3,6-dihydro-2H-1,3,4-oxadiazin-5-yl)-2-(trifluoromethyl)phenyl]azetidine-3-carbonitrile,
5-[4-(3-azabicyclo[3.1.0]hexan-3-yl)-3-(trifluoromethyl)phenyl]-3,6-dihydro-2H-1,3,4-oxadiazin-2-one,
5-[4-(4-ethyl-4-hydroxypiperidin-1-yl)-3-(trifluoromethyl)phenyl]-3,6-dihydro-2H-1,3,4-oxadiazin-2-one,
4-[4-(2-oxo-3,6-dihydro-2H-1,3,4-oxadiazin-5-yl)-2-(trifluoromethyl)anilino]butanenitrile,
6-[4-(2-oxo-3,6-dihydro-2H-1,3,4-oxadiazin-5-yl)-2-(trifluoro-methyl)phenyl]-2lambda$^6$-thia-6-azaspiro[3.3]heptane-2,2-dione,
N$^2$-[4-(2-oxo-3,6-dihydro-2H-1,3,4-oxadiazin-5-yl)-2-(trifluoromethyl)phenyl]glycinamide,
5-{4-[(3R)-3-hydroxypyrrolidin-1-yl]-3-(trifluoromethyl)phenyl}-3,6-dihydro-2H-1,3,4-oxadiazin-2-one,
5-{4-[(2-methoxy-2-methylpropyl)amino]-3-(trifluoromethyl)phenyl}-3,6-dihydro-2H-1,3,4-oxadiazin-2-one
5-[4-({[(2S)-oxolan-2-yl]methyl}amino)-3-(trifluoromethyl)phenyl]-3,6-dihydro-2H-1,3,4-oxadiazin-2-one,
5-{4-[(2-ethoxyethyl)amino]-3-(trifluoromethyl)phenyl}-3,6-dihydro-2H-1,3,4-oxadiazin-2-one,
5-[4-{[(1S,2R)-2-hydroxycyclopentyl]amino}-3-(trifluoromethyl)phenyl]-3,6-dihydro-2H-1,3,4-oxadiazin-2-one,
5-{4-[(oxetan-3-yl)amino]-3-(trifluoromethyl)phenyl}-3,6-dihydro-2H-1,3,4-oxadiazin-2-on,
5-{3-(difluoromethyl)-4-[1-(propan-2-yl)-1H-pyrazol-4-yl]phenyl}-3,6-dihydro-2H-1,3,4-oxadiazin-2-one,
5-[3-fluoro-4-(morpholin-4-yl)-5-(trifluoromethyl)phenyl]-3,6-dihydro-2H-1,3,4-oxadiazin-2-one,
(6S)-6-methyl-5-{3-(trifluoromethyl)-4-[3-(trifluoromethyl)-1H-pyrazol-1-yl]phenyl}-3,6-dihydro-2H-1,3,4-oxadiazin-2-one,
(6S)-6-methyl-5-{3-(trifluoromethyl)-4-[4-(trifluoromethyl)-1H-imidazol-1-yl]phenyl}-3,6-dihydro-2H-1,3,4-oxadiazin-2-one,
5-[4-(3-Methoxypropyl)-3-(trifluoromethyl)phenyl]-3,6-dihydro-2H-1,3,4-oxadiazin-2-one,
5-[4-(2-methylpropyl)-3-(trifluoromethyl)phenyl]-3,6-dihydro-2H-1,3,4-oxadiazin-2-one,
5-[4-(3,3-dimethylbutyl)-3-(trifluoromethyl)phenyl]-3,6-dihydro-2H-1,3,4-oxadiazin-2-one,
5-[4-(Propan-2-yl)-3-(trifluoromethyl)phenyl]-3,6-dihydro-2H-1,3,4-oxadiazin-2-one,
(rac)-5-{4-[oxan-3-yl]-3-(trifluoromethyl)phenyl}-3,6-dihydro-2H-1,3,4-oxadiazin-2-one,
(trans)-5-{4-[4-hydroxycyclohexyl]-3-(trifluoromethyl)phenyl}-3,6-dihydro-2H-1,3,4-oxadiazin-2-one (trans isomer),
(cis)-5-{4-[4-hydroxycyclohexyl]-3-(trifluoromethyl)phenyl}-3,6-dihydro-2H-1,3,4-oxadiazin-2-one, 5-{4-[(2-Aminoethyl)amino]-3-(trifluoromethyl)phenyl}-3,6-dihydro-2H-1,3,4-oxadiazin-2-one-salt with hydrochloric acid, 5-{4-[1-amino-3-azabicyclo[3.1.0]hexan-3-yl]-3-(trifluoromethyl)-phenyl}-3,6-dihydro-2H-1,3,4-oxadiazin-2-one-salt with hydrochloric acid, 5-[4-(methylamino)-3-(trifluoromethyl)phenyl]-3,6-dihydro-2H-1,3,4-oxadiazin-2-one, (6S)-6-methyl-5-[4-(4-methylpiperazin-1-yl)-3-(trifluoromethyl)phenyl]-3,6-dihydro-2H-1,3,4-oxadiazin-2-one, 5-[4-(2-hydroxypropan-2-yl)-3-(trifluoromethyl)phenyl]-3,6-dihydro-2H-1,3,4-oxadiazin-2-one, (6S)-5-[4-(3,3-difluoroazetidin-1-yl)-3-(trifluoromethyl)phenyl]-6-methyl-3,6-dihydro-2H-1,3,4-oxadiazin-2-one and (6S)-5-[4-(3-hydroxy-3-methylazetidin-1-yl)-3-(trifluoromethyl)-phenyl]-6-methyl-3,6-dihydro-2H-1,3,4-oxadiazin-2-one or a stereoisomer, a tautomer, an N-oxide, a hydrate, a solvate, or a salt thereof, or a mixture of same.

In accordance with a further embodiment of the first aspect, the present invention provides compounds of general formula (I): wherein the compound is selected from the group 5-[4-(4,4-Difluoropiperidin-1-yl)-3-fluorophenyl]-3,6-dihydro-2H-1,3,4-oxadiazin-2-one 5-[4'-fluoro-2-(trifluoromethyl)biphenyl-4-yl]-3,6-dihydro-2H-1,3,4-oxadiazin-2-one, 5-(4'-fluoro-2-methylbiphenyl-4-yl)-3,6-dihydro-2H-1,3,4-oxadiazin-2-one, 5-(3',4'-Difluoro-2-methylbiphenyl-4-yl)-3,6-dihydro-2H-1,3,4-oxadiazin-2-one 5-[4'-chloro-2-(trifluoromethyl)biphenyl-4-yl]-3,6-dihydro-2H-1,3,4-oxadiazin-2-one, 5-[4-(1,2-Thiazol-4-yl)-3-(trifluoromethyl)phenyl]-3,6-dihydro-2H-1,3,4-oxadiazin-2-one 5-[4-(2-Methyl-1,3-thiazol-5-yl)-3-(trifluoromethyl)phenyl]-3,6-dihydro-2H-1,3,4-oxadiazin-2-one 5-[4-(Propylamino)-3-(trifluoromethyl)phenyl]-3,6-dihydro-2H-1,3,4-oxadiazin-2-one 5-[4'-Fluoro-2-(trifluoromethoxy)biphenyl-4-yl]-3,6-dihydro-2H-1,3,4-oxadiazin-2-one (6S)-5-[4'-fluoro-2-(trifluoromethyl)biphenyl-4-yl]-6-methyl-3,6-dihydro-2H-1,3,4-oxadiazin-2-one, 5-[4-(Cyclopentylamino)-3-(trifluoromethyl)phenyl]-3,6-dihydro-2H-1,3,4-oxadiazin-2-one 5-{4-[1-(difluoromethyl)-1H-pyrazol-4-yl]-3-(trifluoromethyl)phenyl}-3,6-dihydro-2H-1,3,4-oxadiazin-2-one, 5-[4-(2,5-Dihydrofuran-3-yl)-3-(trifluoromethyl)phenyl]-3,6-dihydro-2H-1,3,4-oxadiazin-2-one 5-[4-(5-Chloropyridin-2-yl)-3-(trifluoromethyl)phenyl]-3,6-dihydro-2H-1,3,4-oxadiazin-2-one (6S)-5-[4-(2-aminopyridin-4-yl)-3-(trifluoromethyl)phenyl]-6-methyl-3,6-dihydro-2H-1,3,4-oxadiazin-2-one and (6S)-5-{4-[1-(difluoromethyl)-1H-pyrazol-4-yl]-3-(trifluoromethyl)-phenyl}-6-methyl-3,6-dihydro-2H-1,3,4-oxadiazin-2-one, 5-{4-[(Morpholin-4-yl)methyl]-3-(trifluoromethyl)phenyl}-3,6-dihydro-2H-1,3,4-oxadiazin-2-one (cis/trans)-5-[4-{[3-hydroxycyclobutyl]amino}-3-(trifluoromethyl)phenyl]-3,6-dihydro-2H-1,3,4-oxadiazin-2-one 5-[4-{[3,3,3-Trifluoro-2(S)-hydroxypropyl]amino}-3-(trifluoromethyl)phenyl]-3,6-dihydro-2H-1,3,4-oxadiazin-2-one, 5-{4-[(2-Hydroxy-2-methylpropyl)amino]-3-(trifluoromethyl)phenyl}-3,6-dihydro-2H-1,3,4-oxadiazin-2-one, 5-{4-[(2-Methoxyethyl)amino]-3-(trifluoromethyl)phenyl}-3,6-dihydro-2H-1,3,4-oxadiazin-2-one, 5-[4-{[(Pyrazin-2-yl)methyl]amino}-3-(trifluoromethyl)phenyl]-3,6-dihydro-2H-1,3,4-oxadiazin-2-one (6S)-6-methyl-5-{3-(trifluoromethyl)-4-[3-(trifluoromethyl)-1H-pyrazol-1-yl]phenyl}-3,6-dihydro-2H-1,3,4-oxadiazin-2-one, 5-[4-(2-Methylpropyl)-3-(trifluoromethyl)phenyl]-3,6-dihydro-2H-1,3,4-oxadiazin-2-one and (6S)-5-[4-(3-Hydroxy-3-methylazetidin-1-yl)-3-(trifluoromethyl)phenyl]-6-methyl-3,6-dihydro-2H-1,3,4-oxadiazin-2-one or a stereoisomer, a tautomer, an N-oxide, a hydrate, a solvate, or a salt thereof, or a mixture of same.

In accordance with a further embodiment of the first aspect, the present invention provides compounds of general formula (I): wherein the compound is selected from the group 5-[4-(4,4-Difluoropiperidin-1-yl)-3-fluorophenyl]-3,6-dihydro-2H-1,3,4-oxadiazin-2-one 5-(3',4'-Difluoro-2-methylbiphenyl-4-yl)-3,6-dihydro-2H-1,3,4-oxadiazin-2-one 5-[4-(1,2-Thiazol-4-yl)-3-(trifluoromethyl)phenyl]-3,6-dihydro-2H-1,3,4-oxadiazin-2-one 5-[4-(2-Methyl-1,3-thiazol-5-yl)-3-(trifluoromethyl)phenyl]-3,6-dihydro-2H-1,3,4-oxadiazin-2-one 5-[4-(Propylamino)-3-(trifluoromethyl)phenyl]-3,6-dihydro-2H-1,3,4-oxadiazin-2-one 5-[4'-Fluoro-2-(trifluoromethoxy)biphenyl-4-yl]-3,6-dihydro-2H-1,3,4-oxadiazin-2-one 5-[4-(Cyclopentylamino)-3-(trifluoromethyl)phenyl]-3,6-dihydro-2H-1,3,4-oxadiazin-2-one 5-[4-(2,5-Dihydrofuran-3-yl)-3-(trifluoromethyl)phenyl]-3,6-dihydro-2H-1,3,4-oxadiazin-2-one 5-[4-(5-Chloropyridin-2-yl)-3-(trifluoromethyl)phenyl]-3,6-dihydro-2H-1,3,4-oxadiazin-2-one 5-{4-[(Morpholin-4-yl)methyl]-3-(trifluoromethyl)phenyl}-3,6-dihydro-2H-1,3,4-oxadiazin-2-one (cis/trans)-5-[4-{[3-hydroxycyclobutyl]amino}-3-(trifluoromethyl)phenyl]-3,6-dihydro-2H-1,3,4-oxadiazin-2-one 5-[4-{[(Pyrazin-2-yl)methyl]amino}-3-(trifluoromethyl)phenyl]-3,6-dihydro-2H-1,3,4-oxadiazin-2-one 5-[4-(2-Methylpropyl)-3-(trifluoromethyl)phenyl]-3,6-dihydro-2H-1,3,4-oxadiazin-2-one (6S)-5-[4-(3-Hydroxy-3-methylazetidin-1-yl)-3-(trifluoromethyl)phenyl]-6-methyl-3,6-dihydro-2H-1,3,4-oxadiazin-2-one or a stereoisomer, a tautomer, an N-oxide, a hydrate, a solvate, or a salt thereof, or a mixture of same.

In accordance with a further embodiment of the first aspect, the present invention provides compounds of general formula (I): wherein the compound is selected from the group 5-[4'-fluoro-2-(trifluoromethyl)biphenyl-4-yl]-3,6-dihydro-2H-1,3,4-oxadiazin-2-one, 5-(4'-fluoro-2-methylbiphenyl-4-yl)-3,6-dihydro-2H-1,3,4-oxadiazin-2-one, 5-[4'-chloro-2-(trifluoromethyl)biphenyl-4-yl]-3,6-dihydro-2H-1,3,4-oxadiazin-2-one, (6S)-5-{4-[1-(difluoromethyl)-1H-pyrazol-4-yl]-3-(trifluoromethyl)-phenyl}-6-methyl-3,6-dihydro-2H-1,3,4-oxadiazin-2-one, 5-[4-{[3,3,3-Trifluoro-2(S)-hydroxypropyl]amino}-3-(trifluoromethyl)phenyl]-3,6-dihydro-2H-1,3,4-oxadiazin-2-one, 5-{4-[(2-Hydroxy-2-methylpropyl)amino]-3-(trifluoromethyl)phenyl}-3,6-dihydro-2H-1,3,4-oxadiazin-2-one, 5-{4-[(2-Methoxyethyl)amino]-3-(trifluoromethyl)phenyl}-3,6-dihydro-2H-1,3,4-oxadiazin-2-one,
(6S)-5-[4'-fluoro-2-(trifluoromethyl)biphenyl-4-yl]-6-methyl-3,6-dihydro-2H-1,3,4-oxadiazin-2-one,
5-{4-[1-(difluoromethyl)-1H-pyrazol-4-yl]-3-(trifluoromethyl)phenyl}-3,6-dihydro-2H-1,3,4-oxadiazin-2-one,
(6S)-5-[4-(2-aminopyridin-4-yl)-3-(trifluoromethyl)phenyl]-6-methyl-3,6-dihydro-2H-1,3,4-oxadiazin-2-one and
(6S)-6-methyl-5-{3-(trifluoromethyl)-4-[3-(trifluoromethyl)-1H-pyrazol-1-yl]phenyl}-3,6-dihydro-2H-1,3,4-oxadiazin-2-one,
or a stereoisomer, a tautomer, an N-oxide, a hydrate, a solvate, or a salt thereof, or a mixture of same.

In accordance with a further embodiment of the first aspect, the present invention provides compounds of general formula (I): wherein the compound is selected from the group
5-[4'-fluoro-2-(trifluoromethyl)biphenyl-4-yl]-3,6-dihydro-2H-1,3,4-oxadiazin-2-one,
5-(4'-fluoro-2-methylbiphenyl-4-yl)-3,6-dihydro-2H-1,3,4-oxadiazin-2-one,
5-[4'-chloro-2-(trifluoromethyl)biphenyl-4-yl]-3,6-dihydro-2H-1,3,4-oxadiazin-2-one and
(6S)-5-[4'-fluoro-2-(trifluoromethyl)biphenyl-4-yl]-6-methyl-3,6-dihydro-2H-1,3,4-oxadiazin-2-one,
or a stereoisomer, a tautomer, an N-oxide, a hydrate, a solvate, or a salt thereof, or a mixture of same.

In accordance with a further embodiment of the first aspect, the present invention provides compounds of general formula (I): wherein the compound is selected from the group
(6S)-5-{4-[1-(difluoromethyl)-1H-pyrazol-4-yl]-3-(trifluoromethyl)-phenyl}-6-methyl-3,6-dihydro-2H-1,3,4-oxadiazin-2-one,
5-[4-{[3,3,3-Trifluoro-2(S)-hydroxypropyl]amino}-3-(trifluoromethyl)phenyl]-3,6-dihydro-2H-1,3,4-oxadiazin-2-one,
5-{4-[(2-Hydroxy-2-methylpropyl)amino]-3-(trifluoromethyl)phenyl}-3,6-dihydro-2H-1,3,4-oxadiazin-2-one,
5-{4-[(2-Methoxyethyl)amino]-3-(trifluoromethyl)phenyl}-3,6-dihydro-2H-1,3,4-oxadiazin-2-one,
5-{4-[1-(difluoromethyl)-1H-pyrazol-4-yl]-3-(trifluoromethyl)phenyl}-3,6-dihydro-2H-1,3,4-oxadiazin-2-one,
(6S)-5-[4-(2-aminopyridin-4-yl)-3-(trifluoromethyl)phenyl]-6-methyl-3,6-dihydro-2H-1,3,4-oxadiazin-2-one and
(6S)-6-methyl-5-{3-(trifluoromethyl)-4-[3-(trifluoromethyl)-1H-pyrazol-1-yl]phenyl}-3,6-dihydro-2H-1,3,4-oxadiazin-2-one,
or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is selected from the group
5-[4'-fluoro-2-(trifluoromethyl)biphenyl-4-yl]-3,6-dihydro-2H-1,3,4-oxadiazin-2-one,
5-(4'-fluoro-2-methylbiphenyl-4-yl)-3,6-dihydro-2H-1,3,4-oxadiazin-2-one,
5-[4'-chloro-2-(trifluoromethyl)biphenyl-4-yl]-3,6-dihydro-2H-1,3,4-oxadiazin-2-one,
(6S)-5-{4-[1-(difluoromethyl)-1H-pyrazol-4-yl]-3-(trifluoromethyl)-phenyl}-6-methyl-3,6-dihydro-2H-1,3,4-oxadiazin-2-one,
5-[4-{[3,3,3-Trifluoro-2(S)-hydroxypropyl]amino}-3-(trifluoromethyl)phenyl]-3,6-dihydro-2H-1,3,4-oxadiazin-2-one,
5-{4-[(2-Hydroxy-2-methylpropyl)amino]-3-(trifluoromethyl)phenyl}-3,6-dihydro-2H-1,3,4-oxadiazin-2-one and
5-{4-[(2-Methoxyethyl)amino]-3-(trifluoromethyl)phenyl}-3,6-dihydro-2H-1,3,4-oxadiazin-2-one,
or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is selected from the group
(6S)-5-[4'-fluoro-2-(trifluoromethyl)biphenyl-4-yl]-6-methyl-3,6-dihydro-2H-1,3,4-oxadiazin-2-one,
5-{4-[1-(difluoromethyl)-1H-pyrazol-4-yl]-3-(trifluoromethyl)phenyl}-3,6-dihydro-2H-1,3,4-oxadiazin-2-one,
(6S)-5-[4-(2-aminopyridin-4-yl)-3-(trifluoromethyl)phenyl]-6-methyl-3,6-dihydro-2H-1,3,4-oxadiazin-2-one and
(6S)-6-methyl-5-{3-(trifluoromethyl)-4-[3-(trifluoromethyl)-1H-pyrazol-1-yl]phenyl}-3,6-dihydro-2H-1,3,4-oxadiazin-2-one,
or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is
(6S)-5-[4'-fluoro-2-(trifluoromethyl)biphenyl-4-yl]-6-methyl-3,6-dihydro-2H-1,3,4-oxadiazin-2-one,
or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is
5-{4-[1-(difluoromethyl)-1H-pyrazol-4-yl]-3-(trifluoromethyl)phenyl}-3,6-dihydro-2H-1,3,4-oxadiazin-2-one,
or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is
(6S)-5-[4-(2-aminopyridin-4-yl)-3-(trifluoromethyl)phenyl]-6-methyl-3,6-dihydro-2H-1,3,4-oxadiazin-2-one and
or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is
(6S)-6-methyl-5-{3-(trifluoromethyl)-4-[3-(trifluoromethyl)-1H-pyrazol-1-yl]phenyl}-3,6-dihydro-2H-1,3,4-oxadiazin-2-one,
or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is
5-[4'-fluoro-2-(trifluoromethyl)biphenyl-4-yl]-3,6-dihydro-2H-1,3,4-oxadiazin-2-one, or a stereoisomer, a tautomer, an N-oxide, a hydrate, a solvate, or a salt thereof, or a mixture of same.

In accordance with a further embodiment of the first aspect, the present invention provides compounds of general formula (I):

wherein the compound is
5-(4'-fluoro-2-methylbiphenyl-4-yl)-3,6-dihydro-2H-1,3,4-oxadiazin-2-one, or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is
5-[4'-chloro-2-(trifluoromethyl)biphenyl-4-yl]-3,6-dihydro-2H-1,3,4-oxadiazin-2-one, or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is
(6S)-5-{4-[1-(difluoromethyl)-1H-pyrazol-4-yl]-3-(trifluoromethyl)-phenyl}-6-methyl-3,6-dihydro-2H-1,3,4-oxadiazin-2-one,
or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is
5-[4-{[3,3,3-Trifluoro-2(S)-hydroxypropyl]amino}-3-(trifluoromethyl)phenyl]-3,6-dihydro-2H-1,3,4-oxadiazin-2-one,
or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is
5-{4-[(2-Hydroxy-2-methylpropyl)amino]-3-(trifluoromethyl)phenyl}-3,6-dihydro-2H-1,3,4-oxadiazin-2-one and
or a stereoisomer, a tautomer, an N-oxide, a hydrate, a solvate, or a salt thereof, or a mixture of same.

In accordance with a further embodiment of the first aspect, the present invention provides compounds of general formula (I):
wherein the compound is
5-{4-[(2-Methoxyethyl)amino]-3-(trifluoromethyl)phenyl}-3,6-dihydro-2H-1,3,4-oxadiazin-2-one,
or a stereoisomer, a tautomer, an N-oxide, a hydrate, a solvate, or a salt thereof, or a mixture of same.

In accordance with a further embodiment of the first aspect, the present invention provides the compounds as specifically exemplified in the experimental section or a stereoisomer, a tautomer, an N-oxide, a hydrate, a solvate, or a salt thereof, or a mixture of same.

In accordance with a further embodiment of the first aspect, the present invention provides compounds of general formula (I):
wherein
$R^1$ is selected from a hydrogen atom, a halogen atom, a cyano group, a $C_1$-$C_3$-alkyl group, a $C_1$-$C_3$-haloalkyl group, and a $C_1$-$C_3$-haloalkoxy group;
$R^2$ is selected from a hydrogen atom and a halogen atom;
$R^3$ is selected from,
a $C_1$-$C_6$-alkyl group which is optionally substituted with one or two substituents and each substituent is independently selected from a hydroxy group, a $C_1$-$C_4$-alkoxy group, and a 3- to 7-membered heterocycloalkyl group,
a $C_2$-$C_6$-alkenyl group which is optionally substituted with an $C_1$-$C_4$-alkoxy group,
a $C_3$-$C_9$-cycloalkyl group, which is optionally substituted with a hydroxy group,
a $C_5$-$C_9$-cycloalkenyl group, which is optionally substituted with a hydroxy group
a 3- to 9-membered heterocycloalkyl group, comprising one, two or three heteroatoms which are independently selected from —O—, —S—, —S(O)—, S(O)$_2$, and —NR$^9$—, and said heterocycloalkyl group optionally further comprising a bridging group
selected from —O—, —NR$^9$—, —CH$_2$—, —CH$_2$—CH$_2$—, —O—CH$_2$—, —CH$_2$—O—, —NR$^9$—CH$_2$—, and —CH$_2$—NR$^9$—;
and said heterocycloalkyl group is optionally substituted with one, two or three substituents and each substituent is independently selected from
a halogen atom;
a oxo(=O) group;
a cyano group;
a hydroxy group;
a $C_1$-$C_3$-alkyl group which is optionally substituted with a hydroxy group;
a $C_1$-$C_3$-haloalkyl group;
a $C_1$-$C_3$-alkoxy group;
a $C_1$-$C_3$-haloalkoxy group;
a C(O)NR$^5$R$^6$ group and
a NR$^5$R$^6$ group
a 5- to 9-membered heterocycloalkyl group which is partially unsaturated and optionally substituted with one, two or three substituents and each substituent is independently selected from an oxo group (=O), a $C_1$-$C_3$-alkyl group, a —C(O)R$^5$R$^6$ group and a halogen atom,
an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a NR$^5$R$^6$ group,
a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a NR$^5$R$^6$ group, with the proviso that said monocyclic heteroaryl group is not a pyridin-4-yl group;
and a NR$^7$R$^8$ group;
$R^4$ is a hydrogen atom;
$R^5/R^6$ is independently selected from a hydrogen atom, a $C_1$-$C_6$-alkyl group, a —$C_1$-$C_5$-alkylene-O—$C_1$-$C_5$-alkyl group, a —$C_1$-$C_5$-alkylene-S—$C_1$-$C_5$-alkyl group, $C_3$-$C_6$-cycloalkyl group, and a $C_3$-$C_5$-heterocycloalkyl group;
$R^7/R^8$ are independently selected from
a hydrogen atom, with the proviso that $R^7$=$R^8$=hydrogen is excluded,
a $C_1$-$C_6$-alkyl group,
which is optionally substituted with one, two, three or four substituents and said substituent is independently selected from
a halogen atom, a cyano group, a hydroxy group, a C(O)NR$^5$R$^6$ group, a NR$^5$R$^6$ group,
a $C_1$-$C_3$-alkoxy group,
a $C_3$-$C_7$-cycloalkyl group which is optionally substituted with one or two substitutents and said substituents are independently selected from a $C_1$-$C_3$-alkyl group, a oxo (=O) group, a hydroxy group, and a $C_1$-$C_3$-hydroxyalkyl group;
- a 3- to 7-membered heterocycloalkyl group which itself is optionally substituted
  with a $C_1$-$C_3$-alkyl group, or an oxo (=O) group
- a heteroaryl group, which itself is optionally substituted with a $C_1$-$C_3$-alkyl group;
- a —$C_1$-$C_5$-alkylene-O—$C_1$-$C_5$-alkyl group,
- a —$C_1$-$C_5$-alkylene-S—$C_1$-$C_5$-alkyl group,
- a —$C_1$-$C_5$-alkylene-NR$^5$—$C_1$-$C_5$-alkyl group,
- a $C_3$-$C_6$-cycloalkyl group which is optionally substituted with a hydroxy group, and
- a 3- to 6-membered heterocycloalkyl group, which is optionally substituted with one or two substituents, said substituent independently selected from $C_1$-$C_3$-alkyl group and a hydroxy group, $R^9$ is a hydrogen atom or a $C_1$-$C_3$-alkyl group or a bond;
or a stereoisomer, a tautomer, an N-oxide, a hydrate, a solvate, or a salt thereof, or a mixture of same.

In accordance with a further embodiment of the first aspect, the present invention provides compounds of general formula (I):
wherein
$R^1$ is selected from a hydrogen atom, a halogen atom, a cyano group, a $C_1$-$C_3$-alkyl group, a $C_1$-$C_3$-haloalkyl group, and a $C_1$-$C_3$-haloalkoxy group;
$R^2$ is selected from a hydrogen atom and a halogen atom,
$R^3$ is selected from a halogen atom,
- a $C_2$-$C_6$-alkenyl group,
- a $C_3$-$C_6$-cycloalkyl group
- a $C_5$-$C_6$-cycloalkenyl group which,
- a $C_3$-$C_7$-heterocycloalkyl group, which is optionally substituted with one, two or three substituents and each substituent is independently selected from a halogen atom and a $C_1$-$C_3$-alkyl group, a hydroxy group, NR$^5$R$^6$ group, a $C_1$-$C_3$-haloalkyl group and a $C_1$-$C_3$-haloalkoxy group,
- a $C_5$-$C_7$-heterocycloalkyl group which is partially unsaturated and optionally substituted with one, two or three substituents and each substituent is independently selected from an oxo group (=O), a $C_1$-$C_3$-alkyl group and a halogen atom,
- an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, $C_1$-$C_3$-alkoxy group, a $C_1$-$C_3$-haloalkoxy group, and a NR$^5$R$^6$ group.
- a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a NR$^5$R$^6$ group, with the proviso that said monocyclic heteroaryl group is not a pyridin-4-yl group;
- and a NR$^7$R$^8$ group, $R^4$ is a hydrogen atom,
$R^5$/$R^6$ is independently selected from a hydrogen atom, a $C_1$-$C_6$-alkyl group, a —$C_1$-$C_5$-alkylene-O—$C_1$-$C_5$-alkyl group, a —$C_1$-$C_5$-alkylene-S—$C_1$-$C_5$-alkyl group, $C_3$-$C_6$-cycloalkyl group, and a $C_3$-$C_5$-heterocycloalkyl group,
$R^7$/$R^8$ is independently selected from a hydrogen atom, and a $C_1$-$C_6$-alkyl group, a —$C_1$—C— alkylene-O—$C_1$-$C_5$-alkyl group, a —$C_1$-$C_5$-alkylene-S—$C_1$-$C_5$ alkyl group, a —$C_1$-$C_5$-alkylene-NR$^5$—$C_1$-$C_5$-alkyl group, a $C_3$-$C_6$-cycloalkyl group, a $C_3$-$C_5$-heterocycloalkyl group,
or $R^7$ and $R^8$ together form a 3-, 4-, 5-, 6- or 7-membered ring optionally containing one or two additional heteroatoms selected from the group consisting of —O—, —S— and —NR$^9$—,
and which is optionally substituted one, two or three times with a substituent selected from a halogen atom, a $C_1$-$C_3$-alkyl group, a hydroxy group, a cyano group, an oxo group (=O), and a NR$^5$R$^6$ group,
and if $R^7$ and $R^8$ together form a 5-, 6- or 7-membered ring, said ring can optionally contain a bridging group selected from —O—, —NR$^9$—, —CH$_2$—, —CH$_2$—CH$_2$—, —O—CH$_2$—, —NR$^9$—CH$_2$—;
$R^9$ is a hydrogen atom or a $C_1$-$C_3$-alkyl group,
or a stereoisomer, a tautomer, an N-oxide, a hydrate, a solvate, or a salt thereof, or a mixture of same.

In accordance with another embodiment of the first aspect, the present invention provides compounds of general formula (I):
wherein
$R^1$ is selected from a hydrogen atom, a halogen atom, a cyano group, a $C_1$-$C_3$-alkyl group, a $C_1$-$C_3$-haloalkyl group, and a $C_1$-$C_3$-haloalkoxy group;
$R^2$ is selected from a hydrogen atom and a halogen atom;
$R^3$ is selected from,
- a $C_1$-$C_6$-alkyl group which is optionally substituted with a substituent which is selected from a hydroxy group, a $C_1$-$C_4$-alkoxy group, and a 3- to 7-membered heterocycloalkyl group,
- a $C_2$-$C_6$-alkenyl group which is optionally substituted with an $C_1$-$C_4$-alkoxy group,
- a $C_3$-$C_7$-cycloalkyl group, which is optionally substituted with a hydroxy group,
- a $C_1$-$C_7$-cycloalkenyl group, which is optionally substituted with a hydroxy group
- a 3- to 7-membered-heterocycloalkyl group, comprising one, or two heteroatoms which are independently selected from —O—, S(O)$_2$, and —NR$^9$—,
  and said heterocycloalkyl group is optionally substituted with one, or two substituents and each substituent is independently selected from
  - a halogen atom;
  - a cyano group;
  - a hydroxy group;
  - a $C_1$-$C_3$-alkyl group which is optionally further substituted with a hydroxy group;
  - a $C_1$-$C_3$-alkoxy group;
  - a C(O)NR$^5$R$^6$ group and
  - a NR$^5$R$^6$ group;
- a 5- to 7-membered-heterocycloalkyl group, comprising a heteroatom which is selected from —O—, —S— and —NR$^9$—, which is partially unsaturated and optionally substituted with a substituent which is selected from a $C_1$-$C_3$-alkyl group and a halogen atom,
- an aryl group which is optionally substituted with one, two, or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, and a NR$^5$R$^6$ group,
- a mono- or bicyclic heteroaryl group which is optionally substituted with a substituent which is selected from a halogen atom, a $C_1$-$C_3$-alkyl group, a cyano group, a $C_1$-$C_3$-haloalkyl group, a $C_1$-$C_3$-alkoxy group, and a NR$^5$R$^6$ group, with the proviso that said monocyclic heteroaryl group is not a pyridin-4-yl group;
and a NR$^7$R$^8$ group;
R$^4$ is a hydrogen atom;
R$^5$/R$^6$ is independently selected from a hydrogen atom and a C$_1$-C$_6$-alkyl group;
R$^7$/R$^8$ are independently selected from
a hydrogen atom, with the proviso that R$^7$=R$^8$=hydrogen is excluded,
a C$_1$-C$_6$-alkyl group, which is optionally substituted with one, two, three or four substituents and said substituent is independently selected from
a halogen atom, a cyano group, a hydroxy group, a C(O)NR$^5$R$^6$ group, a NR$^5$R$^6$ group,
a C$_1$-C$_3$-alkoxy group,
a C$_3$-C$_7$-cycloalkyl group which is optionally further substituted with one or two substituents and said substituents are independently selected from a C$_1$-C$_3$-alkyl group, a oxo (=O) group, a hydroxy group, and a C$_1$-C$_3$-hydroxyalkyl group;
a 3- to 7-membered heterocycloalkyl group, comprising one, two or three heteroatoms which are independently selected from —O— and —NR$^9$—, which is optionally further substituted with a C$_1$-C$_3$-alkyl group,
a heteroaryl group, which is optionally further substituted with a C$_1$-C$_3$-alkyl group
a C$_3$-C$_7$-cycloalkyl group which is optionally substituted with a hydroxy group, or a C$_1$-C$_3$-alkyl group and
a 3- to 6-membered heterocycloalkyl group, which is optionally substituted with one or two substituents, said substituent independently selected from C$_1$-C$_3$-alkyl group and a hydroxy group,
R$^9$ is a hydrogen atom or a C$_1$-C$_3$-alkyl group or a bond;
or a stereoisomer, a tautomer, an N-oxide, a hydrate, a solvate, or a salt thereof, or a mixture of same.

In accordance with another embodiment of the first aspect, the present invention provides compounds of general formula (I):
wherein
R$^1$ is selected from a hydrogen atom, a halogen atom, a cyano group, a C$_1$-C$_3$-alkyl group, a C$_1$-C$_3$-haloalkyl group, and a C$_1$-C$_3$-haloalkoxy group;
R$^2$ is selected from a hydrogen atom and a halogen atom;
R$^3$ is selected from,
a C$_1$-C$_6$-alkyl group which is optionally substituted with a substituent which is selected from a hydroxy group, a C$_1$-C$_4$-alkoxy group, and a 3- to 7-membered heterocycloalkyl group,
a C$_2$-C$_6$-alkenyl group which is optionally substituted with an C$_1$-C$_4$-alkoxy group,
a C$_3$-C$_7$-cycloalkyl group, which is optionally substituted with a hydroxy group,
a C$_5$-C$_7$-cycloalkenyl group, which is optionally substituted with a hydroxy group
a 3- to 7-membered-heterocycloalkyl group, comprising one, or two heteroatoms which are independently selected from —O—, S(O)$_2$, and —NR$^9$—,
and said heterocycloalkyl group is optionally substituted with one, or two substituents and each substituent is independently selected from
a halogen atom;
a cyano group;
a hydroxy group;
a C$_1$-C$_3$-alkyl group which is optionally further substituted with a hydroxy group;
a C$_1$-C$_3$-alkoxy group;
a C(O)NR$^5$R$^6$ group and
a NR$^5$R$^6$ group;

a 5- to 7-membered-heterocycloalkyl group, comprising a heteroatom which is selected from —O—, —S— and —NR$^9$—, which is partially unsaturated and optionally substituted with a substituent which is selected from a C$_1$-C$_3$-alkyl group and a halogen atom,
an aryl group which is optionally substituted with one, two, or three substituents and each substituent is independently selected from a halogen atom, a hydroxy group, a cyano group, a C$_1$-C$_3$-alkyl group, a C$_1$-C$_3$-haloalkyl group, a C$_1$-C$_3$-alkoxy group, and a NR$^5$R$^6$ group,
a mono- or bicyclic heteroaryl group which is optionally substituted with a substituent which is selected from a halogen atom, a C$_1$-C$_3$-alkyl group, a cyano group, a C$_1$-C$_3$-haloalkyl group, a C$_1$-C$_3$-alkoxy group, and a NR$^5$R$^6$ group, with the proviso that said monocyclic heteroaryl group is not a pyridin-4-yl group;
and a NR$^7$R$^8$ group;
R$^4$ is a C$_1$-C$_3$-alkyl group;
R$^5$/R$^6$ is independently selected from a hydrogen atom and a C$_1$-C$_6$-alkyl group;
R$^7$/R$^8$ are independently selected from
a hydrogen atom, with the proviso that R$^7$=R$^8$=hydrogen is excluded,
a C$_1$-C$_6$-alkyl group, which is optionally substituted with one, two, three or four substituents and said substituent is independently selected from
a halogen atom, a cyano group, a hydroxy group, a C(O)NR$^5$R$^6$ group, a NR$^5$R$^6$ group,
a C$_1$-C$_3$-alkoxy group,
a C$_3$-C$_7$-cycloalkyl group which is optionally further substituted with one or two substituents and said substituents are independently selected from a C$_1$-C$_3$-alkyl group, a oxo (=O) group, a hydroxy group, and a C$_1$-C$_3$-hydroxyalkyl group;
a 3- to 7-membered heterocycloalkyl group, comprising one, two or three heteroatoms which are independently selected from —O— and —NR$^9$—, which is optionally further substituted with a C$_1$-C$_3$-alkyl group,
a heteroaryl group, which is optionally further substituted with a C$_1$-C$_3$-alkyl group
a C$_3$-C$_7$-cycloalkyl group which is optionally substituted with a hydroxy group, or a C$_1$-C$_3$-alkyl group and
a 3- to 6-membered heterocycloalkyl group, which is optionally substituted with one or two substituents, said substituent independently selected from C$_1$-C$_3$-alkyl group and a hydroxy group,
R$^9$ is a hydrogen atom or a C$_1$-C$_3$-alkyl group or a bond;
or a stereoisomer, a tautomer, an N-oxide, a hydrate, a solvate, or a salt thereof, or a mixture of same.

In accordance with another embodiment of the first aspect, the present invention provides compounds of general formula (I):
wherein
R$^1$ is selected from a hydrogen atom, a halogen atom, a C$_1$-C$_3$-alkyl group, a C$_1$-C$_3$-haloalkyl group, a C$_1$-C$_3$-haloalkoxy group;
R$^2$ is selected from a hydrogen atom, and a halogen atom,
R$^3$ is selected from a halogen atom
a C$_2$-C$_4$-alkenyl group,
a C$_1$-C$_6$-cycloalkenyl group,
a C$_3$-C$_6$-heterocycloalkyl group, which is optionally substituted with one or two substituents and each substituent is independently selected from a halogen atom and a C$_1$-C$_3$-alkyl group;

a C$_1$-C$_6$-heterocycloalkyl group which is partially unsaturated and optionally substituted with one or two substituents and each substituent is independently selected from an oxo group (=O), a C$_1$-C$_3$-alkyl group and a halogen atom;

an aryl group which is optionally substituted with one, two, or three substituents and each substituent is independently selected from a halogen atom, a hydroxy group, a C$_1$-C$_3$-alkyl group, a C$_1$-C$_3$-haloalkyl group, and a NR$^5$R$^6$ group;

a mono- or bicyclic heteroaryl group which is optionally substituted with one, two or three substituents and each substituent is independently selected from a halogen atom, a C$_1$-C$_3$-alkyl group, a cyano group, a C$_1$-C$_3$-haloalkyl group, a C$_1$-C$_3$-alkoxy group, and a NR$^5$R$^6$ group, with the proviso that said monocyclic heteroaryl group is not a pyridin-4-yl group;

and a NR$^7$R$^8$ group;

R$^4$ is a hydrogen atom,

R$^5$/R$^6$ is independently selected from a hydrogen atom, a C$_1$-C$_6$-alkyl group, a —C$_1$-C$_3$-alkylene-O—C$_1$-C$_3$-alkyl group, a —C$_1$-C$_3$-alkylene-S—C$_1$-C$_3$-alkyl group, and a C$_3$-C$_5$-heterocycloalkyl group, R$^7$/R$^8$ are independently selected from a hydrogen atom, with the proviso that R$^7$=R$^8$=hydrogen is excluded, and a C$_1$-C$_6$-alkyl group, a —C$_1$-C$_3$-alkylene-O—C$_1$-C$_3$-alkyl group, a —C$_1$-C$_3$-alkylene-S—C$_1$-C$_3$-alkyl group, a —C$_1$-C$_3$-alkylene-NR$^5$—C$_1$-C$_3$-alkyl group, a C$_3$-C$_6$-cycloalkyl group, a C$_3$-C$_5$-heterocycloalkyl group, or R$^7$ and R$^8$ together form a 3-, 4-, 5-, 6- or 7-membered ring optionally containing one or two additional heteroatoms selected from the group consisting of —O—, —S— and —NR$^9$—, and which is optionally substituted one, two or three times with a substituent selected from a halogen atom, a C$_1$-C$_3$-alkyl group, a hydroxy group, a cyano group, an oxo group (=O), and a NR$^5$R$^6$ group, R$^9$ is a hydrogen atom or a C$_1$-C$_3$-alkyl group, or a stereoisomer, a tautomer, an N-oxide, a hydrate, a solvate, or a salt thereof, or a mixture of same.

In accordance with yet another embodiment of the first aspect, the present invention provides compounds of general formula (I):

wherein

R$^1$ is selected from CF$_3$, —CH$_3$, —OCF$_3$ and a fluorine atom,

R$^2$ is selected from a hydrogen atom

R$^3$ is selected from a halogen atom, a C$_2$-C$_4$-alkenyl group, a C$_5$-C$_6$-cycloalkyenyl group, a C$_3$-C$_6$-heterocycloalkyl group, which is optionally substituted with one or two substituents and each substituent is independently selected from a halogen atom and a C$_1$-C$_3$-alkyl group;

a C$_1$-C$_6$-heterocycloalkyl group which is partially unsaturated and optionally substituted with an oxo group (=O);

an phenyl group which is optionally substituted with one, two or three substituents and each substituent is independently selected from a halogen atom, a hydroxy group, a C$_1$-C$_3$-alkyl group, a C$_1$-C$_3$-haloalkyl group, and a NR$^5$R$^6$ group;

a mono- or bicyclic heteroaryl group which is optionally substituted with one, two or three substituents and each substituent is independently selected from a halogen atom, a C$_1$-C$_3$-alkyl group, a cyano group, a C$_1$-C$_3$-haloalkyl group, a C$_1$-C$_3$-alkoxy group, and a NR$^5$R$^6$ group;

and a NR$^7$R$^8$ group;

R$^4$ is a hydrogen atom,

R$^5$/R$^6$ is independently selected from a hydrogen atom and a C$_1$-C$_3$-alkyl group; and R$^7$/R$^8$ is independently selected from a hydrogen atom and a C$_1$-C$_6$-alkyl group;

or R$^7$ and R$^8$ together form a 4-, 5-, or 6-membered ring optionally containing one additional oxygen atom, and which is optionally substituted one or two times with a substituent selected from a halogen atom and a C$_1$-C$_3$-alkyl group;

or a stereoisomer, a tautomer, an N-oxide, a hydrate, a solvate, or a salt thereof, or a mixture of same.

In accordance with a further embodiment of the first aspect, the present invention provides compounds of general formula (I):

wherein

R$^1$ is selected from CF$_3$, —CH$_3$, —OCF$_3$ and a fluorine atom,

R$^2$ is selected from a hydrogen atom

R$^3$ is selected from a halogen atom, a prop-1-en-1-yl group which is optionally substituted with a methyl group, a piperidin-1-yl group which is optionally substituted with one or two substitutents and each substituent is independently selected from a fluorine atom and a methyl group a morpholin-4-yl group which is optionally substituted with one or two methyl groups, a pyrrolidin-1-yl group which is optionally substituted with one or two halogen atoms, a 1,2,3,6-tetrahydropyridin-4-yl group which is optionally substituted with a methyl group, an azitidin-1-yl group, a 3,6-dihydro-1H-pyran-4-yl group, a 6-oxo-1,6-dihydropyridin-3-yl group which is optionally substituted with one or two substitutents and each substituent is independently selected from a hydrogen atom and a methyl group, a cyclopent-1en-1-yl group, a phenyl group which is optionally substituted with one, two or three substitutents and each substituent is independently selected from a halogen atom, a hydroxy group, a methyl group, an ethyl group, a CF$_3$, CF$_2$H group, a methoxy group, a CF$_3$O group, a NH$_2$ group and a NHCH$_3$ group, a 2H-pyrrol-1-yl group, which is optionally substituted with one or two substitutents and each substituent is independently selected from a hydrogen atom, a cyano group and a methyl group, a 1H-pyrrazol-4-yl group, which is optionally substituted with one or two substitutents and each substituent is independently selected from a methyl group, an ethyl group or a CF$_3$ group, a 1H-pyrrazol-5-yl group, which is optionally substituted with a methyl group, 1,2-oxazol-4-yl which is optionally substituted with one or two methyl groups, a 1,2-thiazol-4-yl group which is optionally substituted with a methyl group, a 1,3-thiazol-5-yl group which is optionally substituted with a methyl group, a pyridin-3-yl, a pyridin-4-yl and a pyridin 5-yl group each group being optionally substituted with one or two substitutents and each substituent is independently selected from a halogen atom, a methyl group, a $CF_3$ group, a methoxy group and a $NH_2$ group, a pyrimidin-5-yl group which is optionally substituted with a methyl group, a 1H-indol-6-yl group, a 1H-indazol-6-yl group which is optionally substituted with a methyl group, a 1H-benzimidazol-6-yl group which is optionally substituted with a methyl group, a $NH(C_2H_5)$ group, a $NH(C_3H_7)$ group, a $NH(C_4H_9)$ group, a $NCH_3(C_4H_9)$ group, a $NH(C_5H_{11})$ group, a NH(cyclopentyl) group, a $NCH_3$(cyclopentyl) group;

$R^4$ is a hydrogen atom, or a stereoisomer, a tautomer, an N-oxide, a hydrate, a solvate, or a salt thereof, or a mixture of same.

In accordance with a further embodiment of the first aspect, the present invention provides compounds of general formula (I):

wherein $R^1$ is selected from $CF_3$, —$CH_3$, —$OCF_3$ and a fluorine atom, $R^2$ is selected from a hydrogen atom $R^3$ is selected from a prop-1-en-1-yl group which is optionally substituted with a methyl group, a piperidin-1-yl group which is optionally substituted with one or two substitutents and each substituent is independently selected from a fluorine atom and a methyl group a morpholin-4-yl group which is optionally substituted with one or two methyl groups, a pyrrolidin-1-yl group which is optionally substituted with one or two halogen atoms, a 1,2,3,6-tetrahydropyridin-4-yl group which is optionally substituted with a methyl group, an azitidin-1-yl group, a 3,6-dihydro-1H-pyran-4-yl group, a 6-oxo-1,6-dihydropyridin-3-yl group which is optionally substituted with one or two substitutents and each substituent is independently selected from a hydrogen atom and a methyl group, a cyclopent-1en-1-yl group, a phenyl group which is optionally substituted with one, two or three substitutents and each substituent is independently selected from a halogen atom, a hydroxy group, a methyl group, an ethyl group, a $CF_3$, $CF_2H$ group, a methoxy group, a $CF_3O$ group, a $NH_2$ group and a $NHCH_3$ group, a 2H-pyrrol-1-yl group, which is optionally substituted with one or two substitutents and each substituent is independently selected from a hydrogen atom, a cyano group and a methyl group, a 1H-pyrrazol-4-yl group, which is optionally substituted with one or two substitutents and each substituent is independently selected from a methyl group, an ethyl group or a $CF_3$ group, a 1H-pyrrazol-5-yl group, which is optionally substituted with a methyl group, 1,2-oxazol-4-yl which is optionally substituted with one or two methyl groups, a 1,2-thiazol-4-yl group which is optionally substituted with a methyl group, a 1,3-thiazol-5-yl group which is optionally substituted with a methyl group, a pyridin-3-yl, a pyridin-4-yl and a pyridin 5-yl group each group being optionally substituted with one or two substitutents and each substituent is independently selected from a halogen atom, a methyl group, a $CF_3$ group, a methoxy group and a $NH_2$ group, a pyrimidin-5-yl group which is optionally substituted with a methyl group, a 1H-indol-6-yl group, a 1H-indazol-6-yl group which is optionally substituted with a methyl group, a 1H-benzimidazol-6-yl group which is optionally substituted with a methyl group, a $NH(C_2H)$ group, a $NH(C_3H_7)$ group, a $NH(C_4H)$ group, a $NCH_3(C_4H_9)$ group, a $NH(C_5H_{11})$ group, a NH(cyclopentyl) group, a $NCH_3$(cyclopentyl) group;

$R^4$ is a hydrogen atom, or a stereoisomer, a tautomer, an N-oxide, a hydrate, a solvate, or a salt thereof, or a mixture of same.

In accordance with yet another embodiment of the first aspect, the present invention provides compounds of general formula (I):

where $R^1$ is selected from a hydrogen atom, a halogen atom, a $C_1$-$C_3$-alkyl group, a $C_1$-$C_3$-haloalkyl group, and a $C_1$-$C_3$-haloalkoxy group;

$R^2$ is selected from a hydrogen atom and a halogen atom;

$R^3$ is selected from, a $C_1$-$C_6$-alkyl group which is optionally substituted with a substituent which is selected from a hydroxy group, a $C_1$-$C_4$-alkoxy group, and a 3- to 7-membered heterocycloalkyl group, a $C_2$-$C_6$-alkenyl group which is optionally substituted with an $C_1$-$C_4$-alkoxy group, a $C_3$-$C_7$-cycloalkyl group, which is optionally substituted with a hydroxy group, a $C_1$-$C_7$-cycloalkenyl group, a 3- to 7-membered heterocycloalkyl group, comprising one, or two heteroatoms which are independently selected from —O—, and —$NR^9$—, and said heterocycloalkyl group is optionally substituted with one, or two substituents and each substituent is independently selected from a halogen atom;

a cyano group;

a hydroxy group;

a $C_1$-$C_3$-alkyl group which is optionally further substituted with a hydroxy group;

a $C_1$-$C_3$-alkoxy group; and a $C(O)NR^5R^6$ group a 5- to 7-membered-heterocycloalkyl group, comprising a heteroatom which is selected from —O—, and —$NR^9$—, which is partially unsaturated and optionally substituted with a substituent which is selected from a $C_1$-$C_3$-alkyl group and a halogen atom, an aryl group which is optionally substituted with one, two, or three substituents and each substituent is independently selected from a halogen atom, a hydroxy group, a cyano group, a $C_1$-$C_3$-alkyl group, a $C_1$-$C_3$-haloalkyl group, and a $NR^5R^6$ group, a mono- or bicyclic heteroaryl group which is optionally substituted with a substituent which is selected from a halogen atom, a $C_1$-$C_3$-alkyl group a $C_1$-$C_3$-haloalkyl group, a $C_1$-$C_3$-alkoxy group, and a $NR^5R^6$ group, with the proviso that said monocyclic heteroaryl group is not a pyridin-4-yl group;

and a $NR^7R^8$ group;

$R^4$ is a hydrogen atom;
$R^5/R^6$ is independently selected from a hydrogen atom and a $C_1$-$C_6$-alkyl group;
$R^7/R^8$ are independently selected from
  a hydrogen atom, with the proviso that $R^7$=$R^8$=hydrogen is excluded,
  a $C_1$-$C_6$-alkyl group, which is optionally substituted with one, two, three or four substituents and said substituent is independently selected from
    a halogen atom, a cyano group, a hydroxy group, a $NR^5R^6$ group,
    a $C_1$-$C_3$-alkoxy group,
    a $C_3$-$C_7$-cycloalkyl group which is optionally further substituted with one or two substituents and said substituents are independently selected from a $C_1$-$C_3$-alkyl group, a oxo (=O) group, a hydroxy group, and a $C_1$-$C_3$-hydroxyalkyl group;
    a 3- to 7-membered heterocycloalkyl group, comprising one, two or three heteroatoms which are independently selected from —O— and —$NR^9$—, which is optionally further substituted with a $C_1$-$C_3$-alkyl group,
    a heteroaryl group, which is optionally further substituted with a $C_1$-$C_3$-alkyl group
  a $C_3$-$C_7$-cycloalkyl group, which is optionally substituted with a hydroxy group, or a $C_1$-$C_3$-alkyl group and
  a 3- to 6-membered heterocycloalkyl group, which is optionally substituted with one or two substituents, said substituent independently selected from $C_1$-$C_3$-alkyl group and a hydroxy group,
$R^9$ is a hydrogen atom or a $C_1$-$C_3$-alkyl group or a bond;
wherein or a stereoisomer, a tautomer, an N-oxide, a hydrate, a solvate, or a salt thereof, or a mixture of same.

In accordance with yet another embodiment of the first aspect, the present invention provides compounds of general formula (I):
where
$R^1$ is selected from a hydrogen atom, a halogen atom, a $C_1$-$C_3$-alkyl group, a $C_1$-$C_3$-haloalkyl group, and a $C_1$-$C_3$-haloalkoxy group;
$R^2$ is selected from a hydrogen atom and a halogen atom;
$R^3$ is selected from,
  a $C_1$-$C_6$-alkyl group which is optionally substituted with a substituent which is selected from a hydroxy group, a $C_1$-$C_4$-alkoxy group, and a 3- to 7-membered heterocycloalkyl group,
  a $C_2$-$C_6$-alkenyl group which is optionally substituted with an $C_1$-$C_4$-alkoxy group,
  a $C_3$-$C_7$-cycloalkyl group, which is optionally substituted with a hydroxy group,
  a $C_5$-$C_7$-cycloalkenyl group,
  a 3- to 7-membered heterocycloalkyl group, comprising one, or two heteroatoms which are independently selected from —O—, and —$NR^9$—,
    and said heterocycloalkyl group is optionally substituted with one, or two substituents and each substituent is independently selected from
      a halogen atom;
      a cyano group;
      a hydroxy group;
      a $C_1$-$C_3$-alkyl group which is optionally further substituted with a hydroxy group;
      a $C_1$-$C_3$-alkoxy group; and
      a $C(O)NR^5R^6$ group
  a 5- to 7-membered-heterocycloalkyl group, comprising a heteroatom which is selected from —O—, and —$NR^9$—, which is partially unsaturated and optionally substituted with a substituent which is selected from a $C_1$-$C_3$-alkyl group and a halogen atom,
  an aryl group which is optionally substituted with one, two, or three substituents and each substituent is independently selected from a halogen atom, a hydroxy group, a cyano group, a $C_1$-$C_3$-alkyl group, a $C_1$-$C_3$-haloalkyl group, and a $NR^5R^6$ group,
  a mono- or bicyclic heteroaryl group which is optionally substituted with a substituent which is selected from a halogen atom, a $C_1$-$C_3$-alkyl group a $C_1$-$C_3$-haloalkyl group, a $C_1$-$C_3$-alkoxy group, and a $NR^5R^6$ group, with the proviso that said monocyclic heteroaryl group is not a pyridin-4-yl group;
  and a $NR^7R^8$ group;
$R^4$ is a $C_1$-$C_3$-alkyl group;
$R^5/R^6$ is independently selected from a hydrogen atom and a $C_1$-$C_6$-alkyl group;
$R^7/R^8$ are independently selected from
  a hydrogen atom, with the proviso that $R^7$=$R^8$=hydrogen is excluded,
  a $C_1$-$C_6$-alkyl group, which is optionally substituted with one, two, three or four substituents and said substituent is independently selected from
    a halogen atom, a cyano group, a hydroxy group, a $NR^5R^6$ group,
    a $C_1$-$C_3$-alkoxy group,
    a $C_3$-$C_7$-cycloalkyl group which is optionally further substituted with one or two substituents and said substituents are independently selected from a $C_1$-$C_3$-alkyl group, a oxo (=O) group, a hydroxy group, and a $C_1$-$C_3$-hydroxyalkyl group;
    a 3- to 7-membered heterocycloalkyl group, comprising one, two or three heteroatoms which are independently selected from —O— and —$NR^9$—, which is optionally further substituted with a $C_1$-$C_3$-alkyl group,
    a heteroaryl group, which is optionally further substituted with a $C_1$-$C_3$-alkyl group
  a $C_3$-$C_7$-cycloalkyl group, which is optionally substituted with a hydroxy group, or a $C_1$-$C_3$-alkyl group and
  a 3- to 6-membered heterocycloalkyl group, which is optionally substituted with one or two substituents, said substituent independently selected from $C_1$-$C_3$-alkyl group and a hydroxy group,
$R^9$ is a hydrogen atom or a $C_1$-$C_3$-alkyl group or a bond;
wherein or a stereoisomer, a tautomer, an N-oxide, a hydrate, a solvate, or a salt thereof, or a mixture of same.

In accordance with a further embodiment of the first aspect, the present invention provides compounds of general formula (I):
wherein
$R^1$ is selected from a halogen atom, a $C_1$-$C_3$-alkyl group and a $C_1$-$C_3$-haloalkyl group;
$R^2$ is selected from a hydrogen atom and a halogen atom,
$R^3$ is selected from a halogen atom,
  a $C_2$-$C_4$-alkenyl group,
  a $C_5$-$C_6$-cycloalkyenyl group,
  a $C_3$-$C_6$-heterocycloalkyl group, which is optionally substituted with one or two substituents and each substituent is independently selected from a halogen atom and a $C_1$-$C_3$-alkyl group;
  a $C_5$-$C_6$-heterocycloalkyl group which is partially unsaturated and optionally substituted with an oxo group (=O);
  an phenyl group which is optionally substituted with one, two or three substituents and each substituent is independently selected from a halogen atom, a hydroxy group, a $C_1$-$C_3$-alkyl group, a $C_1$-$C_3$-haloalkyl group, and a $NR^5R^6$ group;
a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, and a $NR^5R^6$ group;
and a $NR^7R^8$ group;
$R^4$ is a hydrogen atom,
$R^5/R^6$ is independently selected from a hydrogen atom and a $C_1$-$C_3$-alkyl group; and
$R^7/R^8$ is independently selected from a hydrogen atom, a $C_3$-$C_5$-cycloalkyl group, and a $C_1$-$C_6$-alkyl group;
or $R^7$ and $R^8$ together form a 4-, 5-, or 6-membered ring optionally containing one additional oxygen atom, and which is optionally substituted one or two times with a substituent selected from a halogen atom and a $C_1$-$C_3$-alkyl group;
or a stereoisomer, a tautomer, an N-oxide, a hydrate, a solvate, or a salt thereof, or a mixture of same.

In accordance with yet a further embodiment of the first aspect, the present invention provides compounds of general formula (I):
wherein
$R^1$ is selected from a hydrogen atom, a halogen atom, a $C_1$-$C_3$-alkyl group, a $C_1$-$C_3$-haloalkyl group, and a $C_1$-$C_3$-haloalkoxy group;
$R^2$ is selected from a hydrogen atom and a halogen atom;
$R^3$ is selected from,
a $C_1$-$C_6$-alkyl group which is optionally substituted with a substituent which is selected from a hydroxy group, a $C_1$-$C_4$-alkoxy group, and a 3- to 7-membered heterocycloalkyl group,
a $C_2$-$C_6$-alkenyl group which is optionally substituted with an $C_1$-$C_4$-alkoxy group,
a $C_4$-$C_6$-cycloalkyl group, which is optionally substituted with a hydroxy group,
a $C_5$-$C_7$-cycloalkenyl group,
a 3- to 6-membered heterocycloalkyl group, comprising one, or two heteroatoms which are independently selected from —O—, and —NR$^9$—,
and said heterocycloalkyl group is optionally substituted with one, or two substituents and each substituent is independently selected from
a halogen atom;
a cyano group;
a hydroxy group
a $C_1$-$C_3$-alkyl group which is optionally further substituted with a hydroxy group;
a 5- to 6-membered-heterocycloalkyl group, comprising a heteroatom which is selected from —O—, and —NR$^9$—, which is partially unsaturated and optionally substituted with a substituent which is selected from a $C_1$-$C_3$-alkyl group and a halogen atom,
an aryl group which is optionally substituted with one, or two, substituents and each substituent is independently selected from a halogen atom, a hydroxy group, a cyano group, a $C_1$-$C_3$-alkyl group, a $C_1$-$C_3$-haloalkyl group, and a $NR^5R^6$ group,
a mono- or bicyclic heteroaryl group which is optionally substituted with a substituent which is selected from a halogen atom, a $C_1$-$C_3$-alkyl group a $C_1$-$C_3$-haloalkyl group, a $C_1$-$C_3$-alkoxy group, and a $NR^5R^6$ group, with the proviso that said monocyclic heteroaryl group is not a pyridin-4-yl group;
and a $NR^7R^8$ group;

$R^4$ is a hydrogen atom;
$R^5/R^6$ is independently selected from a hydrogen atom and a $C_1$-$C_6$-alkyl group;
$R^7/R^8$ are independently selected from
a hydrogen atom, with the proviso that $R^7=R^8$=hydrogen is excluded,
a $C_1$-$C_6$-alkyl group, which is optionally substituted with one, two, three or four substituents and said substituent is independently selected from
a halogen atom, a hydroxy group,
a $C_1$-$C_3$-alkoxy group,
a $C_3$-$C_6$-cycloalkyl group which is optionally further substituted with one or two substituents and said substituents are independently selected from a $C_1$-$C_3$-alkyl group and a $C_1$-$C_3$-hydroxyalkyl group;
a 4- to 6-membered heterocycloalkyl group, comprising one, two or three heteroatoms which are independently selected from —O— and —NR$^9$—, which is optionally further substituted with a $C_1$-$C_3$-alkyl group,
a heteroaryl group, which is optionally further substituted with a $C_1$-$C_3$-alkyl group;
a $C_3$-$C_6$-cycloalkyl group, which is optionally substituted with a hydroxy group, or a $C_1$-$C_3$-alkyl group
a 3- to 6-membered heterocycloalkyl group, which is optionally substituted with one or two substituents, said substituent independently selected from $C_1$-$C_3$-alkyl group and a hydroxy group, and
$R^9$ is a hydrogen atom or a $C_1$-$C_3$-alkyl group or a bond;
or a stereoisomer, a tautomer, an N-oxide, a hydrate, a solvate, or a salt thereof, or a mixture of same.

In accordance with yet a further embodiment of the first aspect, the present invention provides compounds of general formula (I):
wherein
$R^1$ is selected from a hydrogen atom, a halogen atom, a $C_1$-$C_3$-alkyl group, a $C_1$-$C_3$-haloalkyl group, and a $C_1$-$C_3$-haloalkoxy group;
$R^2$ is selected from a hydrogen atom and a halogen atom;
$R^3$ is selected from,
a $C_1$-$C_6$-alkyl group which is optionally substituted with a substituent which is selected from a hydroxy group, a $C_1$-$C_4$-alkoxy group, and a 3- to 7-membered heterocycloalkyl group,
a $C_2$-$C_6$-alkenyl group which is optionally substituted with an $C_1$-$C_4$-alkoxy group,
a $C_4$-$C_6$-cycloalkyl group, which is optionally substituted with a hydroxy group,
a $C_5$-$C_7$-cycloalkenyl group,
a 3- to 6-membered heterocycloalkyl group, comprising one, or two heteroatoms which are independently selected from —O—, and —NR$^9$—,
and said heterocycloalkyl group is optionally substituted with one, or two substituents and each substituent is independently selected from
a halogen atom;
a cyano group;
a hydroxy group
a $C_1$-$C_3$-alkyl group which is optionally further substituted with a hydroxy group;
a 5- to 6-membered-heterocycloalkyl group, comprising a heteroatom which is selected from —O—, and —NR$^9$—, which is partially unsaturated and optionally substituted with a substituent which is selected from a $C_1$-$C_3$-alkyl group and a halogen atom, an aryl group which is optionally substituted with one, or two, substituents and each substituent is independently selected from a halogen atom, a hydroxy group, a cyano group, a $C_1$-$C_3$-alkyl group, a $C_1$-$C_3$-haloalkyl group, and a $NR^5R^6$ group, a mono- or bicyclic heteroaryl group which is optionally substituted with a substituent which is selected from a halogen atom, a $C_1$-$C_3$-alkyl group a $C_1$-$C_3$-haloalkyl group, a $C_1$-$C_3$-alkoxy group, and a $NR^5R^6$ group, with the proviso that said monocyclic heteroaryl group is not a pyridin-4-yl group;

and a $NR^7R^8$ group;

$R^4$ is a $C_1$-$C_3$-alkyl group;

$R^5/R^6$ is independently selected from a hydrogen atom and a $C_1$-$C_6$-alkyl group;

$R^7/R^8$ are independently selected from a hydrogen atom, with the proviso that $R^7$=$R^8$=hydrogen is excluded, a $C_1$-$C_6$-alkyl group, which is optionally substituted with one, two, three or four substituents and said substituent is independently selected from a halogen atom, a hydroxy group, a $C_1$-$C_3$-alkoxy group, a $C_3$-$C_6$-cycloalkyl group which is optionally further substituted with one or two substituents and said substituents are independently selected from a $C_1$-$C_3$-alkyl group and a $C_1$-$C_3$-hydroxyalkyl group;

a 4- to 6-membered heterocycloalkyl group, comprising one, two or three heteroatoms which are independently selected from —O— and —$NR^9$—, which is optionally further substituted with a $C_1$-$C_3$-alkyl group, a heteroaryl group, which is optionally further substituted with a $C_1$-$C_3$-alkyl group;

a $C_3$-$C_6$-cycloalkyl group which is optionally substituted with a hydroxy group, or a $C_1$-$C_3$-alkyl group a 3- to 6-membered heterocycloalkyl group, which is optionally substituted with one or two substituents, said substituent independently selected from $C_1$-$C_3$-alkyl group and a hydroxy group, and $R^9$ is a hydrogen atom or a $C_1$-$C_3$-alkyl group or a bond;

or a stereoisomer, a tautomer, an N-oxide, a hydrate, a solvate, or a salt thereof, or a mixture of same.

In accordance with yet a further embodiment of the first aspect, the present invention provides compounds of general formula (I):

wherein $R^1$ is selected from $CF_3$, and a fluorine atom, $R^2$ is selected from a hydrogen atom $R^3$ is selected from a halogen atom, a prop-1-en-1-yl group which is optionally substituted with a methyl group, a piperidin-1-yl group which is optionally substituted with one or two substitutents and each substituent is independently selected from a fluorine atom and a methyl group a morpholin-4-yl group which is optionally substituted with one or two methyl groups, a pyrrolidin-1-yl group which is optionally substituted with one or two halogen atoms, a 1,2,3,6-tetrahydropyridin-4-yl group which is optionally substituted with a methyl group, an azitidin-1-yl group, a 3,6-dihydro-1H-pyran-4-yl group, a 6-oxo-1,6-dihydropyridin-3-yl group which is optionally substituted with one or two each substituent is independently selected from a hydrogen atom and a methyl group, a cyclopent-1en-1-yl group, a phenyl group which is optionally substituted with one, two or three substitutents and each substituent is independently selected from a halogen atom, a hydroxy group, a methyl group, an ethyl group, a $CF_3$, $CF_2H$ group, a methoxy group, a $CF_3O$ group, a $NH_2$ group and a $NHCH_3$ group, a 2H-pyrrol-1-yl group, which is optionally substituted with one or two substitutents and each substituent is independently selected from a hydrogen atom, a cyano group and a methyl group, a 1H-pyrrazol-4-yl group, which is optionally substituted with one or two substitutents and each substituent is independently selected from a methyl group, an ethyl group or a $CF_3$ group, a 1H-pyrrazol-5-yl group, which is optionally substituted with a methyl group, 1,2-oxazol-4-yl which is optionally substituted with one or two methyl groups, a 1,2-thiazol-4-yl group which is optionally substituted with a methyl group, a 1,3-thiazol-5-yl group which is optionally substituted with a methyl group, a pyridin-3-yl, a pyridin-4-yl and a pyridin 5-yl group each group being optionally substituted with one or two substitutents and each substituent is independently selected from a halogen atom, a methyl group, a $CF_3$ group, a methoxy group and a $NH_2$ group, a pyrimidin-5-yl group which is optionally substituted with a methyl group, a 1H-indol-6-yl group, a 1H-indazol-6-yl group which is optionally substituted with a methyl group, a 1H-benzimidazol-6-yl group which is optionally substituted with a methyl group, a $NH(C_2H_5)$ group, a $NH(C_3H_7)$ group, a $NH(C_4H_9)$ group, a $NCH_3(C_4H_9)$ group, a $NH(C_5H_{11})$ group, a NH(cyclopentyl) group, a $NCH_3$(cyclopentyl) group;

$R^4$ is a hydrogen atom, or a stereoisomer, a tautomer, an N-oxide, a hydrate, a solvate, or a salt thereof, or a mixture of same.

In accordance with yet a further embodiment of the first aspect, the present invention provides compounds of general formula (I):

where $R^1$ is selected from a hydrogen atom, a halogen atom, a $C_1$-$C_3$-alkyl group, and a $C_1$-$C_3$-haloalkyl group;

$R^2$ is selected from a hydrogen atom and a halogen atom;

$R^3$ is selected from, a $C_1$-$C_6$-alkyl group which is optionally substituted with one or two substituents and each substituent is independently selected from a hydroxy group, a $C_1$-$C_4$-alkoxy group, and a 3- to 7-membered heterocycloalkyl group, a $C_2$-$C_6$-alkenyl group which is optionally substituted with an $C_1$-$C_3$-alkoxy group, a $C_3$-$C_7$-cycloalkyl group, which is optionally substituted with a hydroxy group, a $C_1$-$C_6$-cycloalkenyl group, which is optionally substituted with a hydroxy group a 3- to 6-membered heterocycloalkyl group, comprising one, two or three heteroatoms which are independently selected from —O— and —$NR^9$—, and said heterocycloalkyl group is optionally substituted with one, two or three substituents and each substituent is independently selected from
a halogen atom;
a oxo(=O) group;
a cyano group;
a hydroxy group;
a $C_1$-$C_3$-alkyl group which is optionally substituted with a hydroxy group;
a 5- to 7-membered heterocycloalkyl group which is partially unsaturated and optionally substituted with one or two substituents and each substituent is independently selected from a $C_1$-$C_3$-alkyl group and a halogen atom,
an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a $NR^5R^6$ group,
a mono- or bicyclic heteroaryl group which is optionally substituted with one or two substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^5R^6$ group, with the proviso that said monocyclic heteroaryl group is not a pyridin-4-yl group;
and a $NR^7R^8$ group;
$R^4$ is a hydrogen atom;
$R^5/R^6$ is independently selected from a hydrogen atom and a $C_1$-$C_6$-alkyl group;
$R^7/R^8$ are independently selected from
a hydrogen atom, with the proviso that $R^7$=$R^8$=hydrogen is excluded,
a $C_1$-$C_6$-alkyl group,
which is optionally substituted with one, two, three or four substituents and said substituent is independently selected from
a halogen atom, a cyano group, and a hydroxy group,
a $C_1$-$C_3$-alkoxy group,
a $C_3$-$C_7$-cycloalkyl group which is optionally substituted with one or two substitutents and said substituents are independently selected from a $C_1$-$C_3$-alkyl group, a hydroxy group, and a $C_1$-$C_3$-hydroxyalkyl group;
a 3- to 7-membered heterocycloalkyl group which itself is optionally substituted with a $C_1$-$C_3$-alkyl group
a heteroaryl group, which is optionally further substituted with a $C_1$-$C_3$-alkyl group;
a $C_3$-$C_6$-cycloalkyl group, which is optionally substituted with a hydroxy group, and
a 3- to 6-membered heterocycloalkyl group, which is optionally substituted with one or two substituents said substituent independently selected from $C_1$-$C_3$-alkyl group and a hydroxy group,
$R^9$ is a hydrogen atom or a $C_1$-$C_3$-alkyl group or a bond;
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is selected from a hydrogen atom, a halogen atom, a $C_1$-$C_3$-alkyl group, and a $C_1$-$C_3$-haloalkyl group;
$R^2$ is selected from a hydrogen atom and a halogen atom;
$R^3$ is selected from,
a $C_1$-$C_6$-alkyl group which is optionally substituted with one or two substituents and each substituent is independently selected from a hydroxy group, a $C_1$-$C_4$-alkoxy group, and a 3- to 7-membered heterocycloalkyl group,
a $C_2$-$C_6$-alkenyl group which is optionally substituted with an $C_1$-$C_3$-alkoxy group,
a $C_3$-$C_7$-cycloalkyl group, which is optionally substituted with a hydroxy group,
a $C_5$-$C_6$-cycloalkenyl group, which is optionally substituted with a hydroxy group
a 3- to 6-membered heterocycloalkyl group, comprising one, two or three heteroatoms which are independently selected from —O— and —$NR^9$—,
and said heterocycloalkyl group is optionally substituted with one, two or three substituents and each substituent is independently selected from
a halogen atom;
a oxo(=O) group;
a cyano group;
a hydroxy group;
a $C_1$-$C_3$-alkyl group which is optionally substituted with a hydroxy group;
a 5- to 7-membered heterocycloalkyl group which is partially unsaturated and optionally substituted with one or two substituents and each substituent is independently selected from a $C_1$-$C_3$-alkyl group and a halogen atom,
an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a $NR^5R^6$ group,
a mono- or bicyclic heteroaryl group which is optionally substituted with one or two substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^5R^6$ group, with the proviso that said monocyclic heteroaryl group is not a pyridin-4-yl group;
and a $NR^7R^8$ group;
$R^4$ is a $C_1$-$C_3$-alkyl group;
$R^5/R^6$ is independently selected from a hydrogen atom and a $C_1$-$C_6$-alkyl group;
$R^7/R^8$ are independently selected from
a hydrogen atom, with the proviso that $R^7$=$R^8$=hydrogen is excluded,
a $C_1$-$C_6$-alkyl group,
which is optionally substituted with one, two, three or four substituents and said substituent is independently selected from a halogen atom, a cyano group, and a hydroxy group,
a $C_1$-$C_3$-alkoxy group,
a $C_3$-$C_7$-cycloalkyl group which is optionally substituted with one or two substitutents and said substituents are independently selected from a $C_1$-$C_3$-alkyl group, a hydroxy group, and a $C_1$-$C_3$-hydroxyalkyl group;
a 3- to 7-membered heterocycloalkyl group which itself is optionally substituted with a $C_1$-$C_3$-alkyl group
a heteroaryl group, which is optionally further substituted with a $C_1$-$C_3$-alkyl group;
a $C_3$-$C_6$-cycloalkyl group, which is optionally substituted with a hydroxy group, and a 3- to 6-membered heterocycloalkyl group, which is optionally substituted with one or two substituents said substituent independently selected from $C_1$-$C_3$-alkyl group and a hydroxy group, $R^9$ is a hydrogen atom or a $C_1$-$C_3$-alkyl group or a bond;

or a stereoisomer, a tautomer, an N-oxide, a hydrate, a solvate, or a salt thereof, or a mixture of same.

In accordance with yet a further embodiment of the first aspect, the present invention provides compounds of general formula (I):

where $R^1$ is selected from a hydrogen atom, a halogen atom, a $C_1$-$C_3$-alkyl group, and a $C_1$-$C_3$-haloalkyl group;

$R^2$ is selected from a hydrogen atom and a halogen atom;

$R^3$ is selected from, a 3- to 6-membered heterocycloalkyl group, comprising one, or two heteroatoms which are independently selected from —O—, and —$NR^9$—, and said heterocycloalkyl group is optionally substituted with one, or two substituents and each substituent is independently selected from a halogen atom;

a hydroxy group a $C_1$-$C_3$-alkyl group which is optionally further substituted with a hydroxy group; an aryl group which is optionally substituted with one, or two, substituents and each substituent is independently selected from a halogen atom, a hydroxy group, and a $C_1$-$C_3$-haloalkyl group, a mono- or bicyclic heteroaryl group which is optionally substituted with a substituent which is selected from a halogen atom, a $C_1$-$C_3$-alkyl group a $C_1$-$C_3$-haloalkyl group and a $NR^5R^6$ group, with the proviso that said monocyclic heteroaryl group is not a pyridin-4-yl group;

and a $NR^7R^8$ group;

$R^4$ is a hydrogen atom;

$R^5/R^6$ is independently selected from a hydrogen atom and a $C_1$-$C_3$-alkyl group;

$R^7/R^8$ are independently selected from a hydrogen atom, with the proviso that $R^7$=$R^8$=hydrogen is excluded, a $C_1$-$C_6$-alkyl group, which is optionally substituted with one or two, three or four substituents and said substituent is independently selected from a halogen atom, a hydroxy group, a $C_1$-$C_3$-alkoxy group, a $C_3$-$C_5$-cycloalkyl group which is optionally further substituted with one or two substituents and said substituents are independently selected from a $C_1$-$C_3$-alkyl group and a $C_1$-$C_3$-hydroxyalkyl group;

a 5- to 6-membered heterocycloalkyl group, comprising one, or two heteroatoms which are independently selected from —O— and —$NR^9$—, which is optionally further substituted with a $C_1$-$C_3$-alkyl group, a heteroaryl group, which is optionally further substituted with a $C_1$-$C_3$-alkyl group;

a $C_3$-$C_6$-cycloalkyl group which is optionally substituted with a hydroxy group, or a $C_1$-$C_3$-alkyl group a 4- to 5-membered heterocycloalkyl group, which is optionally substituted with one or two substituents, said substituent independently selected from $C_1$-$C_3$-alkyl group and a hydroxy group, and $R^9$ is a hydrogen atom or a $C_1$-$C_3$-alkyl group or a bond;

or a stereoisomer, a tautomer, an N-oxide, a hydrate, a solvate, or a salt thereof, or a mixture of same.

In accordance with yet a further embodiment of the first aspect, the present invention provides compounds of general formula (I):

where $R^1$ is selected from a hydrogen atom, a halogen atom, a $C_1$-$C_3$-alkyl group, and a $C_1$-$C_3$-haloalkyl group;

$R^2$ is selected from a hydrogen atom and a halogen atom;

$R^3$ is selected from, a 3- to 6-membered heterocycloalkyl group, comprising one, or two heteroatoms which are independently selected from —O—, and —$NR^9$—, and said heterocycloalkyl group is optionally substituted with one, or two substituents and each substituent is independently selected from a halogen atom;

a hydroxy group a $C_1$-$C_3$-alkyl group which is optionally further substituted with a hydroxy group;

an aryl group which is optionally substituted with one, or two, substituents and each substituent is independently selected from a halogen atom, a hydroxy group, and a $C_1$-$C_3$-haloalkyl group, a mono- or bicyclic heteroaryl group which is optionally substituted with a substituent which is selected from a halogen atom, a $C_1$-$C_3$-alkyl group a $C_1$-$C_3$-haloalkyl group and a $NR^5R^6$ group, with the proviso that said monocyclic heteroaryl group is not a pyridin-4-yl group;

and a $NR^7R^8$ group;

$R^4$ is a $C_1$-$C_3$-alkyl group;

$R^5/R^6$ is independently selected from a hydrogen atom and a $C_1$-$C_3$-alkyl group;

$R^7/R^8$ are independently selected from a hydrogen atom, with the proviso that $R^7$=$R^8$=hydrogen is excluded, a $C_1$-$C_6$-alkyl group, which is optionally substituted with one or two, three or four substituents and said substituent is independently selected from a halogen atom, a hydroxy group, a $C_1$-$C_3$-alkoxy group, a $C_3$-$C_5$-cycloalkyl group which is optionally further substituted with one or two substituents and said substituents are independently selected from a $C_1$-$C_3$-alkyl group and a $C_1$-$C_3$-hydroxyalkyl group;

a 5- to 6-membered heterocycloalkyl group, comprising one, or two heteroatoms which are independently selected from —O— and —$NR^9$—, which is optionally further substituted with a $C_1$-$C_3$-alkyl group, a heteroaryl group, which is optionally further substituted with a $C_1$-$C_3$-alkyl group;

a $C_3$-$C_6$-cycloalkyl group, which is optionally substituted with a hydroxy group, or a $C_1$-$C_3$-alkyl group a 4- to 5-membered heterocycloalkyl group, which is optionally substituted with one or two substituents, said substituent independently selected from $C_1$-$C_3$-alkyl group and a hydroxy group, and $R^9$ is a hydrogen atom or a $C_1$-$C_3$-alkyl group or a bond;

or a stereoisomer, a tautomer, an N-oxide, a hydrate, a solvate, or a salt thereof, or a mixture of same.

In accordance with yet a further embodiment of the first aspect, the present invention provides compounds of general formula (I):

where $R^1$ is selected from $CF_3$ and a fluorine atom;

$R^2$ is a hydrogen atom;

$R^3$ is selected from an aryl group which is optionally substituted with a substituent which is selected from a halogen atom and a $C_1$-$C_3$-haloalkyl group, a monocyclic heteroaryl group substituted with a substituent which is selected from $C_1$-$C_3$-haloalkyl group and $NR^5R^6$ group;
and a $NR^7R^8$ group;
$R^4$ is a hydrogen atom;
$R^5/R^6$ is a hydrogen atom or a methyl group;
$R^7/R^8$ are independently selected from
a hydrogen atom, with the proviso that $R^7=R^8$=hydrogen is excluded,
a $C_1$-$C_3$-alkyl group, which is optionally substituted with one, two or four substituents and said substituent is independently selected from
a halogen atom, a hydroxy group, and a methoxy group,
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is selected from $CF_3$ and a fluorine atom;
$R^2$ is a hydrogen atom;
$R^3$ is selected from
an aryl group which is optionally substituted with a substituent which is selected from a halogen atom and a $C_1$-$C_3$-haloalkyl group,
a monocyclic heteroaryl group substituted with a substituent which is selected from $C_1$-$C_3$-haloalkyl group and $NR^5R^6$ group;
and a $NR^7R^8$ group;
$R^4$ is a $C_1$-$C_3$-alkyl group;
$R^5/R^6$ is a hydrogen atom or a methyl group;
$R^7/R^8$ are independently selected from
a hydrogen atom, with the proviso that $R^7=R^8$=hydrogen is excluded,
a $C_1$-$C_3$-alkyl group, which is optionally substituted with one two or four substituents and said substituent is independently selected from
a halogen atom, a hydroxy group, and a methoxy group,
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is selected from $CF_3$ and a fluorine atom;
$R^2$ is a hydrogen atom;
$R^3$ is selected from
an aryl group which is optionally substituted with a substituent which is selected from a halogen atom and a $C_1$-$C_3$-haloalkyl group,
a monocyclic heteroaryl group substituted with a substituent which is selected from $C_1$-$C_3$-haloalkyl group and $NR^5R^6$ group;
and a $NR^7R^8$ group;
$R^4$ is a methyl group;
$R^5/R^6$ is a hydrogen atom or a methyl group;
$R^7/R^8$ are independently selected from
a hydrogen atom, with the proviso that $R^7=R^8$=hydrogen is excluded,
a $C_1$-$C_3$-alkyl group, which is optionally substituted with one two or four substituents and said substituent is independently selected from
a halogen atom, a hydroxy group, and a methoxy group,
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is selected from $CF_3$ and a fluorine atom;
$R^2$ is a hydrogen atom;
$R^3$ is selected from
an aryl group which is optionally substituted with a substituent which is selected from a halogen atom and a $C_1$-$C_3$-haloalkyl group,
a monocyclic heteroaryl group substituted with a substituent which is selected from $C_1$-$C_3$-haloalkyl group and $NR^5R^6$ group;
and a $NR^7R^8$ group;
$R^4$ is a methyl group having S-configuration;
$R^5/R^6$ is a hydrogen atom or a methyl group;
$R^7/R^8$ are independently selected from
a hydrogen atom, with the proviso that $R^7=R^8$=hydrogen is excluded,
a $C_1$-$C_3$-alkyl group, which is optionally substituted with one two or four substituents and said substituent is independently selected from
a halogen atom, a hydroxy group, and a methoxy group,
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is a $CF_3$ group a fluorine atom a $OCF_3$ group or a $CH_3$ group,
$R^2$ is a hydrogen atom,
$R^3$ is selected from
a $C_1$-$C_4$-alkyl group,
a phenyl group which is optionally substituted with one or two substitutents said substituents selected from a halogen atom,
a 4-6-membered heterocycloalkyl group, which is optionally substituted with one or two substituents said substituents selected from a halogen atom, a methyl group or a hydroxy group,
a 5-membered heterocycloalkyl group which is partially unsaturated,
a heteroaryl group which is optionally substituted with a $C_1$-$C_3$-haloalkyl group, a $NH_2$ group, a methyl group, a chlorine atom, a $C_1$-$C_3$-haloalkyl group, and a $NR^7R^8$ group,
$R^7/R^8$ are independently selected from
a hydrogen atom, with the proviso that $R^7=R^8$=hydrogen is excluded,
a $C_4$-$C_5$-cycloalkyl group or a $C_1$-$C_4$-alkyl group
which is optionally substituted one or more times with substituents and said substituents are independently selected from
a halogen atom, a hydroxy group, a heterocycloalkyl group or a heteroaryl group and
$R^4$ is a hydrogen atom or a methyl group
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is a $CF_3$ group a fluorine atom a $OCF_3$ group or a $CH_3$ group,
$R^2$ is a hydrogen atom, R³ is selected from
a C₁-C₄-alkyl group,
a phenyl group which is optionally substituted with one or two substitutents said substitutents selected from a fluorine atom or a chlorine atom,
a 4-6-membered heterocycloalkyl group, which is optionally substituted with one or two substituents said substituents selected from a fluorine atom, a methyl group or a hydroxy group,
a 5-membered heterocycloalkyl group which is partially unsaturated,
a heteroaryl group which is optionally substituted with a NH₂ group, a methyl group, a chlorine atom, a trifluoromethyl group, and a difluoromethyl group,
a NR⁷R⁸ group,
R⁷/R⁸ are independently selected from
a hydrogen atom, with the proviso that R⁷=R⁸=hydrogen is excluded,
a C₄-C₅-cycloalkyl group or a C₁-C₄-alkyl group
which is optionally substituted one or more times with substituents and said substituents are independently selected from
a fluorine atom, a hydroxy group, a heterocycloalkyl group or a heteroaryl group and
R⁴ is a hydrogen atom or a methyl group
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
R¹ is a CF₃ group or a CH₃ group,
R² is a hydrogen atom,
R³ is selected from a phenyl group which is optionally substituted with a halogen atom, a heteroaryl group which is optionally substituted with a C₁-C₃-haloalkyl group or a NR⁷R⁸ group,
R⁷/R⁸ are independently selected from
a hydrogen atom, with the proviso that R⁷=R⁸=hydrogen is excluded,
or a C₁-C₄-alkyl group
which is optionally substituted one or more times with substituents and said substituents are independently selected from
a halogen atom, a hydroxy group or a C₁-C₃-alkoxy group and
R⁴ is a hydrogen atom or a methyl group
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
R¹ is a CF₃ group or a CH₃ group,
R² is a hydrogen atom,
R³ is selected from a phenyl group which is optionally substituted with a fluorine atom or a chlorine atom, a pyridyl group or a pyrazolyl group which is optionally substituted with a CHF₂ group or a CF₃ group or a NR⁷R⁸ group,
R⁷/R⁸ are independently selected from
a hydrogen atom, with the proviso that R⁷=R⁸=hydrogen is excluded,
or a C₂-C₄-alkyl group
which is optionally substituted one or more times with substituents and said substituents are independently selected from
a fluorine atom, a hydroxy group or a methoxy group and
R⁴ is a hydrogen atom or a methyl group
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
R¹ is a CF₃ group,
R² is a hydrogen atom
R³ is selected from a phenyl group which is optionally substituted with a halogen atom or a heteroaryl group which is optionally substituted with a C₁-C₃-haloalkyl group and
R⁴ is a hydrogen atom or a methyl group
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
R¹ is a CF₃ group,
R² is a hydrogen atom
R³ is selected from a phenyl group which is optionally substituted with a halogen atom or a heteroaryl group which is optionally substituted with a CHF₂ group or a CF₃ group and
R⁴ is a hydrogen atom or a methyl group
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
R¹ is a CF₃ group,
R² is a hydrogen atom
R³ is selected from a phenyl group which is optionally substituted with a halogen atom or a heteroaryl group which is optionally substituted with a C₁-C₃-haloalkyl group and
R⁴ is a hydrogen atom,
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
R¹ is a CF₃ group,
R² is a hydrogen atom
R³ is selected from a phenyl group which is optionally substituted with a halogen atom or a heteroaryl group which is optionally substituted with a C₁-C₃-haloalkyl group and
R⁴ is a methyl group
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
R¹ is a CF₃ group,
R² is a hydrogen atom
R³ is selected from a phenyl group which is optionally substituted with a halogen atom or a 5-membered heteroaryl group which is optionally substituted with a C₁-C₃-haloalkyl group and
R⁴ is a hydrogen atom or a methyl group or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is a $CF_3$ group,
$R^2$ is a hydrogen atom
$R^3$ is selected from a phenyl group which is optionally substituted with a halogen atom or a 6-membered heteroaryl group which is optionally substituted with a $C_1$-$C_3$-haloalkyl group and
$R^4$ is a hydrogen atom or a methyl group
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is a $CF_3$ group,
$R^2$ is a hydrogen atom
$R^3$ is selected from
a phenyl group which is substituted with a fluorine atom or a chlorine atom,
a pyrazolyl group which is substituted with a $CHF_2$ group or a $CF_3$ group and
a pyridine group which is substituted with a $NH_2$ group or a $NHCH_3$ group.
$R^4$ is a hydrogen atom or a methyl group, or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is a $CF_3$ group,
$R^2$ is a hydrogen atom
$R^3$ is selected from
a phenyl group which is substituted with a fluorine atom,
a pyrazolyl group which is substituted with a $CHF_2$ group or a $CF_3$ group and
a pyridine group which is substituted with a $NH_2$ group or a $NHCH_3$ group.
$R^4$ is a hydrogen atom or a methyl group,
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is a $CF_3$ group,
$R^2$ is a hydrogen atom
$R^3$ is selected from
a phenyl group which is substituted with a fluorine atom or a chlorine atom,
a pyrazolyl group which is substituted with a $CHF_2$ group or a $CF_3$ group and
a pyridine group which is substituted with a $NH_2$ group or a $NHCH_3$ group.
$R^4$ is a hydrogen atom,
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is a $CF_3$ group,
$R^2$ is a hydrogen atom
$R^3$ is selected from
a phenyl group which is substituted with a fluorine atom;
a pyrazolyl group which is substituted with a $CHF_2$ group or a $CF_3$ group and
a pyridine group which is substituted with a $NH_2$ group or a $NHCH_3$ group;
$R^4$ is a hydrogen atom;
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is a $CF_3$ group,
$R^2$ is a hydrogen atom
$R^3$ is selected from
a phenyl group which is substituted with a fluorine atom or a chlorine atom,
a pyrazolyl group which is substituted with a $CHF_2$ group or a $CF_3$ group and
a pyridine group which is substituted with a $NH_2$ group or a $NHCH_3$ group.
$R^4$ is a methyl group,
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is a $CF_3$ group,
$R^2$ is a hydrogen atom
$R^3$ is selected from
a phenyl group which is substituted with a fluorine atom,
a pyrazolyl group which is substituted with a $CHF_2$ group or a $CF_3$ group and
a pyridine group which is substituted with a $NH_2$ group or a $NHCH_3$ group.
$R^4$ is a methyl group,
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is a $CF_3$ group,
$R^2$ is a hydrogen atom
$R^3$ is selected from a phenyl group which is substituted with a fluorine atom or a 1H-pyrazol-4-yl group or a 1H-pyrazol-1-yl group which are substituted with a $CHF_2$ group or a $CF_3$ group and
$R^4$ is a hydrogen atom or a methyl group,
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is a $CF_3$ group,
$R^2$ is a hydrogen atom
$R^3$ is selected from a phenyl group which is substituted with a fluorine atom or a 1H-pyrazol-4-yl group or a 1H-pyrazol-1-yl group which are substituted with a $CHF_2$ group or a $CF_3$ group and
$R^4$ is a hydrogen atom, In accordance with yet a further embodiment of the first aspect, the present invention provides compounds of general formula (I):
where
$R^1$ is a $CF_3$ group,
$R^2$ is a hydrogen atom
$R^3$ is selected from a phenyl group which is substituted with a fluorine atom or a 1H-pyrazol-4-yl group or a 1H-pyrazol-1-yl group which are substituted with a $CHF_2$ group or a $CF_3$ group and
$R^4$ is a methyl group,
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is a $CF_3$ group,
$R^2$ is a hydrogen atom
$R^3$ is selected from a phenyl group which is substituted with a fluorine atom or a 1H-pyrazol-4-yl group which is substituted with a $CHF_2$ group or a 1H-pyrazol-1-yl group which is substituted with a $CF_3$ group and
$R^4$ is a hydrogen atom or a methyl group
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is a $CF_3$ group,
$R^2$ is a hydrogen atom
$R^3$ is selected from a phenyl group which is substituted with a fluorine atom or a 1H-pyrazol-4-yl group which is substituted with a $CHF_2$ group or a 1H-pyrazol-1-yl group which is substituted with a $CF_3$ group and
$R^4$ is a hydrogen atom
or a stereoisomer, a tautomer, an N-oxide, a hydrate, a solvate, or a salt thereof, or a mixture of same.

In accordance with yet a further embodiment of the first aspect, the present invention provides compounds of general formula (I):
where
$R^1$ is a $CF_3$ group,
$R^2$ is a hydrogen atom,
$R^3$ is selected from a phenyl group which is substituted with a fluorine atom or a 1H-pyrazol-4-yl group which is substituted with a $CHF_2$ group or a 1H-pyrazol-1-yl group which is substituted with a $CF_3$ group and
$R^4$ is a methyl group
or a stereoisomer, a tautomer, an N-oxide, a hydrate, a solvate, or a salt thereof, or a mixture of same.

Further Embodiments of the Present Invention

In a further embodiment of the first aspect or any embodiment derived therefrom, the present invention provides compounds of formula (I), supra, in which:
$R^1$ is hydrogen atom, a halogen atom, a cyano group, a $C_1$-$C_3$-alkyl group, a $C_1$-$C_3$-haloalkyl group, or a $C_1$-$C_3$-haloalkoxy group and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^1$ is hydrogen atom, a halogen atom, a $C_1$-$C_3$-alkyl group, a $C_1$-$C_3$-haloalkyl group, or a $C_1$-$C_3$-haloalkoxy group and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^1$ is hydrogen atom, a fluorine atom, a methyl group, a trifluormethyl group, or a trifluoromethoxy group and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is a hydrogen atom and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is a halogen atom and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is a $C_1$-$C_3$-haloalkyl group and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is a $CHF_2$ group or a $CF_3$ group and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is a fluorine atom or a trifluoromethyl group and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is a fluorine atom and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is a trifluoromethyl group and stereoisomers, tautomers, N-oxides, hydrates, solvates, and salts thereof, and mixtures of same.

In further embodiments of the first aspect or any embodiment derived therefrom, if $R^1$ and $R^2$ are each independently a halogen atom (e.g., F and/or Cl) and $R^4$ is methyl then $R^3$ is not morpholinyl.

In further embodiments of the first aspect or any embodiment derived therefrom, if $R^1$ and $R^2$ are each independently a halogen atom (e.g., F and/or Cl) or a $C_1$-$C_3$-haloalkyl group and $R^4$ is methyl then $R^3$ is not morpholinyl.

In another embodiment of the first aspect or any embodiment derived therefrom, the present invention provides compounds of formula (I), supra, in which:
$R^2$ is a hydrogen atom or a halogen atom and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is a fluorine atoms or a trifluoromethyl group and $R^2$ is a hydrogen atom or a methyl group and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is a trifluoromethyl group and $R^2$ is a hydrogen atom and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^1$ is a fluorine atom and $R^2$ is a hydrogen atom and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^2$ is a hydrogen atom and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is selected from,
- a $C_1$-$C_6$-alkyl group which is optionally substituted with one or two substituents and each substituent is independently selected from a hydroxy group, a $C_1$-$C_4$-alkoxy group, and a 3- to 7-membered heterocycloalkyl group,
- a $C_2$-$C_6$-alkenyl group which is optionally substituted with an $C_1$-$C_4$-alkoxy group,
- a $C_3$-$C_5$-cycloalkyl group, which is optionally substituted with a hydroxy group,
- a $C_5$-$C_9$-cycloalkenyl group, which is optionally substituted with a hydroxy group
- a 3- to 9-membered heterocycloalkyl group, comprising one, two or three heteroatoms which are independently selected from —O—, —S—, —S(O)—, S(O)$_2$, and —NR$^9$—, and said heterocycloalkyl group optionally further comprising a bridging group selected from —O—, —NR$^9$—, —CH$_2$—, —CH$_2$—CH$_2$—, —O—CH$_2$—, —CH$_2$—O—, —NR$^9$—CH$_2$—, and —CH$_2$—NR$^9$—;
- and said heterocycloalkyl group is optionally substituted with one, two or three substituents and each substituent is independently selected from
  - a halogen atom;
  - a oxo(=O) group;
  - a cyano group;
  - a hydroxy group;
  - a $C_1$-$C_3$-alkyl group which is optionally further substituted with a hydroxy group;
  - a $C_1$-$C_3$-haloalkyl group;
  - a $C_1$-$C_3$-alkoxy group;
  - a $C_1$-$C_3$-haloalkoxy group;
  - a C(O)NR$^5$R$^6$ group and
  - a NR$^5$R$^6$ group
- a 5- to 9-membered heterocycloalkyl group which is partially unsaturated and optionally substituted with one, two or three substituents and each substituent is independently selected from an oxo group (=O), a $C_1$-$C_3$-alkyl group a —C(O)R$^5$R$^6$ group and a halogen atom,
- an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a NR$^5$R$^6$ group,
- a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a NR$^5$R$^6$ group, with the proviso that said monocyclic heteroaryl group is not a pyridin-4-yl group; and
- a NR$^7$R$^8$ group; and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is selected from,
- a $C_1$-$C_6$-alkyl group which is optionally substituted with one or two substituents and each substituent is independently selected from a hydroxy group, a $C_1$-$C_4$-alkoxy group, and a 3- to 7-membered heterocycloalkyl group,
- a $C_2$-$C_6$-alkenyl group which is optionally substituted with an $C_1$-$C_4$-alkoxy group,
- a $C_3$-$C_9$-cycloalkyl group, which is optionally substituted with a hydroxy group,
- a $C_5$-$C_9$-cycloalkenyl group, which is optionally substituted with a hydroxy group
- a 3- to 9-membered heterocycloalkyl group, comprising one, two or three heteroatoms which are independently selected from —O—, —S—, —S(O)—, S(O)$_2$, and —NR$^9$—,
  - and said heterocycloalkyl group optionally further comprising a bridging group selected from —O—, —NR$^9$—, —CH$_2$—, —CH$_2$—CH$_2$—, —O—CH$_2$—, —CH$_2$—O—, —NR$^9$—CH$_2$—, and —CH$_2$—NR$^9$—;
  - and said heterocycloalkyl group is optionally substituted with one, two or three substituents and each substituent is independently selected from
    - a halogen atom;
    - a oxo(=O) group;
    - a cyano group;
    - a hydroxy group;
    - a $C_1$-$C_3$-alkyl group which is optionally further substituted with a hydroxy group;
    - a $C_1$-$C_3$-haloalkyl group;
    - a $C_1$-$C_3$-alkoxy group;
    - a $C_1$-$C_3$-haloalkoxy group;
    - a C(O)NR$^5$R$^6$ group and
    - a NR$^5$R$^6$ group
- a 5- to 9-membered heterocycloalkyl group which is partially unsaturated and optionally substituted with one, two or three substituents and each substituent is independently selected from an oxo group (=O), a $C_1$-$C_3$-alkyl group a —C(O)R$^5$R$^6$ group and a halogen atom,
- an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a $NR^5R^6$ group,
- a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^5R^6$ group, with the proviso that said monocyclic heteroaryl group is not a pyridinyl group; and
- a $NR^7R^8$ group; and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:

$R^3$ is selected from,
- a $C_1$-$C_6$-alkyl group which is optionally substituted with one or two substituents and each substituent is independently selected from a hydroxy group, a $C_1$-$C_4$-alkoxy group, and a 3- to 7-membered heterocycloalkyl group,
- a $C_2$-$C_6$-alkenyl group which is optionally substituted with an $C_1$-$C_4$-alkoxy group,
- a $C_3$-$C_9$-cycloalkyl group, which is optionally substituted with a hydroxy group,
- a $C_5$-$C_9$-cycloalkenyl group, which is optionally substituted with a hydroxy group
- a 3- to 9-membered heterocycloalkyl group, comprising one, two or three heteroatoms which are independently selected from —O—, —S—, —S(O)—, S(O)$_2$, and —NR$^9$—,
  - and said heterocycloalkyl group optionally further comprising a bridging group selected from —O—, —NR$^9$—, —CH$_2$—, —CH$_2$—CH$_2$—, —O—CH$_2$—, —CH$_2$—O—, —NR$^9$—CH$_2$—, and —CH$_2$—NR$^9$—;
  - and said heterocycloalkyl group is optionally substituted with one, two or three substituents and each substituent is independently selected from
  - a halogen atom;
  - a oxo(=O) group;
  - a cyano group;
  - a hydroxy group;
  - a $C_1$-$C_3$-alkyl group which is optionally further substituted with a hydroxy group;
  - a $C_1$-$C_3$-haloalkyl group;
  - a $C_1$-$C_3$-alkoxy group;
  - a $C_1$-$C_3$-haloalkoxy group;
  - a C(O)NR$^5$R$^6$ group and
  - a NR$^5$R$^6$ group
- a 5- to 9-membered heterocycloalkyl group which is partially unsaturated and optionally substituted with one, two or three substituents and each substituent is independently selected from an oxo group (=O), a $C_1$-$C_3$-alkyl group a —C(O)R$^5$R$^6$ group and a halogen atom,
- an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a NR$^5$R$^6$ group,
- a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a NR$^5$R$^6$ group, with the proviso that said monocyclic heteroaryl group is not a pyridin-2-yl group, a pyridin-3-yl group, and a pyridin-4-yl group; and
- a NR$^7$R$^8$ group; and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:

if any R$^3$ is a heterocycloalkyl constituent, said constituent is optionally substituted with one, two or three substituents and each substituent is independently selected from
- a fluorine atom;
- a oxo(=O) group;
- a cyano group;
- a hydroxy group;
- a $C_1$-$C_3$-alkyl group which is optionally further substituted with a hydroxy group;
- a $C_1$-$C_3$-haloalkyl group;
- a $C_1$-$C_3$-alkoxy group;
- a $C_1$-$C_3$-haloalkoxy group;
- a C(O)NR$^5$R$^6$ group and
- a NR$^5$R$^6$ group and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:

if any R$^3$ is a heterocycloalkyl constituent, said constituent is optionally substituted with one, or two substituents and each substituent is independently selected from a fluorine atom;
- a cyano group;
- a hydroxy group;
- a $C_1$-$C_3$-alkyl group which is optionally further substituted with a hydroxy group;
- a $C_1$-$C_3$-alkoxy group;
- a C(O)NR$^5$R$^6$ group and
- a NR$^5$R$^6$ group;
and stereoisomers, tautomers, N-oxides, hydrates, solvates, and salts thereof,
and mixtures of same.

In another embodiment of the first aspect or any embodiment derived therefrom, the present invention provides compounds of formula (I), supra, in which:

if any R$^3$ is a heterocycloalkyl constituent, said constituent is optionally substituted with one, or two substituents and each substituent is independently selected from a fluorine atom;
- a cyano group;
- a hydroxy group;
- a $C_1$-$C_3$-alkyl group which is optionally further substituted with a hydroxy group;
- a $C_1$-$C_3$-alkoxy group; and
- a C(O)NR$^5$R$^6$ group
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:

if any $R^3$ is a heterocycloalkyl constituent, said constituent is optionally substituted with one, or two substituents and each substituent is independently selected from
a fluorine atom;
a cyano group;
a hydroxy group
a $C_1$-$C_3$-alkyl group which is optionally further substituted with a hydroxy group; and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
if any $R^3$ is a heterocycloalkyl constituent, said constituent is optionally substituted with one, two or three substituents and each substituent is independently selected from
a fluorine atom;
a oxo(=O) group;
a cyano group;
a hydroxy group;
a $C_1$-$C_3$-alkyl group which is optionally further substituted with a hydroxy group; and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
if any $R^3$ is a heterocycloalkyl constituent, said constituent is optionally substituted with one, or two substituents and each substituent is independently selected from
a fluorine atom;
a hydroxy group
a $C_1$-$C_3$-alkyl group which is optionally further substituted with a hydroxy group; and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is selected from,
a $C_1$-$C_6$-alkyl group which is optionally substituted with a substituent which is selected from a hydroxy group, a $C_1$-$C_4$-alkoxy group, and a 3- to 7-membered heterocycloalkyl group,
a $C_2$-$C_6$-alkenyl group which is optionally substituted with an $C_1$-$C_4$-alkoxy group,
a $C_3$-$C_7$-cycloalkyl group, which is optionally substituted with a hydroxy group,
a $C_5$-$C_7$-cycloalkenyl group, which is optionally substituted with a hydroxy group
a 3- to 7-membered-heterocycloalkyl group, comprising one, or two heteroatoms which are independently selected from —O—, S(O)$_2$, and —NR$^9$—,
and said heterocycloalkyl group is optionally substituted with one, or two substituents and each substituent is independently selected from
a halogen atom;
a cyano group;
a hydroxy group;
a $C_1$-$C_3$-alkyl group which is optionally further substituted with a hydroxy group;
a $C_1$-$C_3$-alkoxy group;
a C(O)NR$^5$R$^6$ group and
a NR$^5$R$^6$ group;
a 5- to 7-membered-heterocycloalkyl group, comprising a heteroatom which is selected from —O—, —S— and —NR$^9$—, which is partially unsaturated and optionally substituted with a substituent which is selected from a $C_1$-$C_3$-alkyl group a —C(O)R$^5$R$^6$ group and a halogen atom,
an aryl group which is optionally substituted with one, two, or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, and a NR$^5$R$^6$ group,
a mono- or bicyclic heteroaryl group which is optionally substituted with a substituent which is selected from a halogen atom, a $C_1$-$C_3$-alkyl group, a cyano group, a $C_1$-$C_3$-haloalkyl group, a $C_1$-$C_3$-alkoxy group, and a NR$^5$R$^6$ group, with the proviso that said monocyclic heteroaryl group is not a pyridin-4-yl group; and
a NR$^7$R$^8$ group; and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is selected from,
a $C_1$-$C_6$-alkyl group which is optionally substituted with a substituent which is selected from a hydroxy group, a $C_1$-$C_4$-alkoxy group, and a 3- to 7-membered heterocycloalkyl group,
a $C_2$-$C_6$-alkenyl group which is optionally substituted with an $C_1$-$C_4$-alkoxy group,
a $C_3$-$C_7$-cycloalkyl group, which is optionally substituted with a hydroxy group,
a $C_5$-$C_7$-cycloalkenyl group,
a 3- to 7-membered heterocycloalkyl group, comprising one, or two heteroatoms which are independently selected from —O—, and —NR$^9$—,
and said heterocycloalkyl group is optionally substituted with one, or two substituents and each substituent is independently selected from
a halogen atom;
a cyano group;
a hydroxy group;
a $C_1$-$C_3$-alkyl group which is optionally further substituted with a hydroxy group;
a $C_1$-$C_3$-alkoxy group; and
a C(O)NR$^5$R$^6$ group
a 5- to 7-membered-heterocycloalkyl group, comprising a heteroatom which is selected from —O—, and —NR$^9$—, which is partially unsaturated and optionally substituted with a substituent which is selected from a $C_1$-$C_3$-alkyl group and a halogen atom,
an aryl group which is optionally substituted with one, two, or three substituents and each substituent is independently selected from a halogen atom, a hydroxy group, a cyano group, a $C_1$-$C_3$-alkyl group, a $C_1$-$C_3$-haloalkyl group, and a NR$^5$R$^6$ group,
a mono- or bicyclic heteroaryl group which is optionally substituted with a substituent which is selected from a halogen atom, a $C_1$-$C_3$-alkyl group a $C_1$-$C_3$-haloalkyl group, a $C_1$-$C_3$-alkoxy group, and a NR$^5$R$^6$ group, with the proviso that said monocyclic heteroaryl group is not a pyridin-4-yl group; and
a NR$^7$R$^8$ group; and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is selected from,
- a $C_1$-$C_6$-alkyl group which is optionally substituted with a substituent which is selected from a hydroxy group, a $C_1$-$C_4$-alkoxy group, and a 3- to 7-membered heterocycloalkyl group,
- a $C_2$-$C_6$-alkenyl group which is optionally substituted with an $C_1$-$C_4$-alkoxy group,
- a $C_3$-$C_7$-cycloalkyl group, which is optionally substituted with a hydroxy group,
- a $C_5$-$C_7$-cycloalkenyl group,
- a 3- to 7-membered heterocycloalkyl group, comprising one, or two heteroatoms which are independently selected from —O—, and —$NR^9$—,
  and said heterocycloalkyl group is optionally substituted with one, or two substituents and each substituent is independently selected from
  - a halogen atom;
  - a cyano group;
  - a hydroxy group;
  - a $C_1$-$C_3$-alkyl group which is optionally further substituted with a hydroxy group;
  - a $C_1$-$C_3$-alkoxy group; and
  - a $C(O)NR^5R^6$ group
- a 5- to 7-membered-heterocycloalkyl group, comprising a heteroatom which is selected from —O—, and —$NR^9$—, which is partially unsaturated and optionally substituted with a substituent which is selected from a $C_1$-$C_3$-alkyl group and a halogen atom,
- an aryl group which is substituted with one, two, or three substituents and each substituent is independently selected from a halogen atom, a hydroxy group, a cyano group, a $C_1$-$C_3$-alkyl group, a $C_1$-$C_3$-haloalkyl group, and a $NR^5R^6$ group,
- a mono- or bicyclic heteroaryl group which is optionally substituted with a substituent which is selected from a halogen atom, a $C_1$-$C_3$-alkyl group a $C_1$-$C_3$-haloalkyl group, a $C_1$-$C_3$-alkoxy group, and a $NR^5R^6$ group, with the proviso that said monocyclic heteroaryl group is not a pyridin-4-yl group; and
- a $NR^7R^8$ group; and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
- a 3- to 6-membered heterocycloalkyl group, comprising one, or two heteroatoms which are independently selected from —O—, and —$NR^9$—,
  and said heterocycloalkyl group is optionally substituted with one, or two substituents and each substituent is independently selected from
  - a halogen atom;
  - a cyano group;
  - a hydroxy group
  - a $C_1$-$C_3$-alkyl group which is optionally further substituted with a hydroxy group;
- a 5- to 6-membered-heterocycloalkyl group, comprising a heteroatom which is selected from —O—, and —$NR^9$—, which is partially unsaturated and optionally substituted with a substituent which is selected from a $C_1$-$C_3$-alkyl group and a halogen atom,
- an aryl group which is optionally substituted with one, or two, substituents and each substituent is independently selected from a halogen atom, a hydroxy group, a cyano group, a $C_1$-$C_3$-alkyl group, a $C_1$-$C_3$-haloalkyl group, and a $NR^5R^6$ group,
- a mono- or bicyclic heteroaryl group which is optionally substituted with a substituent which is selected from a halogen atom, a $C_1$-$C_3$-alkyl group a $C_1$-$C_3$-haloalkyl group, a $C_1$-$C_3$-alkoxy group, and a $NR^5R^6$ group, with the proviso that said monocyclic heteroaryl group is not a pyridin-4-yl group;
- and a $NR^7R^8$ group;
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
- a 3- to 6-membered heterocycloalkyl group, comprising one, or two heteroatoms which are independently selected from —O—, and —$NR^9$—,
  and said heterocycloalkyl group is optionally substituted with one, or two substituents and each substituent is independently selected from
  - a halogen atom;
  - a cyano group;
  - a hydroxy group
  - a $C_1$-$C_3$-alkyl group which is optionally further substituted with a hydroxy group;
- a 5- to 6-membered-heterocycloalkyl group, comprising a heteroatom which is selected from —O—, and —$NR^9$—, which is partially unsaturated and optionally substituted with a substituent which is selected from a $C_1$-$C_3$-alkyl group and a halogen atom,
- an aryl group which is substituted with one, or two, substituents and each substituent is independently selected from a halogen atom, a hydroxy group, a cyano group, a $C_1$-$C_3$-alkyl group, a $C_1$-$C_3$-haloalkyl group, and a $NR^5R^6$ group,
- a mono- or bicyclic heteroaryl group which is optionally substituted with a substituent which is selected from a halogen atom, a $C_1$-$C_3$-alkyl group a $C_1$-$C_3$-haloalkyl group, a $C_1$-$C_3$-alkoxy group, and a $NR^5R^6$ group, with the proviso that said monocyclic heteroaryl group is not a pyridin-4-yl group;
- and a $NR^7R^8$ group;
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is selected from,
- a $C_1$-$C_6$-alkyl group which is optionally substituted with one or two substituents and each substituent is independently selected from a hydroxy group, a $C_1$-$C_4$-alkoxy group, and a 3- to 7-membered heterocycloalkyl group,
- a $C_2$-$C_6$-alkenyl group which is optionally substituted with an $C_1$-$C_3$-alkoxy group,
- a $C_3$-$C_7$-cycloalkyl group, which is optionally substituted with a hydroxy group,
- a $C_5$-$C_6$-cycloalkenyl group, which is optionally substituted with a hydroxy group
- a 3- to 6-membered heterocycloalkyl group, comprising one, two or three heteroatoms which are independently selected from —O— and —$NR^9$—,
  and said heterocycloalkyl group is optionally substituted with one, two or three substituents and each substituent is independently selected from
  - a halogen atom;
  - a oxo(=O) group;

a cyano group;
a hydroxy group;
a $C_1$-$C_3$-alkyl group which is optionally further substituted with a hydroxy group;
a 5- to 7-membered heterocycloalkyl group which is partially unsaturated and optionally substituted with one or two substituents and each substituent is independently selected from a $C_1$-$C_3$-alkyl group and a halogen atom,
an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a $NR^5R^6$ group,
a mono- or bicyclic heteroaryl group which is optionally substituted with one or two substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^5R^6$ group, with the proviso that said monocyclic heteroaryl group is not a pyridin-4-yl group; and
a $NR^7R^8$ group;
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is selected from,
a $C_1$-$C_6$-alkyl group which is optionally substituted with one or two substituents and each substituent is independently selected from a hydroxy group, a $C_1$-$C_4$-alkoxy group, and a 3- to 7-membered heterocycloalkyl group,
a $C_2$-$C_6$-alkenyl group which is optionally substituted with an $C_1$-$C_3$-alkoxy group,
a $C_3$-$C_7$-cycloalkyl group, which is optionally substituted with a hydroxy group,
a $C_5$-$C_6$-cycloalkenyl group, which is optionally substituted with a hydroxy group
a 3- to 6-membered heterocycloalkyl group, comprising one, two or three heteroatoms which are independently selected from —O— and —$NR^9$—,
and said heterocycloalkyl group is optionally substituted with one, two or three substituents and each substituent is independently selected from
a halogen atom;
a oxo(=O) group;
a cyano group;
a hydroxy group;
a $C_1$-$C_3$-alkyl group which is optionally further substituted with a hydroxy group;
a 5- to 7-membered heterocycloalkyl group which is partially unsaturated and optionally substituted with one or two substituents and each substituent is independently selected from a $C_1$-$C_3$-alkyl group and a halogen atom,
an aryl group which is substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a $NR^5R^6$ group,
a mono- or bicyclic heteroaryl group which is optionally substituted with one or two substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^5R^6$ group, with the proviso that said monocyclic heteroaryl group is not a pyridin-4-yl group; and
a $NR^7R^8$ group;
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is selected from,
a $C_1$-$C_6$-alkyl group which is optionally substituted with one or two substituents and each substituent is independently selected from a hydroxy group, a $C_1$-$C_4$-alkoxy group, and a 3- to 7-membered heterocycloalkyl group,
a $C_2$-$C_6$-alkenyl group which is optionally substituted with an $C_1$-$C_3$-alkoxy group,
a $C_3$-$C_7$-cycloalkyl group, which is optionally substituted with a hydroxy group,
a $C_5$-$C_6$-cycloalkenyl group, which is optionally substituted with a hydroxy group
a 3- to 6-membered heterocycloalkyl group, comprising one, two or three heteroatoms which are independently selected from —O— and —$NR^9$—,
and said heterocycloalkyl group is optionally substituted with one, two or three substituents and each substituent is independently selected from
a halogen atom;
a oxo(=O) group;
a cyano group;
a hydroxy group;
a $C_1$-$C_3$-alkyl group which is optionally further substituted with a hydroxy group;
a 5- to 7-membered heterocycloalkyl group which is partially unsaturated and optionally substituted with one or two substituents and each substituent is independently selected from a $C_1$-$C_3$-alkyl group and a halogen atom,
an aryl group which is substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a $NR^5R^6$ group,
a mono- or bicyclic heteroaryl group which is optionally substituted with one or two substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^5R^6$ group, with the proviso that said monocyclic heteroaryl group is not a pyridin-4-yl group; and
a $NR^7R^8$ group;
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is selected from,
a 3- to 6-membered heterocycloalkyl group, comprising one, or two heteroatoms which are independently selected from —O—, and —$NR^9$—,- and said heterocycloalkyl group is optionally substituted with one, or two substituents and each substituent is independently selected from
a halogen atom;
a hydroxy group
a $C_1$-$C_3$-alkyl group which is optionally further substituted with a hydroxy group;
an aryl group which is optionally substituted with one, or two, substituents and each substituent is independently selected from a halogen atom, a hydroxy group, and a $C_1$-$C_3$-haloalkyl group,
a mono- or bicyclic heteroaryl group which is optionally substituted with a substituent which is selected from a halogen atom, a $C_1$-$C_3$-alkyl group a $C_1$-$C_3$-haloalkyl group and a $NR^5R^6$ group, with the proviso that said monocyclic heteroaryl group is not a pyridin-4-yl group;
and a $NR^7R^8$ group;
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is selected from,
a 3- to 6-membered heterocycloalkyl group, comprising one, or two heteroatoms which are independently selected from —O—, and —$NR^9$—,
and said heterocycloalkyl group is optionally substituted with one, or two substituents and each substituent is independently selected from
a halogen atom;
a hydroxy group
a $C_1$-$C_3$-alkyl group which is optionally further substituted with a hydroxy group;
an phenyl group which is optionally substituted with one, or two, substituents and each substituent is independently selected from a halogen atom, a hydroxy group, and a $C_1$-$C_3$-haloalkyl group,
a mono- or bicyclic heteroaryl group which is optionally substituted with a substituent which is selected from a halogen atom, a $C_1$-$C_3$-alkyl group a $C_1$-$C_3$-haloalkyl group and a $NR^5R^6$ group, with the proviso that said monocyclic heteroaryl group is not a pyridin-4-yl group;
and a $NR^7R^8$ group;
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is selected from,
a 3- to 6-membered heterocycloalkyl group, comprising one, or two heteroatoms which are independently selected from —O—, and —$NR^9$—,
and said heterocycloalkyl group is optionally substituted with one, or two substituents and each substituent is independently selected from
a halogen atom;
a hydroxy group
a $C_1$-$C_3$-alkyl group which is optionally further substituted with a hydroxy group;
an phenyl group which is substituted with one, or two, substituents and each substituent is independently selected from a halogen atom, a hydroxy group, and a $C_1$-$C_3$-haloalkyl group,
a mono- or bicyclic heteroaryl group which is optionally substituted with a substituent which is selected from a halogen atom, a $C_1$-$C_3$-alkyl group a $C_1$-$C_3$-haloalkyl group and a $NR^5R^6$ group, with the proviso that said monocyclic heteroaryl group is not a pyridin-4-yl group;
and a $NR^7R^8$ group;
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which: of
$R^3$ is selected from
an aryl group which is optionally substituted with a substituent which is selected from a halogen atom and a $C_1$-$C_3$-haloalkyl group,
a monocyclic heteroaryl group substituted with a substituent which is selected from $C_1$-$C_3$-haloalkyl group and $NR^5R^6$ group;
and a $NR^7R^8$ group;
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which: of
$R^3$ is selected from
an phenyl group which is optionally substituted with a substituent which is selected from
a halogen atom and a $C_1$-$C_3$-haloalkyl group,
a monocyclic heteroaryl group substituted with a substituent which is selected from $C_1$-$C_3$-haloalkyl group and $NR^5R^6$ group;
and a $NR^7R^8$ group;
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which $R^3$ is
$R^3$ is selected from
a methyl group, a propan-2-yl group, a 2-methylpropyl group, a 2-hydroxypropan-2-yl group, a 3,3-dimethylbutyl group, a 3-methoxypropyl group,
a —$CH_2$-(morpholin-4-yl) group,
a prop-1-en-2-yl group, a 2-methylprop-1-en-1-yl group, a 3,3-dimethylbut-1-en-1-yl group,
a 3-methoxyprop-1-en-1-yl group,
a 4-hydroxycyclohexyl group,
a cyclopent-1-en-1-yl group, a cyclohex-1-en-1-yl group, a bicyclo[2.2.1]hept-2-en-2-yl group
a oxan-3-yl group, a 3,3-difluoroazetidin-1-yl group, azetidin-3-carbocxamide, a 2-hydroxyazetidin-1-yl group, a 3-hydroxy-3-methylazetidin-1-yl group, a 2-(hydroxymethyl)azetidin-1-yl group, a 3-cyano-3-methylazetidin-1-yl group, a 2,4-dimethylazetidin-1-yl group, a -2lambda<sup>6</sup>-thia-6-azaspiro[3.3]heptane-2,2-dione group, a 3-hydroxypyrrolidin-1-yl group, a 3,3-difluoropyrrolidin-1-yl group, a 3-azabicyclo[3.1.0]hexan-3-yl group, a 1-amino-3-azabicyclo[3.1.0]hexan-3-yl group, a 4-fluoropiperidin-1-yl group, 4,4-fluoropiperidin-1-yl group, a 4-cyano-piperidin-1-yl group, a 4-fluoro-4-methylpiperidin-1-yl group, a 4-ethyl-4-hydroxypiperidin-1-yl group, a 4-hydroxypiperidin-1-yl group, a 3-hydroxypiperidin-1-yl group, a 3-aminocarbonylypiperidin-1-yl group, a morpholin-4-yl group, a 2-methylmorpholin-4-yl group, a 2,6-dimethylmorpholin-4-yl group, a 4-methylpiperazin-1-yl group,
a 2,5-dihydrofuran-3-yl group, a 5,6-dihydro-2H-pyran-3-yl group, a 3,6-dihydro-2H-pyran-4-yl group, a 1,2,3,6-tetrahydropyridin-4-yl group, a 1-methyl-1,2,3,6-tetrahydropyridin-4-yl group, a 6-oxo-1,6-dihydropyridin-3-yl group, a phenyl group, 2-methylphenyl group, 2-ethylphenyl group, a 2-fluorophenyl group, a 2-aminophenyl group, a 2-hydroxyphenyl group, a 2-methoxyphenyl group, a 2,4-dimethylphenyl group, a 2-fluoro-4-methylphenyl group, a 2-fluoro-4-aminophenyl group, a 4-cyano-2-methylphenyl group, a 2-chloro-4-fluorophenyl group, a 2,3-difluorophenyl group, a 2-fluoro-3-aminophenyl group, a 2,5-difluorophenyl group, a 2,6-difluorophenyl group, a 4-fluoro-6-methylphenyl group, a (2-difluoromethyl)phenyl group, a 2-cyanophenyl group, a 2,4-difluorophenyl group, a 3-methylphenyl group, a 3-aminophenyl group, a 3-fluorophenyl group, a 3-hydroxyphenyl group, a 3,4-difluorophenyl group, a 3-amino-4-methlyphenyl group, a 3-amino-4-chlorophenyl group, a 3-amino-4-fluorophenyl group, a 3-fluoro-4-methylphenyl group, a 4-amino-3-fluorophenyl group, a 4-fluoro-3-methylphenyl group, a 4-fluoro-3-hydroxyphenyl group, a 3-hydroxy-4-methylphenyl group, a 4-methylphenyl group, a 4-fluorophenyl group, a 4-chlorophenyl group, a 4-(difluoromethyl)phenyl group, a 4-(trifluoromethyl)phenyl group, a 4-cyanophenyl group, a 4-aminophenyl group, a 4-(methylamino)phenyl group, a 4-hydroxyphenyl group, a 4-methoxyphenyl group, a 3,5-difluorophenyl group, a 2,4,5-trifluorophenyl group, a 2,3,4-trifluorophenyl group, a 3,4,5-trifluorophenyl group, a 3-amino-4,6-difluorophenyl group, a 1H-pyrazol-4-yl group, a 1-methyl-1H-pyrazol-4-yl group, a 1-ethyl-a 3-(trifluoromethyl)-1H-pyrazol-1-yl group, 1H-pyrazol-4-yl group, a 1-(propan-2-yl)-1H-pyrazol-4-yl group, a 1-(difluoromethyl)-1H-pyrazol-4-yl group, a 1-methyl-1H-pyrazol-5-yl group, a 3-methyl-1H-pyrazol-4-yl group, a 1,3-dimethyl-1H-pyrazol-4-yl group, a 3,5-dimethyl-1H-pyrazol-4-yl group, a 1-methyl-3-(trifluoromethyl)-1H-pyrazol-4-yl group, a 3-(trifluoromethyl)-1H-pyrazol-4-yl group, 1-methyl-5-cyano-1H-pyrrol-2-yl group, a 1-ethyl-1H-imidazol-4-yl group, a 4-(trifluoromethyl)-1H-imidazol-1-yl group, a 3,5-dimethyl-1,2-oxazol-4-yl group, a 1,2-thiazol-4-yl group, a 2-methyl-1,3-thiazol-5-yl group, a 5-(trifluoromethyl)thiophen-2-yl group, a 5-cyano-4-methyl-thiophen-2-yl group, a 5-(trifluoromethyl)thiophen-3-yl group, a pyridin-2-yl group, a 5-methyl-pyridin-2-yl group, a 5-chloro-pyridin-2-yl group, a 5-fluoro-pyridin-2-yl group, a pyridin-3-yl group, a 4-methylpyridin-3-yl group, a 2-methylpyridin-3-yl group, a 6-fluoropyridin-3-yl group, a 6-methylpyridin-3-yl group, a 6-(trifuoromethyl)pyridin-3-yl group, a 6-aminopyridin-3-yl group, a 6-methoxypyridin-3-yl group, a 5-fluoro-6-methylpyridin-3-yl group, a 2-methoxy-6-methylpyridin-3-yl group, a pyridin-4-yl group, a 2-methylpyridin-4-yl group, a 2-methoxypyridin-4-yl group, a 2-aminopyridin-4-yl group, a 3-methylpyridin-4-yl group, a pyrimidin-5-yl group, 2-methylpyrimidin-5-yl group, a 1-benzothiophen-2-yl group, an imidazo[1,2-a]pyridin-6-yl group, a 1-methyl-1H-benzimidazol-6-yl group, a 1-methyl-1H-indazol-6-yl group, a 1H-indazol-6-yl group, a 1H-indol-6-yl group, a 1H-indol-5-yl group, a methylamino group, a ethylamino group, a (propan-2-yl)amino group, a propylamino group, a butylamino group, a tert-butylamino group, a pentylamino group, a ethyl(methyl)amino group, a (butyl)methylamino group, an aminocarbonylmethyl group, a (2-aminoethyl)amino group, a (2-methylpropyl)amino group, a (3-methylbutyl)amino group, a (2-methoxyethyl)amino group, a (2-ethoxyethyl)amino group, a (3-methoxypropyl)amino group, a (3-cyanopropyl)amino group, a (2-hydroxypropyl)amino group, a (2-hydroxy-2-methylpropyl)amino group, a (2-methoxypropyl)amino group, a (2-ethoxypropyl)amino group, a (3,3,3-trifluoro-2-hydroxypropyl)amino group, a (2-methoxy-2-methylpropyl)amino group, a (2-methoxybutyl)amino group, a (3-hydroxybutyl)amino group, a (1-hydroxybutan-2-yl)amino group, a (4-hydroxybutan-2-yl)amino group, a (1-hydroxypentan-2-yl)amino group, a (3-hydroxy-3-methylbutyl)amino group, a (2-hydroxy-3-methoxypropyl)amino group, a (cyclopropylmethyl)amino group, a (1-cyclopropylethyl)amino group, a ((1-hydroxycyclobutyl)methyl)amino group, a (1-hydroxy-4-methylpentan-2-yl)amino group, a (1,3-dihydroxybutan-2-yl)amino group, a (2,2-dimethylcyclopropyl)methyl]amino group, a (dicyclopropylmethyl)amino group, a (3-hydroxycyclobutyl)amino group, a [1-(hydroxymethyl)cyclobutyl]methyl group, a cyclopentylamino group, a (2-hydroxycyclopentyl)amino group, a (cyclopentyl)(methyl)amino group, a (4-hydroxycyclohexyl)amino group, a bicyclo[2.2.1]heptan-2-yl]amino group, an [(3-methyloxetan-3-yl)methyl]amino group, a (oxetan-3-yl)amino group, an (oxolan-3-yl)methyl)amino group, a (tetrahydrofuran-2-ylmethyl)amino group, a (oxan-4-yl)amino group, a ((oxan-4-yl)methyl)amino group, a ((4-methyloxan-4-yl)methyl)amino group, an (3-methyloxetan-3-yl)methyl]amino group, a [(5-oxopyrrolidin-2-yl)methyl]amino group, a [(6-oxopiperidin-3-yl)methyl]amino group, a [(1-methyl-1H-imidazol-2-yl)methyl]amino group, a [2-(1H-pyrazol-1-yl)ethyl]amino group, a [2-(1H-imidazol-5-yl)ethyl]amino group, a (3-(1H-imidazol-1-yl)propyl)amino group, a [(1-methyl-1H-pyrazol-5-yl)methyl]amino group, a [(1H-pyrazol-3-yl)methyl]aminogroup, a [(1-methyl-1H-pyrazol-3-yl)methyl]amino group, a [(1-methyl-1H-pyrazol-4-yl)methyl]amino group, a [(pyrazin-2-yl)methyl]aminogroup, a [(pyridin-3-yl)methyl]amino group, a [(pyrimidin-5-yl)methyl]amino group, a [(pyrimidin-2-yl)methyl]amino group, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which the aryl group $R^3$ is a phenyl group, which is optionally substituted with one or two fluorine atoms, a chlorine atom or a trifluoromethyl group and stereoisomers, tautomers, N-oxides, hydrates, solvates, and salts thereof, and mixtures of same.

In another embodiment of the first aspect or any embodiment derived therefrom, the present invention provides compounds of formula (I), supra, in which the aryl group $R^3$ is a phenyl group, which is substituted with a fluorine atom and stereoisomers, tautomers, N-oxides, hydrates, solvates, and salts thereof, and mixtures of same.

In another embodiment of the first aspect or any embodiment derived therefrom, the present invention provides compounds of formula (I), supra, in which $R^3$ is a phenyl group which is optionally substituted with one, two, or three substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, and a $NR^5R^6$ group;

a mono- or bicyclic heteroaryl group which is optionally substituted with a substituent which is selected from a halogen atom, a $C_1$-$C_3$-alkyl group, a cyano group, a $C_1$-$C_3$-haloalkyl group, a $C_1$-$C_3$-alkoxy group, and a NR⁵R⁶ group, with the proviso that said monocyclic heteroaryl group is not a pyridin-4-yl group;
and a NR⁷R⁸ group; and stereoisomers, tautomers, N-oxides, hydrates, solvates, and salts thereof, and mixtures of same.

In another embodiment of the first aspect or any embodiment derived therefrom, the present invention provides compounds of formula (I), supra, in which R³ is
a monocyclic heteroaryl group which is optionally substituted with a substituent which is selected from a halogen atom, a $C_1$-$C_3$-alkyl group, a cyano group, a $C_1$-$C_3$-haloalkyl group,
a $C_1$-$C_3$-alkoxy group, and a NR⁵R⁶ group;
or a NR⁷R⁸ group; and stereoisomers, tautomers, N-oxides, hydrates, solvates, and salts thereof, and mixtures of same.

In another embodiment of the first aspect or any embodiment derived therefrom, the present invention provides compounds of formula (I), supra, in which R³ is
a monocyclic heteroaryl group which is optionally substituted with a substituent which is selected from a halogen atom, a $C_1$-$C_3$-alkyl group, a $C_1$-$C_3$-haloalkyl group, and a NR⁵R⁶ group;
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which R³ is
a substituted heterocycloalkyl group, such as a 4,4-difluoropiperidin-1-yl group,
a heterocycloalkyl group which is partially unsaturated, such as a 2,5-dihydrofuran-3-yl group,
a substituted phenyl group, such as a 4-fluorophenyl group, a 3,4-difluorophenyl group, a 4-chlorophenyl group,
a substituted heteroaryl group, such as a 1,2-thiazol-4-yl group, a 2-methyl-1,3-thiazol-5-yl group, a 1-(difluoromethyl)-1H-pyrazol-4-yl group, a 3-(trifluoromethyl)-1H-pyrazol-1-yl group, a 5-chloropyridin-2-yl group, a 2-aminopyridin-4-yl group, a (morpholin-4-yl)methyl group, a 2-hydroxy-2-methylpropyl group, a 2-methylpropyl group, a pyrazin-2-yl)methyl group, a 3-hydroxy-3-methylazetidin-1-yl group, and
a NR⁷R⁸ group, such as a 4-(propylamino) group, a 4-(cyclopentylamino) group; a [3-hydroxycyclobutyl]amino group, a [3,3,3-trifluoro-2-hydroxypropyl]amino group, a 2-methoxyethyl)amino group,
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which R³ is a $C_1$-$C_6$-alkyl group which is optionally substituted with one or two substituents and each substituent is independently selected from a hydroxy group, a $C_1$-$C_4$-alkoxy group, and a 3- to 7-membered heterocycloalkyl group and stereoisomers, tautomers, N-oxides, hydrates, solvates, and salts thereof, and mixtures of same.

In another embodiment of the first aspect or any embodiment derived therefrom, the present invention provides compounds of formula (I), supra, in which R³ is a $C_2$-$C_6$-alkenyl group which is optionally substituted with an $C_1$-$C_4$-alkoxy group, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which R³ is a $C_3$-$C_9$-cycloalkyl group, which is optionally substituted with a hydroxy group, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which R³ is a $C_5$-$C_9$-cycloalkenyl group, C5:150,201, C7:154 (bridged), which is optionally substituted with a hydroxy group and stereoisomers, tautomers, N-oxides, hydrates, solvates, and salts thereof, and mixtures of same. In another embodiment of the first aspect or any embodiment derived therefrom, the present invention provides compounds of formula (I), supra, in which R³ is a 3-9-membered-heterocycloalkyl group, comprising one, 72,234,239, two 207 or three heteroatoms which are independently selected from —O—, —S—, —S(O)—, S(O)₂, and —NR⁹—
and said heterocycloalkyl group may optionally further contain a bridging group selected from —O—, —NR⁹—, —CH₂—, —CH₂—CH₂—, —O—CH₂—, —CH₂—O—, —NR⁹—CH₂—, and —CH₂—NR⁹—;
and said heterocycloalkyl group is optionally substituted with one, 18,239,243,275, two or three substituents and each substituent is independently selected from
a halogen atom;
a oxo(=O) group;
a cyano group;
a hydroxy group;
a $C_1$-$C_3$-alkyl group which is optionally substituted with one, two or three substitutents and said substitutents are independently selected from a hydroxy group;
a $C_1$-$C_3$-haloalkyl group;
a $C_1$-$C_3$-alkoxy group;
a $C_1$-$C_3$-haloalkoxy group;
a $C_1$-$C_3$-hydroxyalkoxy group;
a C(O)NR⁵R⁶ group and NR⁵R⁶ group;
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which R³ is a 5- to 9-membered-heterocycloalkyl group, comprising one, two or three heteroatoms which are independently selected from —O—, —S— and —NR⁹—, which is partially unsaturated and optionally substituted with one, two or three substituents and each substituent is independently selected from an oxo group (=O), a $C_1$-$C_3$-alkyl group, and a halogen atom, and stereoisomers, tautomers, N-oxides, hydrates, solvates, and salts thereof, and mixtures of same. In another embodiment of the first aspect or any embodiment derived therefrom, the present invention provides compounds of formula (I), supra, in which R³ is an aryl group which is optionally substituted with one, three or four substituents and each substituent is independently selected from
a halogen atom,
a hydroxy group,
a cyano group,
a $C_1$-$C_3$-alkyl group,
a $C_1$-$C_3$-haloalkyl group,
a $C_1$-$C_3$-alkoxy group,
a $C_1$-$C_3$-haloalkoxy group, and
a NR⁵R⁶ group,
and stereoisomers, tautomers, N-oxides, hydrates, solvates, and salts thereof, and mixtures of same. In another embodiment of the first aspect or any embodiment derived therefrom, the present invention provides compounds of formula (I), supra, in which R³ is a monoor bicyclic heteroaryl group which is optionally substituted with one, two or three substituents and each substituent is independently selected from
a halogen atom,
a $C_1$-$C_3$-alkyl group,
a cyano group,
a $C_1$-$C_3$-haloalkyl group,
a $C_1$-$C_3$-alkoxy group,
a hydroxy group, and
a $NR^5R^6$ group;
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which R is a 5- to 9-membered-heterocycloalkyl group, comprising one, two or three heteroatoms which are independently selected from —O—, —S— and —$NR^9$, which is partially unsaturated and optionally substituted with one, two or three substituents and each substituent is independently selected from an oxo group (=O), a $C_1$-$C_3$-alkyl group, and a halogen atom, and stereoisomers, tautomers, N-oxides, hydrates, solvates, and salts thereof, and mixtures of same. In another embodiment of the first aspect or any embodiment derived therefrom, the present invention provides compounds of formula (I), supra, in which $R^3$ is an aryl group which is optionally substituted with one, three or four substituents and each substituent is independently selected from
a halogen atom,
a hydroxy group,
a cyano group,
a $C_1$-$C_3$-alkyl group,
a $C_1$-$C_3$-haloalkyl group,
a $C_1$-$C_3$-alkoxy group,
a $C_1$-$C_3$-haloalkoxy group, and
a $NR^5R^6$ group,
and stereoisomers, tautomers, N-oxides, hydrates, solvates, and salts thereof, and mixtures of same. In another embodiment of the first aspect or any embodiment derived therefrom, the present invention provides compounds of formula (I), supra, in which $R^3$ is a monoor bicyclic heteroaryl group which is optionally substituted with one, two or three substituents and each substituent is independently selected from
a halogen atom,
a $C_1$-$C_3$-alkyl group,
a cyano group,
a $C_1$-$C_3$-haloalkyl group,
a $C_1$-$C_3$-alkoxy group,
a hydroxy group, and
a $NR^5R^6$ group;
were the heterocycloalkyl group is a 6-membered ring, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which R is a 5- to 9-membered-heterocycloalkyl group, comprising one, two or three heteroatoms which are independently selected from —O—, —S— and —$NR^9$, which is partially unsaturated and optionally substituted with one, two or three substituents and each substituent is independently selected from an oxo group (=O), a $C_1$-$C_3$-alkyl group, and a halogen atom, and stereoisomers, tautomers, N-oxides, hydrates, solvates, and salts thereof, and mixtures of same. In another embodiment of the first aspect or any embodiment derived therefrom, the present invention provides compounds of formula (I), supra,
in which $R^3$ is an aryl group which is optionally substituted with one, three or four substituents and each substituent is independently selected from
a halogen atom,
a hydroxy group,
a cyano group,
a $C_1$-$C_3$-alkyl group,
a $C_1$-$C_3$-haloalkyl group,
a $C_1$-$C_3$-alkoxy group,
a $C_1$-$C_3$-haloalkoxy group, and
a $NR^5R^6$ group,
and stereoisomers, tautomers, N-oxides, hydrates, solvates, and salts thereof, and mixtures of same. In another embodiment of the first aspect or any embodiment derived therefrom, the present invention provides compounds of formula (I), supra, in which $R^3$ is a monoor bicyclic heteroaryl group which is optionally substituted with one, two or three substituents and each substituent is independently selected from
a halogen atom,
a $C_1$-$C_3$-alkyl group,
a cyano group,
a $C_1$-$C_3$-haloalkyl group,
a $C_1$-$C_3$-alkoxy group,
a hydroxy group, and
a $NR^5R^6$ group;
were the heterocycloalkyl group is a 5-membered ring, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which $R^3$ is a $NR^7R^8$ group; and stereoisomers, tautomers, N-oxides, hydrates, solvates, and salts thereof, and mixtures of same.

In another embodiment of the first aspect or any embodiment derived therefrom, the present invention provides compounds of formula (I), supra, in which $R^3$ is a $NR^7R^8$ group; and $R^7/R^8$ are independently selected from
a hydrogen atom, with the proviso that $R^7=R^8=$hydrogen is excluded,
a $C_1$-$C_6$-alkyl group,
which is optionally substituted with one, two, three or four substituents and said substituent is independently selected from
a halogen atom, a cyano group, a hydroxy group, a $C(O)NR^5R^6$ group, a $NR^5R^6$ group,
a $C_1$-$C_3$-alkoxy group,
a $C_3$-$C_7$-cycloalkyl group which is optionally substituted with one or two substitutents and said substituents are independently selected from a $C_1$-$C_3$-alkyl group, a oxo (=O) group, a hydroxy group, and a $C_1$-$C_3$-hydroxyalkyl group;
a 3- to 7-membered heterocycloalkyl group which itself is optionally substituted with a $C_1$-$C_3$-alkyl group or an oxo (=O) group,
a heteroaryl group, which itself is optionally substituted with a $C_1$-$C_3$-alkyl group;
a —$C_1$-$C_5$-alkylene-O—$C_1$-$C_5$-alkyl group,
a —$C_1$-$C_5$-alkylene-S—$C_1$-$C_5$-alkyl group,
a —$C_1$-$C_5$-alkylene-$NR^5$—$C_1$-$C_5$-alkyl group,
a $C_3$-$C_6$-cycloalkyl group which is optionally substituted with a hydroxy group, and
a 3- to 6-membered heterocycloalkyl group, which is optionally substituted with one or two substituents, said substituent independently selected from $C_1$-$C_3$-alkyl group and a hydroxy group, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which $R^3$ is a $NR^7R^8$ group; and
$R^7/R^8$ are independently selected from
  a hydrogen atom, with the proviso that $R^7=R^8$=hydrogen is excluded,
  a $C_1$-$C_6$-alkyl group, which is optionally substituted with one, two, three or four substituents and said substituent is independently selected from
    a halogen atom, a cyano group, a hydroxy group, a C(O)$NR^5R^6$ group, a $NR^5R^6$ group,
    a $C_1$-$C_3$-alkoxy group,
    a $C_3$-$C_7$-cycloalkyl group which is optionally further substituted with one or two substituents and said substituents are independently selected from a $C_1$-$C_3$-alkyl group, a oxo (=O) group, a hydroxy group, and a $C_1$-$C_3$-hydroxyalkyl group;
    a 3- to 7-membered heterocycloalkyl group, comprising one, two or three heteroatoms which are independently selected from —O— and —$NR^9$—, which is optionally further substituted with a $C_1$-$C_3$-alkyl group,
    a heteroaryl group, which is optionally further substituted with a $C_1$-$C_3$-alkyl group
  a $C_3$-$C_7$-cycloalkyl group which is optionally substituted with a hydroxy group, or a $C_1$-$C_3$-alkyl group and
  a 3- to 6-membered heterocycloalkyl group, which is optionally substituted with one or two substituents, said substituent independently selected from $C_1$-$C_3$-alkyl group and a hydroxy group,
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is a halogen atom,
  a $C_2$-$C_6$-alkenyl group,
  a $C_3$-$C_6$-cycloalkyl group
  a $C_5$-$C_6$-cycloalkenyl group,
  a $C_3$-$C_7$-heterocycloalkyl group, which is optionally substituted with one, two or three substituents and each substituent is independently selected from a halogen atom and a $C_1$-$C_3$-alkyl group, a hydroxy group, $NR^5R^6$ group, a $C_1$-$C_3$-haloalkyl group and a $C_1$-$C_3$-haloalkoxy group,
  a $C_5$-$C_7$-heterocycloalkyl group which is partially unsaturated and optionally substituted with one, two or three substituents and each substituent is independently selected from an oxo group (=O), a $C_1$-$C_3$-alkyl group and a halogen atom,
  an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a $NR^5R^6$ group,
  a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^5R^6$ group;
  and a $NR^7R^8$ group.

In another embodiment of the first aspect or any embodiment derived therefrom, the present invention provides compounds of formula (I), supra, in which:
$R^3$ is a $C_2$-$C_6$-alkenyl group,
  a $C_3$-$C_6$-cycloalkyl group
  a $C_1$-$C_6$-cycloalkenyl group,
  a $C_3$-$C_7$-heterocycloalkyl group, which is optionally substituted with one, two or three substituents and each substituent is independently selected from a halogen atom and a $C_1$-$C_3$-alkyl group, a hydroxy group, $NR^5R^6$ group, a $C_1$-$C_3$-haloalkyl group and a $C_1$-$C_3$-haloalkoxy group,
  a $C_5$-$C_7$-heterocycloalkyl group which is partially unsaturated and optionally substituted with one, two or three substituents and each substituent is independently selected from an oxo group (=O), a $C_1$-$C_3$-alkyl group and a halogen atom,
  an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a $NR^5R^6$ group,
  a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^5R^6$ group, with the proviso that said monocyclic heteroaryl group is not a pyridin-4-yl group;
  and a $NR^7R^8$ group.

In another embodiment of the first aspect or any embodiment derived therefrom, the present invention provides compounds of formula (I), supra, in which:
$R^3$ is a halogen atom,
  a $C_2$-$C_6$-alkenyl group,
  a $C_5$-$C_6$-cycloalkyl group which is optionally partially unsaturated,
  a $C_3$-$C_6$-heterocycloalkyl group, which is optionally substituted with one, two or three substituents and each substituent is independently selected from a halogen atom and a $C_1$-$C_3$-alkyl group,
  a $C_5$-$C_6$-heterocycloalkyl group which is partially unsaturated and optionally substituted with one, two or three substituents and each substituent is independently selected from an oxo group (=O), a $C_1$-$C_3$-alkyl group and a halogen atom,
  an aryl group which is optionally substituted with one, two or three substituents and each substituent is independently selected from a halogen atom, a hydroxy group, a $C_1$-$C_3$-alkyl group, a $C_1$-$C_3$-haloalkyl group, a $C_1$-$C_3$-alkoxy group, a cyano group and a $NR^5R^6$ group; and
  a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, and a $NR^5R^6$ group;
  or a $NR^7R^8$ group,
    and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:

$R^3$ is
- a $C_2$-$C_6$-alkenyl group,
- a $C_5$-$C_6$-cycloalkyl group which is optionally partially unsaturated,
- a $C_3$-$C_6$-heterocycloalkyl group, which is optionally substituted with one, two or three substituents and each substituent is independently selected from a halogen atom and a $C_1$-$C_3$-alkyl group,
- a $C_5$-$C_6$-heterocycloalkyl group which is partially unsaturated and optionally substituted with one, two or three substituents and each substituent is independently selected from an oxo group (=O), a $C_1$-$C_3$-alkyl group and a halogen atom,
- an aryl group which is optionally substituted with one, two or three substituents and each substituent is independently selected from a halogen atom, a hydroxy group, a $C_1$-$C_3$-alkyl group, a $C_1$-$C_3$-haloalkyl group, a $C_1$-$C_3$-alkoxy group, a cyano group and a $NR^5R^6$ group; and
- a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, and a $NR^5R^6$ group, with the proviso that said monocyclic heteroaryl group is not a pyridin-4-yl group;
- or a $NR^7R^8$ group,
  - and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is a halogen atom,
- a $C_2$-$C_6$-alkenyl group,
- a $C_3$-$C_6$-cycloalkyl group
- a $C_5$-$C_6$-cycloalkenyl group which,
- a $C_3$-$C_7$-heterocycloalkyl group, which is optionally substituted with one, two or three substituents and each substituent is independently selected from a halogen atom and a $C_1$-$C_3$-alkyl group, a hydroxy group, $NR^5R^6$ group, a $C_1$-$C_3$-haloalkyl group and a $C_1$-$C_3$-haloalkoxy group,
- a $C_5$-$C_7$-heterocycloalkyl group which is partially unsaturated and optionally substituted with one, two or three substituents and each substituent is independently selected from an oxo group (=O), a $C_1$-$C_3$-alkyl group and a halogen atom,
- a phenyl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a $NR^5R^6$ group,
- a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^5R^6$ group;
- and a $NR^7R^8$ group, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is a $C_2$-$C_6$-alkenyl group,
- a $C_3$-$C_6$-cycloalkyl group
- a $C_1$-$C_6$-cycloalkenyl group which,
- a $C_3$-$C_7$-heterocycloalkyl group, which is optionally substituted with one, two or three substituents and each substituent is independently selected from a halogen atom and a $C_1$-$C_3$-alkyl group, a hydroxy group, $NR^5R^6$ group, a $C_1$-$C_3$-haloalkyl group and a $C_1$-$C_3$-haloalkoxy group,
- a $C_5$-$C_7$-heterocycloalkyl group which is partially unsaturated and optionally substituted with one, two or three substituents and each substituent is independently selected from an oxo group (=O), a $C_1$-$C_3$-alkyl group and a halogen atom,
- a phenyl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a $NR^5R^6$ group,
- a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^5R^6$ group, with the proviso that said monocyclic heteroaryl group is not a pyridin-4-yl group;
- and a $NR^7R^8$ group, and stereoisomers, tautomers, N-oxides, hydrates, solvates, and salts thereof, and mixtures of same.

In yet another embodiment of the first aspect or any embodiment derived therefrom, the present invention provides compounds of formula (I), supra, in which:
$R^3$ is a halogen atom,
- a $C_2$-$C_6$-alkenyl group,
- a $C_1$-$C_6$-cycloalkenyl group,
- a $C_3$-$C_6$-heterocycloalkyl group, which is optionally substituted with one, two or three substituents and each substituent is independently selected from a halogen atom and a $C_1$-$C_3$-alkyl group,
- a $C_1$-$C_6$-heterocycloalkyl group which is partially unsaturated and optionally substituted with one, two or three substituents and each substituent is independently selected from an oxo group (=O), a $C_1$-$C_3$-alkyl group and a halogen atom,
- an phenyl group which is optionally substituted with one, two or three substituents and each substituent is independently selected from a halogen atom, a hydroxy group, a $C_1$-$C_3$-alkyl group, a $C_1$-$C_3$-haloalkyl group, a $C_1$-$C_3$-alkoxy group, a cyano group and a $NR^5R^6$ group; and
- a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, and a $NR^5R^6$ group;
- or a $NR^7R^8$ group,
  - and stereoisomers, tautomers, N-oxides, hydrates, solvates, and salts thereof, and mixtures of same.

In yet another embodiment of the first aspect or any embodiment derived therefrom, the present invention provides compounds of formula (I), supra, in which:
$R^3$ is a $C_2$-$C_6$-alkenyl group,
- a $C_5$-$C_6$-cycloalkenyl group,
- a $C_3$-$C_6$-heterocycloalkyl group, which is optionally substituted with one, two or three substituents and each substituent is independently selected from a halogen atom and a $C_1$-$C_3$-alkyl group, a $C_5$-$C_6$-heterocycloalkyl group which is partially unsaturated and optionally substituted with one, two or three substituents and each substituent is independently selected from an oxo group (=O), a $C_1$-$C_3$-alkyl group and a halogen atom, an phenyl group which is optionally substituted with one, two or three substituents and each substituent is independently selected from a halogen atom, a hydroxy group, a $C_1$-$C_3$-alkyl group, a $C_1$-$C_3$-haloalkyl group, a $C_1$-$C_3$-alkoxy group, a cyano group and a $NR^5R^6$ group; and a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, and a $NR^5R^6$ group, with the proviso that said monocyclic heteroaryl group is not a pyridin-4-yl group;

or a $NR^7R^8$ group, and stereoisomers, tautomers, N-oxides, hydrates, solvates, and salts thereof, and mixtures of same.

In yet another embodiment of the first aspect or any embodiment derived therefrom t, the present invention provides compounds of formula (I), supra, in which:

$R^3$ is a halogen atom,
a $C_2$-$C_6$-alkenyl group,
or a $NR^7R^8$ group,
and stereoisomers, tautomers, N-oxides, hydrates, solvates, and salts thereof, and mixtures of same.

In yet another embodiment of the first aspect or any embodiment derived therefrom, the present invention provides compounds of formula (I), supra, in which:

$R^3$ is a $C_2$-$C_6$-alkenyl group,
or a $NR^7R^8$ group,
and stereoisomers, tautomers, N-oxides, hydrates, solvates, and salts thereof, and mixtures of same.

In yet another embodiment of the first aspect, the present invention provides compounds of formula (I), supra, in which:

$R^3$ is a $C_3$-$C_6$-cycloalkyl group
a $C_5$-$C_6$-cycloalkenyl group which,
a $C_3$-$C_7$-heterocycloalkyl group, which is optionally substituted with one, two or three substituents and each substituent is independently selected from a halogen atom and a $C_1$-$C_3$-alkyl group, a hydroxy group, $NR^5R^6$ group, a $C_1$-$C_3$-haloalkyl group and a $C_1$-$C_3$-haloalkoxy group,
a $C_5$-$C_7$-heterocycloalkyl group which is partially unsaturated and optionally substituted with one, two or three substituents and each substituent is independently selected from an oxo group (=O), a $C_1$-$C_3$-alkyl group and a halogen atom,
a phenyl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a $NR^5R^6$ group,
a mono- or bicyclic heteroaryl group which is optionally substituted with one, two or three substituents and each substituent is independently selected from a halogen atom, a $C_1$-$C_3$-alkyl group, methyl a cyano group, a $C_1$-$C_3$-haloalkyl group, a $C_1$-$C_3$-alkoxy group methoxy, a hydroxy group, and a $NR^5R^6$ group, with the proviso that said monocyclic heteroaryl group is not a pyridin-4-yl group;

and stereoisomers, tautomers, N-oxides, hydrates, solvates, and salts thereof, and mixtures of same.

In yet another embodiment of the first aspect, the present invention provides compounds of formula (I), supra, in which:

$R^3$ is a $C_5$-$C_6$-cycloalkyl group,
a $C_5$-$C_6$-cycloalkenyl group, (cyclopentenyl)
a $C_3$-$C_6$-heterocycloalkyl group, which is optionally substituted with one, two or three substituents and each substituent is independently selected from a halogen atom and a $C_1$-$C_3$-alkyl group,
a $C_5$-$C_6$-heterocycloalkyl group which is partially unsaturated and optionally substituted with one, two or three substituents and each substituent is independently selected from an oxo group (=O), a $C_1$-$C_3$-alkyl group and a halogen atom,
and stereoisomers, tautomers, N-oxides, hydrates, solvates, and salts thereof, and mixtures of same.

In yet another embodiment of the first aspect or any embodiment derived therefrom, the present invention provides compounds of formula (I), supra, in which:

$R^3$ is
a phenyl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a $NR^5R^6$ group.
a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^5R^6$ group, with the proviso that said monocyclic heteroaryl group is not a pyridin-4-yl group;
and stereoisomers, tautomers, N-oxides, hydrates, solvates, and salts thereof, and mixtures of same.

In yet another embodiment of the first aspect or any embodiment derived therefrom, the present invention provides compounds of formula (I), supra, in which:

$R^3$ is
a phenyl group which is optionally substituted with a halogen atom,
a monocyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and
a $NR^7R^8$ group;
where
$R^7$, $R^8$ are independently selected from a hydrogen atom, a $C_2$-$C_3$-alkyl group which is optionally substituted with one or two substitutent independently selected from a hydroxy group, a trifluoromethyl group, or a methoxy group.
and stereoisomers, tautomers, N-oxides, hydrates, solvates, and salts thereof, and mixtures of same.

In yet another embodiment of the first aspect or any embodiment derived therefrom, the present invention provides compounds of formula (I), supra, in which:

$R^3$ is
a phenyl group which is optionally substituted with a halogen atom, a monocyclic heteroaryl group which is optionally substituted with one, two or three substituents and each substituent is independently selected from a halogen atom,
a amino group and a $C_1$-$C_3$-haloalkyl group, and
a $NR^7R^8$ group;
where
$R^7$ is a hydrogen atom and $R^8$ is a $C_1$-$C_6$-alkyl group which is optionally substituted with one or two substitutent independently selected from a hydroxy group, a trifluoromethyl group, or a methoxy group.
and stereoisomers, tautomers, N-oxides, hydrates, solvates, and salts thereof, and mixtures of same.

In yet another embodiment of the first aspect or any embodiment derived therefrom, the present invention provides compounds of formula (I), supra, in which:
$R^3$ is
a phenyl group which is optionally substituted with a halogen atom,
a monocyclic heteroaryl group which is optionally substituted with one, two or three substituents and each substituent is independently selected from a halogen atom, a amino group and a $C_1$-$C_3$-haloalkyl group, and
a $NR^7R^8$ group;
where
$R^7$ is a hydrogen atom and $R^8$ is a $C_2$-$C_3$-alkyl group which is optionally substituted with one or two substitutent independently selected from a hydroxy group, a trifluoromethyl group, or a methoxy group.
and stereoisomers, tautomers, N-oxides, hydrates, solvates, and salts thereof, and mixtures of same.

In yet another embodiment of the first aspect or any embodiment derived therefrom, the present invention provides compounds of formula (I), supra, in which:
$R^3$ is
a $NR^7R^8$ group;
where
$R^7$ is a hydrogen atom and $R^8$ is a $C_2$-$C_3$-alkyl group which is optionally substituted with one or two substitutent independently selected from a hydroxy group, a trifluoromethyl group, or a methoxy group.
and stereoisomers, tautomers, N-oxides, hydrates, solvates, and salts thereof, and mixtures of same.

In yet another embodiment of the first aspect or any embodiment derived therefrom, the present invention provides compounds of formula (I), supra, in which:
$R^3$ is
a monocyclic heteroaryl group which is optionally substituted with one, two or three substituents and each substituent is independently selected from a amino group and a $C_1$-$C_3$-haloalkyl group, and
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is selected from
an aryl group which is optionally substituted with a substituent which is selected from a halogen atom and a $C_1$-$C_3$-haloalkyl group,
a monocyclic heteroaryl group substituted with a substituent which is selected from $C_1$-$C_3$-haloalkyl group and $NR^5R^6$ group;
and a $NR^7R^8$ group;
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is selected from
an phenyl group which is optionally substituted with a substituent which is selected from a fluorine atom or chlorine atom and a $CHF_2$ group and a $CF_3$ group,
a 1H-pyrazol-4-yl group, a 1H-pyrazol-1-yl group a pyridin-4-yl group which are optionally substituted with a substituent which is selected from a $CHF_2$ group, a $CF_3$ group and $NH_2$ group;
a —NH—($CH_2$)—CH(OH)($CH_3$) group, a —NH—($CH_2$)$_2$—O—$CH_3$ group, a —NH—$CH_2$—CH(OH)$CF_3$ group;
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^3$ is selected from
an phenyl group which is optionally substituted with a substituent which is selected from a fluorine atom or chlorine atom and a $CF_3$ group,
a 1H-pyrazol-4-yl group, a 1H-pyrazol-1-yl group a pyridin-4-yl group which are optionally substituted with a substituent which is selected from a $CF_3$ group and $NH_2$ group;
a —NH—($CH_2$)—CH(OH)($CH_3$) group, a —NH—($CH_2$)$_2$—O—$CH_3$ group, a —NH—$CH_2$—CH(OH)$CF_3$ group;
and stereoisomers, tautomers, N-oxides, hydrates, solvates, and salts thereof, and mixtures of same.

In yet another embodiment of the first aspect or any embodiment derived therefrom, the present invention provides compounds of formula (I), supra, in which:
$R^4$ is a hydrogen atom and stereoisomers, tautomers, N-oxides, hydrates, solvates, and salts thereof, and mixtures of same.

In yet a further embodiment of the first aspect or any embodiment derived therefrom, the present invention provides compounds of formula (I), supra, in which:
$R^4$ is a $C_1$-$C_3$-alkyl group and stereoisomers, tautomers, N-oxides, hydrates, solvates, and salts thereof, and mixtures of same.

In yet a further embodiment of the first aspect or any embodiment derived therefrom, the present invention provides compounds of formula (I), supra, in which:
$R^4$ is a methyl group and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^4$ is a $C_1$-$C_3$-alkyl group having S-Konfiguration and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which:
$R^4$ is a methyl group having S-Konfiguration and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:

$R^5/R^6$ is independently selected from a hydrogen atom and a $C_1$-$C_6$-alkyl group and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^5/R^6$ are independently selected from a hydrogen atom and a methyl group and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^5/R^6$ are a hydrogen atom and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^7/R^8$ are independently selected from
  a hydrogen atom, with the proviso that $R^7$=R$=hydrogen is excluded,
  a $C_1$-$C_6$-alkyl group,
  which is optionally substituted with one, two, three or four substituents and said substituent is independently selected from
    a halogen atom, a cyano group, a hydroxy group, a $C(O)NR^5R^6$ group, a $NR^5R^6$ group,
    a $C_1$-$C_3$-alkoxy group,
    a $C_3$-$C_7$-cycloalkyl group which is optionally substituted with one or two substituents and said substituents are independently selected from a $C_1$-$C_3$-alkyl group, a oxo (=O) group, a hydroxy group, and a $C_1$-$C_3$-hydroxyalkyl group;
    a 3- to 7-membered heterocycloalkyl group which itself is optionally substituted
      with a $C_1$-$C_3$-alkyl group or an oxo (=O) group,
    a heteroaryl group, which itself is optionally substituted with a $C_1$-$C_3$-alkyl group
    a —$C_1$-$C_5$-alkylene-O—$C_1$-$C_5$-alkyl group,
    a —$C_1$-$C_5$-alkylene-S—$C_1$-$C_5$-alkyl group,
    a —$C_1$-$C_5$-alkylene-$NR^5$—$C_1$-$C_5$-alkyl group,
    a $C_3$-$C_6$-cycloalkyl group which is optionally substituted with a hydroxy group, and
    a 3- to 6-membered heterocycloalkyl group, which is optionally substituted with one or two substituents, said substituent independently selected from $C_1$-$C_3$-alkyl group and a hydroxy group, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^7$ is a hydrogen atom and $R^8$ is selected from,
  a $C_1$-$C_6$-alkyl group,
  which is optionally substituted with one, two, three or four substituents and said substituent is independently selected from
    a halogen atom, a cyano group, a hydroxy group, a $C(O)NR^5R^6$ group, a $NR^5R^6$ group,
    a $C_1$-$C_3$-alkoxy group,
    a $C_3$-$C_7$-cycloalkyl group which is optionally substituted with one or two substitutents and said substituents are independently selected from a $C_1$-$C_3$-alkyl group, a oxo (=O) group, a hydroxy group, and a $C_1$-$C_3$-hydroxyalkyl group;
    a 3- to 7-membered heterocycloalkyl group which itself is optionally substituted
      with a $C_1$-$C_3$-alkyl group or an oxo (=O) group,
    a heteroaryl group, which itself is optionally substituted with a $C_1$-$C_3$-alkyl group
    a —$C_1$-$C_5$-alkylene-O—$C_1$-$C_5$-alkyl group,
    a —$C_1$-$C_5$-alkylene-S—$C_1$-$C_5$-alkyl group,
    a —$C_1$-$C_5$-alkylene-$NR^5$—$C_1$-$C_5$-alkyl group,
    a $C_3$-$C_6$-cycloalkyl group which is optionally substituted with a hydroxy group, and
    a 3- to 6-membered heterocycloalkyl group, which is optionally substituted with one or two substituents, said substituent independently selected from $C_1$-$C_3$-alkyl group and a hydroxy group, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^7/R^8$ are independently selected from
  a hydrogen atom, with the proviso that $R^7$=$R^8$=hydrogen is excluded,
  a $C_1$-$C_6$-alkyl group, which is optionally substituted with one, two, three or four substituents and said substituent is independently selected from
    a halogen atom, a cyano group, a hydroxy group, a $C(O)NR^5R^6$ group, a $NR^5R^6$ group,
    a $C_1$-$C_3$-alkoxy group,
    a $C_3$-$C_7$-cycloalkyl group which is optionally further substituted with one or two substituents and substituents are independently selected from a $C_1$-$C_3$-alkyl group, a oxo (=O) group, a hydroxy group, and a $C_1$-$C_3$-hydroxyalkyl group;
    a 3- to 7-membered heterocycloalkyl group, comprising one, two or three heteroatoms which are independently selected from —O— and —$NR^9$—, which is optionally further substituted with a $C_1$-$C_3$-alkyl group,
    a heteroaryl group, which is optionally further substituted with a $C_1$-$C_3$-alkyl group
    a $C_3$-$C_7$-cycloalkyl group, which is optionally substituted with a hydroxy group, or a $C_1$-$C_3$-alkyl group and
    a 3- to 6-membered heterocycloalkyl group, which is optionally substituted with one or two substituents, said substituent independently selected from $C_1$-$C_3$-alkyl group and a hydroxy group, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^7$ is a hydrogen atom and $R^8$ is selected from,
  a $C_1$-$C_6$-alkyl group, which is optionally substituted with one, two, three or four substituents and said substituent is independently selected from
    a halogen atom, a cyano group, a hydroxy group, a $C(O)NR^5R^6$ group, a $NR^5R^6$ group,
    a $C_1$-$C_3$-alkoxy group,
    a $C_3$-$C_7$-cycloalkyl group which is optionally further substituted with one or two substituents and substituents are independently selected from a $C_1$-$C_3$-alkyl group, a oxo (=O) group, a hydroxy group, and a $C_1$-$C_3$-hydroxyalkyl group;
    a 3- to 7-membered heterocycloalkyl group, comprising one, two or three heteroatoms which are independently selected from —O— and —NR$^9$—, which is optionally further substituted with a $C_1$-$C_3$-alkyl group,
a heteroaryl group, which is optionally further substituted with a $C_1$-$C_3$-alkyl group
a $C_3$-$C_7$-cycloalkyl group, which is optionally substituted with a hydroxy group, or a $C_1$-$C_3$-alkyl group and
a 3- to 6-membered heterocycloalkyl group, which is optionally substituted with one or two substituents, said substituent independently selected from $C_1$-$C_3$-alkyl group and a hydroxy group, and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^7/R^8$ are independently selected from
a hydrogen atom, with the proviso that $R^7$=$R^8$=hydrogen is excluded,
a $C_1$-$C_6$-alkyl group, which is optionally substituted with one, two, three or four substituents and said substituent is independently selected from
a halogen atom, a cyano group, a hydroxy group, a NR$^5$R$^6$ group,
a $C_1$-$C_3$-alkoxy group,
a $C_3$-$C_7$-cycloalkyl group which is optionally further substituted with one or two substituents and said substituents are independently selected from a $C_1$-$C_3$-alkyl group, a oxo (=O) group, a hydroxy group, and a $C_1$-$C_3$-hydroxyalkyl group;
a 3- to 7-membered heterocycloalkyl group, comprising one, two or three heteroatoms which are independently selected from —O— and —NR$^9$—, which is optionally further substituted with a $C_1$-$C_3$-alkyl group,
a heteroaryl group, which is optionally further substituted with a $C_1$-$C_3$-alkyl group
a $C_3$-$C_7$-cycloalkyl group, which is optionally substituted with a hydroxy group, or a $C_1$-$C_3$-alkyl group and
a 3- to 6-membered heterocycloalkyl group, which is optionally substituted with one or two substituents, said substituent independently selected from $C_1$-$C_3$-alkyl group and a hydroxy group,
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^7$ is a hydrogen atom and $R^8$ is selected from,
a $C_1$-$C_6$-alkyl group, which is optionally substituted with one, two, three or four substituents and said substituent is independently selected from
a halogen atom, a cyano group, a hydroxy group, a NR$^5$R$^6$ group,
a $C_1$-$C_3$-alkoxy group,
a $C_3$-$C_7$-cycloalkyl group which is optionally further substituted with one or two substituents and said substituents are independently selected from a $C_1$-$C_3$-alkyl group, a oxo (=O) group, a hydroxy group, and a $C_1$-$C_3$-hydroxyalkyl group;
a 3- to 7-membered heterocycloalkyl group, comprising one, two or three heteroatoms which are independently selected from —O— and —NR$^9$—, which is optionally further substituted with a $C_1$-$C_3$-alkyl group,
a heteroaryl group, which is optionally further substituted with a $C_1$-$C_3$-alkyl group a $C_3$-$C_7$-cycloalkyl group, which is optionally substituted with a hydroxy group, or a $C_1$-$C_3$-alkyl group and
a 3- to 6-membered heterocycloalkyl group, which is optionally substituted with one or two substituents, said substituent independently selected from $C_1$-$C_3$-alkyl group and a hydroxy group,
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^7/R^8$ are independently selected from
a hydrogen atom, with the proviso that $R^7$=$R^8$=hydrogen is excluded,
a $C_1$-$C_6$-alkyl group, which is optionally substituted with one, two, three or four substituents and said substituent is independently selected from
a halogen atom, a hydroxy group,
a $C_1$-$C_3$-alkoxy group,
a $C_3$-$C_6$-cycloalkyl group which is optionally further substituted with one or two substituents and said substituents are independently selected from a $C_1$-$C_3$-alkyl group and a $C_1$-$C_3$-hydroxyalkyl group;
a 4- to 6-membered heterocycloalkyl group, comprising one, two or three heteroatoms which are independently selected from —O— and —NR$^9$—, which is optionally further substituted with a $C_1$-$C_3$-alkyl group,
a heteroaryl group, which is optionally further substituted with a $C_1$-$C_3$-alkyl group;
a $C_3$-$C_6$-cycloalkyl group, which is optionally substituted with a hydroxy group, or a $C_1$-$C_3$-alkyl group
a 3- to 6-membered heterocycloalkyl group, which is optionally substituted with one or two substituents, said substituent independently selected from $C_1$-$C_3$-alkyl group and a hydroxy group, and
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^7/R^8$ are independently selected from
a hydrogen atom, with the proviso that $R^7$=$R^8$=hydrogen is excluded,
a $C_1$-$C_6$-alkyl group, which is optionally substituted with one, two, three or four substituents and said substituent is independently selected from
a halogen atom, a hydroxy group,
a $C_1$-$C_3$-alkoxy group,
a $C_3$-$C_6$-cycloalkyl group which is optionally further substituted with one or two substituents and said substituents are independently selected from a $C_1$-$C_3$-alkyl group and a $C_1$-$C_3$-hydroxyalkyl group;
a 4- to 6-membered heterocycloalkyl group, comprising one, two or three heteroatoms which are independently selected from —O— and —NR$^9$—, which is optionally further substituted with a $C_1$-$C_3$-alkyl group,
a heteroaryl group, which is optionally further substituted with a $C_1$-$C_3$-alkyl group;
a $C_3$-$C_6$-cycloalkyl group, which is optionally substituted with a hydroxy group, or a $C_1$-$C_3$-alkyl group
a 3- to 6-membered heterocycloalkyl group, which is optionally substituted with one or two substituents, said substituent independently selected from $C_1$-$C_3$-alkyl group and a hydroxy group, and and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^7/R^8$ are independently selected from
a hydrogen atom, with the proviso that $R^7=R^8$=hydrogen is excluded,
a $C_1$-$C_6$-alkyl group,
which is optionally substituted with one, two, three or four substituents and said substituent is independently selected from
a halogen atom, a cyano group, and a hydroxy group,
a $C_1$-$C_3$-alkoxy group,
a $C_3$-$C_7$-cycloalkyl group which is optionally substituted with one or two substitutents and said substituents are independently selected from a $C_1$-$C_3$-alkyl group, a hydroxy group, and a $C_1$-$C_3$-hydroxyalkyl group;
a 3- to 7-membered heterocycloalkyl group which itself is optionally substituted with a $C_1$-$C_3$-alkyl group
a heteroaryl group, which is optionally further substituted with a $C_1$-$C_3$-alkyl group;
a $C_3$-$C_6$-cycloalkyl group, which is optionally substituted with a hydroxy group, and
a 3- to 6-membered heterocycloalkyl group, which is optionally substituted with one or two substituents said substituent independently selected from $C_1$-$C_3$-alkyl group and a hydroxy group,
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^7$ is a hydrogen atom and $R^8$ is selected from,
a $C_1$-$C_6$-alkyl group,
which is optionally substituted with one, two, three or four substituents and said substituent is independently selected from
a halogen atom, a cyano group, and a hydroxy group,
a $C_1$-$C_3$-alkoxy group,
a $C_3$-$C_7$-cycloalkyl group which is optionally substituted with one or two substitutents and said substituents are independently selected from a $C_1$-$C_3$-alkyl group, a hydroxy group, and a $C_1$-$C_3$-hydroxyalkyl group;
a 3- to 7-membered heterocycloalkyl group which itself is optionally substituted with a $C_1$-$C_3$-alkyl group
a heteroaryl group, which is optionally further substituted with a $C_1$-$C_3$-alkyl group;
a $C_3$-$C_6$-cycloalkyl group, which is optionally substituted with a hydroxy group, and
a 3- to 6-membered heterocycloalkyl group, which is optionally substituted with one or two substituents said substituent independently selected from $C_1$-$C_3$-alkyl group and a hydroxy group,
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
R/R$ are independently selected from
a hydrogen atom, with the proviso that $R^7=R^8$=hydrogen is excluded,
a $C_1$-$C_6$-alkyl group, which is optionally substituted with one or two, three or four substituents and said substituent is independently selected from
a halogen atom, a hydroxy group,
a $C_1$-$C_3$-alkoxy group,
a $C_3$-$C_5$-cycloalkyl group which is optionally further substituted with one or two substituents and said substituents are independently selected from a $C_1$-$C_3$-alkyl group and a $C_1$-$C_3$-hydroxyalkyl group;
a 5- to 6-membered heterocycloalkyl group, comprising one, or two heteroatoms which are independently selected from —O— and —$NR^9$—, which is optionally further substituted with a $C_1$-$C_3$-alkyl group,
a heteroaryl group, which is optionally further substituted with a $C_1$-$C_3$-alkyl group;
a $C_3$-$C_6$-cycloalkyl group, which is optionally substituted with a hydroxy group, or a $C_1$-$C_3$-alkyl group
a 4- to 5-membered heterocycloalkyl group, which is optionally substituted with one or two substituents, said substituent independently selected from $C_1$-$C_3$-alkyl group and a hydroxy group, and
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^7$ a hydrogen atom and R is selected from,
a $C_1$-$C_6$-alkyl group, which is optionally substituted with one or two, three or four substituents and said substituent is independently selected from
a halogen atom, a hydroxy group,
a $C_1$-$C_3$-alkoxy group,
a $C_3$-$C_5$-cycloalkyl group which is optionally further substituted with one or two substituents and said substituents are independently selected from a $C_1$-$C_3$-alkyl group and a $C_1$-$C_3$-hydroxyalkyl group;
a 5- to 6-membered heterocycloalkyl group, comprising one, or two heteroatoms which are independently selected from —O— and —$NR^9$—, which is optionally further substituted with a $C_1$-$C_3$-alkyl group,
a heteroaryl group, which is optionally further substituted with a $C_1$-$C_3$-alkyl group;
a $C_3$-$C_6$-cycloalkyl group, which is optionally substituted with a hydroxy group, or a $C_1$-$C_3$-alkyl group
a 4- to 5-membered heterocycloalkyl group, which is optionally substituted with one or two substituents, said substituent independently selected from $C_1$-$C_3$-alkyl group and a hydroxy group, and
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^7/R^8$ are independently selected from
a hydrogen atom, with the proviso that $R^7=R^8$=hydrogen is excluded,
a $C_1$-$C_3$-alkyl group, which is optionally substituted with one two or four substituents and said substituent is independently selected from a halogen atom, a hydroxy group, and a methoxy group,
and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^7$ a hydrogen atom and $R^8$ is selected from,
a $C_1$-$C_3$-alkyl group, which is optionally substituted with one two or four substituents and said substituent is independently selected from a halogen atom, a hydroxy group, and a methoxy group, and stereoisomers, tautomers, N-oxides, hydrates, solvates, and salts thereof, and mixtures of same.

In yet a further embodiment of the first aspect or any embodiment derived therefrom, the present invention provides compounds of formula (I), supra, in which:
$R^7$ is a hydrogen atom and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^7/R^8$ are independently selected from
a hydrogen atom, with the proviso that $R^7=R^8$=hydrogen is excluded,
and a $C_1$-$C_6$-alkyl group and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^7/R^8$ are independently selected from
a hydrogen atom, with the proviso that $R^7=R^8$=hydrogen is excluded,
and a $C_1$-$C_6$-alkyl group which is optionally substituted one or two times with a substituent independently selected from a hydroxy group, a trifluoromethyl group and a methoxy group and stereoisomers, tautomers, N-oxides, hydrates, solvates, and salts thereof, and mixtures of same.

In another embodiment of the first aspect or any embodiment derived therefrom, the present invention provides compounds of formula (I), supra, in which:
$R^7/R^8$ are independently selected from
a hydrogen atom, with the proviso that $R^7=R^8$=hydrogen is excluded,
and a $C_1$-$C_4$-alkyl group which is optionally substituted one or two times with a substituent independently selected from a hydroxy group and a trifluoromethyl group and stereoisomers, tautomers, N-oxides, hydrates, solvates, and salts thereof, and mixtures of same.

In a further embodiment of the first aspect or any embodiment derived therefrom, the present invention provides compounds of formula (I), supra, in which: $R^9$ is a bond whereby said bond constitutes the connection from the nitrogen atom to which $R^9$ is bound to the rest of the molecule.

In another aspect, the invention provides a pharmaceutical composition containing one or more pharmaceutically acceptable carriers or excipients and a compound of formula (I)
or stereoisomers, tautomers, N-oxides, hydrates, solvates, salts thereof, or mixtures of same.

In yet another aspect, the invention provides a pharmaceutical composition containing one or more pharmaceutically acceptable carriers or excipients and a compound of formula (I)
a pharmaceutically acceptable salt or prodrug thereof.

"Reference" in the context of this invention means an average expression in a representative panel of tumor cells or tumor cell lines.

In various embodiments of any aspect delineated herein, the cancer is responsive to a PDE3A- and/or PDE3B-SLFN12 complex modulator.

In various embodiments, the subject has been diagnosed with a cancer responsive to a PDE3A- and/or PDE3B-SLFN12 complex modulator.

In various embodiments of any aspect delineated herein, the cancer is brain cancer (especially glioma, more specifically glioblastoma, astrocytoma), breast cancer (especially ductal carcinoma and adenocarcinoma), cervical cancer, AML (especially erythroleucemia), lung cancer (especially NSCLC adenocarcinoma and SCLC), skin cancer (especially melanoma), oesophagus cancer (especially squamous cell carcinoma), ovarian cancer, (especially teratocarcinoma, adenocarcinoma), pancreas cancer and prostatic cancer.

In various embodiments of any aspect delineated herein, the cancer is brain cancer, breast cancer, cervical cancer, AML, lung cancer, skin cancer, oesophagus cancer, ovarian cancer, pancreas cancer and prostatic cancer In various embodiments, the cancer is a melanoma, endometrium-, lung-, hematopoetic-/lymphoid-ovarian-, cervical, soft-tissue sarcoma, leiomyosarcoma, urinary tract-, pancreas-, thyroid-, kidney-, glioblastoma-, or breast cancer.

In various embodiments, the cancer is a skin cancer, especially melanoma, lung adenocarcinoma or a cervical cancer.

In various embodiments of any aspect delineated herein, the PDE3A- and/or PDE3B-SLFN12 complex modulator is administered orally.

In various embodiments of any aspect delineated herein, the PDE3A- and/or PDE3B-SLFN12 complex modulator is administered by intravenous injection.

The invention provides methods for treating subjects having cancer identified as responsive to treatment with a PDE3A- and/or PDE3B-SLFN12 complex modulator of formula (I) by detecting co-expression of PDE3A and/or PDE3B and Schlafen 12 (SLFN12) polynucleotides or polypeptides and/or a lack of decrease in expression of CREB3L1 polynucleotides or polypeptides in the cancer.

Compositions and articles defined by the invention were isolated or otherwise manufactured in connection with the examples provided below. Other features and advantages of the invention will be apparent from the detailed description, and from the claims.

In a particular further embodiment of the first aspect, the present invention provides combinations of two or more of the above mentioned embodiments under the heading "further embodiments of the first aspect of the present invention".

The present invention provides any sub-combination within any embodiment or aspect of the present invention of compounds of general formula (I), supra.

The present invention provides any sub-combination within any embodiment or aspect of the present invention of intermediate compounds of general formula (I).

The present invention provides the compounds of general formula (I) which are disclosed in the Example Section of this text, infra.

Kits

The invention further provides kits comprising a compound of formula (I) and/or means for characterizing the responsiveness or resistance of a subject to PDE3A- and/or PDE3B-SLFN12 complex modulator, especially to compounds of formula (I) treatment.

Also provided herein are kits that can include the compound of formula (I) in form of a therapeutic composition containing an effective amount of said compound in e.g., a unit dosage form.

In some embodiments, the kit comprises a sterile container which includes a therapeutic or diagnostic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

In one embodiment, if desired, the kit further comprises instructions for measuring PDE3A and/or PDE3B and SLFN12 and/or instructions for administering the PDE3A- and/or PDE3B-SLFN12 complex modulator to a subject having a malignancy, e.g., a malignancy selected as responsive to PDE3A- and/or PDE3B-SLFN12 complex modulator treatment.

In particular embodiments, the instructions include at least one of the following: description of the therapeutic agent; dosage schedule and administration for treatment or prevention of malignancy or symptoms thereof; precautions; warnings; indications; counter-indications; over dosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of the invention.

General Synthesis of the Compounds of Formula (I)

The compounds according to the invention of general formula (I) can be prepared according to the following schemes 1 through 9. The schemes and procedures described below illustrate synthetic routes to the compounds of general formula (I) of the invention and are not intended to be limiting. It is clear to the person skilled in the art that the order of transformations as exemplified in schemes 1 through 9 can be modified in various ways. The order of transformations exemplified in these schemes is therefore not intended to be limiting. In addition, interconversion of any of the substituents, $R^1$, $R^2$, $R^3$, or $R^4$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Specific examples are described in the subsequent paragraphs.

Seven routes for the preparation of compounds of general formula (I) are described in schemes 1 through 9.

Synthesis Routes

Route 1: Synthesis of Compounds of Formula (I) by Transition Metal Catalyzed Reaction, Such as Suzuki Couplings, Negishi Couplings, Kumada Couplings, Stille Couplings, Buchwald-Hartwig Couplings, Preferentially Suzuki Couplings, or by Nucleophilic Aromatic Substitution Part I: Synthesis of Intermediate Compounds of Formula (II)

Scheme 1

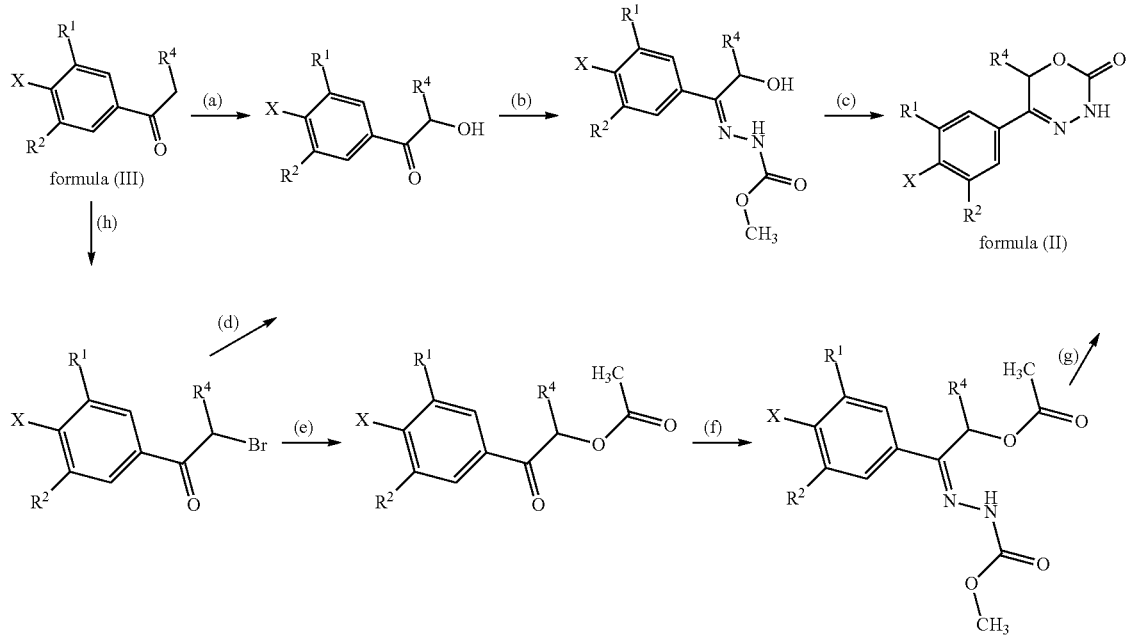

Scheme 1: Route for the preparation of intermediate compounds of formula (II), in which $R^1$, $R^2$ and $R^4$ have the meaning as defined supra; the meaning of X is as defined below in context of Scheme 2 and the paragraphs (i), (j), (k) for compounds of formula (II).

(a) Hydroxy(tosyloxy)iodo)benzene, DMSO, water, RT, 18 h; or iodine, DMSO, 60° C., 18 h. For the preparation of the starting material for steps (a) and (h) see e.g. Scheme 3.
(b) $H_2NNHCOOCH_3$, HCl (aq), MeOH, RT, 5 h;
(c) potassium carbonate, acetonitrile, 60° C., 18 h or NaOEt/EtOH, 0° C., 10 min, or NaH, EtOH, 0° C. 10 min;
(d) sodium formate, sodium hydrogencarbonate, $CH_3CN$, water, 65° C., 24 h;
(e) potassium acetate, potassium iodide, 18 h, RT;
(f) $H_2NNHCOOCH_3$, HCl (aq), MeOH, RT, 5-18 h;
(g) potassium carbonate, $CH_3CN$, 60° C., 18 h or NaOEt/EtOH, 0° C. 10 min, or NaH, EtOH, 0° C. 10 min;
(h) acetic acid, bromine, hydrogen bromide, 18 h, RT; for the preparation of the starting material for steps (a) and (h) see e.g. Scheme 3.

Compounds of formula (II) containing chiral centers can be optionally separated by methods known to the person skilled in the art, such as e.g. chiral chromatography, to obtain individual enantiomers or diastereomers.

Part II: Conversion of the Intermediate Compounds of Formula (II) into Compounds of General Formula (I):

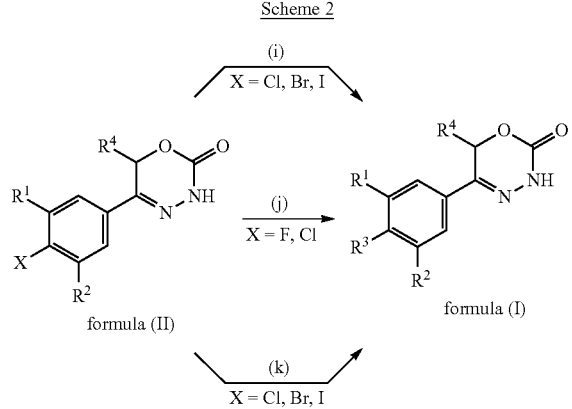

Scheme 2

(j), (k): $R^3$ = $NR^7R^8$, opt. subst. N-linked heterocycloalkyl, partially unsaturated heterocycloalkyl or heteroaryl
(i): $R^3$ = optional substituted alkyl, alkenyl, cycloalkenyl, heterocycloalkyl, part. unsaturated heterocyclalkyl, aryl, heteroaryl Scheme 2: Route for the preparation of compounds of general formula (I) via formula (II) in which $R^1$, $R^2$ and $R^4$ have the meaning as defined supra, in which $R^3$ in general formula (I) is optionally substituted alkyl, alkenyl, cycloalkenyl, heterocycloalkyl, partially unsaturated heterocycloalkyl, aryl, or heteroaryl, as defined in more detail below in paragraph (i); or $R^3$ is $NR^7R^8$, or optionally substituted N-linked heterocycloalkyl, partially unsaturated heterocycloalkyl or heteroaryl, as defined in more detail below in paragraph (j) and (k), respectively; and in which the terms "N-linked heterocycloalkyl", "N-linked, partially unsaturated heterocycloalkyl" and "N-linked heteroaryl" refer to a 3- to 9-membered heterocycloalkyl, a 3- to 9-membered partially unsaturated heterocycloalkyl, or a heteroaryl group, as defined for $R^3$ supra, which is bonded to the rest of the molecule via a nitrogen atom which constitutes a ring atom of said heterocycloalkyl, partially unsaturated heterocycloalkyl or heteroaryl group.

(i) Route 1 Via Suzuki Coupling with Organoboron Compounds

Compounds of general formula (I), in which $R^3$ is $R^x$ as defined below for the formulae (IIIa), (IIIb), and (IIIc), can be obtained by reacting intermediate compounds of formula (II), in which X is Cl, Br, I, (as reflected in scheme 2), or a group selected from ($C_1$-$C_4$-alkylsulfonyl)oxy, ($C_1$-$C_4$-fluoroalkylsulfonyl)oxy and (phenylsulfonyl)oxy, the phenyl present in (phenylsulfonyl)oxy being optionally substituted with one, two, three, four or five substituents, each of them independently selected from halogen, nitro, cyano, $C_1$-$C_4$-alkyl and $C_1$-$C_4$-alkoxy;

$R^1$ or $R^2$ are as defined supra but are different from Cl, Br, I, and $R^4$ is as defined supra, with boronic acids $RB(OH)_2$ (formula (IIIa)), or boronic esters $R^xB(OR^y)_2$ (formula (IIb)), or tetrafluoroborate salts $R^xBF_4$ (formula (IIIc)), in the presence of a base, such as e.g. potassium carbonate or potassium acetate, a palladium catalyst, such as e.g. dichlorobis(triphenylphosphine)palladium, tetrakistriphenylphosphinepalladium (0), palladium(II) acetate/tricyclohexylphosphine, tris(dibenzylideneacetone)dipalladium, bis(diphenylphosphineferrocenyl)palladium(II) chloride, 1,3-bis(2,6-diisopropylphenyl)imidazol-2-ylidene(1,4-naphthoquinone) palladium dimer, allyl(chloro)(1,3-dimesityl-1,3-dihydro-2H-imidazol-2-ylidene)palladium, palladium(II) acetate/dicyclohexyl(2',4',6'-triisopropyl-biphenyl-2-yl)phosphine, [1,1-bis(diphenylphosphino)ferrocene]palladium (II) chloride monodichloromethane adduct, [1,1'-Bis(diphenylphosphino)ferrocene]dichloropalladium(II), chloro(2-dicyclohexylphosphino-2',4',6'-triisopropyl-1,1'-biphenyl)[2-(2'-amino-1,1'-biphenyl)]palladium(II), palladium (II) acetate, (2-dicyclohexylphosphino-2',4',6'-triisopropyl-1,1'-biphenyl)[2-(2'-amino-1,1'-biphenyl)] palladium(II), or chloro(2-dicyclohexylphosphino-2',4',6'-triisopropyl-1,1'-biphenyl)[2-(2'-amino-1,1'-biphenyl)] palladium(II), as a preferred embodiment chloro(2-dicyclohexylphosphino-2',4',6'-triisopropyl-1,1'-biphenyl)[2-(2'-amino-1,1'-biphenyl)]palladium(II), and, optionally, an additional ligand, such as e.g. 2-(dicyclohexylphosphino)-2',4',6'-triisopropylbiphenyl, in a solvent, such as e.g. dioxane, toluene, or water, or a mixture thereof, under nitrogen or argon atmosphere, at 80° C.-120° C., for 2 h-7 d;

whereby $R^x$ is a $C_1$-$C_6$-alkyl group which is optionally substituted with one or two substituents and each substituent is independently selected from a hydroxy group, a $C_1$-$C_4$-alkoxy group, and a 3- to 7-membered heterocycloalkyl group; preferably a methyl group which is optionally substituted with a 3 to 7 membered heterocycloalkyl group, a $C_2$-$C_6$-alkenyl group which is optionally substituted with an $C_1$-$C_4$-alkoxy group, a $C_5$-$C_9$-cycloalkenyl group, which is optionally substituted with a hydroxy group, a 3- to 9-membered heterocycloalkyl group, comprising one, two or three heteroatoms which are independently selected from —O—, —S—, —S(O)—, $S(O)_2$, and —$NR^9$—, and said heterocycloalkyl group optionally further comprising a bridging group selected from —O—, —NR$^9$—, —CH$_2$—, —CH$_2$—CH$_2$—, —O—CH$_2$—, —CH$_2$—O—, —NR$^9$—CH$_2$—, and —CH$_2$—NR$^9$—;

and said heterocycloalkyl group is optionally substituted with one, two or three substituents and each substituent is independently selected from
- a halogen atom;
- a oxo(=O) group;
- a cyano group;
- a hydroxy group;
- a C$_1$-C$_3$-alkyl group which is optionally further substituted with a hydroxy group;
- a C$_1$-C$_3$-haloalkyl group;
- a C$_1$-C$_3$-alkoxy group;
- a C$_1$-C$_3$-haloalkoxy group;
- a C(O)NR$^5$R$^6$ group and
- a NR$^5$R$^6$ group,
- a 5- to 9-membered heterocycloalkyl group which is partially unsaturated and optionally substituted with one, two or three substituents and each substituent is independently selected from an oxo group (=O), a C$_1$-C$_3$-alkyl group a —C(O)R$^5$R$^6$ group and a halogen atom,
- an aryl group which is optionally substituted with one, two, three or four substituents and each substituent is independently selected from a halogen atom, a hydroxy group, a cyano group, a C$_1$-C$_3$-alkyl group, a C$_1$-C$_3$-haloalkyl group, a C$_1$-C$_3$-alkoxy group, a C$_1$-C$_3$-haloalkoxy group, and a NR$^5$R$^6$ group,
- a mono- or bicyclic heteroaryl group which is optionally substituted with one, two or three substituents and each substituent is independently selected from a halogen atom, a C$_1$-C$_3$-alkyl group, a cyano group, a C$_1$-C$_3$-haloalkyl group, a C$_1$-C$_3$-alkoxy group, a hydroxy group, and a NR$^5$R$^6$ group, with the proviso that said monocyclic heteroaryl group is not a pyridin-4-yl group; R$^y$ is C$_1$-C$_6$-alkyl, or the two residues R$^y$ together are a C$_2$-C$_6$-alkylene group, preferably —C(CH$_3$)$_2$—C(CH$_3$)$_2$— to form a pinacol ester.

As readily understood by the person skilled in the art, compounds of general formula (I) prepared e.g. by a Suzuki coupling, in which R$^3$ features a group comprising an olefinic double bond (e.g. if R$^3$ is alkenyl, cycloalkenyl or partially unsaturated heterocycloalkyl), can be readily converted into compounds in which R$^3$ features the corresponding saturated group (e.g. alkyl, cycloalkyl, heterocycloalkyl) by methods known to the person skilled in the art, such as e.g. catalytic hydrogenolysis using a suitable catalyst, such as e.g. palladium on carbon.

(j) Route 1 via nucleophilic aromatic substitution to introduce R$^3$ substituents selected from —NR$^7$R$^8$, a N-linked heterocycloalkyl group, a partially unsaturated N-linked heterocycloalkyl group and a N-linked heteroaryl group, whereby the term "N-linked" is to be understood as described in context of Scheme 2, Compounds of general formula (I), in which R$^3$ is selected from —NR$^7$R$^8$, a N-linked 3- to 9-membered heterocycloalkyl group, a N-linked, partially unsaturated 3- to 9-membered heterocyloalkyl group, and a N-linked heteroaryl group, whereby the term "N-linked" is to be understood as described in context of Scheme 2, and in which the terms "3- to 9-membered heterocycloalkyl", "partially unsaturated 3- to 9-membered heterocycloalkyl", and "heteroaryl" are constituted and optionally substituted as defined for R$^3$, supra, can be obtained by reacting intermediate compounds of formula (II), in which R$^4$ has the meaning as defined supra, X is F or Cl (as reflected in scheme 2), and if X is Cl, R$^1$ or R$^2$ can not be F; preferably X is F;

R$^1$ and R$^2$ have the meaning as defined supra, with the proviso that if X is Cl, R$^1$ or R$^2$ can not be F, and with the proviso that at least one of R$^1$ and R$^2$ exerts an electron withdrawing effect; preferably, R$^1$ is selected from fluorine, a cyano group, and —CF$_3$, and R$^2$ is hydrogen or fluorine; more preferably, R$^1$ is —CF$_3$ and R$^2$ is hydrogen;

with a corresponding amine, optionally as a free base or as a salt, such as e.g. a hydrochloride salt, selected from HNR$^7$R$^8$ and a cyclic amine featuring one N—H as a ring atom, said cyclic amine being selected from a 3- to 9-membered heterocycloalkane, a partially unsaturated 3- to 9-membered heterocyloalkane, and a heteroarene containing one N—H as a ring atom, respectively, optionally in the presence of a base, such as e.g. triethylamine, DIPEA, or cesium carbonate, in an inert solvent, such as e.g. CH$_3$CN, DMF or DMSO, at optionally elevated temperatures ranging from RT to 160° C., preferably from 60° C. to 150° C., for 2 h-7 d;

whereby

R$^7$/R$^8$ are independently selected from
- a hydrogen atom, with the proviso that R$^7$=R$^8$=hydrogen is excluded,
- a C$_1$-C$_6$-alkyl group,
- which is optionally substituted with one, two, three or four substituents and said substituent is independently selected from
  - a halogen atom, a cyano group, a hydroxy group, a C(O)NR$^5$R$^6$ group, a NR$^5$R$^6$ group,
  - a C$_1$-C$_3$-alkoxy group,
  - a C$_3$-C$_7$-cycloalkyl group which is optionally substituted with one or two substitutents and said substituents are independently selected from a C$_1$-C$_3$-alkyl group, a oxo (=O) group, a hydroxy group, and a C$_1$-C$_3$-hydroxyalkyl group;
  - a 3- to 7-membered heterocycloalkyl group which itself is optionally substituted
  - with a C$_1$-C$_3$-alkyl group or an oxo (=O) group,
  - a heteroaryl group, which itself is optionally substituted with a C$_1$-C$_3$-alkyl group;
- a —C$_1$-C$_5$-alkylene-O—C$_1$-C$_5$-alkyl group,
- a —C$_1$-C$_5$-alkylene-S—C$_1$-C$_5$-alkyl group,
- a —C$_1$-C$_5$-alkylene-NR$^5$—C$_1$-C$_5$-alkyl group,
- a C$_3$-C$_6$-cycloalkyl group which is optionally substituted with a hydroxy group, and
- a 3- to 6-membered heterocycloalkyl group which is optionally substituted one or two substituents, said substituent independently selected from C$_1$-C$_3$-alkyl group and a hydroxy group, (k) Alternative Route via transition metal catalyzed, preferably palladium catalyzed amination, to introduce R$^3$ substituents selected from —NR$^7$R$^8$, a N-linked heterocycloalkyl group, a partially unsaturated N-linked heterocyloalkyl group and a N-linked heteroaryl group, whereby the term "N-linked" is to be understood as described in context of Scheme 2, Compounds of general formula (I), in which R$^3$ is selected from —NR$^7$R$^8$, a N-linked 3- to 9-membered heterocycloalkyl group, a N-linked, partially unsaturated 3- to 9-membered heterocycloalkyl group, and a N-linked heteroaryl group, whereby the term "N-linked" is to be understood as described in context of Scheme 2, and in which the terms "3- to 9-membered heterocycloalkyl", "partially unsaturated 3- to 9-membered heterocyloalkyl", and "heteroaryl" are constituted and optionally substituted as defined for $R^3$, supra, can be obtained by reacting intermediate compounds of formula (II), in which X is Cl, Br, I, (as reflected in scheme 2), or a group selected from ($C_1$-$C_4$-alkylsulfonyl)oxy,
($C_1$-$C_4$-fluoroalkylsulfonyl)oxy and (phenylsulfonyl)oxy, the phenyl present in (phenylsulfonyl)oxy being optionally substituted with one, two, three, four or five substituents, each of them independently selected from halogen, nitro, cyano, $C_1$-$C_4$-alkyl and $C_1$-$C_4$-alkoxy;

$R^1$ or $R^2$ are as defined supra but are different from C, Br, I; preferably, $R^1$ is —$CF_3$ and $R^2$ is hydrogen;

$R^4$ has the meaning as defined supra, with a corresponding amine, optionally as a free base or as a salt, such as e.g. a hydrochloride salt, selected from $HNR^7R^8$ and a cyclic amine featuring one N—H as a ring atom, said cyclic amine being selected from a 3- to 9-membered heterocycloalkane, a partially unsaturated 3- to 9-membered heterocyloalkane and a heteroarene containing one N—H as a ring atom, respectively, in the presence of a base, such as e.g. potassium phosphate or cesium carbonate, a palladium catalyst, such as e.g. tris(dibenzylideneacetone)dipalladium(0), a ligand, such as e.g. 2-(dicyclohexylphosphino)-2',4',6'-triisopropyl-1,1'-biphenyl or 2,2'-bis(diphenylphosphino)-1,1'-binaphthalene, in an inert solvent, such as e.g. dioxane or toluene, at elevated temperatures ranging from 60-160° C., for 2 h-7 d; whereby $R^7$/$R^8$ are independently selected from
  a hydrogen atom, with the proviso that $R^7$=$R^8$=hydrogen is excluded,
  a $C_1$-$C_6$-alkyl group,
  which is optionally substituted with one, two, three or four substituents and said substituent is independently selected from
    a halogen atom, a cyano group, a hydroxy group, a C(O)$NR^5R^6$ group, a $NR^5R^6$ group,
    a $C_1$-$C_3$-alkoxy group,
    a $C_3$-$C_7$-cycloalkyl group which is optionally substituted with one or two substitutents and said subtituents are independently selected from a $C_1$-$C_3$-alkyl group, a oxo (=O) group, a hydroxy group, and a $C_1$-$C_3$-hydroxyalkyl group;
    a 3- to 7-membered heterocycloalkyl group which itself is optionally substituted with a $C_1$-$C_3$-alkyl group or an oxo (=O) group,
    a heteroaryl group, which itself is optionally substituted with a $C_1$-$C_3$-alkyl group;
  a —$C_1$-$C_5$-alkylene-O—$C_1$-$C_5$-alkyl group,
  a —$C_1$-$C_5$-alkylene-S—$C_1$-$C_5$-alkyl group,
  a —$C_1$-$C_5$-alkylene-$NR^5$—$C_1$-$C_5$-alkyl group,
  a $C_3$-$C_6$-cycloalkyl group which is optionally substituted with a hydroxy group, and a 3- to 6-membered heterocycloalkyl group which is optionally substituted one or two substituents, said substituent independently selected from $C_1$-$C_3$-alkyl group and a hydroxy group, The thus obtained compounds of formula (I) containing chiral centers can be optionally separated by chiral chromatography to obtain individual enantiomers or diastereomers.

Route 2

Part I: Synthesis of Intermediate Compounds of Formula (III) from Compounds of Formula (IV):

Scheme 3

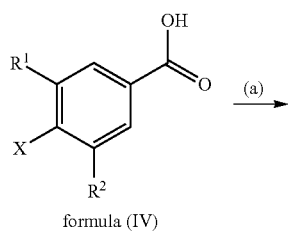

formula (IV)

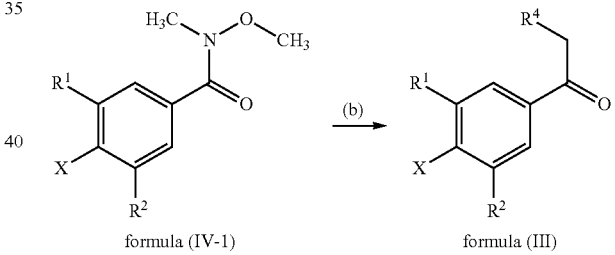

formula (IV-1)    formula (III)

Scheme 3: Route for the preparation of intermediate compounds of formula (III) from compounds of formula (IV), in which $R^1$ and $R^2$ have the meaning as defined supra. Benzoic acids of formula (IV) are well known to the person skilled in the art and are commercially available in considerable structural variety.

Step (a) (IV) to (IV-1)

A compound of formula (IV) and oxalyl chloride, in a solvent such as e.g. DMF/DCM, are reacted at a temperature range of 0° C. to RT, for 1 h-20 h, then HN(OCH$_3$)CH$_3$.HCl, Et$_3$N/CH$_2$Cl$_2$, is added at RT, and the mixture is subsequently reacted for 1 h-3 d, Step (b) (IV-1) to (III)

A compound (IV-1) and $R^4$CH$_2$MgBr, in which $R^4$ is as defined supra, in a solvent such as e.g. THF, are reacted at 0° C. to RT, for 1 h-20 h, in order to obtain an intermediate compound of formula (III);

Part II: Conversion of Intermediate Compounds of Formula (III) into Compounds of General Formula (I)

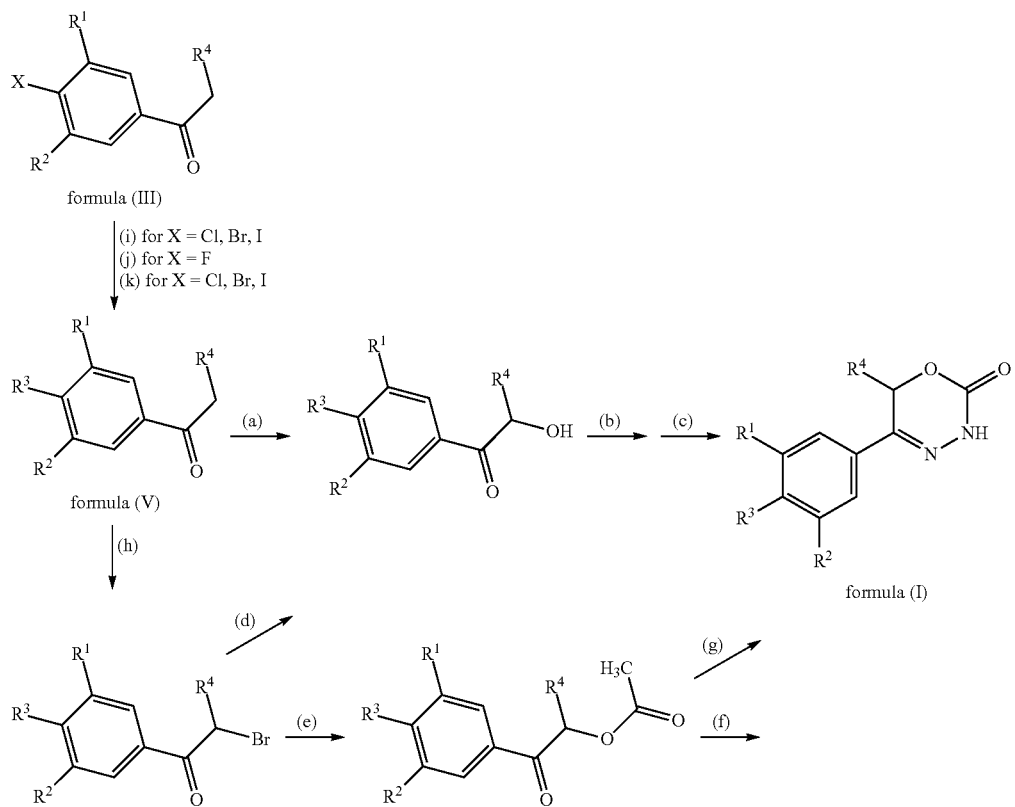

Scheme 4: Route for the preparation of compounds of general formula (I) from intermediate compounds of formula (II) via intermediate compounds of formula (V), in which $R^1$, $R^2$, $R^3$, and $R^4$ have the meaning as defined supra.

Intermediate compounds of formula (III) can be converted into intermediate compounds of formula (V) as described in more detail in the subsequent paragraphs (i), (j) and (k):
(i) Route 1 Via Suzuki Coupling with Organoboron Compounds Intermediate compounds of formula (V), in which $R^3$ is $R^x$ as defined below for the formulae (IIIa), (IIIb), and (IIIc), can be obtained by reacting intermediate compounds of formula (III), in which X is Cl, Br, I, (as reflected in scheme 2), or a group selected from $(C_1$-$C_4$-alkylsulfonyl)oxy, $(C_1$-$C_4$-fluoroalkylsulfonyl)oxy and (phenylsulfonyl)oxy, the phenyl present in (phenylsulfonyl)oxy being optionally substituted with one, two, three, four or five substituents, each of them independently selected from halogen, nitro, cyano, $C_1$-$C_4$-alkyl and $C_1$-$C_4$-alkoxy;

$R^1$ or $R^2$ are as defined supra but are different from Cl, Br, I, and $R^4$ is as defined supra, with boronic acids $R_xB(OH)_2$ (formula (IIIa)), or boronic esters $RB(OR^y)_2$ (formula (IIIb)), or tetrafluoroborate salts $R^xBF_4$ (formula (IIIc)), in the presence of a base, such as e.g. potassium carbonate or potassium acetate, a palladium catalyst, such as e.g. dichlorobis(triphenylphosphine)palladium, tetrakistriphenylphosphinepalladium (0), palladium(II) acetate/triscyclohexylphosphine, tris(dibenzylideneacetone)dipalladium, bis(diphenylphosphineferrocenyl)palladium(II) chloride, 1,3-bis(2,6-diisopropylphenyl)imidazol-2-ylidene(1,4-naphthoquinone)palladium dimer, allyl(chloro)(1,3-dimesityl-1,3-dihydro-2H-imidazol-2-ylidene)palladium, palladium(II) acetate/dicyclohexyl(2',4',6'-triisopropylbiphenyl-2-yl)phosphine, [1,1-bis(diphenylphosphino)ferrocene]palladium(II) chloride monodichloromethane adduct, [1,1'-Bis(diphenylphosphino)ferrocene]dichloropalladium(II), chloro(2-dicyclohexylphosphino-2',4',6'-triisopropyl-1,1'-biphenyl)[2-(2'-amino-1,1'-biphenyl)]palladium(II), palladium (II) acetate and (2-dicyclohexylphosphino-2',4',6'-triisopropyl-1,1'-biphenyl)[2-(2'-amino-1,1'-biphenyl)]palladium(II), as a preferred embodiment chloro(2-dicyclohexylphosphino-2',4',6'-triisopropyl-1,1'-biphenyl)[2-(2'-amino-1,1'-biphenyl)]palladium(I), and, optionally, an additional ligand, such as e.g. 2-(dicyclohexylphosphino)-2',4',6'-triisopropylbiphenyl, in a solvent, such as e.g. dioxane, toluene, or water, or a mixture thereof, under nitrogen or argon atmosphere, at 80° C.-120° C., for 2 h-7 d;

whereby $R^x$ is a $C_1$-$C_6$-alkyl group which is optionally substituted with one or two substituents and each substituent is independently selected from a hydroxy group, a $C_1$-$C_4$-alkoxy group, and a 3- to 7-membered heterocycloalkyl group; preferably a methyl group which is optionally substituted with a 3 to 7 membered heterocycloalkyl group, a $C_2$-$C_6$-alkenyl group which is optionally substituted with an $C_1$-$C_4$-alkoxy group, a $C_5$-$C_8$-cycloalkenyl group, which is optionally substituted with a hydroxy group a 3- to 9-membered heterocycloalkyl group, comprising one, two or three heteroatoms which are independently selected from —O—, —S—, —S(O)—, S(O)$_2$, and —NR$^9$—, and said heterocycloalkyl group optionally further comprising a bridging group selected from —O—, —NR$^9$—, —CH$_2$—, —CH$_2$—CH$_2$—, —O—CH$_2$—, —CH$_2$—O—, —NR$^9$—CH$_2$—, and —CH$_2$—NR$^9$—;

and said heterocycloalkyl group is optionally substituted with one, two or three substituents and each substituent is independently selected from a halogen atom;

a oxo(=O) group;

a cyano group;

a hydroxy group;

a $C_1$-$C_3$-alkyl group which is optionally further substituted with a hydroxy group;

a $C_1$-$C_3$-haloalkyl group;

a $C_1$-$C_3$-alkoxy group;

a $C_1$-$C_3$-haloalkoxy group;

a C(O)NR$^5$R$^6$ group and a NR$^5$R$^6$ group a 5- to 9-membered heterocycloalkyl group which is partially unsaturated and optionally substituted with one, two or three substituents and each substituent is independently selected from an oxo group (=O), a $C_1$-$C_3$-alkyl group a —C(O)R$^5$R$^6$ group and a halogen atom, an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a NR$^5$R$^6$ group, a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a NR$^5$R$^6$ group, with the proviso that said monocyclic heteroaryl group is not a pyridin-4-yl group;

R$^y$ is $C_1$-$C_6$-alkyl, or the two residues R$^y$ together are a $C_2$-$C_6$-alkylene group, preferably —C(CH$_3$)$_2$—C(CH$_3$)$_2$— to form a pinacol ester.

(j) Route 1 via nucleophilic aromatic substitution to introduce R$^3$ substituents selected from —NR$^7$R$^8$, a N-linked heterocycloalkyl group, a partially unsaturated N-linked heterocyloalkyl group and a N-linked heteroaryl group, whereby the term "N-linked" is to be understood as described in context of Scheme 2, Intermediate compounds of formula (V), in which R$^3$ is selected from —NR$^7$R$^8$, a N-linked 3- to 9-membered heterocycloalkyl group, a N-linked, partially unsaturated 3- to 9-membered heterocycloalkyl group, and a N-linked heteroaryl group, whereby the term "N-linked" is to be understood as described in context of Scheme 2, and in which the terms "3- to 9-membered heterocycloalkyl", "partially unsaturated 3- to 9-membered heterocyloalkyl", and "heteroaryl" are constituted and optionally substituted as defined for R$^3$, supra, can be obtained by reacting intermediate compounds of formula (III), in which R$^4$ has the meaning as defined supra, X is F or Cl (as reflected in scheme 2), and if X is Cl, R$^1$ or R$^2$ can not be F; preferably X is F;

R$^1$ and R$^2$ have the meaning as defined supra, with the proviso that if X is Cl, R$^1$ or R$^2$ can not be F, and with the proviso that at least one of R$^1$ and R$^2$ exerts an electron withdrawing effect; preferably, R$^1$ is selected from fluorine, a cyano group, and —CF$_3$, and R$^2$ is hydrogen or fluorine; more preferably, R$^1$ is —CF$_3$ and R$^2$ is hydrogen; with a corresponding amine, optionally as a free base or as a salt, such as e.g. a hydrochloride salt, selected from HNR$^7$R$^8$ and a cyclic amine featuring one N—H as a ring atom, said cyclic amine being selected from a heterocycloalkane, a partially unsaturated heterocyloalkane, and a heteroarene containing one N—H as a ring atom, respectively, optionally in the presence of a base, such as e.g. triethylamine, DIPEA, or cesium carbonate, in an inert solvent, such as e.g. CH$_3$CN, DMF or DMSO, at optionally elevated temperatures ranging from RT to 160° C., preferably from 60° C. to 150° C., for 2 h-7 d; whereby R$^7$/R$^8$ are independently selected from a hydrogen atom, with the proviso that R$^7$=R$^8$=hydrogen is excluded, a $C_1$-$C_6$-alkyl group, which is optionally substituted with one, two, three or four substituents and said substituent is independently selected from a halogen atom, a cyano group, a hydroxy group, a C(O)NR$^5$R$^6$ group, a NR$^5$R$^6$ group, a $C_1$-$C_3$-alkoxy group, a $C_3$-$C_7$-cycloalkyl group which is optionally substituted with one or two substitutents and said substituents are independently selected from a $C_1$-$C_3$-alkyl group, a oxo (=O) group, a hydroxy group, and a $C_1$-$C_3$-hydroxyalkyl group;

a 3- to 7-membered heterocycloalkyl group which itself is optionally substituted with a $C_1$-$C_3$-alkyl group or an oxo (=O) group, a heteroaryl group, which itself is optionally substituted with a $C_1$-$C_3$-alkyl group;

a —$C_1$-$C_5$-alkylene-O—$C_1$-$C_5$-alkyl group, a —$C_1$-$C_5$-alkylene-S—$C_1$-$C_5$-alkyl group, a —$C_1$-$C_5$-alkylene-NR$^5$—$C_1$-$C_5$-alkyl group, a $C_3$-$C_6$-cycloalkyl group which is optionally substituted with a hydroxy group, and a 3- to 6-membered heterocycloalkyl group which is optionally substituted with one or two substituents, said substituent independently selected from $C_1$-$C_3$-alkyl group and a hydroxy group (k) Alternative Route via transition metal catalyzed, preferably palladium catalyzed amination, to introduce R$^3$ substituents selected from —NR$^7$R$^8$, a N-linked heterocycloalkyl group, a partially unsaturated N-linked heterocyloalkyl group and a N-linked heteroaryl group, whereby the term "N-linked" is to be understood as described in context of Scheme 2, Intermediate compounds of formula (V), in which R$^3$ is selected from —NR$^7$R$^8$, a N-linked 3- to 9-membered heterocycloalkyl group, a N-linked, partially unsaturated 3- to 9-membered heterocyloalkyl group, and a N-linked heteroaryl group, whereby the term "N-linked" is to be understood as described in context of Scheme 2, and in which the terms "3- to 9-membered heterocycloalkyl", "partially unsaturated 3- to 9-membered heterocyloalkyl", and "heteroaryl" are constituted and optionally substituted as defined for $R^3$, supra, can be obtained by reacting intermediate compounds of formula (III), in which X is Cl, Br, I, (as reflected in scheme 2), or a group selected from ($C_1$-$C_4$-alkylsulfonyl)oxy, ($C_1$-$C_4$-fluoroalkylsulfonyl)oxy and (phenylsulfonyl)oxy, the phenyl present in (phenylsulfonyl)oxy being optionally substituted with one, two, three, four or five substituents, each of them independently selected from halogen, nitro, cyano, $C_1$-$C_4$-alkyl and $C_1$-$C_4$-alkoxy;

$R^1$ or $R^2$ are as defined supra but are different from C, Br, I; preferably, $R^1$ is —$CF_3$ and $R^2$ is hydrogen;

$R^4$ has the meaning as defined supra, with a corresponding amine, optionally as a free base or as a salt, such as e.g. a hydrochloride salt, selected from $HNR^7R^8$ and a cyclic amine featuring one N—H as a ring atom, said cyclic amine being selected from a 3- to 9-membered heterocycloalkane, a partially unsaturated 3- to 9-membered heterocyloalkane and a heteroarene containing one N—H as a ring atom, respectively, in the presence of a base, such as e.g. potassium phosphate or cesium carbonate, a palladium catalyst, such as e.g. tris(dibenzylideneacetone)dipalladium(0), a ligand, such as e.g. 2-(dicyclohexylphosphino)-2',4',6'-triisopropyl-1,1'-biphenyl or 2,2'-bis(diphenylphosphino)-1,1'-binaphthalene, in an inert solvent, such as e.g. dioxane or toluene, at elevated temperatures ranging from 60-160° C., for 2 h-7 d;

whereby $R^7$/$R^8$ are independently selected from
- a hydrogen atom, with the proviso that $R^7$=$R^8$=hydrogen is excluded,
- a $C_1$-$C_6$-alkyl group,
  which is optionally substituted with one, two, three or four substituents and said substituent is independently selected from
   - a halogen atom, a cyano group, a hydroxy group, a $C(O)NR^5R^6$ group, a $NR^5R^6$ group,
   - a $C_1$-$C_3$-alkoxy group,
   - a $C_3$-$C_7$-cycloalkyl group which is optionally substituted with one or two substitutents and said substituents are independently selected from a $C_1$-$C_3$-alkyl group, a oxo (=O) group, a hydroxy group, and a $C_1$-$C_3$-hydroxyalkyl group;
   - a 3- to 7-membered heterocycloalkyl group which itself is optionally substituted with a $C_1$-$C_3$-alkyl group or an oxo (=O) group,
   - a heteroaryl group, which itself is optionally substituted with a $C_1$-$C_3$-alkyl group;
- a —$C_1$-$C_5$-alkylene-O—$C_1$-$C_5$-alkyl group,
- a —$C_1$-$C_5$-alkylene-S—$C_1$-$C_5$-alkyl group,
- a —$C_1$-$C_5$-alkylene-$NR^5$—$C_1$-$C_5$-alkyl group,
- a $C_3$-$C_6$-cycloalkyl group which is optionally substituted with a hydroxy group, and
- a 3- to 6-membered heterocycloalkyl group which is optionally substituted with one or two substituents, said substituent independently selected from $C_1$-$C_3$-alkyl group and a hydroxy group.

The subsequent conversion of the resulting compounds of formula (V) into compounds of general formula (I) can e.g. be accomplished by the following sequence of reactions according to the steps (a) to (h):

Step (a)
A compound of formula (V) and Hydroxy(tosyloxy)iodo)benzene in a solvent such as e.g. DMSO, water are reacted at RT, for 18 h; or a compound of formula (V) and iodine, in a solvent such as e.g. DMSO, are reacted at 60° C., for 18 h Step (b)
The reaction product of step (a), $H_2NNHCOOCH_3$, and HCl (aq), are reacted in a solvent such as e.g. MeOH, at RT, for 5 h;

Step (c)
The reaction product of step (b) and potassium carbonate are reacted in a solvent such as e.g. acetonitrile, at 60° C., for 18 h or the reaction product of step (b) and NaOEt/EtOH, are reacted at 0° C. for 10 min, or the reaction product of step (b) and NaH, are reacted in EtOH, at 0° C. for 10 min;

Step (d)
The reaction product of step (h), sodium formate and sodium hydrogencarbonate, are reacted in a solvent such as e.g. $CH_3CN$, water, at 65° C., for 24 h in order to obtain the same product as from step (a) which subsequently may be converted to a compound of formula (I) via steps (b) and (c);

Step (e)
The reaction product of step (h), potassium acetate and potassium iodide are reacted for 18 h at RT;

Step (f)
The reaction product of step (e), $H_2NNHCOOCH_3$ and HCl (aq), are reacted in a solvent such as e.g. MeOH, at RT for 5-18 h;

Step (g)
The reaction product of step (f) and potassium carbonate are reacted in a solvent such as e.g. acetonitrile, at 60° C., for about 18 h or the reaction product of step (f) and NaOEt/EtOH, are reacted at 0° C. for 10 min, or the reaction product of step (f) and NaH, are reacted in a solvent such as e.g. EtOH, at 0° C. for 10 min in order to obtain a compound of formula (I);

Step (h)
A compound of formula (V), acetic acid and bromine, hydrogen bromide are reacted for 18 h, at RT.

The resulting compounds of general formula (I), if containing chiral centers, can be optionally separated by chiral chromatography to obtain individual enantiomers or diastereomers.

Route 3: Stereoselective Synthesis of Intermediate Compounds of Formula (IIa), in which $R^4$ is Different from Hydrogen

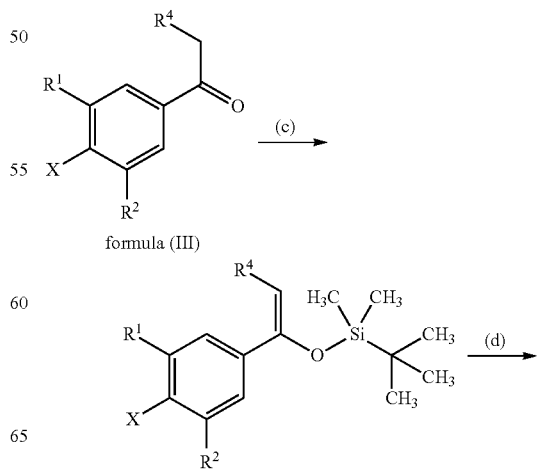

Scheme 5

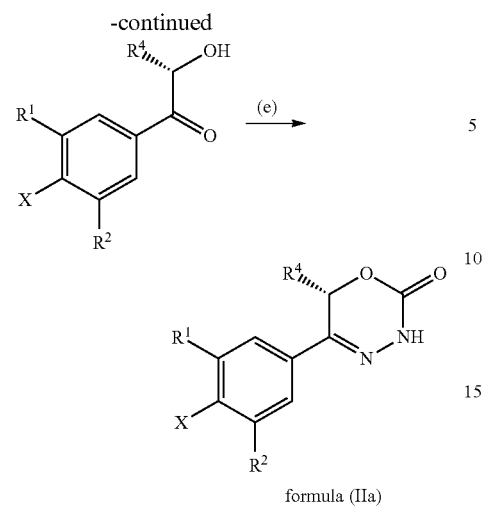

formula (IIa)

Scheme 5: Stereoselective route for the preparation of intermediate compounds of formula (IIa), constituting a sub-set of the intermediate compounds of formula (II), from intermediate compounds of formula (III) in which $R^1$, $R^2$, and $R^4$ have the meaning as defined supra, with the proviso that $R^4$ is different from hydrogen.

(c) LiHMDS/THF, 1 h, −78° C., then tBDMSCl (tert-butyldimethylchloro silane), −78° C. to RT, 15 h-2 d;

(d) AD-Mix-α, CH$_3$SO$_2$NH$_2$/tBuOH/water, 0° C. to RT 15 h-2 d;

(e) 1. H$_2$NNHCOOCH$_3$, HCl, MeOH; 2. NaOEt/EtOH or NaOMe/MeOH or NaH/EtOH;

Route 4: Stereoselective Synthesis of Compounds of Formula (Ia)

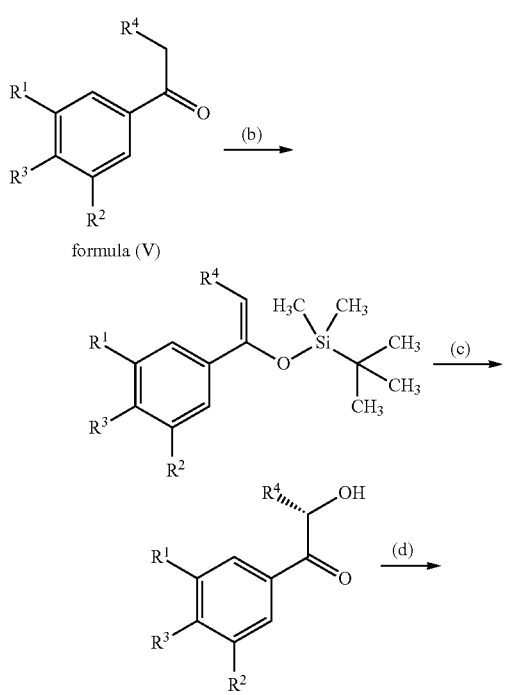

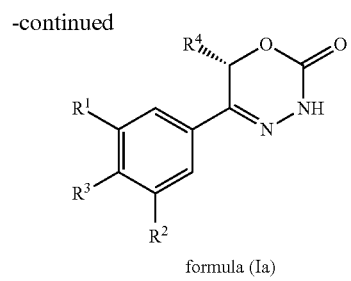

formula (Ia)

Scheme 6: Stereoselective route for the preparation of compounds of formula (Ia), constituting a sub-set of general formula (I), from intermediate compounds of formula (V), in which $R^1$, $R^2$, $R^3$ and $R^4$ have the meaning as defined supra, with the proviso that $R^4$ is different from hydrogen.

(b) LiHMDS/THF, 1 h, −78° C., then tBDMSCl (tert-butyldimethylchloro silane), −78° C. to RT, 15 h-2 d;

(c) AD-Mix-α, CH$_3$SO$_2$NH$_2$/tBuOH/water, 0° C. to RT, 15 h-2 d;

(d) 1. methyl hydrazino-carboxylate, HCl (aq)/MeOH, 60° C., 1 h; 2. NaOEt/EtOH or NaOMe/MeOH, RT, 1-2 h.

Route 5: Synthesis of Compounds of Formula (Ic)

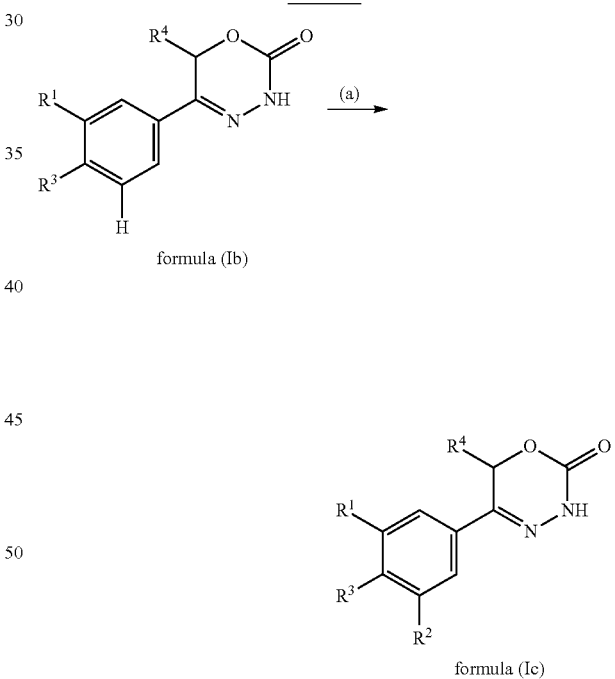

Scheme 7: Route for the preparation of compounds of formula (Ic) from compounds of formula (Ib), in which $R^1$ and $R^4$ have the meaning as defined supra, and $R^3$ is $NR^7R^8$ or a 3- to 7-membered heterocycloalkyl group. Both formulae (Ib) and (Ic) constitute sub-sets of general formula (I); compounds of formula (Ib) are readily available according to the other synthesis routes discussed in this chapter, and in the Experimental Section below.

(a) N-chloro succinimide (NCS, 1-Chloro-pyrrolidin-2,5-dione), THF, RT, 18 h, or, NaOCl/HOAc, 10-15° C., 1-2 h;

133

Route 6: Alternative Synthesis of Intermediate Compounds of Formula (II)

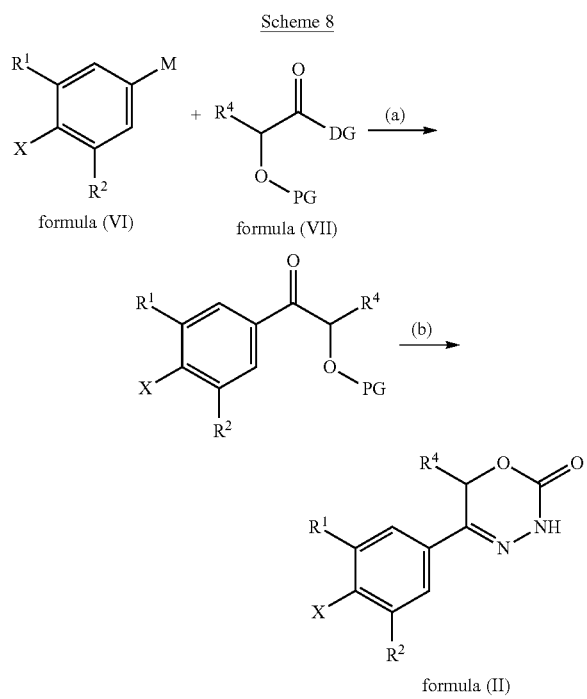

formula (II)

Scheme 8: Route for the preparation of intermediate compounds of formula (II) from compounds of formulae (VI) and (VII), in which $R^1$, $R^2$ and $R^4$ have the meaning as defined supra and M is a metal-containing group, such as e.g. Li, or MgBr, or MgCl; and X is F, Cl, or Br; and DG is a group displacable from compounds of formula (VII) with reactands of formula (VI), selected from morpholinyl or N(OCH$_3$)CH$_3$ (Weinreb amide); and PG is a protecting group suitable for hydroxy groups, e.g. a tri-(C$_1$-C$_4$-alkyl)-silyl group such as e.g. tert-butyl-dimethylsilyl. Compounds of formulae (VI) and (VII) are known to the person skilled in the art and can be readily prepared from commercially available precursors by known methods.

(a) THF, −20° C.-20° C., 1 h-24 h, (b) 1. H$_2$NNHCOOCH$_3$, HCl, MeOH; 2. TBAF (tetrabutylammonium fluoride), THF; 3. NaOEt/EtOH or NaOMe/MeOH;

Compounds of formula (II) can be converted to compounds of general formula (I) as described above in context of Scheme 2.

Route 7: Alternative Synthesis of Compounds of General Formula (I)

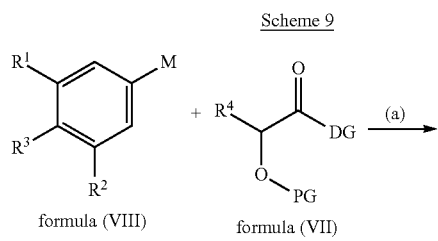

134

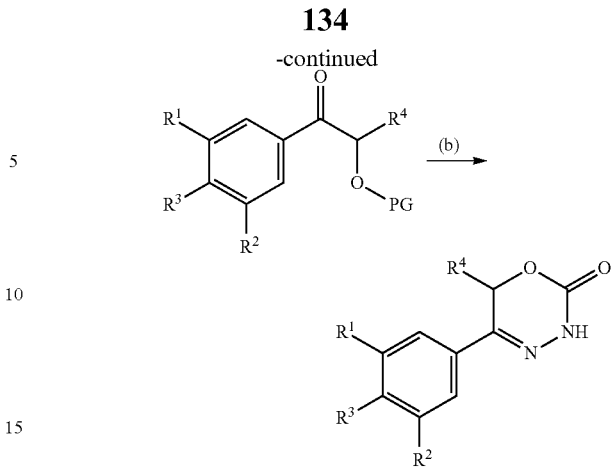

formula (I)

Scheme 9: Route for the preparation of compounds of general formula (I) from compounds of formulae (VIII) and (VII), in which $R^1$, $R^2$, $R^3$, and $R^4$ have the meaning as defined supra and M is a metal-containing group, such as e.g. Li, or MgBr, or MgCl; and DG is a group displacable from compounds of formula (VII) by reactands of formula (VIII), selected from morpholinyl or N(OCH$_3$)CH$_3$ (Weinreb amide); and PG is a protecting group suitable for hydroxy groups, e.g. a tri-(C$_1$-C$_4$-alkyl)-silyl group such as e.g. tert-butyl-dimethylsilyl. Compounds of formulae (VIII) and (VII) are known to the person skilled in the art and can be readily prepared from commercially available precursors by known methods.

(a) THF, −20° C.-20° C., 1 h-24 h, (b) 1. H$_2$NNHCOOCH$_3$, HC, MeOH; 2. TBAF, THF; 3.

NaOEt/EtOH or NaOMe/MeOH;

Some further aspects of the invention are the synthesis routes according to the schemes 1-9 above whereby R$^x$ and/or R$^7$/R$^8$ respectively are defined analogously as described supra but limited according to claims 2-7.

The present invention further provides methods of preparing compounds of the present invention of general formula (I), said methods comprising the steps as described in the Experimental Section herein.

The present invention in particular provides a method of preparing a compound of general formula (I) as defined supra, said method comprising

EITHER the step A of allowing an intermediate compound of general formula (II)

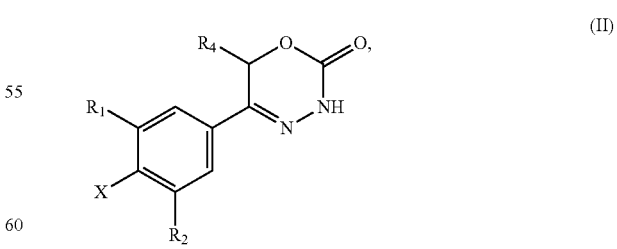

in which

X is Cl, Br, I, or a group selected from (C$_1$-C$_4$-alkylsulfonyl)oxy, (C$_1$-C$_4$-fluoroalkylsulfonyl)oxy and (phenylsulfonyl)oxy, the phenyl present in (phenylsulfonyl)oxy being optionally substituted with one, two, three, four or five substituents, each of them independently selected from halogen, nitro, cyano, $C_1$-$C_4$-alkyl and $C_1$-$C_4$-alkoxy;

$R^1$ is selected from a hydrogen atom, a fluorine atom, a cyano group, a $C_1$-$C_3$-alkyl group, a $C_1$-$C_3$-haloalkyl group, and a $C_1$-$C_3$-haloalkoxy group;

$R^2$ is selected from a hydrogen atom, a fluorine atom;

$R^4$ is selected from a hydrogen atom, and a $C_1$-$C_3$-alkyl group;

to react under transition metal catalysed coupling conditions such as e.g. Suzuki couplings, Negishi couplings, Kumada couplings, Stille couplings, preferably Suzuki couplings, by allowing said intermediate compound of formula (II) to react with an organoboron compound selected from a boronic acid of formula (IIIa)

$$(R^x)B(OH)_2 \quad (IIIa),$$

a boronic ester of formula $$(R^x)B(OR^y)_2 \quad (IIIb),$$

and a tetrafluoroborate salt of formula $$(R^x)BF_4 \quad (IIIc),$$

whereby $R^x$ is a $C_1$-$C_6$-alkyl group which is optionally substituted with one or two substituents and each substituent is independently selected from a hydroxy group, a $C_1$-$C_4$-alkoxy group, and a 3- to 7-membered heterocycloalkyl group; preferably a methyl group which is optionally substituted with a 3 to 7 membered heterocycloalkyl group, a $C_2$-$C_6$-alkenyl group which is optionally substituted with an $C_1$-$C_4$-alkoxy group, a $C_5$-$C_9$-cycloalkenyl group, which is optionally substituted with a hydroxy group, a 3- to 9-membered heterocycloalkyl group, comprising one, two or three heteroatoms which are independently selected from —O—, —S—, —S(O)—, $S(O)_2$, and —$NR^9$—, and said heterocycloalkyl group optionally further comprising a bridging group selected from —O—, —$NR^9$—, —$CH_2$—, —$CH_2$—$CH_2$—, —O—$CH_2$—, —$CH_2$—O—, —$NR^9$—$CH_2$—, and —$CH_2$—$NR^9$—;

and said heterocycloalkyl group is optionally substituted with one, two or three substituents and each substituent is independently selected from a halogen atom;

a oxo(=O) group;

a cyano group;

a hydroxy group;

a $C_1$-$C_3$-alkyl group which is optionally further substituted with a hydroxy group;

a $C_1$-$C_3$-haloalkyl group;

a $C_1$-$C_3$-alkoxy group;

a $C_1$-$C_3$-haloalkoxy group;

a $C(O)NR^5R^6$ group and a $NR^5R^6$ group, a 5- to 9-membered heterocycloalkyl group which is partially unsaturated and optionally substituted with one, two or three substituents and each substituent is independently selected from an oxo group (=O), a $C_1$-$C_3$-alkyl group a —$C(O)R^5R^6$ group and a halogen atom, an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a $NR^5R^6$ group, a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^5R^6$ group, with the proviso that said monocyclic heteroaryl group is not a pyridin-4-yl group;

$R^y$ is $C_1$-$C_6$-alkyl, or the two residues $R^y$ together are a $C_2$-$C_6$-alkylene group, preferably —$C(CH_3)_2$—$C(CH_3)_2$— to form a pinacol ester, in the presence of a base, in a preferred embodiment potassium carbonate or potassium acetate, a palladium catalyst selected from:

dichlorobis(triphenylphosphine)palladium, tetrakistriphenylphosphinepalladium(0), palladium(II) acetate/triscyclohexylphosphine, tris(dibenzylideneacetone)dipalladium, bis(diphenylphosphineferrocenyl)palladium(II) chloride, 1,3-bis(2,6-diisopropylphenyl)imidazol-2-ylidene(1,4-naphthoquinone)palladium dimer, allyl (chloro)(1,3-dimesityl-1,3-dihydro-2H-imidazol-2-ylidene)palladium, palladium(II) acetate/dicyclohexyl(2',4',6'-triisopropyl-biphenyl-2-yl)phosphine, [1,1-bis(diphenylphosphino)ferrocene]palladium(II) chloride monodichloromethane adduct, [1,1'-Bis(diphenylphosphino)ferrocene]dichloropalladium(II), chloro(2-dicyclohexylphosphino-2',4',6'-triisopropyl-1,1'-biphenyl)[2-(2'-amino-1,1'-biphenyl)]palladium(II), palladium (II) acetate and (2-dicyclohexylphosphino-2',4',6'-triisopropyl-1,1'-biphenyl)[2-(2'-amino-1,1'-biphenyl)]palladium (II), or chloro(2-dicyclohexylphosphino-2',4',6'-triisopropyl-1,1'-biphenyl)[2-(2'-amino-1,1'-biphenyl)]palladium (II), as a preferred embodiment chloro(2-dicyclohexylphosphino-2',4',6'-triisopropyl-1,1'-biphenyl)[2-(2'-amino-1,1'-biphenyl)]palladium(II), and, optionally, an additional ligand such as e.g. 2-(dicyclohexylphosphino)-2',4',6'-triisopropylbiphenyl,

OR said method comprising the step B of allowing an intermediate compound of general formula (II)

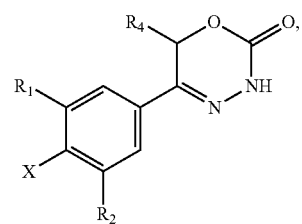

in which $R^4$ has the meaning as defined supra,

X is F or C, with the proviso that if X is Cl, $R^1$ or $R^2$ can not be F; preferably X is F;

$R^1$ is selected from a hydrogen atom, a halogen atom, a cyano group, a $C_1$-$C_3$-alkyl group, a $C_1$-$C_3$-haloalkyl group, and a $C_1$-$C_3$-haloalkoxy group;

preferably $R^1$ is selected from a fluorine atom, a cyano group, and a —$CF_3$ group, and with the proviso that if X is Cl, $R^1$ can not be a fluorine atom; more preferably, $R^1$ is —$CF_3$;

R² is selected from a hydrogen atom and a halogen atom with the proviso that if X is Cl, R² can not be a fluorine atom; more preferably, R² is hydrogen;

with the further proviso that at least one of R¹ and R² exerts an electron withdrawing effect;

R⁴ is selected from a hydrogen atom, and a $C_1$-$C_3$-alkyl group;

to react with a corresponding amine, optionally as a free base or as a salt, such as e.g. a hydrochloride salt, selected from $HNR^7R^8$ and a cyclic amine featuring one N—H as a ring atom, said cyclic amine being selected from a 3- to 9-membered heterocycloalkane, a partially unsaturated 3- to 9-membered heterocyloalkane, and a heteroarene, containing one N—H as a ring atom, respectively, in which $R^7/R^8$ are independently selected from a hydrogen atom, with the proviso that $R^7=R^8$=hydrogen is excluded, a $C_1$-$C_6$-alkyl group, which is optionally substituted with one, two, three or four substituents and said substituent is independently selected from a halogen atom, a cyano group, a hydroxy group, a $C(O)NR^5R^6$ group, a $NR^5R^6$ group, a $C_1$-$C_3$-alkoxy group, a $C_3$-$C_7$-cycloalkyl group which is optionally substituted with one or two substitutents and said substituents are independently selected from a $C_1$-$C_3$-alkyl group, a oxo (=O) group, a hydroxy group, and a $C_1$-$C_3$-hydroxyalkyl group;

a 3- to 7-membered heterocycloalkyl group which itself is optionally substituted with a $C_1$-$C_3$-alkyl group or an oxo (=O) group, a heteroaryl group, which itself is optionally substituted with a $C_1$-$C_3$-alkyl group;

a —$C_1$-$C_5$-alkylene-O—$C_1$-$C_5$-alkyl group, a —$C_1$-$C_5$-alkylene-S—$C_1$-$C_5$-alkyl group, a —$C_1$-$C_5$-alkylene-NR⁵—$C_1$-$C_5$-alkyl group, a $C_3$-$C_6$-cycloalkyl group which is optionally substituted with a hydroxy group, and a 3- to 6-membered heterocycloalkyl group which is optionally substituted with one or two substitutents, said substituent independently selected from $C_1$-$C_3$-alkyl group and a hydroxy group, a 3- to 9-membered heterocycloalkane containing one N—H as a ring atom is to be understood as a cyclic amine corresponding to a 3- to 9-membered heterocycloalkyl group as defined for R³ supra, with the proviso it contains one N—H as a ring atom, a partially unsaturated 3- to 9-membered heterocycloalkane containing one N—H as a ring atom is to be understood as a cyclic amine corresponding to a partially unsaturated 3- to 9-membered heterocycloalkyl group, as defined for R³ supra, with the proviso it contains one N—H as a ring atom, and a heteroarene containing one N—H as a ring atom is to be understood as a cyclic amine corresponding to a heteroaryl group as defined for R³ supra, with the proviso it contains one N—H as a ring atom, optionally in the presence of a base, and optionally the presence of an inert solvent, and at temperature ranging from RT to 160° C.,

OR said method comprising the step C of allowing an intermediate compound of general formula (II)

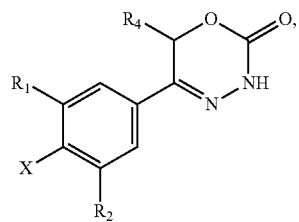

(II)

in which

X is Cl, Br, I, or a group selected from ($C_1$-$C_4$-alkylsulfonyl)oxy, ($C_1$-$C_4$-fluoroalkylsulfonyl)oxy and (phenylsulfonyl)oxy, the phenyl present in (phenylsulfonyl)oxy being optionally substituted with one, two, three, four or five substituents, each of them independently selected from halogen, nitro, cyano, $C_1$-$C_4$-alkyl and $C_1$-$C_4$-alkoxy;

R¹ is selected from a hydrogen atom, a fluorine atom, a cyano group, a $C_1$-$C_3$-alkyl group, a $C_1$-$C_3$-haloalkyl group, and a $C_1$-$C_3$-haloalkoxy group;

R² is selected from a hydrogen atom, a fluorine atom;

R⁴ is selected from a hydrogen atom, and a $C_1$-$C_3$-alkyl group;

to react with a corresponding amine, optionally as a free base or as a salt, such as e.g. a hydrochloride salt, selected from $HNR^7R^8$ and cyclic amine featuring one N—H as a ring atom, said cyclic amine being selected from a 3- to 9-membered heterocycloalkane, a partially unsaturated 3- to 9-membered heterocyloalkane, and a heteroarene, containing one N—H as a ring atom, respectively, in which $R^7/R^8$ are independently selected from a hydrogen atom, with the proviso that $R^7=R^8$=hydrogen is excluded, a $C_1$-$C_6$-alkyl group, which is optionally substituted with one, two, three or four substituents and said substituent is independently selected from a halogen atom, a cyano group, a hydroxy group, a $C(O)NR^5R^6$ group, a $NR^5R^6$ group, a $C_1$-$C_3$-alkoxy group, a $C_3$-$C_7$-cycloalkyl group which is optionally substituted with one or two substitutents and said substituents are independently selected from a $C_1$-$C_3$-alkyl group, a oxo (=O) group, a hydroxy group, and a $C_1$-$C_3$-hydroxyalkyl group;

a 3- to 7-membered heterocycloalkyl group which itself is optionally substituted with a $C_1$-$C_3$-alkyl group or an oxo (=O) group, a heteroaryl group, which itself is optionally substituted with a $C_1$-$C_3$-alkyl group;

a —$C_1$-$C_5$-alkylene-O—$C_1$-$C_5$-alkyl group, a —$C_1$-$C_5$-alkylene-S—$C_1$-$C_5$-alkyl group, a —$C_1$-$C_5$-alkylene-NR⁵—$C_1$-$C_5$-alkyl group, a $C_3$-$C_6$-cycloalkyl group which is optionally substituted with a hydroxy group, and a 3- to 6-membered heterocycloalkyl group which is optionally substituted with one or two substitutents, said substituent independently selected from $C_1$-$C_3$-alkyl group and a hydroxy group, a 3- to 9-membered heterocycloalkane containing one N—H as a ring atom is to be understood as a cyclic amine corresponding to a 3- to 9-membered heterocycloalkyl group as defined for $R^3$ supra, with the proviso it contains one N—H as a ring atom, a partially unsaturated 3- to 9-membered heterocycloalkane containing one N—H as a ring atom is to be understood as a cyclic amine corresponding to a partially unsaturated 3- to 9-membered heterocycloalkyl group, as defined for $R^3$ supra, with the proviso it contains one N—H as a ring atom, and a heteroarene containing one N—H as a ring atom is to be understood as a cyclic amine corresponding to a heteroaryl group as defined for $R^3$ supra, with the proviso it contains one N—H as a ring atom, in the presence of a base, and of a palladium catalyst, such as e.g. tris(dibenzylideneacetone)dipalladium(0), a ligand, such as e.g. 2-(dicyclohexylphosphino)-2',4',6'-triisopropyl-1,1'-biphenyl or 2,2'-bis(diphenylphosphino)-1,1'-binaphthalene, in an inert solvent, and in the presence of an inert solvent, and at a temperature ranging from 60° C. to 160° C., in order to obtain a compound of formula (I) using one of said steps.

Some further aspects of the invention are the methods A, B, or C as outlined directly above starting with a compound of general formula (II) and providing two further alternative routes whereby R and/or $R^7/R^8$ are defined analogously as described supra, but limited according to claims 2-7 or any of the embodiments defined infra.

In some aspects the invention provides methods of preparing a compound of general formula (I) as outlined above, said methods comprising for compound (II): $R^1$ is trifluoromethyl and $R^2$ is a hydrogen atom, for step A:

Suzuki coupling conditions are used and the palladium catalyst is chloro(2-dicyclohexylphosphino-2',4',6'-triisopropyl-1,1'-biphenyl)[2-(2'-amino-1,1'-biphenyl)]palladium(II), and the ligand is 2-(dicyclohexylphosphino)-2',4',6'-triisopropylbiphenyl and/or for step B:
two residues $R^y$ together are —C(CH$_3$)$_2$—C(CH$_3$)$_2$— to form a pinacol ester, the base is potassium carbonate or potassium acetate, and/or for step C:
the palladium catalyst is tris(dibenzylideneacetone)dipalladium(0) and the ligand is 2-(dicyclohexylphosphino)-2',4',6'-triisopropyl-1,1'-biphenyl or 2,2'-bis(diphenylphosphino)-1,1'-binaphthalene.

In some aspects the invention provides a method as outlined above wherein for compound (II): $R^1$ is trifluoromethyl and $R^2$ is a hydrogen atom, for step A:
Suzuki coupling conditions are used and the palladium catalyst is chloro(2-dicyclohexylphosphino-2',4',6'-triisopropyl-1,1'-biphenyl)[2-(2'-amino-1,1'-biphenyl)]palladium(II), and the ligand is 2-(dicyclohexylphosphino)-2',4',6'-triisopropylbiphenyl and/or for step B:
two residues $R^y$ together are —C(CH$_3$)$_2$—C(CH$_3$)$_2$— to form a pinacol ester, the base is potassium carbonate or potassium acetate, and/or for step C:
the palladium catalyst is tris(dibenzylideneacetone)dipalladium(0) and the ligand is 2-(dicyclohexylphosphino)-2',4',6'-triisopropyl-1,1'-biphenyl or 2,2'-bis(diphenylphosphino)-1,1'-binaphthalene.

The present invention in particular provides a method of preparing a compound of general formula (I) according to any one of claims 1 to 8, said method comprising the step A of allowing an intermediate compound of general formula (II)

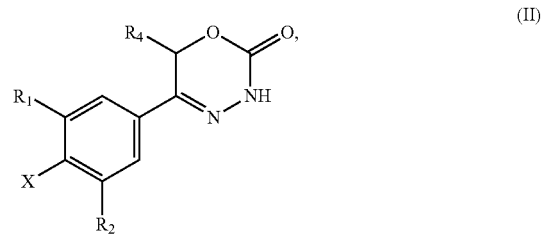

in which $R^1$, $R^2$ and $R^4$ have the meaning as defined for the compound of general formula (I) supra and X=F, Cl, Br, I to react a) if X=Cl, Br, I, and with the prerequisite that R/R$^2$ is not Cl, Br, I, under transmetal catalysed coupling conditions such as e.g. Suzuki couplings, Negishi couplings, Kumada couplings, Stille couplings, but preferentially Suzuki couplings with a boronic acid of formula (R$^x$)B(OH)$_2$      (IIIa)

whereby R$^x$ is a C$_2$-C$_6$-alkenyl group, a C$_5$-C$_6$-cycloalkyl group which is optionally partially unsaturated, a C$_3$-C$_7$-heterocycloalkyl group, which is optionally substituted with one, two or three substituents and each substituent is independently selected from a halogen atom and a C$_1$-C$_3$-alkyl group, a hydroxy group, NR$^5$R$^6$ group, a C$_1$-C$_3$-haloalkyl group and a C$_1$-C$_3$-haloalkoxy group, a C$_5$-C$_7$-heterocycloalkyl group which is partially unsaturated and optionally substituted with one, two or three substituents and each substituent is independently selected from an oxo group, a C$_1$-C$_3$-alkyl group a —C(O)R$^5$R$^6$ group and a halogen atom, an aryl group which is optionally substituted with one, two, three or four substituents and each substituent is independently selected from a halogen atom, a hydroxy group, a cyano group, a C$_1$-C$_3$-alkyl group, a C$_1$-C$_3$-haloalkyl group, a C$_1$-C$_3$-alkoxy group, a C$_1$-C$_3$-haloalkoxy group, and NR$^5$R$^6$ group;

and a mono- or bicyclic heteroaryl group which is optionally substituted with one, two a or three substituents and each substituent is independently selected from a halogen atom, a C$_1$-C$_3$-alkyl group, a cyano group, a C$_1$-C$_3$-haloalkyl group, a C$_1$-C$_3$-alkoxy group, a hydroxy group, and a NR$^5$R$^6$ group, with the proviso that said monocyclic heteroaryl group is not a pyridin-4-yl group;

or a boronic ester of formula (R$^x$)B(OR$^y$)$_2$      (IIIb)

wherein R$^x$ is as defined for the boronic acid supra and R$^y$ is C$_1$-C$_6$-alkyl, or the two residues R$^y$ together form a pinacol ester, or other suitable boronic esters employed in this reaction by people skilled in the art/potassium carbonate/a palladium catalyst from the following list:

dichlorobis(triphenylphosphine)palladium, tetrakistriphenylphosphinepalladium(0), palladium(II) acetate/triscyclohexylphosphine, tris(dibenzylideneacetone)dipalladium, bis(diphenylphosphineferrocenyl)palladium(II) chloride, 1,3-bis(2,6-diisopropylphenyl)imidazol-2-ylidene(1,4-naphthoquinone)palladium dimer, allyl(chloro)(1,3-dimesityl-1,3-dihydro-2H-imidazol-2-ylidene)palladium, palladium(II) acetate/dicyclohexyl(2',4',6'-triisopropyl-biphenyl-2-yl)phosphine, [1,1-bis(diphenylphosphino)ferrocene]palladium(II) chloride monodichloromethane adduct, [1,1'-Bis(diphenylphosphino)ferrocene]dichloropalladium(II), chloro(2-dicyclohexylphosphino-2',4',6'-triisopropyl-1,1'-biphenyl)[2-(2'-amino-1,1'-biphenyl)]palladium(II), or (2-Dicyclohexylphosphino-2',4',6'-triisopropyl-1,1'-biphenyl)[2-(2'-amino-1,1'-biphenyl)]palladium(II), as a preferred embodiment chloro(2-dicyclohexylphosphino-2',4',6'-triisopropyl-1,1'-biphenyl)[2-(2'-amino-1,1'-biphenyl)]palladium(II).

in order to obtain a compound of formula (I) wherein $R^3$ is R
or
b) if X=F, and with the prerequisite that R/$R^2$ exert, at least partially, electron withdrawing effects, preferentially $R^1$ is F, $CF_3$, CN, and $R^2$ is F or $CF_3$, even more particularly $R^1$ is F or $CF_3$, $R^2$=H, F
to react with

HNR$^7$R$^8$ wherein $R^7$ and $R^8$ have the meaning as defined in anyone of claim 1-7,
optionally in the precence of a base, and optionally the presence of an inert solvent, and optionally heating up to the boiling temperature of the present base or the present solvent, preferentially RT-150° C. in order to obtain a compound of formula (I).

A suitable solvent for the methods above is an inert solvent as known to the skilled person, such as e.g. dimethylformamide, or mixtures of dioxane/water or any solvent is disclosed in the example section.

In accordance with a further aspect, the present invention provides intermediate compounds which are useful for the preparation of the compounds of general formula (I), supra.

Particularly, the invention provides the intermediate compounds of general formula (II)

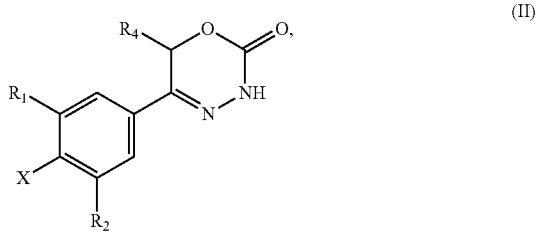

(II)

in which $R^1$, $R^2$ and $R^4$ have the meaning as defined for the compound of general formula (I) supra and X=F, C. Br, I with the proviso that if X=Cl, Br, I, R/$R^2$ is not C. Br, I.

Particularly, the invention provides the intermediate compounds of general formula (II), in which $R^1$ is selected from a fluorine atom, a cyano group, a $OCF_3$ group and —$CF_3$, $R^2$ is a hydrogen atom or a fluorine atom, and $R^4$ is a hydrogen atom or a methyl group, preferably the methyl group having (S)-configuration More particularly, the invention provides the intermediate compounds of general formula (II), in which $R^1$ is selected from a fluorine atom, a cyano group and a trifluoromethyl group, $R^2$ is a hydrogen atom or a fluorine atom, and $R^4$ is a hydrogen atom or a methyl group.

More particularly, the invention provides the intermediate compounds of general formula (II), in which $R^1$ is a fluorine atom or a trifluoromethyl group, $R^2$ is a hydrogen atom or a fluorine atom, and $R^4$ is a hydrogen atom or a methyl group.

Even more particularly, the invention provides the intermediate compounds of general formula (II), in which $R^1$ is a trifluoromethyl group, $R^2$ is a hydrogen atom, and $R^4$ is hydrogen atom or a methyl group Particularly, the invention further provides the intermediate compounds of general formula (II) in particular intermediate 63, intermediate 64, intermediate 76, intermediate 65, intermediate 73, intermediate 66, intermediate 68, and intermediate 74 as exemplified in the experimental section.

Furthermore, the invention provides the intermediate compounds of general formula (II) in particular intermediate 50, intermediate 57, intermediate 63, intermediate 64, intermediate 65, intermediate 66, intermediate 68, intermediate 73, intermediate 74, intermediate 75 and intermediate 76 as exemplified in the experimental section.

Furthermore, the invention provides the intermediate compounds of general formula (II) in particular intermediate 49, intermediate 51, intermediate 57, intermediate 58, intermediate 62, intermediate 63, intermediate 64, intermediate 65, intermediate 66, intermediate 68, intermediate 73, intermediate 74, intermediate 75, intermediate 76 and intermediate 78 as exemplified in the experimental section.

Even more particularly, the invention provides the intermediate compounds of general formula (II) in particular intermediate 50, intermediate 57, intermediate 64, intermediate 66, intermediate 74, intermediate 75.

In a further aspect the invention provides intermediate compounds of general formula (II), in particular intermediate 64, intermediate 66, intermediate 74 and intermediate 75.

In a further aspect the invention provides intermediate compounds of general formula (II), in particular intermediate 64, intermediate 74 and intermediate 75.

One aspect of the invention is a method for the preparation of compounds of formula (I), said method comprising
EITHER
the step A of allowing an intermediate compound of formula (IIb)

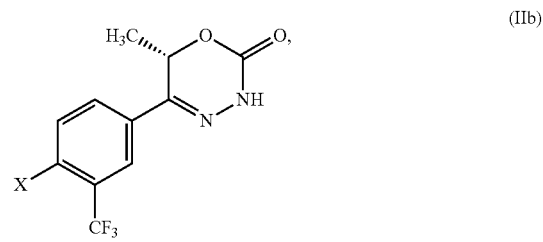

(IIb)

or an intermediate compound of formula (IIc)

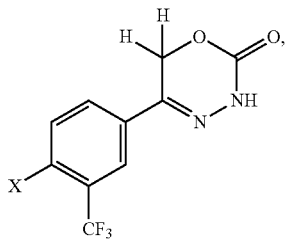
(IIc)

in which X is selected from $C_1$, Br and I
to react, in a Suzuki coupling reaction,
with a boronic acid of formula (IIId)

$(R^x)B(OH)_2$ (IIId), whereby $R^x$ is selected from
a phenyl group which is substituted with one or two substituents independently selected from a fluorine atom and a chlorine atom,
a pyrazolyl group which is substituted with one difluoromethyl group or one trifluoromethyl group, and
a pyridyl group, which is substituted with one $NH_2$ group, or
with a boronic ester of formula $(R^x)B(OR^y)_2$ (IIIe), wherein $R^x$ is as defined for the boronic acid of formula (IIId), supra, and $R^y$ is $C_1$-$C_6$-alkyl, or the two residues $R^y$ together form a $C_2$-$C_6$-alkylene group, preferably —C($CH_3$)$_2$—C($CH_3$)$_2$- to form a pinacol ester,
in the presence of a base, preferably potassium carbonate, and of a palladium catalyst selected from:
dichlorobis(triphenylphosphine)palladium, tetrakistriphenylphosphinepalladium(0), palladium(II) acetate/tricyclohexylphosphine, tris(dibenzylideneacetone)dipalladium, bis(diphenylphosphineferrocenyl)palladium(II) chloride, 1,3-bis(2,6-diisopropylphenyl)imidazol-2-ylidene(1,4-naphthoquinone)palladium dimer, allyl(chloro)(1,3-dimesityl-1,3-dihydro-2H-imidazol-2-ylidene)palladium, palladium(II) acetate/dicyclohexyl(2',4',6'-triisopropyl-biphenyl-2-yl)phosphine, [1,1-bis(diphenylphosphino)ferrocene]palladium(II) chloride monodichloromethane adduct, [1,1'-Bis(diphenylphosphino)ferrocene]dichloropalladium(II), chloro(2-dicyclohexylphosphino-2',4',6'-triisopropyl-1,1'-biphenyl)[2-(2'-amino-1,1'-biphenyl)]palladium(II), and (2-dicyclohexylphosphino-2',4',6'-triisopropyl-1,1'-biphenyl)[2-(2'-amino-1,1'-biphenyl)]palladium(II),
as a preferred embodiment chloro(2-dicyclohexylphosphino-2',4',6'-triisopropyl-1,1'-biphenyl)[2-(2'-amino-1,1'-biphenyl)]palladium(II),
optionally in the presence of an additional ligand, preferably 2-(dicyclohexylphosphino)-2',4',6'-triisopropylbiphenyl,
in the presence of a solvent, preferably dioxane or water, or a mixture thereof, at a temperature ranging from 80° C. to 120° C.,
in order to obtain a compound of formula (I) wherein $R^1$ is a trifluoromethyl group, $R^2$ is a hydrogen atom, $R^3$ is $R^x$ as defined above for formula (IId) and $R^4$ is a hydrogen atom or a methyl group,
OR said method comprising
the step B of allowing an intermediate compound of formula (IIb)

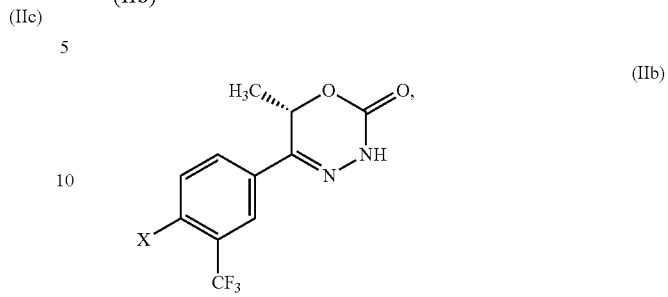
(IIb)

or said intermediate compound of formula (IIc)

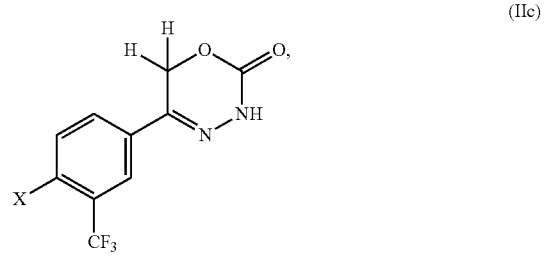
(IIc)

in which X is a fluorine atom,
to react with an amine $HNR^7R^8$ wherein $R^7$ is a hydrogen atom, and $R^8$ is a 3,3,3-trifluoro-2-hydroxypropyl group, a 2-hydroxy-2-methylpropyl group or a 2-methoxyethyl group,
or with a 1H-pyrazole which is substituted with a trifluoromethyl group and is unsubstituted at N–1,
optionally in the presence of a base, preferably cesium carbonate, and optionally the presence of an inert solvent, preferably DMF, and optionally heating up to the boiling temperature of the present base or the present solvent, preferably RT-150° C.
in order to obtain a compound of formula (I) wherein $R^1$ is a trifluoromethyl group, $R^2$ is a hydrogen atom, $R^3$ is a $NR^7R^8$ group, whereby $R^7$ is hydrogen and $R^8$ is 3,3,3-trifluoro-2-hydroxypropyl, 2-hydroxy-2-methylpropyl or 2-methoxyethyl,
or $R^3$ is a 1H-pyrazol-1-yl group, which is substituted with a trifluoromethyl group,
and $R^4$ is a hydrogen atom or a methyl group,
OR
said method comprising
the step C of allowing an intermediate compound of formula (IIb)

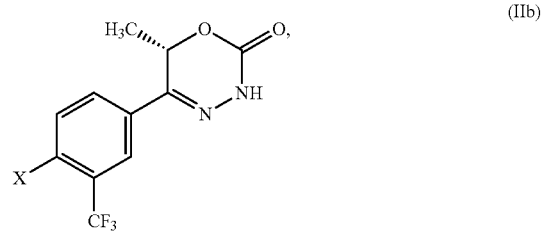
(IIb)

or said intermediate compound of formula (IIc)

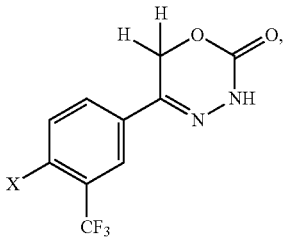

in which X is a chlorine atom,
to react with
an amine, which is a cyclic amine, in a preferred embodiment selected from 3-hydroxy-3-methylazetidine, 3,3-difluoroazetidine, 4,4-difluoropiperidin and 3-(trifluoromethyl)-1H-pyrazol, as a free base or as hydrochloride salt,
in the presence of a base, in a preferred embodiment potassium phosphate, a palladium catalyst, preferably tris(dibenzylideneacetone)dipalladium(0), a ligand, in a preferred embodiment 2-(dicyclohexylphosphino)-2',4',6'-triisopropyl-1,1'-biphenyl and in the presence of an inert solvent, in a preferred embodiment 1,4-dioxane, at a temperature ranging from 80° C. to 120° C.,
in order to obtain a compound of formula (I) wherein $R^1$ is a trifluoromethyl group, $R^2$ is a hydrogen atom, $R^3$ is a group selected from 3-hydroxy-3-methylazetidin-1-yl and 3,3-difluoroazetidin-1-yl-, and $R^4$ is a hydrogen atom or a methyl group.

One further aspect of the invention is a method for the preparation of compounds of formula (I),
said method comprising
EITHER
the step A of allowing an intermediate compound of formula (IIb)

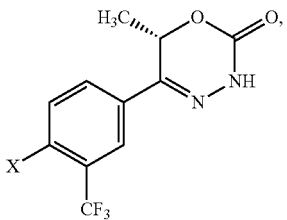

or an intermediate compound of formula (IIc)

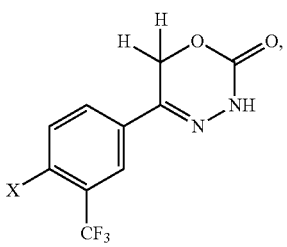

in which X is selected from $C_1$, Br and I
to react, in a Suzuki coupling reaction,
with a boronic acid of formula (IIId)

$$(R^x)B(OH)_2 \quad (IIId),$$

whereby $R^x$ is selected from
a phenyl group which is substituted with one or two substituents independently selected from a halogen atom, a $C_1$-$C_3$-alkyl group and a $NR^5R^6$ group,
a heteroaryl group which is substituted with a substituent selected from a $C_1$-$C_3$-alkyl group, a $C_1$-$C_3$-haloalkyl group and a $NR^5R^6$ group,
or
with a boronic ester of formula $$(R^x)B(OR^y)_2 \quad (IIIe),$$

wherein $R^x$ is as defined for the boronic acid of formula (IIId), supra, and $R^y$ is $C_1$-$C_6$-alkyl, or the two residues $R^y$ together form a $C_2$-$C_6$-alkylene group, in a preferred embodiment —C(CH$_3$)$_2$—C(CH$_3$)$_2$— to form a pinacol ester,
in the presence of a base, preferably potassium carbonate, and of a palladium catalyst selected from: dichlorobis(triphenylphosphine)palladium, tetrakistriphenylphosphinepalladium(0), palladium(II) acetate/triscyclohexylphosphine, tris(dibenzylideneacetone)dipalladium, bis(diphenylphosphineferrocenyl)palladium(II) chloride, 1,3-bis(2,6-diisopropylphenyl)imidazol-2-ylidene(1,4-naphthoquinone)palladium dimer, allyl(chloro)(1,3-dimesityl-1,3-dihydro-2H-imidazol-2-ylidene)palladium, palladium(II) acetate/dicyclohexyl(2',4',6'-triisopropyl-biphenyl-2-yl)phosphine, [1,1-bis(diphenylphosphino)ferrocene]palladium(II) chloride monodichloromethane adduct, [1,1'-Bis(diphenylphosphino)ferrocene]dichloropalladium(II), chloro(2-dicyclohexylphosphino-2',4',6'-triisopropyl-1,1'-biphenyl)[2-(2'-amino-1,1'-biphenyl)]palladium(II), and (2-dicyclohexylphosphino-2',4',6'-triisopropyl-1,1'-biphenyl)[2-(2'-amino-1,1'-biphenyl)]palladium(II), as a preferred embodiment chloro(2-dicyclohexylphosphino-2',4',6'-triisopropyl-1,1'-biphenyl)[2-(2'-amino-1,1'-biphenyl)]palladium(II),
optionally in the presence of an additional ligand such as e.g. 2-(dicyclohexylphosphino)-2',4',6'-triisopropylbiphenyl,
in the presence of a solvent, such as e.g. dioxane or water, or a mixture thereof, at a temperature ranging from 80° C. to 120° C.,
in order to obtain a compound of formula (I) wherein $R^1$ is a trifluoromethyl group, $R^2$ is a hydrogen atom, $R^3$ is $R^x$ as defined above for formula (IId) and $R^4$ is a hydrogen atom or a methyl group,
OR
said method comprising
the step B of allowing an intermediate compound of formula (IIb)

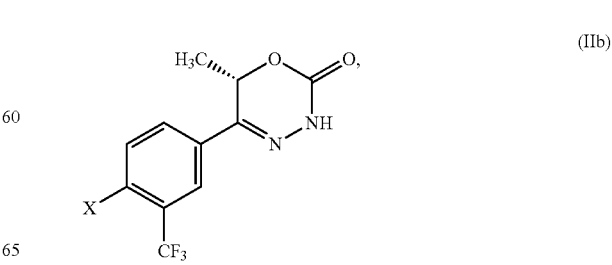

or said intermediate compound of formula (IIc)

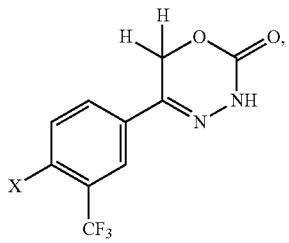

in which X is a fluorine atom,
to react with an amine HNR$^7$R$^8$
wherein R$^7$ is a hydrogen atom, and R$^8$ is selected from
C$_1$-C$_6$-alkyl group, which is optionally substituted with a substituent and said substituent is independently selected from
a halogen atom, a hydroxy group,
a C$_1$-C$_3$-alkoxy group,
a C$_3$-C$_7$-cycloalkyl group which is optionally further substituted with one or two substituents and said substituents are independently selected from a C$_1$-C$_3$-alkyl, group, a hydroxy group, and a C$_1$-C$_3$-hydroxyalkyl group;
a 3- to 7-membered heterocycloalkyl group, comprising one or two heteroatoms which are independently selected from —O—, —S— and —NR$^9$—, which is optionally further substituted with a C$_1$-C$_3$-alkyl group or an oxo (=O) group;
a heteroaryl group, which is optionally further substituted with a C$_1$-C$_3$-alkyl group;
a C$_3$-C$_7$-cycloalkyl group which is optionally substituted with a hydroxy group, or a C$_1$-C$_3$-alkyl group and
a 3- to 6-membered heterocycloalkyl group, which is optionally substituted with one or two substituents said substituent independently selected from C$_1$-C$_3$-alkyl group and a hydroxy group.
and bear an unsubstituted nitrogen atom at N–1,
optionally in the presence of a base, such as e.g. cesium carbonate, and optionally the presence of an inert solvent, such as e.g. DMF, and optionally heating up to the boiling temperature of the present base or the present solvent, preferentially RT-150° C.
in order to obtain a compound of formula (I) wherein R$^1$ is a trifluoromethyl group, R$^2$ is a hydrogen atom,
R$^3$ is a NR$^7$R$^8$ group, whereby R$^7$ is hydrogen and R$^8$ is as defined above,
and R$^4$ is a hydrogen atom or a methyl group.
One further aspect of the invention is a method for the preparation of compounds of formula (I),
said method comprising
EITHER
the step A of allowing an intermediate compound of formula (IIb)

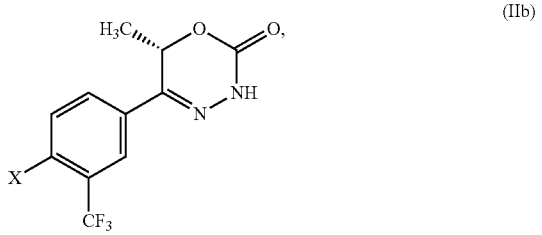

or an intermediate compound of formula (IIc)

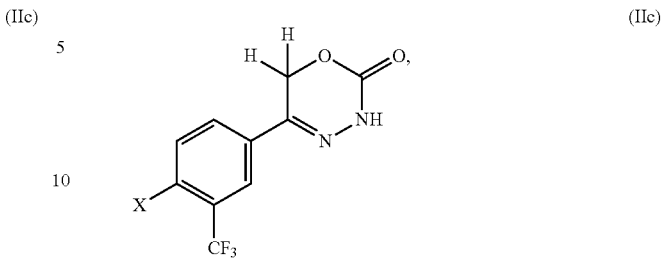

in which X is selected from C$_1$, Br and I
to react, in a Suzuki coupling reaction,
with a boronic acid of formula (IIId)

(R$^x$)B(OH)$_2$     (IIId), whereby R$^x$ is selected from
a phenyl group which is substituted with one or two substituents independently selected from a fluorine atom and a chlorine atom,
a pyrazolyl group which is substituted with one difluoromethyl group or one trifluoromethyl group, and
a pyridyl group, which is substituted with one NH$_2$ group,
or
with a boronic ester of formula (R$^x$)B(OR$^y$)$_2$     (IIIe), wherein R$^x$ is as defined for the boronic acid of formula (IIId), supra, and R$^y$ is C$_1$-C$_6$-alkyl, or the two residues R$^y$ together form a C$_2$-C$_6$-alkylene group, in a preferred embodiment —C(CH$_3$)$_2$—C(CH$_3$)$_2$— to form a pinacol ester,
in the presence of a base, preferably potassium carbonate, and of a palladium catalyst selected from: dichlorobis(triphenylphosphine)palladium, tetrakistriphenylphosphinepalladium(0), palladium(II) acetate/triscyclohexylphosphine, tris(dibenzylideneacetone)dipalladium, bis(diphenylphosphineferrocenyl)palladium(II) chloride, 1,3-bis(2,6-diisopropylphenyl)imidazol-2-ylidene(1,4-naphthoquinone)palladium dimer, allyl(chloro)(1,3-dimesityl-1,3-dihydro-2H-imidazol-2-ylidene)palladium, palladium(II) acetate/dicyclohexyl(2',4',6'-triisopropyl-biphenyl-2-yl)phosphine, [1,1-bis(diphenylphosphino)ferrocene]palladium(II) chloride monodichloromethane adduct, [1,1'-Bis(diphenylphosphino)ferrocene]dichloropalladium(II), chloro(2-dicyclohexylphosphino-2',4',6'-triisopropyl-1,1'-biphenyl)[2-(2'-amino-1,1'-biphenyl)]palladium(II), and (2-dicyclohexylphosphino-2',4',6'-triisopropyl-1,1'-biphenyl)[2-(2'-amino-1,1'-biphenyl)]palladium(II), as a preferred embodiment chloro(2-dicyclohexylphosphino-2',4',6'-triisopropyl-1,1'-biphenyl)[2-(2'-amino-1,1'-biphenyl)]palladium(II),
optionally in the presence of an additional ligand such as e.g. 2-(dicyclohexylphosphino)-2',4',6'-triisopropylbiphenyl,
in the presence of a solvent, such as e.g. dioxane or water, or a mixture thereof, at a temperature ranging from 80° C. to 120° C.,
in order to obtain a compound of formula (I) wherein R$^1$ is a trifluoromethyl group, R$^2$ is a hydrogen atom, R$^3$ is R$^x$ as defined above for formula (IId) and R$^4$ is a hydrogen atom or a methyl group,
OR said method comprising
the step B of allowing an intermediate compound of formula (IIb)

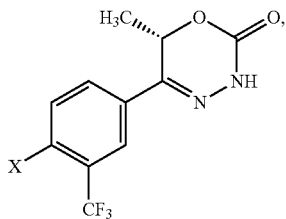

or said intermediate compound of formula (IIc)

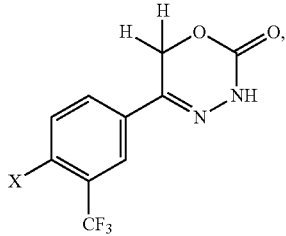

in which X is a fluorine atom,
to react with an amine HNR⁷R⁸
wherein $R^7$ is a hydrogen atom, and $R^8$ is a 3,3,3-trifluoro-2-hydroxypropyl group, a 2-hydroxy-2-methylpropyl group or a 2-methoxyethyl group,
or with a 1H-pyrazole which is substituted with a trifluoromethyl group and is unsubstituted at N–1,
optionally in the presence of a base, such as e.g. cesium carbonate, and optionally the presence of an inert solvent, such as e.g. DMF, and optionally heating up to the boiling temperature of the present base or the present solvent, preferentially RT-150° C. in order to obtain a compound of formula (I) wherein
$R^1$ is a trifluoromethyl group, $R^2$ is a hydrogen atom,
$R^3$ is a NR⁷R⁸ group, whereby $R^7$ is hydrogen and $R^8$ is 3,3,3-trifluoro-2-hydroxypropyl, 2-hydroxy-2-methylpropyl or 2-methoxyethyl,
or $R^3$ is a 1H-pyrazol-1-yl group, which is substituted with a trifluoromethyl group,
and $R^4$ is a hydrogen atom or a methyl group.

In accordance with another aspect, the present invention provides the use of said intermediate compound of formulae (II), (IIa) and (IIb) as defined supra for the preparation of a compound of general formula (I) as defined supra.

The present invention provides the intermediate compounds which are disclosed in the Example Section of this text, infra.

The present invention provides any sub-combination within any embodiment or aspect of the present invention of intermediate compounds of general formula (I), supra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Utility

Compounds of general formula (I) of the present invention demonstrate a valuable pharmacological spectrum of action, which could not have been predicted. Compounds of the present invention have surprisingly been found to effectively modulate PDE3A and it is possible therefore that said compounds be used for the treatment or prophylaxis of diseases, more particularly hyperproliferative diseases, even more particularly cancer diseases in humans and animals. More particularly the compounds of formula (I) are suitable for the treatment of a patient having a cancer that is sensitive to treatment with a phosphodiesterase 3A/B (PDE3A/B)-SLF12 complex modulator by detecting co-expression of PDE3A and/or PDE3B and Schlafen 12 (SLFN12) and/or SLFN12L mRNA, polynucleotides or polypeptides and/or a lack of decrease in expression of CREB3L1 mRNA, polynucleotides or polypeptides in a cancer cell derived from such patients.

Compounds of the present invention can be utilized to inhibit, block, reduce, decrease, etc., cell proliferation and/or cell division, and/or produce apoptosis. This method comprises administering to a mammal in need thereof, including a human, an amount of a compound of general formula (I) of the present invention, or a pharmaceutically acceptable salt, isomer, polymorph, metabolite, hydrate, solvate or ester thereof, which is effective to treat the disease.

The present compounds of formula (I) may additionally show improved physicochemical properties and/or improved safety pharmacological properties.

Thus a further aspect of the invention are compounds if formula (I) which show improved physicochemical properties compared to compounds of the state of the art.

Another aspect of the invention are those compounds of formula (I) which show an improved safety pharmacological properties.

Further Definitions

By "alteration" is meant a change (increase or decrease) in the expression levels or activity of a gene or polypeptide as detected by standard art known methods such as those described herein. As used herein, in one embodiment an alteration includes an about 10% change in expression levels, preferably an about 25% change, more preferably an about 40% change, and most preferably an about 50% or greater (e.g., 60% or greater, 70% or greater, 80% or greater, 90% or greater) change in expression levels. In certain embodiments an alteration includes a 10% or less (including 10%) change in expression levels, preferably a 25% or less (including 25%) change, more preferably a 40% or less (including 40%) change, and most preferably a 50% or less (including 50%) or greater change in expression levels. In other embodiments an alteration includes a 9%-11% (including 9% and 11%) change in expression levels, preferably a 10%-25% (including 10% and 25%) change, more preferably a 25%-40% (including 25% and 40%) change, and most preferably a 40%-50% (including 40%-50%) or greater than 50% (including 50%) change in expression levels. In other certain embodiments an alteration includes a 9%-11% (including 9% and 11%) change in expression levels, preferably a 22%-28% (including 22% and 28%) change, more preferably a 35%-45% (including 35% and 45%) change, and most preferably a 45%-55% (including 45%-55%) or a greater or equal to 55% change in expression levels By "fragment" is meant a portion of a polypeptide or nucleic acid molecule. This portion contains, preferably, at least about 10%, about 20%, about 30%, about 40%, about 50%, about 60%, about 70%, about 80%, or about 90% of the entire length of the reference nucleic acid molecule or polypeptide. In certain embodiments this portion contains, preferably, at least 9%-11% (including 9% and 11%), 18%-22% (including 18% ands 22%), 27%-33% (including 27% and 33%), 36%-44% (including 36% and 44%), 45%-55% (including 45% and 55%), 54%-66% (including 54% and 66%), 63%-77% (including 63% and 77%), 72%-88% (including 72% and 88%), or 81%-99% (including 81% and 99%) of the entire length of the reference nucleic acid molecule or polypeptide A fragment may contain about 10, about 20, about 30, about 40, about 50, about 60, about 70, about 80, about 90, about 100, about 200, about 300, about 400, about 500, about 600, about 700, about 800, about 900, or about 1000 nucleotides or amino acids. In certain embodiments a fragment may contain 9-11, about 18-22, 27-33, 36-44, 45-55, 54-66, 63-77, 72-88, 81-99, 90-110, 180-220, 270-330, 360-440, 450-550, 540-660, 630-770, 720-880, 810-990, or 900-1100 nucleotides or amino acids (including for each the mentioned limitation e.g. for "9-11" means including 9 and 11.

"Hematopoietic hyperproliferative diseases" also known as myoproliferative diseases include e.g. polycythemia vera, essential thrombocytosis, thrombocytosis, primary myelofibrosis, and others.

"Hyperproliferative diseases" include, but are not limited to, for example: psoriasis, keloids, and other hyperplasias affecting the skin, benign hyperproliferative diseases, hematopoietic hyperproliferative diseases (including polycythemia vera, essential thrombocytosis, primary myelofibrosis), benign prostate hyperplasia (BPH), cancer (especially metastatic or malignant tumors, more specifically solid tumors and haematological tumors).

"Benign hyperproliferative diseases" include for example, endometriosis, leiomyoma and benign prostate hyperplasia.

By "marker" or "biomarker" is meant any protein or polynucleotide having an alteration in expression level or activity (e.g., at the protein or mRNA level) that is associated with a disease or disease. In particular embodiments, a marker of the invention is PDE3A/PBE3B or SLFN12 or CREB3L1 polypeptide or polynucleotide.

By "modulator" is meant any agent that binds to a polypeptide and alters a biological function or activity of the polypeptide. A modulator includes, without limitation, agents that reduce or eliminate a biological function or activity of a polypeptide (e.g., an "inhibitor"). For example, a modulator may inhibit a catalytic activity of a polypeptide. A modulator includes, without limitation, agents that increase or decrease binding of a polypeptide to another agent. For example, a modulator may promote binding of a polypeptide to another polypeptide. In some embodiments, the modulator of PDE3A/PDE3B polypeptide is a compound of formula (I).

"Solid tumours" are such as e.g. cancers of the breast, brain, digestive tract, eye, head and neck, liver, parathyroid, reproductive organs, respiratory tract, skin, thyroid, urinary tract, and their distant metastases. Those diseases also include lymphomas, sarcomas, and leukaemias.

Examples of breast cancers include, but are not limited to, invasive ductal carcinoma, invasive lobular carcinoma, ductal carcinoma in situ, and lobular carcinoma in situ.

Examples of "brain cancers" include, but are not limited to, brain stem and hypophtalmic glioma, cerebellar and cerebral astrocytoma, medulloblastoma, ependymoma, as well as neuroectodermal and pineal tumour.

Tumours of the "digestive tract" include, but are not limited to, anal, colon, colorectal, oesophageal, gallbladder, gastric, pancreatic, rectal, small-intestine, and salivary gland cancers.

"Eye cancers" include, but are not limited to, intraocular melanoma and retinoblastoma.

"Head-and-neck cancers" include, but are not limited to, laryngeal, hypopharyngeal, nasopharyngeal, oropharyngeal cancer, lip and oral cavity cancer and squamous cell.

Examples of "liver cancers" include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Examples of cancers of the "respiratory tract" include, but are not limited to, small-cell and non-small-cell lung carcinoma, as well as bronchial adenoma and pleuropulmonary blastoma.

"Reproductive organs" include female- and male reproductive organs.

"Tumours of the female reproductive organs" include, but are not limited to, endometrial, cervical, ovarian, vaginal, and vulvar cancer, as well as sarcoma of the uterus. T"umours of the male reproductive organs" include, but are not limited to, prostate and testicular cancer.

"Skin cancers" include, but are not limited to, squamous cell carcinoma, Kaposi's sarcoma, malignant melanoma (melanoma), Merkel cell skin cancer, and non-melanoma skin cancer.

"Tumours of the urinary tract" include, but are not limited to, bladder, penile, kidney, renal pelvis, ureter, urethral and human papillary renal cancers.

"Lymphomas" include, but are not limited to, AIDS-related lymphoma, non-Hodgkin's lymphoma, cutaneous T-cell lymphoma, Burkitt lymphoma, Hodgkin's disease, and lymphoma of the central nervous system.

"Sarcomas" include, but are not limited to, sarcoma of the soft tissue, osteosarcoma, malignant fibrous histiocytoma, lymphosarcoma, and rhabdomyosarcoma.

"Leukemias" include, but are not limited to, acute myeloid leukemia (AML), acute lymphoblastic leukemia, chronic lymphocytic leukemia, chronic myelogenous leukemia, and hairy cell leukemia.

By "subject" is meant a mammal, including, but not limited to, a human or non-human mammal, such as e.g. a bovine, equine, canine, ovine, or feline.

As used herein, the terms "treat," treating," "treatment," and the like refer to reducing or ameliorating a disease and/or symptoms associated therewith. It will be appreciated that, although not precluded, treating a disease or condition does not require that the disease, condition or symptoms associated therewith be completely eliminated.

Any compositions or methods provided herein can be combined with one or more of any of the other compositions and methods provided herein.

The term "treating" or "treatment" as stated throughout this document is used conventionally, for example the management or care of a subject for the purpose of combating, alleviating, reducing, relieving, improving the condition of a disease or disease, such as e.g. a carcinoma. These diseases have been well characterized in humans, but also exist with a similar etiology in other mammals, and can be treated by administering pharmaceutical compositions of the present invention.

The compounds of the present invention can be used in particular in therapy and prevention, i.e. prophylaxis, of hyperproliferative diseases, more particularly of cancer diseases, e.g. heamatological cancer diseases and tumour growth and metastasis, especially in solid tumours and heamatological cancer diseases of all indications and stages with or without pre-treatment of the tumour.

Generally, the use of chemotherapeutic agents and/or anti-cancer agents in combination with a compound or pharmaceutical composition of the present invention will serve to:
1. yield better efficacy in reducing the growth of a tumour or even eliminate the tumour as compared to administration of either agent alone,
2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other cancer agent combinations produce antagonistic effects.

In another aspect, the cell is in vitro. In another embodiment, the cell is in vivo.

Optionally, an anti-neoplasia therapeutic (e.g., compounds of general formula (I)) may be administered in combination with any other standard anti-neoplasia therapy or conventional chemotherapeutic agent, such as e.g. an alkylating agent; such methods are known to the skilled artisan and described in Remington's Pharmaceutical Sciences by E. W. Martin. If desired, agents of the invention are administered in combination with any conventional anti-neoplastic therapy, including but not limited to, surgery, radiation therapy, or chemotherapy for the treatment of a neoplasia (e.g., melanoma, lung adenocarcinoma or a cervical cancer).

The present invention also provides compounds of formula (I) for methods of treating hyperproliferative diseases, more particularly cancer diseases including hematological cancer diseases and solid tumors.

In one embodiment the invention provides methods of treatment mentioned above where tumors are selected from list given above, more particularly the tumors are: tumors of the anus, the brain, the breast, the bones, the central and peripheral nervous system, the colon, the eye, the kidney, the endocrine glands (e.g., thyroid and adrenal cortex), the endometrium, the esophagus, the gastrointestinal tract (including gastrointestinal stromal tumors), the germ cells, the head and the neck, the kidney, the liver, the larynx and hypopharynx, the lung, the mesothelioma, the pancreas, the prostate, the rectum, the reproductive organs (e.g., cervix, ovary, prostate), the respiratory tract, the small intestine, the skin, the soft tissue, the stomach, the testis, the thyroid gland, the parathyroid gland, ureter, the urogenital tract, vagina and vulva and the connective tissue and metastases of these tumors. Malignant neoplasias include inherited cancers exemplified by Retinoblastoma and Wilms tumor.

In another embodiment the invention provides methods of treatment of cancer or the use of the compounds formula (I) for the treatment of a cancer disease, where said cancer disease is selected from brain cancer, e.g. glioma, more specifically astrocytoma or glioblastoma; breast cancer, more specifically ductal carcinoma, adenocarcinoma; cervical cancer; leukemia, such as e.g. acute myeloid leukemia (AML); lung cancer, more specifically non small cell lung cancer (NSCLC) or small cell lung cancer (SCLC); skin cancer, more specifically melanoma; oesophagal cancer, more specifically squamous cell carcinoma; ovarian cancer, more specifically teratocarcinoma, adenocarcinoma; pancreas cancer and prostate cancer.

In another embodiment the invention provides methods of treatment of cancer or the use of the compounds formula (I) for the treatment of a cancer disease, where said cancer disease is selected from glioma, more specifically astrocytoma or glioblastoma; breast ductal carcinoma, breast adenocarcinoma; cervical cancer; acute myeloid leukemia (AML); non small cell lung cancer (NSCLC), small cell lung cancer (SCLC), melanoma, squamous cell carcinoma, ovarian teratocarcinoma, ovarian adenocarcinoma, pancreas cancer and prostate cancer.

In one embodiment the invention provides methods of treatment of cancer or the use of the compounds formula (I) for the treatment of a cancer disease, where said cancer disease is selected from melanoma, AML, cervical cancer and ovarian cancer, more particularly ovarian teratocarcioma.

In one embodiment the invention provides methods of treatment of cancer or the use of the compounds formula (I) for the treatment of a cancer disease, where said cancer disease is selected from melanoma and cervical cancer.

In one embodiment the invention provides methods of treatment of cancer or the use of the compounds formula (I) for the treatment of a cancer disease, where said cancer disease is melanoma.

These diseases have been well characterized in humans, but also exist with a similar etiology in other mammals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as e.g. cancer.

The compounds of the present invention can be used in particular in therapy and prevention, i.e. prophylaxis, of hyperproliferative diseases, more particularly cancer diseases.

In accordance with a further aspect, the present invention provides compounds of general formula (I), as described supra, or stereoisomers, tautomers, N-oxides, hydrates, solvates, and salts thereof, particularly pharmaceutically acceptable salts thereof, or mixtures of same, for use in the treatment or prophylaxis of diseases, in particular hyperproliferative diseases.

The pharmaceutical activity of the compounds according to the invention can be explained by their activity by modulation of phosphodiesterase 3A/B (PDE3A/B).

Thus a further aspect of the invention is a method of treatment comprising administering a compound of formula (I) or a pharmaceutical composition thereof to a patient suffering from a cancer disease being sensitive to a treatment with a PDE3A/PDE3B modulator.

Another aspect of the invention is a method of treatment comprising the steps of
deriving cancer cells from a patient,
detecting co-expression of PDE3A and/or
detecting co-expression of PDE3B and detecting co-expression of Schlafen 12 (SLFN12) and/or SLFN12L mRNA, polynucleotides or polypeptides and/or a lack of decrease in expression of CREB3L1 mRNA, polynucleotides or polypeptides in said cancer cells, summarizing the overall results whether the data collected indicate that said cancer cells are sensitive to the treatment with a compound of formula (I), and administering a compound of formula (I) to said patient.

In accordance with a further aspect, the present invention provides the use of compounds of general formula (I), as described supra, or stereoisomers, tautomers, N-oxides, hydrates, solvates, and salts thereof, particularly pharmaceutically acceptable salts thereof, or mixtures of same, for the treatment or prophylaxis of diseases, in particular hyperproliferative diseases, particularly cancer diseases.

In accordance with a further aspect, the present invention provides the a compound of formula (I), described supra, or a stereoisomer, a tautomer, an N-oxide, a hydrate, a solvate, or a salt thereof, particularly a pharmaceutically acceptable salt thereof, or a mixture of same, for use in the prophylaxis or treatment of diseases, in particular hyperproliferative diseases, particularly cancer diseases.

In accordance with a further aspect, the present invention provides the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prophylaxis of diseases, in particular hyperproliferative diseases, particularly cancer diseases.

In accordance with a further aspect, the present invention provides use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular hyperproliferative diseases, particularly cancer diseases.

In accordance with a further aspect, the present invention provides a method of treatment or prophylaxis of diseases, in particular hyperproliferative diseases, particularly cancer diseases, comprising administering an effective amount of a compound of general formula (I), as described supra, or stereoisomers, tautomers, N-oxides, hydrates, solvates, and salts thereof, particularly pharmaceutically acceptable salts thereof, or mixtures of same to a patient in need thereof Pharmaceutical Composition In accordance with a further aspect, the present invention provides pharmaceutical compositions, in particular a medicament, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore provides pharmaceutical compositions, in particular medicaments, which comprise at least one compound according to the invention, conventionally together with one or more pharmaceutically suitable excipients, and for their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides, fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

Combinations

In accordance with another aspect, the present invention provides pharmaceutical combinations, in particular medicaments, comprising at least one compound of general formula (I) of the present invention and at least one or more further active ingredients, in particular for the treatment and/or prophylaxis of a hyperproliferative disease, a cancer disease.

Particularly, the present invention provides a pharmaceutical combination, which comprises:

one or more first active ingredients, in particular compounds of general formula (I) as defined supra, and one or more further active ingredients, in particular a hyperproliferative disease, a cancer disease.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as e.g. in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also provides such pharmaceutical combinations. For example, the compounds of the present invention can be combined with known anti-cancer-agents, said anti-cancer agents including but not limited to:

131I-chTNT, abarelix, abemaciclib, abiraterone, acalabrutinib, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, apalutamide, aprepitant, arcitumomab, arglabin, arsenic trioxide, asparaginase, atezolizumab, avelumab, axicabtagene ciloleucel, axitinib, azacitidine, basiliximab, belotecan, bendamustine, besilesomab, belinostat, bevacizumab, bexarotene, bicalutamide, bisantrene, bleomycin, blinatumomab, bortezomib, bosutinib, buserelin, brentuximab vedotin, brigatinib, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, durvalumab, eculizumab, edrecolomab, elliptinium acetate, elotuzumab, eltrombopag, enasidenib, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, Iansoprazole, ibandronic acid, ibritumomab tiuxetan, ibrutinib, idarubicin, ifosfamide, imatinib, imiquimod, improsulfan, indisetron, incadronic acid, ingenol mebutate, inotuzumab ozogamicin, interferon alfa, interferon beta, interferon gamma, iobitridol, iobenguane (123I), iomeprol, ipilimumab, irinotecan, Itraconazole, ixabepilone, ixazomib, Ianreotide, Iansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, lutetium Lu 177 dotatate, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, midostaurin, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, mvasi, nabilone, nabiximols, nafarelin, naloxone+pentazocine, naltrexone, nartograstim, necitumumab, nedaplatin, nelarabine, neratinib, neridronic acid, netupitant/palonosetron, nivolumab, pentetreotide, nilotinib, nilutamide, nimorazole, nimotuzumab, nimustine, nintedanib, niraparib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, ribociclib, risedronic acid, rhenium-186 etidronate, rituximab, rolapitant, romidepsin, romiplostim, romurtide, rucaparib, samarium (153Sm) lexidronam, sargramostim, sarilumab, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tisagenlecleucel, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Based upon standard laboratory techniques known to evaluate compounds useful for the treatment of hyperproliferative diseases, more particularly cancer diseases by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 500 mg/kg body weight per day, particularly about 0.001 mg/kg to about 200 mg/kg body weight per day, and more particularly from about 0.01 mg/kg to about 50 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight. For oral administration the dosing schedule may be once or two time or three times daily and a dose range as referred to above for general dosing is possible.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXAMPLES

Experimental Section

NMR peak forms are stated as they appear in the spectra, possible higher order effects have not been considered.

The $^1$H-NMR data of selected compounds are listed in the form of $^1$H-NMR peaklists. Therein, for each signal peak the δ value in ppm is given, followed by the signal intensity, reported in round brackets. The δ value-signal intensity pairs from different peaks are separated by commas. Therefore, a peaklist is described by the general form: $δ_1$ (intensity$_1$), $δ_2$ (intensity$_2$), ..., $δ_i$ (intensity$_i$), ..., $δ_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of the particular target compound, peaks of impurities, $^{13}$C satellite peaks, and/or spinning sidebands. The peaks of stereoisomers, and/or peaks of impurities are typically displayed with a lower intensity compared to the peaks of the target compound (e.g., with a purity of >90%). Such stereoisomers and/or impurities may be typical for the particular manufacturing process, and therefore their peaks may help to identify a reproduction of the manufacturing process on the basis of "byproduct fingerprints". An expert who calculates the peaks of the target compound by known methods (MestReC, ACD simulation, or by use of empirically evaluated expectation values), can isolate the peaks of the target compound as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. http://www.researchdisclosure.com/searching-disclosures, Research Disclosure Database Number 605005, 2014, 1 Aug. 2014). In the peak picking routine, as described in the Research Disclosure Database Number 605005, the parameter "MinimumHeight" can be adjusted between 1% and 4%. However, depending on the chemical structure and/or depending on the concentration of the measured compound it may be reasonable to set the parameter "MinimumHeight"<1%.

Chemical names were generated using the ACD/Name software from ACD/Labs. In some cases generally accepted names of commercially available reagents were used in place of ACD/Name generated names.

The following table 1 lists the abbreviations used in this paragraph and in the Examples section as far as they are not explained within the text body. Other abbreviations have their meanings customary per se to the skilled person.

TABLE 1

| Abbreviations | |
|---|---|
| [α] | specific rotation value |
| EtOH | Ethanol |
| THF | Tetrahydrofurane |
| DAD | Diode array detector |
| δ | NMR shift in ppm |
| d | doublet (NMR coupling pattern) |
| DMSO | dimethylsulfoxide |
| M | Molar or molecular Mass |
| ESI | electrospray ionisation (MS) |
| LiHMDS | Lithium 1,1,1,3,3,3-hexamethyldisilazan-2-ide |
| LC-MS | liquid chromatography coupled to mass spectrometry |
| m | multiplet (NMR coupling pattern) |
| MS | mass spectrometry |
| MHz | Megahertz |
| NMR | nuclear magnetic resonance |
| q | quartet (NMR coupling pattern) |
| $R_t$, Rt | retention time |
| RT | room temperature |
| s | singlet (NMR coupling pattern) |
| t | triplet (NMR coupling pattern) |
| UPLC | Ultra Performance Liquid Chromatography |
| UV | ultraviolet |
| WL | wavelength |
| DIPEA | N,N-diisopropylethylamine |
| UPLC-MS | Ultra High Preformance Liquid Chromatography Mass Spectroscopy |
| pH | Potential of Hydrogen |
| MTBE | Methyl tert-butyl ether |
| EtOAc, EA | Ethyl acetate |
| MeCN, ACN | Acetonitrile |
| Et | Ethyl |
| Me | Methyl |
| Pr | Propyl |
| AMC | Automated Medicinal Chemistry |
| DMF | Dimethylformamide |
| MeOH | methanol |
| HOAc | Acetic Acid |
| PE | Petroleum Ether |
| DCM | dichloromethane |
| J | coupling constant (in NMR spectra) |
| NaOMe | sodium methoxide |
| NaOEt | sodium ethoxide |
| HCl | hydrochloric acid, hydrogen chloride |
| aq | aqueous |
| Pd/C | Palladium on carbon |
| IPA | Isopropyl alcohol |
| v:v | ratio by volume |

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as e.g. gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as e.g. gradients of water and acetonitrile which may contain additives such as e.g. trifluoroacetic acid, formic acid or aqueous ammonia.

In some cases, purification methods as described above can provide those compounds of the present invention which possess a sufficiently basic or acidic functionality in the form of a salt, such as e.g., in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC-MS Standard Procedures

Analytical UPLC-MS was performed as described below. The masses (m/z) are reported from the positive mode electrospray ionisation unless the negative mode is indicated (ESI−). In most of the cases method 1 is used. If not, it is indicated.

Experimental Section—General Procedures

Analytical LC-MS Methods:
Method 1:
Instrument: Waters Acquity UPLC-MS SingleQuad; column: Acquity UPLC BEH C18 1.7 µm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.
Method 2:
Instrument: Waters Acquity UPLC-MS SingleQuad; Column: Acquity UPLC BEH C18 1.7 µm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; DAD scan: 210-400 nm.
Method 3:
Instrument: SHIMADZU LCMS-UFLC 20-AD-LCMS 2020 MS detector; Column: Waters Atlantis dC18 3 µm, 2.1×100 mm; eluent A: water+0.1% formic acid (v/v), eluent B: acetonitrile+0.1% formic acid (v/v); gradient: 0-5.00 min 5-100% B 5.00-5.40 min 100% B; flow: 0.6 mL/min; temperature: 40° C.; PDA scan: 210-420 nm.
Method 4:
Instrument Waters Acquity UPLCMS SingleQuad; Column: Phenomenex Kinetix-XB C18 1.7 µm, 2.1×100 mm; eluent A: water+0.1% formic acid (v/v), eluent B: acetonitrile+0.1% formic acid (v/v); gradient: 0-5.30 min 5-100% B, 5.30-5.80 min 100% B; flow: 0.6 mL/min; temperature: 40° C.; PDA scan: 200-400 nm.
Method 5:
Tandem Liquid Chromatography/Mass Spectrometry (LC/MS) was performed on a Waters 2795 separations module and 3100 mass detector with a Waters Symmetry C18 column (3.5 µm, 4.6×100 mm) with a gradient of 0-100% $CH_3CN$ in water over 2.5 min with constant 0.1% formic acid.

Preparative LC-MS Methods:

Unless otherwise noted compounds were purified using mass-triggered preparative HPLC (Waters Autopurification-system; Column: Waters XBridge C18 5µ 100×30 mm; DAD scan: 210-400 nm, flow: 150 mL/min) or UV triggered preparative HPLC (pump: Labomatic HD-5000 or HD-3000, head HDK 280, lowpressure gradient module ND-B1000; manual injection valve: Rheodyne 3725i038; detector: Knauer Azura UVD 2.15; collector: Labomatic Labocol Vario-4000; column: Chromatorex RP C-18 10 µm, 125×30 mm, flow: 70 mL/min)

Acidic conditions: Eluent A: water+0.1 vol-% formic acid, Eluent B: acetonitrile+0.1 vol-% formic acid;

Basic conditions: Eluent A: water+0.2 Vol-% aqueous ammonia (32%), Eluent B: acetonitrile;

Experimental Section—General Procedures

General Details

All reactions were carried out under nitrogen ($N_2$) atmosphere. All reagents and solvents were purchased from commercial vendors and used as received. Nuclear magnetic resonance (NMR) spectra were recorded on a Bruker (300 or 400 MHz $^1$H, 75 or 101 MHz $^{13}$C) spectrometer. Proton and carbon chemical shifts are reported in ppm (δ) referenced to the NMR solvent. Data are reported as follows: chemical shifts, multiplicity (br=broad, s=singlet, d=doublet, t=triplet, q=quartet, m=multiplet; coupling constant(s) in Hz). Flash chromatography was performed using 40-60 µm Silica Gel (60 Å mesh) on a Teledyne Isco Combiflash Rf or a Biotage Isolera. Analytical thin layer chromatography (TLC) was performed on EM Reagent 0.25 mm silica gel 60-F plates.

Experimental Section—Intermediates

Intermediate 1

4-Chloro-N-methoxy-N-methyl-3-(trifluoromethyl) benzamide

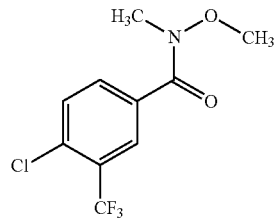 [SMILES: CON(C)C(=O)c1ccc(Cl)c(C(F)(F)F)c1]

A mixture of 15 g (66.7 mmol) of 4-chloro-3-trifluoromethyl benzoic acid (CAS 1737-36-6) in 100 ml of DCM was cooled in an ice bath before addition of 6.73 mL (80 mmol) of oxalyl chloride and a drop of DMF. The reaction was stirred overnight, warming to room temperature before concentration, and addition of $CHCl_3$ followed by concentration (twice) to remove oxalyl chloride. The crude product was dissolved in 100 mL of $CH_2Cl_2$. In a separate flask, 7.14 g of N,O-dimethylhydroxylamine HCl (73.3 mmol) was added to 100 mL of $CH_2Cl_2$ and 37 mL of $Et_3N$ (266 mmol). After stirring 15 min the mixture was filtered and added to the acid chloride solution and the mixture was stirred 3 d. The reaction mixture was then transferred to a separatory funnel and the CH₂Cl₂ was rinsed with water, then aqueous NaHCO₃ solution, before drying and concentrating to an oil. Chromatography with 0-20% EtOAc in hexane yielded 14.1 g of the title compound as an oil (79%).

¹H NMR (300 MHz, CDCl₃) δ 8.08 (d, J=2.0 Hz, 1H), 7.85 (dd, J=8.1, 1.8 Hz, 1H), 7.56 (d, J=8.3 Hz, 1H), 3.55 (s, 3H), 3.39 (s, 3H). Mass 268 (M+1)+.

Intermediate 2

1-(4-Chloro-3-(trifluoromethyl)phenyl)propan-1-one

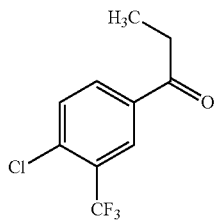

4-chloro-N-methoxy-N-methyl-3-(trifluoromethyl)benzamide (14.1 g, 52.6 mmol, Intermediate 1) was dissolved in 200 mL of THF and cooled in an ice bath before dropwise addition of 44 mL of 3 M EtMgBr solution (132 mmol, ether). Once addition was complete the ice bath was removed and the reaction stirred 3 h before cooling with an ice bath and quenching with NH₄Cl solution. The mixture was transferred to a separatory funnel, EtOAc and water were added. The organic layer was separated and dried and concentrated to a tan solid. Chromatography with 0-10% EtOAc in hexane yielded 10.1 g of product as a white solid (81%).

¹H NMR (400 MHz, CDCl₃) δ 8.29 (d, J=1.9 Hz, 1H), 8.08 (dd, J=8.3, 1.9 Hz, 1H), 7.64 (d, J=8.3 Hz, 1H), 3.03 (q, J=7.2 Hz, 2H), 1.27 (t, J=7.2 Hz, 3H). ¹F NMR (376 MHz, CDCl₃) δ -62.87.

Intermediate 3

1-[3,5-Difluoro-4-(morpholin-4-yl)phenyl]ethanone

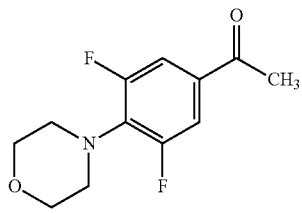 [SMILES: CC(=O)c1cc(F)c(N2CCOCC2)c(F)c1]

A solution of morpholine (480 µL, 5.6 mmol) and 1-(3,4,5-trifluorophenyl)ethanone (440 mg, 2.53 mmol, CAS 220141-73-1) in N,N-diisopropylethylamine (660 µL, 3.8 mmol) was stirred at 100° C. overnight. The reaction mixture was concentrated in vacuo, diluted with water and extracted three times with ethyl acetate. The combined organic phases were concentrated in vacuo to obtain 560 mg (42% yield) of the desired title compound, which was used in the next step without any further purification.

LC-MS (Method 1): R$_t$=1.06 min, MS (ESIpos): m/z=242 [M+H]⁺

¹H-NMR (400 MHz, DMSO-d6) δ[ppm]: 2.491 (4.95), 2.496 (10.90), 2.500 (16.00), 2.505 (11.73), 2.509 (5.31), 2.597 (0.55), 3.224 (1.82), 3.230 (1.81), 3.236 (2.59), 3.244 (1.94), 3.247 (2.03), 3.328 (4.68), 3.681 (3.37), 3.693 (3.40), 3.705 (3.03), 7.584 (2.54), 7.587 (1.37), 7.589 (1.06), 7.609 (1.43), 7.612 (2.54).

Intermediate 4

5-Acetyl-2-(morpholin-4-yl)benzonitrile

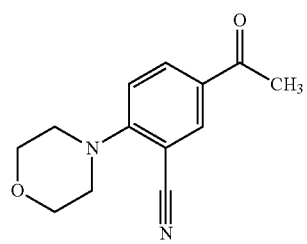 [SMILES: CC(=O)c1ccc(N2CCOCC2)c(C#N)c1]

A solution of morpholine (5.3 mL) and 5-acetyl-2-fluorobenzonitrile (2.00 g, 12.3 mmol CAS: 288309-07-9) in N,N-diisopropylethylamine (6.4 mL) was stirred at 100° C. overnight. For work up, the reaction mixture was concentrated in vacuo, diluted with water and extracted three times with ethyl acetate. The combined organic phases were concentrated in vacuo, to obtain 3.00 g (quant.) of the desired title compound, which was used in the next step without any further purification.

LC-MS (Method 1): R$_t$=0.90 min, MS (ESIpos): m/z=231 [M+H]⁺

Intermediate 5

1-(3-Fluoro-4-morpholinophenyl)propan-1-one

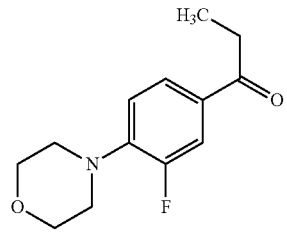 [SMILES: CCC(=O)c1ccc(N2CCOCC2)c(F)c1]

To a 1 L one-neck flask was added 40 g of 3,4-difluoropropiophenone (235 mmol, CAS 23384-72-7), 400 mL of CH₃CN, 250 mL of morpholine (2.86 mol), and 50 mL of DIPEA (360 mmol) and the solution was heated at 100° C. overnight. The next day the reaction was cooled and concentrated. The mixture was dissolved in CH₂Cl₂ and rinsed several times with water, then brine, and was dried (MgSO₄), filtered and concentrated. Most of the crude product dissolved in approx. 1 L of hot hexane and was cooled overnight. Upon filtration, more crystals appeared in the mother liquors. The mother liquors were concentrated and recrystallized from hexane. A total of 52.5 g of dry white solid was obtained (94%).

¹H NMR (400 MHz, CDCl₃) δ 7.72 (dd, J=8.4, 1.9 Hz, 1H), 7.66 (dd, J=14.0, 2.0 Hz, 1H), 6.93 (t, J=8.5 Hz, 1H), 3.94-3.85 (m, 4H), 3.26-3.17 (m, 4H), 2.94 (q, J=7.3 Hz, 2H), 1.23 (t, J=7.3 Hz, 3H). ¹⁹F NMR (376 MHz, CDCl₃) δ −121.48. MS: 238 [M+H]⁺

Intermediate 6

1-(4-Morpholino-3-(trifluoromethyl)phenyl)propan-1-one

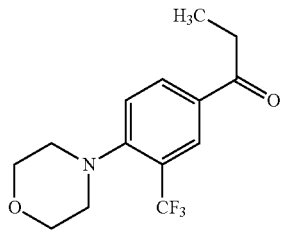 [SMILES: CCC(=O)c1ccc(N2CCOCC2)c(C(F)(F)F)c1]

A solution of 10 g of 1-(4-fluoro-3-(trifluoromethyl)phenyl)propan-1-one (45 mmol, CAS 239107-27-8), 40 mL of morpholine (450 mmol) and 16 mL of DIPEA (90 mmol) were heated at reflux temperature overnight. The next day another 20 mL of morpholine and 10 mL of DIPEA were added and heating continued several hours before cooling and concentrating. Water was added to the crude reaction mixture which was then rinsed several times with CH₂Cl₂, the combined CH₂C₂ layers were rinsed with brine, dried and concentrated. Chromatography with 0-20% EtOAc in hexane yielded 6.0 g of product as a white solid (46%).

¹H NMR (400 MHz, CDCl₃) δ 8.25 (s, 1H), 8.13 (d, J=8.4 Hz, 1H), 7.34 (d, J=8.4 Hz, 1H), 3.87 (s, 4H), 3.05 (s, 4H), 3.02-2.95 (m, 2H), 1.25 (t, J=7.2 Hz, 3H). ¹⁹F NMR (376 MHz, CDCl₃) δ −60.02. MS: 288 (M+1)+.

Intermediate 7

1-[4-Amino-3-fluoro-5-(trifluoromethyl)phenyl]ethan-1-one

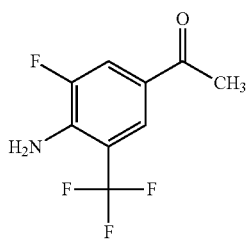

To a solution of 4-bromo-2-fluoro-6-(trifluoromethyl)benzenamine (21.60 g, 83.7 mmol, CAS 875664-46-3), in 250 mL of 1,4-dioxane were added tributyl(1-ethoxyvinyl)stannane, 45.35 g (125.6 mmol), and tetrakis(triphenylphosphine)palladium(0), 4.84 g (4.19 mmol). The resulting mixture was stirred at 120° C. for overnight. After cooled to room temperature, 100 mL of the hydrochloric acid solution (1 M) was added. The resulting mixture was stirred at room temperature for further 4 hours. Upon completion of the reaction, the reaction mixture was extracted with ethyl acetate. The combined organic layer was washed with brine, water and dried over anhydrous sodium sulfate. The solvent was removed in vacuo, and the residue purified with silica gel column chromatography (PE/EA=5:1) to give 16.00 g (69.8%) of the product as a yellow solid. MS(ESIpos): m/z=222 (M+H)+.

Intermediate 8

1-[4-Chloro-3-fluoro-5-(trifluoromethyl)phenyl]ethan-1-one

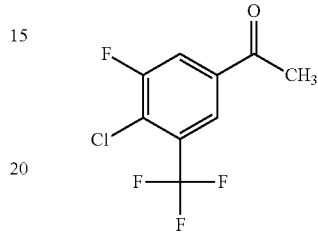

To a solution of 1-[4-amino-3-fluoro-5-(trifluoromethyl)phenyl]ethan-1-one (15.80 g, 71.4 mmol, Intermediate 7) in 200 mL of acetonitrile was added copper(II) chloride, 12.49 g (92.9 mmol), tert-butyl nitrite, 9.58 g (92.9 mmol). The resulting mixture was stirred at room temperature for 2 hours. Upon completion of the reaction, ice water was added and the resulting mixture was extracted with ethyl acetate. The combined organic layer was washed with saturated ammonium chloride solution, brine and dried over anhydrous sodium sulfate. The solvent was removed in vacuo, the residue was purified with silica gel column chromatography (ethyl acetate: petroleum ether=1:20) to give 16.0 g (83.8%) of the product as a yellow oil.

¹H-NMR (400 MHz, DMSO-de): 5 [ppm]=8.26 (d, 1H), 8.07 (s, 1H), 2.65 (s, 3H)

Intermediate 9

1-[4-Bromo-3-fluoro-5-(trifluoromethyl)phenyl]ethan-1-one

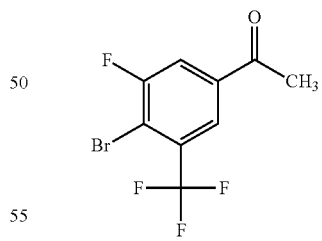

To a solution of 1-(4-amino-3-fluoro-5-(trifluoromethyl)phenyl)ethanone, 15.00 g (67.8 mmol, Intermediate 7), bromotrichloromethane, 26.90 g (135.7 mmol), and sodium nitrite, 23.40 g (339.1 mmol), in 300 mL of dichloromethane/water (v:v=1:1) was added HOAc, 81.46 g (1.4 mol), in one portion. The resulting mixture was stirred at room temperature for 2 hours. Upon completion of the reaction, the reaction mixture was extracted with ethyl acetate. The combined organic layer was washed with brine, water and dried over anhydrous sodium sulfate. The solvent was removed in vacuo, and the residue was purified with silica gel column chromatography (PE/EA=10:1) to give 16.70 g (86%) of the product as a yellow oil.

¹H-NMR (300 MHz, CDCl₃): δ [ppm]=8.09-8.03 (m, 1H), 7.86 (dd, 1H), 2.64 (s, 3H)

Intermediate 10

(E)-tert-Butyl((1-(4-chloro-3-(trifluoromethyl)phenyl)prop-1-en-1-yl)oxy)dimethylsilane

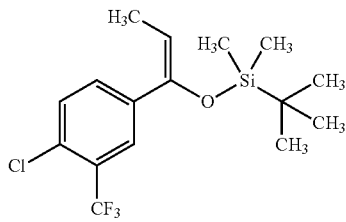 [SMILES: C/C=C(/O[Si](C)(C)C(C)(C)C)c1ccc(Cl)c(C(F)(F)F)c1]

1-(4-chloro-3-(trifluoromethyl)phenyl)propan-1-one (10.1 g, 42.6 mmol, Intermediate 2) was dissolved in 80 mL of THF and cooled in a dry ice bath before addition of 42.6 mL (42.6 mmol) of 1 N lithium hexamethyldisilazane (in THF). After 1 h, a solution of 6.42 g of tert-butyldimethylsilane (42.6 mmol) in 10 mL THF was added dropwise and the reaction was stirred, warming to room temperature. After 3 d, the reaction mixture was concentrated and hexane was added and the mixture was stirred 30 min before filtering and concentrating. Chromatography with hexane on silica gel pretreated with Et₃N yielded 11.2 g of product (75%).

¹H NMR (400 MHz, CDCl₃) δ 7.80 (d, J=2.0 Hz, 1H), 7.55 (dd, J=8.4, 2.0 Hz, 1H), 7.43 (d, J=8.4 Hz, 1H), 5.33 (q, J=6.9 Hz, 1H), 1.77 (d, J=6.9 Hz, 3H), 1.02 (s, 9H), 0.00 (s, 6H). ¹⁹F NMR (376 MHz, CDCl₃) δ −62.68.

Intermediate 11 tert-Butyl-[(E)-1-(3-fluoro-4-morpholino-phenyl)prop-1-enoxy]-dimethyl-silane

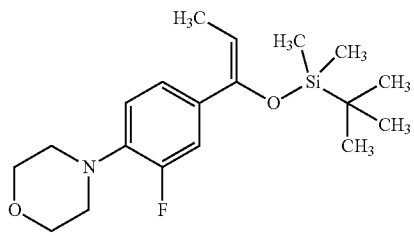 [SMILES: C/C=C(/O[Si](C)(C)C(C)(C)C)c1ccc(N2CCOCC2)c(F)c1]

A solution of 749 mg (3.16 mmol) 1-(3-fluoro-4-morpholinophenyl)propan-1-one (Intermediate 5) dissolved in 10 mL THF was cooled in a −78° C. dry ice bath and to it was added 3.16 mL (3.16 mmol) of a 1 N THF solution of LiHMDS. After stirring cold for 1 h, a solution of 476 mg (3.16 mmol) of tert-butyldimethylsilyl chloride (tBDMSCl), dissolved in 2 mL of THF, was added and the solution was stirred overnight, warming to room temperature. After 2 d, ca. 50 mL of hexane was added, the mixture was filtered over a short plug of silica gel pretreated with some Et₃N in hexane. Elution with hexane and 5% EtOAc in hexane isolated 670 mg clear oil (60%).

¹H NMR (400 MHz, CDCl₃) δ 7.19-7.09 (m, 2H), 6.86 (t, J=8.6 Hz, 1H), 5.16 (q, J=6.7 Hz, 1H), 3.95-3.80 (m, 4H), 3.17-3.05 (m, 4H), 1.73 (d, J=6.8 Hz, 3H), 1.01 (s, 9H), 0.00 (s, 6H). ¹⁹F NMR (376 MHz, CDCl₃) δ −123.51.

Intermediate 12 tert-Butyl-[(E)-1-(3,5-difluoro-4-morpholino-phenyl)prop-1-enoxy]-dimethyl-silane

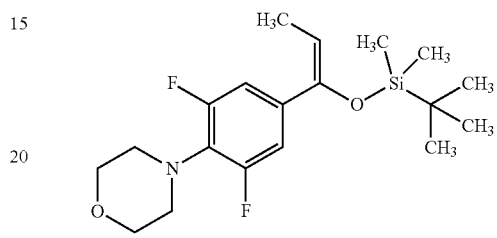

A solution of 2.20 g (8.61 mmol) of 1-(3,5-difluoro-4-morpholinophenyl)propan-1-one (Intermediate 3) was dissolved in 20 mL THF and cooled with a −78° C. ice bath. To this was added 8.61 mL (8.61 mmol) of a 1 N (THF) LiHMDS solution. The solution was stirred cold 1 h before addition of 1.29 g (8.61 mmol) TBDMSCl, dissolved in 10 mL THF, and the ice bath was removed and stirring continued overnight. The next day hexane was added and the mixture was filtered over a short plug of silica gel pretreated with Et₃N in hexane. Elution with hexane and 5% EtOAc in hexane isolated 2.94 g of product (89%).

¹H NMR (400 MHz, CDCl₃) δ 6.94 (d, J=10.4 Hz, 2H), 5.20 (q, J=6.8 Hz, 1H), 3.90-3.74 (m, 4H), 3.22 (s, 4H), 1.73 (d, J=6.9 Hz, 3H), 1.02 (s, 9H), 0.02 (s, 6H). ¹⁹F NMR (376 MHz, CDCl₃) δ −120.79.

Intermediate 13

(E)-4-(4-(1-((tert-Butyldimethylsilyl)oxy)prop-1-en-1-yl)-2-(trifluoromethyl)phenyl)morpholine

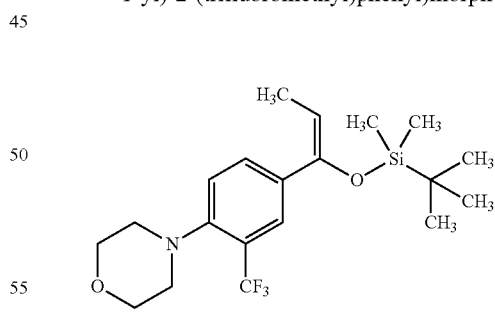

A solution of 5.00 g (17.4 mmol) of 1-(4-morpholino-3-(trifluoromethyl)phenyl)propan-1-one (Intermediate 6) was dissolved in 30 mL THF and cooled with a −78° C. ice bath. To this was added 17.4 mL (17.4 mmol) of a 1 N (THF) LiHMDS solution. The solution was stirred cold 1 h before addition of 2.62 g (17.4 mmol) TBDMSCl, dissolved in 5 mL THF, and the ice bath was removed and stirring continued overnight. The next day ca. 200 mL of hexane was added and the mixture was stirred several hours before filtering and concentration. Chromatography with 0-10%

EtOAc in hexane on a column pretreated with Et₃N yielded 4.87 g of product as a clear oil (70%).

¹H NMR (400 MHz, CDCl₃) δ 7.74 (s, 1H), 7.60 (d, J=8.2 Hz, 1H), 7.28 (d, J=7.0 Hz, 1H), 5.27 (q, J=6.6 Hz, 1H), 3.85 (s, 4H), 2.95 (s, 4H), 1.76 (d, J=6.8 Hz, 3H), 1.02 (s, 9H), −0.00 (s, 6H).

Intermediate 14

(E)-tert-Butyl((1-(4-fluoro-3-(trifluoromethyl)phenyl)prop-1-en-1-yl)oxy)dimethylsilane

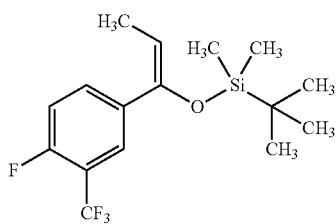 [SMILES: C/C=C(/O[Si](C)(C)C(C)(C)C)c1ccc(F)c(C(F)(F)F)c1]

A solution of 4-fluoro-3-trifluoromethylpropiophenone (12 g, 55 mmol, CAS 239107-27-8) was dissolved in 60 mL of THF and cooled in a dry ice bath before addition of 60 mL (60 mmol) of 1 N lithium hexamethyldisilazane (in THF). After 1 h, a solution of 9.0 g of tert-butyldimethylsilane (60 mmol) in 15 mL THF was added dropwise and the reaction was stirred, warming to room temperature overnight. The next day, the reaction mixture was concentrated and stirred in 500 mL of hexane for 30 min before filtering and concentrating. Chromatography with hexane on silica gel pretreated with Et₃N yielded 15.3 g product (84%).

¹H NMR (400 MHz, CDCl₃) δ 7.71 (dd, J=6.9, 2.1 Hz, 1H), 7.62 (ddd, J=7.3, 4.7, 2.2 Hz, 1H), 7.13 (t, J=9.4 Hz, 1H), 5.26 (q, J=6.9 Hz, 1H), 1.76 (d, J=6.9 Hz, 3H), 1.02 (s, 9H), −0.00 (s, 6H). ¹⁹F NMR (376 MHz, CDCl₃) δ −61.49 (d, J=12.7 Hz), −116.85 (q, J=12.8 Hz).

Intermediate 15

1-[3-Fluoro-4-(morpholin-4-yl)-5-(trifluoromethyl)phenyl]ethan-1-one

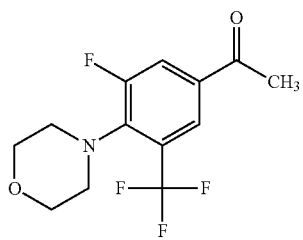 [SMILES: CC(=O)c1cc(F)c(N2CCOCC2)c(C(F)(F)F)c1]

To a solution of 1-(4-bromo-3-fluoro-5-(trifluoromethyl)phenyl)ethanone, 16.00 g (56.1 mmol, Intermediate 9, in 300 mL of toluene were added morpholine, 9.78 g (112.3 mmol), cesium carbonate, 54.87 g (168.4 mmol), tris(dibenzylideneacetone)dipalladium, 2.57 g (2.8 mmol), and 2,2'-bis(diphenylphosphino)-1,1'-binaphthalene, 1.75 g (2.8 mmol). The resulting mixture was stirred at 80° C. for overnight under nitrogen atmosphere. After cooled to room temperature, water was added, and extracted with ethyl acetate. The combined organic layer was washed with brine, and dried over anhydrous sodium sulfate, the solvent was removed in vacuo, and the residue was purified with silica gel column chromatography (PE/EA=5:1) to give 10.10 g (58%) of the product as a yellow oil. MS(ESIpos): m/z=292 (M+H)+.

Intermediate 16

1-[4-Bromo-3-(difluoromethyl)phenyl]ethan-1-one

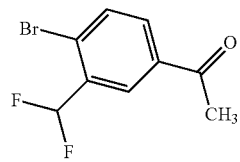

The title compound was synthesized analogously to Intermediate 7 from 1-bromo-4-iodo-2-(trifluoromethyl)benzene (CAS 1261496-16-5).

¹H-NMR (400 MHz, DMSO-d₆): δ [ppm]=8.18-8.10 (m, 1H), 8.07-8.00 (m, 1H), 8.00-7.90 (m, 1H), 7.40-7.03 (m, 1H), 2.63 (s, 3H)

Intermediate 17

2-Bromo-1-[4-chloro-3-(trifluoromethyl)phenyl]ethanone

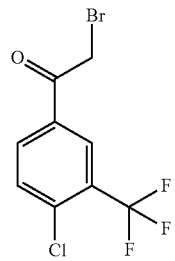 [SMILES: O=C(CBr)c1ccc(Cl)c(C(F)(F)F)c1]

1-[4-chloro-3-(trifluoromethyl)phenyl]ethanone (3.76 g, 16.9 mmol, CAS 129825-11-2) was dissolved in acetic acid (15.5 mL), and bromine (870 μL, 17 mmol) and hydrogen bromide (46 μL, 840 μmol) were added. The reaction mixture was stirred overnight at room temperature. Then the reaction was poured into iced water, adjusted to pH 5 with aqueous sodium hydrogencarbonate solution, the brown precipitate was filtered off, washed with water and dried, to obtain 3.50 g of the crude title compound LC-MS (Method 1): R$_t$=1.29 min, MS (ESIpos): m/z=301 [M+H]⁺

Intermediate 18

2-Bromo-1-[4-chloro-3-fluoro-5-(trifluoromethyl)phenyl]ethan-1-one

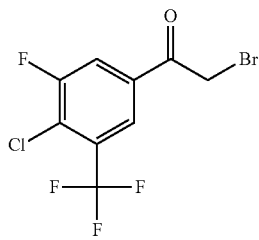 [SMILES: O=C(CBr)c1cc(F)c(Cl)c(C(F)(F)F)c1]

To a solution of 1-[4-chloro-3-fluoro-5-(trifluoromethyl)phenyl]ethan-1-one (15.00 g, 62 mmol, Intermediate 8) in 300 mL of HOAc was added hydrobromic acid, 0.03 g (0.3 mmol), bromine, 8.97 g (56.1 mmol), The mixture was stirred at room temperature for 3 hours. Upon completion of the reaction, ice water was added and the resulting mixture was extracted with ethyl acetate. The combined organic layer was washed with brine and dried over anhydrous sodium sulfate. The solvent was removed in vacuo to give 18 g (crude) of the product as a yellow oil.

$^1$H-NMR (400 MHz, DMSO-d$_6$): δ [ppm]=8.43-8.35 (m, 1H), 8.23-8.14 (m, 1H), 5.07 (s, 2H)

Intermediate 19

2-Bromo-1-[3,5-difluoro-4-(morpholin-4-yl)phenyl]ethanone

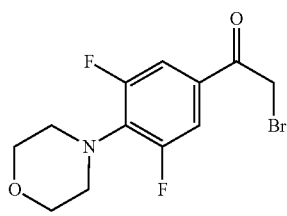 [SMILES: O=C(CBr)c1cc(F)c(N2CCOCC2)c(F)c1]

1-[3,5-difluoro-4-(morpholin-4-yl)phenyl]ethanone (540 mg, 2.24 mmol, Intermediate 3) was dissolved in acetic acid (5.3 mL) and bromine (120 μL, 2.2 mmol) and hydrogen bromide (13 μL, 48% purity, 110 μmol) were added. The reaction mixture was stirred overnight at room temperature. Then the reaction was poured into iced water, adjusted to pH 5 with aqueous sodium hydrogencarbonate solution. The yellow precipitate was filtered off, washed with water and dried, to obtain 580 mg (81% yield) of the crude title compound.

LC-MS (Method 1): $R_t$=1.18 min, MS (ESIpos): m/z=320 [M+H]$^+$

Intermediate 20

(rac)-2-Bromo-1-(3,4,5-trifluorophenyl)propan-1-one

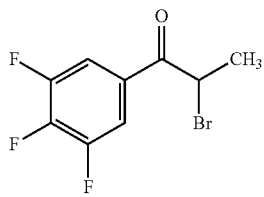

1-(3,4,5-trifluorophenyl)propan-1-one (1.48 g, 7.87 mmol, CAS 220227-74-7) was dissolved in acetic acid (15 mL) and bromine (410 μL, 7.9 mmol) and hydrogen bromide (89 μL, 790 μmol, 48% purity) were added. The reaction mixture was stirred overnight at room temperature. Then the reaction was poured into iced water, adjusted to pH 5 with aqueous sodium hydrogencarbonate solution and the aqueous phase was extracted with dichloromethane. The organic phase was concentrated in vacuo, to obtain 1.6 g (quant.) of the crude title compound.

LC-MS (Method 1): $R_t$=1.33 min: MS (ESIpos): m/z=mass not detectable.

1H NMR (400 MHz, DMSO-d6) δ ppm 1.78 (d, J=6.34 Hz, 3H) 5.85 (q, J=6.59 Hz, 1H) 7.88-8.06 (m, 2H).

Intermediate 21

2-Bromo-1-[4-fluoro-3-(trifluoromethyl)phenyl]ethanone

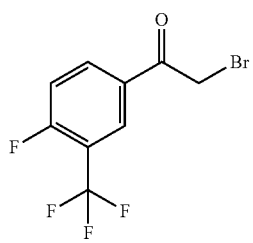 [SMILES: O=C(CBr)c1ccc(F)c(C(F)(F)F)c1]

1-[4-Fluoro-3-(trifluoromethyl)phenyl]ethanone (380 μL, 100% purity, 2.4 mmol, CAS 208173-24-4) was dissolved in acetic acid (3.7 mL) at room temperature. Bromine (120 μL, 100% purity, 2.4 mmol) was added dropwise into the reaction mixture, which was stirred overnight, its colour turned from brown to orange. The mixture was concentrated under reduced pressure and used as crude material in the next step.

Intermediate 22

2-Bromo-1-[4-chloro-3-(trifluoromethoxy)phenyl]ethanone

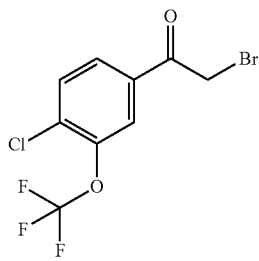 [SMILES: O=C(CBr)c1ccc(Cl)c(OC(F)(F)F)c1]

1-[4-chloro-3-(trifluoromethoxy)phenyl]ethanone (2.28 g, 9.56 mmol, CAS 886501-62-8) was dissolved in acetic acid (5.0 ml, 87 mmol) at room temperature. Bromine (490 µl, 9.6 mmol) and hydrobromic acid (54 µl, 48% purity, 480 µmol) were added dropwise into the reaction mixture, which was stirred overnight, its colour turned from brown to orange. The mixture was pured on ice water, set to pH5 with aqueous sodium carbonate solution and extracted three times with dichloromethane. The combined organic phases were concentrated under reduced pressure and obtained as crude material (2.80 g, 92% yield).

Intermediate 23

(rac)-2-Bromo-1-[4-chloro-3-(trifluoromethyl)phenyl]propan-1-one

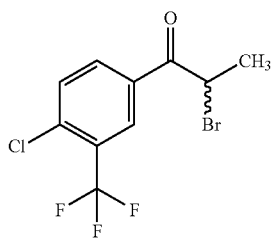 [SMILES: CC(Br)C(=O)c1ccc(Cl)c(C(F)(F)F)c1]

1-[4-chloro-3-(trifluoromethyl)phenyl]propan-1-one (500 mg, 2.11 mmol, Intermediate 2) was dissolved in acetic acid (5 mL), and bromine (109 µL, 2.11 mmol) and hydrogen bromide (23.9 µL, 0.21 mmol, 48% purity) were added. The reaction mixture was stirred overnight at RT. Then the reaction was poured into iced water, adjusted to pH 5 with sat. aq. NaHCO$_3$ and the aqueous phase was extracted with DCM (3×20 mL). The organic phase was dried over anhydrous MgSO$_4$, filtered and concentrated in vacuo to afford 605 mg (86% yield, 95% purity) of the title compound as a pale yellow free-flowing oil. LCMS (Method 3, 1.7 min) 95% @ Rt=1.34 min, MS (ESIpos): m/z=mass not detectable $^1$H NMR (500 MHz, Chloroform-d) δ 1.92 (d, J=6.6 Hz, 3H), 5.21 (q, J=6.6 Hz, 1H), 7.65 (d, J=8.4 Hz, 1H), 8.12 (dd, J=2.0, 8.4 Hz, 1H), 8.35 (d, J=1.8 Hz, 1H).

Intermediate 24

2-Bromo-1-[3-fluoro-4-(morpholin-4-yl)-5-(trifluoromethyl)phenyl]ethan-1-one

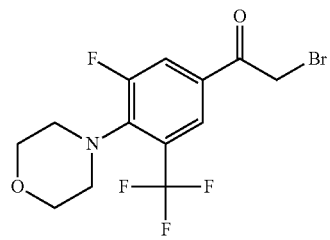 [SMILES: O=C(CBr)c1cc(F)c(N2CCOCC2)c(C(F)(F)F)c1]

The title compound was synthesized analogously to Intermediate 19 from Intermediate 15. MS(ESIpos): m/z=370 (M+H)+.

Intermediate 25

2-Bromo-1-[4-bromo-3-(difluoromethyl)phenyl]ethan-1-one

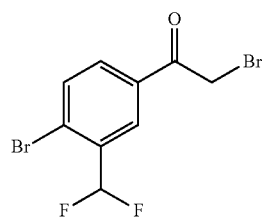 [SMILES: O=C(CBr)c1ccc(Br)c(C(F)F)c1]

The title compound was synthesized analogously to Intermediate 19 from Intermediate 16.

Intermediate 26

2-Bromo-1-[4-bromo-3-(trifluoromethyl)phenyl]ethan-1-one

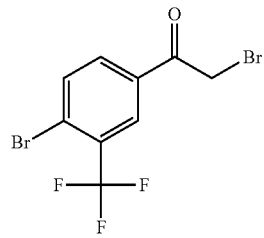 [SMILES: O=C(CBr)c1ccc(Br)c(C(F)(F)F)c1]

The title compound was synthesized analogously to Intermediate 19 from 1-(4-bromo-3-(trifluoromethyl)phenyl)ethanone (CAS 120077-70-5).

Intermediate 27

1-(3,4-Difluorophenyl)-2-hydroxyethanone

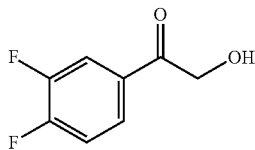

To a solution of 2-bromo-1-(3,4-difluorophenyl)ethanone (1.62 g, 6.89 mmol, CAS: 40706-98-7) in acetonitrile (9.3 mL), sodium formate (563 mg, 8.27 mmol), sodium bicarbonate (811 mg, 9.65 mmol) and water (4.4 mL) were added and the mixture was stirred for 24 h at 65° C. The organic phase was separated. The aqueous phase was extracted three times with ethyl acetate. All collected organic phases were evaporated and dried in vacuo. Purification via column chromatography (silica gel, hexane/ethyl acetate, gradient: 12%→93% ethyl acetate) afforded the title compound (450 mg, 38% yield).

LC-MS (Method 1): $R_t$=0.77 min: MS (ESIpos): m/z=173 [M+H]$^+$

Intermediate 28

1-[4-Chloro-3-(trifluoromethyl)phenyl]-2-hydroxyethanone

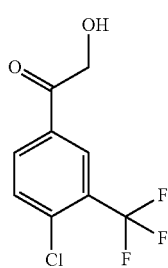

To a solution of 2-bromo-1-[4-chloro-3-(trifluoromethyl)phenyl]ethanone (8.00 g, 26.5 mmol, Intermediate 17) in acetonitrile (23 mL), sodium formate (1.8 g, 26.5 mmol), sodium hydrogencarbonate (2.23 g, 26.5 mmol) and water (8 mL) were added and the mixture was stirred for 4 h at 65° C. The organic phase was separated. The aqueous phase was extracted three times with ethyl acetate. All collected organic phases were evaporated and dried in vacuo. Purification via column chromatography (silica gel, hexane/ethyl acetate, gradient: 12%→92% ethyl acetate) afforded the title compound (700 mg, 11% yield) in a purity of 67%.

LC-MS (Method 1): $R_t$=1.03 min, MS (ESIpos): m/z=239 [M+H]$^+$

Intermediate 29

(rac)-2-Hydroxy-1-(3,4,5-trifluorophenyl)propan-1-one

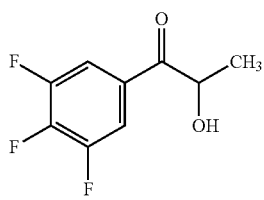

To a solution of (rac)-2-bromo-1-(3,4,5-trifluorophenyl)propan-1-one (2.00 g, 7.49 mmol, Intermediate 20) in acetonitrile (10 mL), sodium formate (611 mg, 8.99 mmol), sodium hydrogencarbonate (881 mg, 10.5 mmol) and water (4.8 mL) were added and the mixture was stirred for 24 h at 65° C. The organic phase was separated. The aqueous phase was extracted three times with ethyl acetate. All collected organic phases were evaporated and dried in vacuo. Purification via column chromatography (silica gel, hexane/ethyl acetate, gradient: 12%→100% ethyl acetate) afforded the title compound (1.62 g, quant.).

LC-MS (Method 2): $R_t$=0.94 min: MS (ESIneg): m/z=203 [M−H]

$^1$H-NMR (400 MHz, DMSO-d6) δ[ppm]: 1.261 (15.24), 1.278 (16.00), 2.518 (0.60), 2.523 (0.43), 4.981 (0.51), 4.998 (2.16), 5.015 (3.40), 5.031 (2.17), 5.048 (0.51), 5.579 (5.93), 5.595 (5.34), 7.899 (0.42), 7.909 (2.91), 7.916 (0.61), 7.926 (3.03), 7.931 (3.03), 7.941 (0.58), 7.948 (2.94), 7.958 (0.42).

Intermediate 30

(rac)-1-(4-Bromophenyl)-2-hydroxypropan-1-one

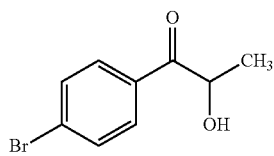

To a solution of (rac)-2-bromo-1-(4-bromophenyl)propan-1-one (2.78 g, 9.52 mmol, CAS: 38786-67-3) in acetonitrile (13 mL), sodium formate (777 mg, 11.4 mmol), sodium hydrogencarbonate (1.12 g, 13.3 mmol) and water (6.1 mL) were added and the mixture was stirred for 24 h at 65° C. The organic phase was separated. The aqueous phase was extracted three times with ethyl acetate. All collected organic phases were evaporated and dried in vacuo. Purification via column chromatography (silica gel, hexane/ethyl acetate gradient: 2%→100% ethyl acetate) afforded the title compound (1.15 g, 53% yield).

LC-MS (Method 1): $R_t$=0.98 min, MS (ESIpos): m/z=229 [M+H]$^+$

Intermediate 31

1-[3,5-Difluoro-4-(morpholin-4-yl)phenyl]-2-hydroxyethanone

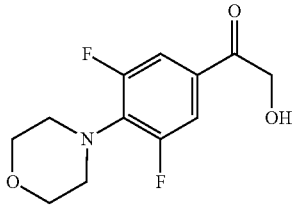 [SMILES: O=C(CO)c1cc(F)c(N2CCOCC2)c(F)c1]

A solution of 2-bromo-1-[3,5-difluoro-4-(morpholin-4-yl)phenyl]ethanone (580 mg, 50% purity, 0.90 mmol, Intermediate 19) in acetonitrile (1.5 mL) and water (0.5 mL) was stirred 1 h in a microwave vial. Then sodium formate (61.6 mg, 0.906 mmol) and sodium hydrogencarbonate (76.1 mg, 0.906 mmol) were added and stirred 4 h at 65° C. The reaction mixture was diluted with water and extracted three times with ethyl acetate. All collected organic phases were evaporated and dried in vacuo. Purification via column chromatography (silica gel, hexane/ethyl acetate, gradient: 12%→100% ethyl acetate) afforded the title compound 60.0 mg (26% yield).

LC-MS (Method 1): $R_t$=0.87 min; MS (ESIpos): m/z=258 [M+H]$^+$

Intermediate 32

5-(Hydroxyacetyl)-2-(morpholin-4-yl)benzonitrile

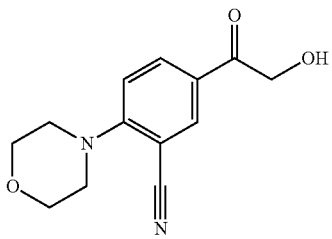 [SMILES: N#Cc1cc(C(=O)CO)ccc1N1CCOCC1]

To a solution of 5-acetyl-2-(morpholin-4-yl)benzonitrile (1.77 g, 7.68 mmol, Intermediate 4) in DMSO (36 mL) and water (7.4 mL) was added hydroxy(tosyloxy)iodo]benzene (18.1 g, 46.1 mmol) and the mixture was stirred at room temperature over night. The reaction mixture was diluted with water and the aqueous phase was extracted three times with ethyl acetate. The combined organic phases were concentrated in vacuo and purified by column chromatography (silica gel, hexane/ethyl acetate, gradient: 15%→100% ethyl acetate) afforded the title compound 570 mg (28% yield).

LC-MS (Method 1): $R_t$=0.73 min; MS (ESIpos): m/z=247 [M+H]$^+$

1H NMR (400 MHz, DMSO-d6) δ ppm 3.34-3.39 (m, 4H) 3.71-3.81 (m, 4H) 4.73 (d, J=5.83 Hz, 2H) 5.12 (t, 1H) 7.22 (d, J=8.87 Hz, 1H) 8.07 (dd, J=8.87, 2.03 Hz, 1H) 8.24 (d, J=2.03 Hz, 1H).

Intermediate 33

(rac)-1-(3-Fluoro-4-morpholinophenyl)-2-hydroxypropan-1-one

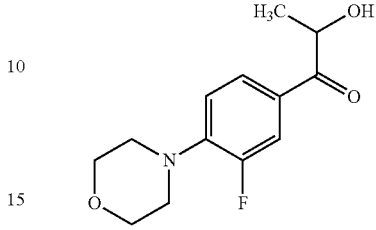

Following a literature procedure (Org. Lett. 2015, 17, 876), to 930 mg (3.91 mmol) of 1-(3-fluoro-4-morpholinophenyl)propan-1-one (Intermediate 5) dissolved in 6 mL of dry DMSO was added 198 mg of iodine (0.782 mmol) and the reaction was heated at 60° C. overnight. The next day the reaction was cooled, water was added and the mixture was rinsed several times with EtOAc, the combined EtOAc layers were rinsed with brine, dried, concentrated and chromatographed with 0-40% EtOAc in hexane to isolate 240 mg of product as a yellow oil which solidified with time (24%).

$^1$H NMR (400 MHz, CDCl$_3$) δ 7.62-7.70 (m, 2H), 6.95 (t, J=8.4 Hz, 1H), 5.07 (p, J=6.7 Hz, 1H), 3.89 (s, 4H), 3.77 (d, J=6.3 Hz, 1H), 3.27 (s, 4H), 1.46 (d, J=6.9 Hz, 3H). $^{19}$F NMR (376 MHz, CDCl$_3$) δ −120.60. MS: 254 [M+H]$^+$

Intermediate 34

(rac)-1-[4-Chloro-3-(trifluoromethyl)phenyl]-2-hydroxypropan-1-one

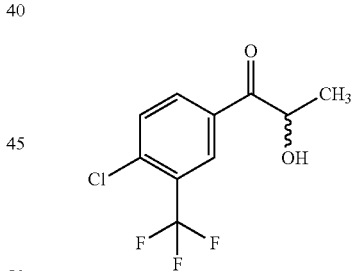

To a solution of (rac)-2-bromo-1-[4-chloro-3-(trifluoromethyl)phenyl]propan-1-one (605 mg, 1.82 mmol, Intermediate 23) in MeCN (2.5 mL), sodium formate (149 mg, 2.19 mmol), sodium hydrogencarbonate (214 mg, 2.55 mmol) and water (1.25 mL) were added and the mixture was stirred for 24 h at 65° C. The reaction mixture was diluted with water (10 mL) and then extracted with EtOAc (10 mL×3). The organic layers were combined, washed with sodium thiosulfate (sat. aq. sol. 50% diluted in H$_2$O), dried over anhydrous MgSO$_4$, filtered and dried in vacuo to obtain a crude residue. The crude residue was purified by Biotage Isolera™ chromatography (25 g KP-Sil, eluting with heptanes-EtOAc, 1:0 to 1:1) to afford 404.4 mg (67% yield, >75% purity by NMR) of the title compound as a pale yellow free-flowing oil. LCMS (Method 3, 1.7 min) 87% @ Rt=1.10 min, MS (ESIpos): m/z=mass not detectable $^1$H NMR (500 MHz, Chloroform-d) δ 1.46 (d, J=7.1 Hz, 3H), 3.55 (d, J=6.5 Hz, 1H), 5.08-5.18 (m, 1H), 7.67 (d, J=8.4 Hz, 1H), 8.02 (dd, J=2.0, 8.3 Hz, 1H), 8.26 (d, J=1.7 Hz, 1H) [contains 10% w/w EtOAc and trace heptane by NMR].

Intermediate 35

2-(4-Chloro-3-methylphenyl)-2-oxoethyl acetate

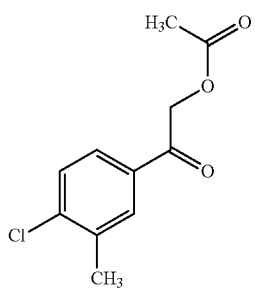

To a solution of 2-bromo-1-(4-chloro-3-methylphenyl)ethanone (247 mg, 998 μmol, CAS 205178-80-9) in DMF (4.0 mL) were added potassium acetate (294 mg, 2.99 mmol) and potassium iodide (166 mg, 998 μmol) and the mixture was stirred at room temperature overnight. The reaction mixture was poured into water and extracted three times with ethyl acetate. The combined organic phases were dried and concentrated in vacuo, to obtain 200 mg (88% yield) of the crude title compound.

LC-MS (Method 1): R$_f$=1.16 min, MS (ESIpos): m/z=227 [M+H]$^+$ $^1$H-NMR (400 MHz, DMSO-d6) δ[ppm]: 2.147 (16.00), 2.408 (9.14), 2.728 (1.85), 2.888 (2.32), 5.444 (9.67), 7.597 (1.85), 7.618 (2.27), 7.780 (0.91), 7.784 (0.96), 7.799 (0.71), 7.804 (0.79), 7.962 (1.48), 7.966 (1.38).

Intermediate 36

(S)-1-(3-Fluoro-4-morpholinophenyl)-2-hydroxypropan-1-one

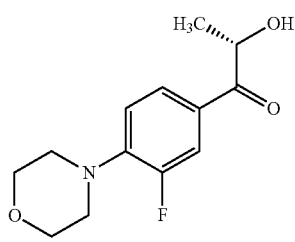 [SMILES: CC(O)C(=O)c1ccc(N2CCOCC2)c(F)c1]

Following a literature procedure (J. Org. Chem. 1992, 57, 5067), to 10 mL of tert-butanol and 10 mL water was added 190 mg methanesulfonamide, and 2.7 g AD-mix-α (Aldrich) and the mixture was cooled on an ice bath before addition of the 670 mg of tert-butyl-[(E)-1-(3-fluoro-4-morpholino-phenyl)prop-1-enoxy]-dimethyl-silane (Intermediate 11). The mixture was kept cold for several hours and warmed to room temperature overnight. The next day the mixture was cooled on an ice bath, 2 g of sodium sulfite was added and stirred 30 min. Water and EtOAc were added and the EtOAc separated, dried, and concentrated. Chromatography with 0-50% EtOAc yielded 363 mg white solid (75%).

$^1$H NMR (400 MHz, CDCl$_3$) δ 7.75-7.56 (m, 2H), 6.95 (t, J=8.4 Hz, 1H), 5.08 (q, J=6.4 Hz, 1H), 3.90 (t, J=4.5 Hz, 4H), 3.77 (br s, 1H), 3.34-3.17 (m, 4H), 1.46 (d, J=7.0 Hz, 3H). $^{19}$F NMR (376 MHz, CDCl$_3$) δ -120.60. MS: 254 [M+H]$^+$

Intermediate 37

(S)-1-(3,5-Difluoro-4-morpholinophenyl)-2-hydroxypropan-1-one

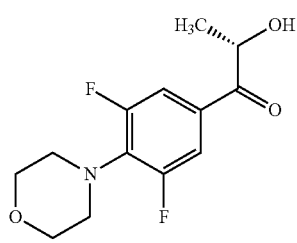 [SMILES: C[C@H](O)C(=O)c1cc(F)c(N2CCOCC2)c(F)c1]

Following a literature procedure (J. Org. Chem. 1992, 57, 5067), to 40 mL of water and 40 mL of tert-BuOH was added 11.2 g of AD-mix-α (Aldrich) and 760 mg of methanesulfonamide (8 mmol). The mixture was cooled in an ice bath and to this was added the 2.94 g of tert-butyl-[(E)-1-(3,5-difluoro-4-morpholino-phenyl)prop-1-enoxy]-dimethyl-silane (7.95 mmol, Intermediate 12). The mixture was kept on an ice bath for several hours before warming to room temperature overnight. Water and EtOAc were added, the EtOAc layer was dried, concentrated, and chromatographed with 0-30% EtOAc in hexane to yield 1.68 g of oil which solidified with sitting (68%).

$^1$H NMR (400 MHz, CDCl$_3$) δ 7.45 (d, J=9.5 Hz, 2H), 5.02 (p, J=6.8 Hz, 1H), 3.83 (t, J=4.4 Hz, 4H), 3.65 (d, J=6.5 Hz, 1H), 3.38 (s, 4H), 1.46 (d, J=7.0 Hz, 3H). $^{19}$F NMR (376 MHz, CDCl$_3$) δ -119.20. MS: 272 [M+H]$^+$

Intermediate 38

2-(4-Chloro-3-fluorophenyl)-2-oxoethyl acetate

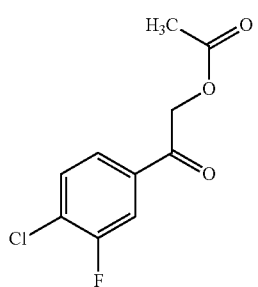

To a solution of 2-bromo-1-(4-chloro-3-fluorophenyl)ethanone (5.20 g, 20.7 mmol, CAS 231297-62-4) in DMF (31 mL) were added potassium acetate (4.06 g, 41.4 mmol) and potassium iodide (3.43 g, 20.7 mmol) and the mixture was stirred at room temperature over night. The reaction mixture was poured into water and extracted three times with ethyl acetate. The combined organic phases were dried and concentrated in vacuo, to obtain 5.40 g (113% yield) of the crude title compound.

LC-MS (Method 1): R$_t$=1.07 min; MS (ESIpos): m/z=189 [M+H]$^+$

Intermediate 39

2-[4-Fluoro-3-(trifluoromethyl)phenyl]-2-oxoethyl acetate

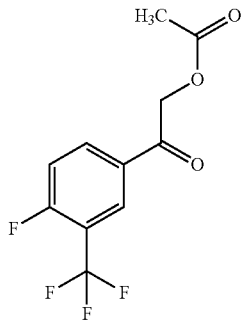

2-Bromo-1-[4-fluoro-3-(trifluoromethyl)phenyl]ethanone (500 mg, 1.75 mmol, Intermediate 21) was dissolved in dimethyl formamide (2.6 mL) under nitrogen, potassium acetate (516 mg, 5.26 mmol) and potassium iodide (291 mg, 1.75 mmol) were added and the mixture was stirred at room temperature overnight. The mixture was diluted with water and extracted with ethyl acetate three times. The combined organic layers were dried using a water-resistant filter and the filtrate was concentrated under reduced pressure. The crude material was used without further purification.

LC-MS (Method 1): R$_t$=1.14 min; MS (ESIneg): m/z=263 [M−H]$^−$

Intermediate 40

(rac)-2-Hydroxy-1-(4-morpholino-3-(trifluoromethyl)phenyl)propan-1-one

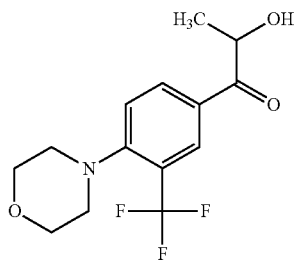 [SMILES: CC(O)C(=O)c1ccc(N2CCOCC2)c(C(F)(F)F)c1]

A solution of 200 mg of 1-(4-morpholino-3-(trifluoromethyl)phenyl)propan-1-one (0.7 mmol, Intermediate 6) and 35 mg of iodine (0.035 mmol) were heated at 60° C. overnight in 2 mL of DMSO. After cooling, the reaction mixture was transferred to a separatory funnel. Water and EtOAc were added, addition of sodium sulfite solution dissipated most of the color. The EtOAc layer was rinsed with brine, dried, concentrated and chromatographed with 20-70% EtOAc in hexane to yield 104 mg of a clear yellow oil (49%).

$^1$H NMR (400 MHz, CDCl$_3$) δ 8.23 (s, 1H), 8.07 (d, J=10.5 Hz, 1H), 7.33 (d, J=8.5 Hz, 1H), 5.13 (q, J=7.0 Hz, 1H), 3.93-3.81 (m, 4H), 3.74 (s, 1H), 3.10 (q, J=3.9 Hz, 4H), 1.47 (d, J=7.0 Hz, 3H). $^{19}$F NMR (376 MHz, CDCl$_3$) δ −59.94. Mass 304 (M+1)+.

Intermediate 41

(S)-2-Hydroxy-1-(4-morpholino-3-(trifluoromethyl)phenyl)propan-1-one

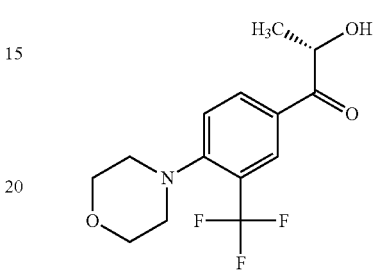

Following a literature procedure (J. Org. Chem. 1992, 57, 5067), to 50 mL of tert-butanol and 50 mL water was added 1 g methanesulfonamide, and 14 g AD-mix-α (Aldrich) and the mixture was cooled on an ice bath before addition of the 4.87 g of (E)-4-(4-(1-((tert-Butyldimethylsilyl)oxy)prop-1-en-1-yl)-2-(trifluoromethyl)phenyl)morpholine (Intermediate 13). The mixture was kept cold for several hours and warmed to room temperature overnight. The next day the mixture was cooled on an ice bath, 10 g of sodium sulfite was added and stirred 30 min. Water and EtOAc were added and the EtOAc separated, dried, and concentrated. Chromatography with 0-50% EtOAc yielded 3.3 g white solid (90%). $^1$H NMR (400 MHz, CDCl$_3$) δ 8.24 (s, 1H), 8.08 (d, J=8.5 Hz, 1H), 7.34 (d, J=8.5 Hz, 1H), 5.15 (s, 1H), 3.88 (s, 4H), 3.71 (s, 1H), 3.17-3.03 (m, 4H), 1.48 (d, J=7.0 Hz, 3H). $^{19}$F NMR (376 MHz, CDCl$_3$) δ −59.94. MS: 304 (M+1)+.

Intermediate 42

(S)-1-(4-Chloro-3-(trifluoromethyl)phenyl)-2-hydroxypropan-1-one

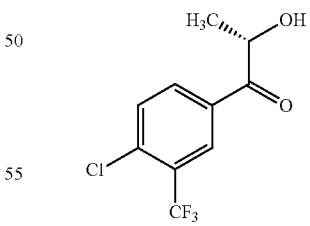

Following a literature procedure (J. Org. Chem. 1992, 57, 5067), to 150 mL of tert-butanol and 150 mL of water was added 3 g methanesulfonamide, and 45 g AD-mix-α (Aldrich) and the mixture was cooled on an ice bath before addition of the 11.2 g of (E)-tert-Butyl((1-(4-chloro-3-(trifluoromethyl)phenyl)prop-1-en-1-yl)oxy)dimethylsilane (31.9 mmol, Intermediate 10). The mixture was kept cold for several hours and warmed to room temperature overnight. The next day the mixture was cooled on an ice bath, 30 g of sodium sulfite was added and stirred 30 min. The mixture was filtered and water and EtOAc were added and the EtOAc was separated, dried, and concentrated. Chromatography with 0-25% EtOAc yielded 5.2 g of pale yellow oil (65%). Mass 253 (M+1)+.

Intermediate 43

(S)-1-(4-Fluoro-3-(trifluoromethyl)phenyl)-2-hydroxypropan-1-one

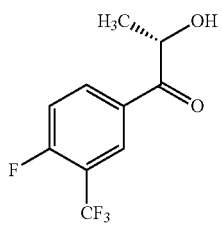

Following a literature procedure (*J. Org. Chem.* 1992, 57, 5067), to 90 mL of tert-butanol and 90 mL water was added 1.8 g methanesulfonamide, and 26 g AD-mix-α (Aldrich) and the mixture was cooled on an ice bath before addition of the 6.0 g of (E)-tert-Butyl((1-(4-fluoro-3-(trifluoromethyl)phenyl)prop-1-en-1-yl)oxy)dimethylsilane (18 mmol, Intermediate 14). The mixture was kept cold for several hours and warmed to room temperature overnight. The next day the mixture was cooled on an ice bath, 18 g of sodium sulfite was added and stirred 30 min. Water and CH$_2$Cl$_2$ were added and the CH$_2$Cl$_2$ was separated, dried, and concentrated before chromatography with 0-30% EtOAc yielded 3.5 g of product as an oil (82%).

$^1$H NMR (400 MHz, CDCl$_3$) δ 8.25 (dd, J=6.7, 1.7 Hz, 1H), 8.17 (ddd, J=8.3, 4.6, 2.2 Hz, 1H), 7.38 (t, J=9.2 Hz, 1H), 5.15 (q, J=6.5 Hz, 1H), 3.62 (s, 1H), 1.48 (d, J=7.0 Hz, 3H). $^{19}$F NMR (376 MHz, CDCl$_3$) δ −61.78 (d, J=12.5 Hz), −104.89 (q, J=12.5 Hz). Mass 237 (M+1)+.

Intermediate 44

2-[4-Chloro-3-(trifluoromethoxy)phenyl]-2-oxoethyl acetate

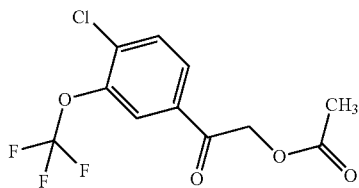 [SMILES: CC(=O)OCC(=O)c1ccc(Cl)c(OC(F)(F)F)c1]

2-bromo-1-[4-chloro-3-(trifluoromethoxy)phenyl]ethanone (2.80 g, 8.82 mmol, Intermediate 22), was dissolved in acetonitrile (4.8 ml) under nitrogen, potassium acetate (2.60 g, 26.5 mmol) and potassium iodide (1.46 g, 8.82 mmol) were added and the mixture was stirred at room temperature overnight. The mixture was diluted with water and extracted with ethyl acetate three times. The combined organic layers were dried using a water-resistant filter and the filtrate was concentrated under reduced pressure. The crude material 2.50 g (96% yield) was used without further purification.

LC-MS (Method 1): R$_t$=1.14 min, MS (ESIneg): m/z=263 [M−H]$^−$

Intermediate 45

2-[4-Chloro-3-fluoro-5-(trifluoromethyl)phenyl]-2-oxoethyl acetate

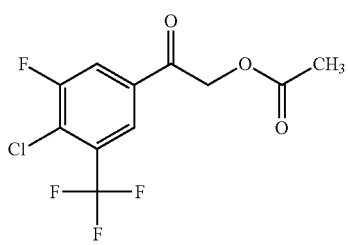 [SMILES: CC(=O)OCC(=O)c1cc(F)c(Cl)c(C(F)(F)F)c1]

To a solution of 2-bromo-1-[4-chloro-3-fluoro-5-(trifluoromethyl)phenyl]ethan-1-one (18 g, 56 mmol, Intermediate 18) in 200 mL of N,N-dimethylformamide was added potassium acetate, 11.1 g (113 mmol), potassium iodide, 9.4 g (56.3 mmol), The mixture was stirred at room temperature for overnight. Upon completion of the reaction, ice water was added and the resulting mixture was extracted with ethyl acetate. The combined organic layer was washed with brine and dried over anhydrous sodium sulfate. The solvent was removed in vacuo to give 16.4 g (crude) of the product as a yellow oil.

$^1$H-NMR (400 MHz, DMSO-d$_6$): δ [ppm]=8.39-8.31 (m, 1H), 8.13 (s, 1H), 5.54 (s, 2H), 2.16 (s, 3H)

Intermediate 46

2-[3-Fluoro-4-(morpholin-4-yl)-5-(trifluoromethyl)phenyl]-2-oxoethyl acetate

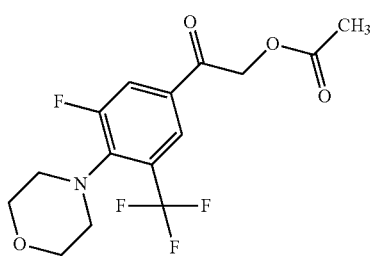 [SMILES: CC(=O)OCC(=O)c1cc(F)c(N2CCOCC2)c(C(F)(F)F)c1]

The title compound was synthesized analogously to Intermediate 45 from Intermediate 24.

MS(ESIpos): m/z=350 (M+H)+.

Intermediate 47

2-[4-Bromo-3-(difluoromethyl)phenyl]-2-oxoethyl acetate

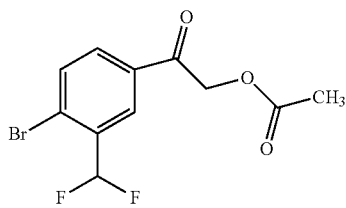 [SMILES: CC(=O)OCC(=O)c1ccc(Br)c(C(F)F)c1]

The title compound was as synthesized analogously to Intermediate 45 from Intermediate 25.

¹H-NMR (400 MHz, DMSO-$d_6$): δ [ppm]=8.14 (s, 1H), 8.08-7.96 (m, 2H), 7.40-7.03 (m, 1H), 5.51 (s, 2H), 2.16 (s, 3H)

Intermediate 48

2-[4-Bromo-3-(trifluoromethyl)phenyl]-2-oxoethyl-acetate

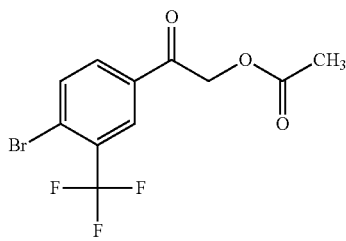 [SMILES: CC(=O)OCC(=O)c1ccc(Br)c(C(F)(F)F)c1]

The title compound was as synthesized analogously to Intermediate 45 from Intermediate 26.

Intermediate 49

Methyl 2-[1-(3,4-difluorophenyl)-2-hydroxyethylidene]hydrazinecarboxylate

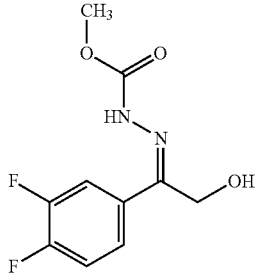 [SMILES: COC(=O)N/N=C(/CO)c1ccc(F)c(F)c1]

1-(3,4-difluorophenyl)-2-hydroxyethanone (1.20 g, 6.97 mmol, Intermediate 27) was dissolved in methanol. Methyl hydrazinecarboxylate (1.13 g, 12.5 mmol) and aqueous hydrochloric acid (1N) were added until pH value 5.5 was reached. The reaction mixture was stirred 5 h at room temperature and concentrated in vacuo, to obtain the crude title compound (2.4 g, quant.), which was used in the next step without any further purification.

LC-MS (Method 1): $R_t$=0.85 min, MS (ESIpos): m/z=245 [M+H]⁺

Intermediate 50

Methyl 2-{1-[4-chloro-3-(trifluoromethyl)phenyl]-2-hydroxyethylidene}hydrazinecarboxylate

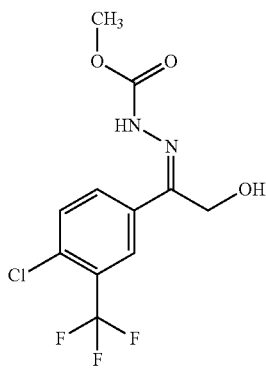 [SMILES: COC(=O)N/N=C(/CO)c1ccc(Cl)c(C(F)(F)F)c1]

To a solution of 1-[4-chloro-3-(trifluoromethyl)phenyl]-2-hydroxyethanone (700 mg, 2.93 mmol, Intermediate 28) in methanol (7.0 mL) was added methyl hydrazinecarboxylate (396 mg, 4.40 mmol) and with aqueous hydrochloric acid (1N) a pH of 5.5 was adjusted. The reaction mixture was stirred 24 h at room temperature. The reaction mixture was concentrated in vacuo, to obtain 1.2 g of the crude title compound.

LC-MS (Method 1): $R_t$=1.04 min: MS (ESIpos): m/z=311 [M+H]

Intermediate 51

Methyl 2-[2-(acetyloxy)-1-(4-chloro-3-methylphenyl)ethylidene]hydrazinecarboxylate

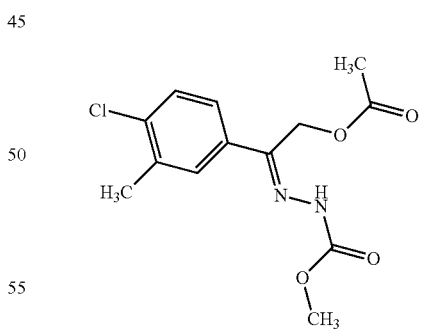

To a solution of 2-(4-chloro-3-methylphenyl)-2-oxoethyl acetate (2.80 g, 12.4 mmol, Intermediate 35) in methanol (32.0 mL) was added methyl hydrazinecarboxylate (1.78 g, 19.8 mmol) and a pH of 5.5 was adjusted with aqueous hydrochloric acid (1N). The reaction mixture was stirred at room temperature overnight. The reaction mixture was concentrated in vacuo, to obtain 3.6 g (98% yield) of the crude title compound, which was used in the next step without any further purification.

Intermediate 52

(rac)-Methyl 2-[2-hydroxy-1-(3,4,5-trifluorophenyl)propylidene]hydrazinecarboxylate

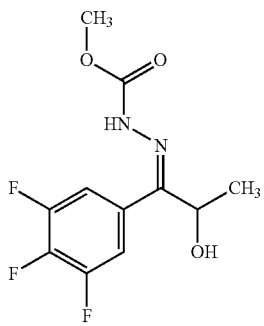 [SMILES: COC(=O)N/N=C(\c1cc(F)c(F)c(F)c1)C(C)O]

(rac)-2-Hydroxy-1-(3,4,5-trifluorophenyl)propan-1-one (1.62 g, 7.94 mmol, Intermediate 29) was dissolved in methanol. Methyl hydrazinecarboxylate (1.29 g, 14.3 mmol) and aqueous hydrochloric acid (1N) was added until pH value 5.5 was reached. The reaction mixture was stirred 24 h at room temperature and concentrated in vacuo and the residue was purified by column chromatography (silica gel, hexane/ethyl acetate, gradient: 12%→100% ethyl acetate) afforded the title compound (950 mg, 43% yield).

LC-MS (Method 2): $R_t$=1.03 min: MS (ESIneg): m/z=275 [M−H]$^-$

Intermediate 53

(rac)-Ethyl 2-[-1-(4-bromophenyl)-2-hydroxypropylidene]hydrazinecarboxylate

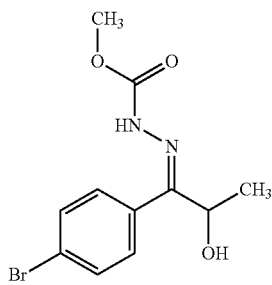 [SMILES: COC(=O)N/N=C(\c1ccc(Br)cc1)C(C)O]

(rac)-1-(4-Bromophenyl)-2-hydroxypropan-1-one (1.15 g, 5.02 mmol, Intermediate 30) was dissolved in methanol. Methyl hydrazinecarboxylate (814 mg, 9.04 mmol) and aqueous hydrochloric acid (1N) was added until pH value 5.5 was reached. The reaction mixture was stirred 24 h at room temperature and concentrated in vacuo. Purification via column chromatography (silica gel, hexane/ethyl acetate gradient: 2%→100% ethyl acetate) afforded the title compound (600 mg, 40% yield).

LC-MS (Method 1): $R_t$=1.05 min, MS (ESIpos): m/z=229 [M+H]$^+$

Intermediate 54

Methyl 2-{1-[3,5-difluoro-4-(morpholin-4-yl)phenyl]-2-hydroxyethylidene}hydrazinecarboxylate

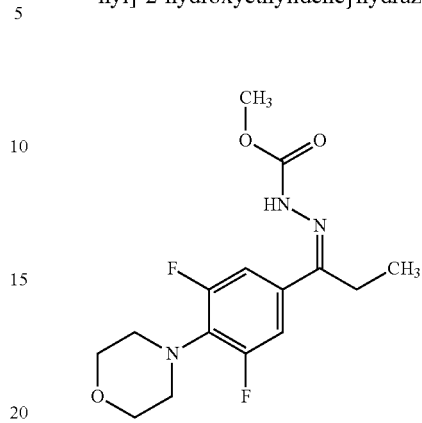

1-[3,5-Difluoro-4-(morpholin-4-yl)phenyl]-2-hydroxyethanone (460 mg, 1.79 mmol, Intermediate 31) was dissolved in methanol (4.0 mL). Methyl hydrazinecarboxylate (290 mg, 3.22 mmol) and aqueous hydrochloric acid (18 µl, 1.0 M, 18 µmol) was added until pH value 5.5 was reached. The reaction mixture was stirred 5 h at room temperature and concentrated in vacuo, to obtain the crude title compound (30 mg, 5% yield), which was used in the next step without any further purification.

LC-MS (Method 1): $R_t$=0.91 min: MS (ESIpos): m/z=330 [M+H]$^+$

Intermediate 55

Methyl 2-{1-[3-cyano-4-(morpholin-4-yl)phenyl]-2-hydroxyethylidene}hydrazinecarboxylate

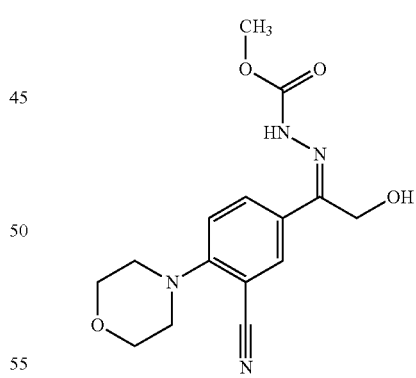

5-(Hydroxyacetyl)-2-(morpholin-4-yl)benzonitrile (570 mg, 2.31 mmol, Intermediate 32) was dissolved in methanol. Methyl hydrazinecarboxylate (375 mg, 4.17 mmol) and aqueous hydrochloric acid (1N) was added until pH value 5.5 was reached. The reaction mixture was stirred 24 h at room temperature and then concentrated in vacuo, to obtain the crude title compound 600 mg (81% yield), which was used in the next step without any further purification.

LC-MS (Method 1): $R_t$=0.80 min, MS (ESIpos): m/z=319 [M+H]$^+$

Intermediate 56

Methyl 2-[2-(acetyloxy)-1-(4-chloro-3-fluorophenyl)ethylidene]hydrazinecarboxylate

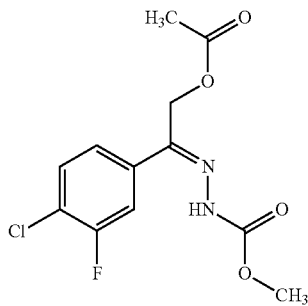 [SMILES: COC(=O)N/N=C(/COC(C)=O)c1ccc(Cl)c(F)c1]

2-(4-chloro-3-fluorophenyl)-2-oxoethyl acetate (5.40 g, 23.4 mmol, Intermediate 38) was dissolved in methanol (16 ml, 380 mmol). Methyl hydrazinecarboxylate (3.80 g, 42.1 mmol) and aqueous hydrochloric acid (1N) was added until pH value 5.5 was reached. The reaction mixture was stirred 24 h at room temperature and concentrated in vacuo, to obtain the crude title compound (7 g, quant.), which was used in the next step without any further purification.

LC-MS (Method 1): $R_t$=1.11 min; MS (ESIpos): m/z=303 [M+H]$^+$

Intermediate 57

Methyl(2)-2-{2-(acetyloxy)-1-[4-fluoro-3-(trifluoromethyl)phenyl]ethylidene}hydrazinecarboxylate

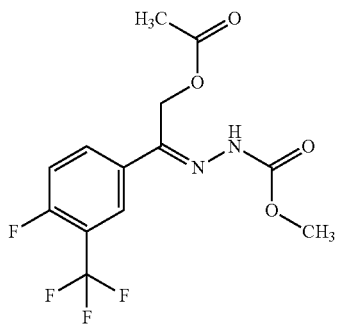 [SMILES: COC(=O)N/N=C(\COC(C)=O)c1ccc(F)c(C(F)(F)F)c1]

2-[4-Fluoro-3-(trifluoromethyl)phenyl]-2-oxoethyl acetate (95.0 mg, 360 μmol, Intermediate 39) was dissolved in methanol (2.0 mL) and acidified to pH 5 using aqueous hydrochloric acid (1M). Then methyl hydrazinecarboxylate (32.4 mg, 360 μmol) was added and the mixture was stirred 72 hours at room temperature. The mixture was concentrated and the crude material was used without further purification.

LC-MS (Method 1): $R_t$=1.15 min; MS (ESIneg): m/z=335 [M–H]$^-$

Intermediate 58

Methyl (2)-2-{2-(acetyloxy)-1-[4-chloro-3-(trifluoromethoxy)phenyl]ethylidene}hydrazinecarboxylate

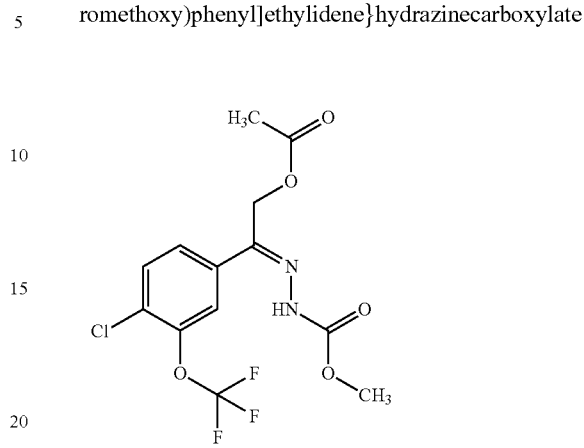

2-[4-chloro-3-(trifluoromethoxy)phenyl]-2-oxoethyl acetate (2.50 g, 8.43 mmol, Intermediate 44), was dissolved in methanol (11 ml, 270 mmol) and acidified to pH 5 using aqueous hydrochloric acid (1M). Then methyl hydrazinecarboxylate (1.37 g, 15.2 mmol) was added and the mixture was stirred 1 hour at room temperature. The mixture was concentrated and the crude material 2.2 g (71% yield) was used without further purification.

LC-MS (Method 1): $R_t$=1.26 min; MS (ESIneg): m/z=367 [M–H]$^-$

Intermediate 59

Methyl(2Z)-2-{2-(acetyloxy)-1-[4-chloro-3-fluoro-5-(trifluoromethyl)phenyl]ethylidene}hydrazine-1-carboxylate

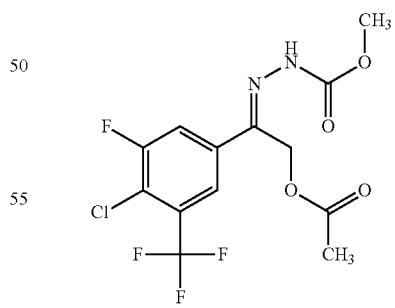

The title compound was synthesized analogously to Intermediate 58 from Intermediate 45.

MS (ESIpos):m/z=371 (M+H)+

Intermediate 60

Methyl(2Z)-2-{2-(acetyloxy)-1-[3-fluoro-4-(morpholin-4-yl)-5-(trifluoromethyl)phenyl]ethylidene}hydrazine-1-carboxylate

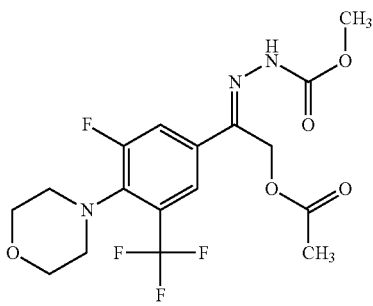 [SMILES: COC(=O)N/N=C(\COC(C)=O)c1cc(F)c(N2CCOCC2)c(C(F)(F)F)c1]

The title compound was synthesized analogously to Intermediate 58 from Intermediate 46.
MS(ESIpos): m/z=422 (M+H)+.

Intermediate 61

Methyl (2E)-2-{2-(acetyloxy)-1-[4-bromo-3-(difluoromethyl)phenyl]ethylidene}hydrazine-1-carboxylate

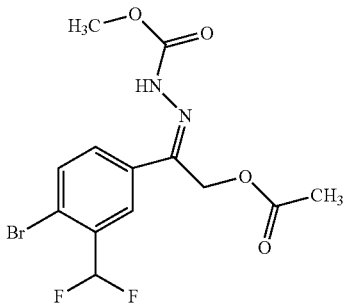 [SMILES: COC(=O)N/N=C(/COC(C)=O)c1ccc(Br)c(C(F)F)c1]

The title compound was synthesized analogously to Intermediate 58 from Intermediate 47.
MS (ESIpos): m/z=379 [M+H]$^+$.

Intermediate 62

Methyl(2Z)-2-{2-(acetyloxy)-1-[4-bromo-3-(trifluoromethyl)phenyl]ethylidene}hydrazine-1-carboxylate

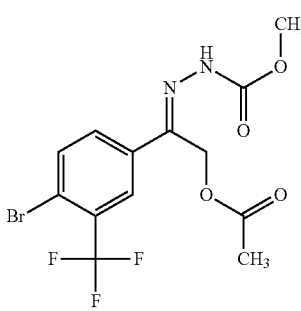

The title compound was synthesized analogously to Intermediate 58 from Intermediate 48.
MS(ESIpos): m/z=398 (M+H)+.

Intermediate 63

5-(3,4-Difluorophenyl)-3,6-dihydro-2H-1,3,4-oxadiazin-2-one

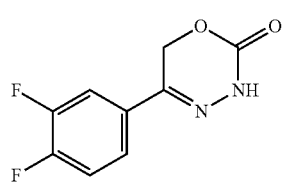 [SMILES: O=C1NN=C(c2ccc(F)c(F)c2)CO1]

To a solution of methyl 2-[1-(3,4-difluorophenyl)-2-hydroxyethylidene]hydrazinecarboxylate (2.40 g, 9.83 mmol, Intermediate 49) in acetonitrile (20 mL) was added potassium carbonate (2.04 g, 14.7 mmol) and the mixture was stirred at 60° C. overnight. The reaction mixture was concentrated in vacuo and diluted with water. The precipitate was filtered off, washed with water and dried, to obtain 1.20 g (58% yield) of the desired title compound.

LC-MS (Method 1): R$_t$=0.87 min; MS (ESIpos): m/z=213 [M+H]$^+$ $^1$H-NMR (400 MHz, DMSO-d6) δ[ppm]: 2.074 (0.66), 2.518 (0.81), 2.523 (0.52), 5.354 (16.00), 7.514 (0.58), 7.535 (1.33), 7.539 (0.65), 7.555 (1.45), 7.561 (1.43), 7.568 (1.29), 7.572 (1.29), 7.580 (2.74), 7.585 (1.75), 7.595 (0.49), 7.607 (0.41), 7.747 (0.91), 7.752 (0.87), 7.767 (0.94), 7.772 (0.94), 7.778 (0.92), 7.782 (0.85), 7.798 (0.79), 7.801 (0.73), 11.168 (2.49).

Intermediate 64

5-[4-Chloro-3-(trifluoromethyl)phenyl]-3,6-dihydro-2H-1,3,4-oxadiazin-2-one

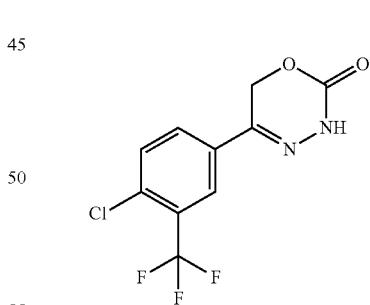

To a solution of methyl 2-{1-[4-chloro-3-(trifluoromethyl)phenyl]-2-hydroxyethylidene}hydrazinecarboxylate (1.10 g, 3.54 mmol, Intermediate 50) in acetonitrile (9 mL) was added potassium carbonate (489 mg, 3.54 mmol) and the mixture was stirred 3 h at 60° C. The reaction mixture was diluted with water and concentrated in vacuo. The precipitate was filtered off, washed with water and dried, to obtain 700 mg (71% yield, 90% purity) of the desired title compound.

LC-MS (Method 1): R$_t$=1.11 min; MS (ESIpos): m/z=279 [M+H]$^+$

¹H-NMR (400 MHz, DMSO-d6) δ[ppm]: 2.074 (4.51), 2.518 (0.60), 2.523 (0.42), 5.427 (16.00), 7.827 (1.88), 7.848 (2.46), 7.979 (1.39), 7.984 (1.44), 8.000 (1.05), 8.005 (1.14), 8.081 (2.49), 8.087 (2.21), 11.267 (1.72).

Intermediate 65

5-(4-Chloro-3-fluorophenyl)-3,6-dihydro-2H-1,3,4-oxadiazin-2-one

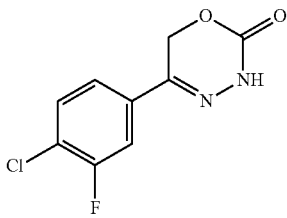 [SMILES: O=C1NN=C(c2ccc(Cl)c(F)c2)CO1]

To a solution of methyl 2-[2-(acetyloxy)-1-(4-chloro-3-fluorophenyl)ethylidene]hydrazinecarboxylate (4.15 g, 13.7 mmol, Intermediate 56) in ethanol (21 ml) was added sodium ethanolate (7.7 ml, 21% in EtOH, 21 mmol) and the mixture was stirred 17 h at RT. Water was added, the precipitate was filtered off and dried to obtain 1.60 g (51% yield) of the desired title compound.

LC-MS (Method 1): R$_t$=0.97 min; MS (ESIpos): m/z=229 [M+H]$^+$

¹H-NMR (400 MHz, DMSO-d6) δ[ppm]: 2.518 (0.57), 5.361 (16.00), 7.571 (1.23), 7.575 (1.31), 7.593 (1.77), 7.597 (1.79), 7.675 (2.38), 7.695 (2.83), 7.716 (3.58), 7.720 (2.03), 7.742 (2.00), 7.747 (1.86), 11.223 (1.69).

Intermediate 66

5-[4-Fluoro-3-(trifluoromethyl)phenyl]-3,6-dihydro-2H-1,3,4-oxadiazin-2-one

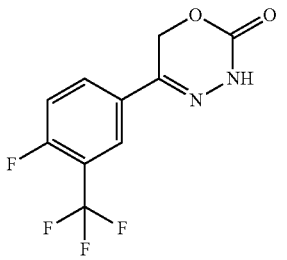 [SMILES: O=C1NN=C(c2ccc(F)c(C(F)(F)F)c2)CO1]

Methyl (2)-2-{2-(acetyloxy)-1-[4-fluoro-3-(trifluoromethyl)phenyl]ethylidene}hydrazinecarboxy-late (3.30 g, 9.81 mmol, Intermediate 57) was suspended in ethanol (83 mL) under nitrogen and sodium ethylate solution in ethanol (5.5 mL, 21% purity, 15 mmol) was added. It was stirred at room temperature for 30 min. The reaction mixture was diluted with aqueous saturated ammonium chloride solution and water and stirred for 1 hour. Precipitated product was filtered off. The filter cake was washed with water and dried under vacuo to give 2.50 g (95% purity) of the title compound.

LC-MS (Method 1): R$_t$=1.03 min; MS (ESIneg): m/z=261 [M−H]$^-$

¹H-NMR (400 MHz, DMSO-d6) δ[ppm]: 1.228 (0.61), 1.246 (1.18), 1.264 (0.57), 2.327 (0.49), 2.669 (0.50), 4.164 (0.49), 4.181 (0.47), 4.631 (1.19), 5.421 (16.00), 7.617 (1.38), 7.640 (2.05), 7.665 (1.50), 8.028 (2.22), 8.045 (2.02), 8.060 (1.16), 8.066 (1.06), 8.072 (1.26), 8.081 (1.28), 8.088 (1.01), 8.094 (1.06), 11.215 (0.91).

Intermediate 67 tert-Butyl {2-[4-(2-oxo-3,6-dihydro-2H-1,3,4-oxadiazin-5-yl)-2-(trifluoromethyl)anilino]ethyl} carbamate

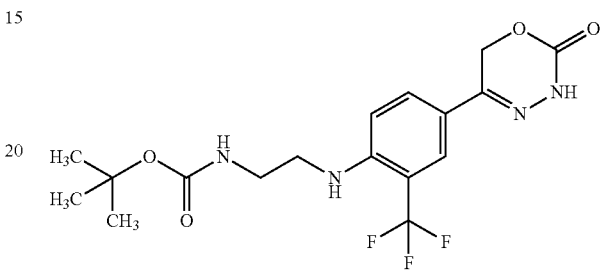

5-[4-Fluoro-3-(trifluoromethyl)phenyl]-3,6-dihydro-2H-1,3,4-oxadiazin-2-one (150 mg, 572 μmol, Intermediate 66) was dissolved in DMSO (500 μl) and tert-butyl (2-aminoethyl)carbamate (200 μl, 1.3 mmol) was added. The mixture was stirred at 100° C. for 16 h. DMSO (2 ml) and water (0.5 ml) were added. The mixture was extracted three times with MTBE and the combined organic phases were dried in vacuo. The precipitate was suspended in dichloromethane, filtered, and washed with MTBE. The precipitate was dissolved in ethyl acetate, washed with aqueous saturated ammonium chloride solution, the organic phases were then concentrated in vacuo. The precipitate was suspended in MTBE, filtered, and washed with MTBE and water. After drying in vacuo 95.0 mg (95% purity, 39% yield) of the title compound was obtained.

LC-MS (Method 1): R$_t$=1.12 min, MS (ESIpos): m/z=403 [M+H]$^+$

¹H-NMR (400 MHz, DMSO-d6) δ[ppm]: 1.376 (16.00), 2.518 (0.78), 2.522 (0.49), 3.137 (0.54), 3.152 (0.62), 3.247 (0.60), 3.261 (0.54), 5.299 (4.30), 6.043 (0.46), 6.916 (0.51), 6.939 (0.52), 7.051 (0.45), 7.733 (1.74), 7.752 (0.41), 10.884 (1.04).

Intermediate 68

(rac)-5-[4-Chloro-3-(trifluoromethyl)phenyl]-6-methyl-3,6-dihydro-2H-1,3,4-oxadiazin-2-one

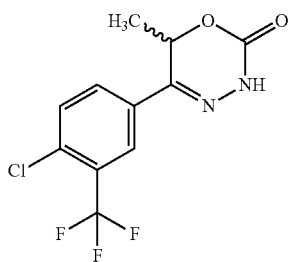 [SMILES: CC1OC(=O)NN=C1c1ccc(Cl)c(C(F)(F)F)c1]

To a solution of (rac)-1-[4-chloro-3-(trifluoromethyl)phenyl]-2-hydroxypropan-1-one (400 mg, 1.19 mmol, Intermediate 34) in MeOH (1.2 mL) was added methyl hydrazinocarboxylate (118 mg, 1.31 mmol) and 0.1M aqueous hydrogen chloride solution (2 drops, 2.02 µmol). The resulting mixture was heated at reflux for 1 h. The reaction mixture was concentrated in vacuo and the residual material azeotroped with MeOH (×2). Freshly prepared methanolic NaOMe solution [Na (109 mg, 4.75 mmol) consumed in MeOH (3.1 mL)] was added and the mixture stirred at RT for 2 h. Additional freshly prepared methanolic NaOMe solution [Na (109 mg, 4.75 mmol) consumed in MeOH (3.1 mL)] was added and the mixture stirred at RT for a further 2 h. AcOH (506 µL, 8.84 mmol) was added and the solution was concentrated and partitioned between EtOAc and water. The EtOAc was isolated, washed with brine, dried over anhydrous $MgSO_4$, filtered and concentrated in vacuo to obtain a crude residue. The residue was purified by Biotage Isolera™ chromatography (25 g KP-Sil, eluting with heptanes-EtOAc, 1:0 to 1:1). The obtained impure solid was re-purified by Biotage Isolera™ chromatography (10 g KP-Sil, eluting with heptanes-EtOAc, 1:0 to 1:1) to afford the title compound (185.7 mg, 49% yield, 92% purity) as a off-white solid. LCMS (Method 3, 2 min) 94% @ Rt=1.14 min, MS (ESIpos): m/z=292.8 (M+H)+[Weak ionisation] LCMS (Method 4, 7 min) 92% @ Rt=3.18 min, MS (ESIpos): m/z=292.9 (M+H)+[Weak ionisation] $^1$H NMR (500 MHz, Chloroform-d) δ 1.63 (d, J=7.0 Hz, 3H), 5.53 (q, J=7.0 Hz, 1H), 7.59 (d, J=8.4 Hz, 1H), 7.73 (dd, J=2.1, 8.4 Hz, 1H), 7.99 (d, J=1.9 Hz, 1H), 8.20 (br. s, 1H). Chiral analysis: Column: Cellulose-3 25 cm, Mobile phase: 20% IPA: 80% $CO_2$, Flow rate: 4 mL/min, UV at 280 nm, Runtime: 7 min, Neg ion MS LC-MS (Method 4, 7 min): $R_t$=3.18 min, MS (ESIpos): m/z=293 [M+H]$^+$ Intermediate 69

5-[4-Chloro-3-fluoro-5-(trifluoromethyl)phenyl]-3,6-dihydro-2H-1,3,4-oxadiazin-2-one

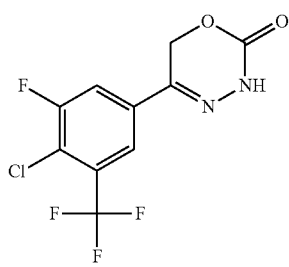 [SMILES: O=C1NN=C(c2cc(F)c(Cl)c(C(F)(F)F)c2)CO1]

To a solution of methyl (2Z)-2-{2-(acetyloxy)-1-[4-chloro-3-fluoro-5-(trifluoromethyl)phenyl]ethylidene}hydrazine-1-carboxylate (20 g, 36% purity, Intermediate 59), in 200 mL of ethanol, was added sodium hydride, 0.39 g (9.7 mmol, 60% purity), then the resulting mixture was stirred at 0° C. for 2 hours under nitrogen. Upon completion of the reaction, the mixture was acidified to pH=1 with HCl (1N). The solvent was removed in vacuo directly, the residue was purified by C18 reversed phase column chromatography: [Mobile Phase A: Waters (0.1% NH4HCO3), Mobile Phase B: ACN; Flow rate: 80 mL/min; Gradient: 40% B to 70% B in 25 min] to give 2.01 g (34.4%) of the product as a white solid.

$^1$H-NMR (400 MHz, DMSO-$d_6$): δ [ppm]=11.35 (br s, 1H), 8.07 (dd, 1H), 7.97 (s, 1H), 5.43 (s, 2H)

Intermediate 70

5-[4-Acetyl-3-(trifluoromethyl)phenyl]-3,6-dihydro-2H-1,3,4-oxadiazin-2-one

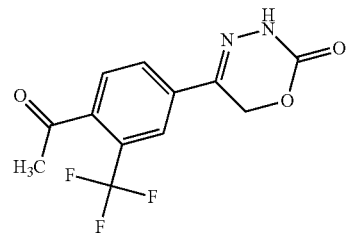 [SMILES: CC(=O)c1ccc(C2=NNC(=O)OC2)cc1C(F)(F)F]

To a solution of 5-[4-bromo-3-(trifluoromethyl)phenyl]-3,6-dihydro-2H-1,3,4-oxadiazin-2-one (500 mg, 1.5 mmol, Intermediate 78), in 30 mL of 1,4-dioxane were added tributyl(1-ethoxyvinyl)stannane, 838 mg (2.3 mmol), and tetrakis(triphenylphosphine)palladium(0), 89 mg (0.08 mmol). The resulting mixture was stirred at 110° C. for overnight. After cooled to room temperature, 15 mL of the hydrochloric acid solution (1 M) was added. The resulting mixture was stirred at room temperature for further 4 hours. Upon completion of the reaction, the reaction mixture was extracted with ethyl acetate. The combined organic layer was washed with brine, water and dried over anhydrous sodium sulfate. The solvent was removed in vacuo, and the residue purified with silica gel column chromatography (PE/EA=3:1) to give 320 mg (65%) of the product as a yellow solid.

MS(ESIpos): m/z=287 (M+H)+.

Intermediate 71

(rac)-6-Methyl-5-(3,4,5-trifluorophenyl)-3,6-dihydro-2H-1,3,4-oxadiazin-2-one

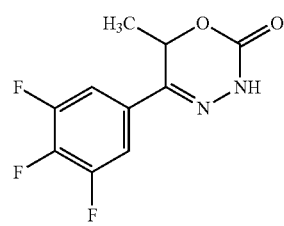 [SMILES: CC1OC(=O)NN=C1c1cc(F)c(F)c(F)c1]

To a solution of (rac)-methyl 2-[2-hydroxy-1-(3,4,5-trifluorophenyl)propylidene]hydrazinecarboxylate (95.0 mg, 344 µmol, Intermediate 52) in toluene (2.0 mL) was added potassium carbonate (143 mg, 1.03 mmol) and this mixture was stirred at 50° C. overnight. The reaction mixture was concentrated in vacuo and the residue was diluted with dichloromethane. The precipitate was filtered off and washed with dichloromethane. The filtrate was concentrated in vacuo and the residue was purified by preparative HPLC, to obtain 5.00 mg (95% purity, 6% yield) of the desired title compound.

LC-MS (Method 1): $R_t$=1.02 min, MS (ESIpos): m/z=245 [M+H]+

1H-NMR (400 MHz, DMSO-d6) δ[ppm]: 1.400 (16.00), 1.417 (15.92), 2.074 (1.45), 2.518 (9.20), 2.523 (6.26), 5.768 (1.18), 5.785 (4.51), 5.802 (4.43), 5.820 (1.15), 7.668 (0.50), 7.679 (3.67), 7.695 (3.93), 7.702 (4.09), 7.719 (3.89), 7.730 (0.53), 11.337 (5.65).

Intermediate 72

(rac)-5-(4-Bromophenyl)-6-methyl-3,6-dihydro-2H-1,3,4-oxadiazin-2-one

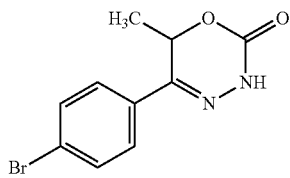

(rac)-Methyl 2-[-1-(4-bromophenyl)-2-hydroxypropylidene]hydrazinecarboxylate (600 mg, 1.99 mmol, Intermediate 53) and potassium carbonate (826 mg, 5.98 mmol) were dissolved in acetonitrile (9 mL) and the mixture was stirred at 50° C. overnight. The reaction mixture was concentrated in vacuo and the residue was diluted with dichloromethane. The precipitate was filtered off and the filtrate was concentrated in vacuo, to obtain 430 mg (95% purity, 76% yield) of the desired title compound.

LC-MS (Method 1): $R_t$=1.04 min; MS (ESIneg): m/z=269 [M−H]−

1H-NMR (400 MHz, DMSO-d6) δ[ppm]: 1.404 (14.54), 1.421 (14.87), 2.518 (1.89), 2.523 (1.26), 5.754 (1.10), 5.758 (0.51), 5.771 (4.34), 5.789 (4.17), 5.806 (1.06), 7.647 (0.53), 7.650 (2.93), 7.652 (2.17), 7.656 (1.32), 7.667 (2.22), 7.673 (16.00), 7.677 (3.81), 7.681 (3.98), 7.684 (15.37), 7.691 (2.09), 7.701 (1.39), 7.705 (2.06), 7.707 (2.93), 11.196 (1.47).

Intermediate 73

5-[4-Chloro-3-(trifluoromethoxy)phenyl]-3,6-dihydro-2H-1,3,4-oxadiazin-2-one

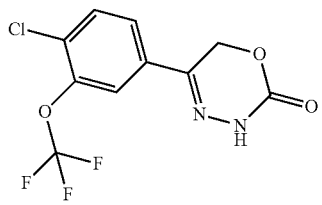 [SMILES: O=C1NN=C(c2ccc(Cl)c(OC(F)(F)F)c2)CO1]

Methyl (2)-2-{2-(acetyloxy)-1-[4-chloro-3-(trifluoromethoxy)phenyl]ethylidene}hydrazinecarboxylate (892 mg, 2.42 mmol, Intermediate 58) was dissolved in ethanol (10 ml) and cooled to 0° C. Sodium hydride (290 mg, 60% purity, 7.26 mmol) was added slowly and the mixture was stirred at 0° C. for 10 min. The solvent was removed in vacuo and water was added. The aqueous phase was extracted three times with ethyl acetate. The combined organic phases were filtered with a water-resistant filter and concentrated in vacuo. The residue was purified by chromatography to obtain 160 mg (90% purity, 20% yield) of the desired title compound.

LC-MS (Method 1): $R_t$=1.15 min; MS (ESIpos): m/z=295 [M+H]+

1H-NMR (400 MHz, DMSO-d6) δ[ppm]: 1.154 (0.47), 1.172 (0.89), 1.190 (0.49), 1.987 (1.79), 2.518 (1.28), 2.523 (0.86), 4.034 (0.40), 5.393 (16.00), 7.734 (1.70), 7.739 (1.86), 7.755 (3.02), 7.760 (3.48), 7.803 (5.56), 7.825 (2.96), 7.844 (1.95), 7.848 (2.51), 7.851 (1.79), 11.245 (3.27).

Intermediate 74

(6S)-5-[4-chloro-3-(trifluoromethyl)phenyl]-6-methyl-3,6-dihydro-2H-1,3,4-oxadiazin-2-one

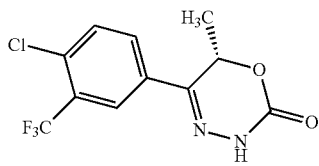 [SMILES: C[C@@H]1OC(=O)NN=C1c1ccc(Cl)c(C(F)(F)F)c1]

To 5.0 g of (S)-1-(4-chloro-3-(trifluoromethyl)phenyl)-2-hydroxypropan-1-one (Intermediate 42) in 20 mL of MeOH was added 1.94 g of methyl hydrazinecarboxylate (21.6 mmol) and 12 drops of 0.1 N HCl solution (J. Med. Chem. 1992, 35, 163) and the mixture was heated at reflux temperature for 1 h. After cooling, the reaction was concentrated, MeOH was added and concentrated to remove HCl and water (twice). To this was added a NaOMe solution (2.26 g Na (98.4 mmol) consumed in 60 mL MeOH). After 1 h 40 min, 5.9 mL of HOAc (98 mmol) was added and the solution was concentrated and partitioned between EtOAc and water. The EtOAc was removed, dried, and concentrated. Chromatography with 0-20% EtOAc in hexane followed by recrystallization from CH2Cl2 and hexane yielded 3.55 g of product as a white solid (62%).

1H NMR (400 MHz, CDCl3) δ 8.46 (s, 1H), 8.02 (d, J=1.7 Hz, 1H), 7.75 (dd, J=8.4, 2.0 Hz, 1H), 7.61 (d, J=8.5 Hz, 1H), 5.56 (q, J=7.0 Hz, 1H), 1.65 (d, J=7.0 Hz, 3H). 19F NMR (376 MHz, CDCl3) δ −62.93. LC-MS (Method 5): Mass 293 (M+1)+. Chiral SFC analysis (Column: ChiralPak AS-H, 250×4.6 mm, 5 um, Mobile Phase Modifier: 100% Methanol, Gradient: 5 to 50% Methanol over 10 min, Flow Rate: 4 mL/min, Back Pressure: 100 bar, Column Temperature: 40° C. UV detection was from 200-400 nm) showed retention times of separated enantiomers at 5.54 and 5.95 min in 98.9:1.1 ratio.

Intermediate 75

(6S)-5-(-[(4-Fluoro-3-(trifluoromethyl)phenyl)-)]-6-methyl-3,6-dihydro-2H-1,3,4-oxadiazin-2-one

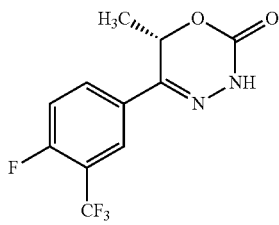 [SMILES: C[C@@H]1OC(=O)NN=C1c1ccc(F)c(C(F)(F)F)c1]

To 3.4 g of (S)-1-(4-fluoro-3-(trifluoromethyl)phenyl)-2-hydroxypropan-1-one (14 mmol, Intermediate 43) in 15 mL of MeOH and 1.41 g of methyl hydrazinecarboxylate (15.7 mmol) was added 9 drops of 0.1 N HCl solution (J. Med. Chem. 1992, 35, 163) and the mixture was heated at reflux 1 h. After cooling, the reaction was concentrated, MeOH was added and concentrated to remove HCl and water (twice). To this was added a NaOMe solution (1.64 g Na (71.5 mmol) consumed in 45 mL MeOH). After 2 h, 4.3 mL of HOAc (72 mmol) was added and the solution was concentrated and partitioned between EtOAc and water. The EtOAc was removed, dried, and concentrated. Chromatography with 10-40% EtOAc in hexane yielded the product as an oil which solidified upon standing overnight, 2.25 g (57%). $^1$H NMR (400 MHz, CDCl$_3$) δ 8.57 (s, 1H), 7.95 (dd, J=6.6, 2.0 Hz, 1H), 7.85 (ddd, J=8.3, 4.4, 2.3 Hz, 1H), 7.31 (t, J=9.2 Hz, 1H), 5.56 (q, J=7.0 Hz, 1H), 1.65 (d, J=7.0 Hz, 4H). $^{19}$F NMR (376 MHz, CDCl$_3$) δ −61.68 (d, J=12.6 Hz), −110.74 (q, J=12.7 Hz). LC-MS (Method 5): Mass 277 (M+1)+.

Intermediate 76

5-(4-Chloro-3-methylphenyl)-3,6-dihydro-2H-1,3,4-oxadiazin-2-one

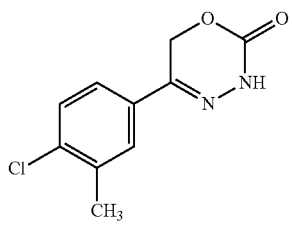

To a solution of methyl 2-[2-(acetyloxy)-1-(4-chloro-3-methylphenyl)ethylidene]hydrazinecarboxylate (3.60 g, 12.1 mmol, Intermediate 51) in acetonitrile (63 mL) was added potassium carbonate (1.67 g, 12.1 mmol) and the mixture was stirred for 3 h at 50° C. The reaction mixture was diluted with water and concentrated in vacuo. The precipitate was filtered off, washed with water, stirred in MTBE, filtered off and dried, to obtain 500 mg (19% yield, 97% purity) of the desired title compound.

LC-MS (Method 1): R$_t$=1.04 min, MS (ESIpos): m/z=225 [M+H]$^+$ $^1$H-NMR (400 MHz, DMSO-d6) δ[ppm]: 2.074 (0.97), 2.363 (14.47), 2.518 (0.67), 2.522 (0.51), 5.344 (16.00), 7.485 (2.22), 7.506 (4.13), 7.548 (1.82), 7.553 (1.83), 7.569 (0.93), 7.574 (1.01), 7.701 (2.51), 7.705 (2.30), 11.114 (1.64).

Intermediate 77

5-[4-Bromo-3-(difluoromethyl)phenyl]-3,6-dihydro-2H-1,3,4-oxadiazin-2-one

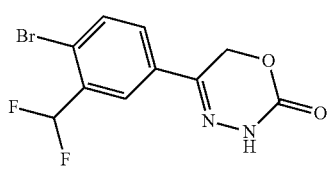 [SMILES: O=C1NN=C(c2ccc(Br)c(C(F)F)c2)CO1]

To a solution of methyl 2-(2-acetoxy-1-(4-bromo-3-(difluoromethyl)phenyl)ethylidene)-hydrazinecarboxylate, 8 g (21.0 mmol, Intermediate 61), in 100 mL of ethanol, was added sodium hydride, 0.8 g (33.3 mmol). The resulting mixture was stirred at 0° C. for 3 hours. Upon completion of the reaction (monitored by TLC), the reaction mixture was diluted with water and extracted with ethyl acetate. The combined organic layer was washed with brine, water and dried over anhydrous sodium sulfate. The solvent was removed in vacuo and the residue was purified with silica gel column chromatography (petroleum ether: ethyl acetate=3:1) to give 4.2 g of the product, as a yellow solid. 100 mg was purified by Prep-HPLC [Column: Xbridge prep C18 5 um 19*150 m; Mobile phase A: Waters (0.1% NH4HCO3), Mobile phase B: ACN; Flow rate: 20 ml/min; Gradient: 30% B to 55% B in 8 min; 254 & 220 nm; t=7.12 min] to give 44.4 mg of product as a white solid. MS(ESIpos): m/z=303 (M−H)+.

Intermediate 78

5-[4-Bromo-3-(trifluoromethyl)phenyl]-3,6-dihydro-2H-1,3,4-oxadiazin-2-one

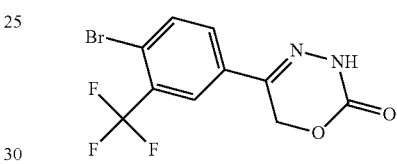

To a solution of methyl 2-(2-acetoxy-1-(4-bromo-3-(trifluoromethyl)phenyl)ethylidene)-hydrazinecarboxylate, 1.4 g (2.7 mmol, Intermediate 62), in 50 mL of ethanol, was added sodium hydride, 0.2 g (4.1 mmol, 60% purity) at 0° C. The resulting mixture was stirred at 0° C. for 2 hours under nitrogen atmosphere. Upon completion of the reaction, the pH value was adjusted to 6-7 with 1N hydrogen chloride solution, then, water was added and the resulting mixture was extracted with ethyl acetate. The combined organic layer was washed with brine, dried over anhydrous sodium. The solvent was removed in vacuo and the residue was purified with silica gel column chromatography (EA/PE=1/1) to give 0.43 g (49%) of the product as a yellow solid.

$^1$H-NMR (400 MHz, DMSO-d$_6$): δ [ppm]=11.27 (s, 1H), 8.06 (d, 1H), 7.99 (d, 1H), 7.88 (dd, 1H), 5.43 (s, 2H)

EXPERIMENTAL SECTION—EXAMPLES

Example 1

5-[4-(4,4-Difluoropiperidin-1-yl)-3-fluorophenyl]-3,6-dihydro-2H-1,3,4-oxadiazin-2-one

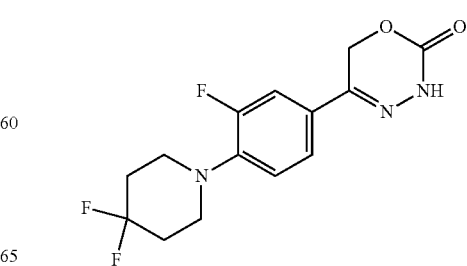

To a solution of 5-(3,4-difluorophenyl)-3,6-dihydro-2H-1,3,4-oxadiazin-2-one (160 mg, 754 µmol, Intermediate 63) in N,N-diisopropylethylamine (530 µL, 3.1 mmol) were added 4,4-difluoropiperidine hydrochloride (1:1) (357 mg, 2.26 mmol) and a small amount of calcium carbonate. The reaction mixture was stirred for 6 days at 110° C. Then water was added and the aqueous phase was extracted three times with ethyl acetate. The combined organic phases were filtered with a water-resistant filter and concentrated in vacuo. The residue was purified by preparative HPLC to obtain 25.0 mg (95% purity, 10% yield) of the desired title compound.

LC-MS (Method 1): $R_t$=1.09 min, MS (ESIpos): m/z=314 [M+H]$^+$ $^1$H-NMR (400 MHz, DMSO-d6) δ[ppm]: 2.069 (0.91), 2.074 (2.12), 2.082 (1.38), 2.104 (1.99), 2.118 (2.69), 2.132 (1.99), 2.153 (1.38), 2.166 (0.91), 2.518 (4.19), 2.523 (2.66), 3.206 (3.71), 3.221 (4.90), 3.234 (3.52), 5.307 (16.00), 7.126 (1.37), 7.148 (2.40), 7.170 (1.61), 7.448 (1.73), 7.453 (2.00), 7.469 (1.37), 7.475 (2.17), 7.482 (2.44), 7.487 (1.47), 7.517 (2.05), 7.523 (1.78), 11.025 (5.03).

Example 3

5-[4'-Fluoro-2-(trifluoromethyl)biphenyl-4-yl]-3,6-dihydro-2H-1,3,4-oxadiazin-2-one

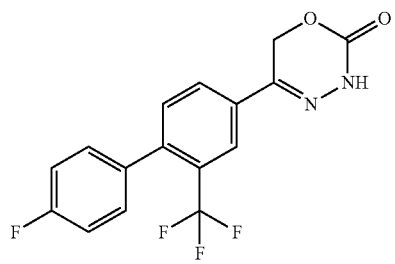 [SMILES: O=C1NN=C(c2ccc(-c3ccc(F)cc3)c(C(F)(F)F)c2)CO1]

To 5-[4-chloro-3-(trifluoromethyl)phenyl]-3,6-dihydro-2H-1,3,4-oxadiazin-2-one (90.0 mg, 323 µmol, Intermediate 64), (4-fluorophenyl)boronic acid (45.2 mg, 323 µmol), potassium carbonate (89.3 mg, 646 µmol) and 2-(dicyclohexylphosphino)-2',4',6'-triisopropylbiphenyl (9.24 mg, 19.4 µmol) in 1,4-dioxane (830 µL) and water (250 µL) (nitrogen atmosphere) was added chloro(2-dicyclohexylphosphino-2',4',6'-triisopropyl-1,1'-biphenyl)[2-(2'-amino-1,1'-biphenyl)]palladium(II) (7.62 mg, 9.69 µmol) and the mixture was stirred 2 h at 80° C. The reaction mixture was poured into water and extracted three times with ethyl acetate. The combined organic phases were filtered with a water-resistant filter and concentrated in vacuo. The residue was diluted with DMSO, filtered and purified by preparative HPLC, to obtain 39.0 mg (90% purity, 32% yield) of the desired title compound.

LC-MS (Method 1): $R_t$=1.25 min; MS (ESIpos): m/z=339 [M+H]$^+$

1H-NMR (400 MHz, DMSO-d6): δ [ppm]=11.25 (s, 1H), 8.10 (d, 1H), 8.01 (dd, 1H), 7.52 (d, 1H), 7.41-7.35 (m, 2H), 7.35-7.28 (m, 2H), 5.47 (s, 2H)

Example 4

5-[3-Fluoro-4-(morpholin-4-yl)phenyl]-3,6-dihydro-2H-1,3,4-oxadiazin-2-one

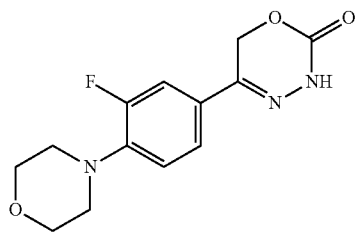 [SMILES: O=C1NN=C(c2ccc(N3CCOCC3)c(F)c2)CO1]

5-(3,4-difluorophenyl)-3,6-dihydro-2H-1,3,4-oxadiazin-2-one (160 mg, 754 µmol, Intermediate 63) in morpholine (3.3 ml, 38 mmol) was stirred 18 h at 110° C. The reaction mixture was concentrated in vacuo and purified by column chromatography (silica gel, hexane/ethyl acetate, gradient: 25%→100% ethyl acetate) to afford the title compound (47.0 mg, 21% yield) in a purity of 95%.

LC-MS (Method 1): $R_t$=0.84 min; MS (ESIpos): m/z=280 [M+H]$^+$ $^1$H-NMR (400 MHz, DMSO-d6) δ[ppm]: 1.988 (0.44), 2.518 (1.55), 2.523 (1.03), 3.063 (4.44), 3.075 (5.51), 3.087 (4.72), 3.730 (4.99), 3.741 (5.47), 3.752 (4.67), 5.304 (16.00), 5.759 (0.42), 7.052 (1.25), 7.075 (2.47), 7.097 (1.51), 7.457 (1.53), 7.463 (2.35), 7.470 (2.13), 7.475 (2.25), 7.480 (1.82), 7.483 (1.59), 7.507 (2.04), 7.512 (1.63), 11.017 (4.58).

Example 5

5-[3-Fluoro-4-(4-fluoro-4-methylpiperidin-1-yl)phenyl]-3,6-dihydro-2H-1,3,4-oxadiazin-2-one

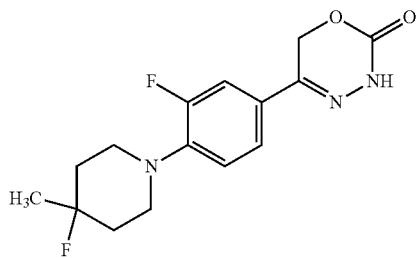 [SMILES: CC1(F)CCN(c2ccc(C3=NNC(=O)OC3)cc2F)CC1]

To a solution of 5-(3,4-difluorophenyl)-3,6-dihydro-2H-1,3,4-oxadiazin-2-one (149 mg, 702 µmol, Intermediate 63) in N,N-diisopropylethylamine (490 µL, 2.8 mmol) was added 4-fluoro-4-methylpiperidine hydrochloride (1:1) (216 mg, 1.40 mmol) and the reaction mixture was stirred for 3 days at 100° C. Then water was added and the aqueous phase was extracted three times with ethyl acetate. The combined organic phases were filtered with a water-resistant filter and concentrated in vacuo. The residue was purified by preparative HPLC to obtain 39.0 mg (95% purity, 17% yield) of the desired title compound.

LC-MS (Method 1): $R_t$=1.12 min, MS (ESIpos): m/z=310 [M+H]$^+$

¹H NMR (400 MHz, DMSO-d6) δ ppm 1.38 (d, J=21.60 Hz, 3H) 1.87 (m, 4H) 2.90-3.06 (m, 2H) 3.27 (m, J=12.42 Hz, 2H) 5.30 (s, 2H) 7.05-7.18 (m, 1H) 7.40-7.54 (m, 2H) 11.00 (s, 1H).

Example 6

5-[3-Fluoro-4-(4-fluoropiperidin-1-yl)phenyl]-3,6-dihydro-2H-1,3,4-oxadiazin-2-one

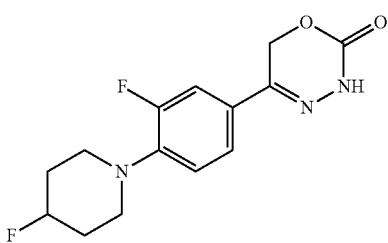 [SMILES: O=C1NN=C(c2ccc(N3CCC(F)CC3)c(F)c2)CO1]

To a solution of 5-(3,4-difluoropheny)-3,6-dihydro-2H-1,3,4-oxadiazin-2-one (102 mg, 481 μmol, Intermediate 63) in N,N-diisopropylethylamine (330 μL, 1.9 mmol) was added 4-fluoropiperidine hydrochloride (1:1) (134 mg, 962 μmol) and the reaction mixture was stirred at 80° C. over the weekend. Then acetonitrile was added and the mixture was stirred at 90° C. over a weekend again. Then water was added and the aqueous phase was extracted three times with ethyl acetate. The combined organic phases were filtered with a water-resistant filter and concentrated in vacuo. The residue was purified by preparative HPLC to obtain 20.0 mg (95% purity, 13% yield) of the desired title compound.

LC-MS (Method 1): $R_t$=1.03 min; MS (ESIpos): m/z=296 [M+H]⁺

¹H-NMR (400 MHz, DMSO-d6) δ[ppm]: 1.809 (0.47), 1.818 (0.74), 1.826 (0.82), 1.835 (1.03), 1.843 (1.16), 1.851 (1.22), 1.860 (0.99), 1.868 (1.02), 1.877 (0.69), 1.886 (0.41), 1.950 (0.61), 1.960 (0.64), 1.971 (0.74), 1.981 (0.63), 1.993 (0.47), 2.004 (0.69), 2.014 (0.75), 2.024 (0.63), 2.036 (0.73), 2.045 (0.62), 2.058 (0.46), 2.075 (5.42), 2.518 (2.16), 2.523 (1.42), 3.026 (0.83), 3.036 (1.01), 3.044 (0.97), 3.055 (1.64), 3.067 (1.34), 3.074 (1.35), 3.084 (1.06), 3.198 (1.12), 3.221 (1.46), 3.247 (0.76), 4.783 (0.50), 4.791 (0.63), 4.800 (0.48), 4.905 (0.50), 4.913 (0.62), 4.922 (0.49), 5.299 (16.00), 7.083 (0.99), 7.107 (2.27), 7.129 (1.56), 7.435 (1.65), 7.440 (2.08), 7.459 (4.84), 7.492 (2.10), 7.497 (1.72), 11.007 (4.72).

Example 7

5-(4'-Fluoro-2-methylbiphenyl-4-yl)-3,6-dihydro-2H-1,3,4-oxadiazin-2-one

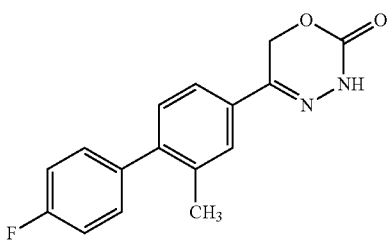 [SMILES: Cc1cc(C2=NNC(=O)OC2)ccc1-c1ccc(F)cc1]

The title compound was synthesized analogously to Example 3 from Intermediate 76 from 4-fluorophenyl)boronic acid.

LC-MS (Method 1): $R_t$=1.21 min; MS (ESIpos): m/z=285 [M+H]⁺

¹H-NMR (400 MHz, DMSO-d₆): δ [ppm]=11.09 (s, 1H), 7.66 (d, 1H), 7.60 (dd, 1H), 7.41 (t, 2H), 7.32-7.26 (m, 3H), 5.38 (s, 2H), 2.26 (s, 3H)

Example 8

5-(3',4'-Difluoro-2-methylbiphenyl-4-yl)-3,6-dihydro-2H-1,3,4-oxadiazin-2-one

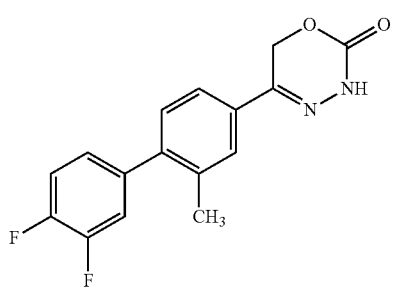 [SMILES: Cc1cc(C2=NNC(=O)OC2)ccc1-c1ccc(F)c(F)c1]

The title compound was synthesized analogously to Example 3 from Intermediate 76.

LC-MS (Method 1): $R_t$=1.24 min; MS (ESIpos): m/z=303 [M+H]⁺

¹H-NMR (400 MHz, DMSO-d6) δ[ppm]: 2.074 (0.85), 2.278 (15.36), 2.518 (1.87), 2.523 (1.22), 5.384 (16.00), 7.204 (0.69), 7.208 (0.73), 7.215 (0.75), 7.219 (0.89), 7.226 (0.88), 7.229 (0.87), 7.236 (0.80), 7.240 (0.65), 7.301 (3.13), 7.320 (3.58), 7.477 (0.97), 7.483 (1.70), 7.497 (1.08), 7.505 (2.78), 7.511 (1.94), 7.526 (1.78), 7.532 (2.39), 7.554 (0.81), 7.599 (1.61), 7.602 (1.77), 7.619 (1.34), 7.622 (1.60), 7.666 (3.03), 11.103 (4.86).

Example 9

5-(4'-Fluoro-2,2'-dimethylbiphenyl-4-yl)-3,6-dihydro-2H-1,3,4-oxadiazin-2-one

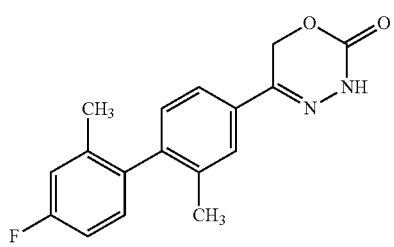 [SMILES: Cc1cc(F)ccc1-c1ccc(C2=NNC(=O)OC2)cc1C]

The title compound was synthesized analogously to Example 3 from Intermediate 76.

LC-MS (Method 1): $R_t$=1.28 min; MS (ESIpos): m/z=299 [M+H]⁺

¹H-NMR (400 MHz, DMSO-d6) δ[ppm]: 1.173 (0.74), 1.232 (0.71), 2.000 (16.00), 2.027 (14.86), 2.323 (0.49), 2.327 (0.66), 2.331 (0.50), 2.522 (3.19), 2.665 (0.49), 2.669 (0.66), 2.673 (0.50), 5.389 (13.67), 7.076 (1.45), 7.082 (1.74), 7.092 (2.67), 7.097 (1.77), 7.103 (2.09), 7.108 (2.77), 7.128 (0.46), 7.145 (2.99), 7.165 (3.29), 7.173 (1.61), 7.179 (1.47), 7.199 (1.43), 7.204 (1.39), 7.579 (1.67), 7.582 (1.73), 7.599 (1.52), 7.602 (1.62), 7.672 (3.16), 11.082 (4.13).

Example 10

5-[4-(3,6-Dihydro-2H-pyran-4-yl)-3-methylphenyl]-3,6-dihydro-2H-1,3,4-oxadiazin-2-one

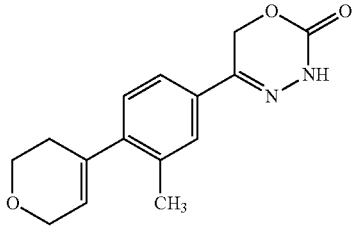 [SMILES: Cc1cc(C2=NNC(=O)OC2)ccc1C1=CCOCC1]

The title compound was synthesized analogously to Example 3 from Intermediate 76.

LC-MS (Method 1): $R_t$=0.94 min; MS (ESIpos): m/z=273 [M+H]$^+$ $^1$H-NMR (400 MHz, DMSO-d6) δ[ppm]: 2.266 (1.67), 2.273 (2.29), 2.278 (2.32), 2.284 (1.79), 2.291 (1.33), 2.304 (16.00), 2.518 (1.39), 2.523 (0.91), 3.798 (2.85), 3.812 (6.11), 3.825 (2.73), 4.182 (1.67), 4.188 (4.45), 4.195 (4.45), 4.202 (1.71), 5.334 (15.96), 5.675 (1.70), 5.678 (2.51), 5.682 (1.73), 7.174 (3.10), 7.193 (3.46), 7.495 (1.62), 7.499 (1.80), 7.515 (1.35), 7.520 (1.65), 7.553 (3.14), 11.038 (4.63).

Example 11

5-[3-Methyl-4-(1H-pyrazol-4-yl)phenyl]-3,6-dihydro-2H-1,3,4-oxadiazin-2-one

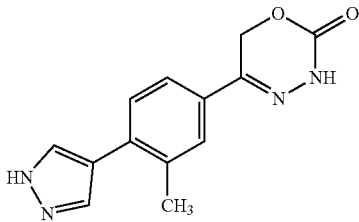 [SMILES: Cc1cc(C2=NNC(=O)OC2)ccc1-c1cn[nH]c1]

The title compound was synthesized analogously to Example 3 from Intermediate 76.

LC-MS (Method 2): $R_t$=0.69 min; MS (ESIpos): m/z=257 [M+H]$^+$ $^1$H-NMR (400 MHz, DMSO-d6) δ[ppm]: 2.074 (1.80), 2.327 (0.48), 2.425 (16.00), 2.522 (1.35), 2.539 (1.74), 2.669 (0.43), 5.356 (14.98), 7.490 (2.11), 7.511 (4.61), 7.538 (2.33), 7.542 (2.46), 7.559 (0.99), 7.562 (1.17), 7.606 (3.22), 7.811 (0.62), 8.060 (0.61), 11.033 (5.10), 13.065 (0.47).

Example 12

5-[3-Methyl-4-(6-oxo-1,6-dihydropyridin-3-yl)phenyl]-3,6-dihydro-2H-1,3,4-oxadiazin-2-one

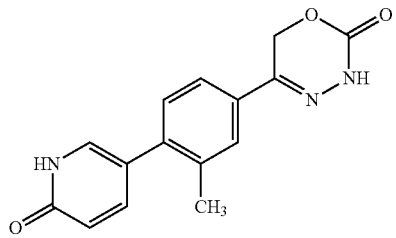 [SMILES: Cc1cc(C2=NNC(=O)OC2)ccc1-c1ccc(=O)[nH]c1]

The title compound was synthesized analogously to Example 3 from Intermediate 76.

LC-MS (Method 2): $R_t$=0.62 min; MS (ESIpos): m/z=284 [M+H]$^+$ $^1$H-NMR (400 MHz, DMSO-d6) δ[ppm]: 1.052 (0.76), 1.070 (0.42), 2.073 (4.95), 2.251 (0.91), 2.299 (15.80), 2.322 (0.85), 2.327 (1.18), 2.518 (3.08), 2.523 (2.05), 2.539 (1.31), 2.665 (0.58), 2.669 (0.82), 2.673 (0.58), 5.363 (16.00), 6.385 (3.14), 6.408 (3.19), 7.273 (3.32), 7.293 (3.74), 7.392 (2.30), 7.398 (2.52), 7.504 (2.67), 7.511 (2.34), 7.528 (2.45), 7.535 (2.25), 7.555 (1.76), 7.559 (1.92), 7.576 (1.45), 7.580 (1.67), 7.626 (3.23), 7.629 (2.90), 11.073 (5.50).

Example 13

5-[3-Methyl-4-(pyridin-3-yl)phenyl]-3,6-dihydro-2H-1,3,4-oxadiazin-2-one

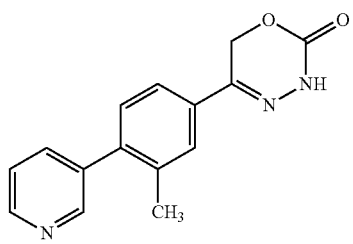 [SMILES: Cc1cc(C2=NNC(=O)OC2)ccc1-c1cccnc1]

The title compound was synthesized analogously to Example 3 from Intermediate 76.

LC-MS (Method 1): $R_t$=0.63 min; MS (ESIpos): m/z=269 [M+H]$^+$ $^1$H-NMR (400 MHz, DMSO-d6) δ[ppm]: 0.881 (0.51), 0.897 (0.57), 1.149 (0.58), 1.154 (0.62), 1.166 (0.64), 1.171 (0.76), 1.190 (0.46), 1.232 (1.40), 1.237 (0.80), 1.245 (0.59), 1.249 (1.17), 1.254 (0.57), 1.987 (1.11), 2.286 (14.79), 2.518 (2.63), 2.522 (1.86), 3.565 (14.67), 5.395 (16.00), 6.302 (0.81), 6.552 (0.70), 6.926 (0.50), 7.339 (3.03), 7.359 (3.43), 7.478 (1.32), 7.480 (1.35), 7.490 (1.34), 7.492 (1.40), 7.498 (1.50), 7.500 (1.52), 7.510 (1.45), 7.512 (1.47), 7.632 (1.61), 7.636 (1.75), 7.652 (1.35), 7.656 (1.55), 7.700 (2.93), 7.703 (2.67), 7.821 (1.27), 7.825 (1.67), 7.831 (1.30), 7.841 (1.16), 7.846 (1.52), 7.851 (1.09), 8.589 (2.72), 8.594 (4.18), 8.598 (2.45), 8.606 (1.96), 8.609 (1.78), 11.112 (4.34).

Example 14

5-[3-Methyl-4-(pyrimidin-5-yl)phenyl]-3,6-dihydro-2H-1,3,4-oxadiazin-2-one

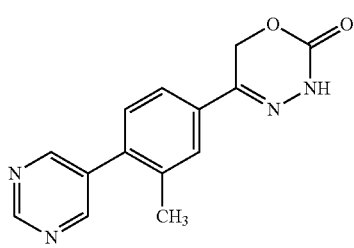 [SMILES: Cc1cc(C2=NNC(=O)OC2)ccc1-c1cncnc1]

The title compound was synthesized analogously to Example 3 from Intermediate 76.

LC-MS (Method 2): $R_t$=0.73 min; MS (ESIpos): m/z=269 [M+H]$^+$ $^1$H-NMR (400 MHz, DMSO-d6) δ[ppm]: 2.319 (12.30), 2.332 (0.49), 2.518 (1.72), 2.523 (1.21), 2.669 (0.43), 5.403 (12.20), 7.419 (2.41), 7.439 (2.83), 7.663 (1.35), 7.667 (1.42), 7.683 (1.09), 7.686 (1.22), 7.730 (2.45), 8.899 (16.00), 9.229 (6.75), 11.138 (3.44).

Example 15

5-(3'-Fluoro-2-methylbiphenyl-4-yl)-3,6-dihydro-2H-1,3,4-oxadiazin-2-one

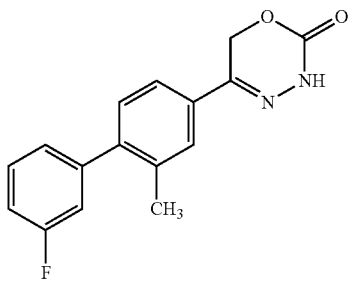 [SMILES: Cc1cc(C2=NNC(=O)OC2)ccc1-c1cccc(F)c1]

The title compound was synthesized analogously to Example 3 from Intermediate 76.

LC-MS (Method 1): $R_t$=1.21 min; MS (ESIpos): m/z=285 [M+H]$^+$ $^1$H-NMR (400 MHz, DMSO-d6) δ[ppm]: 2.075 (2.59), 2.281 (15.90), 2.518 (2.55), 2.523 (1.79), 5.387 (16.00), 7.195 (1.20), 7.197 (2.06), 7.200 (1.75), 7.212 (1.77), 7.215 (3.98), 7.219 (3.51), 7.228 (1.73), 7.234 (1.62), 7.237 (1.60), 7.240 (1.45), 7.245 (1.67), 7.250 (1.96), 7.257 (0.46), 7.305 (3.31), 7.325 (3.65), 7.476 (0.88), 7.492 (1.19), 7.494 (1.03), 7.499 (1.04), 7.503 (0.54), 7.506 (0.46), 7.511 (1.00), 7.514 (1.02), 7.517 (1.02), 7.533 (0.76), 7.603 (1.67), 7.607 (1.80), 7.623 (1.38), 7.627 (1.60), 7.670 (3.10), 11.099 (4.72).

Example 17

(rac)-5-[3,5-Difluoro-4-(morpholin-4-yl)phenyl]-6-methyl-3,6-dihydro-2H-1,3,4-oxadiazin-2-one

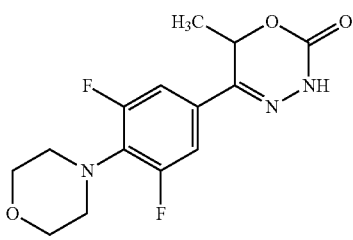 [SMILES: CC1OC(=O)NN=C1c1cc(F)c(N2CCOCC2)c(F)c1]

(rac)-6-methyl-5-(3,4,5-trifluorophenyl)-3,6-dihydro-2H-1,3,4-oxadiazin-2-one (50.0 mg, 205 μmol, Intermediate 71) in morpholine (0.45 mL) was stirred at 100° C. overnight. The reaction mixture was concentrated in vacuo and purified by preparative HPLC afforded the title compound 15.0 mg (95% purity, 22% yield).

LC-MS (Method 1): $R_t$=0.97 min, MS (ESIpos): m/z=312 [M+H]$^+$ $^1$H-NMR (400 MHz, DMSO-d6) δ[ppm]: 1.232 (0.71), 1.380 (14.79), 1.397 (16.00), 1.411 (3.93), 2.075 (2.64), 2.332 (3.00), 2.336 (1.36), 2.518 (14.71), 2.523 (9.79), 2.673 (3.00), 2.678 (1.29), 3.069 (0.93), 3.079 (2.00), 3.090 (2.00), 3.170 (7.79), 3.181 (5.86), 3.675 (8.79), 3.686 (9.57), 3.698 (8.14), 3.735 (1.93), 3.747 (3.07), 3.758 (1.79), 5.730 (1.07), 5.748 (4.36), 5.765 (4.29), 5.783 (1.07), 5.805 (1.07), 5.823 (1.07), 7.167 (0.57), 7.185 (0.50), 7.386 (0.71), 7.394 (1.07), 7.409 (6.36), 7.437 (6.21), 7.452 (0.79), 7.460 (0.57), 11.198 (9.64).

Example 18

5-{3,5-Difluoro-4-[2-methylmorpholin-4-yl]phenyl}-6-methyl-3,6-dihydro-2H-1,3,4-oxadiazin-2-one (Mixture of stereoisomers)

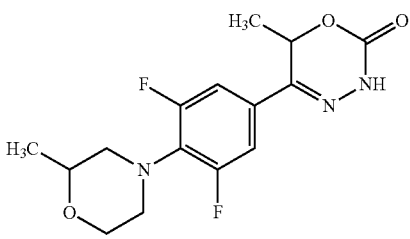 [SMILES: CC1CN(c2c(F)cc(C3=NNC(=O)OC3C)cc2F)CCO1]

(rac)-6-methyl-5-(3,4,5-trifluorophenyl)-3,6-dihydro-2H-1,3,4-oxadiazin-2-one (100 mg, 70% purity, 287 μmol, Intermediate 71) and (rac)-2-methylmorpholine (87.0 mg, 860 μmol) were dissolved in acetonitrile (1.0 mL) and the mixture was stirred at 100° C. overnight. The reaction mixture was concentrated in vacuo and the residue was extracted three times with ethyl acetate. The combined organic layers were concentrated in vacuo and purified by preparative HPLC to obtain 22.0 mg (95% purity, 22% yield) of the desired title compound.

LC-MS (Method 1): $R_t$=1.09 min; MS (ESIpos): m/z=326 [M+H]$^+$

¹H-NMR (400 MHz, DMSO-d6) δ[ppm]: 1.075 (15.75), 1.091 (16.00), 1.123 (3.56), 1.125 (3.68), 1.139 (3.64), 1.141 (3.72), 1.232 (0.45), 1.379 (13.42), 1.396 (14.69), 1.409 (5.24), 1.417 (1.51), 2.336 (0.82), 2.518 (14.28), 2.523 (9.17), 2.539 (1.72), 2.563 (0.45), 2.678 (0.82), 2.808 (1.06), 2.813 (0.94), 2.839 (1.84), 2.844 (1.35), 2.867 (1.47), 2.872 (1.39), 3.082 (0.70), 3.112 (2.21), 3.155 (2.91), 3.186 (1.88), 3.259 (0.45), 3.290 (0.86), 3.582 (0.78), 3.590 (1.02), 3.609 (2.46), 3.618 (2.25), 3.628 (1.47), 3.636 (2.01), 3.645 (1.96), 3.669 (1.23), 3.675 (1.23), 3.686 (0.53), 3.699 (0.82), 3.812 (1.96), 3.816 (1.64), 3.833 (1.27), 3.839 (1.60), 3.865 (0.74), 3.892 (0.57), 5.731 (0.94), 5.748 (3.72), 5.765 (3.76), 5.782 (1.06), 5.809 (1.02), 5.827 (0.98), 7.165 (0.70), 7.181 (0.74), 7.362 (0.41), 7.384 (0.78), 7.391 (1.15), 7.406 (5.77), 7.434 (5.57), 7.449 (0.74), 7.457 (0.49), 11.196 (9.70).

Example 20

(rac)-6-Methyl-5-[4-(morpholin-4-yl)phenyl]-3,6-dihydro-2H-1,3,4-oxadiazin-2-one

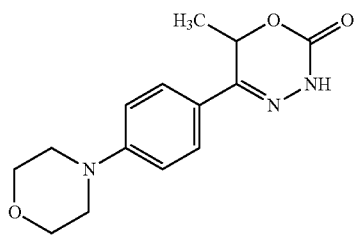 [SMILES: CC1OC(=O)NN=C1c1ccc(N2CCOCC2)cc1]

To (rac)-5-(4-bromophenyl)-6-methyl-3,6-dihydro-2H-1,3,4-oxadiazin-2-one (78.0 mg, 290 µmol, Intermediate 72) in THF (1.3 mL), morpholine (51 µL, 580 µmol), 2-dicyclohexylphosphino-2',6'-diisopropoxybiphenyl (6.76 mg, 14.5 µmol) (argon atmosphere) and finally lithium bis (trimethylsilyl)amide (930 µL, 1.0 M, 930 µmol) and dicyclolhexylphosphino-2',6'-diisopropyl-1,1'-biphenyl)(2-(2-aminoethyl)phenyl)palladium(II) (11.8 mg, 14.5 µmol) were added. The mixture was stirred 4 h at 80° C. in a microwave oven. The reaction mixture was diluted with methanol, filtered off and concentrated in vacuo. The residue was diluted with DMSO, filtered and purified by preparative HPLC to obtain 15.0 mg (95% purity, 18% yield) of the desired title compound.

LC-MS (Method 1): $R_t$=0.83 min; MS (ESIpos): m/z=276 [M+H]⁺

¹H-NMR (400 MHz, DMSO-d6) δ[ppm]: 1.357 (1.77), 1.384 (15.47), 1.402 (16.00), 1.419 (0.41), 2.318 (0.53), 2.456 (0.44), 2.461 (0.71), 2.466 (0.86), 2.470 (1.04), 2.518 (6.00), 2.523 (4.11), 2.660 (0.50), 3.140 (0.41), 3.152 (0.56), 3.164 (0.56), 3.186 (7.42), 3.198 (9.17), 3.211 (7.96), 3.718 (8.70), 3.731 (9.94), 3.743 (8.01), 5.695 (1.09), 5.712 (4.58), 5.729 (4.55), 5.746 (1.09), 6.973 (7.78), 6.996 (8.28), 7.596 (9.38), 7.619 (8.43), 10.895 (5.71).

Example 21

5-[3,5-Difluoro-4-(morpholin-4-yl)phenyl]-3,6-dihydro-2H-1,3,4-oxadiazin-2-one

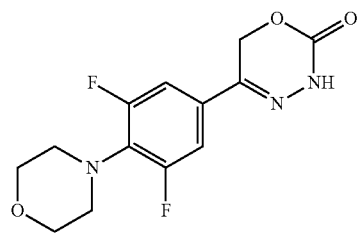 [SMILES: O=C1NN=C(c2cc(F)c(N3CCOCC3)c(F)c2)CO1]

Methyl 2-{1-[3,5-difluoro-4-(morpholin-4-yl)phenyl]-2-hydroxyethylidene}hydrazinecarboxylate (70.0 mg, 213 µmol, Intermediate 54) and potassium carbonate (88.1 mg, 0.64 mmol) were dissolved in acetonitrile (0.5 mL) and the mixture was stirred 4 h at 65° C. The reaction mixture was diluted with water and extracted three times with ethyl acetate. The combined organic layers were concentrated in vacuo and purified by preparative HPLC to obtain 49.0 mg (95% purity, 74% yield) of the desired title compound.

LC-MS (Method 1): $R_t$=0.93 min, MS (ESIpos): m/z=298 [M+H]⁺

¹H-NMR (400 MHz, DMSO-d6) δ[ppm]: 2.074 (2.47), 2.518 (7.37), 2.523 (5.54), 2.674 (0.72), 3.167 (5.67), 3.178 (4.32), 3.621 (0.42), 3.674 (6.41), 3.687 (7.16), 3.697 (5.99), 5.304 (16.00), 7.367 (0.58), 7.382 (3.99), 7.410 (3.94), 7.425 (0.58), 7.433 (0.42), 11.140 (4.55).

Example 22

2-(Morpholin-4-yl)-5-(2-oxo-3,6-dihydro-2H-1,3,4-oxadiazin-5-yl)benzonitrile

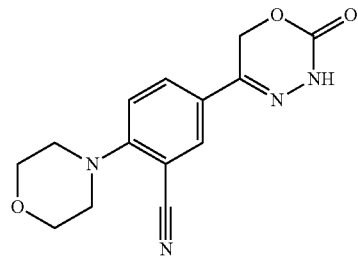 [SMILES: N#Cc1cc(C2=NNC(=O)OC2)ccc1N1CCOCC1]

To a solution of methyl 2-{1-[3-cyano-4-(morpholin-4-yl)phenyl]-2-hydroxyethylidene}hydrazinecarboxylate (600 mg, 1.88 mmol, Intermediate 55) in acetonitrile (5 mL) was added potassium carbonate (781 mg, 5.65 mmol) and the mixture was stirred at 60° C. over night. The reaction mixture was diluted with water and extracted three times with ethyl acetate. The combined organic layers were concentrated in vacuo. The residue was treated with dichloromethane. The precipitate was filtered off to obtain the title compound 150 mg (95% purity, 26% yield).

LC-MS (Method 1): $R_t$=0.80 min; MS (ESIpos): m/z=287 [M+H]⁺

¹H-NMR (400 MHz, DMSO-d6) δ[ppm]: 2.074 (0.44), 2.518 (1.22), 2.523 (0.84), 2.994 (3.48), 3.238 (4.31), 3.250 (5.44), 3.262 (4.75), 3.752 (5.00), 3.764 (5.40), 3.775 (4.58), 5.338 (16.00), 7.215 (3.21), 7.238 (3.38), 7.933 (2.04), 7.938 (2.41), 7.954 (1.74), 7.960 (2.39), 7.990 (4.64), 7.995 (3.60), 11.083 (4.34).

Example 23

3-Chloro-2-(morpholin-4-yl)-5-(2-oxo-3,6-dihydro-2H-1,3,4-oxadiazin-5-yl)benzonitrile

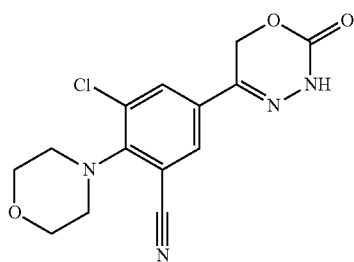 [SMILES: N#Cc1cc(C2=NNC(=O)OC2)cc(Cl)c1N1CCOCC1]

To a solution of 2-(morpholin-4-yl)-5-(2-oxo-3,6-dihydro-2H-1,3,4-oxadiazin-5-yl)benzonitrile (60.0 mg, 210 µmol, Example 22) in THF (2.1 mL) was added 1-chloropyrrolidine-2,5-dione (30.8 mg, 231 µmol) and the mixture was stirred at room temperature overnight. The reaction mixture was concentrated in vacuo and purified by preparative HPLC to obtain 14.0 mg (95% purity, 20% yield) of the desired title compound.

LC-MS (Method 1): $R_t$=0.94 min; MS (ESIpos): m/z=321 [M+H]$^+$ $^1$H-NMR (400 MHz, DMSO-d6) δ[ppm]: 2.518 (1.02), 2.523 (0.70), 3.323 (1.86), 3.328 (16.00), 3.345 (1.66), 3.730 (1.64), 3.741 (1.83), 3.752 (1.47), 5.353 (4.79), 7.998 (1.28), 8.003 (2.14), 8.019 (2.05), 8.024 (1.33), 11.224 (1.46).

Example 24

5-{4-[2,6-Dimethylmorpholin-4-yl]-3-fluorophenyl}-3,6-dihydro-2H-1,3,4-oxadiazin-2-one

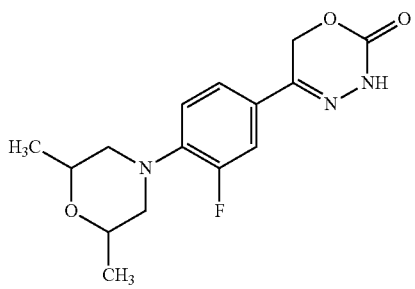 [SMILES: CC1CN(c2ccc(C3=NNC(=O)OC3)cc2F)CC(C)O1]

To a solution of 5-(3,4-difluorophenyl)-3,6-dihydro-2H-1,3,4-oxadiazin-2-one (70.0 mg, 330 µmol, Intermediate 63) in N,N-diisopropylethylamine (570 µL) was added 2,6-dimethylmorpholine (57.0 mg, 495 µmol) and the reaction mixture was stirred for 5 days at 120° C. The reaction mixture was concentrated in vacuo and purified by preparative HPLC to obtain 6.00 mg (95% purity, 6% yield) of the desired title compound.

LC-MS (Method 1): $R_t$=1.04 min, MS (ESIpos): m/z=308 [M+H]$^+$ $^1$H-NMR (400 MHz, DMSO-d6) δ[ppm]: 1.115 (16.00), 1.131 (15.50), 1.209 (2.57), 1.225 (2.74), 2.075 (0.62), 2.336 (1.01), 2.383 (1.51), 2.412 (2.18), 2.439 (1.79), 2.518 (11.75), 2.523 (8.39), 2.678 (0.95), 3.359 (2.07), 3.717 (0.90), 3.722 (1.01), 3.732 (1.06), 3.738 (1.23), 3.742 (1.23), 3.748 (1.12), 3.758 (1.01), 3.764 (0.84), 5.303 (14.10), 5.348 (0.39), 7.044 (1.01), 7.067 (2.01), 7.089 (1.23), 7.445 (1.45), 7.450 (1.79), 7.463 (1.90), 7.467 (3.13), 7.499 (1.79), 7.504 (1.40), 11.010 (4.31).

Example 25-1

(6S)-5-(3-Fluoro-4-morpholinophenyl)-6-methyl-3,6-dihydro-2H-1,3,4-oxadiazin-2-one

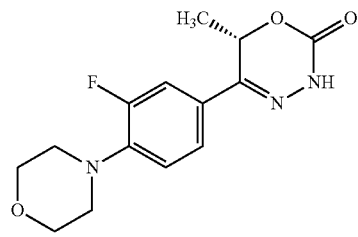 [SMILES: C[C@@H]1OC(=O)NN=C1c1cc(F)c(N2CCOCC2)c(F)c1]

Following a literature procedure (J. Med. Chem. 1990, 35, 163), to 320 mg of 1-(3-fluoro-4-morpholinophenyl)-2-hydroxypropan-1-one (1.26 mmol, Intermediate 36) in 2 mL EtOH and 2 drops of 0.1 N HCl were added 113 mg (1.26 mmol) of methyl hydrazinecarboxylate and the reaction mixture was heated at reflux. After 40 min another 11 mg of methyl hydrazinecarboxylate was added and heat was continued another 20 min. After cooling, the mixture was concentrated, and more MeOH followed by concentration was done twice to remove residual water and acid. The crude product was dissolved in 1 mL EtOH and to the crude mixture was added a NaOEt solution (289 mg of sodium consumed in 4 mL EtOH) and the mixture was stirred 2 h before being filtered. The solid was added to a mixture of slightly acidic (HCl) water and EtOAc. The EtOAc layer was separated, dried and concentrated to give 125 mg (34%) of the product as an off-white solid.

$^1$H NMR (400 MHz, CDCl$_3$) δ 8.28 (s, 1H), 7.44 (d, J=14.1 Hz, 1H), 7.30 (d, J=12.5 Hz, 1H), 6.94 (t, J=8.6 Hz, 1H), 5.50 (q, J=6.9 Hz, 1H), 3.97-3.81 (m, 4H), 3.25-3.05 (m, 4H), 1.62 (d, J=7.0 Hz, 3H). $^{19}$F NMR (376 MHz, CDCl$_3$) δ −120.67. LC-MS (Method 5): 294 [M+H]$^+$ Chiral SCF chromatography separated the enantiomers: Column: ChiralPak AS-H, 250×4.6 mm, 5 um, Mobile Phase Modifier: 100% Methanol, Gradient: 5 to 50% Methanol over 10 minutes, Flow Rate: 4 mL/min, Back Pressure: 100 bar, Column Temperature: 40° C. UV detection was from 200-400 nm. Retention times of separated enantiomers: 6.58 and 6.92 min. Analysis of product from enantioselective synthesis showed a ratio of 2.5 (6.58 min): 97.5 (6.93 min).

Example 25-2

(6S)-5-(3,5-Difluoro-4-morpholinophenyl)-6-methyl-3,6-dihydro-2H-1,3,4-oxadiazin-2-one

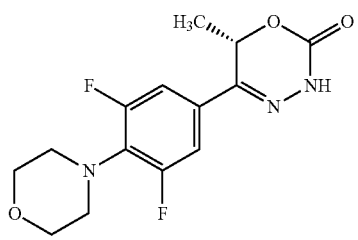

Following a literature procedure (J. Med. Chem. 1990, 35, 163), to 1 g of (S)-1-(3,5-difluoro-4-morpholinophenyl)-2-hydroxypropan-1-one (5.34 mmol, Intermediate 37) in 5 mL of MeOH and 3 drops of 0.1 N HCl was added 481 mg of methyl hydrazinecarboxylate (5.34 mmol) and the reaction mixture was heated at reflux 3 h before cooling, concentrating and twice adding more MeOH and concentrating to remove residual water and HCl. Little of the crude product dissolved in ca. 10 mL MeOH, the solid was filtered and rinsed with MeOH, 935 mg of solid was collected. This solid was stirred in 6 mL EtOH and to it was added a NaOEt solution (600 mg Na consumed in 15 mL EtOH). All solids quickly dissolved but after 30 min copious precipitate appeared and was filtered and rinsed with cold EtOH. The 490 mg solid was dissolved in EtOAc, rinsed with slightly acidic (HCl) water, the EtOAc layer is dried and concentrated to 433 mg white solid product (51%).

$^1$H NMR (400 MHz, CDCl$_3$) δ 8.44 (s, 1H), 7.17 (d, J=9.9 Hz, 2H), 5.44 (q, J=7.0 Hz, 1H), 3.92-3.75 (m, 4H), 3.29 (s, 4H), 1.62 (d, J=7.0 Hz, 3H). $^{19}$F NMR (376 MHz, CDCl$_3$) δ −118.99. LC-MS (Method 5): 312 [M+H]$^+$ Chiral SCF chromatography separated the enantiomers: Column: ChiralPak AS-H, 250×4.6 mm, 5 um, Mobile Phase Modifier: 100% Methanol, Gradient: 5 to 50% Methanol over 10 minutes, Flow Rate: 4 mL/min, Back Pressure: 100 bar, Column Temperature: 40° C. UV detection was from 200-400 nm. Retention times of separated enantiomers: 5.77 and 5.92 min. Analysis of product from enantioselective synthesis showed only the 5.92 min peak.

Example 26

5-[4-(3,3-Difluoropyrrolidin-1-yl)-3-fluorophenyl]-3,6-dihydro-2H-1,3,4-oxadiazin-2-one

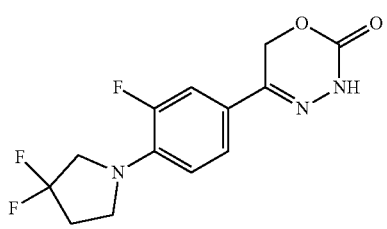 [SMILES: O=C1NN=C(c2ccc(N3CCC(F)(F)C3)c(F)c2)CO1]

To a solution of 5-(3,4-difluorophenyl)-3,6-dihydro-2H-1,3,4-oxadiazin-2-one one (115 mg, 542 μmol, Intermediate 63) in N,N-diisopropylethylamine (280 μl, 1.6 mmol) and acetonitrile (1.0 ml, 19 mmol) were added 3,3-difluoropyrrolidine hydrochloride (1:1) (233 mg, 1.63 mmol). The reaction mixture was stirred for 16 h at 95° C., then 10 d at RT. Then water was added and the aqueous phase was extracted three times with ethyl acetate. The combined organic phases were filtered with a water-resistant filter and concentrated in vacuo. The residue was purified by preparative HPLC to obtain 25.0 mg (95% purity, 15% yield) of the desired title compound.

LC-MS (Method 1): R$_t$=1.06 min, MS (ESIpos): m/z=300 [M+H]$^+$ $^1$H-NMR (400 MHz, DMSO-d6) δ[ppm]: 2.074 (3.04), 2.440 (0.55), 2.459 (1.13), 2.477 (1.85), 2.518 (3.17), 2.522 (2.01), 2.530 (1.21), 2.549 (0.59), 3.593 (1.52), 3.596 (1.61), 3.611 (2.90), 3.615 (2.95), 3.629 (1.52), 3.632 (1.46), 3.802 (1.13), 3.808 (1.21), 3.835 (2.28), 3.842 (2.33), 3.869 (1.15), 3.875 (1.12), 5.283 (16.00), 6.811 (1.40), 6.833 (2.27), 6.856 (1.52), 7.407 (1.79), 7.412 (2.06), 7.428 (1.56), 7.433 (2.03), 7.450 (2.39), 7.455 (1.74), 7.488 (2.10), 7.493 (1.91), 10.945 (4.54).

Example 27

5-(2-Methylbiphenyl-4-yl)-3,6-dihydro-2H-1,3,4-oxadiazin-2-one

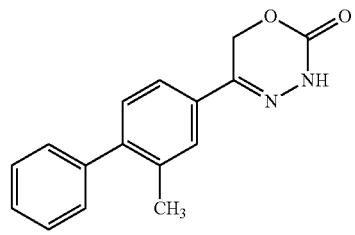 [SMILES: Cc1cc(C2=NNC(=O)OC2)ccc1-c1ccccc1]

The title compound was synthesized analogously to Example 3 from Intermediate 76.

LC-MS (Method 1): R$_t$=1.19 min; MS (ESIpos): m/z=267 [M+H]$^+$ $^1$H-NMR (400 MHz, DMSO-d6) δ[ppm]: 2.273 (14.45), 2.518 (2.88), 2.522 (1.87), 5.385 (16.00), 7.279 (2.96), 7.299 (3.38), 7.350 (2.25), 7.353 (3.50), 7.357 (1.60), 7.364 (0.99), 7.370 (5.69), 7.374 (4.65), 7.383 (0.75), 7.388 (2.34), 7.395 (0.58), 7.404 (1.42), 7.407 (1.78), 7.411 (0.82), 7.445 (3.64), 7.449 (1.40), 7.461 (2.34), 7.464 (4.34), 7.469 (1.00), 7.478 (0.65), 7.482 (1.54), 7.485 (0.91), 7.596 (1.46), 7.599 (1.58), 7.615 (1.21), 7.619 (1.47), 7.661 (2.73), 7.665 (2.41), 11.083 (4.11).

Example 28

5-[3-Methyl-4-(2-methylpyrimidin-5-yl)phenyl]-3,6-dihydro-2H-1,3,4-oxadiazin-2-one

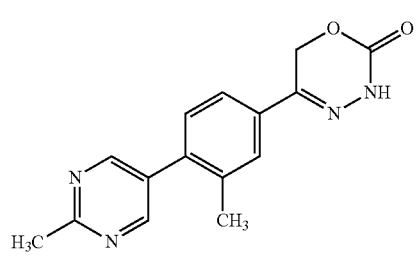 [SMILES: Cc1ncc(-c2ccc(C3=NNC(=O)OC3)cc2C)cn1]

The title compound was synthesized analogously to Example 3 from Intermediate 76.

LC-MS (Method 1): $R_t$=0.80 min; MS (ESIpos): m/z=283 [M+H]$^+$ $^1$H-NMR (400 MHz, DMSO-d6) δ[ppm]: 2.075 (0.60), 2.309 (14.06), 2.322 (0.90), 2.327 (1.04), 2.332 (0.75), 2.517 (3.94), 2.522 (2.64), 2.665 (0.81), 2.669 (1.16), 2.674 (1.14), 2.684 (16.00), 5.396 (12.61), 7.384 (2.72), 7.404 (3.11), 7.645 (1.46), 7.649 (1.64), 7.665 (1.20), 7.669 (1.43), 7.713 (2.82), 8.762 (14.78), 11.125 (4.23).

Example 29

5-[3-Methyl-4-(1-methyl-1H-pyrazol-5-yl)phenyl]-3,6-dihydro-2H-1,3,4-oxadiazin-2-one

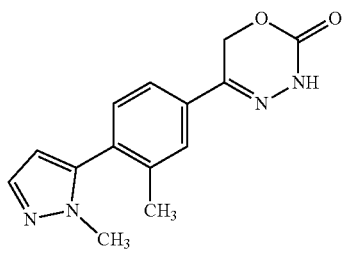 [SMILES: Cc1cc(C2=NNC(=O)OC2)ccc1-c1ccnn1C]

The title compound was synthesized analogously to Example 3 from Intermediate 76.

LC-MS (Method 1): $R_t$=0.84 min; MS (ESIpos): m/z=271 [M+H]$^+$ $^1$H-NMR (400 MHz, DMSO-d6) δ[ppm]: 2.180 (10.00), 2.518 (1.44), 2.522 (0.92), 3.607 (16.00), 5.396 (9.67), 6.307 (3.52), 6.311 (3.58), 7.347 (1.98), 7.367 (2.26), 7.509 (3.43), 7.513 (3.50), 7.622 (1.08), 7.626 (1.14), 7.642 (0.91), 7.646 (1.00), 7.717 (1.97), 11.136 (2.85).

Example 30

5-(2,4'-Difluorobiphenyl-4-yl)-3,6-dihydro-2H-1,3,4-oxadiazin-2-one

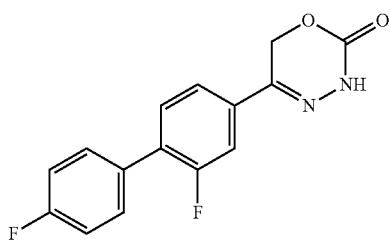 [SMILES: O=C1NN=C(c2ccc(-c3ccc(F)cc3)c(F)c2)CO1]

The title compound was synthesized analogously to Example 3 from Intermediate 65.

LC-MS (Method 1): $R_t$=1.16 min; MS (ESIpos): m/z=289 [M+H]$^+$ $^1$H-NMR (400 MHz, DMSO-d6) δ[ppm]: 2.518 (1.62), 2.523 (1.13), 5.402 (16.00), 7.322 (3.02), 7.327 (0.94), 7.338 (1.15), 7.344 (6.59), 7.350 (1.08), 7.361 (0.99), 7.366 (3.44), 7.615 (0.62), 7.627 (1.86), 7.634 (4.89), 7.637 (3.92), 7.644 (5.15), 7.650 (6.98), 7.658 (1.19), 7.664 (3.32), 7.667 (3.42), 11.200 (4.60).

Example 31

5-[4'-Chloro-2-(trifluoromethyl)biphenyl-4-yl]-3,6-dihydro-2H-1,3,4-oxadiazin-2-one

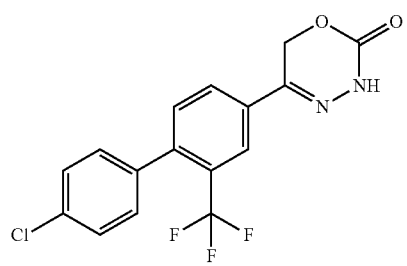 [SMILES: O=C1NN=C(c2ccc(-c3ccc(Cl)cc3)c(C(F)(F)F)c2)CO1]

To 5-[4-chloro-3-(trifluoromethyl)phenyl]-3,6-dihydro-2H-1,3,4-oxadiazin-2-one (107 mg, 384 μmol, Intermediate 64), 2-(4-chlorophenyl)-4,4,5,5-tetramethyl-1,3,2-dioxaborolane (137 mg, 576 μmol), potassium carbonate (106 mg, 768 μmol) and 2-(dicyclohexylphosphino)-2',4',6'-triisopropylbiphenyl (11.0 mg, 23.0 μmol) in 1,4-dioxane (990 μl) and water (300 μl) (nitrogen atmosphere) was added chloro(2-dicyclohexylphosphino-2',4',6'-triisopropyl-1,1'-biphenyl)[2-(2'-amino-1,1'-biphenyl)]palladium(II) (9.06 mg, 11.5 μmol) and the mixture was stirred 2 h at 80° C. The reaction mixture was poured into water and extracted three times with ethyl acetate. The combined organic phases were filtered off a water-resistant filter and concentrated in vacuo. The residue was diluted with DMSO, filtered and purified by preparative HPLC, to obtain 41.0 mg (95% purity, 29% yield) of the desired title compound.

LC-MS (Method 1): $R_t$=1.33 min, MS (ESIpos): m/z=355 [M+H]$^+$

1H-NMR (400 MHz, DMSO-d6): δ [ppm]=11.26 (s, 1H), 8.11 (d, 1H), 8.02 (dd, 1H), 7.56-7.50 (m, 3H), 7.36 (d, 2H), 5.47 (s, 2H)

Example 32

5-[4-(6-Methylpyridin-3-yl)-3-(trifluoromethyl)phenyl]-3,6-dihydro-2H-1,3,4-oxadiazin-2-one

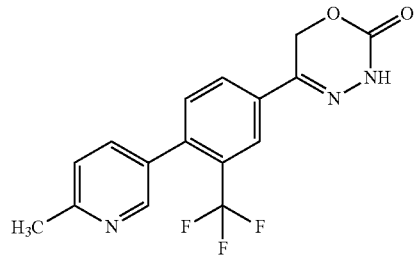

In a reaction vessel, 5-[4-chloro-3-(trifluoromethyl)phenyl]-3,6-dihydro-2H-1,3,4-oxadiazin-2-one (95.0 mg, 341 μmol, Intermediate 64), 2-methyl-5-(4,4,5,5-tetramethyl-1,3,2-dioxaborolan-2-yl)pyridine (112 mg, 511 μmol), potassium carbonate (94.2 mg, 682 μmol) and 2-(dicyclohexylphosphino)-2',4',6'-triisopropylbiphenyl (9.75 mg, 20.5 μmol) were suspended in 870 μL 1,4-dioxane and 260 μL water. The mixture was degassed with nitrogen for 5 min. Then, chloro(2-dicyclohexylphosphino-2',4',6'-triisopropyl- 1,1'-biphenyl)[2-(2'-amino-1,1'-biphenyl)]palladium(II) (8.05 mg, 10.2 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 21.0 mg (95% purity, 17% yield) of the title compound.

LC-MS (Method 1): $R_t$=0.78 min, MS (ESIpos): m/z=336 [M+H]$^+$ $^1$H-NMR (400 MHz, DMSO-d6) δ[ppm]: 2.074 (3.23), 2.327 (0.93), 2.331 (0.67), 2.518 (3.71), 2.523 (2.56), 2.539 (16.00), 2.669 (0.92), 2.673 (0.67), 5.477 (14.23), 7.357 (2.41), 7.377 (2.68), 7.545 (2.26), 7.566 (2.43), 7.660 (1.42), 7.666 (1.42), 7.680 (1.24), 7.686 (1.25), 8.029 (1.51), 8.033 (1.59), 8.049 (1.34), 8.052 (1.48), 8.128 (3.04), 8.133 (2.84), 8.396 (2.36), 8.401 (2.32), 11.260 (4.73).

Example 33

5-[4-(Pyridin-3-yl)-3-(trifluoromethyl)phenyl]-3,6-dihydro-2H-1,3,4-oxadiazin-2-one

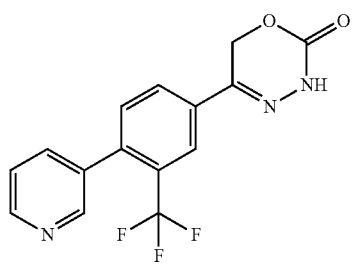 [SMILES: O=C1NN=C(c2ccc(-c3cccnc3)c(C(F)(F)F)c2)CO1]

In a reaction vessel, 5-[4-chloro-3-(trifluoromethyl)phenyl]-3,6-dihydro-2H-1,3,4-oxadiazin-2-one (86.0 mg, 309 µmol, Intermediate 64), 3-(4,4,5,5-tetramethyl-1,3,2-dioxaborolan-2-yl)pyridine (94.9 mg, 463 µmol), potassium carbonate (85.3 mg, 617 µmol) and 2-(dicyclohexylphosphino)-2',4',6'-triisopropylbiphenyl (8.83 mg, 18.5 µmol) were suspended in 790 µL 1,4-dioxane and 240 µL water. The mixture was degassed with nitrogen for 5 min. Then, chloro (2-dicyclohexylphosphino-2',4',6'-triisopropyl-1,1'-biphenyl)[2-(2'-amino-1,1'-biphenyl)]palladium(II) (7.29 mg, 9.26 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO. filtered and purified by preparative HPLC, to give 55.0 mg (95% purity, 53% yield) of the title compound.

LC-MS (Method 2): $R_t$=0.93 min; MS (ESIpos): m/z=322 [M+H]$^+$ $^1$H-NMR (400 MHz, DMSO-d6) δ[ppm]: 1.232 (0.44), 2.327 (0.81), 2.331 (0.60), 2.518 (3.34), 2.522 (2.08), 2.669 (0.82), 2.673 (0.60), 5.485 (16.00), 7.502 (1.57), 7.504 (1.58), 7.514 (1.64), 7.516 (1.65), 7.521 (1.79), 7.523 (1.76), 7.533 (1.79), 7.535 (1.79), 7.580 (2.69), 7.600 (2.89), 7.791 (1.75), 7.811 (1.50), 8.046 (1.84), 8.050 (1.92), 8.066 (1.64), 8.070 (1.77), 8.145 (3.63), 8.148 (3.42), 8.545 (2.93), 8.550 (2.86), 8.654 (2.67), 8.658 (2.74), 8.666 (2.69), 8.670 (2.53), 11.271 (5.14).

Example 34

5-[4'-Amino-2-(trifluoromethyl)biphenyl-4-yl]-3,6-dihydro-2H-1,3,4-oxadiazin-2-one

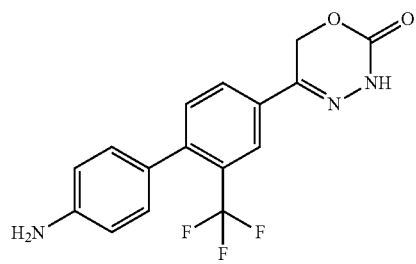 [SMILES: Nc1ccc(-c2ccc(C3=NNC(=O)OC3)cc2C(F)(F)F)cc1]

In a reaction vessel, 5-[4-chloro-3-(trifluoromethyl)phenyl]-3,6-dihydro-2H-1,3,4-oxadiazin-2-one (95.0 mg, 341 µmol, Intermediate 64), 4-(4,4,5,5-tetramethyl-1,3,2-dioxaborolan-2-yl)aniline (112 mg, 511 µmol), potassium carbonate (94.2 mg, 682 µmol) and 2-(icyclohexylphosphino)-2',4',6'-triisopropylbiphenyl (9.75 mg, 20.5 µmol) were suspended in 870 µL 1,4-dioxane and 260 µL water. The mixture was degassed with nitrogen for 5 min. Then, chloro (2-dicyclohexylphosphino-2',4',6'-triisopropyl-1,1'-biphenyl)[2-(2'-amino-1,1'-biphenyl)]palladium(II) (8.05 mg, 10.2 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 15.0 mg (95% purity, 12% yield) of the title compound.

LC-MS (Method 2): $R_t$=0.98 min; MS (ESIpos): m/z=336 [M+H]$^+$ $^1$H-NMR (400 MHz, DMSO-d6) δ[ppm]: 2.518 (2.00), 2.522 (1.38), 5.314 (6.31), 5.444 (16.00), 6.589 (0.68), 6.596 (5.91), 6.601 (1.80), 6.612 (1.95), 6.617 (6.48), 6.623 (0.68), 6.989 (4.19), 7.010 (3.67), 7.425 (2.50), 7.445 (2.66), 7.929 (1.64), 7.932 (1.70), 7.949 (1.45), 7.953 (1.59), 8.037 (3.39), 8.041 (3.14), 11.191 (5.48).

Example 35

5-[3'-Hydroxy-4'-methyl-2-(trifluoromethyl)biphenyl-4-yl]-3,6-dihydro-2H-1,3,4-oxadiazin-2-one

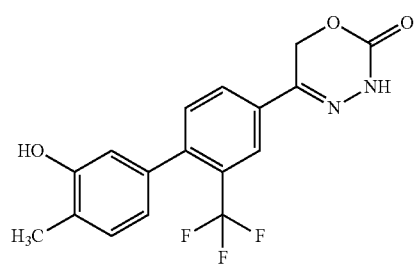 [SMILES: Cc1ccc(-c2ccc(C3=NNC(=O)OC3)cc2C(F)(F)F)cc1O]

In a reaction vessel, 5-[4-chloro-3-(trifluoromethyl)phenyl]-3,6-dihydro-2H-1,3,4-oxadiazin-2-one (97.0 mg, 348 µmol, Intermediate 64), (3-hydroxy-4-methylphenyl)boronic acid (79.4 mg, 522 µmol), potassium carbonate (96.2 mg, 696 µmol) and 2-(dicyclohexylphosphino)-2',4',6'-triisopropylbiphenyl (9.96 mg, 20.9 µmol) were suspended in 890 µL 1,4-dioxane and 270 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (8.22 mg, 10.4 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 41.0 mg (90% purity, 30% yield) of the title compound.

LC-MS (Method 1): $R_t$=1.12 min, MS (ESIpos): m/z=351 [M+H]$^+$ $^1$H-NMR (400 MHz, DMSO-d6) δ[ppm]: 2.074 (1.11), 2.123 (1.92), 2.160 (15.29), 2.518 (1.75), 2.523 (1.16), 5.459 (16.00), 6.635 (1.73), 6.654 (1.85), 6.737 (3.58), 6.948 (0.43), 6.952 (0.40), 7.110 (2.75), 7.129 (2.57), 7.447 (2.70), 7.467 (2.86), 7.964 (1.82), 7.968 (1.89), 7.984 (1.62), 7.988 (1.75), 8.067 (3.65), 8.071 (3.42), 9.362 (0.76), 9.495 (7.97), 11.225 (5.99).

Example 36

5-{3-(Trifluoromethyl)-4-[6-(trifluoromethyl)pyridin-3-yl]phenyl}-3,6-dihydro-2H-1,3,4-oxadiazin-2-one

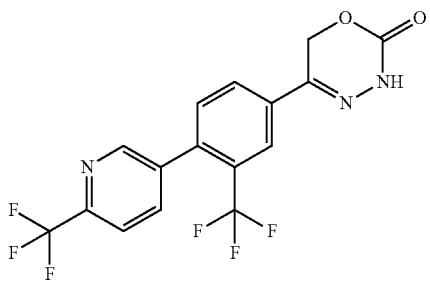 [SMILES: O=C1NN=C(c2ccc(-c3ccc(C(F)(F)F)nc3)c(C(F)(F)F)c2)CO1]

In a reaction vessel, 5-[4-chloro-3-(trifluoromethyl)phenyl]-3,6-dihydro-2H-1,3,4-oxadiazin-2-one (95.0 mg, 341 µmol, Intermediate 64), 5-(4,4,5,5-tetramethyl-1,3,2-dioxaborolan-2-yl)-2-(trifluoromethyl)pyridine (140 mg, 511 µmol), potassium carbonate (94.2 mg, 682 µmol) and 2-(dicyclohexylphosphino)-2',4',6'-triisopropylbiphenyl (9.75 mg, 20.5 µmol) were suspended in 870 µL 1,4-dioxane and 260 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium (II) (8.05 mg, 10.2 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 59.0 mg (95% purity, 42% yield) of the title compound.

LC-MS (Method 2): $R_t$=1.20 min, MS (ESIpos): m/z=390 [M+H]$^+$ $^1$H-NMR (400 MHz, DMSO-d6) δ[ppm]: 2.074 (2.93), 2.518 (1.68), 2.522 (1.10), 5.496 (16.00), 7.660 (2.40), 7.680 (2.60), 8.044 (2.01), 8.046 (2.07), 8.064 (3.56), 8.066 (3.56), 8.084 (1.65), 8.088 (1.73), 8.109 (2.17), 8.133 (0.98), 8.138 (0.97), 8.178 (3.24), 8.182 (3.03), 8.774 (2.61), 11.297 (4.59).

Example 37

5-[4'-Fluoro-3'-hydroxy-2-(trifluoromethyl)biphenyl-4-yl]-3,6-dihydro-2H-1,3,4-oxadiazin-2-one

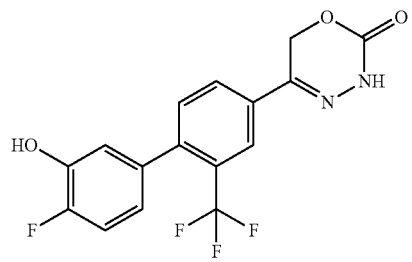 [SMILES: O=C1NN=C(c2ccc(-c3ccc(F)c(O)c3)c(C(F)(F)F)c2)CO1]

In a reaction vessel, 5-[4-chloro-3-(trifluoromethyl)phenyl]-3,6-dihydro-2H-1,3,4-oxadiazin-2-one (90.0 mg, 323 µmol, Intermediate 64), (4-fluoro-3-hydroxyphenyl)boronic acid (75.5 mg, 485 µmol), potassium carbonate (89.3 mg, 646 µmol) and 2-(dicyclohexylphosphino)-2',4',6'-triisopropylbiphenyl (9.24 mg, 19.4 µmol) were suspended in 1.5 mL 1,4-dioxane and 500 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (7.62 mg, 9.69 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 38.0 mg (95% purity, 32% yield) of the title compound.

LC-MS (Method 1): $R_t$=1.04 min, MS (ESIpos): m/z=355 [M+H]$^+$ $^1$H-NMR (400 MHz, DMSO-d6) δ[ppm]: 2.074 (3.59), 2.461 (0.40), 2.466 (0.50), 2.471 (0.66), 2.518 (2.53), 2.522 (1.58), 5.462 (16.00), 6.709 (0.76), 6.714 (0.90), 6.719 (0.91), 6.725 (0.90), 6.730 (0.96), 6.735 (1.01), 6.740 (0.91), 6.746 (0.85), 6.887 (1.58), 6.893 (1.52), 6.909 (1.60), 6.914 (1.47), 7.189 (2.17), 7.210 (2.15), 7.217 (2.27), 7.238 (2.02), 7.483 (2.61), 7.503 (2.77), 7.975 (1.74), 7.980 (1.80), 7.995 (1.55), 7.999 (1.65), 8.077 (3.52), 8.081 (3.23), 10.097 (2.17), 11.238 (5.47).

Example 38

5-[5'-Amino-2',4'-difluoro-2-(trifluoromethyl)biphenyl-4-yl]-3,6-dihydro-2H-1,3,4-oxadiazin-2-one

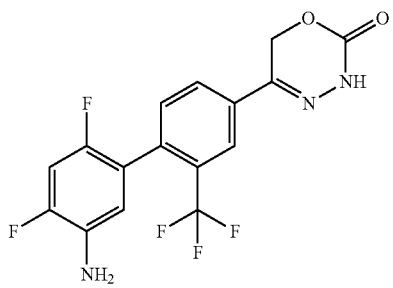 [SMILES: Nc1cc(-c2ccc(C3=NNC(=O)OC3)cc2C(F)(F)F)c(F)cc1F]

In a reaction vessel, 5-[4-chloro-3-(trifluoromethyl)phenyl]-3,6-dihydro-2H-1,3,4-oxadiazin-2-one (94.0 mg, 337 µmol, Intermediate 64), (5-amino-2,4-difluorophenyl)boronic acid hydrochloride (1:1) (106 mg, 506 µmol), potassium carbonate (140 mg, 1.01 mmol) and 2-(dicyclohexylphosphino)-2',4',6'-triisopropylbiphenyl (9.65 mg, 20.2 µmol) were suspended in 1.5 mL 1,4-dioxane and 500 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (7.96 mg, 10.1 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 62.0 mg (95% purity, 47% yield) of the title compound.

LC-MS (Method 2): $R_t$=1.08 min, MS (ESIpos): m/z=372 [M+H]$^-$ $^1$H-NMR (400 MHz, DMSO-d6) δ[ppm]: 2.074 (9.18), 2.518 (1.73), 2.523 (1.22), 5.154 (5.11), 5.468 (16.00), 6.634 (1.32), 6.653 (1.50), 6.658 (1.44), 6.678 (1.30), 7.125 (1.76), 7.150 (1.95), 7.154 (1.94), 7.177 (1.76), 7.501 (2.48), 7.521 (2.63), 7.995 (1.70), 7.999 (1.76), 8.015 (1.51), 8.019 (1.66), 8.093 (3.39), 8.097 (3.16), 11.249 (4.52).

Example 39

5-[4'-Amino-3'-fluoro-2-(trifluoromethyl)biphenyl-4-yl]-3,6-dihydro-2H-1,3,4-oxadiazin-2-one

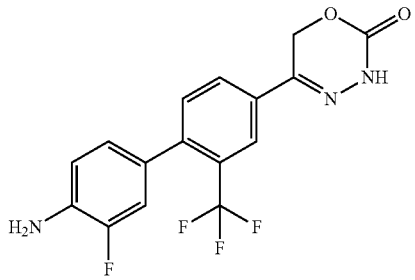 [SMILES: Nc1ccc(-c2ccc(C3=NNC(=O)OC3)cc2C(F)(F)F)cc1F]

In a reaction vessel, 5-[4-chloro-3-(trifluoromethyl)phenyl]-3,6-dihydro-2H-1,3,4-oxadiazin-2-one (98.0 mg, 352 µmol, Intermediate 64), 2-fluoro-4-(4,4,5,5-tetramethyl-1,3,2-dioxaborolan-2-yl)aniline (125 mg, 528 µmol), potassium carbonate (97.2 mg, 703 µmol) and 2-(dicyclohexylphosphino)-2',4',6'-triisopropylbiphenyl (10.1 mg, 21.1 µmol) were suspended in 900 µL 1,4-dioxane and 270 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (8.30 mg, 10.6 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 41.0 mg (90% purity, 30% yield) of the title compound.

LC-MS (Method 2): $R_t$=1.04 min, MS (ESIpos): m/z=354 [M+H]$^+$ $^1$H-NMR (400 MHz, DMSO-d6) δ[ppm]: 1.245 (5.29), 2.074 (13.20), 2.327 (1.00), 2.331 (0.72), 2.518 (3.88), 2.523 (2.65), 2.669 (1.01), 2.673 (0.74), 5.391 (6.65), 5.451 (16.00), 6.787 (1.32), 6.808 (2.68), 6.830 (2.53), 6.852 (2.30), 6.856 (2.25), 6.872 (1.01), 6.877 (1.07), 6.968 (1.65), 6.973 (1.50), 6.999 (1.63), 7.469 (2.58), 7.489 (2.73), 7.694 (0.50), 7.949 (1.74), 7.953 (1.79), 7.969 (1.55), 7.973 (1.65), 8.054 (3.57), 8.058 (3.33), 11.213 (2.58).

Example 40

5-[4-(6-Aminopyridin-3-yl)-3-(trifluoromethyl)phenyl]-3,6-dihydro-2H-1,3,4-oxadiazin-2-one

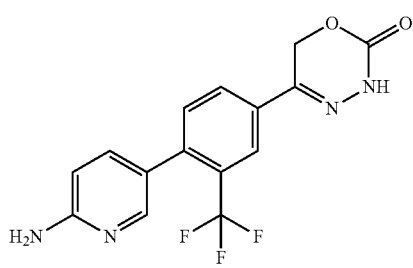

In a reaction vessel, 5-[4-chloro-3-(trifluoromethyl)phenyl]-3,6-dihydro-2H-1,3,4-oxadiazin-2-one (80.0 mg, 287 µmol, Intermediate 64), 5-(4,4,5,5-tetramethyl-1,3,2-dioxaborolan-2-yl)pyridin-2-amine (94.8 mg, 431 µmol), potassium carbonate (79.4 mg, 574 µmol) and 2-(dicyclohexylphosphino)-2',4',6'-triisopropylbiphenyl (8.21 mg, 17.2 µmol) were suspended in 740 µL 1,4-dioxane and 220 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (6.78 mg, 8.61 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 34.0 mg (95% purity, 33% yield) of the title compound.

LC-MS (Method 2): $R_t$=0.85 min: MS (ESIpos): m/z=337 [M+H]$^+$ $^1$H-NMR (400 MHz, DMSO-d6) δ[ppm]: 2.074 (1.71), 2.518 (2.18), 2.522 (1.50), 5.454 (16.00), 6.179 (6.07), 6.487 (3.09), 6.489 (3.09), 6.509 (3.08), 6.511 (3.03), 7.348 (1.30), 7.354 (1.31), 7.369 (1.22), 7.374 (1.23), 7.479 (2.34), 7.500 (2.49), 7.852 (2.54), 7.858 (2.51), 7.967 (1.55), 7.971 (1.61), 7.988 (1.36), 7.991 (1.49), 8.072 (3.19), 8.076 (2.96), 11.216 (5.06).

Example 41

5-[3'-Amino-4'-chloro-2-(trifluoromethyl)biphenyl-4-yl]-3,6-dihydro-2H-1,3,4-oxadiazin-2-one

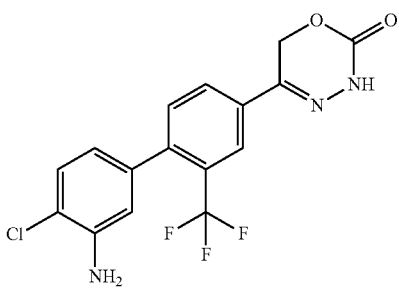 [SMILES: Nc1cc(-c2ccc(C3=NNC(=O)OC3)cc2C(F)(F)F)ccc1Cl]

In a reaction vessel, 5-[4-chloro-3-(trifluoromethyl)phenyl]-3,6-dihydro-2H-1,3,4-oxadiazin-2-one (94.0 mg, 337 μmol, Intermediate 64), (3-amino-4-chlorophenyl)boronic acid (86.7 mg, 506 μmol), potassium carbonate (93.3 mg, 675 μmol) and 2-(dicyclohexylphosphino)-2',4',6'-triisopropylbiphenyl (9.65 mg, 20.2 μmol) were suspended in 870 μL 1,4-dioxane and 260 μL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (7.96 mg, 10.1 μmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 46.0 mg (95% purity, 35% yield) of the title compound.

LC-MS (Method 2): $R_t$=1.18 min, MS (ESIpos): m/z=370 [M+H]$^+$ $^1$H-NMR (400 MHz, DMSO-d6) δ[ppm]: 2.074 (16.00), 5.460 (7.51), 5.512 (2.42), 6.452 (0.76), 6.457 (0.77), 6.473 (0.78), 6.478 (0.78), 6.728 (1.65), 6.733 (1.55), 7.234 (2.26), 7.255 (2.09), 7.460 (1.24), 7.480 (1.31), 7.973 (0.83), 7.977 (0.87), 7.993 (0.74), 7.997 (0.80), 8.071 (1.68), 8.075 (1.54), 11.234 (1.84).

Example 42

5-[3'-Amino-4'-methyl-2-(trifluoromethyl)biphenyl-4-yl]-3,6-dihydro-2H-1,3,4-oxadiazin-2-one

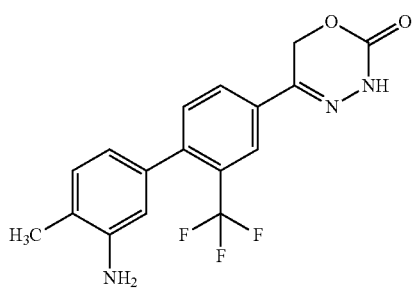 [SMILES: Cc1ccc(-c2ccc(C3=NNC(=O)OC3)cc2C(F)(F)F)cc1N]

In a reaction vessel, 5-[4-chloro-3-(trifluoromethyl)phenyl]-3,6-dihydro-2H-1,3,4-oxadiazin-2-one (102 mg, 366 μmol, Intermediate 64), (3-amino-4-methylphenyl)boronic acid (82.9 mg, 549 μmol), potassium carbonate (101 mg, 732 μmol) and 2-(dicyclohexylphosphino)-2',4',6'-triisopropylbiphenyl (10.5 mg, 22.0 μmol) were suspended in 940 μL 1,4-dioxane and 280 μL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (8.64 mg, 11.0 μmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 81.0 mg (95% purity, 60% yield) of the title compound.

LC-MS (Method 2): $R_t$=1.10 min, MS (ESIpos): m/z=350 [M+H]$^+$ $^1$H-NMR (400 MHz, DMSO-d6) δ[ppm]: 2.074 (2.86), 2.086 (13.85), 2.518 (1.16), 2.523 (0.79), 4.975 (4.73), 5.454 (16.00), 6.388 (1.53), 6.406 (1.61), 6.555 (3.24), 6.558 (3.06), 6.955 (2.54), 6.975 (2.44), 7.420 (2.52), 7.440 (2.64), 7.947 (1.68), 7.951 (1.73), 7.968 (1.48), 7.971 (1.62), 8.051 (3.40), 8.054 (3.14), 11.213 (5.28).

Example 43

5-[3'-Amino-2'-fluoro-2-(trifluoromethyl)biphenyl-4-yl]-3,6-dihydro-2H-1,3,4-oxadiazin-2-one

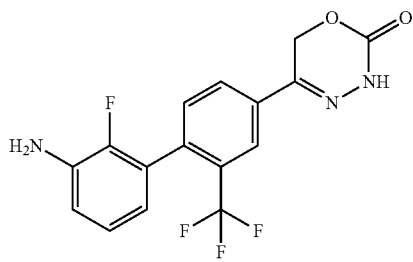 [SMILES: Nc1cccc(-c2ccc(C3=NNC(=O)OC3)cc2C(F)(F)F)c1F]

In a reaction vessel, 5-[4-chloro-3-(trifluoromethyl)phenyl]-3,6-dihydro-2H-1,3,4-oxadiazin-2-one (80.2 mg, 288 μmol, Intermediate 64), 2-fluoro-3-(4,4,5,5-tetramethyl-1,3, 2-dioxaborolan-2-yl)aniline (102 mg, 432 µmol), potassium carbonate (79.6 mg, 576 µmol) and 2-(dicyclohexylphosphino)-2',4',6'-triisopropylbiphenyl (8.23 mg, 17.3 µmol) were suspended in 740 µL 1,4-dioxane and 220 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (6.79 mg, 8.64 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 51.0 mg (95% purity, 48% yield) of the title compound.

LC-MS (Method 2): $R_t$=1.04 min, MS (ESIpos): m/z=354 [M+H]$^+$ $^1$H-NMR (400 MHz, DMSO-d6) δ[ppm]: 2.074 (16.00), 2.323 (0.46), 2.327 (0.60), 2.331 (0.45), 2.518 (2.03), 2.522 (1.33), 2.665 (0.44), 2.669 (0.59), 2.673 (0.43), 5.253 (4.94), 5.472 (13.69), 6.369 (0.89), 6.385 (1.64), 6.401 (0.86), 6.797 (0.79), 6.801 (0.82), 6.817 (1.69), 6.821 (1.64), 6.838 (1.19), 6.842 (1.07), 6.896 (1.87), 6.916 (2.66), 6.936 (1.09), 7.493 (2.29), 7.513 (2.43), 7.992 (1.64), 7.995 (1.68), 8.016 (1.57), 8.096 (3.24), 8.099 (3.06).

Example 44

5-[4'-Amino-2'-fluoro-2-(trifluoromethyl)biphenyl-4-yl]-3,6-dihydro-2H-1,3,4-oxadiazin-2-one

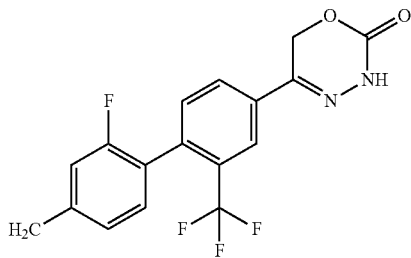

In a reaction vessel, 5-[4-chloro-3-(trifluoromethyl)phenyl]-3,6-dihydro-2H-1,3,4-oxadiazin-2-one (82.0 mg, 294 µmol, Intermediate 64), 3-fluoro-4-(4,4,5,5-tetramethyl-1,3,2-dioxaborolan-2-yl)aniline (105 mg, 441 µmol), potassium carbonate (81.3 mg, 589 µmol) and 2-(dicyclohexylphosphino)-2',4',6'-triisopropylbiphenyl (8.42 mg, 17.7 µmol) were suspended in 760 µL 1,4-dioxane and 230 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (6.95 mg, 8.83 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC to give 9.00 mg (95% purity, 8% yield) of the title compound.

LC-MS (Method 2): $R_t$=1.00 min, MS (ESIneg): m/z=352 [M−H]$^-$ $^1$H-NMR (400 MHz, DMSO-d6) δ[ppm]: 2.074 (0.73), 2.332 (1.24), 2.336 (0.55), 2.518 (5.59), 2.522 (3.67), 2.539 (0.67), 2.673 (1.24), 2.678 (0.55), 5.454 (16.00), 5.603 (5.98), 6.363 (1.85), 6.368 (2.13), 6.394 (1.58), 6.399 (2.43), 6.409 (2.88), 6.415 (1.70), 6.430 (2.52), 6.435 (2.09), 6.882 (1.31), 6.905 (2.31), 6.925 (1.15), 7.441 (2.40), 7.461 (2.55), 7.951 (1.70), 7.955 (1.76), 7.971 (1.49), 7.975 (1.61), 8.057 (3.49), 8.062 (3.22), 11.215 (5.56).

Example 45

5-[4-(1-Methyl-1H-pyrazol-4-yl)-3-(trifluoromethyl)phenyl]-3,6-dihydro-2H-1,3,4-oxadiazin-2-one

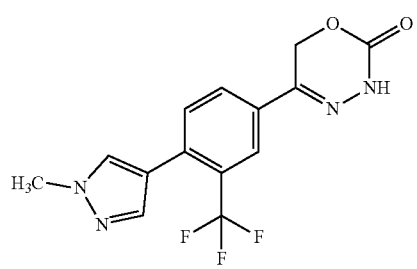 [SMILES: Cn1cc(-c2ccc(C3=NNC(=O)OC3)cc2C(F)(F)F)cn1]

In a reaction vessel, 5-[4-chloro-3-(trifluoromethyl)phenyl]-3,6-dihydro-2H-1,3,4-oxadiazin-2-one (94.0 mg, 337 µmol, Intermediate 64), 1-methyl-4-(4,4,5,5-tetramethyl-1,3,2-dioxaborolan-2-yl)-1H-pyrazole (105 mg, 506 µmol), potassium carbonate (93.3 mg, 675 µmol) and 2-(dicyclohexylphosphino)-2',4',6'-triisopropylbiphenyl (9.65 mg, 20.2 µmol) were suspended in 870 µL 1,4-dioxane and 260 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (7.96 mg, 10.1 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 47.0 mg (95% purity, 41% yield) of the title compound.

LC-MS (Method 2): $R_t$=0.91 min, MS (ESIpos): m/z=325 [M+H]$^+$ $^1$H-NMR (400 MHz, DMSO-d6) δ[ppm]: 2.522 (0.64), 3.888 (0.63), 3.903 (16.00), 5.441 (11.08), 7.621 (1.97), 7.636 (3.95), 7.949 (1.37), 7.952 (1.44), 7.973 (4.85), 8.061 (2.56), 8.065 (2.43), 11.204 (2.04).

Example 46

5-[4-(3-Methyl-1H-pyrazol-4-yl)-3-(trifluoromethyl)phenyl]-3,6-dihydro-2H-1,3,4-oxadiazin-2-one

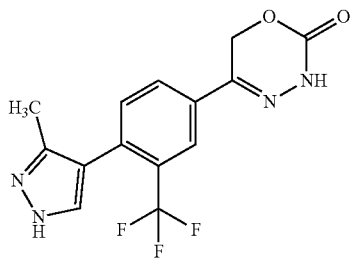

In a reaction vessel, 5-[4-chloro-3-(trifluoromethyl)phenyl]-3,6-dihydro-2H-1,3,4-oxadiazin-2-one (80.0 mg, 287 µmol, Intermediate 64), (3-methyl-1H-pyrazol-4-yl)boronic acid (54.2 mg, 431 µmol), potassium carbonate (79.4 mg, 574 µmol) and 2-(dicyclohexylphosphino)-2',4',6'-triisopropylbiphenyl (8.21 mg, 17.2 µmol) were suspended in 740 µL 1,4-dioxane and 220 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (6.78 mg, 8.61 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 17.0 mg (95% purity, 17% yield) of the title compound.

LC-MS (Method 2): $R_t$=0.83 min, MS (ESIpos): m/z=325 [M+H]$^+$ $^1$H-NMR (400 MHz, DMSO-d6) δ[ppm]: 2.050 (1.20), 2.074 (0.83), 2.137 (2.21), 2.322 (0.54), 2.327 (0.73), 2.331 (0.53), 2.518 (2.70), 2.522 (1.78), 2.539 (1.91), 2.665 (0.54), 2.669 (0.74), 2.673 (0.54), 5.453 (16.00), 7.376 (0.65), 7.473 (1.29), 7.493 (1.38), 7.952 (1.89), 7.955 (1.96), 7.972 (1.69), 7.976 (1.81), 8.077 (3.55), 11.210 (4.03), 12.800 (0.50).

Example 47

5-[4-(1H-Indazol-6-yl)-3-(trifluoromethyl)phenyl]-3,6-dihydro-2H-1,3,4-oxadiazin-2-one

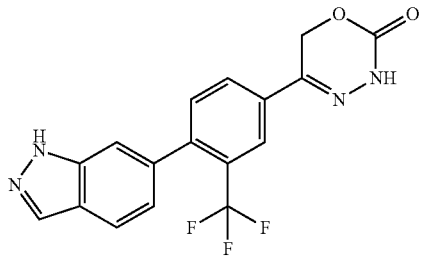 [SMILES: O=C1NN=C(c2ccc(-c3ccc4cn[nH]c4c3)c(C(F)(F)F)c2)CO1]

In a reaction vessel, 5-[4-chloro-3-(trifluoromethyl)phenyl]-3,6-dihydro-2H-1,3,4-oxadiazin-2-one (115 mg, 413 µmol, Intermediate 64), 1H-indazol-6-ylboronic acid (100 mg, 619 µmol), potassium carbonate (114 mg, 825 µmol) and 2-(dicyclohexylphosphino)-2',4',6'-triisopropylbiphenyl (11.8 mg, 24.8 µmol) were suspended in 1.1 mL 1,4-dioxane and 320 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (9.74 mg, 12.4 µmol) was added. Nitrogen was passed through the reaction mixture. It was stirred at 80° C. for 2 hours in a heating block. Because of incomplete conversion 1H-indazol-6-ylboronic acid (66 mg, 408 µmol) and chloro(2-dicyclohexylphosphino-2',4',6'-triisopropyl-1,1'-biphenyl)[2-(2'-amino-1,1'-biphenyl)]palladium(II) (324.3 mg, 412.9 µmol) were added again and the mixture was heated at 80° C. overnight. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 38.0 mg (95% purity, 24% yield) of the title compound.

LC-MS (Method 2): $R_t$=1.00 min, MS (ESIpos): m/z=361 [M+H]$^+$ $^1$H-NMR (400 MHz, DMSO-d6) δ[ppm]: 2.074 (4.84), 2.518 (1.55), 2.523 (1.01), 5.489 (16.00), 7.051 (1.77), 7.072 (1.89), 7.468 (3.18), 7.575 (2.44), 7.596 (2.61), 7.824 (2.77), 7.845 (2.62), 8.017 (1.64), 8.021 (1.68), 8.037 (1.41), 8.041 (1.54), 8.126 (3.35), 8.131 (3.20), 8.147 (3.03), 11.252 (2.35), 13.190 (1.81).

Example 48

5-[4-(5-Fluoro-6-methylpyridin-3-yl)-3-(trifluoromethyl)phenyl]-3,6-dihydro-2H-1,3,4-oxadiazin-2-one

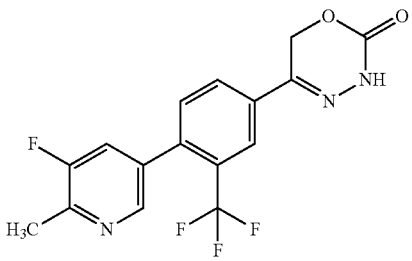 [SMILES: Cc1ncc(-c2ccc(C3=NNC(=O)OC3)cc2C(F)(F)F)cc1F]

In a reaction vessel, 5-[4-chloro-3-(trifluoromethyl)phenyl]-3,6-dihydro-2H-1,3,4-oxadiazin-2-one (95.0 mg, 341 µmol, Intermediate 64), (5-fluoro-6-methylpyridin-3-yl)boronic acid (79.2 mg, 511 µmol), potassium carbonate (94.2 mg, 682 µmol) and 2-(dicyclohexylphosphino)-2',4',6'-triisopropylbiphenyl (9.75 mg, 20.5 µmol) were suspended in 1.5 mL 1,4-dioxane and 510 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (8.05 mg, 10.2 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 16.0 mg (95% purity, 13% yield) of the title compound.

LC-MS (Method 2): $R_t$=1.10 min; MS (ESIpos): m/z=354 [M+H]$^+$

¹H-NMR (400 MHz, DMSO-d6) δ[ppm]: 2.074 (2.62), 2.518 (9.97), 2.522 (5.37), 2.526 (8.33), 2.673 (0.58), 5.428 (3.94), 5.482 (16.00), 7.594 (2.25), 7.615 (2.41), 7.715 (1.42), 7.719 (1.42), 7.741 (1.41), 7.745 (1.42), 7.830 (0.46), 7.852 (0.60), 8.047 (1.49), 8.050 (1.57), 8.067 (1.31), 8.071 (1.46), 8.083 (0.62), 8.089 (0.55), 8.142 (2.98), 8.146 (2.76), 8.281 (2.75), 11.276 (3.96).

Example 49

5-[4-(1,2-Thiazol-4-yl)-3-(trifluoromethyl)phenyl]-3,6-dihydro-2H-1,3,4-oxadiazin-2-one

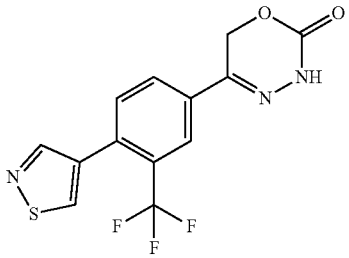 [SMILES: O=C1NN=C(c2ccc(-c3cnsc3)c(C(F)(F)F)c2)CO1]

In a reaction vessel, 5-[4-chloro-3-(trifluoromethyl)phenyl]-3,6-dihydro-2H-1,3,4-oxadiazin-2-one (108 mg, 388 μmol, Intermediate 64), 4-(4,4,5,5-tetramethyl-1,3,2-dioxaborolan-2-yl)-1,2-thiazole (123 mg, 581 μmol), potassium carbonate (107 mg, 775 μmol) and 2-(dicyclohexylphosphino)-2',4',6'-triisopropylbiphenyl (11.1 mg, 23.3 μmol) were suspended in 1.7 mL 1,4-dioxane and 580 μL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (9.15 mg, 11.6 μmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 49.0 mg (95% purity, 37% yield) of the title compound.

LC-MS (Method 2): $R_t$=1.03 min; MS (ESIpos): m/z=328 [M+H]⁺

¹H-NMR (400 MHz, DMSO-d6) δ[ppm]: 2.074 (0.96), 2.518 (0.74), 2.523 (0.54), 5.477 (16.00), 7.648 (2.03), 7.668 (2.24), 8.029 (1.38), 8.033 (1.43), 8.050 (1.22), 8.053 (1.32), 8.137 (2.69), 8.141 (2.50), 8.644 (4.81), 9.156 (5.87), 11.267 (1.51).

Example 50

1-Methyl-5-[4-(2-oxo-3,6-dihydro-2H-1,3,4-oxadiazin-5-yl)-2-(trifluoromethyl)phenyl]-1H-pyrrole-2-carbonitrile

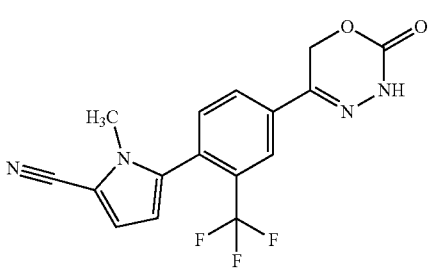 [SMILES: Cn1c(C#N)ccc1-c1ccc(C2=NNC(=O)OC2)cc1C(F)(F)F]

In a reaction vessel, 5-[4-chloro-3-(trifluoromethyl)phenyl]-3,6-dihydro-2H-1,3,4-oxadiazin-2-one (133 mg, 476 μmol, Intermediate 64), (5-cyano-1-methyl-1H-pyrrol-2-yl)boronic acid (107 mg, 714 μmol), potassium carbonate (132 mg, 953 μmol) and 2-(dicyclohexylphosphino)-2',4',6'-triisopropylbiphenyl (13.6 mg, 28.6 μmol) were suspended in 2.1 mL 1,4-dioxane and 710 μL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (11.2 mg, 14.3 μmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 100 mg (95% purity, 57% yield) of the title compound.

LC-MS (Method 2): $R_t$=1.11 min, MS (ESIneg): m/z=347 [M−H]⁻

¹H-NMR (400 MHz, DMSO-d6) δ[ppm]: 2.074 (1.15), 2.518 (1.22), 2.522 (0.78), 3.330 (16.00), 3.635 (0.51), 5.482 (14.16), 6.264 (2.68), 6.274 (2.75), 7.064 (5.04), 7.074 (4.86), 7.673 (2.28), 7.693 (2.48), 8.060 (1.59), 8.064 (1.68), 8.080 (1.40), 8.083 (1.53), 8.159 (3.14), 8.162 (3.01), 11.303 (4.44).

Example 51

5-[2,4'-Bis(trifluoromethyl)biphenyl-4-yl]-3,6-dihydro-2H-1,3,4-oxadiazin-2-one

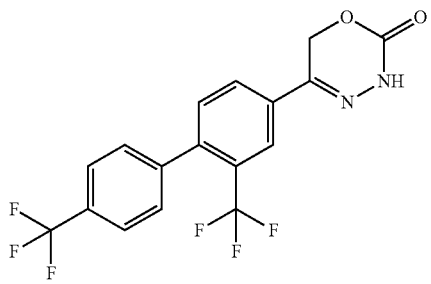 [SMILES: O=C1NN=C(c2ccc(-c3ccc(C(F)(F)F)cc3)c(C(F)(F)F)c2)CO1]

In a reaction vessel, 5-[4-chloro-3-(trifluoromethyl)phenyl]-3,6-dihydro-2H-1,3,4-oxadiazin-2-one (118 mg, 424 μmol, Intermediate 64), 4,4,5,5-tetramethyl-2-[4-(trifluoromethyl)phenyl]-1,3,2-dioxaborolane (173 mg, 635 μmol), potassium carbonate (117 mg, 847 μmol) and 2-(dicyclohexylphosphino)-2',4',6'-triisopropylbiphenyl (12.1 mg, 25.4 μmol) were suspended in 1.9 mL 1,4-dioxane and 630 μL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (10.0 mg, 12.7 μmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 41.0 mg (95% purity, 24% yield) of the title compound.

LC-MS (Method 2): $R_t$=1.34 min, MS (ESIneg): m/z=387 [M−H]⁻

¹H-NMR (400 MHz, DMSO-d6) δ[ppm]: 2.074 (0.60), 2.518 (1.30), 2.522 (0.87), 5.485 (16.00), 7.558 (2.86), 7.573 (4.04), 7.578 (4.21), 7.592 (4.18), 7.840 (4.85), 7.861 (4.14), 8.040 (1.89), 8.044 (1.99), 8.064 (1.84), 8.139 (3.75), 8.142 (3.55), 11.272 (5.26).

Example 52

5-[4-(1,3-Dimethyl-1H-pyrazol-4-yl)-3-(trifluoromethyl)phenyl]-3,6-dihydro-2H-1,3,4-oxadiazin-2-one

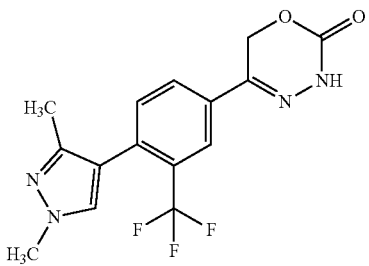 [SMILES: Cc1nn(C)cc1-c1ccc(C2=NNC(=O)OC2)cc1C(F)(F)F]

In a reaction vessel, 5-[4-chloro-3-(trifluoromethyl)phenyl]-3,6-dihydro-2H-1,3,4-oxadiazin-2-one (105 mg, 377 µmol, Intermediate 64), 1,3-dimethyl-4-(4,4,5,5-tetramethyl-1,3,2-dioxaborolan-2-yl)-1H-pyrazole (126 mg, 565 µmol), potassium carbonate (104 mg, 754 µmol) and 2-(dicyclohexylphosphino)-2',4',6'-triisopropylbiphenyl (10.8 mg, 22.6 µmol) were suspended in 1.5 mL 1,4-dioxane and 500 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium (II) (8.90 mg, 11.3 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 46.0 mg (95% purity, 34% yield) of the title compound.

LC-MS (Method 2): R$_t$=0.93 min, MS (ESIpos): m/z=339 [M+H]$^+$

¹H-NMR (400 MHz, DMSO-d6) δ[ppm]: 2.016 (16.00), 2.518 (0.93), 2.522 (0.63), 3.331 (14.15), 5.451 (11.97), 7.476 (1.92), 7.497 (2.06), 7.657 (3.25), 7.951 (1.30), 7.955 (1.34), 7.971 (1.16), 7.975 (1.25), 8.070 (2.59), 8.074 (2.44), 11.213 (3.27).

Example 53

5-[4-(2-Methoxy-6-methylpyridin-3-yl)-3-(trifluoromethyl)phenyl]-3,6-dihydro-2H-1,3,4-oxadiazin-2-one

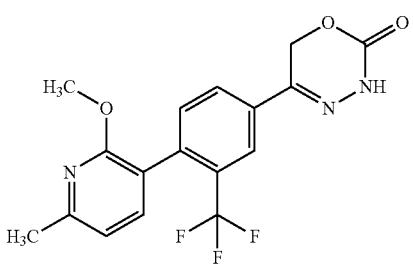 [SMILES: COc1nc(C)ccc1-c1ccc(C2=NNC(=O)OC2)cc1C(F)(F)F]

In a reaction vessel, 5-[4-chloro-3-(trifluoromethyl)phenyl]-3,6-dihydro-2H-1,3,4-oxadiazin-2-one (150 mg, 538 µmol, Intermediate 64), (2-methoxy-6-methylpyridin-3-yl)boronic acid (135 mg, 808 µmol), potassium carbonate (149 mg, 1.08 mmol) and 2-(dicyclohexylphosphino)-2',4',6'-triisopropylbiphenyl (15.4 mg, 32.3 µmol) were suspended in 2.4 mL 1,4-dioxane and 810 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (12.7 mg, 16.2 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 87.0 mg (95% purity, 42% yield) of the title compound.

LC-MS (Method 2): R$_t$=1.24 min, MS (ESIpos): m/z=366 [M+H]$^+$

¹H-NMR (400 MHz, DMSO-d6) δ[ppm]: 2.073 (2.23), 2.456 (14.29), 2.522 (0.48), 3.335 (16.00), 5.464 (12.60), 6.926 (2.62), 6.944 (2.85), 7.446 (2.39), 7.453 (2.89), 7.466 (2.72), 7.471 (2.82), 7.970 (1.51), 7.974 (1.61), 7.990 (1.37), 7.994 (1.51), 8.069 (3.06), 8.072 (2.92), 11.230 (4.14).

Example 54

5-[4-(2-Methyl-1,3-thiazol-5-yl)-3-(trifluoromethyl)phenyl]-3,6-dihydro-2H-1,3,4-oxadiazin-2-one

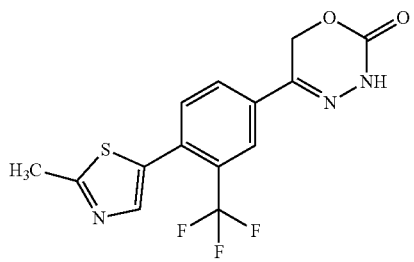 [SMILES: Cc1ncc(-c2ccc(C3=NNC(=O)OC3)cc2C(F)(F)F)s1]

In a reaction vessel, 5-[4-chloro-3-(trifluoromethyl)phenyl]-3,6-dihydro-2H-1,3,4-oxadiazin-2-one (115 mg, 413 µmol, Intermediate 64), 2-methyl-5-(4,4,5,5-tetramethyl-1,3,2-dioxaborolan-2-yl)-1,3-thiazole (139 mg, 619 µmol), potassium carbonate (114 mg, 825 µmol) and 2-(dicyclohexylphosphino)-2',4',6'-triisopropylbiphenyl (11.8 mg, 24.8 µmol) were suspended in 1.9 mL 1,4-dioxane and 620 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (9.74 mg, 12.4 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 31.0 mg (95% purity, 21% yield) of the title compound.

LC-MS (Method 2): R$_t$=1.02 min: MS (ESIpos): m/z=342 [M+H]$^+$

¹H-NMR (400 MHz, DMSO-d6) δ[ppm]: 2.074 (3.55), 2.518 (1.43), 2.522 (0.95), 2.715 (16.00), 5.462 (12.09), 7.675 (5.53), 7.694 (2.05), 8.007 (1.29), 8.012 (1.33), 8.028 (1.10), 8.032 (1.17), 8.125 (2.43), 8.130 (2.27), 11.280 (1.79).

Example 55

5-[4'-(Methylamino)-2-(trifluoromethyl)biphenyl-4-yl]-3,6-dihydro-2H-1,3,4-oxadiazin-2-one

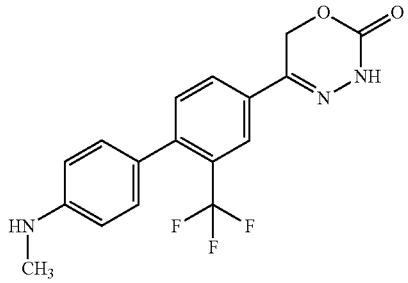 [SMILES: CNc1ccc(-c2ccc(C3=NNC(=O)OC3)cc2C(F)(F)F)cc1]

In a reaction vessel, 5-[4-chloro-3-(trifluoromethyl)phenyl]-3,6-dihydro-2H-1,3,4-oxadiazin-2-one (167 mg, 599 µmol, Intermediate 64), N-methyl-4-(4,4,5,5-tetramethyl-1,3,2-dioxaborolan-2-yl)aniline (210 mg, 899 µmol), potassium carbonate (166 mg, 1.20 mmol) and 2-(dicyclohexylphosphino)-2',4',6'-triisopropylbiphenyl (17.1 mg, 36.0 µmol) were suspended in 2.7 mL 1,4-dioxane and 900 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (14.1 mg, 18.0 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 41.0 mg (95% purity, 19% yield) of the title compound.

LC-MS (Method 1): $R_t$=1.08 min, MS (ESIpos): m/z=350 [M+H]$^+$ $^1$H-NMR (400 MHz, DMSO-d6) δ[ppm]: 2.074 (1.18), 2.518 (1.55), 2.522 (1.04), 2.701 (10.67), 2.714 (10.49), 5.447 (16.00), 5.897 (0.58), 5.909 (1.81), 5.922 (1.81), 5.934 (0.57), 6.578 (5.57), 6.599 (6.07), 7.068 (4.60), 7.089 (4.12), 7.436 (2.75), 7.456 (2.97), 7.935 (1.84), 7.939 (1.91), 7.955 (1.71), 7.959 (1.79), 8.045 (3.75), 8.049 (3.51), 11.196 (6.11).

Example 56

5-[3'-Amino-4'-fluoro-2-(trifluoromethyl)biphenyl-4-yl]-3,6-dihydro-2H-1,3,4-oxadiazin-2-one

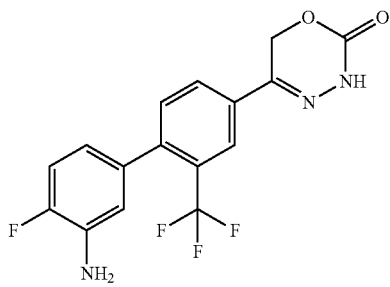 [SMILES: Nc1cc(-c2ccc(C3=NNC(=O)OC3)cc2C(F)(F)F)ccc1F]

In a reaction vessel, 5-[4-chloro-3-(trifluoromethyl)phenyl]-3,6-dihydro-2H-1,3,4-oxadiazin-2-one (90.0 mg, 323 µmol, Intermediate 64), (3-amino-4-fluorophenyl)boronic acid (75.1 mg, 485 µmol), potassium carbonate (89.3 mg, 646 µmol) and 2-(dicyclohexylphosphino)-2',4',6'-triisopropylbiphenyl (9.24 mg, 19.4 µmol) were suspended in 830 µL 1,4-dioxane and 250 µL water. The mixture was degassed with nitrogen for 5 min. Then, chloro(2-dicyclohexylphosphino-2',4',6'-triisopropyl-1,1'-biphenyl)[2-(2'-amino-1,1'-biphenyl)]palladium(II) (7.62 mg, 9.69 µmol) was added. Nitrogen was passed through the reaction mixture. It was stirred at 80° C. for 2 hours in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC, to give 41.0 mg (95% purity, 34% yield) of the title compound.

LC-MS (Method 2): $R_t$=1.09 min, MS (ESIpos): m/z=354 [M+H]$^-$ $^1$H-NMR (400 MHz, DMSO-d6) δ[ppm]: 2.075 (1.25), 2.518 (1.63), 2.523 (1.10), 5.295 (5.00), 5.458 (16.00), 6.412 (0.70), 6.417 (0.82), 6.422 (0.84), 6.432 (0.92), 6.438 (0.92), 6.442 (0.85), 6.448 (0.80), 6.694 (1.51), 6.699 (1.50), 6.715 (1.54), 6.720 (1.48), 7.017 (1.89), 7.038 (1.92), 7.046 (2.02), 7.067 (1.81), 7.452 (2.49), 7.473 (2.66), 7.960 (1.65), 7.964 (1.75), 7.981 (1.48), 7.984 (1.64), 8.062 (3.35), 8.066 (3.21), 11.226 (1.14).

Example 58

5-[3',4',5'-Trifluoro-2-(trifluoromethyl)biphenyl-4-yl]-3,6-dihydro-2H-1,3,4-oxadiazin-2-one

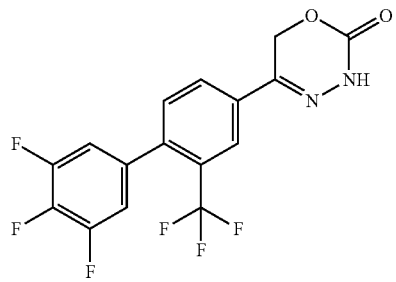 [SMILES: O=C1NN=C(c2ccc(-c3cc(F)c(F)c(F)c3)c(C(F)(F)F)c2)CO1]

In a reaction vessel, 5-[4-chloro-3-(trifluoromethyl)phenyl]-3,6-dihydro-2H-1,3,4-oxadiazin-2-one (115 mg, 413 µmol, Intermediate 64), (3,4,5-trifluorophenyl)boronic acid (109 mg, 619 µmol), potassium carbonate (114 mg, 825 µmol) and dicyclohexyl[2',4',6'-tri(propan-2-yl)biphenyl-2-yl]phosphane (11.8 mg, 24.8 µmol) were suspended in 1,4-dioxane (1.9 mL) and water (620 µL). The mixture was degassed with nitrogen for 5 min. Afterwards chloro(2-dicyclohexylphosphino-2',4',6'-triisopropyl-1,1'-biphenyl)[2-(2'-amino-1,1'-biphenyl)]palladium(II) (9.74 mg, 12.4 µmol) was added. Again nitrogen was passed through the reaction mixture. It was stirred at 80° C. overnight in a heating block. The mixture was diluted with water and extracted with ethyl acetate three times. The combined organic layers were dried using a water-resistant filter and the filtrate was concentrated under reduced pressure. The crude material was purified by flash chromatography using a silica column, gradient hexane/ethyl acetate 12-100%. Obtained product fractions were concentrated and the residue was suspended in a mixture of 10 mL hexane and 1 mL tert-butyl methyl ether. The precipitated product was filtered. The filter cake was washed with hexane and dried under vacuo to give 96.0 mg (95% purity, 59% yield) of the title compound.

LC-MS (Method 1): $R_t$=1.32 min, MS (ESIneg): m/z=373 [M−H]⁻

¹H-NMR (400 MHz, DMSO-d6) δ[ppm]: 1.154 (0.48), 1.172 (0.93), 1.189 (0.47), 1.986 (1.46), 2.518 (1.55), 2.523 (1.01), 5.475 (16.00), 5.488 (0.51), 7.388 (1.93), 7.405 (2.31), 7.409 (2.33), 7.426 (2.00), 7.557 (2.42), 7.578 (2.58), 8.028 (1.60), 8.032 (1.69), 8.049 (1.42), 8.052 (1.62), 8.116 (3.22), 8.120 (2.98), 11.275 (4.90).

Example 59

5-[2',5'-Difluoro-2-(trifluoromethyl)biphenyl-4-yl]-3,6-dihydro-2H-1,3,4-oxadiazin-2-one

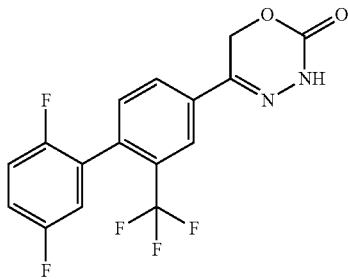 [SMILES: O=C1NN=C(c2ccc(-c3cc(F)ccc3F)c(C(F)(F)F)c2)CO1]

In a reaction vessel, 5-[4-chloro-3-(trifluoromethyl)phenyl]-3,6-dihydro-2H-1,3,4-oxadiazin-2-one (115 mg, 413 µmol, Intermediate 64), (2,5-difluorophenyl)boronic acid (97.8 mg, 619 µmol), potassium carbonate (114 mg, 825 µmol) and dicyclohexyl[2',4',6'-tri(propan-2-yl)biphenyl-2-yl]phosphane (11.8 mg, 24.8 µmol) were suspended in 1,4-dioxane (1.9 mL) and water (620 µL). The mixture was degassed with nitrogen for 5 min. Afterwards, chloro(2-dicyclohexylphosphino-2',4',6'-triisopropyl-1,1'-biphenyl)[2-(2'-amino-1,1'-biphenyl)]palladium(II) (9.74 mg, 12.4 µmol) was added. Again nitrogen was passed through the reaction mixture. It was stirred at 80° C. overnight in a heating block. The mixture was diluted with water and extracted with ethyl acetate three times. The combined organic layers were dried using a water-resistant filter and the filtrate was concentrated under reduced pressure. The crude material was purified by flash chromatography using a silica column, gradient hexane/ethyl acetate 12-100%. The obtained product fractions were concentrated and the residue was suspended in a mixture of 10 mL hexane and 1 mL tert-butyl methyl ether. The precipitated product was filtered. The filter cake was washed with hexane and dried under vacuo to give 95.0 mg (95% purity, 61% yield) of the title compound.

LC-MS (Method 1): $R_t$=1.23 min, MS (ESIpos): m/z=357 [M+H]⁺

¹H-NMR (400 MHz, DMSO-d6) δ[ppm]: 2.518 (1.91), 2.523 (1.24), 5.482 (16.00), 7.284 (0.71), 7.293 (0.71), 7.299 (1.21), 7.313 (0.64), 7.320 (0.66), 7.370 (1.06), 7.376 (2.19), 7.381 (1.30), 7.388 (2.61), 7.393 (2.36), 7.397 (1.70), 7.408 (1.66), 7.588 (2.39), 7.608 (2.55), 8.042 (1.66), 8.045 (1.74), 8.062 (1.47), 8.066 (1.61), 8.134 (3.31), 8.138 (3.06), 11.275 (4.91).

Example 60

5-[3'-Amino-4'-fluoro-2-(trifluoromethoxy)biphenyl-4-yl]-3,6-dihydro-2H-1,3,4-oxadiazin-2-one

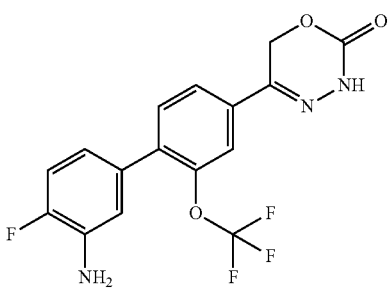 [SMILES: Nc1cc(-c2ccc(C3=NNC(=O)OC3)cc2OC(F)(F)F)ccc1F]

In a reaction vessel, 5-[4-chloro-3-(trifluoromethoxy)phenyl]-3,6-dihydro-2H-1,3,4-oxadiazin-2-one (105 mg, 356 µmol, Intermediate 73), (3-amino-4-fluorophenyl)boronic acid (82.8 mg, 535 µmol), potassium carbonate (98.5 mg, 713 µmol) and dicyclohexyl[2',4',6'-tri(propan-2-yl)biphenyl-2-yl]phosphane (10.2 mg, 21.4 µmol) were suspended in 1,4-dioxane (910 µL) and water (270 µL). The mixture was degassed with nitrogen for 5 min. Afterwards chloro(2-dicyclohexylphosphino-2',4',6'-triisopropyl-1,1'-biphenyl)[2-(2'-amino-1,1'-biphenyl)]palladium(II) (8.41 mg, 10.7 µmol) was added. Again nitrogen was passed through the reaction mixture. It was stirred at 80° C. overnight in a heating block. The mixture was diluted with water and extracted with ethyl acetate three times. The combined organic layers were dried using a water-resistant filter and the filtrate was concentrated under reduced pressure. The crude material was purified by flash chromatography using a silica column, gradient hexane/ethyl acetate 12-100%. The obtained product fractions were concentrated and the residue was suspended in a mixture of 10 mL hexane and 1 mL tert-butyl methyl ether. The precipitated product was filtered. The filter cake was washed with hexane and dried under vacuo to give 51.0 mg (90% purity, 35% yield) of the title compound.

LC-MS (Method 2): $R_t$=1.12 min, MS (ESIpos): m/z=370 [M+H]⁺

¹H-NMR (400 MHz, DMSO-d6) δ[ppm]: 1.172 (0.48), 1.987 (0.76), 2.518 (1.80), 2.523 (1.13), 5.306 (5.02), 5.419 (16.00), 6.591 (1.05), 6.596 (1.16), 6.601 (1.20), 6.607 (1.22), 6.611 (1.28), 6.617 (1.36), 6.622 (1.21), 6.628 (1.21), 6.870 (2.07), 6.875 (2.02), 6.891 (2.11), 6.897 (2.03), 7.063 (2.07), 7.084 (1.98), 7.091 (2.14), 7.112 (1.90), 7.545 (4.04), 7.555 (0.51), 7.566 (4.74), 7.745 (1.91), 7.750 (3.58), 7.756 (2.74), 7.760 (3.47), 7.764 (2.97), 7.766 (4.07), 7.771 (1.30), 11.205 (5.80).

Example 61

5-[3',4'-Difluoro-2-(trifluoromethyl)biphenyl-4-yl]-3,6-dihydro-2H-1,3,4-oxadiazin-2-one

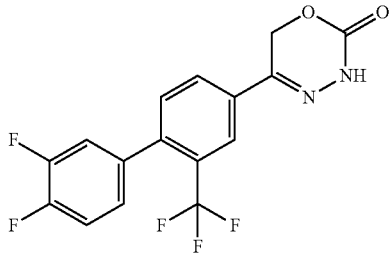 [SMILES: O=C1NN=C(c2ccc(-c3ccc(F)c(F)c3)c(C(F)(F)F)c2)CO1]

In a reaction vessel, 5-[4-chloro-3-(trifluoromethyl)phenyl]-3,6-dihydro-2H-1,3,4-oxadiazin-2-one (120 mg, 431 µmol, Intermediate 64), (3,4-difluorophenyl)boronic acid (136 mg, 861 µmol), potassium carbonate (119 mg, 861 µmol) and dicyclohexyl[2',4',6'-tri(propan-2-yl)biphenyl-2-yl]phosphane (12.3 mg, 25.8 µmol) were suspended in 1,4-dioxane (1.9 mL) and water (650 µL). The mixture was degassed with nitrogen for 5 min. Afterwards chloro(2-dicyclohexylphosphino-2',4',6'-triisopropyl-1,1'-biphenyl)[2-(2'-amino-1,1'-biphenyl)]palladium(II) (10.2 mg, 12.9 µmol) was added. Again nitrogen was passed through the reaction mixture. It was stirred at 80° C. overnight in a heating block. The mixture was diluted with water and extracted with ethyl acetate three times. The combined organic layers were dried using a water-resistant filter and the filtrate was concentrated under reduced pressure. The crude material was purified by flash chromatography using a silica column, gradient hexane/ethyl acetate 12-100%. The obtained product fractions were concentrated and the residue was suspended in a mixture of 10 mL hexane and 1 mL tert-butyl methyl ether. The precipitated product was filtered off. The filter cake was washed with hexane and dried under vacuo to give 103 mg (95% purity, 64% yield) of the title compound.

LC-MS (Method 1): $R_t$=1.27 min, MS (ESIpos): m/z=357 [M+H]$^+$ $^1$H-NMR (400 MHz, DMSO-d6) δ[ppm]: 2.518 (1.54), 2.522 (0.94), 5.474 (16.00), 5.758 (0.65), 7.188 (0.95), 7.204 (0.99), 7.466 (0.85), 7.471 (0.86), 7.485 (0.95), 7.493 (1.14), 7.499 (0.95), 7.514 (1.84), 7.535 (2.22), 7.541 (3.81), 7.562 (4.67), 7.583 (0.86), 8.015 (1.87), 8.018 (1.97), 8.035 (1.65), 8.038 (1.80), 8.110 (3.71), 8.114 (3.49), 11.262 (5.28).

Example 62

5-[4-(1H-Indol-6-yl)-3-(trifluoromethyl)phenyl]-3,6-dihydro-2H-1,3,4-oxadiazin-2-one

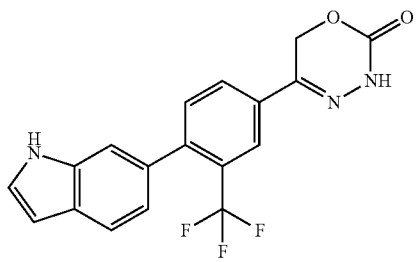 [SMILES: O=C1NN=C(c2ccc(-c3ccc4cc[nH]c4c3)c(C(F)(F)F)c2)CO1]

In a reaction vessel, 5-[4-chloro-3-(trifluoromethyl)phenyl]-3,6-dihydro-2H-1,3,4-oxadiazin-2-one (109 mg, 391 µmol, Intermediate 64), 1H-indol-6-ylboronic acid (94.5 mg, 587 µmol), potassium carbonate (108 mg, 782 µmol) and dicyclohexyl[2',4',6'-tri(propan-2-yl)biphenyl-2-yl]phosphane (11.2 mg, 23.5 µmol) were suspended in 1,4-dioxane (1.8 mL) and water (500 µL). The mixture was degassed with nitrogen for 5 min. Afterwards chloro(2-dicyclohexylphosphino-2',4',6'-triisopropyl-1,1'-biphenyl)[2-(2'-amino-1,1'-biphenyl)]palladium(II) (9.23 mg, 11.7 µmol) was added. Again, nitrogen was passed through the reaction mixture. It was stirred at 80° C. overnight in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC to give 69.0 mg (95% purity, 47% yield) of the title compound.

LC-MS (Method 2): $R_t$=1.17 min, MS (ESIneg): m/z=358 [M–H]$^-$ $^1$H-NMR (400 MHz, DMSO-d6) δ[ppm]: 2.074 (1.77), 2.518 (1.22), 2.522 (0.80), 5.480 (16.00), 6.478 (1.51), 6.480 (1.82), 6.483 (1.90), 6.485 (2.79), 6.488 (2.05), 6.490 (1.81), 6.493 (1.60), 6.944 (1.76), 6.946 (1.75), 6.964 (1.86), 6.966 (1.84), 7.351 (3.49), 7.421 (2.64), 7.428 (3.33), 7.435 (2.70), 7.539 (2.53), 7.559 (2.71), 7.587 (3.29), 7.608 (3.02), 7.986 (1.66), 7.989 (1.76), 8.006 (1.46), 8.010 (1.62), 8.102 (3.35), 8.107 (3.22), 11.227 (7.36).

Example 63

5-[4-(2-Methylprop-1-en-1-yl)-3-(trifluoromethyl)phenyl]-3,6-dihydro-2H-1,3,4-oxadiazin-2-one

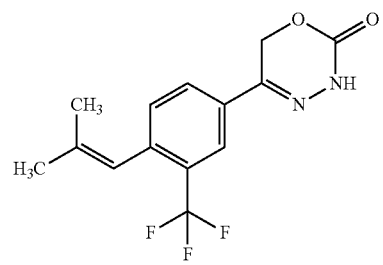 [SMILES: CC(C)=Cc1ccc(C2=NNC(=O)OC2)cc1C(F)(F)F]

In a reaction vessel, 5-[4-chloro-3-(trifluoromethyl)phenyl]-3,6-dihydro-2H-1,3,4-oxadiazin-2-one (112 mg, 402 µmol, Intermediate 64), 4,4,5,5-tetramethyl-2-(2-methylprop-1-en-1-yl)-1,3,2-dioxaborolane (110 mg, 603 µmol), potassium carbonate (111 mg, 804 µmol) and dicyclohexyl[2',4',6'-tri(propan-2-yl)biphenyl-2-yl]phosphane (11.5 mg, 24.1 µmol) were suspended in 1,4-dioxane (1.8 mL) and water (600 µL). The mixture was degassed with nitrogen for 5 min. Afterwards chloro(2-dicyclohexylphosphino-2',4',6'-triisopropyl-1,1'-biphenyl)[2-(2'-amino-1,1'-biphenyl)]palladium(II) (9.49 mg, 12.1 µmol) was added. Again, nitrogen was passed through the reaction mixture. It was stirred at 80° C. overnight in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC to give 43.0 mg (95% purity, 34% yield) of the title compound.

LC-MS (Method 2): $R_t$=1.27 min, MS (ESIneg): m/z=297 [M−H]⁻

¹H-NMR (400 MHz, DMSO-d6) δ[ppm]: 1.700 (10.62), 1.703 (10.58), 1.912 (9.28), 1.915 (9.39), 2.518 (1.56), 2.522 (1.02), 5.422 (16.00), 6.379 (1.51), 7.457 (2.02), 7.478 (2.17), 7.916 (1.43), 7.920 (1.55), 7.940 (1.44), 7.988 (2.99), 7.992 (2.72), 11.182 (4.02).

Example 64

5-[2',3'-Difluoro-2-(trifluoromethyl)biphenyl-4-yl]-3,6-dihydro-2H-1,3,4-oxadiazin-2-one

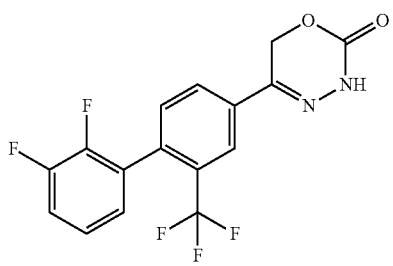 [SMILES: O=C1NN=C(c2ccc(-c3cccc(F)c3F)c(C(F)(F)F)c2)CO1]

In a reaction vessel, 5-[4-chloro-3-(trifluoromethyl)phenyl]-3,6-dihydro-2H-1,3,4-oxadiazin-2-one (130 mg, 467 μmol, Intermediate 64), (2,3-difluorophenyl)boronic acid (111 mg, 700 μmol), potassium carbonate (129 mg, 933 μmol) and dicyclohexyl[2',4',6'-tri(propan-2-yl)biphenyl-2-yl]phosphane (13.3 mg, 28.0 μmol) were suspended in 1,4-dioxane (2.1 mL) and water (700 μL). The mixture was degassed with nitrogen for 5 min. Afterwards chloro(2-dicyclohexylphosphino-2',4',6'-triisopropyl-1,1'-biphenyl)[2-(2'-amino-1,1'-biphenyl)]palladium(II) (11.0 mg, 14.0 μmol) was added. Again, nitrogen was passed through the reaction mixture. It was stirred at 80° C. overnight in a heating block. The mixture was diluted with water and extracted with ethyl acetate three times. The combined organic layers were dried using a water-resistant filter and the filtrate was concentrated under reduced pressure. The crude material was purified by flash chromatography using a silica column, gradient hexane/ethyl acetate 12-100%. The obtained product fractions were concentrated and the residue was suspended in a mixture of 10 mL hexane and 1 mL tert-butyl methyl ether. The precipitated product was filtered. The filter cake was washed with hexane and dried under vacuo to give 81.0 mg (95% purity, 46% yield) of the titled compound.

LC-MS (Method 2): $R_t$=1.22 min; MS (ESIneg): m/z=355 [M−H]⁻

¹H-NMR (400 MHz, DMSO-d6) δ[ppm]: 1.172 (0.73), 1.986 (1.43), 2.518 (1.33), 2.523 (0.87), 5.486 (16.00), 7.168 (0.70), 7.187 (1.29), 7.203 (0.90), 7.292 (0.55), 7.295 (0.52), 7.305 (0.63), 7.308 (0.67), 7.313 (1.02), 7.325 (1.01), 7.329 (0.91), 7.332 (0.62), 7.336 (0.50), 7.345 (0.54), 7.349 (0.47), 7.527 (0.47), 7.531 (0.49), 7.550 (0.94), 7.557 (0.62), 7.567 (0.56), 7.573 (0.95), 7.576 (0.86), 7.594 (0.49), 7.597 (0.47), 7.612 (2.25), 7.633 (2.43), 8.052 (1.60), 8.056 (1.65), 8.073 (1.41), 8.077 (1.51), 8.149 (3.16), 8.153 (2.90), 11.280 (4.37).

Example 65

5-[4-(Morpholin-4-yl)-3-(trifluoromethyl)phenyl]-3,6-dihydro-2H-1,3,4-oxadiazin-2-one

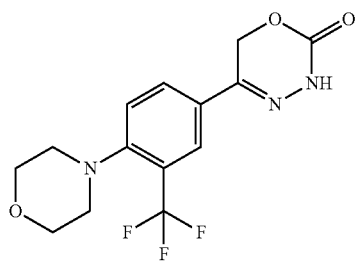 [SMILES: O=C1NN=C(c2ccc(N3CCOCC3)c(C(F)(F)F)c2)CO1]

5-[4-Fluoro-3-(trifluoromethyl)phenyl]-3,6-dihydro-2H-1,3,4-oxadiazin-2-one (100 mg, 381 μmol, Intermediate 66) was dissolved in DMSO (1.0 mL), and morpholine (170 μL, 1.9 mmol) was added. The mixture was stirred at 80° C. overnight and then at 150° C. overnight. The reaction mixture was diluted with DMSO, filtered and purified by preparative HPLC to give 20.0 mg (95% purity, 15% yield) of the title compound.

LC-MS (Method 1): $R_t$=1.03 min; MS (ESIpos): m/z=330 [M+H]⁺

¹H-NMR (400 MHz, DMSO-d6) δ[ppm]: 2.074 (0.49), 2.331 (0.67), 2.518 (4.11), 2.522 (2.52), 2.539 (0.51), 2.673 (0.68), 2.897 (4.65), 2.908 (5.70), 2.919 (4.90), 3.699 (5.05), 3.711 (5.60), 3.721 (4.98), 5.396 (16.00), 7.596 (1.76), 7.618 (1.98), 7.938 (1.29), 7.943 (1.97), 7.962 (6.78), 11.134 (4.65).

Example 66

5-[4-(Butylamino)-3-(trifluoromethyl)phenyl]-3,6-dihydro-2H-1,3,4-oxadiazin-2-one

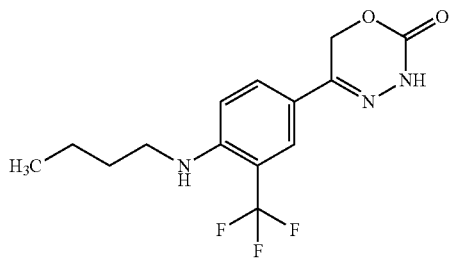 [SMILES: CCCCNc1ccc(C2=NNC(=O)OC2)cc1C(F)(F)F]

5-[4-Fluoro-3-(trifluoromethyl)phenyl]-3,6-dihydro-2H-1,3,4-oxadiazin-2-one (105 mg, 401 μmol, Intermediate 66) was dissolved in DMSO (1.0 mL), and butan-1-amine (44 μL, 440 μmol) was added. The mixture was stirred at 100° C. for 2 hours. More butan-1-amine (44 μL, 440 μmol) was added and stirring was continued at 100° C. overnight. The reaction mixture was diluted with DMSO, filtered and purified by preparative HPLC to give 77.0 mg (95% purity, 58% yield) of the title compound.

LC-MS (Method 1): $R_t$=1.27 min, MS (ESIpos): m/z=316 [M+H]⁺

¹H-NMR (400 MHz, DMSO-d6) δ[ppm]: 0.879 (5.19), 0.897 (13.15), 0.915 (6.10), 1.297 (1.33), 1.315 (2.20), 1.334 (2.25), 1.353 (1.52), 1.372 (0.43), 1.487 (0.71), 1.506

(1.67), 1.518 (1.27), 1.524 (2.25), 1.542 (1.41), 1.560 (0.50), 2.518 (1.62), 2.522 (1.02), 3.216 (1.04), 3.233 (2.23), 3.249 (2.24), 3.265 (1.01), 5.289 (16.00), 5.903 (0.75), 5.917 (1.49), 5.931 (0.73), 6.861 (2.11), 6.882 (2.20), 7.719 (4.74), 7.742 (1.52), 7.747 (1.15), 10.869 (4.91).

Example 67

5-[4-(Ethylamino)-3-(trifluoromethyl)phenyl]-3,6-dihydro-2H-1,3,4-oxadiazin-2-one

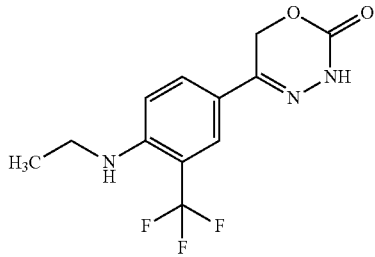 [SMILES: CCNc1ccc(C2=NNC(=O)OC2)cc1C(F)(F)F]

5-[4-Fluoro-3-(trifluoromethyl)phenyl]-3,6-dihydro-2H-1,3,4-oxadiazin-2-one (155 mg, 591 µmol, Intermediate 66) was dissolved in DMSO (1.0 mL), and ethanamine (330 µL, 2.0 M in tetrahydrofuran, 650 µmol) was added. The mixture was stirred at 60° C. overnight. Again ethanamine (180 µL, 2.0 M in tetrahydrofuran, 355 µmol) was added and stirring was continued at 60° C. overnight. A second time more ethanamine (180 µL, 2.0 M in tetrahydrofuran, 355 µmol) was added and it was heated at 60° C. overnight again. The reaction mixture was diluted with DMSO, filtered and purified by preparative HPLC to give 75.0 mg (95% purity, 42% yield) of the title compound.

LC-MS (Method 1): $R_t$=1.08 min, MS (ESIpos): m/z=288 [M+H]$^+$ $^1$H-NMR (400 MHz, DMSO-d6) δ[ppm]: 1.121 (5.12), 1.139 (12.23), 1.156 (5.23), 2.074 (1.79), 2.518 (2.25), 2.522 (1.36), 3.247 (0.59), 3.264 (1.98), 3.280 (2.39), 3.297 (1.97), 3.314 (0.66), 5.292 (16.00), 5.905 (0.72), 5.919 (1.42), 5.933 (0.71), 6.865 (2.11), 6.887 (2.22), 7.725 (3.88), 7.751 (1.46), 7.756 (1.12), 10.873 (4.44).

Example 68

5-[4-(1-Methyl-1H-pyrazol-4-yl)-3-(trifluoromethoxy)phenyl]-3,6-dihydro-2H-1,3,4-oxadiazin-2-one

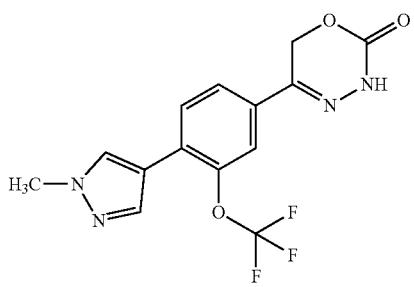 [SMILES: Cn1cc(-c2ccc(C3=NNC(=O)OC3)cc2OC(F)(F)F)cn1]

In a reaction vessel, 5-[4-chloro-3-(trifluoromethoxy)phenyl]-3,6-dihydro-2H-1,3,4-oxadiazin-2-one (135 mg, 458 µmol, Intermediate 73), (1-methyl-1H-pyrazol-4-yl)boronic acid (86.6 mg, 687 µmol), potassium carbonate (127 mg, 916 µmol) and dicyclohexyl[2',4',6'-tri(propan-2-yl)biphenyl-2-yl]phosphane (13.1 mg, 27.5 µmol) were suspended in 1,4-dioxane (1.5 mL) and water (500 µL). The mixture was degassed with nitrogen for 5 min. Afterwards chloro(2-dicyclohexylphosphino-2',4',6'-triisopropyl-1,1'-biphenyl)[2-(2'-amino-1,1'-biphenyl)]palladium(II) (10.8 mg, 13.7 µmol) was added. Again, nitrogen was passed through the reaction mixture. It was stirred at 60° C. for 2 h in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC to give 21.0 mg (95% purity, 13% yield) of the title compound.

LC-MS (Method 1): $R_t$=0.95 min: MS (ESIpos): m/z=341 [M+H]$^+$ $^1$H-NMR (400 MHz, DMSO-d6) δ[ppm]: 1.154 (0.52), 1.172 (0.91), 1.190 (0.57), 1.231 (0.74), 1.987 (1.41), 2.323 (0.77), 2.326 (1.01), 2.331 (0.76), 2.539 (0.74), 2.665 (0.77), 2.669 (1.01), 2.673 (0.74), 3.910 (16.00), 5.397 (11.22), 7.686 (1.50), 7.690 (1.70), 7.706 (1.73), 7.710 (2.31), 7.731 (2.73), 7.847 (3.32), 7.867 (2.56), 7.921 (5.07), 8.187 (4.85), 11.160 (4.16).

Example 69

5-[4-(Propylamino)-3-(trifluoromethyl)phenyl]-3,6-dihydro-2H-1,3,4-oxadiazin-2-one

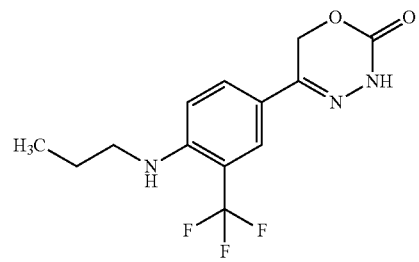 [SMILES: CCCNc1ccc(C2=NNC(=O)OC2)cc1C(F)(F)F]

5-[4-Fluoro-3-(trifluoromethyl)phenyl]-3,6-dihydro-2H-1,3,4-oxadiazin-2-one (125 mg, 477 µmol, Intermediate 66) was dissolved in DMSO (1.0 mL), and propan-1-amine (43 µl, 520 µmol) was added. The mixture was stirred at 100° C. for 18 h. Again propan-1-amine (43 µl, 520 µmol) was added and stirring was continued at 100° C. for 2 h. The reaction mixture was diluted with DMSO, filtered and purified by preparative HPLC to give 62.0 mg (95% purity, 41% yield) of the title compound.

LC-MS (Method 1): $R_t$=1.18 min, MS (ESIpos): m/z=302 [M+H]$^+$ $^1$H-NMR (400 MHz, DMSO-d6) δ[ppm]: 0.866 (4.91), 0.885 (12.24), 0.903 (5.74), 1.525 (1.47), 1.543 (2.53), 1.561 (2.53), 1.579 (1.44), 2.518 (2.77), 2.522 (2.03), 3.183 (1.10), 3.198 (2.27), 3.217 (2.34), 3.233 (1.14), 5.289 (16.00), 5.935 (0.76), 5.950 (1.51), 5.964 (0.79), 6.865 (2.02), 6.887 (2.14), 7.717 (5.83), 7.740 (1.63), 7.745 (1.23), 10.871 (4.72).

Example 70

5-[4-(6-Methylpyridin-3-yl)-3-(trifluoromethoxy)phenyl]-3,6-dihydro-2H-1,3,4-oxadiazin-2-one

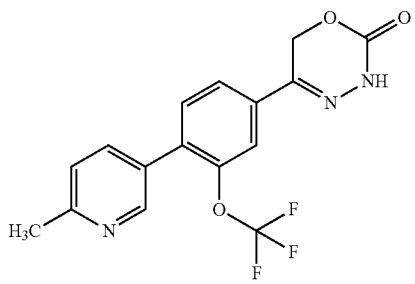 [SMILES: Cc1ccc(-c2ccc(C3=NNC(=O)OC3)cc2OC(F)(F)F)cn1]

In a reaction vessel, 5-[4-chloro-3-(trifluoromethoxy)phenyl]-3,6-dihydro-2H-1,3,4-oxadiazin-2-one (90.0 mg, 305 µmol, Intermediate 73), (6-methylpyridin-3-yl)boronic acid (62.8 mg, 458 µmol), potassium carbonate (84.4 mg, 611 µmol) and dicyclohexyl[2',4',6'-tri(propan-2-yl)biphenyl-2-yl]phosphane (8.74 mg, 18.3 µmol) were suspended in 1,4-dioxane (780 µl) and water (240 µl). The mixture was degassed with nitrogen for 5 min. Afterwards chloro(2-dicyclohexylphosphino-2',4',6'-triisopropyl-1,1'-biphenyl)[2-(2'-amino-1,1'-biphenyl)]palladium(II) (10.8 mg, 13.7 µmol) was added. Again, nitrogen was passed through the reaction mixture. It was stirred at 60° C. for 2 h in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC to give 21.0 mg (95% purity, 19% yield) of the title compound.

LC-MS (Method 1): $R_t$=1.04 min, MS (ESIpos): m/z=352 [M+H]$^+$ $^1$H-NMR (400 MHz, DMSO-d6) δ[ppm]: 2.327 (0.93), 2.331 (0.69), 2.518 (4.00), 2.523 (2.78), 2.536 (16.00), 2.669 (0.96), 2.673 (0.70), 5.439 (14.58), 7.388 (2.55), 7.408 (2.74), 7.692 (3.17), 7.714 (4.28), 7.808 (2.01), 7.812 (3.15), 7.822 (2.47), 7.829 (6.74), 7.834 (3.20), 7.848 (1.94), 7.854 (2.01), 8.577 (2.82), 8.581 (2.84), 11.239 (4.67).

Example 71

5-[4'-Chloro-2-(trifluoromethoxy)biphenyl-4-yl]-3,6-dihydro-2H-1,3,4-oxadiazin-2-one

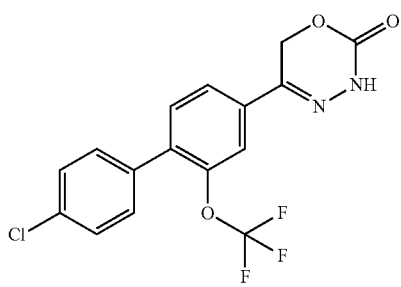 [SMILES: O=C1NN=C(c2ccc(-c3ccc(Cl)cc3)c(OC(F)(F)F)c2)CO1]

In a reaction vessel, 5-[4-chloro-3-(trifluoromethoxy)phenyl]-3,6-dihydro-2H-1,3,4-oxadiazin-2-one (135 mg, 458 µmol, Intermediate 73), (4-chlorophenyl)boronic acid (107 mg, 687 µmol), potassium carbonate (127 mg, 916 µmol) and dicyclohexyl[2',4',6'-tri(propan-2-yl)biphenyl-2-yl]phosphane (13.1 mg, 27.5 µmol) were suspended in 1,4-dioxane (1.5 ml) and water (500 µl). The mixture was degassed with nitrogen for 5 min. Afterwards chloro(2-dicyclohexylphosphino-2',4',6'-triisopropyl-1,1'-biphenyl)[2-(2'-amino-1,1'-biphenyl)]palladium(II) (10.8 mg, 13.7 µmol) was added. Again, nitrogen was passed through the reaction mixture. It was stirred at 60° C. for 2 h in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC to give 44.0 mg (95% purity, 25% yield) of the title compound.

LC-MS (Method 1): $R_t$=1.37 min, MS (ESIpos): m/z=371 [M+H]$^+$ $^1$H-NMR (400 MHz, DMSO-d6) δ[ppm]: 2.074 (0.80), 2.518 (3.98), 2.522 (2.72), 5.435 (16.00), 7.522 (0.44), 7.526 (3.04), 7.533 (1.36), 7.543 (2.03), 7.549 (9.55), 7.554 (2.06), 7.565 (1.96), 7.569 (10.05), 7.575 (2.12), 7.586 (1.42), 7.592 (3.22), 7.651 (3.61), 7.661 (0.48), 7.672 (4.83), 7.795 (1.81), 7.799 (3.79), 7.805 (2.72), 7.809 (3.36), 7.813 (2.75), 7.816 (3.69), 7.820 (1.38), 11.235 (4.85).

Example 72

5-[4-(Azetidin-1-yl)-3-(trifluoromethyl)phenyl]-3,6-dihydro-2H-1,3,4-oxadiazin-2-one

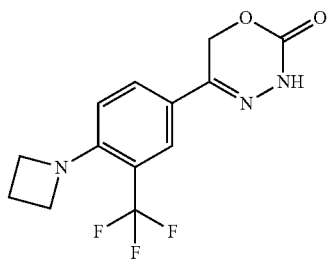 [SMILES: O=C1NN=C(c2ccc(N3CCC3)c(C(F)(F)F)c2)CO1]

5-[4-Fluoro-3-(trifluoromethyl)phenyl]-3,6-dihydro-2H-1,3,4-oxadiazin-2-one (100 mg, 381 µmol, Intermediate 66) was dissolved in DMSO (1.0 mL) and azetidine (57 µl, 840 µmol) was added. The mixture was stirred at 100° C. for 3 d. The reaction mixture was diluted with DMSO, filtered and purified by preparative HPLC to give 37.0 mg (95% purity, 31% yield) of the title compound.

LC-MS (Method 1): $R_t$=1.14 min: MS (ESIpos): m/z=300 [M+H]$^+$ $^1$H-NMR (400 MHz, DMSO-d6) δ[ppm]: 2.074 (0.56), 2.260 (0.51), 2.278 (1.44), 2.297 (2.23), 2.316 (1.60), 2.322 (0.64), 2.327 (0.58), 2.335 (0.65), 2.518 (1.50), 2.523 (1.06), 4.067 (2.57), 4.085 (4.57), 4.103 (2.46), 5.305 (16.00), 6.588 (2.04), 6.609 (2.12), 7.737 (1.31), 7.742 (1.84), 7.764 (5.76), 10.908 (3.53).

Example 73

5-[4-(1-Methyl-1H-benzimidazol-6-yl)-3-(trifluoromethyl)phenyl]-3,6-dihydro-2H-1,3,4-oxadiazin-2-one

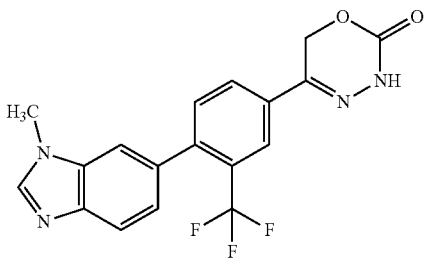 [SMILES: Cn1cnc2ccc(-c3ccc(C4=NNC(=O)OC4)cc3C(F)(F)F)cc21]

In a reaction vessel, 5-[4-chloro-3-(trifluoromethyl)phenyl]-3,6-dihydro-2H-1,3,4-oxadiazin-2-one (136 mg, 488 µmol, Intermediate 64), (1-methyl-1H-benzimidazol-6-yl)boronic acid (129 mg, 732 µmol), potassium carbonate (135 mg, 976 µmol) and dicyclohexyl[2',4',6'-tri(propan-2-yl)biphenyl-2-yl]phosphane (14.0 mg, 29.3 µmol) were suspended in 1,4-dioxane (2.2 ml) and water (730 µl). The mixture was degassed with nitrogen for 5 min. Afterwards chloro(2-dicyclohexylphosphino-2',4',6'-triisopropyl-1,1'-biphenyl)[2-(2'-amino-1,1'-biphenyl)]palladium(II) (11.5 mg, 14.6 µmol) was added. Again, nitrogen was passed through the reaction mixture. It was stirred at 80° C. for 3 h in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC to give 90.4 mg (50% yield) of the titled compound.

LC-MS (Method 2): $R_t$=0.92 min, MS (ESIpos): m/z=375 [M+H]+

1H-NMR (400 MHz, DMSO-d6) δ[ppm]: 1.154 (0.66), 1.171 (1.28), 1.189 (0.61), 1.987 (2.41), 2.518 (1.12), 2.522 (0.72), 3.885 (1.32), 4.017 (0.54), 4.034 (0.56), 4.061 (16.00), 5.494 (9.20), 7.074 (1.10), 7.095 (1.15), 7.587 (1.46), 7.607 (1.58), 7.630 (2.17), 7.808 (1.88), 7.810 (1.85), 7.829 (1.81), 7.830 (1.78), 8.033 (0.99), 8.036 (1.03), 8.053 (0.85), 8.057 (0.93), 8.119 (3.84), 8.122 (3.57), 8.137 (1.94), 8.142 (1.83), 11.258 (3.14).

Example 74

5-[4-(Pentylamino)-3-(trifluoromethyl)phenyl]-3,6-dihydro-2H-1,3,4-oxadiazin-2-one

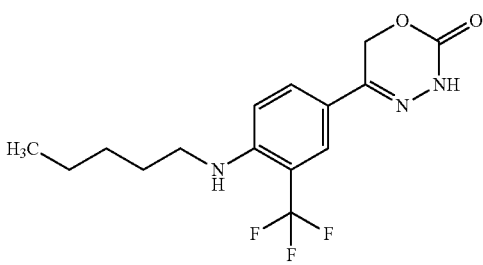 [SMILES: CCCCCNc1ccc(C2=NNC(=O)OC2)cc1C(F)(F)F]

5-[4-Fluoro-3-(trifluoromethyl)phenyl]-3,6-dihydro-2H-1,3,4-oxadiazin-2-one (115 mg, 439 µmol, Intermediate 66) was dissolved in DMSO (920 µl), and pentan-1-amine (55 µl, 480 µmol) was added. The mixture was stirred at 100° C. for 18 h. Again pentan-1-amine (55 µl, 480 µmol) was added and stirring was continued at 100° C. for 2 h. The reaction mixture was diluted with DMSO, filtered and purified by preparative HPLC to give 71.0 mg (95% purity, 47% yield) of the title compound.

LC-MS (Method 1): $R_t$=1.35 min, MS (ESIpos): m/z=330 [M+H]+

1H-NMR (400 MHz, DMSO-d6) δ[ppm]: 0.847 (2.92), 0.864 (9.07), 0.881 (3.05), 1.282 (2.81), 1.291 (4.88), 1.300 (3.93), 1.309 (2.93), 1.331 (0.52), 1.504 (0.45), 1.522 (1.41), 1.539 (2.00), 1.557 (1.36), 2.518 (1.91), 2.522 (1.17), 3.206 (1.06), 3.223 (2.26), 3.240 (2.27), 3.256 (1.03), 5.289 (16.00), 5.914 (0.82), 5.928 (1.62), 5.943 (0.80), 6.855 (2.16), 6.877 (2.28), 7.718 (5.77), 7.742 (1.64), 10.870 (5.21).

Example 75

5-[4-(1-Methyl-1H-indazol-6-yl)-3-(trifluoromethyl)phenyl]-3,6-dihydro-2H-1,3,4-oxadiazin-2-one

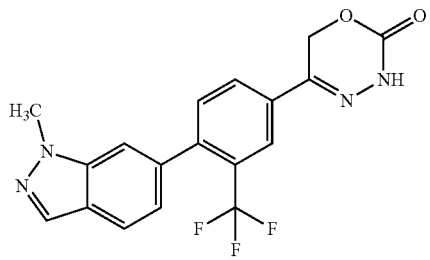 [SMILES: Cn1ncc2ccc(-c3ccc(C4=NNC(=O)OC4)cc3C(F)(F)F)cc21]

In a reaction vessel, 5-[4-chloro-3-(trifluoromethyl)phenyl]-3,6-dihydro-2H-1,3,4-oxadiazin-2-one (114 mg, 409 µmol, Intermediate 64), (1-methyl-1H-indazol-6-yl)boronic acid (108 mg, 614 µmol), potassium carbonate (113 mg, 818 µmol) and dicyclohexyl[2',4',6'-tri(propan-2-yl)biphenyl-2-yl]phosphane (11.7 mg, 24.5 µmol) were suspended in 1,4-dioxane (1.8 ml) and water (610 µl). The mixture was degassed with nitrogen for 5 min. Afterwards chloro(2-dicyclohexylphosphino-2',4',6'-triisopropyl-1,1'-biphenyl)[2-(2'-amino-1,1'-biphenyl)]palladium(II) (9.66 mg, 12.3 µmol) was added. Again, nitrogen was passed through the reaction mixture. It was stirred at 80° C. for 18 h in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC to give 63.0 mg (90% purity, 37% yield) of the title compound.

LC-MS Method 1): $R_t$=1.10 min, MS (ESIpos): m/z=375 [M+H]+

1H-NMR (400 MHz, DMSO-d6) δ[ppm]: 1.154 (0.66), 1.171 (1.28), 1.189 (0.61), 1.987 (2.41), 2.518 (1.12), 2.522 (0.72), 3.885 (1.32), 4.017 (0.54), 4.034 (0.56), 4.061 (16.00), 5.494 (9.20), 7.074 (1.10), 7.095 (1.15), 7.587 (1.46), 7.607 (1.58), 7.630 (2.17), 7.808 (1.88), 7.810 (1.85), 7.829 (1.81), 7.830 (1.78), 8.033 (0.99), 8.036 (1.03), 8.053 (0.85), 8.057 (0.93), 8.119 (3.84), 8.122 (3.57), 8.137 (1.94), 8.142 (1.83), 11.258 (3.14).

Example 76

5-[4'-Fluoro-2-(trifluoromethoxy)biphenyl-4-yl]-3,6-dihydro-2H-1,3,4-oxadiazin-2-one

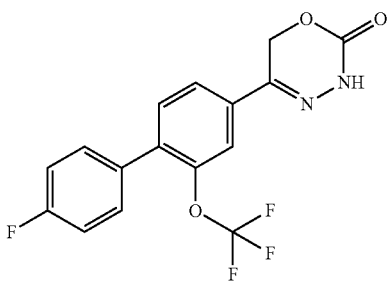 [SMILES: O=C1NN=C(c2ccc(-c3ccc(F)cc3)c(OC(F)(F)F)c2)CO1]

In a reaction vessel, 5-[4-chloro-3-(trifluoromethoxy)phenyl]-3,6-dihydro-2H-1,3,4-oxadiazin-2-one (180 mg, 611 µmol, Intermediate 73), (4-fluorophenyl)boronic acid (128 mg, 916 µmol), potassium carbonate (169 mg, 1.22 mmol) and dicyclohexyl[2',4',6'-tri(propan-2-yl)biphenyl-2-yl]phosphane (17.5 mg, 36.7 µmol) were suspended in 1,4-dioxane (1.6 ml) and water (470 µl). The mixture was degassed with nitrogen for 5 min. Afterwards chloro(2-dicyclohexylphosphino-2',4',6'-triisopropyl-1,1'-biphenyl)[2-(2'-amino-1,1'-biphenyl)]palladium(II) (14.4 mg, 18.3 µmol) was added. Again, nitrogen was passed through the reaction mixture. It was stirred at 60° C. for 2 h in a heating block. The mixture was diluted with water and extracted with ethyl acetate three times. The combined organic layers were dried using a water-resistant filter and the filtrate was concentrated under reduced pressure. The residue was dissolved in DMSO, filtered and dried in vacuo. It was purified by chromatography to give 121 mg (95% purity, 53% yield) of the title compound.

LC-MS (Method 1): $R_t$=1.28 min; MS (ESIpos): m/z=355 [M+H]$^+$ $^1$H-NMR (400 MHz, DMSO-d6) δ[ppm]: 1.172 (0.72), 1.987 (1.44), 2.518 (1.57), 2.523 (1.10), 5.433 (16.00), 7.325 (2.97), 7.331 (0.88), 7.341 (1.10), 7.347 (6.45), 7.353 (1.07), 7.364 (1.01), 7.369 (3.40), 7.543 (3.25), 7.549 (1.30), 7.557 (3.71), 7.566 (3.07), 7.573 (1.08), 7.579 (2.79), 7.640 (3.66), 7.661 (4.66), 7.785 (1.97), 7.789 (3.47), 7.794 (1.05), 7.797 (2.31), 7.801 (3.17), 7.806 (4.24), 11.225 (4.88).

Example 77

5-[3-Fluoro-4-(6-fluoropyridin-3-yl)phenyl]-3,6-dihydro-2H-1,3,4-oxadiazin-2-one

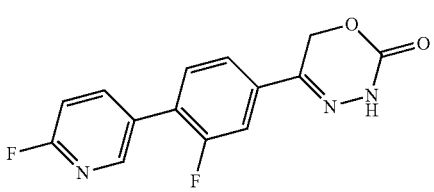 [SMILES: O=C1NN=C(c2ccc(-c3ccc(F)nc3)c(F)c2)CO1]

The title compound was synthesized analogously to the procedure described in Example 3 from 5-(4-chloro-3-fluorophenyl)-3,6-dihydro-2H-1,3,4-oxadiazin-2-one (Intermediate 65) and 4-fluoropyridin-3-yl boronic acid.

LC-MS (Method 11): $R_t$=0.91 min; MS (ESIpos): m/z=290 [M+H]$^+$

Example 78

5-[3-Fluoro-4-(3-methylpyridin-4-yl)phenyl]-3,6-dihydro-2H-1,3,4-oxadiazin-2-one

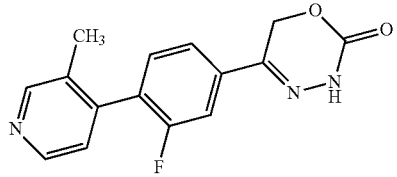 [SMILES: Cc1cnccc1-c1ccc(C2=NNC(=O)OC2)cc1F]

The title compound was synthesized analogously to Example 3 from Intermediate 65.

LC-MS (Method 1): $R_t$=0.53 min; MS (ESIpos): m/z=286 [M+H]$^+$

Example 79

5-[3-Fluoro-4-(2-methylpyridin-4-yl)phenyl]-3,6-dihydro-2H-1,3,4-oxadiazin-2-one

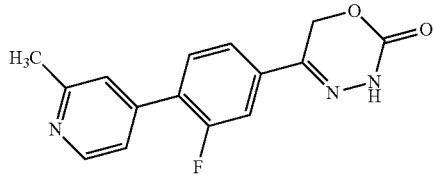 [SMILES: Cc1cc(-c2ccc(C3=NNC(=O)OC3)cc2F)ccn1]

The title compound was synthesized analogously to Example 3 from Intermediate 65.

LC-MS (Method 1): $R_t$=0.50 min; MS (ESIpos): m/z=286 [M+H]$^+$

Example 80

5-(4'-Amino-2-fluorobiphenyl-4-yl)-3,6-dihydro-2H-1,3,4-oxadiazin-2-one

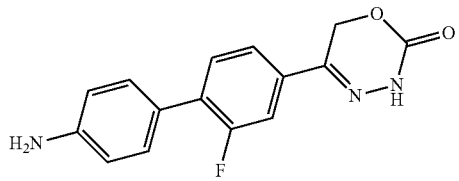 [SMILES: Nc1ccc(-c2ccc(C3=NNC(=O)OC3)cc2F)cc1]

The title compound was synthesized analogously to Example 3 from Intermediate 65.

LC-MS (Method 1): $R_t$=0.72 min; MS (ESIpos): m/z=286 [M+H]$^+$

Example 81

5-(2-Fluoro-2'-methylbiphenyl-4-yl)-3,6-dihydro-2H-1,3,4-oxadiazin-2-one

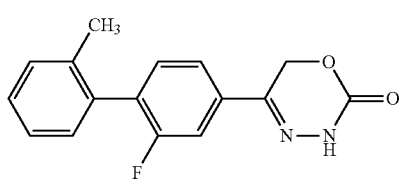 [SMILES: Cc1ccccc1-c1ccc(C2=NNC(=O)OC2)cc1F]

The title compound was synthesized analogously to Example 3 from Intermediate 65.

LC-MS (Method 1): $R_t$=1.15 min; MS (ESIpos): m/z=285 [M+H]$^+$

Example 82

5-(2'-Chloro-2,4'-difluorobiphenyl-4-yl)-3,6-dihydro-2H-1,3,4-oxadiazin-2-one

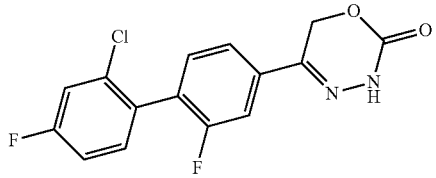 [SMILES: O=C1NN=C(c2ccc(-c3ccc(F)cc3Cl)c(F)c2)CO1]

The title compound was synthesized analogously to Example 3 from Intermediate 65.

LC-MS (Method 1): $R_t$=1.16 min; MS (ESIpos): m/z=323 [M+H]$^+$

Example 83

5-[4-(Cyclopent-1-en-1-yl)-3-fluorophenyl]-3,6-dihydro-2H-1,3,4-oxadiazin-2-one

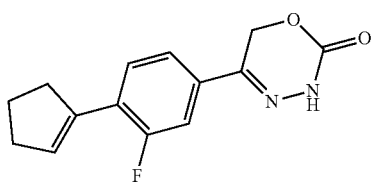 [SMILES: O=C1NN=C(c2ccc(C3=CCCC3)c(F)c2)CO1]

The title compound was synthesized analogously to Example 3 from Intermediate 65.

LC-MS (Method 1): $R_t$=1.19 min; MS (ESIpos): m/z=261 [M+H]$^+$

Example 84

5-(2'-Ethyl-2-fluorobiphenyl-4-yl)-3,6-dihydro-2H-1,3,4-oxadiazin-2-one

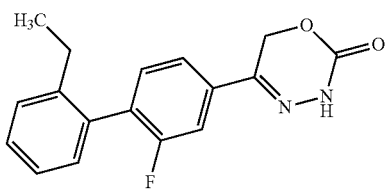 [SMILES: CCc1ccccc1-c1ccc(C2=NNC(=O)OC2)cc1F]

The title compound was synthesized analogously to Example 3 from Intermediate 65.

LC-MS (Method 1): $R_t$=1.21 min; MS (ESIpos): m/z=299 [M+H]$^+$

Example 85

5-[3-Fluoro-4-(6-methoxypyridin-3-yl)phenyl]-3,6-dihydro-2H-1,3,4-oxadiazin-2-one

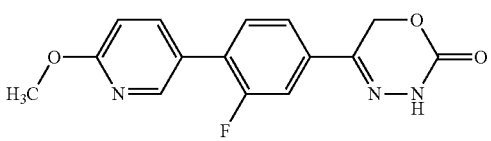 [SMILES: COc1ccc(-c2ccc(C3=NNC(=O)OC3)cc2F)cn1]

The title compound was synthesized analogously to Example 3 from Intermediate 65.

LC-MS (Method 1): $R_t$=0.97 min; MS (ESIpos): m/z=302 [M+H]$^+$

Example 86

5-(2,4'-Difluoro-3'-methylbiphenyl-4-yl)-3,6-dihydro-2H-1,3,4-oxadiazin-2-one

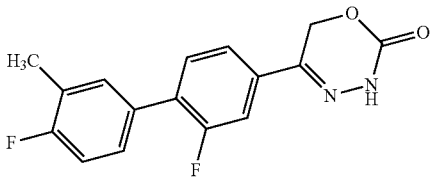 [SMILES: Cc1cc(-c2ccc(C3=NNC(=O)OC3)cc2F)ccc1F]

The title compound was synthesized analogously to Example 3 from Intermediate 65.

LC-MS (Method 1): $R_t$=1.20 min: MS (ESIpos): m/z=303 [M+H]$^+$

Example 87

5-(2-Fluoro-3'-methylbiphenyl-4-yl)-3,6-dihydro-2H-1,3,4-oxadiazin-2-one

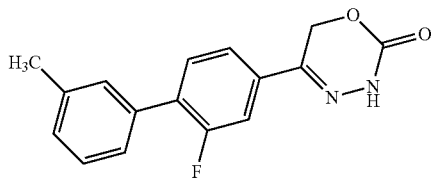 [SMILES: Cc1cccc(-c2ccc(C3=NNC(=O)OC3)cc2F)c1]

The title compound was synthesized analogously to Example 3 from Intermediate 65.
LC-MS (Method 1): $R_t$=1.18 min; MS (ESIpos): m/z=285 [M+H]$^+$ Example 88

5-(2-Fluoro-4'-methylbiphenyl-4-yl)-3,6-dihydro-2H-1,3,4-oxadiazin-2-one

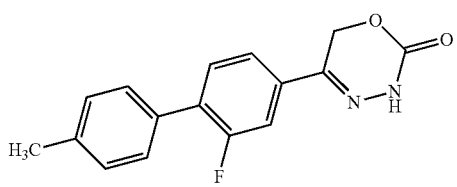 [SMILES: Cc1ccc(-c2ccc(C3=NNC(=O)OC3)cc2F)cc1]

The title compound was synthesized analogously to Example 3 from Intermediate 65.
LC-MS (Method 1): $R_t$=1.18 min; MS (ESIpos): m/z=285 [M+H]$^+$ Example 89

5-(2-Fluorobiphenyl-4-yl)-3,6-dihydro-2H-1,3,4-oxadiazin-2-one

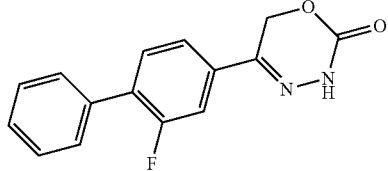 [SMILES: O=C1NN=C(c2ccc(-c3ccccc3)c(F)c2)CO1]

The title compound was synthesized analogously to Example 3 from Intermediate 65.
LC-MS (Method 1): $R_t$=1.09 min; MS (ESIpos): m/z=271 [M+H]$^+$ The following examples Example 90-Example 118 were prepared in analogy to example 89 from Intermediate 65 by reacting with the respective corresponding boronic acid or the corresponding 4,4,5,5-tetramethyl-1,3,2-dioxaboroan-2-yl ester which were purchased from commercial sources unless stated otherwise Example 90

5-[4-(2-Aminopyridin-4-yl)-3-fluorophenyl]-3,6-dihydro-2H-1,3,4-oxadiazin-2-one

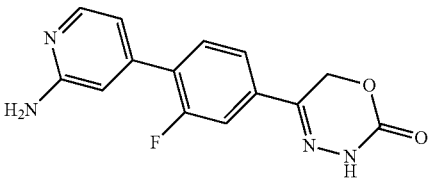 [SMILES: Nc1cc(-c2ccc(C3=NNC(=O)OC3)cc2F)ccn1]

LC-MS (Method 1): $R_t$=0.47 min; MS (ESIpos): m/z=287 [M+H]$^+$

Example 91

5-[4-(3-Aminophenyl)-3-fluoro-phenyl]-3,6-dihydro-1,3,4-oxadiazin-2-one

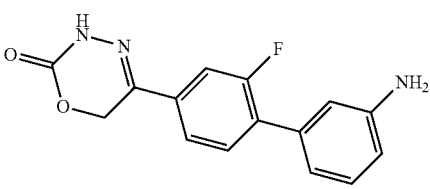 [SMILES: Nc1cccc(-c2ccc(C3=NNC(=O)OC3)cc2F)c1]

LC-MS (Method 1): $R_t$=0.47 min; MS (ESIpos): m/z=286 [M+H]$^+$

Example 92

5-[4'-(Difluoromethyl)-2-fluoro[1,1'-biphenyl]-4-yl]-3,6-dihydro-2H-1,3,4-oxadiazin-2-one

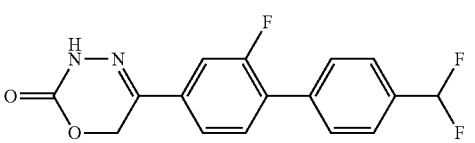 [SMILES: O=C1NN=C(c2ccc(-c3ccc(C(F)F)cc3)c(F)c2)CO1]

LC-MS (Method 1): $R_t$=1.10 min; MS (ESIpos): m/z=321 [M+H]$^+$

Example 93

5-[3-Fluoro-4-(pyridin-4-yl)phenyl]-3,6-dihydro-2H-1,3,4-oxadiazin-2-one

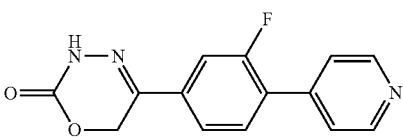 [SMILES: O=C1NN=C(c2ccc(-c3ccncc3)c(F)c2)CO1]

LC-MS (Method 1): R$_t$=0.50 min; MS (ESIpos): m/z=272 [M+H]$^+$

Example 94

5-[3-Fluoro-4-(2-methylpyrimidin-5-yl)phenyl]-3,6-dihydro-2H-1,3,4-oxadiazin-2-one

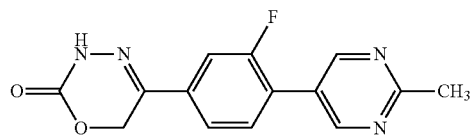 [SMILES: Cc1ncc(-c2ccc(C3=NNC(=O)OC3)cc2F)cn1]

LC-MS (Method 1): R$_t$=0.72 min; MS (ESIpos): m/z=287 [M+H]$^+$

Example 95

5-[3-Fluoro-4-(2-methoxypyridin-4-yl)phenyl]-3,6-dihydro-2H-1,3,4-oxadiazin-2-one

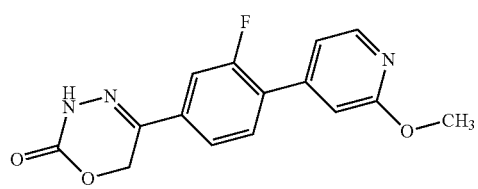 [SMILES: COc1cc(-c2ccc(C3=NNC(=O)OC3)cc2F)ccn1]

LC-MS (Method 1): R$_t$=0.95 min; MS (ESIpos): m/z=302 [M+H]$^+$

Example 96

5-[3-Fluoro-4-(2-methylpyridin-3-yl)phenyl]-3,6-dihydro-2H-1,3,4-oxadiazin-2-one

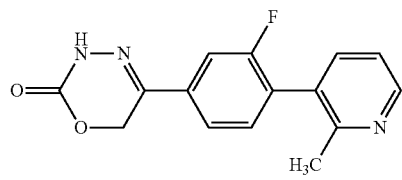 [SMILES: Cc1ncccc1-c1ccc(C2=NNC(=O)OC2)cc1F]

LC-MS (Method 1): R$_t$=0.51 min; MS (ESIpos): m/z=286 [M+H]$^+$

Example 97

5-[3-Fluoro-4-(6-methylpyridin-3-yl)phenyl]-3,6-dihydro-2H-1,3,4-oxadiazin-2-one

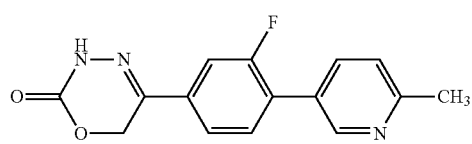

LC-MS (Method 1): R$_t$=0.56 min; MS (ESIpos): m/z=286 [M+H]$^+$

Example 98

5-(2,2',4',5'-Tetrafluoro[1,1'-biphenyl]-4-yl)-3,6-dihydro-2H-1,3,4-oxadiazin-2-one

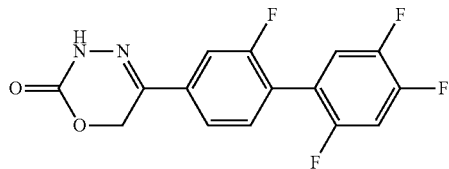 [SMILES: O=C1NN=C(c2ccc(-c3cc(F)c(F)cc3F)c(F)c2)CO1]

LC-MS (Method 1): R$_t$=1.14 min; MS (ESIpos): m/z=325 [M+H]$^+$

Example 99

5-(2,2',3',4'-Tetrafluoro[1,1'-biphenyl]-4-yl)-3,6-dihydro-2H-1,3,4-oxadiazin-2-one

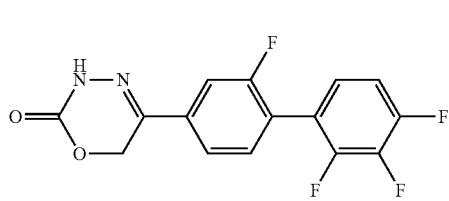 [SMILES: O=C1NN=C(c2ccc(-c3ccc(F)c(F)c3F)c(F)c2)CO1]

LC-MS (Method 1): R$_t$=1.15 min; MS (ESIpos): m/z=325 [M+H]$^+$

Example 100

5-(2,2',5'-Trifluoro[1,1'-biphenyl]-4-yl)-3,6-dihydro-2H-1,3,4-oxadiazin-2-one

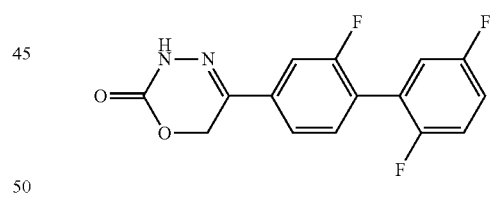

LC-MS (Method 1): R$_t$=1.09 min; MS (ESIpos): m/z=307 [M+H]$^+$

Example 101

2'-Fluoro-4'-(2-oxo-3,6-dihydro-2H-1,3,4-oxadiazin-5-yl)[1,1'-biphenyl]-4-carbonitrile

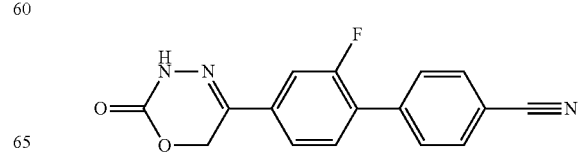

LC-MS (Method 1): $R_t$=0.98 min; MS (ESIpos): m/z=296 [M+H]$^+$

Example 102

5-(2'-Amino-2-fluoro[1,1'-biphenyl]-4-yl)-3,6-dihydro-2H-1,3,4-oxadiazin-2-one

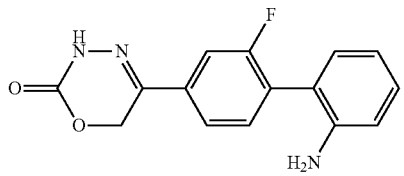 [SMILES: Nc1ccccc1-c1ccc(C2=NNC(=O)OC2)cc1F]

LC-MS (Method 1): $R_t$=0.89 min; MS (ESIpos): m/z=286 [M+H]$^+$

Example 103

5-(3'-Amino-2-fluoro-4'-methyl[1,1'-biphenyl]-4-yl)-3,6-dihydro-2H-1,3,4-oxadiazin-2-one

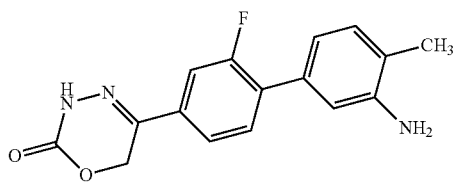 [SMILES: Cc1ccc(-c2ccc(C3=NNC(=O)OC3)cc2F)cc1N]

LC-MS (Method 1): $R_t$=0.87 min; MS (ESIpos): m/z=300 [M+H]$^+$

Example 104

5-(2-Fluoro-3'-hydroxy[1,1'-biphenyl]-4-yl)-3,6-dihydro-2H-1,3,4-oxadiazin-2-one

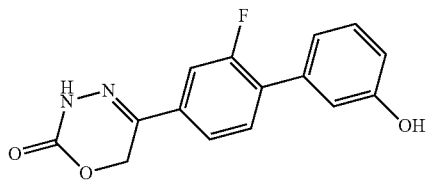 [SMILES: O=C1NN=C(c2ccc(-c3cccc(O)c3)c(F)c2)CO1]

LC-MS (Method 1): $R_t$=0.86 min; MS (ESIpos): m/z=287 [M+H]$^+$

Example 105

5-(2-Fluoro-4'-hydroxy[1,1'-biphenyl]-4-yl)-3,6-dihydro-2H-1,3,4-oxadiazin-2-one

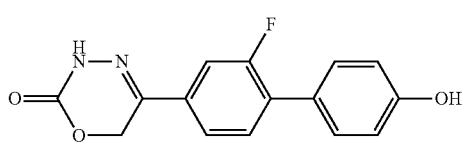

LC-MS (Method 1): $R_t$=0.82 min; MS (ESIpos): m/z=287 [M+H]$^+$

Example 106

5-(2-Fluoro-2'-hydroxy[1,1'-biphenyl]-4-yl)-3,6-dihydro-2H-1,3,4-oxadiazin-2-one

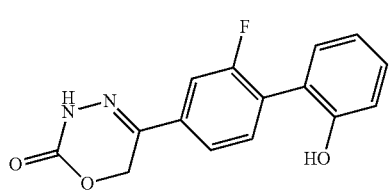 [SMILES: O=C1NN=C(c2ccc(-c3ccccc3O)c(F)c2)CO1]

LC-MS (Method 1): $R_t$=0.90 min; MS (ESIpos): m/z=287 [M+H]$^+$

Example 107

5-(2,3',4'-Trifluoro[1,1'-biphenyl]-4-yl)-3,6-dihydro-2H-1,3,4-oxadiazin-2-one

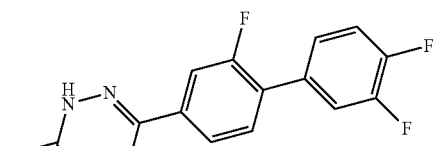

LC-MS (Method 1): $R_t$=1.14 min; MS (ESIpos): m/z=307 [M+H]$^+$

Example 108

5-[3-Fluoro-4-(pyridin-3-yl)phenyl]-3,6-dihydro-2H-1,3,4-oxadiazin-2-one

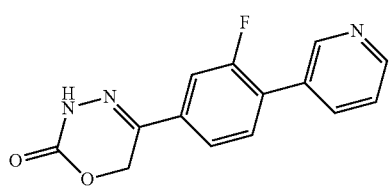 [SMILES: O=C1NN=C(c2ccc(-c3cccnc3)c(F)c2)CO1]

LC-MS (Method 1): $R_t$=0.59 min; MS (ESIpos): m/z=272 [M+H]$^+$

Example 109

5-(2,2',3'-Trifluoro[1,1'-biphenyl]-4-yl)-3,6-dihydro-2H-1,3,4-oxadiazin-2-one

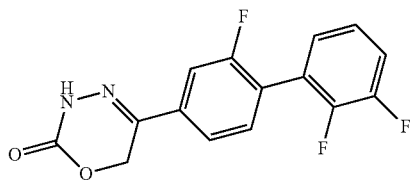 [SMILES: O=C1NN=C(c2ccc(-c3cccc(F)c3F)c(F)c2)CO1]

LC-MS (Method 1): $R_t$=1.10 min; MS (ESIpos): m/z=307 [M+H]$^+$

Example 110

5-(2,3',5'-Trifluoro[1,1'-biphenyl]-4-yl)-3,6-dihydro-2H-1,3,4-oxadiazin-2-one

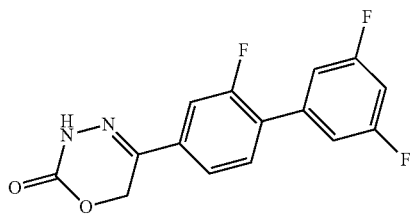 [SMILES: O=C1NN=C(c2ccc(-c3cc(F)cc(F)c3)c(F)c2)CO1]

LC-MS (Method 1): $R_t$=1.15 min; MS (ESIpos): m/z=307 [M+H]$^+$

Example 111

5-(2,2',4'-Trifluoro[1,1'-biphenyl]-4-yl)-3,6-dihydro-2H-1,3,4-oxadiazin-2-one

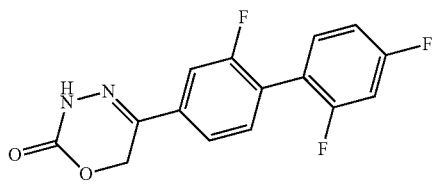 [SMILES: O=C1NN=C(c2ccc(-c3ccc(F)cc3F)c(F)c2)CO1]

LC-MS (Method 1): $R_t$=1.11 min; MS (ESIpos): m/z=307 [M+H]$^+$

Example 112

5-(2-Fluoro-2',4'-dimethyl[1,1'-biphenyl]-4-yl)-3,6-dihydro-2H-1,3,4-oxadiazin-2-one

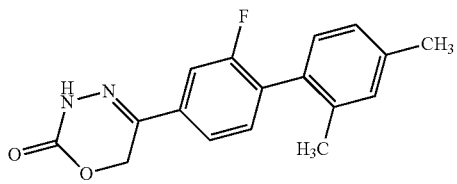 [SMILES: Cc1ccc(-c2ccc(C3=NNC(=O)OC3)cc2F)c(C)c1]

LC-MS (Method 1): $R_t$=1.23 min; MS (ESIpos): m/z=299 [M+H]$^+$

Example 113

5-(2,3'-Difluoro-4'-methyl[1,1'-biphenyl]-4-yl)-3,6-dihydro-2H-1,3,4-oxadiazin-2-one

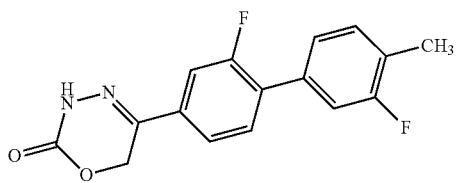 [SMILES: Cc1ccc(-c2ccc(C3=NNC(=O)OC3)cc2F)cc1F]

LC-MS (Method 1): $R_t$=1.20 min; MS (ESIpos): m/z=303 [M+H]$^+$

Example 114

5-(2,2'-Difluoro[1,1'-biphenyl]-4-yl)-3,6-dihydro-2H-1,3,4-oxadiazin-2-one

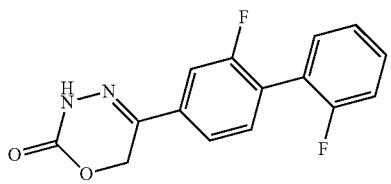 [SMILES: O=C1NN=C(c2ccc(-c3ccccc3F)c(F)c2)CO1]

LC-MS (Method 1): $R_t$=1.07 min; MS (ESIpos): m/z=289 [M+H]$^+$

Example 115

5-(2,2',6'-Trifluoro[1,1'-biphenyl]-4-yl)-3,6-dihydro-2H-1,3,4-oxadiazin-2-one

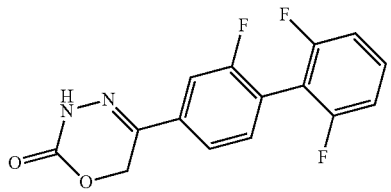 [SMILES: O=C1NN=C(c2ccc(-c3c(F)cccc3F)c(F)c2)CO1]

LC-MS (Method 1): $R_t$=1.07 min; MS (ESIpos): m/z=307 [M+H]$^+$

Example 116

5-(2-Fluoro-2'-methoxy[1,1'-biphenyl]-4-yl)-3,6-dihydro-2H-1,3,4-oxadiazin-2-one

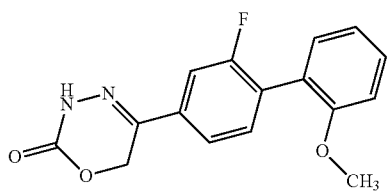 [SMILES: COc1ccccc1-c1ccc(C2=NNC(=O)OC2)cc1F]

LC-MS (Method 1): $R_t$=1.07 min; MS (ESIpos): m/z=301 [M+H]$^+$

Example 117

5-(2,3'-Difluoro[1,1'-biphenyl]-4-yl)-3,6-dihydro-2H-1,3,4-oxadiazin-2-one

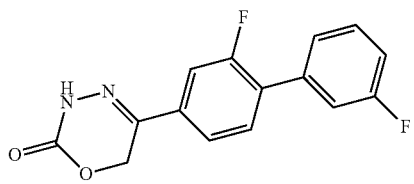 [SMILES: O=C1NN=C(c2ccc(-c3cccc(F)c3)c(F)c2)CO1]

LC-MS (Method 1): R=1.11 min; MS (ESIpos): m/z=289 [M+H]$^+$

Example 118

5-[3-Fluoro-4-(4-methylpyridin-3-yl)phenyl]-3,6-dihydro-2H-1,3,4-oxadiazin-2-one

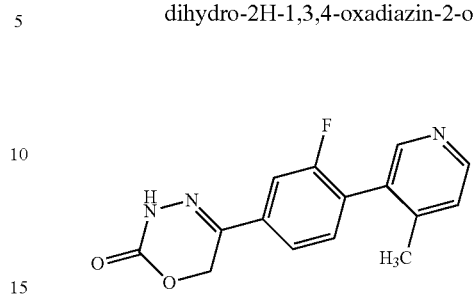

LC-MS (Method 1): $R_t$=0.55 min, MS (ESIpos): m/z=286 [M+H]$^+$

Example 119

(rac)-5-(3-Fluoro-4-morpholinophenyl)-6-methyl-3,6-dihydro-2H-1,3,4-oxadiazin-2-one

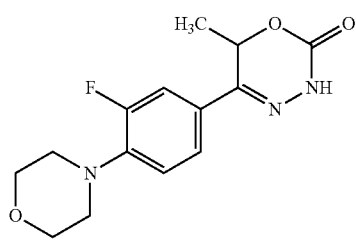 [SMILES: CC1OC(=O)NN=C1c1ccc(N2CCOCC2)c(F)c1]

Following a literature procedure (J. Med. Chem. 1990, 35, 163), to 370 mg of (rac)-1-(3-fluoro-4-morpholinophenyl)-2-hydroxypropan-1-one (1.46 mmol, Intermediate 33) in 4 mL EtOH and 5-6 drops of 0.1 N HCl were added 131 mg (1.46 mmol) of methyl hydrazinecarboxylate and the reaction was heated at reflux 1 h. After cooling, the mixture was concentrated, and more EtOH followed by concentration was done twice to remove residual water and acid. To the crude mixture was added a NaOEt solution (350 mg of sodium consumed in 5 mL EtOH) and the mixture was stirred overnight. The next day the solid was filtered off and added to a mixture of slightly acidic (HCl) water and EtOAc. The EtOAc layer was separated, dried and concentrated to give 107 mg (25%) of product as an off-white solid.

1H NMR (400 MHz, CDCl$_3$) δ 8.19 (s, 1H), 7.44 (d, J=14.1 Hz, 1H), 7.30 (d, J=12.1 Hz, 1H), 6.94 (t, J=8.4 Hz, 1H), 5.50 (q, J=6.9 Hz, 1H), 3.90 (s, 4H), 3.19 (s, 4H), 1.62 (d, J=6.9 Hz, 3H). 19F NMR (376 MHz, CDCl$_3$) δ −120.66. LC-MS (Method 5): 294 [M+H]$^+$

Example 120

(6S)-6-Methyl-5-[4-(morpholin-4-yl)-3-(trifluoromethyl)phenyl]-3,6-dihydro-2H-1,3,4-oxadiazin-2-one

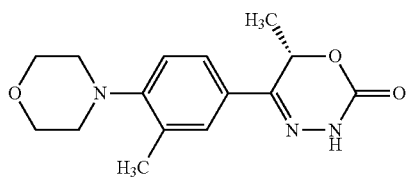 [SMILES: Cc1cc(C2=NNC(=O)O[C@H]2C)ccc1N1CCOCC1]

To 3.30 g of (S)-2-hydroxy-1-(4-morpholino-3-(trifluoromethyl)phenyl)propan-1-one (10.8 mmol, Intermediate 41) and 972 mg of methyl hydrazinecarboxylate (10.8 mmol) in 10 mL MeOH were added 6 drops of 0.1 N HCl (aq), and the reaction was heated at reflux temperature 1 h. After cooling, the mixture was concentrated, MeOH was added and concentrated to remove water and HCl (twice). The crude reaction mixture was dissolved in ca. 20 mL EtOH and added to a solution of NaOEt (12.4 g of sodium (54 mmol) consumed in 30 mL EtOH). After 90 min, 3 mL of acetic acid were added resulting in copious precipitation. The solids were filtered and rinsed with EtOH, dissolved in EtOAc and washed with water. The EtOAc was dried, concentrated, to give 980 mg of the title compound as white solid (26%) which was recrystallized from EtOH.

$^1$H NMR (400 MHz, CDCl$_3$) δ 8.34 (s, 1H), 7.96 (s, 1H), 7.80 (d, J=8.4 Hz, 1H), 7.38 (d, J=8.5 Hz, 1H), 5.56 (q, J=6.9 Hz, 1H), 3.87 (s, 4H), 3.01 (s, 4H), 1.65 (d, J=6.9 Hz, 3H). $^{19}$F NMR (376 MHz, CDCl$_3$) δ −60.29. $^{13}$C NMR (101 MHz, CDCl$_3$) δ 153.72, 148.98, 146.92, 129.73, 127.71, 127.11 (q, J=29.4 Hz), 125.04 (q, J=5.0, 4.4 Hz), 123.83, 119.53, 71.87, 67.12, 53.45, 17.36. MS: 344 (M+1)+.

Chiral SCF chromatography separated the enantiomers: Column: ChiralPak AD-H, 250×4.6 mm, 5 um, Mobile Phase Modifier: 100% Methanol, Gradient: 3 to 50% Methanol over 8 minutes, Flow Rate: 4 mL/min, Back Pressure: 100 bar, Column Temperature: 40° C. UV detection was from 200-400 nm. Ratio of peaks corresponding to enantiomers at 6.36 and 7.15 min was 99.61:0.39.

Example 121

(6S)-5-(-[(3-Chloro-4-(morpholin-4-yl)-5-(trifluoromethyl)phenyl)-)]-6-methyl-3,6-dihydro-2H-1,3,4-oxadiazin-2-one

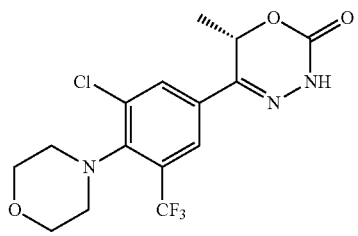 [SMILES: C[C@@H]1OC(=O)NN=C1c1cc(Cl)c(N2CCOCC2)c(C(F)(F)F)c1]

A solution of 104 mg (0.304 mmol) of (S)-6-methyl-5-(4-morpholino-3-(trifluoromethyl)phenyl)-3,6-dihydro-2H-1,3,4-oxadiazin-2-one (Example 120) was dissolved in 2 mL HOAc and the solution was cooled to 15-20° C. with an ice bath. To this was added 0.295 mL of a NaOCl solution (10-15% available chlorine, Aldrich). After ca. 30 min another 100 µL of NaOCl solution was added. After another 30 min the reaction contents were transferred to a separatory funnel along with water and CH$_2$Cl$_2$. The CH$_2$Cl$_2$ layer was separated and rinsed with a Na$_2$SO$_3$ solution, then brine, before drying and concentrating. Chromatography with 20-40% EtOAc (twice) yielded 19 mg of clean product (17%).

$^1$H NMR (400 MHz, CDCl$_3$) δ 8.25 (s, 1H), 7.86 (d, J=1.7 Hz, 1H), 7.83 (d, J=1.9 Hz, 1H), 5.53 (q, J=7.0 Hz, 1H), 3.88 (d, J=9.5 Hz, 2H), 3.84-3.63 (m, 4H), 2.74 (d, J=10.4 Hz, 2H), 1.65 (d, J=7.0 Hz, 3H). $^{19}$F NMR (376 MHz, CDCl$_3$) δ −61.14. LC-MS (Method 5): Mass 378 (M+1)+.

Example 126

(rac)-6-Methyl-5-(4-morpholino-3-(trifluoromethyl)phenyl)-3,6-dihydro-2H-1,3,4-oxadiazin-2-one

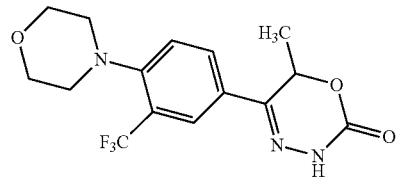 [SMILES: CC1OC(=O)NN=C1c1ccc(N2CCOCC2)c(C(F)(F)F)c1]

A solution of 100 mg of (rac)-2-hydroxy-1-(4-morpholino-3-(trifluoromethyl)phenyl)propan-1-one (0.33 mmol, Intermediate 40), 33 mg of methyl hydrazinecarboxylate (0.36 mmol) and 2 drops of 0.1 N HCl in 1 mL MeOH was heated at 60° C. for 1 h. After cooling, the reaction was concentrated, MeOH was twice added followed by concentration to remove residual water and HCl. The crude product was dissolved in 1 mL MeOH and to it was added a NaOMe solution (75 mg Na consumed in 1 mL MeOH) and the solution was stirred 2 h before addition of 200 µL of HOAc. The precipitates dissolve with stirring and were transferred to a separatory funnel with water and EtOAc. The EtOAc layer was separated, dried, concentrated and chromatographed with 20-50% EtOAc to yield 39 mg of product as a white solid (35%).

$^1$H NMR (400 MHz, Chloroform-d) b 8.22 (s, 1H), 7.96 (d, J=2.1 Hz, 1H), 7.80 (dd, J=8.5, 2.1 Hz, 1H), 7.39 (d, J=8.5 Hz, 1H), 5.56 (q, J=7.0 Hz, 1H), 3.92-3.81 (m, 4H), 3.05-2.96 (m, 4H), 1.65 (d, J=7.0 Hz, 3H).

$^{19}$F NMR (376 MHz, CDCl$_3$) δ −60.29. LC-MS (Method 5): 344 (M+1)+.

Chiral SCF chromatography separated the enantiomers of example 126: Column: ChiralPak AD-H, 250×4.6 mm, 5 um, Mobile Phase Modifier: 100% Methanol, Gradient: 3 to 50% Methanol over 8 minutes, Flow Rate: 4 mL/min, Back Pressure: 100 bar, Column Temperature: 40° C. UV detection was from 200-400 nm. Retention time of enantiomers: 6.30 and 7.10 min.

The following examples Example 127-Example 130 were prepared in analogy to Example 3 from Intermediate 64 by reacting with the respective corresponding boronic acid or the corresponding 4,4,5,5-tetramethyl-1,3,2-dioxaborolan-2-yl ester which were purchased from commercial sources unless stated otherwise.

Example 127

5-{4-[1-Methyl-3-(trifluoromethyl)-1H-pyrazol-4-yl]-3-(trifluoromethyl)phenyl}-3,6-dihydro-2H-1,3,4-oxadiazin-2-one

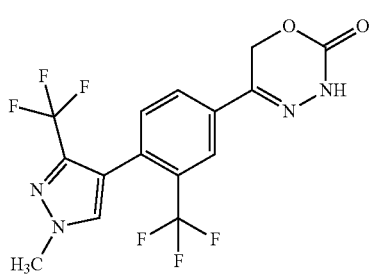 [SMILES: Cn1cc(-c2ccc(C3=NNC(=O)OC3)cc2C(F)(F)F)c(C(F)(F)F)n1]

LC-MS (Method 2): $R_t$=1.09 min, MS (ESIpos): m/z=393 [M+H]$^+$ $^1$H-NMR (400 MHz, DMSO-d6) δ[ppm]: 2.518 (2.02), 2.522 (1.30), 3.987 (14.22), 5.464 (16.00), 7.511 (2.16), 7.531 (2.32), 7.986 (1.57), 7.990 (1.64), 8.007 (1.39), 8.010 (1.52), 8.063 (3.50), 8.094 (3.14), 8.098 (2.96), 11.253 (4.82).

Example 128

5-[4-(3,5-Dimethyl-1H-pyrazol-4-yl)-3-(trifluoromethyl)phenyl]-3,6-dihydro-2H-1,3,4-oxadiazin-2-one

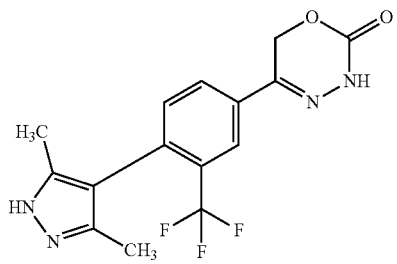 [SMILES: Cc1n[nH]c(C)c1-c1ccc(C2=NNC(=O)OC2)cc1C(F)(F)F]

LC-MS (Method 2): $R_t$=0.85 min; MS (ESIpos): m/z=339 [M+H]$^+$ $^1$H-NMR (400 MHz, DMSO-d6) δ[ppm]: 1.875 (1.00), 1.947 (0.99), 2.518 (1.20), 2.523 (0.87), 2.539 (16.00), 5.462 (6.32), 7.370 (0.92), 7.390 (0.95), 7.962 (0.61), 7.966 (0.62), 7.983 (0.54), 7.986 (0.58), 8.085 (1.23), 8.089 (1.15), 11.215 (1.68), 12.345 (0.47).

Example 129

5-[4-(3,5-Dimethyl-1,2-oxazol-4-yl)-3-(trifluoromethyl)phenyl]-3,6-dihydro-2H-1,3,4-oxadiazin-2-one

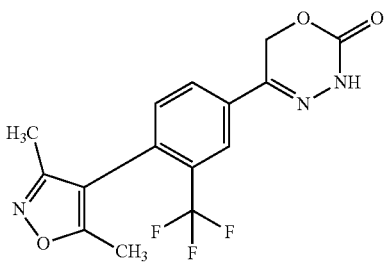 [SMILES: Cc1noc(C)c1-c1ccc(C2=NNC(=O)OC2)cc1C(F)(F)F]

LC-MS (Method 2): $R_t$=1.04 min; MS (ESIpos): m/z=340 [M+H]$^+$ $^1$H-NMR (400 MHz, DMSO-d6) δ[ppm]: 1.966 (16.00), 2.074 (7.48), 2.169 (12.93), 2.518 (0.86), 2.523 (0.59), 5.476 (12.53), 7.542 (1.69), 7.562 (1.79), 8.045 (1.11), 8.048 (1.16), 8.065 (0.99), 8.068 (1.09), 8.143 (2.21), 8.148 (2.04).

Example 130

5-{3-(Trifluoromethyl)-4-[3-(trifluoromethyl)-1H-pyrazol-4-yl]phenyl}-3,6-dihydro-2H-1,3,4-oxadiazin-2-one

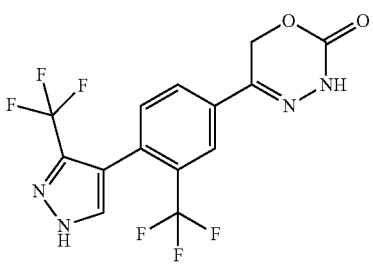 [SMILES: O=C1NN=C(c2ccc(-c3c[nH]nc3C(F)(F)F)c(C(F)(F)F)c2)CO1]

LC-MS (Method 2): $R_t$=0.95 min; MS (ESIneg): m/z=377 [M−H]$^-$ $^1$H-NMR (400 MHz, DMSO-d6) δ[ppm]: 2.074 (1.45), 2.518 (1.64), 2.523 (1.09), 5.466 (16.00), 7.513 (2.08), 7.533 (2.23), 7.984 (1.53), 7.988 (1.58), 8.004 (1.34), 8.008 (1.47), 8.081 (3.12), 8.094 (3.11), 8.098 (2.90), 11.248 (1.64).

Example 131

5-[4-(1-Ethyl-1H-pyrazol-4-yl)-3-(trifluoromethyl)phenyl]-3,6-dihydro-2H-1,3,4-oxadiazin-2-one

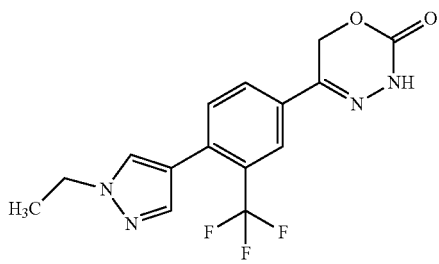 [SMILES: CCn1cc(-c2ccc(C3=NNC(=O)OC3)cc2C(F)(F)F)cn1]

In a reaction vessel, 5-[4-chloro-3-(trifluoromethyl)phenyl]-3,6-dihydro-2H-1,3,4-oxadiazin-2-one (120 mg, 431 µmol, Intermediate 64), (1-ethyl-1H-pyrazol-4-yl)boronic acid (90.4 mg, 646 µmol), potassium carbonate (119 mg, 861 µmol) and dicyclohexyl[2',4',6'-tri(propan-2-yl)biphenyl-2-yl]phosphane (12.3 mg, 25.8 µmol) were suspended in 1,4-dioxane (1.9 mL) and water (650 µL). The mixture was degassed with nitrogen for 5 min. Afterwards chloro(2-dicyclohexylphosphino-2',4',6'-triisopropyl-1,1'-biphenyl)[2-(2'-amino-1,1'-biphenyl)]palladium(II) (10.2 mg, 12.9 µmol) was added. Again, nitrogen was passed through the reaction mixture. It was stirred at 80° C. overnight in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC to give 45.0 mg (95% purity, 29% yield) of the title compound.

LC-MS (Method 1): $R_t$=1.00 min, MS (ESIpos): m/z=339 [M+H]$^+$ $^1$H-NMR (400 MHz, DMSO-d6) δ[ppm]: 1.388 (6.84), 1.406 (14.43), 1.424 (6.92), 2.075 (1.76), 2.518 (3.48), 2.523 (2.49), 4.168 (1.84), 4.187 (5.81), 4.205 (5.52), 4.223 (1.78), 5.443 (16.00), 7.639 (2.44), 7.648 (4.66), 7.660 (2.64), 7.949 (1.60), 7.953 (1.67), 7.969 (1.37), 7.974 (1.48), 8.017 (4.66), 8.061 (3.08), 8.066 (2.91), 11.201 (3.48).

Example 132

5-{4-[Cyclopentyl(methyl)amino]-3-(trifluoromethyl)phenyl}-3,6-dihydro-2H-1,3,4-oxadiazin-2-one

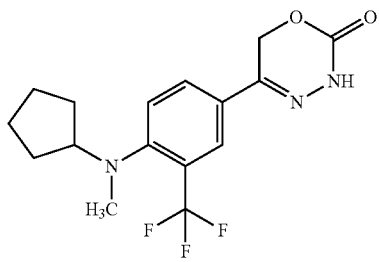 [SMILES: CN(c1ccc(C2=NNC(=O)OC2)cc1C(F)(F)F)C1CCCC1]

5-[4-Fluoro-3-(trifluoromethyl)phenyl]-3,6-dihydro-2H-1,3,4-oxadiazin-2-one (100 mg, 381 µmol, Intermediate 66) was dissolved in DMSO (1.0 mL), and N-methylcyclopentanamine (99 µl, 840 µmol) was added. The mixture was stirred at 100° C. for 3 d. The reaction mixture was diluted with DMSO, filtered and purified by preparative HPLC to give 2.40 mg (95% purity, 2% yield) of the title compound.

LC-MS (Method 2): $R_t$=1.41 min, MS (ESIpos): m/z=342 [M+H]$^+$ $^1$H-NMR (400 MHz, DMSO-d6) δ[ppm]: 1.326 (0.78), 1.345 (1.03), 1.354 (1.09), 1.374 (1.03), 1.393 (0.48), 1.457 (0.54), 1.466 (0.74), 1.473 (1.26), 1.485 (1.36), 1.492 (1.20), 1.503 (1.05), 1.572 (0.50), 1.586 (0.99), 1.603 (1.42), 1.613 (1.14), 1.624 (0.76), 1.647 (0.76), 1.665 (0.99), 1.677 (1.14), 1.694 (1.05), 1.705 (0.76), 2.332 (0.80), 2.518 (4.29), 2.523 (3.01), 2.539 (0.78), 2.565 (16.00), 3.496 (0.68), 3.513 (0.97), 3.532 (0.62), 5.396 (14.95), 7.641 (1.63), 7.663 (1.88), 7.927 (4.79), 7.932 (2.46), 7.943 (1.61), 7.948 (0.85), 11.124 (3.94).

Example 133

5-[4-(1-Methyl-1,2,3,6-tetrahydropyridin-4-yl)-3-(trifluoromethyl)phenyl]-3,6-dihydro-2H-1,3,4-oxadiazin-2-one

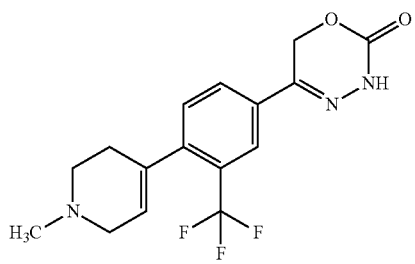 [SMILES: CN1CC=C(c2ccc(C3=NNC(=O)OC3)cc2C(F)(F)F)CC1]

In a reaction vessel, 5-[4-chloro-3-(trifluoromethyl)phenyl]-3,6-dihydro-2H-1,3,4-oxadiazin-2-one (109 mg, 391 µmol, Intermediate 64), 1-methyl-4-(4,4,5,5-tetramethyl-1,3,2-dioxaborolan-2-yl)-1,2,3,6-tetrahydropyridine (131 mg, 587 µmol), potassium carbonate (108 mg, 782 µmol) and dicyclohexyl[2',4',6'-tri(propan-2-yl)biphenyl-2-yl]phosphane (11.2 mg, 23.5 µmol) were suspended in 1,4-dioxane (1.5 mL) and water (500 µL). The mixture was degassed with nitrogen for 5 min. Afterwards chloro(2-dicyclohexylphosphino-2',4',6'-triisopropyl-1,1'-biphenyl)[2-(2'-amino-1,1'-biphenyl)]palladium(II) (9.23 mg, 11.7 µmol) was added. Again, nitrogen was passed through the reaction mixture. It was stirred at 80° C. overnight in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC to give 61.0 mg (95% purity, 44% yield) of the title compound.

LC-MS (Method 1): $R_t$=0.56 min; MS (ESIpos): m/z=340 [M+H]$^+$ $^1$H-NMR (400 MHz, DMSO-d6) δ[ppm]: 2.075 (0.64), 2.276 (15.55), 2.311 (2.18), 2.316 (2.25), 2.322 (1.96), 2.518 (1.45), 2.523 (1.12), 2.536 (2.66), 2.549 (4.64), 2.563 (1.94), 2.951 (3.63), 2.958 (3.57), 5.418 (16.00), 5.563 (1.89), 7.431 (2.37), 7.451 (2.55), 7.910 (1.67), 7.914 (1.76), 7.931 (1.43), 7.934 (1.64), 7.981 (3.40), 7.985 (3.07).

Example 134

5-{4-[Butyl(methyl)amino]-3-(trifluoromethyl)phenyl}-3,6-dihydro-2H-1,3,4-oxadiazin-2-one

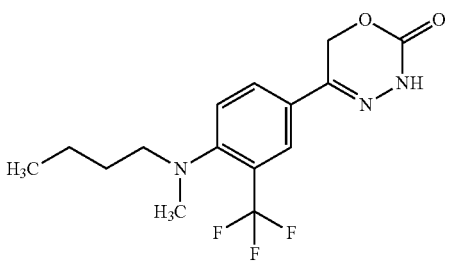 [SMILES: CCCCN(C)c1ccc(C2=NNC(=O)OC2)cc1C(F)(F)F]

5-[4-Fluoro-3-(trifluoromethyl)phenyl]-3,6-dihydro-2H-1,3,4-oxadiazin-2-one (100 mg, 381 µmol, Intermediate 66) was dissolved in DMSO (1.0 mL), and N-methylbutan-1-amine (99 µl, 840 µmol) was added. The mixture was stirred at 100° C. for 3 d. The reaction mixture was diluted with DMSO, filtered and purified by preparative HPLC to give 32.0 mg (95% purity, 24% yield) of the title compound.

LC-MS (Method 1): $R_t$=1.37 min; MS (ESIpos): m/z=330 [M+H]$^+$ $^1$H-NMR (400 MHz, DMSO-d6) δ[ppm]: 0.814 (4.69), 0.833 (11.78), 0.850 (5.68), 1.223 (1.11), 1.240 (1.92), 1.260 (2.01), 1.279 (1.38), 1.297 (0.42), 1.361 (0.68), 1.375 (0.99), 1.380 (1.33), 1.399 (1.84), 1.413 (0.85), 1.418 (1.11), 1.435 (0.42), 2.323 (0.49), 2.327 (0.72), 2.332 (0.52), 2.518 (2.56), 2.523 (1.91), 2.673 (16.00), 2.943 (2.08), 2.962 (2.58), 2.980 (1.98), 5.382 (15.03), 7.517 (1.94), 7.538 (2.11), 7.890 (1.22), 7.895 (1.63), 7.920 (3.73), 7.925 (1.96), 11.095 (4.03).

Example 135

(6S)-5-[4'-Fluoro-2-(trifluoromethyl)biphenyl-4-yl]-6-methyl-3,6-dihydro-2H-1,3,4-oxadiazin-2-one

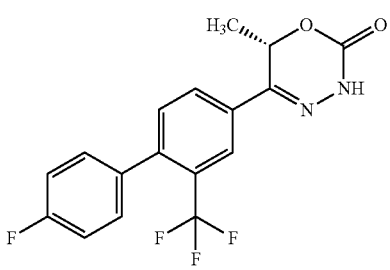 [SMILES: C[C@@H]1OC(=O)NN=C1c1ccc(-c2ccc(F)cc2)c(C(F)(F)F)c1]

In a reaction vessel, (6S)-5-[4-chloro-3-(trifluoromethyl)phenyl]-6-methyl-3,6-dihydro-2H-1,3,4-oxadiazin-2-one (96.0 mg, 328 µmol, Intermediate 74), (4-fluorophenyl)boronic acid (68.9 mg, 492 µmol), potassium carbonate (90.7 mg, 656 µmol) and dicyclohexyl[2',4',6'-tri(propan-2-yl)biphenyl-2-yl]phosphane (9.38 mg, 19.7 µmol) were suspended in 1,4-dioxane (1.5 mL) and water (500 µL). The mixture was degassed with nitrogen for 5 min. Afterwards chloro(2-dicyclohexylphosphino-2',4',6'-triisopropyl-1,1'-biphenyl)[2-(2'-amino-1,1'-biphenyl)]palladium(II) (7.74 mg, 9.84 µmol) was added. Again, nitrogen was passed through the reaction mixture. It was stirred at 80° C. overnight in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC to give 65.0 mg (95% purity, 53% yield) of the title compound.

Rotational angle: −303.9° (DMSO, 1.0000 g/100 ml, 20° C., 589 nm)

LC-MS (Method 2): $R_t$=1.28 min, MS (ESIneg): m/z=351 [M−H]$^−$ $^1$H-NMR (400 MHz, DMSO-de): δ [ppm]=11.32 (s, 1H), 8.15 (d, 1H), 8.05 (dd, 1H), 7.52 (d, 1H), 7.42-7.35 (m, 2H), 7.35-7.28 (m, 2H), 5.98-5.92 (m, 1H), 1.47 (d, 3H)

Example 136

5-[4-(Cyclopentylamino)-3-(trifluoromethyl)phenyl]-3,6-dihydro-2H-1,3,4-oxadiazin-2-one

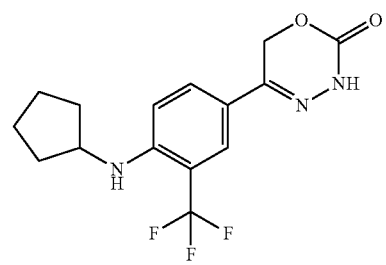 [SMILES: O=C1NN=C(c2ccc(NC3CCCC3)c(C(F)(F)F)c2)CO1]

5-[4-Fluoro-3-(trifluoromethyl)phenyl]-3,6-dihydro-2H-1,3,4-oxadiazin-2-one (100 mg, 381 µmol, Intermediate 66) was dissolved in DMSO (1.0 mL), and cyclopentanamine (83 µl, 840 µmol) was added. The mixture was stirred at 100° C. for 3 d. The reaction mixture was diluted with DMSO, filtered and purified by preparative HPLC to give 59.0 mg (95% purity, 45% yield) of the title compound.

LC-MS Method 1): $R_t$=1.30 min; MS (ESIpos): m/z=328 [M+H]$^+$ $^1$H-NMR (400 MHz, DMSO-d6) δ[ppm]: 1.498 (0.84), 1.515 (1.31), 1.531 (1.56), 1.546 (2.28), 1.556 (2.19), 1.574 (1.62), 1.581 (1.20), 1.589 (1.27), 1.593 (1.23), 1.605 (0.51), 1.609 (0.52), 1.614 (0.67), 1.629 (0.56), 1.633 (0.49), 1.637 (0.49), 1.659 (1.46), 1.674 (1.72), 1.688 (1.12), 1.959 (0.59), 1.976 (1.28), 1.988 (1.45), 2.005 (1.58), 2.018 (0.99), 2.074 (0.98), 2.518 (4.95), 2.523 (3.46), 3.916 (0.51), 3.932 (0.97), 3.948 (1.00), 3.963 (0.57), 5.108 (1.49), 5.125 (1.44), 5.301 (16.00), 6.942 (2.14), 6.964 (2.28), 7.738 (3.92), 7.744 (2.52), 7.766 (1.60), 7.771 (1.31), 10.898 (4.59).

Example 137

5-[4-(Propan-2-ylamino)-3-(trifluoromethyl)phenyl]-3,6-dihydro-2H-1,3,4-oxadiazin-2-one

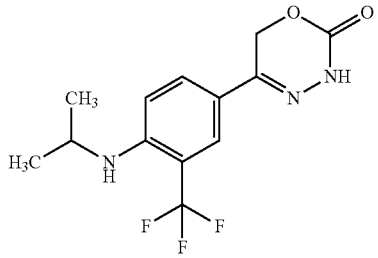 [SMILES: CC(C)Nc1ccc(C2=NNC(=O)OC2)cc1C(F)(F)F]

5-[4-Fluoro-3-(trifluoromethyl)phenyl]-3,6-dihydro-2H-1,3,4-oxadiazin-2-one (100 mg, 381 µmol, Intermediate 66) was dissolved in DMSO (1.0 mL), and propan-2-amine (46 µl, 550 µmol) was added. The mixture was stirred at 100° C. for 3 d. The reaction mixture was diluted with DMSO, filtered and purified by preparative HPLC to give 35.0 mg (95% purity, 22% yield) of the title compound.

LC-MS (Method 1): $R_t$=1.18 min; MS (ESIpos): m/z=302 [M+H]$^+$ $^1$H-NMR (400 MHz, DMSO-d6) δ[ppm]: 1.195 (15.78), 1.211 (16.00), 1.232 (0.44), 2.518 (2.46), 2.522 (1.54), 3.806 (0.43), 3.822 (0.66), 3.841 (0.67), 3.857 (0.44), 5.018 (1.03), 5.038 (1.00), 5.297 (12.01), 6.936 (1.55), 6.957 (1.64), 7.737 (3.71), 7.761 (1.17), 10.890 (3.44).

Example 138

5-[3'-Fluoro-2-(trifluoromethyl)biphenyl-4-yl]-3,6-dihydro-2H-1,3,4-oxadiazin-2-one

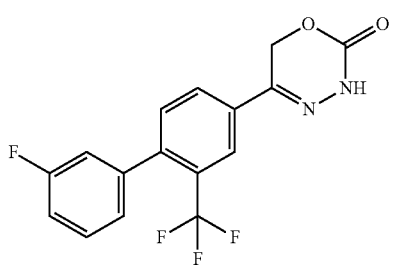 [SMILES: O=C1NN=C(c2ccc(-c3cccc(F)c3)c(C(F)(F)F)c2)CO1]

In a reaction vessel, 5-[4-chloro-3-(trifluoromethyl)phenyl]-3,6-dihydro-2H-1,3,4-oxadiazin-2-one (136 mg, 487 µmol, Intermediate 64), 2-(3-fluorophenyl)-4,4,5,5-tetramethyl-1,3,2-dioxaborolane (162 mg, 731 µmol), potassium carbonate (135 mg, 974 µmol) and dicyclohexyl[2',4',6'-tri(propan-2-yl)biphenyl-2-yl]phosphane (13.9 mg, 29.2 µmol) were suspended in 1,4-dioxane (2.2 mL) and water (370 µL). The mixture was degassed with nitrogen for 5 min. Afterwards chloro(2-dicyclohexylphosphino-2',4',6'-triisopropyl-1,1'-biphenyl)[2-(2'-amino-1,1'-biphenyl)]palladium(II) (11.5 mg, 14.6 µmol) was added. Again, nitrogen was passed through the reaction mixture. It was stirred at 80° C. for 3 h in a heating block. The mixture was diluted with water and extracted with ethyl acetate three times. The combined organic layers were dried using a water-resistant filter and the filtrate was concentrated under reduced pressure. The residue was dissolved in DMSO, filtered and purified by preparative HPLC to give 93.0 mg (95% purity, 54% yield) of the title compound.

LC-MS (Method 2): $R_t$=1.23 min, MS (ESIneg): m/z=337 [M–H]$^-$ $^1$H-NMR (400 MHz, DMSO-d6) δ[ppm]: 1.153 (0.76), 1.171 (1.52), 1.189 (0.73), 1.986 (2.93), 2.518 (1.50), 2.522 (0.92), 4.016 (0.63), 4.034 (0.63), 5.475 (16.00), 7.171 (1.74), 7.192 (2.71), 7.199 (1.44), 7.223 (1.29), 7.284 (0.68), 7.288 (0.65), 7.290 (0.67), 7.305 (1.39), 7.311 (1.34), 7.325 (0.83), 7.327 (0.83), 7.331 (0.80), 7.334 (0.73), 7.490 (1.02), 7.505 (1.32), 7.509 (1.45), 7.524 (1.55), 7.530 (1.08), 7.538 (2.61), 7.545 (1.03), 7.558 (2.72), 8.014 (1.67), 8.019 (1.78), 8.035 (1.49), 8.038 (1.66), 8.113 (3.37), 8.118 (3.19), 11.259 (4.93).

The following compounds of Example 139 to Example 156 were prepared in analogy to the procedure described in Example 3 from Intermediate 64 by reacting with the respective corresponding boronic acid or the corresponding 4,4,5,5-tetramethyl-1,3,2-dioxaborolan-2-yl ester which were purchased from commercial sources unless stated otherwise.

Example 139

5-[4-Methyl-3-(trifluoromethyl)phenyl]-3,6-dihydro-2H-1,3,4-oxadiazin-2-one

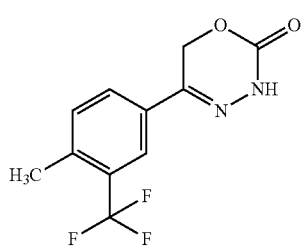 [SMILES: Cc1ccc(C2=NNC(=O)OC2)cc1C(F)(F)F]

LC-MS (Method 2): $R_t$=1.08 min; MS (ESIneg): m/z=257 [M–H]$^-$ $^1$H-NMR (400 MHz, DMSO-d6) δ[ppm]: 2.074 (0.96), 2.474 (6.67), 2.478 (6.66), 2.518 (0.94), 2.522 (0.57), 5.403 (16.00), 7.538 (1.74), 7.558 (1.96), 7.859 (1.42), 7.863 (1.50), 7.883 (1.33), 7.953 (2.78), 11.155 (3.34).

Example 140

5-{4-[3-Methoxyprop-1-en-1-yl]-3-(trifluoromethyl)phenyl}-3,6-dihydro-2H-1,3,4-oxadiazin-2-one

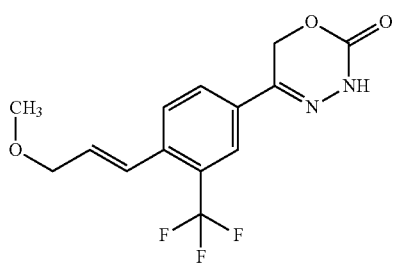 [SMILES: COC/C=C/c1ccc(C2=NNC(=O)OC2)cc1C(F)(F)F]

LC-MS (Method 2): $R_t$=1.08 min; MS (ESIneg): m/z=313 [M–H]$^-$

¹H-NMR (400 MHz, DMSO-d6) δ[ppm]: 2.518 (1.27), 2.522 (0.83), 3.319 (16.00), 3.331 (13.80), 4.105 (1.72), 4.109 (1.86), 4.117 (1.86), 4.122 (1.83), 5.424 (7.79), 6.556 (0.61), 6.595 (0.81), 6.835 (0.54), 6.841 (0.55), 6.874 (0.42), 6.880 (0.42), 7.938 (4.05), 7.976 (1.82), 11.203 (2.37).

Example 141

(rac)-5-[4'-Hydroxy-2-(trifluoromethyl)-2',3',4',5'-tetrahydro[1,1'-biphenyl]-4-yl]-3,6-dihydro-2H-1,3,4-oxadiazin-2-one

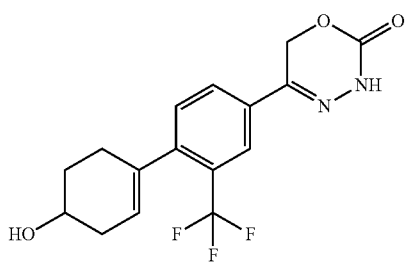 [SMILES: O=C1NN=C(c2ccc(C3=CCC(O)CC3)c(C(F)(F)F)c2)CO1]

LC-MS (Method 2): R_t=0.93 min; MS (ESIneg): m/z=339 [M−H]⁻

¹H-NMR (400 MHz, DMSO-d6) δ[ppm]: 1.064 (1.48), 1.177 (0.71), 1.563 (0.63), 1.575 (0.49), 1.582 (0.52), 1.588 (0.73), 1.594 (0.86), 1.606 (0.49), 1.618 (0.79), 1.836 (0.79), 1.845 (0.83), 1.855 (0.66), 1.865 (0.64), 1.876 (0.64), 1.949 (0.50), 1.956 (0.57), 1.968 (0.55), 1.975 (0.55), 1.993 (0.63), 2.000 (0.66), 2.012 (0.68), 2.019 (0.62), 2.278 (2.23), 2.327 (0.73), 2.331 (0.71), 2.340 (0.87), 2.384 (0.68), 2.518 (0.85), 2.522 (0.55), 2.539 (0.51), 3.771 (0.43), 3.782 (0.68), 3.790 (0.85), 3.796 (0.78), 3.801 (0.82), 4.724 (4.22), 4.735 (3.92), 5.411 (16.00), 5.440 (1.74), 7.407 (2.63), 7.427 (2.78), 7.892 (1.82), 7.896 (1.93), 7.912 (1.60), 7.916 (1.79), 7.964 (3.75), 7.968 (3.41), 11.178 (5.86).

Example 142

5-[4-(5,6-Dihydro-2H-pyran-3-yl)-3-(trifluoromethyl)phenyl]-3,6-dihydro-2H-1,3,4-oxadiazin-2-one

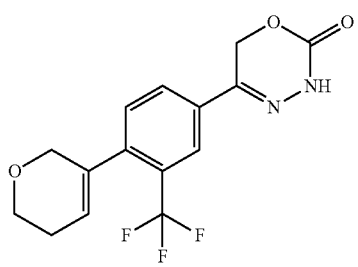 [SMILES: O=C1NN=C(c2ccc(C3=CCCOC3)c(C(F)(F)F)c2)CO1]

LC-MS (Method 2): R_t=1.06 min; MS (ESIneg): m/z=325 [M−H]⁻

¹H-NMR (400 MHz, DMSO-d6) δ[ppm]: 2.074 (3.94), 2.204 (2.14), 2.214 (2.16), 2.518 (1.14), 2.523 (0.73), 3.753 (2.48), 3.767 (5.24), 3.780 (2.38), 4.151 (4.13), 4.156 (4.10), 5.421 (16.00), 5.763 (1.71), 7.497 (2.48), 7.518 (2.69), 7.922 (1.72), 7.925 (1.81), 7.942 (1.52), 7.946 (1.67), 8.009 (3.48), 8.013 (3.21), 11.206 (4.88).

Example 143

5-[4-(Imidazo[1,2-a]pyridin-6-yl)-3-(trifluoromethyl)phenyl]-3,6-dihydro-2H-1,3,4-oxadiazin-2-one

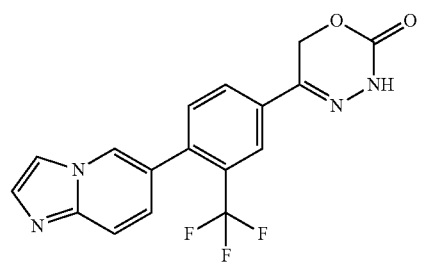 [SMILES: O=C1NN=C(c2ccc(-c3ccc4nccn4c3)c(C(F)(F)F)c2)CO1]

LC-MS (Method 2): R_t=0.89 min; MS (ESIpos): m/z=361 [M+H]⁺

¹H-NMR (400 MHz, DMSO-d6) δ[ppm]: 2.518 (2.21), 2.522 (1.42), 5.491 (16.00), 7.180 (1.78), 7.204 (1.95), 7.630 (3.35), 7.649 (6.76), 7.652 (9.28), 7.675 (2.96), 8.005 (5.24), 8.048 (1.88), 8.052 (1.96), 8.068 (1.65), 8.071 (1.79), 8.147 (3.72), 8.150 (3.50), 8.630 (3.88), 11.276 (5.50).

Example 144

5-{4-[3,3-Dimethylbut-1-en-1-yl]-3-(trifluoromethyl)phenyl}-3,6-dihydro-2H-1,3,4-oxadiazin-2-one

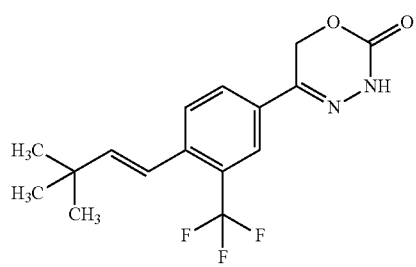 [SMILES: CC(C)(C)/C=C/c1ccc(C2=NNC(=O)OC2)cc1C(F)(F)F]

LC-MS (Method 1): R_t=1.43 min; MS (ESIpos): m/z=327 [M+H]⁺

¹H-NMR (400 MHz, DMSO-d6) δ[ppm]: 1.112 (16.00), 2.074 (0.56), 5.420 (3.54), 6.553 (1.48), 7.877 (0.71), 7.922 (0.56), 7.943 (0.48), 7.950 (0.91), 11.187 (1.16).

Example 145

5-{3-(Trifluoromethyl)-4-[5-(trifluoromethyl)thiophen-3-yl]phenyl}-3,6-dihydro-2H-1,3,4-oxadiazin-2-one

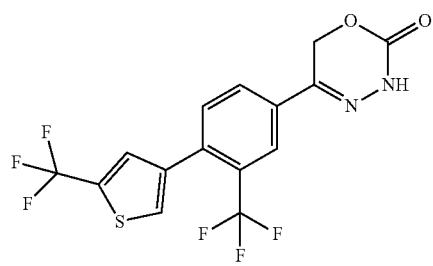 [SMILES: O=C1NN=C(c2ccc(-c3csc(C(F)(F)F)c3)c(C(F)(F)F)c2)CO1]

LC-MS (Method 2): R$_t$=1.34 min; MS (ESIneg): m/z=393 [M−H]$^−$ $^1$H-NMR (400 MHz, DMSO-d6) δ[ppm]: 2.074 (3.07), 2.518 (1.51), 2.523 (0.90), 5.472 (16.00), 7.640 (2.38), 7.660 (2.58), 7.801 (2.85), 8.016 (1.70), 8.020 (1.81), 8.029 (4.25), 8.033 (4.41), 8.040 (1.69), 8.118 (3.18), 8.122 (2.97), 11.268 (5.08).

Example 146

5-{4-[1-(Difluoromethyl)-1H-pyrazol-4-yl]-3-(trifluoromethyl)phenyl}-3,6-dihydro-2H-1,3,4-oxadiazin-2-one

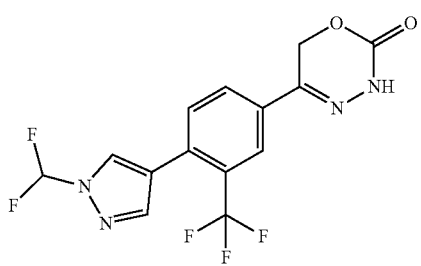 [SMILES: O=C1NN=C(c2ccc(-c3cnn(C(F)F)c3)c(C(F)(F)F)c2)CO1]

To 5-[4-chloro-3-(trifluoromethyl)phenyl]-3,6-dihydro-2H-1,3,4-oxadiazin-2-one (900.0 mg, 3.2 mmol, Intermediate 64), 1-(difluoromethyl)-4-(4,4,5,5-tetramethyl-1,3,2-dioxaborolan-2-yl)-1H-pyrazole (946 mg, 3.88 mmol, CAS 1206640-82-5), potassium carbonate (892 mg, 6.5 mmol) and 2-(dicyclohexylphosphino)-2',4',6'-triisopropylbiphenyl (92 mg, 194 μmol) in 1,4-dioxane (15 mL) and water (5 mL) (nitrogen atmosphere) was added chloro(2-dicyclohexylphosphino-2',4',6'-triisopropyl-1,1'-biphenyl)[2-(2'-amino-1,1'-biphenyl)]palladium(II) (76 mg, 97 μmol) and the mixture was stirred 15 h at 80° C. The reaction mixture was poured into water and extracted four times with ethyl acetate. The combined organic phases were dried over sodium sulfate, filtered, and concentrated in vacuo. The residue was diluted with DMSO, filtered and purified by preparative HPLC (acidic conditions), to obtain 766 mg (99% purity, 65% yield) of the desired title compound.

LC-MS (Method 1): R$_t$=1.04 min; MS (ESIpos): m/z=361 [M+H]$^+$ $^1$H-NMR (400 MHz, DMSO-d$_6$): δ [ppm]=11.25 (s, 1H), 8.49 (s, 1H), 8.11 (d, 1H), 8.02 (dd, 1H), 7.99 (s, 1H), 7.90 (t, 1H), 7.69 (d, 1H), 5.46 (s, 2H)

Example 147

5-[4-(Prop-1-en-2-yl)-3-(trifluoromethyl)phenyl]-3,6-dihydro-2H-1,3,4-oxadiazin-2-one

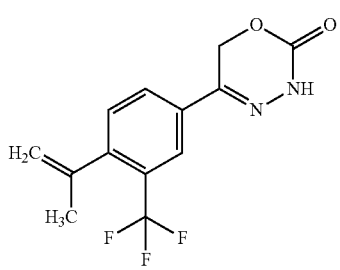 [SMILES: C=C(C)c1ccc(C2=NNC(=O)OC2)cc1C(F)(F)F]

LC-MS (Method 2): R$_t$=1.20 min; MS (ESIneg): m/z=283 [M−H]$^−$ $^1$H-NMR (400 MHz, DMSO-d6) δ[ppm]: 2.050 (11.86), 2.074 (0.50), 2.518 (1.27), 2.522 (0.78), 4.863 (3.04), 5.295 (2.22), 5.299 (3.26), 5.303 (2.18), 5.424 (16.00), 7.474 (2.45), 7.494 (2.62), 7.928 (1.66), 7.932 (1.81), 7.948 (1.47), 7.952 (1.69), 7.992 (3.47), 7.995 (3.05), 11.198 (4.16).

Example 148

5-[4-(1-Benzothiophen-2-yl)-3-(trifluoromethyl)phenyl]-3,6-dihydro-2H-1,3,4-oxadiazin-2-one

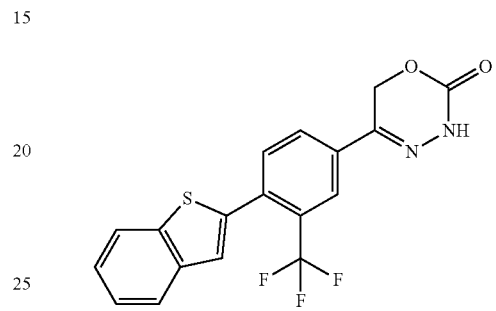

LC-MS (Method 1): R$_t$=1.36 min; MS (ESIpos): m/z=377 [M+H]$^−$ $^1$H-NMR (400 MHz, DMSO-d6) δ[ppm]: 2.074 (0.57), 2.327 (0.51), 2.522 (1.96), 2.669 (0.51), 5.486 (16.00), 7.410 (0.44), 7.414 (0.74), 7.428 (2.23), 7.434 (2.91), 7.443 (4.69), 7.451 (3.14), 7.457 (2.43), 7.471 (0.80), 7.475 (0.47), 7.525 (5.46), 7.774 (2.77), 7.794 (3.15), 7.925 (2.05), 7.934 (1.26), 7.942 (1.75), 7.948 (1.82), 8.025 (1.93), 8.031 (1.79), 8.040 (1.11), 8.048 (3.61), 8.070 (1.77), 8.074 (1.90), 8.162 (3.87), 8.166 (3.76), 11.297 (5.22).

Example 149

5-[4-(2,5-Dihydrofuran-3-yl)-3-(trifluoromethyl)phenyl]-3,6-dihydro-2H-1,3,4-oxadiazin-2-one

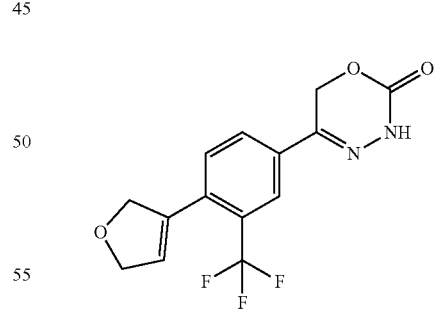

LC-MS (Method 1): R$_t$=1.00 min; MS (ESIpos): m/z=313 [M+H]$^+$ $^1$H-NMR (400 MHz, DMSO-d6) δ[ppm]: 2.327 (0.45), 2.518 (1.74), 2.523 (1.11), 2.669 (0.46), 4.746 (1.09), 4.757 (2.48), 4.760 (2.45), 4.764 (2.22), 4.770 (3.35), 4.792 (2.88), 4.805 (2.24), 4.815 (0.92), 5.433 (16.00), 5.437 (2.82), 6.102 (2.35), 7.597 (2.34), 7.617 (2.56), 7.949 (1.69), 7.953 (1.74), 7.969 (1.46), 7.973 (1.56), 8.054 (3.27), 8.057 (3.02), 11.230 (4.55).

Example 150

5-[4-(Cyclopent-1-en-1-yl)-3-(trifluoromethyl)phenyl]-3,6-dihydro-2H-1,3,4-oxadiazin-2-one

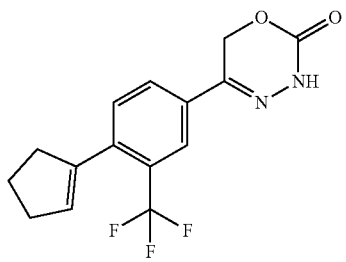 [SMILES: O=C1NN=C(c2ccc(C3=CCCC3)c(C(F)(F)F)c2)CO1]

LC-MS (Method 1): R$_t$=1.33 min; MS (ESIpos): m/z=311 [M+H]$^+$ $^1$H-NMR (400 MHz, DMSO-d6) δ[ppm]: 1.940 (0.63), 1.959 (2.02), 1.978 (2.99), 1.996 (2.24), 2.015 (0.77), 2.074 (4.02), 2.470 (1.87), 2.477 (2.41), 2.518 (2.20), 2.522 (1.26), 2.615 (1.28), 2.620 (1.39), 2.634 (2.18), 2.639 (2.08), 2.652 (1.26), 2.658 (1.13), 2.664 (0.69), 2.668 (0.50), 5.420 (16.00), 5.781 (2.28), 7.497 (2.46), 7.517 (2.66), 7.906 (1.75), 7.909 (1.81), 7.926 (1.54), 7.930 (1.66), 7.997 (3.48), 8.000 (3.21), 11.191 (4.59).

Example 151

5-[4-(1-Ethyl-1H-imidazol-4-yl)-3-(trifluoromethyl)phenyl]-3,6-dihydro-2H-1,3,4-oxadiazin-2-one

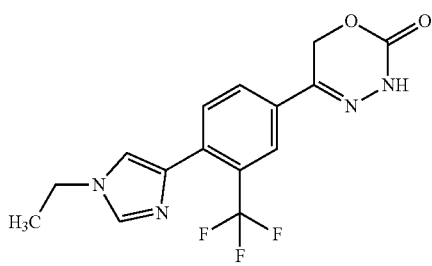 [SMILES: CCn1cnc(-c2ccc(C3=NNC(=O)OC3)cc2C(F)(F)F)c1]

LC-MS (Method 2): R$_t$=0.93 min; MS (ESIpos): m/z=339 [M+H]$^+$ $^1$H-NMR (400 MHz, CHLOROFORM-d) δ [ppm]: 0.000 (6.19), 1.438 (6.42), 1.456 (13.18), 1.475 (6.58), 1.555 (2.58), 1.942 (0.65), 3.969 (1.94), 3.987 (5.59), 4.005 (5.47), 4.024 (1.78), 5.213 (16.00), 7.520 (4.84), 7.711 (1.85), 7.715 (1.93), 7.732 (2.06), 7.736 (2.12), 7.922 (3.82), 8.055 (3.05), 8.076 (2.69), 8.284 (1.68).

Example 152

3-Methyl-5-[4-(2-oxo-3,6-dihydro-2H-1,3,4-oxadiazin-5-yl)-2-(trifluoromethyl)phenyl]thiophene-2-carbonitrile

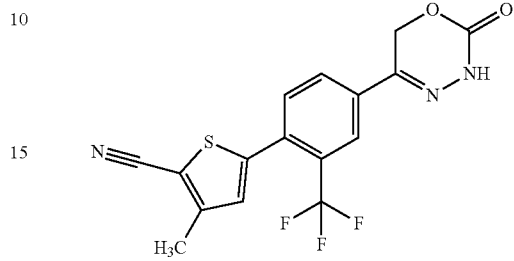

LC-MS (Method 1): R$_t$=1.21 min; MS (ESIpos): m/z=366 [M+H]$^+$ $^1$H-NMR (400 MHz, DMSO-d6) δ[ppm]: 2.074 (1.81), 2.442 (16.00), 2.518 (1.66), 2.523 (1.09), 5.470 (11.67), 7.264 (3.83), 7.713 (1.86), 7.734 (2.07), 8.040 (1.30), 8.044 (1.35), 8.060 (1.11), 8.064 (1.21), 8.149 (2.53), 8.152 (2.40), 11.311 (3.61).

Example 153

5-{4-[1-(Propan-2-yl)-1H-pyrazol-4-yl]-3-(trifluoromethyl)phenyl}-3,6-dihydro-2H-1,3,4-oxadiazin-2-one

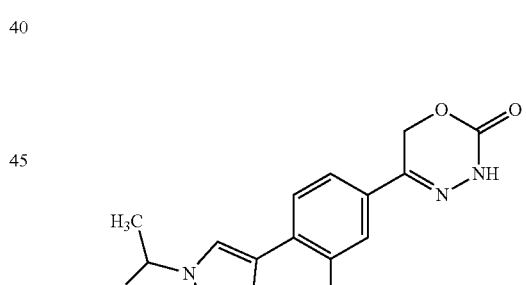

LC-MS (Method 1): R$_t$=1.08 min; MS (ESIpos): m/z=353 [M+H]$^+$ $^1$H-NMR (400 MHz, DMSO-d6) δ[ppm]: 1.442 (15.58), 1.459 (16.00), 2.074 (0.44), 2.326 (0.54), 2.331 (0.41), 2.522 (1.75), 2.668 (0.54), 2.673 (0.41), 4.551 (1.01), 4.568 (1.37), 4.584 (0.99), 5.444 (9.60), 7.644 (2.97), 7.653 (1.70), 7.674 (1.71), 7.947 (1.06), 7.951 (1.19), 7.968 (0.90), 7.972 (1.06), 8.033 (3.24), 8.059 (2.07), 8.063 (2.11), 11.200 (3.20).

Example 154

(rac)-5-[4-(Bicyclo[2.2.1]hept-2-en-2-yl)-3-(trifluoromethyl)phenyl]-3,6-dihydro-2H-1,3,4-oxadiazin-2-one

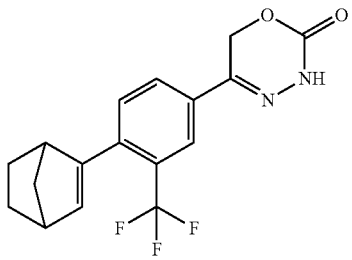 [SMILES: O=C1NN=C(c2ccc(C3=CC4CCC3C4)c(C(F)(F)F)c2)CO1]

LC-MS (Method 2): R$_t$=1.39 min; MS (ESIneg): m/z=335 [M−H]$^-$ $^1$H-NMR (400 MHz, DMSO-d6) δ[ppm]: 1.103 (1.01), 1.122 (0.42), 1.127 (0.42), 1.143 (1.33), 1.165 (1.23), 1.181 (1.16), 1.204 (1.33), 1.226 (0.57), 1.239 (1.91), 1.259 (2.01), 1.552 (1.41), 1.568 (1.00), 1.573 (1.23), 1.728 (0.77), 1.736 (1.30), 1.743 (0.97), 1.755 (1.97), 1.762 (1.94), 1.772 (0.88), 1.779 (1.17), 1.787 (0.72), 2.327 (0.40), 2.518 (1.66), 2.523 (0.99), 2.669 (0.42), 3.014 (1.99), 3.017 (1.99), 3.115 (2.26), 5.416 (16.00), 6.148 (2.52), 6.155 (2.43), 7.420 (2.58), 7.440 (2.74), 7.899 (1.83), 7.902 (1.88), 7.919 (1.62), 7.923 (1.72), 7.999 (3.61), 8.003 (3.32), 11.193 (4.98).

Example 155

5-[2'-Fluoro-2-(trifluoromethyl)[1,1'-biphenyl]-4-yl]-3,6-dihydro-2H-1,3,4-oxadiazin-2-one

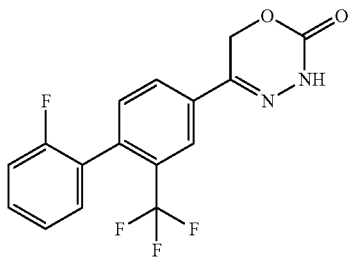 [SMILES: O=C1NN=C(c2ccc(-c3ccccc3F)c(C(F)(F)F)c2)CO1]

LC-MS (Method 2): R$_t$=1.20 min; MS (ESIneg): m/z=337 [M−H]$^-$ $^1$H-NMR (400 MHz, DMSO-d6) δ[ppm]: 2.074 (2.38), 2.518 (1.38), 2.523 (0.93), 5.482 (16.00), 7.279 (0.79), 7.282 (0.85), 7.298 (1.94), 7.301 (2.29), 7.306 (1.21), 7.318 (2.17), 7.326 (2.53), 7.329 (2.48), 7.344 (1.32), 7.350 (2.10), 7.362 (0.54), 7.367 (0.44), 7.490 (0.61), 7.495 (0.54), 7.504 (0.72), 7.508 (1.04), 7.511 (0.90), 7.516 (0.66), 7.521 (0.73), 7.527 (0.82), 7.528 (1.00), 7.534 (0.55), 7.546 (2.33), 7.566 (2.26), 8.026 (1.43), 8.030 (1.52), 8.047 (1.29), 8.050 (1.41), 8.128 (2.88), 8.132 (2.71), 11.261 (0.84).

Example 156

5-{3-(Trifluoromethyl)-4-[5-(trifluoromethyl)thiophen-2-yl]phenyl}-3,6-dihydro-2H-1,3,4-oxadiazin-2-one

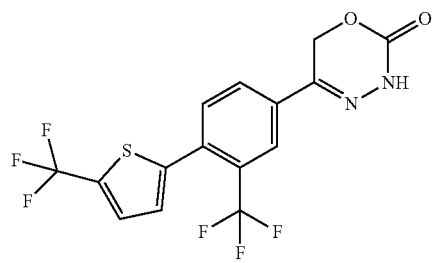 [SMILES: O=C1NN=C(c2ccc(-c3ccc(C(F)(F)F)s3)c(C(F)(F)F)c2)CO1]

LC-MS (Method 1): R$_t$=1.36 min; MS (ESIneg): m/z=393 [M−H]$^-$ $^1$H-NMR (400 MHz, DMSO-d6) δ[ppm]: 2.518 (2.71), 2.523 (1.80), 5.476 (16.00), 5.758 (0.90), 7.308 (1.89), 7.316 (1.94), 7.757 (2.58), 7.777 (3.04), 7.785 (2.32), 7.788 (2.37), 7.792 (1.65), 7.795 (2.22), 7.797 (2.14), 8.041 (1.87), 8.045 (1.91), 8.062 (1.57), 8.066 (1.68), 8.159 (3.53), 8.162 (3.35), 11.307 (4.85).

Example 157

5-[4-(5-Methylpyridin-2-yl)-3-(trifluoromethyl)phenyl]-3,6-dihydro-2H-1,3,4-oxadiazin-2-one

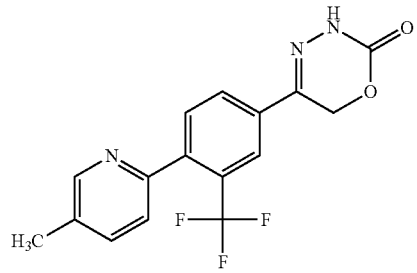 [SMILES: Cc1ccc(-c2ccc(C3=NNC(=O)OC3)cc2C(F)(F)F)nc1]

To a solution of 5-(4-bromo-3-(trifluoromethyl)phenyl)-3H-1,3,4-oxadiazin-2(6H)-one (100 mg, 0.3 mmol, Intermediate 78), in 3 mL of N,N-dimethylformamide were added 5-methylpyridin-2-ylboronic acid (85 mg, 0.6 mmol), cesium carbonate (303 mg, 0.9 mmol), palladium(II) acetate (7 mg, 0.03 mmol), 1,1'-bis(diphenylphosphino)ferrocene (34 mg, 0.03 mmol), and copper(I) chloride (31 mg, 0.3 mmol). The resulting mixture was stirred at 100° C. overnight under nitrogen atmosphere. Upon completion of the reaction, the reaction mixture was diluted with water and extracted with ethyl acetate. The combined organic layer were washed with saturated aq. ammonium chloride solution, followed by water, and were then dried over anhydrous sodium sulfate. The solvent was removed in vacuo, and the residue was purified by prep-HPLC (Column: Xbridge prep C18 5 μm 19*150 mm; Mobile phase A: Water (0.1% TFA), Mobile phase B: ACN; Flow rate: 20 ml/min; Gradient: 25% B to 52% B in 8 min; 254 & 220 nm; Rt:7.23 min). The solvent was removed by lyophilization to give 11 mg (11%) of the title compound as a white solid. MS(ESIpos): m/z=336 (M+H)+.

¹H-NMR (400 MHz, DMSO-de): δ [ppm]=11.26 (s, 1H), 8.51 (s, 1H), 8.12 (s, 1H), 8.05 (d, 1H), 7.74 (dd, 1H), 7.63 (d, 1H), 7.43 (d, 1H), 5.49 (s, 2H), 2.38 (s, 3H)

Example 158

5-[4-(5-Fluoropyridin-2-yl)-3-(trifluoromethyl)phenyl]-3,6-dihydro-2H-1,3,4-oxadiazin-2-one

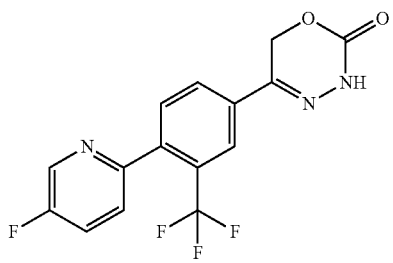

The title compound was prepared in analogy to Example 157 from Intermediate 78.
MS(ESIpos): m/z=340 (M+H)⁺.

Example 159

5-[4-(5-Chloropyridin-2-yl)-3-(trifluoromethyl)phenyl]-3,6-dihydro-2H-1,3,4-oxadiazin-2-one

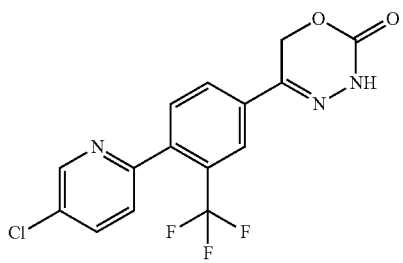 [SMILES: O=C1NN=C(c2ccc(-c3ccc(Cl)cn3)c(C(F)(F)F)c2)CO1]

The title compound was prepared in analogy to Example 157 from Intermediate 78.
MS(ESIpos): m/z=356 (M+H)⁺.

Example 160

5-[4-(Pyridin-2-yl)-3-(trifluoromethyl)phenyl]-3,6-dihydro-2H-1,3,4-oxadiazin-2-one

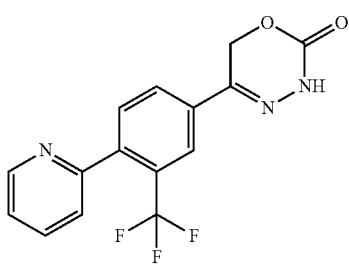 [SMILES: O=C1NN=C(c2ccc(-c3ccccn3)c(C(F)(F)F)c2)CO1]

The title compound was prepared in analogy to Example 157 from Intermediate 78.
MS(ESIpos): m/z=322 (M+H)⁺.

Example 161

5-[2'-(Difluoromethyl)-2-fluoro[1,1'-biphenyl]-4-yl]-3,6-dihydro-2H-1,3,4-oxadiazin-2-one

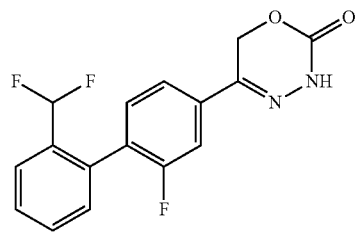 [SMILES: O=C1NN=C(c2ccc(-c3ccccc3C(F)F)c(F)c2)CO1]

The title compound was synthesized analogously to Example 3 from Intermediate 65.
LC-MS (Method 1): R$_t$=1.15 min: MS (ESIpos): m/z=321 [M+H]⁺
¹H-NMR (400 MHz, DMSO-d6) δ[ppm]: 2.327 (0.56), 2.332 (0.41), 2.518 (3.66), 2.522 (2.23), 2.539 (0.72), 2.673 (0.42), 5.420 (16.00), 6.640 (1.33), 6.776 (2.59), 6.913 (1.22), 7.395 (1.43), 7.411 (1.68), 7.435 (1.39), 7.456 (2.95), 7.475 (1.80), 7.613 (0.51), 7.628 (1.57), 7.631 (1.66), 7.644 (3.75), 7.647 (4.44), 7.651 (7.09), 7.656 (3.06), 7.668 (2.39), 7.672 (2.33), 7.680 (2.78), 7.684 (1.97), 7.749 (1.67), 7.754 (1.82), 7.770 (1.35), 11.225 (4.66).

Example 162

5-(2,4'-Difluoro-2'-methyl[1,1'-biphenyl]-4-yl)-3,6-dihydro-2H-1,3,4-oxadiazin-2-one

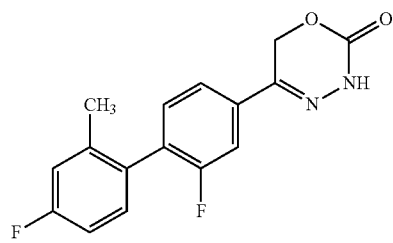 [SMILES: Cc1cc(F)ccc1-c1ccc(C2=NNC(=O)OC2)cc1F]

The title compound was synthesized analogously to Example 3 from Intermediate 65.
LC-MS (Method 1): R$_t$=1.21 min, MS (ESIpos): m/z=303 [M+H]⁺
¹H-NMR (400 MHz, DMSO-d6) δ[ppm]: 2.145 (11.95), 2.327 (0.69), 2.331 (0.49), 2.518 (2.83), 2.523 (1.78), 2.669 (0.70), 2.673 (0.51), 5.409 (16.00), 7.103 (0.60), 7.110 (0.70), 7.125 (1.41), 7.131 (1.66), 7.146 (1.37), 7.153 (0.94), 7.164 (0.43), 7.167 (0.41), 7.207 (1.43), 7.214 (1.29), 7.232 (1.48), 7.239 (1.33), 7.247 (1.80), 7.262 (1.88), 7.269 (1.46), 7.284 (1.30), 7.372 (0.66), 7.376 (0.51), 7.390 (0.52), 7.393 (0.64), 7.397 (1.36), 7.417 (2.96), 7.436 (1.60), 7.464 (0.83), 7.484 (0.55), 7.627 (4.67), 7.630 (2.19), 7.650 (4.12), 8.095 (0.52), 8.115 (0.49), 11.198 (4.49).

Example 163

2'-Fluoro-2-methyl-4'-(2-oxo-3,6-dihydro-2H-1,3,4-oxadiazin-5-yl)[1,1'-biphenyl]-4-carbonitrile

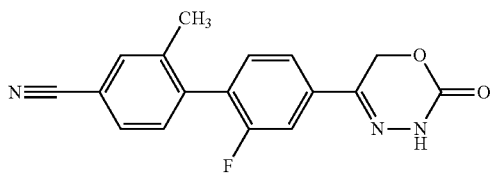 [SMILES: Cc1cc(C#N)ccc1-c1ccc(C2=NNC(=O)OC2)cc1F]

The title compound was synthesized analogously to Example 3 from Intermediate 65.

LC-MS (Method 1): $R_t$=1.09 min: MS (ESIpos): m/z=310 [M+H]$^+$ $^1$H-NMR (400 MHz, DMSO-d6) δ[ppm]: 2.186 (14.22), 2.326 (0.41), 2.522 (1.38), 2.669 (0.42), 5.416 (16.00), 7.440 (3.40), 7.447 (1.50), 7.460 (3.99), 7.467 (3.36), 7.487 (1.93), 7.665 (6.13), 7.684 (2.12), 7.687 (2.88), 7.691 (2.86), 7.759 (2.10), 7.762 (2.17), 7.779 (1.83), 7.782 (1.94), 7.866 (3.86), 11.224 (5.70).

Example 164

5-[4-(2-Methylprop-1-en-1-yl)-3-(trifluoromethoxy) phenyl]-3,6-dihydro-2H-1,3,4-oxadiazin-2-one

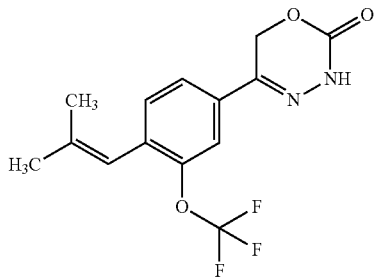 [SMILES: CC(C)=Cc1ccc(C2=NNC(=O)OC2)cc1OC(F)(F)F]

The title compound was synthesized analogously to Example 3 from Intermediate 73.

LC-MS (Method 1): $R_t$=1.31 min, MS (ESIpos): m/z=315 [M+H]$^+$ $^1$H-NMR (400 MHz, DMSO-d6) δ[ppm]: 1.765 (12.45), 1.767 (12.30), 1.922 (10.62), 1.925 (10.53), 2.075 (0.51), 2.518 (1.75), 2.523 (1.16), 5.385 (16.00), 6.238 (2.53), 7.463 (2.46), 7.484 (3.00), 7.669 (5.19), 7.674 (3.38), 7.677 (2.32), 7.686 (2.32), 7.690 (1.32), 11.160 (4.38).

Example 165

(6S)-5-[4-(2-Aminopyridin-4-yl)-3-(trifluoromethyl) phenyl]-6-methyl-3,6-dihydro-2H-1,3,4-oxadiazin-2-one

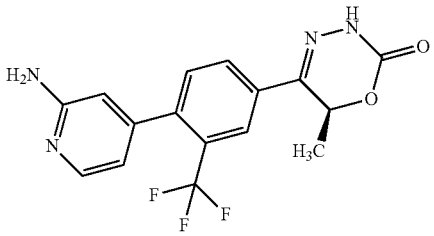 [SMILES: C[C@@H]1OC(=O)NN=C1c1ccc(-c2ccnc(N)c2)c(C(F)(F)F)c1]

(6S)-5-[4-chloro-3-(trifluoromethyl)phenyl]-6-methyl-3,6-dihydro-2H-1,3,4-oxadiazin-2-one (97%, 200 mg, 0.66 mmol, Intermediate 74), 2-aminopyridine-4-boronic acid pinacol ester (219 mg, 0.66 mmol), 2-(Dicyclohexylphosphino)-2',4',6'-triisopropylbipheny [XPhos](19 mg, 39.78 μmol) and K$_2$CO$_3$ (0.88 mL, 1.33 mmol) were stirred in 1,4-Dioxane (2.65 mL). The mixture was thoroughly degassed with nitrogen for 5 mins. Chloro(2-dicyclohexylphosphino-2',4',6'-triisopropyl-1,1'-biphenyl)[2-(2'-amino-1,1'-biphenyl)]palladium(II), X-Phos aminobiphenyl palladium chloride precatalyst [XPhos-Pd-G2] (31 mg, 19.89 μmol) was then added and the resulting mixture was heated in a sealed tube at 80° C. for 1 h. The mixture was allowed to cool to RT then was diluted with EtOAc (10 mL) and washed with brine (10 mL). The aqueous layer was washed with EtOAc (10 mL), the organics combined, dried over anhydrous Na$_2$SO$_4$, filtered and concentrated in vacuo. The residue was purified by Biotage Isolera™ chromatography (10 g KP-Sil, eluting with heptanes-EtOAc, 1:0 to 0:1) to afford the title compound (146.3 mg, 61%, 97% purity) as a beige solid.

LCMS (Method 4, 7 min) $R_t$=1.33 min, MS (ESIPos): m/z=351.1 (M+H)$^+$ $^1$H-NMR (400 MHz, DMSO-d6): δ [ppm]=11.32 (s, 1H), 8.14 (d, 1H), 8.04 (dd, 1H), 7.95 (d, 1H), 7.49 (d, 1H), 6.43 (d, 1H), 6.36 (s, 1H), 6.10 (s, 2H), 6.00-5.86 (m, 1H), 1.46 (d, 3H)

Example 166

(6S)-6-Methyl-5-[4-(pyridin-4-yl)-3-(trifluoromethyl)phenyl]-3,6-dihydro-2H-1,3,4-oxadiazin-2-one

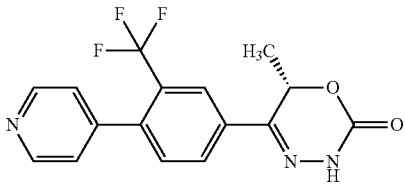 [SMILES: C[C@@H]1OC(=O)NN=C1c1ccc(-c2ccncc2)c(C(F)(F)F)c1]

The title compound was synthesized analogously to Example 3 from Intermediate 74.

LC-MS (Method 1): $R_t$=0.74 min, MS (ESIpos): m/z=336 [M+H]$^+$

Example 167

(6S)-6-Methyl-5-[4-(6-methylpyridin-3-yl)-3-(trifluoromethyl)phenyl]-3,6-dihydro-2H-1,3,4-oxadiazin-2-one

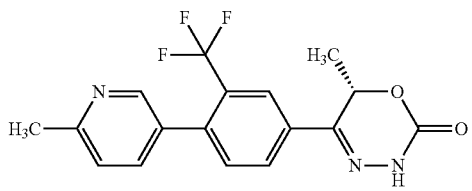 [SMILES: Cc1ccc(-c2ccc(C3=NNC(=O)O[C@H]3C)cc2C(F)(F)F)cn1]

The title compound was synthesized analogously to Example 3 from Intermediate 74.

LC-MS (Method 1): $R_t$=0.78 min: MS (ESIpos): m/z=350 [M+H]$^+$

Example 168

(6S)-5-[2'-Fluoro-4'-methyl-2-(trifluoromethyl)[1,1'-biphenyl]-4-yl]-6-methyl-3,6-dihydro-2H-1,3,4-oxadiazin-2-one

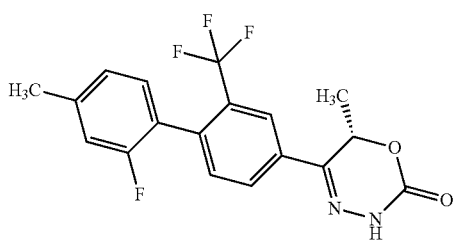 [SMILES: Cc1ccc(-c2ccc(C3=NNC(=O)O[C@H]3C)cc2C(F)(F)F)c(F)c1]

The title compound was synthesized analogously to Example 3 from Intermediate 74.

LC-MS (Method 1): $R_t$=1.27 min; MS (ESIpos): m/z=367 [M+H]$^+$

Example 169

(6S)-6-Methyl-5-[2',4',5'-trifluoro-2-(trifluoromethyl)[1,1'-biphenyl]-4-yl]-3,6-dihydro-2H-1,3,4-oxadiazin-2-one

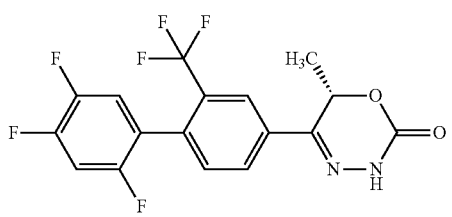

The title compound was synthesized analogously to Example 3 from Intermediate 74.

LC-MS (Method 1): $R_t$=1.25 min; MS (ESIpos): m/z=389 [M+H]$^+$

Example 170

(6S)-6-Methyl-5-[2',3',4'-trifluoro-2-(trifluoromethyl)[1,1'-biphenyl]-4-yl]-3,6-dihydro-2H-1,3,4-oxadiazin-2-one

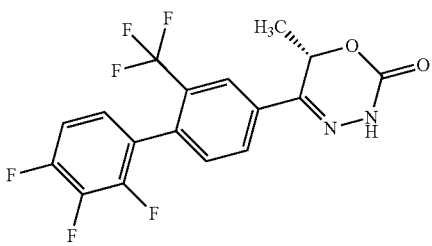 [SMILES: C[C@@H]1OC(=O)NN=C1c1ccc(-c2ccc(F)c(F)c2F)c(C(F)(F)F)c1]

The title compound was synthesized analogously to Example 3 from Intermediate 74.

LC-MS (Method 1): $R_t$=1.26 min: MS (ESIpos): m/z=389 [M+H]$^+$

Example 171

(6S)-5-[2',5'-Difluoro-2-(trifluoromethyl)[1,1'-biphenyl]-4-yl]-6-methyl-3,6-dihydro-2H-1,3,4-oxadiazin-2-one

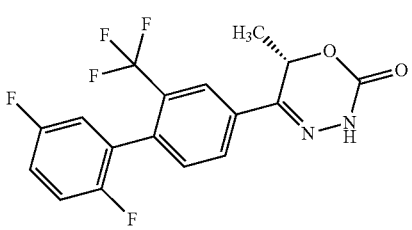 [SMILES: C[C@@H]1OC(=O)NN=C1c1ccc(-c2cc(F)ccc2F)c(C(F)(F)F)c1]

The title compound was synthesized analogously to Example 3 from Intermediate 74.

LC-MS (Method 1): $R_t$=1.21 min; MS (ESIpos): m/z=371 [M+H]$^+$

Example 172

4'-[(6S)-6-Methyl-2-oxo-3,6-dihydro-2H-1,3,4-oxadiazin-5-yl]-2'-(trifluoromethyl)[1,1'-biphenyl]-2-carbonitrile

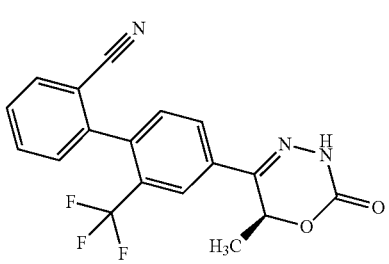 [SMILES: C[C@@H]1OC(=O)NN=C1c1ccc(-c2ccccc2C#N)c(C(F)(F)F)c1]

The title compound was synthesized analogously to Example 3 from Intermediate 74.
LC-MS (Method 1): $R_t$=1.09 min; MS (ESIpos): m/z=360 [M+H]$^+$ Example 173

(6S)-5-[4-(1H-Indol-5-yl)-3-(trifluoromethyl)phenyl]-6-methyl-3,6-dihydro-2H-1,3,4-oxadiazin-2-one

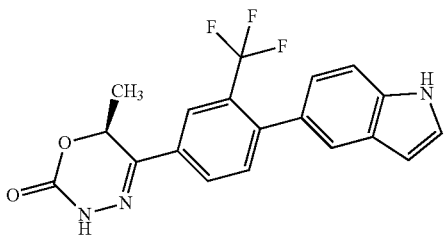 [SMILES: C[C@@H]1OC(=O)NN=C1c1ccc(-c2ccc3[nH]ccc3c2)c(C(F)(F)F)c1]

The title compound was synthesized analogously to Example 3 from Intermediate 74.
LC-MS (Method 1): $R_t$=1.09 min: MS (ESIpos): m/z=374 [M+H]$^+$ Example 174

(6S)-5-[4'-Hydroxy-2-(trifluoromethyl)[1,1'-biphenyl]-4-yl]-6-methyl-3,6-dihydro-2H-1,3,4-oxadiazin-2-one

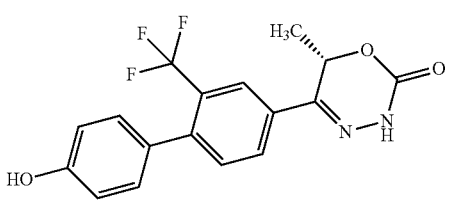 [SMILES: C[C@@H]1OC(=O)NN=C1c1ccc(-c2ccc(O)cc2)c(C(F)(F)F)c1]

The title compound was synthesized analogously to Example 3 from Intermediate 74.
LC-MS (Method 1): $R_t$=0.96 min; MS (ESIpos): m/z=351 [M+H]$^+$ Example 175

(6S)-5-[3'-Hydroxy-2-(trifluoromethyl)[1,1'-biphenyl]-4-yl]-6-methyl-3,6-dihydro-2H-1,3,4-oxadiazin-2-one

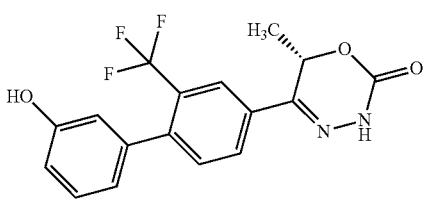 [SMILES: C[C@@H]1OC(=O)NN=C1c1ccc(-c2cccc(O)c2)c(C(F)(F)F)c1]

The title compound was synthesized analogously to Example 3 from Intermediate 74.

LC-MS (Method 1): $R_t$=1.00 min; MS (ESIpos): m/z=351 [M+H]$^+$

Example 176

(6S)-5-[3'-Amino-2-(trifluoromethyl)[1,1'-biphenyl]-4-yl]-6-methyl-3,6-dihydro-2H-1,3,4-oxadiazin-2-one

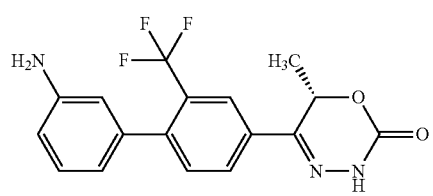 [SMILES: C[C@@H]1OC(=O)NN=C1c1ccc(-c2cccc(N)c2)c(C(F)(F)F)c1]

The title compound was synthesized analogously to Example 3 from Intermediate 74.
LC-MS (Method 1): $R_t$=0.94 min; MS (ESIpos): m/z=350 [M+H]$^+$ Example 177

(6S)-5-[2',4'-Difluoro-2-(trifluoromethyl)[1,1'-biphenyl]-4-yl]-6-methyl-3,6-dihydro-2H-1,3,4-oxadiazin-2-one

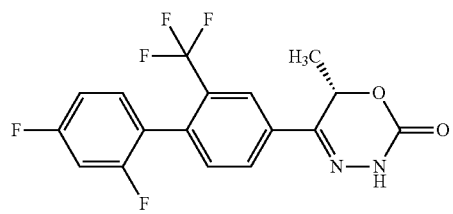 [SMILES: C[C@@H]1OC(=O)NN=C1c1ccc(-c2ccc(F)cc2F)c(C(F)(F)F)c1]

The title compound was synthesized analogously to Example 3 from Intermediate 74.
LC-MS (Method 1): $R_t$=1.23 min; MS (ESIpos): m/z=371 [M+H]$^+$ Example 178

(6S)-5-[3'-Fluoro-4'-methyl-2-(trifluoromethyl)[1,1'-biphenyl]-4-yl]-6-methyl-3,6-dihydro-2H-1,3,4-oxadiazin-2-one

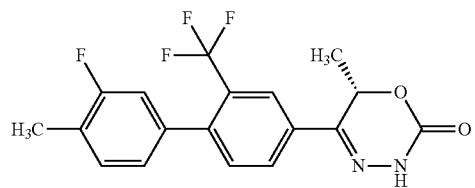 [SMILES: Cc1ccc(-c2ccc(C3=NNC(=O)O[C@H]3C)cc2C(F)(F)F)cc1F]

The title compound was synthesized analogously to Example 3 from Intermediate 74.
LC-MS (Method 1): $R_t$=1.31 min; MS (ESIpos): m/z=367 [M+H]$^+$

Example 179

(6S)-5-[2'-Fluoro-2-(trifluoromethyl)[1,1'-biphenyl]-4-yl]-6-methyl-3,6-dihydro-2H-1,3,4-oxadiazin-2-one

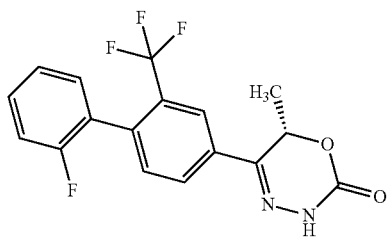 [SMILES: C[C@@H]1OC(=O)NN=C1c1ccc(-c2ccccc2F)c(C(F)(F)F)c1]

The title compound was synthesized analogously to Example 3 from Intermediate 74.
LC-MS (Method 1): $R_t$=1.19 min; MS (ESIpos): m/z=353 [M+H]$^+$

Example 180

(6S)-5-[2'-Methoxy-2-(trifluoromethyl)[1,1'-biphenyl]-4-yl]-6-methyl-3,6-dihydro-2H-1,3,4-oxadiazin-2-one

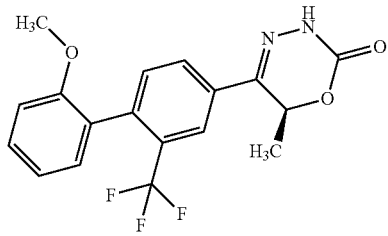 [SMILES: COc1ccccc1-c1ccc(C2=NNC(=O)O[C@H]2C)cc1C(F)(F)F]

The title compound was synthesized analogously to Example 3 from Intermediate 74.
LC-MS (Method 1): $R_t$=1.19 min; MS (ESIpos): m/z=365 [M+H]$^+$

Example 181

(6S)-5-[3'-Fluoro-2-(trifluoromethyl)[1,1'-biphenyl]-4-yl]-6-methyl-3,6-dihydro-2H-1,3,4-oxadiazin-2-one

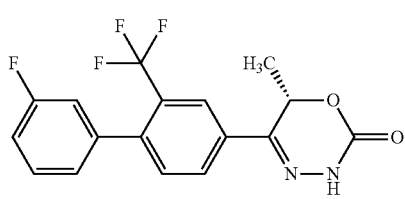 [SMILES: C[C@@H]1OC(=O)NN=C1c1ccc(-c2cccc(F)c2)c(C(F)(F)F)c1]

The title compound was synthesized analogously to Example 3 from Intermediate 74.
LC-MS (Method 1): $R_t$=1.23 min; MS (ESIpos): m/z=353 [M+H]$^+$

Example 182

(6S)-6-Methyl-5-[4-(4-methylpyridin-3-yl)-3-(trifluoromethyl)phenyl]-3,6-dihydro-2H-1,3,4-oxadiazin-2-one

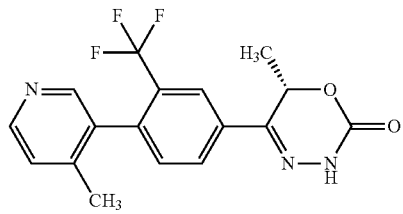 [SMILES: Cc1ccncc1-c1ccc(C2=NNC(=O)O[C@H]2C)cc1C(F)(F)F]

The title compound was synthesized analogously to Example 3 from Intermediate 74.
LC-MS (Method 1): $R_t$=0.73 min; MS (ESIpos): m/z=350 [M+H]$^+$

Example 183

(6S)-6-Methyl-5-[4-(3-methylpyridin-4-yl)-3-(trifluoromethyl)phenyl]-3,6-dihydro-2H-1,3,4-oxadiazin-2-one

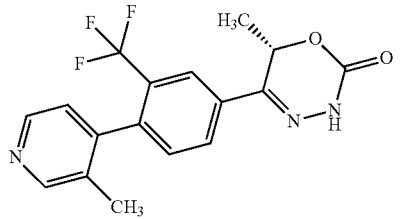 [SMILES: Cc1cnccc1-c1ccc(C2=NNC(=O)O[C@H]2C)cc1C(F)(F)F]

The title compound was synthesized analogously to Example 3 from Intermediate 74.
LC-MS (Method 1): $R_t$=0.72 min; MS (ESIpos): m/z=350 [M+H]$^+$

Example 184

(6S)-6-Methyl-5-[4-(2-methylpyridin-4-yl)-3-(trifluoromethyl)phenyl]-3,6-dihydro-2H-1,3,4-oxadiazin-2-one

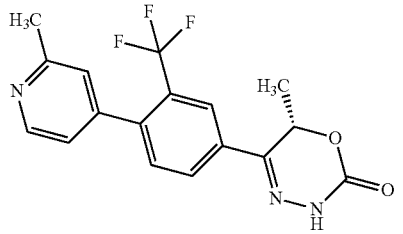 [SMILES: Cc1cc(-c2ccc(C3=NNC(=O)O[C@H]3C)cc2C(F)(F)F)ccn1]

The title compound was synthesized analogously to Example 3 from Intermediate 74.
LC-MS (Method 1): $R_t$=0.68 min; MS (ESIpos): m/z=350 [M+H]$^+$

Example 185

(6S)-5-[4-(1H-Indol-6-yl)-3-(trifluoromethyl)phenyl]-6-methyl-3,6-dihydro-2H-1,3,4-oxadiazin-2-one

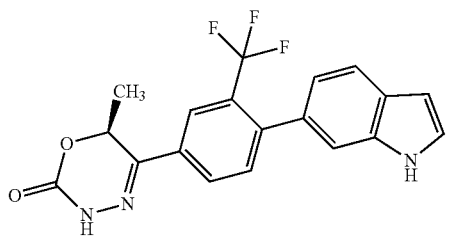 [SMILES: C[C@@H]1OC(=O)NN=C1c1ccc(-c2ccc3cc[nH]c3c2)c(C(F)(F)F)c1]

The title compound was synthesized analogously to Example 3 from Intermediate 74.

LC-MS (Method 1): $R_t$=1.15 min; MS (ESIpos): m/z=374 [M+H]$^+$

Example 186

(6S)-5-[2'-Ethyl-2-(trifluoromethyl)[1,1'-biphenyl]-4-yl]-6-methyl-3,6-dihydro-2H-1,3,4-oxadiazin-2-one

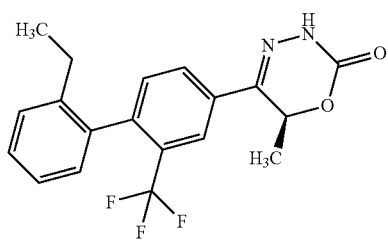 [SMILES: CCc1ccccc1-c1ccc(C2=NNC(=O)O[C@H]2C)cc1C(F)(F)F]

The title compound was synthesized analogously to Example 3 from Intermediate 74.

LC-MS (Method 1): $R_t$=1.32 min; MS (ESIpos): m/z=363 [M+H]$^+$

Example 187

(6S)-5-[4-(6-Methoxypyridin-3-yl)-3-(trifluoromethyl)phenyl]-6-methyl-3,6-dihydro-2H-1,3,4-oxadiazin-2-one

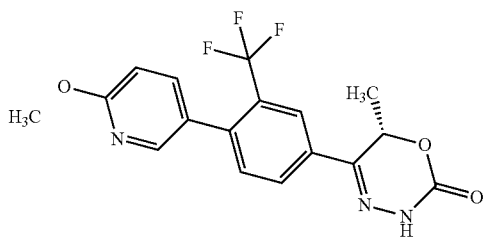

The title compound was synthesized analogously to Example 3 from Intermediate 74.

LC-MS (Method 1): $R_t$=1.12 min; MS (ESIpos): m/z=366 [M+H]$^+$

Example 188

(6S)-5-[4'-Methoxy-2-(trifluoromethyl)[1,1'-biphenyl]-4-yl]-6-methyl-3,6-dihydro-2H-1,3,4-oxadiazin-2-one

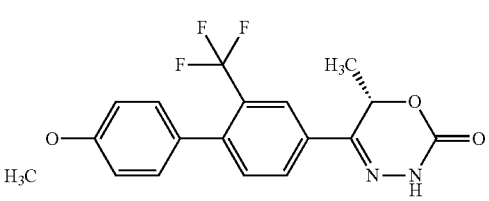

The title compound was synthesized analogously to Example 3 from Intermediate 74.

LC-MS (Method 1): $R_t$=1.20 min; MS (ESIpos): m/z=365 [M+H]$^+$

Example 189

(6S)-6-Methyl-5-[4'-methyl-2-(trifluoromethyl)[1,1'-biphenyl]-4-yl]-3,6-dihydro-2H-1,3,4-oxadiazin-2-one

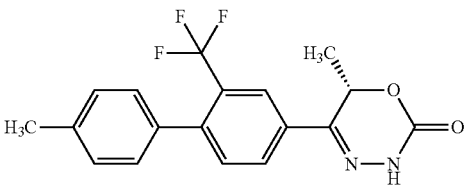

The title compound was synthesized analogously to Example 3 from Intermediate 74.

LC-MS (Method 1): $R_t$=1.30 min, MS (ESIpos): m/z=349 [M+H]$^+$

Example 190

(6S)-5-{4-[1-(Difluoromethyl)-1H-pyrazol-4-yl]-3-(trifluoromethyl)phenyl}-6-methyl-3,6-dihydro-2H-1,3,4-oxadiazin-2-one

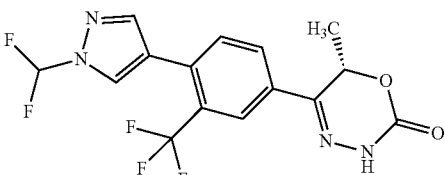

The title compound was synthesized analogously to Example 3 from Intermediate 74.

LCMS (Method 3, 2 min) 100% @ Rt=1.10 mins, MS (ESIPos): m/z=374.90 (M+H)$^+$

LCMS (Method 3, 7 min) 100% @ Rt=3.83 mins, MS (ESIPos): m/z=374.85 (M+H)+

¹H NMR (250 MHz, Chloroform-d) δ=1.68 (d, J=7.0 Hz, 3H), 5.62 (q, J=7.0 Hz, 1H), 7.02-7.52 (m, 1H), 7.54 (d, J=8.2 Hz, 1H), 7.76-7.90 (m, 1H), 7.99 (s, 1H), 8.10 (s, 1H), 8.35 (s, 1H).

Example 191

(rac)-5-{4-[1-(Difluoromethyl)-1H-pyrazol-4-yl]-3-(trifluoromethyl)phenyl}-6-methyl-3,6-dihydro-2H-1,3,4-oxadiazin-2-one

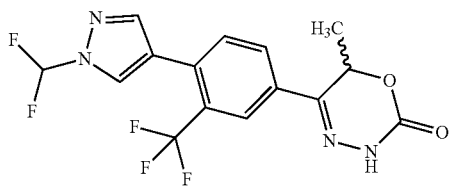 [SMILES: CC1OC(=O)NN=C1c1ccc(-c2cnn(C(F)F)c2)c(C(F)(F)F)c1]

The title compound was synthesized analogously to Example 3 from Intermediate 68.

LCMS (Method 3, 7 min) 100% @ Rt=2.97 mins, MS (ESIPos): m/z=375.1 (M+H)+

¹H NMR (500 MHz, DMSO-d6) δ 1.45 (d, J=6.9 Hz, 3H), 5.93 (q, J=6.9 Hz, 1H), 7.69 (d, J=8.2 Hz, 1H), 7.76-8.01 (m, 2H), 8.04 (dd, J=1.7, 8.2 Hz, 1H), 8.16 (d, J=1.5 Hz, 1H), 8.48 (s, 1H), 11.30 (br. s, 1H).

Example 192

(rac)-5-[4'-Fluoro-2-(trifluoromethyl)[1,1'-biphenyl]-4-yl]-6-methyl-3,6-dihydro-2H-1,3,4-oxadiazin-2-one

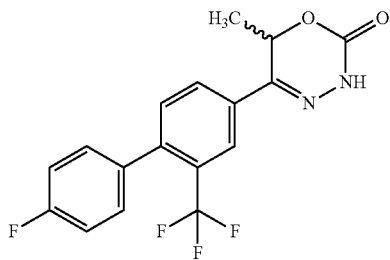 [SMILES: CC1OC(=O)NN=C1c1ccc(-c2ccc(F)cc2)c(C(F)(F)F)c1]

The title compound was synthesized analogously to Example 3 from Intermediate 68.

LCMS (Method 4, 7 min) Rt=3.62 min, MS (ESIPos): m/z=353.1 (M+H)+

¹H NMR (500 MHz, DMSO-d6) δ 1.44-1.50 (m, 3H), 5.94 (q, J=6.9 Hz, 1H), 7.28-7.33 (m, 2H), 7.37-7.41 (m, 2H), 7.52 (d, J=8.1 Hz, 1H), 8.04 (dd, J=1.4, 8.1 Hz, 1H), 8.15 (d, J=1.4 Hz, 1H), 11.30 (s, 1H).

Chiral Analysis conditions: Column: Cellulose-3 25 cm, Mobile phase: 25% Ethanol: 75% CO₂, Flow rate: 4 mL/min, UV at 280 nm, Runtime: 5 min, Neg ion MS Example 193

5-{4-[1-(Difluoromethyl)-1H-pyrazol-4-yl]-3-fluoro-5-(trifluoromethyl)phenyl}-3,6-dihydro-2H-1,3,4-oxadiazin-2-one

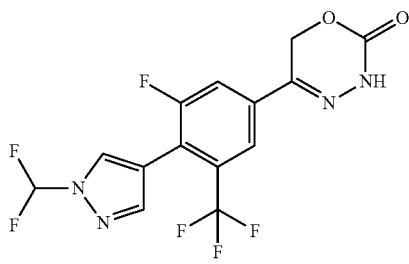 [SMILES: O=C1NN=C(c2cc(F)c(-c3cnn(C(F)F)c3)c(C(F)(F)F)c2)CO1]

The title compound was synthesized analogously to Example 3 from Intermediate 69. LC-MS (Method 1): R_t=1.06 min; MS (ESIpos): m/z=379 [M+H]+

¹H-NMR (400 MHz, DMSO-d6) δ[ppm]: 2.518 (2.77), 2.523 (2.01), 5.458 (16.00), 7.764 (1.60), 7.911 (3.39), 7.950 (4.30), 7.965 (1.44), 7.969 (1.74), 7.991 (7.30), 8.059 (1.39), 8.506 (5.10), 11.345 (4.91).

Example 195

5-{3-(Difluoromethyl)-4-[1-(difluoromethyl)-1H-pyrazol-4-yl]phenyl}-3,6-dihydro-2H-1,3,4-oxadiazin-2-one

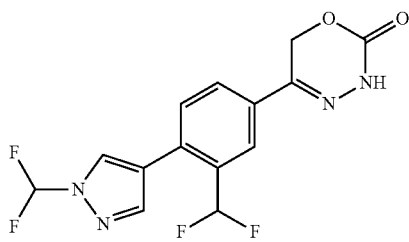 [SMILES: O=C1NN=C(c2ccc(-c3cnn(C(F)F)c3)c(C(F)F)c2)CO1]

The title compound was synthesized analogously to Example 3 from Intermediate 77.

LC-MS (Method 1): R_t=0.98 min; MS (ESIpos): m/z=343 [M+H]+

¹H-NMR (400 MHz, DMSO-d6) δ[ppm]: 2.323 (0.47), 2.327 (0.66), 2.522 (5.80), 2.665 (0.49), 2.669 (0.67), 5.442 (16.00), 7.007 (1.44), 7.143 (3.09), 7.279 (1.29), 7.677 (2.23), 7.697 (2.73), 7.755 (1.76), 7.897 (2.13), 7.901 (4.21), 7.916 (1.69), 8.049 (4.88), 8.085 (6.78), 8.505 (6.67), 11.194 (4.98).

Example 196

(6S)-6-Methyl-5-{4-[(morpholin-4-yl)methyl]-3-(trifluoromethyl)phenyl}-3,6-dihydro-2H-1,3,4-oxadiazin-2-one

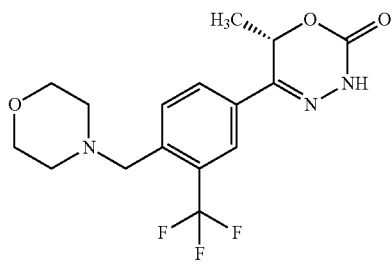 [SMILES: C[C@@H]1OC(=O)NN=C1c1ccc(CN2CCOCC2)c(C(F)(F)F)c1]

A biphasic mixture of (6S)-5-[4-chloro-3-(trifluoromethyl)phenyl]-6-methyl-3,6-dihydro-2H-1,3,4-oxadiazin-2-one (200 mg, 0.68 mmol, Intermediate 74), potassium (morpholin-4-yl)methyltrifluoroborate (212 mg, 1.03 mmol), potassium acetate (201 mg, 2.05 mmol), palladium (II) acetate (20.2 mg, 0.03 mmol) and 2-dicyclohexylphosphino-2',6'-di-i-propoxy-1,1'-biphenyl/RuPhos (31.9 mg, 0.07 mmol) in toluene/water (12:1 v:v; 3.4 mL) was degassed via nitrogen-filled balloon for 5 minutes. The resulting mixture was heated at 100° C. for 16 hours. After this time, the reaction mixture was diluted with EtOAc and water and was filtered through a pad of Celite. The organic layer was isolated, washed with saturated aqueous sodium chloride solution, dried (MgSO$_4$), filtered and concentrated in vacuo. The residual material was purified by Biotage Isolera™ chromatography (silica gel, eluting with heptanes-EtOAc, 1:0 to 0:1), with the desired fractions combined and concentrated in vacuo. The resulting gum was dissolved in diethyl ether and concentrated in vacuo to afford the desired compound (135 mg, 53%) as a yellow solid.

LCMS (Method 3, 2 min) 100% @ Rt=0.79 min, MS (ESIpos): m/z=358.05 (M+H)$^+$.

LCMS (Method 3, 7 min) 96% @ Rt=2.41 min, MS (ESIpos): m/z=358.05 (M+H)$^+$.

$^1$H NMR (500 MHz, Chloroform-d) δ=1.66 (d, J=7.0 Hz, 3H), 2.49-2.54 (m, 4H), 3.71 (s, 2H), 3.73-3.79 (m, 4H), 5.58 (q, J=7.0 Hz, 1H), 7.78 (dd, J=8.2, 1.7 Hz, 1H), 7.87-7.99 (m, 2H), 8.18 (s, 1H); the material thus obtained contained 2.5% Et$_2$O (by NMR signal integration)

Example 197

5-{4-[(Morpholin-4-yl)methyl]-3-(trifluoromethyl)phenyl}-3,6-dihydro-2H-1,3,4-oxadiazin-2-one

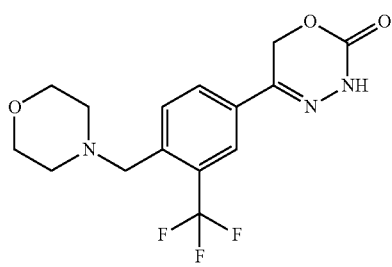 [SMILES: O=C1NN=C(c2ccc(CN3CCOCC3)c(C(F)(F)F)c2)CO1]

The title compound was prepared in analogy to Example 196 from Intermediate 64.

LC-MS (Method 1): R$_t$=0.62 min; MS (ESIpos): m/z=344 [M+H]$^+$ $^1$H-NMR (400 MHz, DMSO-d6) δ[ppm]: 2.388 (4.77), 2.399 (3.58), 2.518 (1.63), 2.523 (1.06), 3.581 (4.43), 3.592 (6.01), 3.604 (4.27), 3.640 (5.70), 5.416 (16.00), 7.858 (1.56), 7.879 (2.28), 7.959 (2.28), 7.977 (6.36), 11.182 (4.83).

Example 198

5-[2-(Difluoromethyl)-4'-fluoro[1,1'-biphenyl]-4-yl]-3,6-dihydro-2H-1,3,4-oxadiazin-2-one

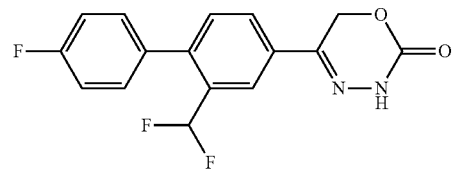 [SMILES: O=C1NN=C(c2ccc(-c3ccc(F)cc3)c(C(F)F)c2)CO1]

To a solution of 5-(4-bromo-3-(difluoromethyl)phenyl)-3H-1,3,4-oxadiazin-2(6H)-one (100 mg, 0.3 mmol, Intermediate 77) in dioxane/water (5 mL, v:v=5:1) were added 1,1'-bis(diphenylphosphino)ferrocenepalladium(II) chloride (26 mg (0.03 mmol), sodium carbonate solid (100 mg, 1.0 mmol) and 4-fluorophenylboronic acid (91 mg, 0.6 mmol), and the mixture was stirred at 100° C. overnight under nitrogen atmosphere. Upon completion of the reaction, the solvent was removed in vacuo and the residue was diluted with water. The resulting mixture was extracted with ethyl acetate and the combined organic layers were dried over anhydrous sodium sulfate. The solvent was removed in vacuo and the residue was purified with silica gel column chromatography (petroleum ether: ethyl acetate=2:1) to give 40 mg of the still impure title compound, which was then re-purified by Prep-HPLC [Column:XBridge C18 19*150; Mobile Phase A: Water/10 mmol/L NH$_4$HCO$_3$, Mobile Phase B: ACN, Flow rate: 20 mL/min; Gradient: 35% B to 60% B in 8 min] to give 10.8 mg (10% yield) of the title compound as a white solid.

MS(ESIpos): m/z=319 (M−H)*.

Example 199

5-[4'-Chloro-2-(difluoromethyl)[1,1'-biphenyl]-4-yl]-3,6-dihydro-2H-1,3,4-oxadiazin-2-one

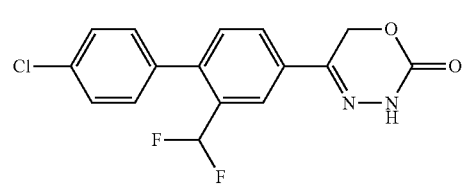 [SMILES: O=C1NN=C(c2ccc(-c3ccc(Cl)cc3)c(C(F)F)c2)CO1]

The title compound was prepared in analogy to Example 198 from Intermediate 77.

MS(ESIpos): m/z=335 (M−H)*.

Example 200

5-[3-(Difluoromethyl)-4-(6-methylpyridin-3-yl)phenyl]-3,6-dihydro-2H-1,3,4-oxadiazin-2-one

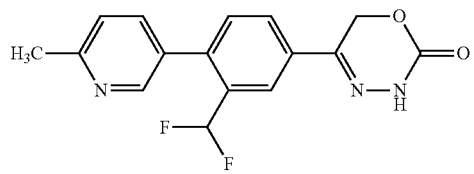 [SMILES: Cc1ccc(-c2ccc(C3=NNC(=O)OC3)cc2C(F)F)cn1]

The title compound was prepared in analogy to Example 198 from Intermediate 77.

MS(ESIpos): m/z=318 (M+H)$^+$.

Example 201

5-[4-(Cyclopent-1-en-1-yl)-3-(difluoromethyl)phenyl]-3,6-dihydro-2H-1,3,4-oxadiazin-2-one

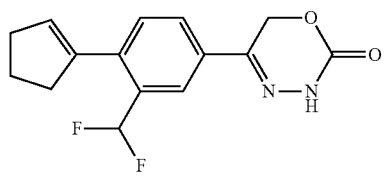 [SMILES: O=C1NN=C(c2ccc(C3=CCCC3)c(C(F)F)c2)CO1]

The title compound was prepared in analogy to Example 198 from Intermediate 77.

MS(ESIpos): m/z=291 (M−H)$^+$.

Example 202

5-[3-(Difluoromethyl)-4-(1H-pyrazol-4-yl)phenyl]-3,6-dihydro-2H-1,3,4-oxadiazin-2-one

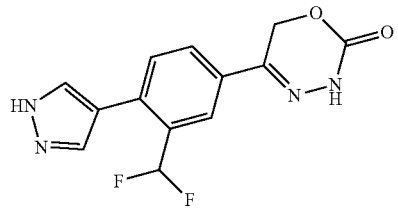 [SMILES: O=C1NN=C(c2ccc(-c3cn[nH]c3)c(C(F)F)c2)CO1]

The title compound was prepared in analogy to Example 198 from Intermediate 77.

MS(ESIpos): m/z=293 (M+H)$^+$.

Example 203

5-[4-(3-Hydroxy-3-methylazetidin-1-yl)-3-(trifluoromethyl)phenyl]-3,6-dihydro-2H-1,3,4-oxadiazin-2-one

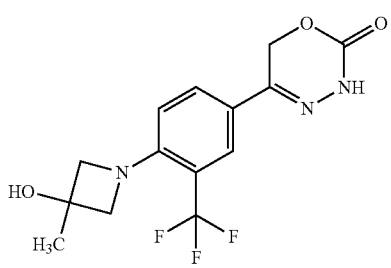 [SMILES: CC1(O)CN(c2ccc(C3=NNC(=O)OC3)cc2C(F)(F)F)C1]

5-[4-Fluoro-3-(trifluoromethyl)phenyl]-3,6-dihydro-2H-1,3,4-oxadiazin-2-one (160 mg, 610 µmol, Intermediate 66) was dissolved in DMSO (2.0 ml), and 3-methylazetidin-3-ol hydrogen chloride (113 mg, 915 µmol) and potassium carbonate (253 mg, 1.83 mmol) were added. The mixture was stirred at 100° C. overnight. The reaction mixture was diluted with DMSO, filtered and purified by preparative HPLC to give 69.0 mg (95% purity, 33% yield) of the title compound.

LC-MS (Method 1): $R_t$=0.92 min; MS (ESIpos): m/z=330 [M+H]$^+$ $^1$H-NMR (400 MHz, DMSO-d6) δ[ppm]: 1.439 (16.00), 2.074 (0.54), 2.323 (0.62), 2.326 (0.83), 2.331 (0.62), 2.665 (0.62), 2.669 (0.81), 2.673 (0.62), 3.892 (2.29), 3.912 (4.58), 3.946 (5.07), 3.967 (2.44), 5.311 (14.85), 5.639 (4.09), 6.619 (2.76), 6.642 (2.83), 7.736 (1.79), 7.742 (2.15), 7.764 (2.33), 7.778 (4.22), 7.782 (3.22), 10.918 (5.44).

Example 204

(rac)-5-[4-{[3,3,3-trifluoro-2-hydroxypropyl]amino}-3-(trifluoromethyl)phenyl]-3,6-dihydro-2H-1,3,4-oxadiazin-2-one

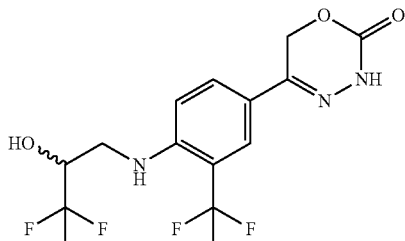

The title compound was prepared analogously to Example 203 from Intermediate 66.

LC-MS (Method 1): $R_t$=1.00 min; MS (ESIpos): m/z=372 [M+H]$^+$ $^1$H-NMR (400 MHz, DMSO-d6) δ[ppm]: 2.074 (1.23), 2.522 (0.95), 3.366 (0.46), 3.380 (0.59), 3.385 (0.60), 3.400 (1.07), 3.419 (0.85), 3.434 (0.64), 3.547 (0.67), 3.559 (0.99), 3.572 (0.78), 3.581 (0.58), 3.593 (0.68), 3.607 (0.47), 4.233 (0.69), 4.244 (0.79), 4.251 (0.77), 4.261 (0.70), 5.309

(16.00), 5.838 (0.83), 5.852 (1.62), 5.867 (0.82), 6.615 (3.02), 6.632 (3.00), 6.975 (2.08), 6.997 (2.16), 7.759 (7.02), 7.780 (1.72), 10.911 (5.36).

Example 205

5-{4-[(Oxan-4-yl)amino]-3-(trifluoromethyl)phenyl}-3,6-dihydro-2H-1,3,4-oxadiazin-2-one

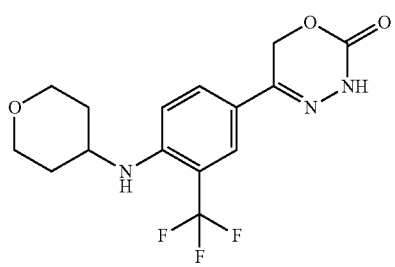 [SMILES: O=C1NN=C(c2ccc(NC3CCOCC3)c(C(F)(F)F)c2)CO1]

5-[4-Fluoro-3-(trifluoromethyl)phenyl]-3,6-dihydro-2H-1,3,4-oxadiazin-2-one (291 mg, 1.11 mmol, Intermediate 66) was dissolved in DMSO (2.0 ml), and oxan-4-amine (225 mg, 2.22 mmol) was added. The mixture was stirred overnight at 100° C. Another portion of oxan-4-amine (113 mg, 1.11 mmol) was added and stirred overnight at 100° C. The reaction mixture was diluted with DMSO, filtered and purified by preparative HPLC to give 139 mg (95% purity, 35% yield) of the title compound.

LC-MS (Method 1): $R_t$=1.01 min, MS (ESIpos): m/z=344 [M+H]$^+$ $^1$H-NMR (400 MHz, DMSO-d6) δ[ppm]: 1.535 (0.43), 1.546 (0.50), 1.567 (1.09), 1.575 (1.16), 1.594 (1.29), 1.606 (1.17), 1.624 (0.65), 1.634 (0.56), 1.818 (1.67), 1.824 (1.69), 1.850 (1.33), 1.855 (1.31), 2.518 (1.10), 2.522 (0.69), 3.401 (1.24), 3.406 (1.50), 3.430 (2.82), 3.434 (2.82), 3.459 (1.61), 3.463 (1.33), 3.731 (0.61), 3.741 (0.56), 3.750 (0.60), 3.845 (1.68), 3.865 (1.26), 3.871 (1.50), 5.162 (1.41), 5.183 (1.37), 5.302 (16.00), 7.039 (1.85), 7.064 (1.98), 7.736 (4.97), 7.741 (2.83), 7.752 (1.74), 10.898 (5.13).

Example 206

(cis/trans)-5-[4-{[3-hydroxycyclobutyl]amino}-3-(trifluoromethyl)phenyl]-3,6-dihydro-2H-1,3,4-oxadiazin-2-one

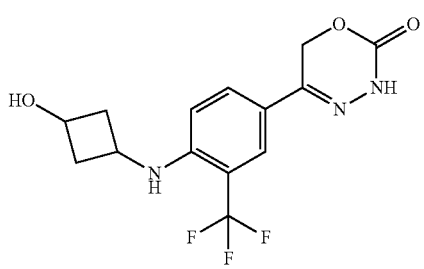 [SMILES: O=C1NN=C(c2ccc(NC3CC(O)C3)c(C(F)(F)F)c2)CO1]

5-[4-Fluoro-3-(trifluoromethyl)phenyl]-3,6-dihydro-2H-1,3,4-oxadiazin-2-one (130 mg, 496 μmol, Intermediate 66) was dissolved in DMSO (1.0 ml), N,N-diisopropylethylamine (260 μl. 1.5 mmol), and (cis/trans)-3-aminocyclobutan-1-ol hydrogen chloride (135 mg, 1.09 mmol) were added.

The mixture was stirred at 100° C. overnight and then 2 another days at 100° C. The reaction mixture was diluted with DMSO, filtered and purified by preparative HPLC to give 70.0 mg (95% purity, 41% yield) of the title compound.

LC-MS (Method 1): $R_t$=0.84 min; MS (ESIpos): m/z=330 [M+H]$^+$ $^1$H-NMR (400 MHz, DMSO-d6) δ[ppm]: 1.805 (0.77), 1.812 (0.59), 1.825 (1.72), 1.833 (1.60), 1.846 (1.64), 1.853 (1.84), 1.867 (0.64), 1.874 (0.83), 2.254 (0.49), 2.518 (3.34), 2.523 (2.22), 2.539 (0.94), 2.696 (0.74), 2.703 (0.76), 2.713 (1.64), 2.720 (1.60), 2.725 (1.29), 2.730 (1.35), 2.735 (1.63), 2.742 (1.61), 2.752 (0.76), 2.759 (0.77), 3.449 (0.46), 3.468 (0.85), 3.484 (0.83), 3.501 (0.44), 3.855 (0.59), 3.873 (1.13), 3.890 (1.13), 3.907 (0.56), 5.095 (2.90), 5.103 (0.87), 5.111 (2.78), 5.271 (0.50), 5.296 (16.00), 5.621 (1.65), 5.636 (1.87), 6.759 (1.96), 6.782 (2.04), 7.726 (1.87), 7.742 (5.61), 10.897 (4.98).

Example 207

(rac)-5-{4-[2,4-Dimethylazetidin-1-yl]-3-(trifluoromethyl)phenyl}-3,6-dihydro-2H-1,3,4-oxadiazin-2-one

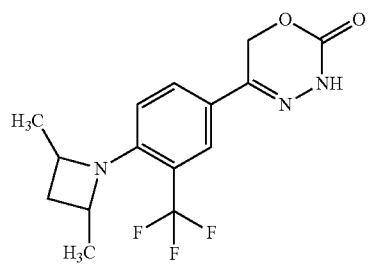 [SMILES: CC1CC(C)N1c1ccc(C2=NNC(=O)OC2)cc1C(F)(F)F]

5-[4-fluoro-3-(trifluoromethyl)phenyl]-3,6-dihydro-2H-1,3,4-oxadiazin-2-one (150 mg, 572 μmol, Intermediate 66) was dissolved in DMSO (1.0 ml), and (rac)-2,4-dimethylazetidine hydrogen chloride (153 mg, 1.26 mmol) was added. The mixture was stirred at 100° C. overnight. The reaction mixture was diluted with DMSO, filtered and purified by preparative HPLC to give 34.0 mg (95% purity, 17% yield) of the title compound.

LC-MS (Method 1): $R_t$=1.28 min; MS (ESIpos): m/z=328 [M+H]$^+$ $^1$H-NMR (400 MHz, DMSO-d6) δ[ppm]: 1.180 (15.90), 1.196 (16.00), 1.331 (8.34), 1.346 (8.44), 1.371 (0.78), 1.452 (0.51), 1.467 (0.99), 1.478 (0.71), 1.482 (0.68), 1.493 (0.99), 1.508 (0.54), 1.905 (0.71), 2.037 (1.87), 2.327 (1.97), 2.331 (1.43), 2.518 (8.14), 2.523 (5.45), 2.665 (1.57), 2.669 (2.14), 2.674 (2.21), 2.696 (0.68), 2.701 (0.95), 2.722 (0.48), 4.106 (0.58), 4.122 (0.99), 4.140 (0.99), 4.156 (0.61), 4.457 (2.35), 4.471 (2.31), 5.289 (1.19), 5.326 (14.33), 5.332 (13.92), 5.339 (9.02), 5.370 (1.06), 6.897 (4.09), 6.919 (4.26), 7.196 (1.19), 7.220 (1.23), 7.768 (2.76), 7.773 (3.06), 7.790 (2.45), 7.795 (3.00), 7.822 (3.03), 7.828 (7.76), 7.834 (5.79), 8.026 (0.68), 8.031 (0.61), 10.970 (8.10), 10.997 (2.55).

Example 208

(cis or trans)-5-{4-[2,4-Dimethylazetidin-1-yl]-3-(trifluoromethyl)phenyl}-3,6-dihydro-2H-1,3,4-oxadiazin-2-one

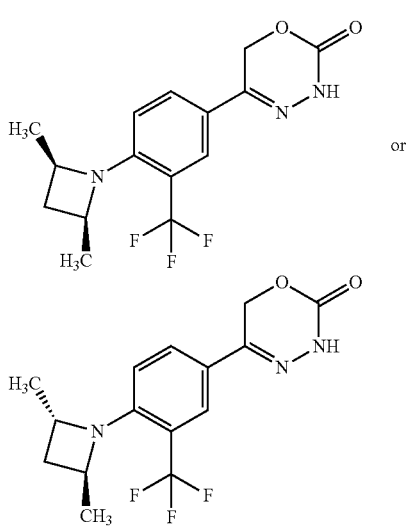

Byproduct from example 207, single stereoisomer: 32.0 mg (95% purity, 16% yield).

LC-MS (Method 1): $R_t$=1.30 min, MS (ESIpos): m/z=328 [M+H]$^+$ $^1$H-NMR (400 MHz, DMSO-d6) δ[ppm]: 1.180 (0.55), 1.196 (0.50), 1.330 (16.00), 1.346 (15.95), 1.452 (0.85), 1.467 (1.64), 1.478 (1.09), 1.482 (1.09), 1.493 (1.66), 1.508 (0.84), 2.323 (0.53), 2.326 (0.68), 2.331 (0.50), 2.522 (2.13), 2.653 (0.82), 2.674 (2.18), 2.679 (1.27), 2.696 (1.18), 2.700 (1.66), 2.721 (0.76), 4.105 (1.18), 4.122 (2.02), 4.140 (1.94), 4.156 (1.10), 5.339 (15.37), 7.196 (2.28), 7.219 (2.38), 7.821 (4.79), 7.827 (3.48), 7.836 (2.35), 10.997 (4.38).

Example 209

5-[4-{[3,3,3-Trifluoro-(2S)-hydroxypropyl]amino}-3-(trifluoromethyl)phenyl]-3,6-dihydro-2H-1,3,4-oxadiazin-2-one

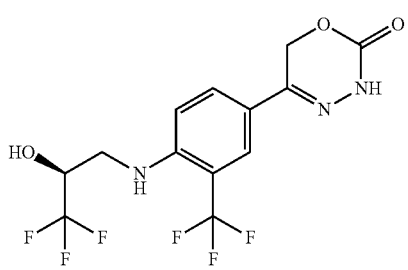 [SMILES: O=C1NN=C(c2ccc(NC[C@H](O)C(F)(F)F)c(C(F)(F)F)c2)CO1]

5-[4-Fluoro-3-(trifluoromethyl)phenyl]-3,6-dihydro-2H-1,3,4-oxadiazin-2-one (530 mg, 1.86 mmol, Intermediate 66) was dissolved in DMSO (9 mL), and (2S)-3-amino-1,1,1-trifluoropropan-2-ol hydrochloride (1:1) (1.4 g, 7.8 mmol) was added, followed by calcium carbonate (0.8 g, 7.7 mmol). The mixture was stirred at 100° C. for 3 days. The reaction mixture was filtered and purified by preparative HPLC (Basic, Gradient: 0.00-0.50 min 17% B (40->70 mL/min), 0.51-5.50 min 33-34% B (70 mL/min)) to give 237 mg (99% purity, 16% yield) of the title compound.

LC-MS (Method 1): $R_t$=1.00 min; MS (ESIpos): m/z=372 [M+H]$^+$ $^1$H-NMR (400 MHz, DMSO-d$_6$): δ [ppm]=10.91 (s, 1H), 7.76 (s, 1H), 7.77 (d, 1H), 6.99 (d, 1H), 6.64 (d, 1H), 5.85 (br t, 1H), 5.31 (s, 2H), 4.25 (br d, 1H), 3.58 (dt, 1H), 3.44-3.36 (m, 1H)

Example 210

5-{4-[(2-Hydroxy-2-methylpropyl)amino]-3-(trifluoromethyl)phenyl}-3,6-dihydro-2H-1,3,4-oxadiazin-2-one

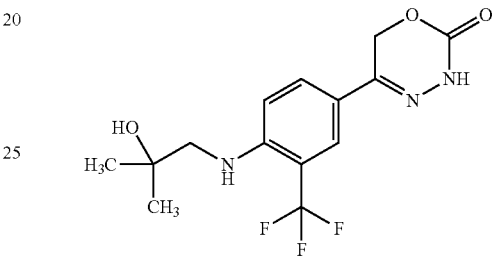

5-[4-Fluoro-3-(trifluoromethyl)phenyl]-3,6-dihydro-2H-1,3,4-oxadiazin-2-one (3.2 g, 12.3 mmol, Intermediate 66) was dissolved in DMSO (22 mL), and 1-amino-2-methylpropan-2-ol (2.2 g, 24.6 mmol) was added, followed by calcium carbonate (1.23 g, 12.3 mmol). The mixture was stirred at 100° C. for 5 days. The reaction mixture was filtered and purified by preparative HPLC (acidic conditions) to give 3.1 g (99% purity, 76% yield) of the title compound.

LC-MS (Method 1): $R_t$=0.95 min; MS (ESIpos): m/z=332 [M+H]$^+$ $^1$H-NMR (400 MHz, DMSO-d$_6$): δ [ppm]=10.89 (s, 1H), 7.74 (s, 1H), 7.75 (d, 1H), 6.94 (d, 1H), 5.40-5.34 (m, 1H), 5.30 (s, 2H), 4.82 (s, 1H), 3.12 (d, 2H), 1.23-1.14 (m, 6H)

Example 211

(trans)-5-[4-{[4-Hydroxycyclohexyl]amino}-3-(trifluoromethyl)phenyl]-3,6-dihydro-2H-1,3,4-oxadiazin-2-one

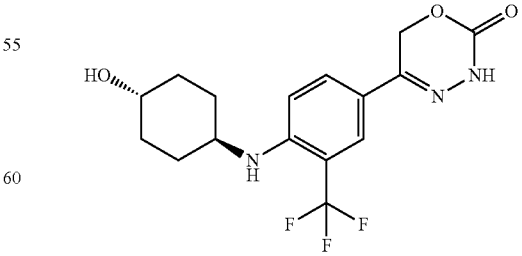

5-[4-Fluoro-3-(trifluoromethyl)phenyl]-3,6-dihydro-2H-1,3,4-oxadiazin-2-one (320 mg, 97% purity, 1.18 mmol, Intermediate 66) was dissolved in DMSO (3.0 ml), and (trans)-4-aminocyclohexan-1-ol (273 mg, 2.37 mmol) was added. The mixture was stirred at 100° C. for 3 d. The reaction mixture was diluted with DMSO, filtered and purified by preparative HPLC to give 234 mg (97% purity, 54% yield) of the title compound.

LC-MS (Method 2): $R_t$=0.93 min, MS (ESIneg): m/z=356 [M–H]⁻

¹H-NMR (400 MHz, DMSO-d6) δ[ppm]: 1.290 (1.19), 1.297 (1.06), 1.322 (2.77), 1.352 (2.73), 1.378 (1.12), 1.384 (1.27), 1.416 (0.42), 1.802 (1.57), 1.828 (1.98), 1.880 (2.09), 1.906 (1.44), 2.073 (0.98), 2.518 (1.45), 2.522 (0.91), 3.409 (0.73), 3.420 (1.09), 3.431 (1.29), 3.442 (1.17), 3.456 (1.01), 3.465 (0.85), 4.590 (3.68), 4.601 (3.59), 4.946 (1.58), 4.966 (1.54), 5.294 (16.00), 6.968 (2.28), 6.991 (2.43), 7.717 (4.14), 7.726 (2.26), 7.749 (1.67), 10.889 (6.00).

Example 212

5-{4-[(Cyclopropylmethyl)amino]-3-(trifluoromethyl)phenyl}-3,6-dihydro-2H-1,3,4-oxadiazin-2-one

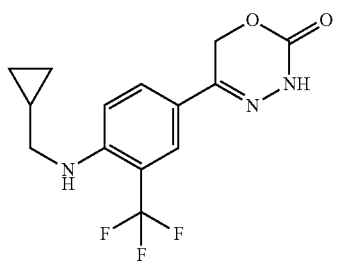 [SMILES: O=C1NN=C(c2ccc(NCC3CC3)c(C(F)(F)F)c2)CO1]

5-[4-Fluoro-3-(trifluoromethyl)phenyl]-3,6-dihydro-2H-1,3,4-oxadiazin-2-one (150 mg, 572 μmol, Intermediate 66) was dissolved in DMSO (1.0 ml), and 1-cyclopropymethanamine (110 μl, 1.3 mmol) was added. The mixture was stirred at 100° C. overnight. The reaction mixture was diluted with DMSO, filtered and purified by preparative HPLC to give 102 mg (95% purity, 54% yield) of the title compound.

LC-MS (Method 1): $R_t$=1.19 min: MS (ESIpos): m/z=314 [M+H]⁺

¹H-NMR (400 MHz, DMSO-d6) δ[ppm]: 0.233 (0.90), 0.245 (3.25), 0.248 (2.94), 0.257 (3.23), 0.260 (3.07), 0.271 (1.18), 0.422 (1.20), 0.432 (2.85), 0.436 (3.03), 0.442 (1.50), 0.447 (1.41), 0.452 (3.06), 0.457 (2.84), 0.467 (0.95), 1.084 (0.61), 1.088 (0.61), 1.092 (0.62), 1.096 (0.52), 1.104 (1.00), 1.112 (0.51), 1.116 (0.58), 1.121 (0.58), 1.124 (0.54), 2.518 (2.09), 2.523 (1.38), 3.118 (2.18), 3.133 (3.59), 3.149 (2.08), 5.295 (16.00), 5.888 (0.75), 5.902 (1.47), 5.916 (0.72), 6.936 (2.04), 6.958 (2.15), 7.729 (5.36), 7.752 (1.52), 7.757 (1.12), 10.879 (4.64).

Example 213

5-[4-{[(3-Methyloxetan-3-yl)methyl]amino}-3-(trifluoromethyl)phenyl]-3,6-dihydro-2H-1,3,4-oxadiazin-2-one

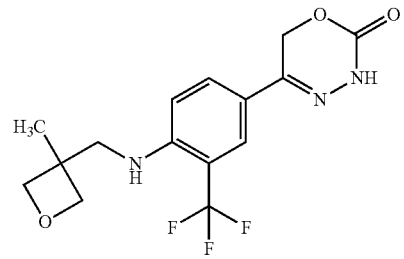 [SMILES: CC1(CNc2ccc(C3=NNC(=O)OC3)cc2C(F)(F)F)COC1]

5-[4-Fluoro-3-(trifluoromethyl)phenyl]-3,6-dihydro-2H-1,3,4-oxadiazin-2-one (120 mg, 458 μmol, Intermediate 66) was dissolved in DMSO (800 μl), and 1-(3-methyloxetan-3-yl)methanamine (92.6 mg, 915 μmol) was added. The mixture was stirred at 100° C. for 3 d. The reaction mixture was diluted with DMSO, filtered and purified by preparative HPLC to give 93.0 mg (95% purity, 56% yield) of the title compound.

LC-MS (Method 1): $R_t$=1.00 min, MS (ESIpos): m/z=344 [M+H]⁺

¹H-NMR (400 MHz, DMSO-d6) δ[ppm]: 1.275 (16.00), 2.518 (1.01), 2.523 (0.62), 3.417 (3.57), 3.432 (3.59), 4.196 (6.36), 4.211 (6.95), 4.449 (5.85), 4.464 (5.27), 5.302 (13.69), 5.943 (0.63), 5.957 (1.27), 5.972 (0.63), 6.991 (1.48), 7.013 (1.59), 7.725 (1.51), 7.744 (5.58), 10.890 (4.43).

Example 214

5-{4-[(3-Methoxypropyl)amino]-3-(trifluoromethyl)phenyl}-3,6-dihydro-2H-1,3,4-oxadiazin-2-one

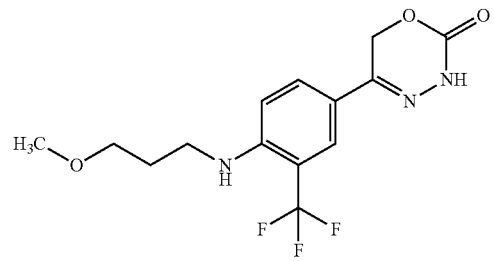 [SMILES: COCCCNc1ccc(C2=NNC(=O)OC2)cc1C(F)(F)F]

5-[4-Fluoro-3-(trifluoromethyl)phenyl]-3,6-dihydro-2H-1,3,4-oxadiazin-2-one (260 mg, 992 μmol, Intermediate 66) was dissolved in DMSO (2.0 ml), and 3-methoxypropan-1-amine (200 μl, 2.0 mmol) was added. The mixture was stirred at 100° C. for 64 h. The reaction mixture was diluted with DMSO, filtered and purified by preparative HPLC to give 267 mg (99% purity, 80% yield) of the title compound.

LC-MS (Method 1): $R_t$=1.05 min; MS (ESIpos): m/z=332 [M+H]⁺

¹H-NMR (400 MHz, DMSO-d6) δ[ppm]: 1.786 (0.98), 1.801 (1.53), 1.817 (1.01), 2.073 (0.41), 2.518 (0.61), 3.243 (16.00), 3.270 (0.53), 3.286 (1.28), 3.301 (1.29), 3.316

(0.64), 3.410 (1.50), 3.425 (2.89), 3.439 (1.42), 5.293 (7.70), 6.066 (0.75), 6.852 (1.05), 6.874 (1.09), 7.730 (2.05), 7.756 (0.75), 10.878 (2.38).

Example 215

(rac)-5-[4-({[Oxolan-2-yl]methyl}amino)-3-(trifluoromethyl)phenyl]-3,6-dihydro-2H-1,3,4-oxadiazin-2-one

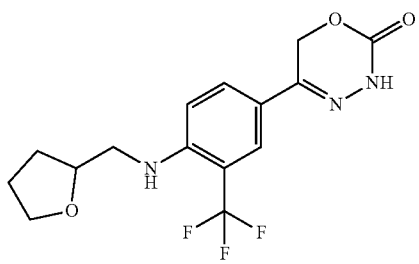 [SMILES: O=C1NN=C(c2ccc(NCC3CCCO3)c(C(F)(F)F)c2)CO1]

5-[4-Fluoro-3-(trifluoromethyl)phenyl]-3,6-dihydro-2H-1,3,4-oxadiazin-2-one (150 mg, 572 μmol, Intermediate 66) was dissolved in DMSO (1.0 ml), and (rac)-1-[oxolan-2-yl]methanamine (130 μl, 1.3 mmol) was added. The mixture was stirred at 100° C. overnight. The reaction mixture was diluted with DMSO, filtered and purified by preparative HPLC to give 108 mg (95% purity, 52% yield) of the title compound.

LC-MS (Method 1): $R_t$=1.09 min; MS (ESIpos): m/z=344 [M+H]$^+$ $^1$H-NMR (400 MHz, DMSO-d6) δ[ppm]: 1.591 (0.79), 1.603 (0.56), 1.611 (0.99), 1.619 (0.88), 1.628 (0.67), 1.636 (0.62), 1.641 (1.02), 1.657 (0.57), 1.783 (0.50), 1.798 (1.22), 1.815 (1.68), 1.819 (1.63), 1.829 (1.49), 1.836 (1.72), 1.846 (0.93), 1.850 (1.20), 1.866 (0.59), 1.885 (0.69), 1.902 (0.89), 1.906 (0.56), 1.914 (0.99), 1.923 (0.64), 1.931 (0.72), 1.934 (0.68), 1.945 (0.55), 2.327 (0.41), 2.518 (1.66), 2.523 (1.12), 2.669 (0.40), 3.212 (0.48), 3.226 (0.65), 3.245 (0.96), 3.261 (1.15), 3.275 (0.85), 3.352 (1.06), 3.359 (0.66), 3.372 (0.72), 3.386 (0.49), 3.610 (0.75), 3.630 (1.56), 3.647 (2.03), 3.664 (1.09), 3.732 (1.03), 3.748 (1.82), 3.765 (1.50), 3.768 (1.38), 3.785 (0.81), 4.026 (1.18), 4.038 (1.37), 4.042 (1.23), 4.054 (1.15), 5.298 (16.00), 5.690 (0.81), 5.703 (1.49), 5.717 (0.78), 6.965 (1.95), 6.987 (2.02), 7.731 (6.98), 7.752 (1.70), 10.890 (5.24).

Example 216

5-[4-{[(2R)-2-Hydroxypropyl]amino}-3-(trifluoromethyl)phenyl]-3,6-dihydro-2H-1,3,4-oxadiazin-2-one

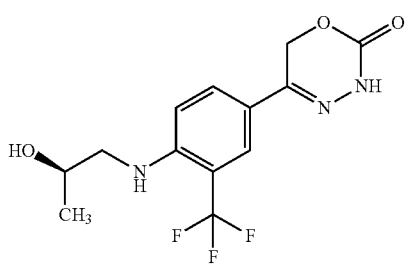 [SMILES: C[C@@H](O)CNc1ccc(C2=NNC(=O)OC2)cc1C(F)(F)F]

5-[4-Fluoro-3-(trifluoromethyl)phenyl]-3,6-dihydro-2H-1,3,4-oxadiazin-2-one (260 mg, 992 μmol, Intermediate 66) was dissolved in DMSO (2.5 ml), and (2R)-1-aminopropan-2-ol (160 μl, 2.0 mmol) was added. The mixture was stirred at 100° C. overnight. The reaction mixture was diluted with DMSO, filtered and purified by preparative HPLC to give 218 mg (95% purity, 66% yield) of the title compound.

LC-MS (Method 1): $R_t$=0.87 min, MS (ESIpos): m/z=318 [M+H]$^+$ $^1$H-NMR (400 MHz, DMSO-d6) δ[ppm]: 1.103 (10.18), 1.118 (10.29), 2.518 (1.03), 2.522 (0.64), 3.029 (0.52), 3.041 (0.61), 3.047 (0.62), 3.060 (1.03), 3.072 (0.84), 3.079 (0.87), 3.090 (0.74), 3.197 (0.72), 3.210 (1.13), 3.224 (0.93), 3.242 (0.79), 3.256 (0.52), 3.821 (0.41), 3.834 (0.85), 3.850 (1.11), 3.866 (0.78), 4.950 (3.78), 4.962 (3.73), 5.300 (16.00), 5.644 (0.86), 5.657 (1.44), 5.670 (0.84), 6.910 (1.93), 6.932 (1.99), 7.737 (7.21), 7.757 (1.77), 10.888 (5.40).

Example 217

5-[4-{[(3R)-3-Hydroxybutyl]amino}-3-(trifluoromethyl)phenyl]-3,6-dihydro-2H-1,3,4-oxadiazin-2-one

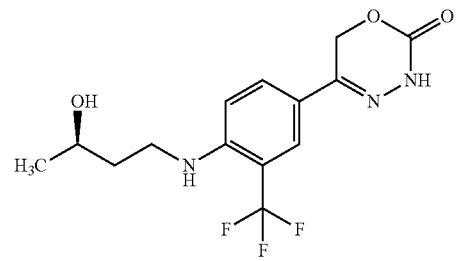 [SMILES: C[C@@H](O)CCNc1ccc(C2=NNC(=O)OC2)cc1C(F)(F)F]

5-[4-Fluoro-3-(trifluoromethyl)phenyl]-3,6-dihydro-2H-1,3,4-oxadiazin-2-one (150 mg, 572 μmol, Intermediate 66) was dissolved in DMSO (1000 μl), and (2R)-4-aminobutan-2-ol (102 mg, 1.14 mmol) was added. The mixture was stirred at 100° C. overnight. The reaction mixture was diluted with DMSO, filtered and purified by preparative HPLC to give 86.0 mg (95% purity, 43% yield) of the title compound.

LC-MS (Method 1): $R_t$=0.92 min, MS (ESIpos): m/z=332 [M+H]$^+$ $^1$H-NMR (400 MHz, DMSO-d6) δ[ppm]: 1.087 (10.42), 1.102 (10.69), 1.532 (0.62), 1.551 (0.91), 1.566 (1.16), 1.586 (1.04), 1.603 (0.41), 1.643 (0.40), 1.658 (0.96), 1.668 (1.02), 1.676 (0.77), 1.685 (0.73), 1.693 (0.63), 1.702 (0.57), 2.327 (0.45), 2.522 (1.03), 2.669 (0.45), 3.268 (0.73), 3.284 (1.69), 3.299 (2.38), 3.314 (1.99), 3.742 (0.91), 3.747 (0.91), 3.758 (0.91), 4.773 (3.53), 4.784 (3.42), 5.292 (16.00), 6.218 (0.94), 6.231 (1.79), 6.243 (0.92), 6.851 (2.46), 6.873 (2.55), 7.726 (4.84), 7.752 (1.77), 10.871 (5.39).

Example 218

5-[4-{[(2S)-2-Hydroxypropyl]amino}-3-(trifluoromethyl)phenyl]-3,6-dihydro-2H-1,3,4-oxadiazin-2-one

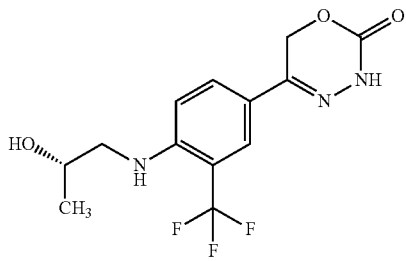 [SMILES: C[C@H](O)CNc1ccc(C2=NNC(=O)OC2)cc1C(F)(F)F]

5-[4-Fluoro-3-(trifluoromethyl)phenyl]-3,6-dihydro-2H-1,3,4-oxadiazin-2-one (150 mg, 97% purity, 555 µmol, Intermediate 66) was dissolved in DMSO (1.0 ml), and (2S)-1-aminopropan-2-ol (99 µl, 98% purity, 1.2 mmol) was added. The mixture was stirred at 100° C. for 18 h. The reaction mixture was diluted with DMSO, filtered and purified by preparative HPLC to give 152 mg (98% purity, 85% yield) of the title compound.

LC-MS (Method 1): $R_t$=0.87 min: MS (ESIpos): m/z=318 [M+H]$^+$ $^1$H-NMR (400 MHz, DMSO-d6) δ[ppm]: 1.102 (10.45), 1.118 (10.65), 2.522 (0.80), 3.029 (0.54), 3.040 (0.63), 3.046 (0.65), 3.060 (1.08), 3.072 (0.87), 3.079 (0.90), 3.090 (0.77), 3.196 (0.73), 3.210 (1.18), 3.224 (0.95), 3.241 (0.81), 3.256 (0.54), 3.821 (0.44), 3.833 (0.89), 3.850 (1.17), 3.866 (0.83), 3.878 (0.41), 4.950 (4.60), 4.962 (4.59), 5.300 (16.00), 5.645 (0.89), 5.657 (1.48), 5.669 (0.87), 6.910 (2.00), 6.932 (2.06), 7.737 (7.43), 7.756 (1.82), 10.888 (5.53).

Example 219

5-[4-{[(1-Hydroxycyclobutyl)methyl]amino}-3-(trifluoromethyl)phenyl]-3,6-dihydro-2H-1,3,4-oxadiazin-2-one

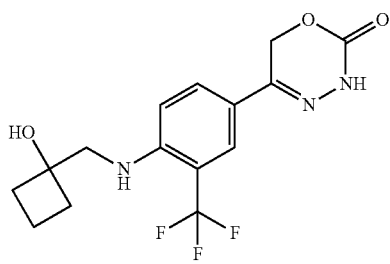 [SMILES: O=C1NN=C(c2ccc(NCC3(O)CCC3)c(C(F)(F)F)c2)CO1]

5-[4-Fluoro-3-(trifluoromethyl)phenyl]-3,6-dihydro-2H-1,3,4-oxadiazin-2-one (320 mg, 1.22 mmol, Intermediate 66) was dissolved in DMSO (2.0 ml), and 1-(aminomethyl)cyclobutan-1-ol (247 mg, 2.44 mmol) was added. The mixture was stirred at 100° C. overnight. The reaction mixture was diluted with DMSO, filtered and purified by preparative HPLC to give 231 mg (95% purity, 52% yield) of the title compound.

LC-MS (Method 1): $R_t$=1.00 min, MS (ESIpos): m/z=344 [M+H]$^+$ $^1$H-NMR (400 MHz, DMSO-d6) δ[ppm]: 1.546 (0.74), 1.569 (1.05), 1.591 (0.73), 1.637 (0.72), 1.644 (0.54), 1.654 (0.80), 1.665 (0.53), 1.976 (4.50), 1.993 (4.03), 1.998 (5.17), 2.015 (2.05), 2.074 (14.34), 2.518 (1.22), 2.522 (0.84), 3.279 (4.02), 3.291 (4.05), 5.278 (1.45), 5.308 (16.00), 5.527 (3.57), 7.000 (2.21), 7.022 (2.34), 7.746 (3.95), 7.752 (2.30), 7.774 (1.55), 7.779 (1.23), 10.898 (5.51).

Example 220

5-{4-[(3-Methylbutyl)amino]-3-(trifluoromethyl)phenyl}-3,6-dihydro-2H-1,3,4-oxadiazin-2-one

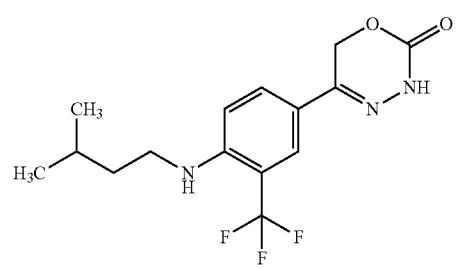 [SMILES: CC(C)CCNc1ccc(C2=NNC(=O)OC2)cc1C(F)(F)F]

5-[4-Fluoro-3-(trifluoromethyl)phenyl]-3,6-dihydro-2H-1,3,4-oxadiazin-2-one (150 mg, 572 µmol, Intermediate 66) was dissolved in DMSO (1.0 ml), and 3-methylbutan-1-amine (150 µl, 1.3 mmol) was added. The mixture was stirred at 100° C. overnight. The reaction mixture was diluted with DMSO, filtered and purified by preparative HPLC to give 106 mg (95% purity, 53% yield) of the title compound.

LC-MS (Method 1): $R_t$=1.34 min, MS (ESIpos): m/z=330 [M+H]$^+$ $^1$H-NMR (400 MHz, DMSO-d6) δ[ppm]: 0.898 (15.35), 0.914 (16.00), 1.413 (0.60), 1.430 (1.37), 1.449 (1.39), 1.467 (0.77), 1.606 (0.67), 1.623 (0.77), 1.640 (0.58), 2.518 (1.24), 2.523 (0.87), 3.227 (0.56), 3.242 (1.04), 3.263 (1.05), 3.278 (0.55), 5.289 (9.24), 5.866 (0.41), 5.880 (0.82), 5.894 (0.41), 6.849 (1.20), 6.871 (1.25), 7.715 (1.22), 7.720 (2.09), 7.727 (1.19), 7.749 (0.82), 7.754 (0.65), 10.871 (2.70).

Example 221

5-{4-[(2-Methylpropyl)amino]-3-(trifluoromethyl)phenyl}-3,6-dihydro-2H-1,3,4-oxadiazin-2-one

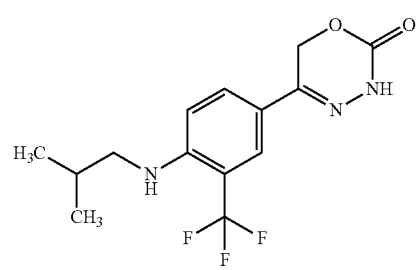 [SMILES: CC(C)CNc1ccc(C2=NNC(=O)OC2)cc1C(F)(F)F]

5-[4-Fluoro-3-(trifluoromethyl)phenyl]-3,6-dihydro-2H-1,3,4-oxadiazin-2-one (150 mg, 572 µmol, Intermediate 66) was dissolved in DMSO (1.0 ml), and 2-methylpropan-1-amine (130 µl, 1.3 mmol) was added. The mixture was stirred at 100° C. overnight. The reaction mixture was diluted with DMSO, filtered and purified by preparative HPLC to give 115 mg (95% purity, 61% yield) of the title compound.

LC-MS (Method 1): $R_t$=1.26 min: MS (ESIpos): m/z=316 [M+H]$^+$ $^1$H-NMR (400 MHz, DMSO-d6) δ[ppm]: 0.875 (15.59), 0.892 (16.00), 1.895 (0.77), 1.912 (0.95), 1.928 (0.73), 2.518 (2.28), 2.522 (1.46), 2.669 (0.50), 3.046 (1.72), 3.062 (2.63), 3.078 (1.65), 5.287 (12.60), 5.958 (0.63), 5.972 (1.23), 5.987 (0.61), 6.865 (1.49), 6.889 (1.55), 7.712 (5.25), 7.730 (1.38), 10.870 (3.92).

Example 222

5-{4-[(2-Methoxyethyl)amino]-3-(trifluoromethyl)phenyl}-3,6-dihydro-2H-1,3,4-oxadiazin-2-one

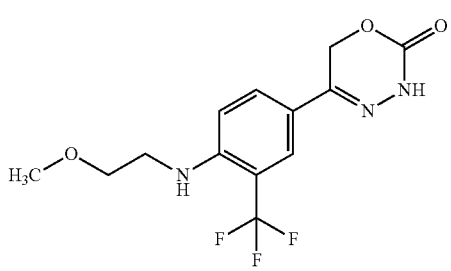 [SMILES: COCCNc1ccc(C2=NNC(=O)OC2)cc1C(F)(F)F]

5-[4-Fluoro-3-(trifluoromethyl)phenyl]-3,6-dihydro-2H-1,3,4-oxadiazin-2-one (1.05 g, 92% purity, 3.68 mmol, Intermediate 66) was dissolved in DMSO (7.0 ml), and 2-methoxyethan-1-amine (710 μl, 99% purity, 8.1 mmol) was added. The mixture was stirred at 100° C. for 16 h. The reaction mixture was diluted with DMSO, filtered and purified by preparative HPLC (acidic conditions) to give 786 mg (100% purity, 67% yield) of the title compound.

LC-MS (Method 1): $R_t$=1.01 min, MS (ESIpos): m/z=318 [M+H]$^+$ $^1$H-NMR (400 MHz, DMSO-d$_6$): δ [ppm]=10.89 (s, 1H), 7.73 (s, 1H), 7.75 (d, 1H), 6.95 (d, 1H), 5.76 (br t, 1H), 5.30 (s, 2H), 3.55-3.46 (m, 2H), 3.41 (q, 2H), 3.27 (s, 3H)

Example 223

5-{4-[Ethyl(methyl)amino]-3-(trifluoromethyl)phenyl}-3,6-dihydro-2H-1,3,4-oxadiazin-2-one

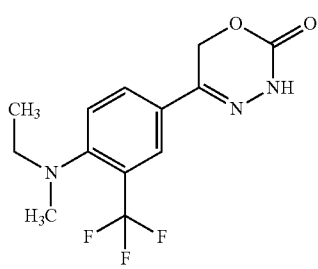 [SMILES: CCN(C)c1ccc(C2=NNC(=O)OC2)cc1C(F)(F)F]

5-[4-Fluoro-3-(trifluoromethyl)phenyl]-3,6-dihydro-2H-1,3,4-oxadiazin-2-one (150 mg, 572 μmol, Intermediate 66) was dissolved in DMSO (1.0 ml), and N-methylethanamine (110 μl, 1.3 mmol) was added. The mixture was stirred at 100° C. overnight. The reaction mixture was diluted with DMSO, filtered and purified by preparative HPLC to give 73.0 mg (95% purity, 40% yield) of the title compound.

LC-MS (Method 1): $R_t$=1.20 min; MS (ESIpos): m/z=302 [M+H]$^+$ $^1$H-NMR (400 MHz, DMSO-d6) δ[ppm]: 0.964 (4.46), 0.981 (10.06), 0.999 (4.62), 2.074 (0.54), 2.518 (1.54), 2.523 (0.99), 2.666 (16.00), 2.967 (1.15), 2.985 (3.62), 3.002 (3.54), 3.020 (1.08), 5.387 (14.58), 7.533 (1.84), 7.554 (2.02), 7.904 (1.16), 7.910 (1.65), 7.931 (5.31), 11.105 (3.70).

Example 224

5-[4-(tert-Butylamino)-3-(trifluoromethyl)phenyl]-3,6-dihydro-2H-1,3,4-oxadiazin-2-one

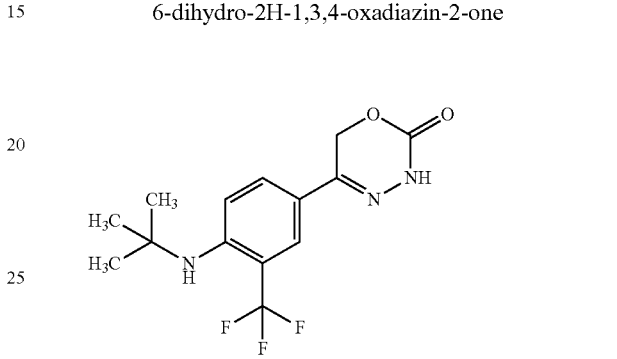

The title compound was prepared analogously to Example 205 from Intermediate 66.

LC-MS (Method 1): $R_t$=1.26 min; MS (ESIpos): m/z=316 [M+H]$^+$ $^1$H-NMR (400 MHz, DMSO-d6) δ[ppm]: 1.400 (16.00), 1.412 (1.99), 1.428 (2.69), 2.522 (1.01), 4.320 (0.50), 4.628 (0.62), 5.302 (4.05), 7.153 (0.66), 7.176 (0.70), 7.740 (0.77), 7.745 (1.05), 7.750 (0.95), 7.757 (0.61), 10.918 (1.26).

Example 225

5-[4-({[(2R)-Oxolan-2-yl]methyl}amino)-3-(trifluoromethyl)phenyl]-3,6-dihydro-2H-1,3,4-oxadiazin-2-one

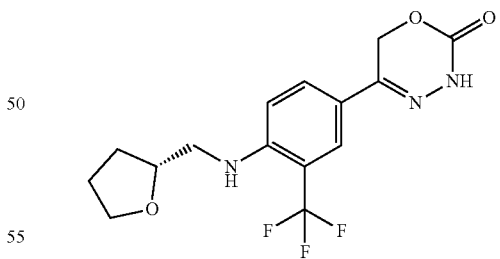

The title compound was prepared analogously to Example 205 from Intermediate 66.

LC-MS (Method 1): $R_t$=1.09 min; MS (ESIpos): m/z=344 [M+H]$^+$ $^1$H-NMR (400 MHz, DMSO-d6) δ[ppm]: 1.591 (0.72), 1.594 (0.54), 1.603 (0.49), 1.607 (0.56), 1.611 (0.92), 1.619 (0.83), 1.628 (0.62), 1.635 (0.55), 1.641 (0.98), 1.657 (0.54), 1.782 (0.47), 1.797 (1.10), 1.802 (0.80), 1.815 (1.49), 1.818 (1.44), 1.829 (1.32), 1.836 (1.57), 1.845 (0.82), 1.850 (1.09), 1.866 (0.56), 1.885 (0.62), 1.901 (0.83), 1.906 (0.50), 1.914

(0.93), 1.919 (0.43), 1.923 (0.58), 1.928 (0.64), 1.930 (0.65), 1.934 (0.62), 1.945 (0.50), 1.950 (0.46), 2.518 (1.37), 2.522 (0.83), 3.212 (0.44), 3.225 (0.57), 3.245 (0.88), 3.261 (1.03), 3.275 (0.76), 3.352 (0.87), 3.359 (0.54), 3.371 (0.62), 3.386 (0.43), 3.609 (0.72), 3.630 (1.47), 3.647 (1.89), 3.664 (1.05), 3.732 (1.00), 3.749 (1.69), 3.752 (1.06), 3.765 (1.42), 3.768 (1.25), 3.785 (0.82), 4.026 (1.09), 4.038 (1.26), 4.042 (1.15), 4.054 (1.08), 5.298 (16.00), 5.422 (1.05), 5.690 (0.73), 5.704 (1.37), 5.718 (0.70), 6.965 (1.80), 6.987 (1.88), 7.731 (6.58), 7.752 (1.56), 10.890 (5.06).

Example 226

5-[4-{[(Pyrazin-2-yl)methyl]amino}-3-(trifluoromethyl)phenyl]-3,6-dihydro-2H-1,3,4-oxadiazin-2-one

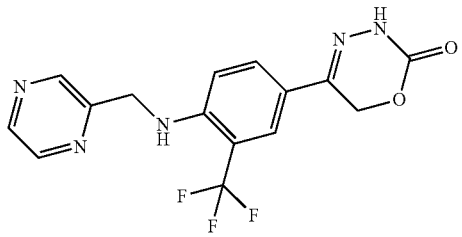 [SMILES: O=C1NN=C(c2ccc(NCc3cnccn3)c(C(F)(F)F)c2)CO1]

5-[4-Fluoro-3-(trifluoromethyl)phenyl]-3,6-dihydro-2H-1,3,4-oxadiazin-2-one one (39.3 mg, 150 μmol, Intermediate 66) was dissolved in DMSO (2.0 ml), and 1-(pyrazin-2-yl)methanamine (32.7 mg, 300 μmol) and N,N-diisopropylethylamine (77.5 mg, 600 μmol) were added. The mixture was stirred at 120° C. overnight. The reaction mixture was filtered through a pad of Celite and purified by prep HPLC.

LC-MS (Method 1): $R_t$=0.88 min; MS (ESIneg): m/z=350 [M–H]$^-$ $^1$H-NMR (400 MHz, DMSO-d6) δ[ppm]: 2.074 (3.21), 2.083 (2.28), 2.458 (0.58), 2.518 (2.41), 2.522 (1.52), 2.539 (0.67), 4.667 (3.73), 4.681 (3.71), 5.276 (16.00), 6.788 (2.49), 6.810 (3.40), 6.825 (1.81), 6.839 (0.85), 7.666 (1.52), 7.670 (1.62), 7.687 (1.41), 7.693 (1.52), 7.782 (3.37), 7.787 (3.09), 8.541 (3.63), 8.547 (4.20), 8.589 (3.98), 8.593 (4.86), 8.616 (3.59), 8.620 (3.29), 8.623 (3.38), 8.626 (2.54), 10.896 (5.03).

Example 227

5-[4-(4-Hydroxypiperidin-1-yl)-3-(trifluoromethyl)phenyl]-3,6-dihydro-2H-1,3,4-oxadiazin-2-one

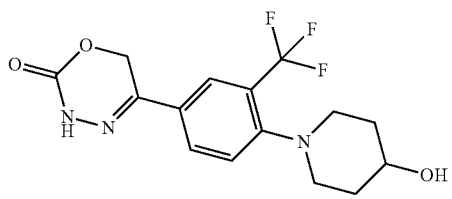 [SMILES: O=C1NN=C(c2ccc(N3CCC(O)CC3)c(C(F)(F)F)c2)CO1]

The title compound was prepared analogously to Example 226 from Intermediate 66.
LC-MS (Method 1): $R_t$=0.90 min; MS (ESIpos): m/z=344 [M+H]$^+$ Example 228

5-[4-{[(2S)-1-Hydroxybutan-2-yl]amino}-3-(trifluoromethyl)phenyl]-3,6-dihydro-2H-1,3,4-oxadiazin-2-one

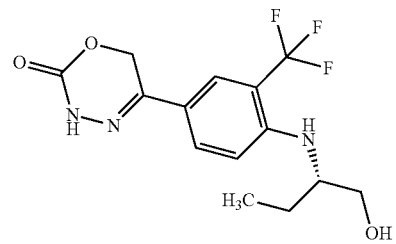 [SMILES: CC[C@@H](CO)Nc1ccc(C2=NNC(=O)OC2)cc1C(F)(F)F]

The title compound was prepared analogously to Example 226 from Intermediate 66.
LC-MS (Method 1): $R_t$=0.95 min; MS (ESIpos): m/z=332 [M+H]$^+$ Example 229

(rac)-5-[4-(3-hydroxypiperidin-1-yl)-3-(trifluoromethyl)phenyl]-3,6-dihydro-2H-1,3,4-oxadiazin-2-one

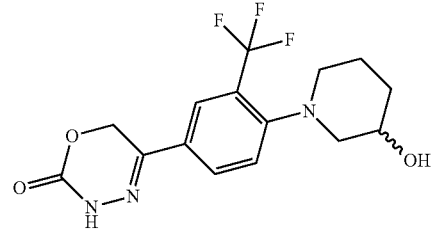 [SMILES: O=C1NN=C(c2ccc(N3CCCC(O)C3)c(C(F)(F)F)c2)CO1]

The title compound was prepared analogously to Example 226 from Intermediate 66.
LC-MS (Method 1): $R_t$=0.96 min; MS (ESIpos): m/z=344 [M+H]$^+$ Example 230

(rac)-1-[4-(2-Oxo-3,6-dihydro-2H-1,3,4-oxadiazin-5-yl)-2-(trifluoromethyl)phenyl]piperidine-3-carboxamide

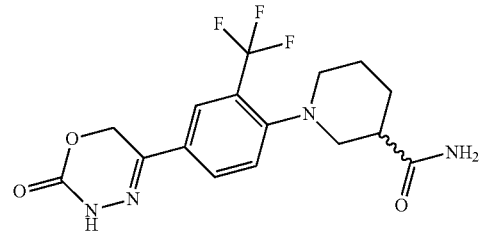 [SMILES: NC(=O)C1CCCN(c2ccc(C3=NNC(=O)OC3)cc2C(F)(F)F)C1]

The title compound was prepared analogously to Example 226 from Intermediate 66.

LC-MS (Method 1): R$_t$=0.87 min; MS (ESIpos): m/z=371 [M+H]$^+$

Example 231

5-{4-[(3-Hydroxy-2,2-dimethylpropyl)amino]-3-(trifluoromethyl)phenyl}-3,6-dihydro-2H-1,3,4-oxadiazin-2-one

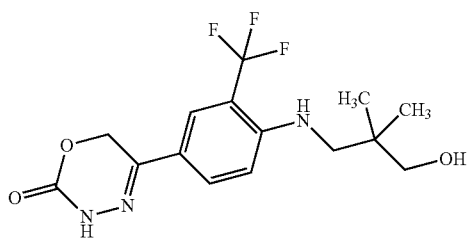 [SMILES: CC(C)(CO)CNc1ccc(C2=NNC(=O)OC2)cc1C(F)(F)F]

The title compound was prepared analogously to Example 226 from Intermediate 66.
LC-MS (Method 1): R$_t$=1.02 min; MS (ESIpos): m/z=346 [M+H]$^+$

Example 232

5-[4-(4,4-Difluoropiperidin-1-yl)-3-(trifluoromethyl)phenyl]-3,6-dihydro-2H-1,3,4-oxadiazin-2-one

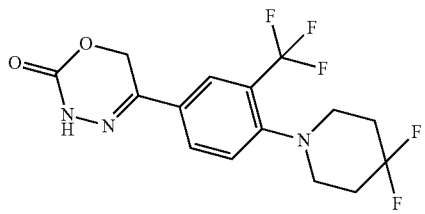 [SMILES: O=C1NN=C(c2ccc(N3CCC(F)(F)CC3)c(C(F)(F)F)c2)CO1]

The title compound was prepared analogously to Example 226 from Intermediate 66.
LC-MS (Method 1): R$_t$=1.21 min; MS (ESIpos): m/z=364 [M+H]$^+$

Example 233

5-[4-{[(1R,2R,4R)-Bicyclo[2.2.1]heptan-2-yl]amino}-3-(trifluoromethyl)phenyl]-3,6-dihydro-2H-1,3,4-oxadiazin-2-one

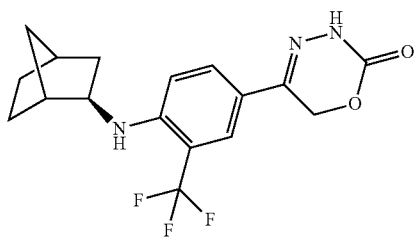 [SMILES: O=C1NN=C(c2ccc(N[C@@H]3CC4CCC3C4)c(C(F)(F)F)c2)CO1]

The title compound was prepared analogously to Example 226 from Intermediate 66.

LC-MS (Method 1): R$_t$=1.38 min; MS (ESIpos): m/z=354 [M+H]$^+$

Example 234

5-{4-[(3S)-3-Hydroxypyrrolidin-1-yl]-3-(trifluoromethyl)phenyl}-3,6-dihydro-2H-1,3,4-oxadiazin-2-one

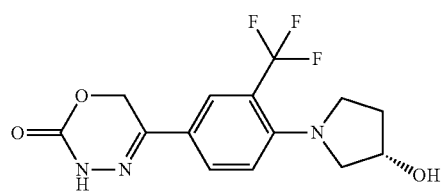 [SMILES: O=C1NN=C(c2ccc(N3CC[C@H](O)C3)c(C(F)(F)F)c2)CO1]

The title compound was prepared analogously to Example 226 from Intermediate 66.
LC-MS (Method 1): R$_t$=0.87 min; MS (ESIpos): m/z=330 [M+H]$^+$

Example 235

(rac)-5-{4-[(2-Hydroxy-3-methoxypropyl)amino]-3-(trifluoromethyl)phenyl}-3,6-dihydro-2H-1,3,4-oxadiazin-2-one

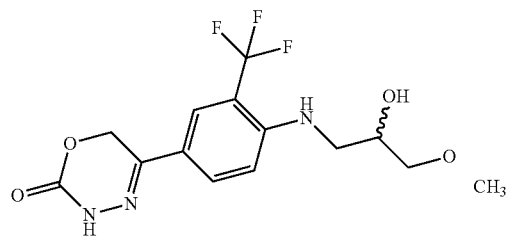

The title compound was prepared analogously to Example 226 from Intermediate 66.
LC-MS (Method 1): R$_t$=0.84 min; MS (ESIpos): m/z=348 [M+H]$^+$

Example 236

5-[4-{[(1-Methyl-1H-pyrazol-5-yl)methyl]amino}-3-(trifluoromethyl)phenyl]-3,6-dihydro-2H-1,3,4-oxadiazin-2-one

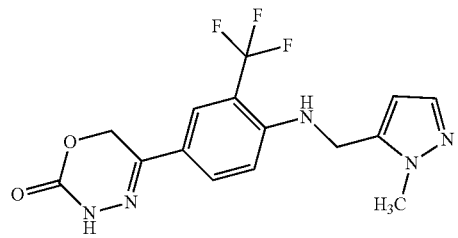 [SMILES: Cn1nccc1CNc1ccc(C2=NNC(=O)OC2)cc1C(F)(F)F]

The title compound was prepared analogously to Example 226 from Intermediate 66.

LC-MS (Method 1): $R_t$=0.88 min; MS (ESIpos): m/z=354 [M+H]$^+$

Example 237

5-[4-{[(1H-Pyrazol-3-yl)methyl]amino}-3-(trifluoromethyl)phenyl]-3,6-dihydro-2H-1,3,4-oxadiazin-2-one

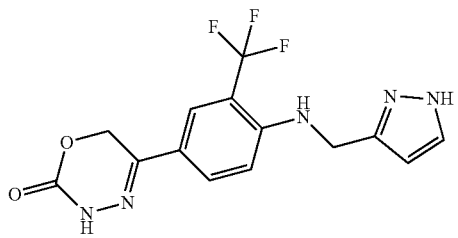 [SMILES: O=C1NN=C(c2ccc(NCc3cc[nH]n3)c(C(F)(F)F)c2)CO1]

The title compound was prepared analogously to Example 226 from Intermediate 66.
LC-MS (Method 1): $R_t$=0.84 min; MS (ESIpos): m/z=340 [M+H]$^+$ Example 238

5-[4-{[2-(1H-Pyrazol-1-yl)ethyl]amino}-3-(trifluoromethyl)phenyl]-3,6-dihydro-2H-1,3,4-oxadiazin-2-one

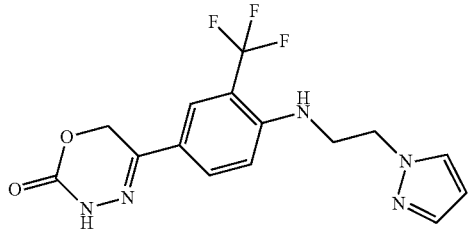 [SMILES: O=C1NN=C(c2ccc(NCCn3cccn3)c(C(F)(F)F)c2)CO1]

The title compound was prepared analogously to Example 226 from Intermediate 66.
LC-MS (Method 1): $R_t$=0.93 min: MS (ESIpos): m/z=354 [M+H]$^+$ Example 239

1-[4-(2-Oxo-3,6-dihydro-2H-1,3,4-oxadiazin-5-yl)-2-(trifluoromethyl)phenyl]piperidine-4-carbonitrile

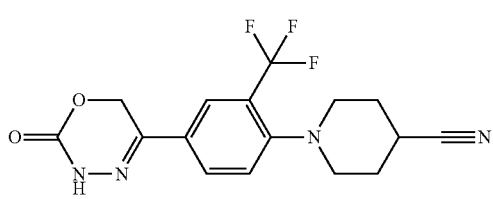 [SMILES: N#CC1CCN(c2ccc(C3=NNC(=O)OC3)cc2C(F)(F)F)CC1]

The title compound was prepared analogously to Example 226 from Intermediate 66.

LC-MS (Method 1): $R_t$=1.07 min; MS (ESIpos): m/z=353 [M+H]$^+$

Example 240

(rac)-5-{4-[(1-cyclopropylethyl)amino]-3-(trifluoromethyl)phenyl}-3,6-dihydro-2H-1,3,4-oxadiazin-2-one

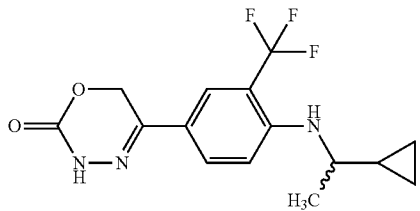 [SMILES: CC(Nc1ccc(C2=NNC(=O)OC2)cc1C(F)(F)F)C1CC1]

The title compound was prepared analogously to Example 226 from Intermediate 66.
LC-MS (Method 1): $R_t$=1.24 min; MS (ESIpos): m/z=328 [M+H]$^+$ Example 241

(rac)-5-{4-[(2-Ethoxypropyl)amino]-3-(trifluoromethyl)phenyl}-3,6-dihydro-2H-1,3,4-oxadiazin-2-one

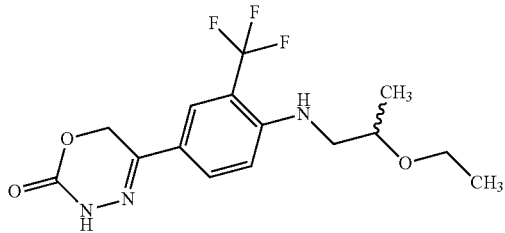 [SMILES: CCOC(C)CNc1ccc(C2=NNC(=O)OC2)cc1C(F)(F)F]

The title compound was prepared analogously to Example 226 from Intermediate 66.
LC-MS (Method 1): $R_t$=1.16 min: MS (ESIpos): m/z=346 [M+H]$^+$ Example 242

(rac)-5-{4-[(2-Methoxypropyl)amino]-3-(trifluoromethyl)phenyl}-3,6-dihydro-2H-1,3,4-oxadiazin-2-one

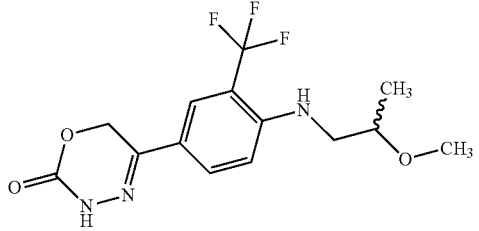 [SMILES: COC(C)CNc1ccc(C2=NNC(=O)OC2)cc1C(F)(F)F]

The title compound was prepared analogously to Example 226 from Intermediate 66.

LC-MS (Method 1): R$_t$=1.07 min; MS (ESIpos): m/z=332 [M+H]$^+$

Example 243

5-[4-(3-Ethoxyazetidin-1-yl)-3-(trifluoromethyl)phenyl]-3,6-dihydro-2H-1,3,4-oxadiazin-2-one

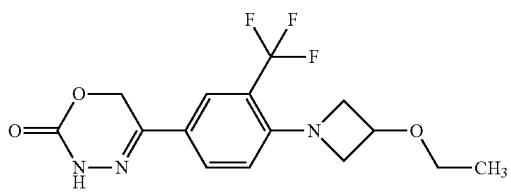 [SMILES: CCOC1CN(c2ccc(C3=NNC(=O)OC3)cc2C(F)(F)F)C1]

The title compound was prepared analogously to Example 226 from Intermediate 66.
LC-MS (Method 1): R$_t$=1.13 min; MS (ESIpos): m/z=344 [M+H]$^+$ Example 244

5-[4-{[(Pyrimidin-2-yl)methyl]amino}-3-(trifluoromethyl)phenyl]-3,6-dihydro-2H-1,3,4-oxadiazin-2-one

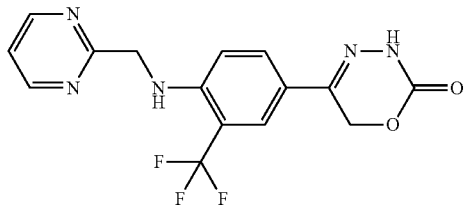 [SMILES: O=C1NN=C(c2ccc(NCc3ncccn3)c(C(F)(F)F)c2)CO1]

The title compound was prepared analogously to Example 226 from Intermediate 66.
LC-MS (Method 1): R$_t$=0.92 min: MS (ESIpos): m/z=352 [M+H]$^+$ Example 245

(rac)-5-[4-{[(Oxolan-3-yl)methyl]amino}-3-(trifluoromethyl)phenyl]-3,6-dihydro-2H-1,3,4-oxadiazin-2-one

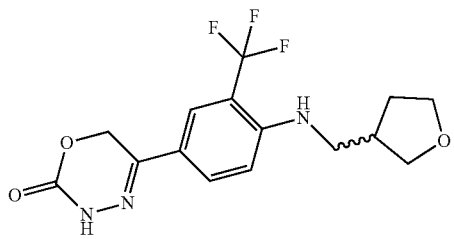 [SMILES: O=C1NN=C(c2ccc(NCC3CCOC3)c(C(F)(F)F)c2)CO1]

The title compound was prepared analogously to Example 226 from Intermediate 66.

LC-MS (Method 1): R$_t$=0.97 min; MS (ESIpos): m/z=344 [M+H]$^+$

Example 246

5-[4-{[(2S)-4-Hydroxybutan-2-yl]amino}-3-(trifluoromethyl)phenyl]-3,6-dihydro-2H-1,3,4-oxadiazin-2-one

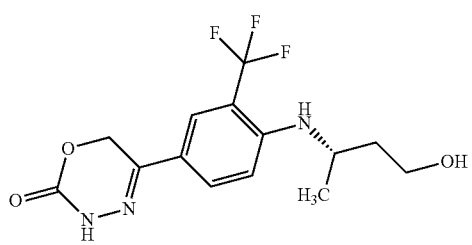 [SMILES: C[C@@H](CCO)Nc1ccc(C2=NNC(=O)OC2)cc1C(F)(F)F]

The title compound was prepared analogously to Example 226 from Intermediate 66.
LC-MS (Method 1): R$_t$=0.92 min; MS (ESIpos): m/z=332 [M+H]$^+$ Example 247

(rac)-5-[4-{[(6-Oxopiperidin-3-yl)methyl]amino}-3-(trifluoromethyl)phenyl]-3,6-dihydro-2H-1,3,4-oxadiazin-2-one

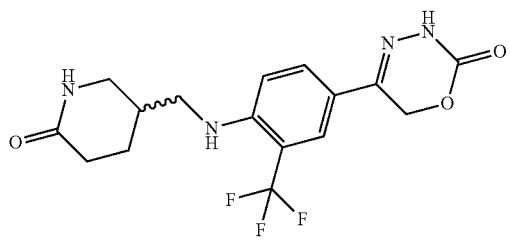 [SMILES: O=C1CCC(CNc2ccc(C3=NNC(=O)OC3)cc2C(F)(F)F)CN1]

The title compound was prepared analogously to Example 226 from Intermediate 66.
LC-MS (Method 1): R$_t$=0.78 min: MS (ESIpos): m/z=371 [M+H]$^+$ Example 248

(rac)-5-[4-{[(2,2-Dimethylcyclopropyl)methyl]amino}-3-(trifluoromethyl)phenyl]-3,6-dihydro-2H-1,3,4-oxadiazin-2-one

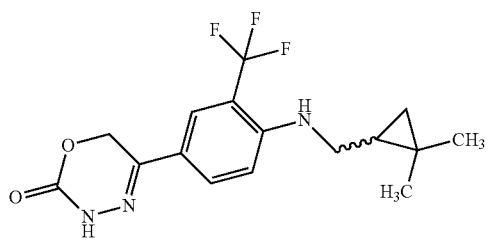 [SMILES: CC1(C)CC1CNc1ccc(C2=NNC(=O)OC2)cc1C(F)(F)F]

The title compound was prepared analogously to Example 226 from Intermediate 66.
LC-MS (Method 1): $R_t$=1.33 min; MS (ESIpos): m/z=342 [M+H]$^+$ Example 249

5-[4-({[1-(Hydroxymethyl)cyclobutyl]methyl}amino)-3-(trifluoromethyl)phenyl]-3,6-dihydro-2H-1,3,4-oxadiazin-2-one

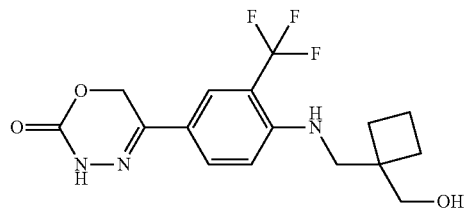 [SMILES: O=C1NN=C(c2ccc(NCC3(CO)CCC3)c(C(F)(F)F)c2)CO1]

The title compound was prepared analogously to Example 226 from Intermediate 66.
LC-MS (Method 1): $R_t$=1.06 min; MS (ESIpos): m/z=358 [M+H]$^+$ Example 250

5-{4-[(2S)-2-(Hydroxymethyl)azetidin-1-yl]-3-(trifluoromethyl)phenyl}-3,6-dihydro-2H-1,3,4-oxadiazin-2-one

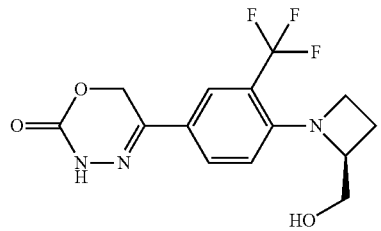 [SMILES: O=C1NN=C(c2ccc(N3CC[C@H]3CO)c(C(F)(F)F)c2)CO1]

The title compound was prepared analogously to Example 226 from Intermediate 66.
LC-MS (Method 1): $R_t$=0.91 min: MS (ESIpos): m/z=330 [M+H]$^+$ Example 251

3-Methyl-1-[4-(2-oxo-3,6-dihydro-2H-1,3,4-oxadiazin-5-yl)-2-(trifluoromethyl)phenyl]azetidine-3-carbonitrile

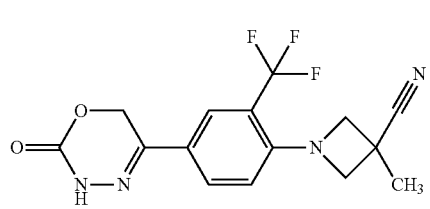 [SMILES: CC1(C#N)CN(c2ccc(C3=NNC(=O)OC3)cc2C(F)(F)F)C1]

The title compound was prepared analogously to Example 226 from Intermediate 66.
LC-MS (Method 1): $R_t$=1.03 min; MS (ESIpos): m/z=339 [M+H]$^+$ Example 252

5-[4-(3-Azabicyclo[3.1.0]hexan-3-yl)-3-(trifluoromethyl)phenyl]-3,6-dihydro-2H-1,3,4-oxadiazin-2-one

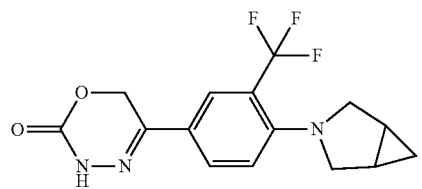 [SMILES: O=C1NN=C(c2ccc(N3CC4CC4C3)c(C(F)(F)F)c2)CO1]

The title compound was prepared analogously to Example 226 from Intermediate 66.
LC-MS (Method 1): $R_t$=1.24 min; MS (ESIpos): m/z=326 [M+H]$^+$ Example 253

5-[4-(4-Ethyl-4-hydroxypiperidin-1-yl)-3-(trifluoromethyl)phenyl]-3,6-dihydro-2H-1,3,4-oxadiazin-2-one

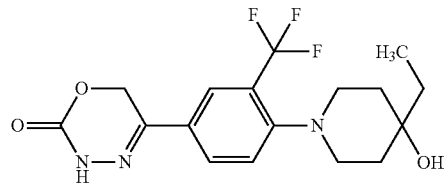 [SMILES: CCC1(O)CCN(c2ccc(C3=NNC(=O)OC3)cc2C(F)(F)F)CC1]

The title compound was prepared analogously to Example 226 from Intermediate 66.
LC-MS (Method 1): $R_t$=1.12 min; MS (ESIpos): m/z=372 [M+H]$^+$ Example 254

4-[4-(2-Oxo-3,6-dihydro-2H-1,3,4-oxadiazin-5-yl)-2-(trifluoromethyl)anilino]butanenitrile

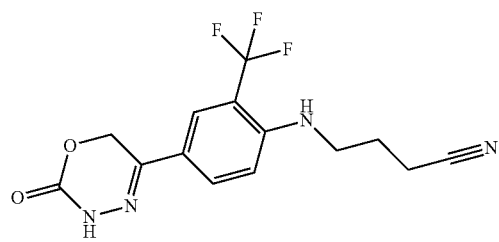 [SMILES: N#CCCCNc1ccc(C2=NNC(=O)OC2)cc1C(F)(F)F]

The title compound was prepared analogously to Example 226 from Intermediate 66.
LC-MS (Method 1): $R_t$=0.92 min; MS (ESIpos): m/z=327 [M+H]$^+$

Example 255

6-[4-(2-Oxo-3,6-dihydro-2H-1,3,4-oxadiazin-5-yl)-2-(trifluoromethyl)phenyl]-2λ⁶-thia-6-azaspiro[3.3]heptane-2,2-dione

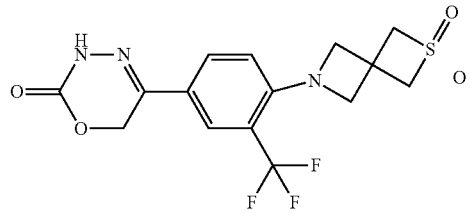

The title compound was prepared analogously to Example 226 from Intermediate 66.

LC-MS (Method 1): $R_t$=0.88 min; MS (ESIpos): m/z=390 [M+H]⁺

Example 256

N²-[4-(2-Oxo-3,6-dihydro-2H-1,3,4-oxadiazin-5-yl)-2-(trifluoromethyl)phenyl]glycinamide

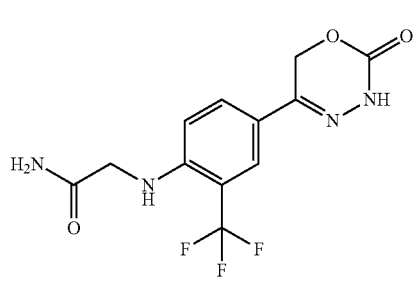 [SMILES: NC(=O)CNc1ccc(C2=NNC(=O)OC2)cc1C(F)(F)F]

The title compound was prepared analogously to Example 226 from Intermediate 66.

LC-MS (Method 1): $R_t$=0.71 min; MS (ESIpos): m/z=317 [M+H]⁺

¹H-NMR (400 MHz, DMSO-d6) δ[ppm]: 2.074 (0.54), 2.323 (0.49), 2.327 (0.64), 2.331 (0.47), 2.522 (1.98), 2.665 (0.49), 2.669 (0.64), 2.673 (0.46), 3.809 (4.91), 3.822 (4.81), 5.304 (16.00), 5.411 (1.30), 6.085 (1.06), 6.097 (2.01), 6.109 (1.01), 6.637 (2.32), 6.661 (2.34), 7.301 (2.21), 7.528 (2.20), 7.763 (7.67), 7.781 (2.11), 7.992 (0.67), 10.907 (6.07).

Example 257

5-{4-[(3R)-3-Hydroxypyrrolidin-1-yl]-3-(trifluoromethyl)phenyl}-3,6-dihydro-2H-1,3,4-oxadiazin-2-one

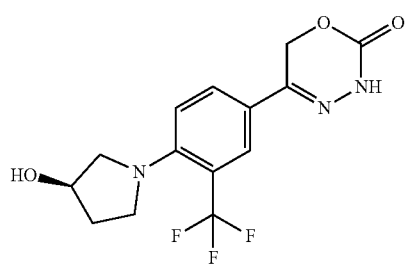 [SMILES: O=C1NN=C(c2ccc(N3CC[C@@H](O)C3)c(C(F)(F)F)c2)CO1]

The title compound was prepared analogously to Example 226 from Intermediate 66.

LC-MS (Method 2): $R_t$=0.88 min, MS (ESIpos): m/z=330 [M+H]⁺

¹H-NMR (400 MHz, DMSO-d6) δ[ppm]: 1.845 (0.62), 1.855 (0.68), 1.877 (1.00), 1.884 (1.00), 1.892 (0.93), 1.939 (0.52), 1.950 (0.57), 1.959 (0.84), 1.969 (1.12), 1.981 (0.93), 1.993 (1.03), 2.003 (0.62), 2.012 (0.43), 2.074 (0.82), 2.331 (0.77), 2.518 (3.97), 2.523 (2.39), 2.673 (0.75), 3.153 (1.35), 3.179 (1.51), 3.367 (1.55), 3.551 (0.68), 3.575 (1.43), 3.593 (2.16), 3.611 (1.30), 4.368 (1.59), 5.021 (1.07), 5.320 (16.00), 7.009 (2.74), 7.032 (2.89), 7.727 (1.94), 7.733 (2.05), 7.749 (1.73), 7.755 (1.89), 7.855 (4.15), 7.861 (3.85), 8.335 (0.53), 10.925 (5.42).

Example 258

5-{4-[(2-Methoxy-2-methylpropyl)amino]-3-(trifluoromethyl)phenyl}-3,6-dihydro-2H-1,3,4-oxadiazin-2-one

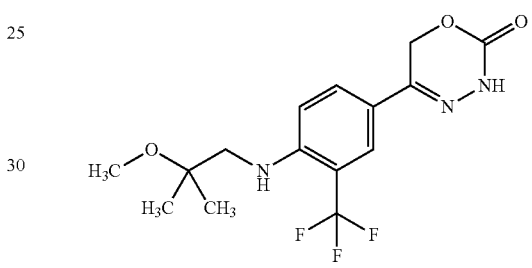

The title compound was prepared analogously to Example 226 from Intermediate 66.

LC-MS (Method 1): $R_t$=1.19 min: MS (ESIpos): m/z=346 [M+H]⁺

¹H-NMR (400 MHz, DMSO-d6) δ[ppm]: 1.173 (16.00), 3.122 (11.15), 3.229 (2.00), 3.241 (1.94), 5.125 (0.66), 5.307 (6.19), 6.949 (0.91), 6.971 (0.95), 7.754 (2.50), 7.778 (0.71), 10.904 (2.14).

Example 259

5-[4-({[(2S)-Oxolan-2-yl]methyl}amino)-3-(trifluoromethyl)phenyl]-3,6-dihydro-2H-1,3,4-oxadiazin-2-one

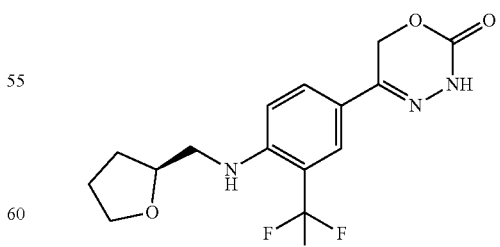

The title compound was prepared analogously to Example 226 from Intermediate 66.

LC-MS (Method 1): $R_t$=1.09 min, MS (ESIpos): m/z=344 [M+H]⁺

¹H-NMR (400 MHz, DMSO-d6) δ[ppm]: 1.591 (0.74), 1.603 (0.50), 1.611 (0.95), 1.619 (0.85), 1.628 (0.64), 1.636 (0.58), 1.641 (1.00), 1.657 (0.55), 1.782 (0.47), 1.797 (1.12), 1.815 (1.55), 1.819 (1.50), 1.829 (1.39), 1.836 (1.64), 1.850 (1.13), 1.866 (0.57), 1.885 (0.65), 1.901 (0.85), 1.906 (0.52), 1.914 (0.96), 1.923 (0.60), 1.931 (0.68), 1.934 (0.65), 1.945 (0.52), 2.518 (1.86), 2.523 (1.15), 3.212 (0.45), 3.225 (0.61), 3.245 (0.91), 3.261 (1.08), 3.275 (0.78), 3.352 (0.91), 3.359 (0.58), 3.372 (0.65), 3.386 (0.46), 3.609 (0.73), 3.630 (1.51), 3.647 (1.96), 3.664 (1.07), 3.732 (1.01), 3.748 (1.75), 3.752 (1.11), 3.765 (1.44), 3.768 (1.32), 3.785 (0.83), 4.026 (1.13), 4.038 (1.31), 4.042 (1.21), 4.054 (1.12), 5.298 (16.00), 5.422 (0.75), 5.691 (0.77), 5.705 (1.44), 5.718 (0.74), 6.965 (1.88), 6.987 (1.97), 7.731 (6.79), 7.752 (1.62), 10.890 (5.13).

Example 260

5-{4-[(2-Ethoxyethyl)amino]-3-(trifluoromethyl)phenyl}-3,6-dihydro-2H-1,3,4-oxadiazin-2-one

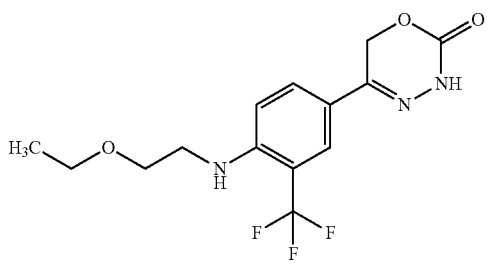 [SMILES: CCOCCNc1ccc(C2=NNC(=O)OC2)cc1C(F)(F)F]

The title compound was prepared analogously to Example 226 from Intermediate 66.

LC-MS (Method 1): $R_t$=1.11 min; MS (ESIpos): m/z=332 [M+H]⁺

¹H-NMR (400 MHz, DMSO-d6) δ[ppm]: 1.082 (6.73), 1.099 (13.49), 1.116 (6.96), 3.377 (1.78), 3.391 (4.78), 3.405 (5.37), 3.418 (2.53), 3.431 (2.74), 3.449 (6.91), 3.466 (6.79), 3.483 (2.36), 3.534 (4.56), 3.548 (7.56), 3.563 (3.32), 5.300 (16.00), 5.739 (2.79), 6.936 (3.28), 6.958 (3.43), 7.739 (8.49), 7.764 (2.77), 10.894 (6.48).

Example 261

5-[4-{[(1S,2R)-2-Hydroxycyclopentyl]amino}-3-(trifluoromethyl)phenyl]-3,6-dihydro-2H-1,3,4-oxadiazin-2-one

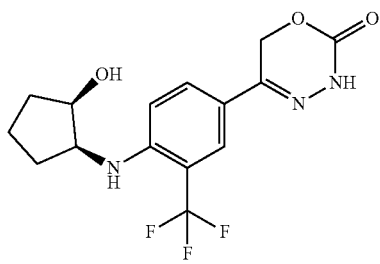 [SMILES: O=C1NN=C(c2ccc(N[C@H]3CCC[C@H]3O)c(C(F)(F)F)c2)CO1]

The title compound was prepared analogously to Example 226 from Intermediate 66.

LC-MS (Method 1): $R_t$=1.01 min; MS (ESIpos): m/z=344 [M+H]⁺

¹H-NMR (400 MHz, DMSO-d6) δ[ppm]: 1.336 (0.59), 1.347 (0.44), 1.358 (0.85), 1.367 (0.79), 1.378 (0.57), 1.389 (0.83), 1.409 (0.48), 1.489 (0.46), 1.497 (0.57), 1.510 (0.74), 1.518 (0.81), 1.530 (0.83), 1.539 (0.83), 1.549 (0.63), 1.560 (0.79), 1.578 (0.90), 1.592 (0.79), 1.599 (0.81), 1.604 (0.96), 1.612 (0.94), 1.624 (0.79), 1.631 (0.72), 1.637 (0.66), 1.644 (0.63), 1.715 (0.55), 1.722 (0.68), 1.730 (0.85), 1.740 (0.88), 1.747 (0.85), 1.758 (0.88), 1.770 (0.83), 1.776 (0.66), 1.787 (0.55), 1.796 (0.81), 1.810 (0.85), 1.818 (0.77), 1.827 (0.88), 1.831 (0.81), 1.841 (0.66), 1.848 (0.68), 1.858 (0.48), 1.863 (0.46), 2.075 (0.44), 2.089 (0.59), 2.100 (0.85), 2.107 (0.55), 2.119 (0.88), 2.130 (0.53), 2.332 (0.88), 2.518 (4.25), 2.523 (3.11), 2.540 (0.70), 2.673 (0.88), 3.727 (0.70), 3.742 (0.94), 3.758 (0.74), 4.124 (1.05), 5.302 (16.00), 5.355 (0.77), 5.677 (1.23), 5.693 (1.18), 6.911 (1.88), 6.933 (1.95), 7.740 (5.98), 7.762 (1.47), 8.354 (1.27), 10.889 (3.26).

Example 262

5-{4-[(Oxetan-3-yl)amino]-3-(trifluoromethyl)phenyl}-3,6-dihydro-2H-1,3,4-oxadiazin-2-one

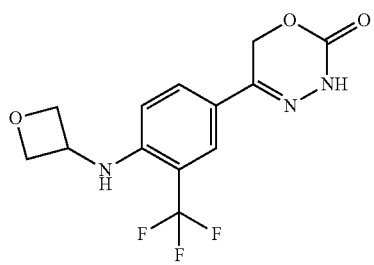 [SMILES: O=C1NN=C(c2ccc(NC3COC3)c(C(F)(F)F)c2)CO1]

The title compound was prepared analogously to Example 226 from Intermediate 66.

LC-MS (Method 1): $R_t$=0.87 min, MS (ESIpos): m/z=316 [M+H]⁺

¹H-NMR (400 MHz, DMSO-d6) δ[ppm]: 2.518 (2.13), 2.523 (1.57), 2.539 (3.28), 4.554 (2.34), 4.570 (5.65), 4.585 (3.91), 4.660 (0.55), 4.674 (0.90), 4.688 (0.90), 4.703 (0.56), 4.820 (3.06), 4.837 (5.21), 4.853 (2.56), 5.305 (16.00), 6.321 (1.57), 6.332 (1.54), 6.539 (2.11), 6.561 (2.18), 7.713 (1.22), 7.719 (1.39), 7.736 (1.14), 7.741 (1.37), 7.782 (2.88), 7.787 (2.47), 10.925 (4.42).

Example 263

5-{3-(Difluoromethyl)-4-[1-(propan-2-yl)-1H-pyrazol-4-yl]phenyl}-3,6-dihydro-2H-1,3,4-oxadiazin-2-one

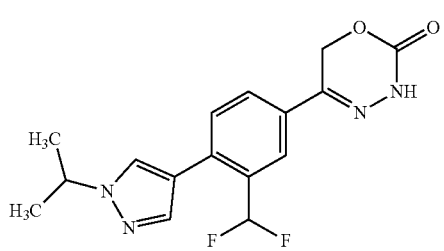 [SMILES: CC(C)n1cc(-c2ccc(C3=NNC(=O)OC3)cc2C(F)F)cn1]

To a solution of 5-(3-(difluoromethyl)-4-(1H-pyrazol-4-yl)phenyl)-3H-1,3,4-oxadiazin-2(6H)-one (100 mg, 0.32 mmol, Example 202) in dioxane/water (5 ml, v:v=5:1) was added 1,1'-bis(diphenylphosphino)ferrocenepalladium(II) chloride (26 mg, 0.03 mmol), sodium carbonate (101 mg, 1.0 mmol), 2-iodopropane (90 mg, 0.7 mmol) and the mixture was stirred at 100° C. overnight under nitrogen atmosphere. Upon completion of the reaction, the solvent was removed in vacuo and the residue was diluted with water. The resulting mixture was extracted with ethyl acetate and the combined organic layers were dried over anhydrous sodium sulfate. The solvent was removed in vacuo and the residue was purified with Prep-HPLC [Column:XBridge C18 19*150; Mobile Phase A: Water/10 mmol/L NH$_4$HCO$_3$, Mobile Phase B: MeCN; Flow rate: 20 mL/min; Gradient: 20% B to 60% B in 8 min], to give 9.9 mg (8% yield) of the title compound as a white solid.

MS(ESIpos): m/z=335 (M+H)$^+$.

Example 264

5-[3-Fluoro-4-(morpholin-4-yl)-5-(trifluoromethyl)phenyl]-3,6-dihydro-2H-1,3,4-oxadiazin-2-one

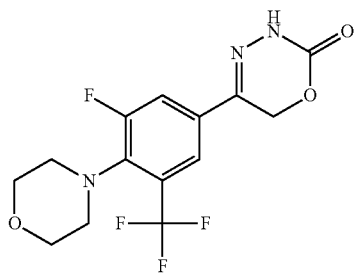 [SMILES: O=C1NN=C(c2cc(F)c(N3CCOCC3)c(C(F)(F)F)c2)CO1]

To a solution of methyl 2-(2-acetoxy-1-(3-fluoro-4-morpholino-5-(trifluoromethyl)phenyl)ethylidene)hydrazinecarboxylate (300 mg, 0.7 mmol, Intermediate 60) in 20 mL of ethanol was added sodium hydride (28 mg, 0.7 mmol, 60% purity), then the resulting mixture was stirred at room temperature overnight. After the reaction, the solvent was removed in vacuo, and water was added, and the mixture was then extracted with ethyl acetate. The combined organic layers were washed with brine, water, and were then dried over anhydrous sodium sulfate. The solvent was removed in vacuo, and the residue was purified by Prep-HPLC (Column: Xbridge Prep C18, 5 um, 19*150 mm; Mobile Phase A:Water (0.1% TFA), Mobile Phase B: ACN; Flow rate: 20 mL/min; Gradient: 25% B to 64% B in 8 min; 254 nm & 220 nm; t: 7.18 min), to give 61.4 mg (25%) of the title compound as a white solid.

MS(ESIpos): m/z=348 (M+H)$^+$.

Example 265

(6S)-6-Methyl-5-{3-(trifluoromethyl)-4-[3-(trifluoromethyl)-1H-pyrazol-1-yl]phenyl}-3,6-dihydro-2H-1,3,4-oxadiazin-2-one

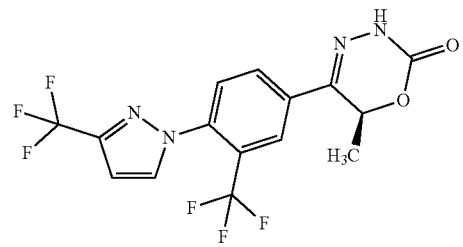 [SMILES: C[C@@H]1OC(=O)NN=C1c1ccc(-n2ccc(C(F)(F)F)n2)c(C(F)(F)F)c1]

To (6S)-5-(4-fluoro-3-(trifluoromethyl)phenyl)-6-methyl-3,6-dihydro-2H-1,3,4-oxadiazin-2-one (3.0 g, 11 mmol, Intermediate 75) and 7.3 g of 3-trifluoromethyl pyrazole (54 mmol), dissolved in 20 mL of DMF, was added 7.0 g of powdered Cs$_2$CO$_3$ (22 mmol), and the mixture was heated at 60° C. for 5 h and then stirred at room temperature overnight. Water was added and the mixture was washed several times with EtOAc, the combined EtOAc layers were washed with water and brine, dried (MgSO$_4$), concentrated and chromatographed on silica with 10-40% EtOAc in hexanes to isolate 3.7 g of product as an off-white solid (87%). The material was recrystallized from hot CH$_2$Cl$_2$/hexane to yield white crystals. Chiral SFC analysis (Chiral Pak AD-H column, 3-50% MeOH over 8 min, flow 4 mL/min) showed a 0.06:99.94 enantiomer ratio, retention times 4.18 and 4.74 min.

$^1$H NMR (400 MHz, CDCl$_3$) δ 8.81 (s, 1H), 8.17 (d, J=1.6 Hz, 1H), 7.95 (dd, J=8.4, 1.9 Hz, 1H), 7.79 (s, 1H), 7.70 (d, J=8.4 Hz, 1H), 6.77 (d, J=2.5 Hz, 1H), 5.63 (q, J=7.0 Hz, 1H), 1.68 (d, J=7.0 Hz, 3H).
$^{19}$F NMR (376 MHz, CDCl$_3$) δ −59.33, −62.28. 13C NMR (101 MHz, CDCl$_3$) δ 148.37, 145.71, 144.81 (q, J=38.7 Hz), 138.73, 133.45-133.21 (m), 133.13, 129.84, 129.53, 126.81 (q, J=32.2 Hz), 124.56 (q, J=5.2 Hz), 123.78-120.91 (m), 119.68-116.75 (m), 105.80, 71.84, 17.38.
LC-MS (Method 5): Mass 277 (M+1).

Example 266

(6S)-6-Methyl-5-{3-(trifluoromethyl)-4-[4-(trifluoromethyl)-1H-imidazol-1-yl]phenyl}-3,6-dihydro-2H-1,3,4-oxadiazin-2-one

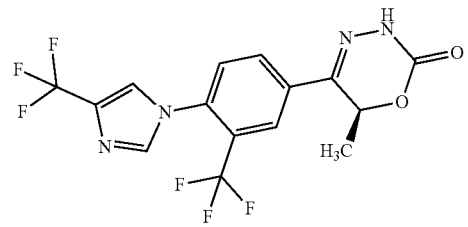 [SMILES: C[C@@H]1OC(=O)NN=C1c1ccc(-n2cnc(C(F)(F)F)c2)c(C(F)(F)F)c1]

To 100 mg (0.36 mmol) of (S)-5-(4-fluoro-3-(trifluoromethyl)phenyl)-6-methyl-3,6-dihydro-2H-1,3,4-oxadiazin-2-one (Intermediate 75) and 73 mg of 4-trifluoromethyl imidazole (0.54 mmol) dissolved in 2 mL of DMF was added 235 mg of powdered Cs2 CO3 (0.72 mmol) and the mixture was heated at 80° C. for 5 h before cooling to room temperature. Water was added and the mixture was rinsed several times with EtOAc, the combined EtOAc was rinsed with water and brine, dried (MgSO4), and concentrated. Dichloromethane was added and the starting 4-trifluoromethyl imidazole was not soluble and was filtered off. Chromatography with 0-70% EtOAc isolated impure product which was dissolved in EtOAc and extracted with 1 N HCl before drying and concentrating to yield 53 mg of the title product as a white solid (38%). 1H NMR (400 MHz, CDCl$_3$) δ 8.66 (s, 1H), 8.21 (s, 1H), 7.97 (d, J=8.3 Hz, 1H), 7.70 (s, 1H), 7.54 (d, J=8.3 Hz, 1H), 7.48 (s, 1H), 5.63 (q, J=6.9 Hz, 1H), 1.70 (d, J=7.0 Hz, 3H). 19F NMR (376 MHz, CDCl$_3$) δ −59.59, −63.01. Mass 393 (M+1)

Example 267

5-[4-(3-Methoxypropyl)-3-(trifluoromethyl)phenyl]-3,6-dihydro-2H-1,3,4-oxadiazin-2-one

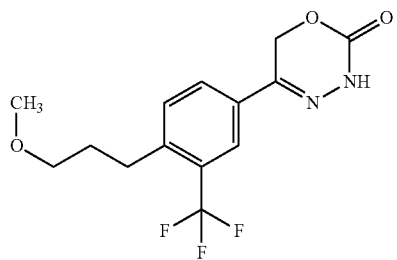

5-{4-[3-Methoxyprop-1-en-1-yl]-3-(trifluoromethyl)phenyl}-3,6-dihydro-2H-1,3,4-oxadiazin-2-one (45.0 mg, 143 μmol, Example 140) was dissolved in ethanol (2.0 ml) under an atmosphere of argon, then Pd/C (8.59 mg, 14.3 μmol) was added and the mixture was stirred for 4 hours under a hydrogen atmosphere. The catalyst was removed over celite, washed with dichloromethane and the organic phase was evaporated in vacuo to yield 37.3 mg (95% purity, 78% yield) of the title compound.

LC-MS (Method 1): R$_t$=1.11 min, MS (ESIpos): m/z=317 [M+H]$^+$ $^1$H-NMR (400 MHz, DMSO-d6) δ[ppm]: 1.764 (0.51), 1.780 (1.40), 1.799 (1.64), 1.819 (1.46), 1.835 (0.56), 2.669 (0.41), 2.787 (1.49), 2.807 (1.97), 2.826 (1.37), 3.331 (16.00), 3.357 (2.50), 3.372 (4.84), 3.388 (2.33), 5.406 (11.07), 7.576 (1.87), 7.597 (2.10), 7.902 (1.69), 7.923 (1.55), 7.950 (3.05), 11.160 (3.49).

Example 268

5-[4-(2-Methylpropyl)-3-(trifluoromethyl)phenyl]-3,6-dihydro-2H-1,3,4-oxadiazin-2-one

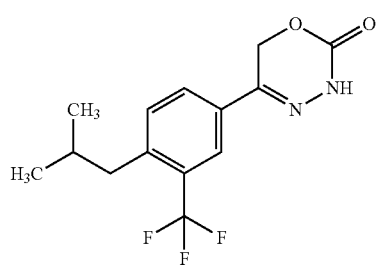 [SMILES: CC(C)Cc1ccc(C2=NNC(=O)OC2)cc1C(F)(F)F]

The title compound was synthesized analogously to Example 267 from Example 63.

LC-MS (Method 1): R$_t$=1.33 min; MS (ESIpos): m/z=301 [M+H]$^+$ $^1$H-NMR (400 MHz, DMSO-d6) δ[ppm]: 0.879 (14.98), 0.896 (15.48), 1.928 (0.57), 1.945 (0.70), 1.962 (0.56), 2.518 (1.14), 2.523 (0.79), 2.646 (2.31), 2.664 (2.39), 5.411 (16.00), 7.554 (1.79), 7.574 (2.00), 7.897 (1.28), 7.901 (1.42), 7.917 (1.08), 7.922 (1.30), 7.958 (2.77), 7.962 (2.39), 11.162 (3.15).

Example 269

5-[4-(3,3-Dimethylbutyl)-3-(trifluoromethyl)phenyl]-3,6-dihydro-2H-1,3,4-oxadiazin-2-one

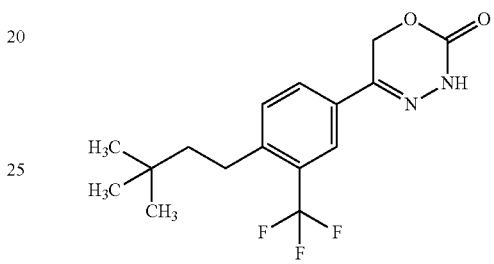

The title compound was synthesized analogously to Example 267 from Example 144.

LC-MS (Method 1): R$_t$=1.47 min; MS (ESIpos): m/z=329 [M+H]$^+$ $^1$H-NMR (400 MHz, DMSO-d6) δ[ppm]: 0.939 (1.27), 0.948 (16.00), 1.399 (0.56), 1.411 (0.41), 1.421 (0.48), 1.432 (0.41), 1.443 (0.58), 2.518 (0.41), 2.698 (0.44), 5.404 (4.21), 7.552 (0.60), 7.573 (0.67), 7.891 (0.50), 7.911 (0.46), 7.935 (0.95), 11.151 (1.28).

Example 270

5-[4-(Propan-2-yl)-3-(trifluoromethyl)phenyl]-3,6-dihydro-2H-1,3,4-oxadiazin-2-one

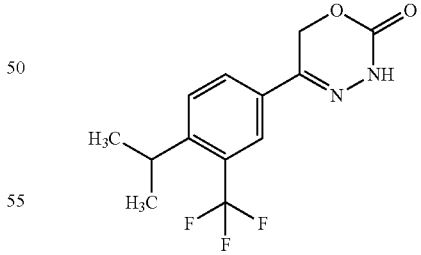

5-[4-(Prop-1-en-2-yl)-3-(trifluoromethyl)phenyl]-3,6-dihydro-2H-1,3,4-oxadiazin-2-one (90.0 mg, 317 μmol, Example 147) was dissolved in ethanol (4.0 ml) under an atmosphere of argon, then Pd/C (19.0 mg, 31.7 μmol) was added and the mixture was stirred for 2 hours under an atmosphere of hydrogen. The catalyst was removed over celite, washed with dichloromethane and the organic phase was evaporated in vacuo to yield 72.0 mg (95% purity, 75% yield) of the title compound.

LC-MS (Method 1): R$_t$=1.25 min, MS (ESIpos): m/z=287 [M+H]$^+$ $^1$H-NMR (400 MHz, DMSO-d6) δ[ppm]: 1.241 (15.87), 1.258 (16.00), 2.518 (1.04), 2.523 (0.68), 3.224 (0.69), 3.240 (0.90), 3.256 (0.66), 5.406 (15.12), 7.740 (2.07), 7.760 (2.48), 7.926 (4.00), 7.932 (2.51), 7.953 (1.55), 11.150 (3.85).

Example 271

(rac)-5-{4-[Oxan-3-yl]-3-(trifluoromethyl)phenyl}-3,6-dihydro-2H-1,3,4-oxadiazin-2-one

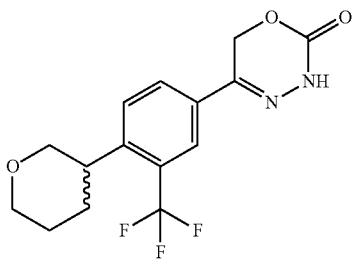 [SMILES: O=C1NN=C(c2ccc(C3CCCOC3)c(C(F)(F)F)c2)CO1]

In an autoclave vessel, 5-[4-(5,6-dihydro-2H-pyran-3-yl)-3-(trifluoromethyl)phenyl]-3,6-dihydro-2H-1,3,4-oxadiazin-2-one (40.0 mg, 123 µmol, Example 142) was dissolved in ethanol (2.0 ml) and THF (0.4 mL) under an atmosphere of argon, then Pd/C (15.0 mg, 31.7 µmol) was added. The vessel was pressurized with hydrogen (26.2 bar) and stirred for 21 hours at room temperature. The catalyst was filtered off, and the organic phase was evaporated in vacuo. The crude product was purified using mass-triggered prep-HPLC to yield 16.0 mg (95% purity, 38% yield) of the title compound.

LC-MS (Method 1): R$_t$=1.09 min: MS (ESIpos): m/z=329 [M+H]$^+$ $^1$H-NMR (400 MHz, DMSO-d6) δ[ppm]: 1.307 (0.41), 1.324 (0.40), 1.674 (1.60), 1.843 (1.21), 1.863 (1.70), 2.518 (2.74), 2.523 (1.86), 3.082 (0.63), 3.435 (0.66), 3.445 (0.62), 3.463 (2.10), 3.471 (1.19), 3.489 (2.63), 3.499 (0.69), 3.516 (1.19), 3.702 (1.10), 3.711 (0.97), 3.729 (0.89), 3.738 (0.77), 3.887 (0.97), 3.913 (0.77), 5.408 (16.00), 7.756 (1.93), 7.777 (2.40), 7.929 (1.78), 7.950 (1.49), 7.969 (3.43), 11.172 (4.69).

Example 272

(trans)-5-{4-[4-hydroxycyclohexyl]-3-(trifluoromethyl)phenyl}-3,6-dihydro-2H-1,3,4-oxadiazin-2-one

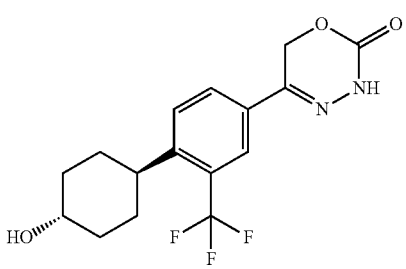 [SMILES: O=C1NN=C(c2ccc([C@H]3CC[C@H](O)CC3)c(C(F)(F)F)c2)CO1]

The title compound was synthesized analogously to Example 271 from Example 141.

LC-MS (Method 1): R$_t$=0.93 min, MS (ESIpos): m/z=343 [M+H]$^-$ $^1$H-NMR (400 MHz, DMSO-d6) δ[ppm]: 1.206 (0.45), 1.225 (1.07), 1.236 (1.26), 1.253 (1.14), 1.265 (1.22), 1.284 (0.52), 1.295 (0.48), 1.615 (1.03), 1.652 (1.96), 1.670 (2.65), 1.933 (1.39), 1.957 (1.34), 2.331 (0.91), 2.336 (0.43), 2.518 (4.32), 2.523 (2.73), 2.673 (0.89), 2.760 (0.66), 3.504 (0.50), 3.520 (0.81), 3.531 (0.81), 3.542 (0.43), 4.622 (4.07), 4.634 (3.95), 5.399 (16.00), 5.412 (1.18), 7.701 (1.88), 7.721 (2.23), 7.897 (1.57), 7.902 (1.86), 7.925 (4.57), 11.146 (5.52).

Example 273

(cis)-5-{4-[4-Hydroxycyclohexyl]-3-(trifluoromethyl)phenyl}-3,6-dihydro-2H-1,3,4-oxadiazin-2-one

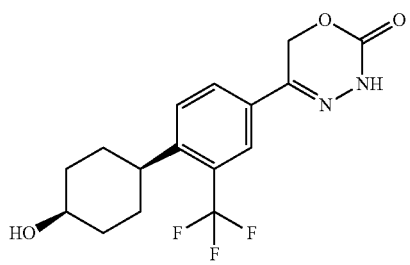 [SMILES: O=C1NN=C(c2ccc([C@H]3CC[C@@H](O)CC3)c(C(F)(F)F)c2)CO1]

The title compound was isolated during the synthesis of Example 272 as a side product.

LC-MS (Method 1): R$_t$=1.04 min; MS (ESIpos): m/z=343 [M+H]$^+$ $^1$H-NMR (400 MHz, DMSO-d6) δ[ppm]: 1.408 (1.39), 1.436 (1.46), 1.487 (0.67), 1.521 (1.58), 1.555 (1.02), 1.762 (1.69), 1.793 (1.28), 1.892 (0.53), 1.923 (1.32), 1.949 (1.23), 1.980 (0.46), 2.331 (0.97), 2.336 (0.46), 2.518 (5.45), 2.522 (3.25), 2.669 (1.37), 2.673 (1.00), 2.678 (0.46), 2.801 (0.44), 2.829 (0.77), 3.914 (1.37), 3.921 (1.37), 4.485 (3.52), 4.495 (3.48), 5.402 (16.00), 7.677 (1.97), 7.698 (2.27), 7.929 (3.83), 7.938 (2.13), 7.959 (1.51), 11.150 (5.15).

Example 274

5-{4-[(2-Aminoethyl)amino]-3-(trifluoromethyl)phenyl}-3,6-dihydro-2H-1,3,4-oxadiazin-2-one-salt with hydrochloric acid

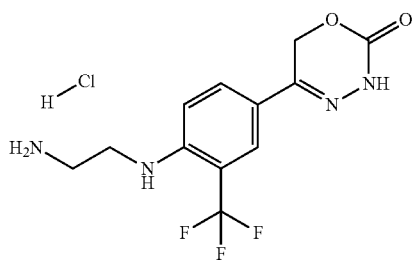

tert-Butyl {2-[4-(2-oxo-3,6-dihydro-2H-1,3,4-oxadiazin-5-yl)-2-(trifluoromethyl)anilino]ethyl} carbamate (86.0 mg, 214 µmol, Intermediate 67) was dissolved in 1,4-dioxane (3.0 ml), then hydrochloric acid in 1,4-dioxane (530 µl, 4.0 M, 2.1 mmol) was added and stirred for 3 d. Afterwards, further portions of 1,4-dioxane (2.0 ml) and hydrochloric acid in 1,4-dioxane (270 µl, 4.0 M, 1.1 mmol) were added and the mixture was stirred overnight. The reaction mixture was dried in vacuo to yield 72.0 mg (95% purity, 94% yield).

LC-MS (Method 1): R$_t$=0.56 min; MS (ESIpos): m/z=303 [M+H]$^+$ $^1$H-NMR (400 MHz, DMSO-d6) δ[ppm]: 2.518 (1.33), 2.523 (0.83), 2.933 (0.66), 2.948 (0.67), 3.513 (0.85), 3.529 (0.83), 3.565 (16.00), 5.317 (5.64), 6.183 (0.59), 7.003 (0.74), 7.027 (0.78), 7.767 (1.39), 7.772 (1.21), 7.780 (0.74), 7.949 (0.78), 10.922 (2.06).

Example 275

(rac)-5-{4-[1-amino-3-azabicyclo[3.1.0]hexan-3-yl]-3-(trifluoromethyl)phenyl}-3,6-dihydro-2H-1,3,4-oxadiazin-2-one-salt with hydrochloric acid

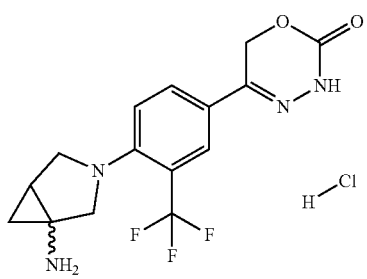 [SMILES: NC12CC1CN(c1ccc(C3=NNC(=O)OC3)cc1C(F)(F)F)C2 ; Cl]

STEP 1: tert-Butyl {3-[4-(2-oxo-3,6-dihydro-2H-1,3,4-oxadiazin-5-yl)-2-(trifluoromethyl)phenyl]-3-azabicyclo[3.1.0]hexan-1-yl}carbamate was prepared analogously to Example 205 from Intermediate 66

STEP 2: tert-Butyl {3-[4-(2-oxo-3,6-dihydro-2H-1,3,4-oxadiazin-5-yl)-2-(trifluoromethyl)phenyl]-3-azabicyclo[3.1.0]hexan-1-yl}carbamate was deprotected analogously to Example 274 to yield the title compound LC-MS (Method 2): R$_t$=0.92 min, MS (ESIpos): m/z=341 [M+H]$^+$ $^1$H-NMR (400 MHz, DMSO-d6) δ[ppm]: 3.328 (0.40), 3.351 (0.77), 3.435 (0.55), 3.458 (0.55), 3.565 (16.00), 3.618 (0.46), 5.363 (2.05), 7.906 (0.57), 7.912 (0.46), 8.789 (0.70), 11.078 (0.83).

Example 276

5-[4-(Methylamino)-3-(trifluoromethyl)phenyl]-3,6-dihydro-2H-1,3,4-oxadiazin-2-one

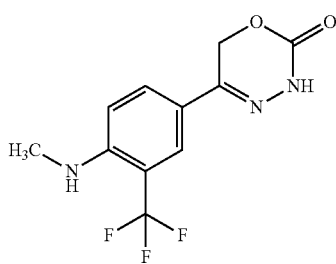 [SMILES: CNc1ccc(C2=NNC(=O)OC2)cc1C(F)(F)F]

5-[4-Fluoro-3-(trifluoromethyl)phenyl]-3,6-dihydro-2H-1,3,4-oxadiazin-2-one (150 mg, 572 µmol, Intermediate 66) was dissolved in DMSO (1.0 ml), and (methylamino)acetonitrile (96 µl, 1.3 mmol) was added. The mixture was stirred overnight at 100° C. (Methylamino)acetonitrile (96 µl, 1.3 mmol) was added again and stirred overnight at 100° C. The mixture was diluted with water and extracted with ethyl acetate three times. The combined organic layers were dried using a water-resistant filter and the filtrate was concentrated under reduced pressure. The residue was diluted with DMSO, filtered and purified by preparative HPLC to give 5.60 mg (95% purity, 3% yield) of the title compound.

LC-MS (Method 1): R$_t$=0.96 min, MS (ESIpos): m/z=274 [M+H]$^+$ $^1$H-NMR (400 MHz, DMSO-d6) δ[ppm]: 2.518 (1.46), 2.523 (1.03), 2.808 (8.32), 2.820 (8.21), 5.297 (16.00), 6.160 (1.14), 6.172 (1.13), 6.782 (2.23), 6.805 (2.34), 7.725 (2.45), 7.730 (3.10), 7.754 (1.58), 7.759 (1.18), 7.777 (1.40), 7.782 (1.18), 10.873 (4.35).

Example 277

(6S)-6-Methyl-5-[4-(4-methylpiperazin-1-yl)-3-(trifluoromethyl)phenyl]-3,6-dihydro-2H-1,3,4-oxadiazin-2-one

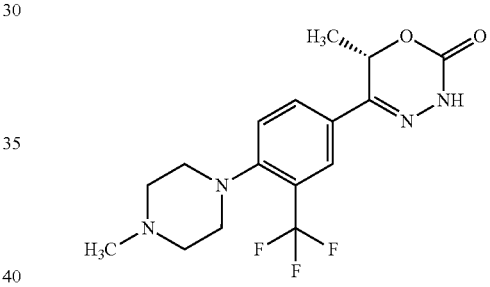

A solution of (6S)-5-[4-chloro-3-(trifluoromethyl)phenyl]-6-methyl-3,6-dihydro-2H-1,3,4-oxadiazin-2-one (200 mg, 0.68 mmol, Intermediate 74) and 1-methylpiperazine (1.52 mL, 13.67 mmol) in N,N-dimethylacetamide (0.6 mL) was heated at 140° C. for 16 hours. The reaction mixture was partitioned between EtOAc and saturated aqueous sodium chloride solution, with the organic layer isolated and washed with saturated aqueous sodium chloride solution (×4), dried (MgSO$_4$), filtered and concentrated in vacuo. The residual material was purified by Biotage Isolera™ chromatography (silica gel, eluting with MeOH/DCM, 0:1 to 1:9), with the desired fractions combined and concentrated in vacuo to afford impure desired material (66 mg @ 83% purity). This material was further purified by reverse phase Biotage Isolera™ chromatography (C$_{18}$, eluting with MeCN-Water, 1:9 to 1:0), with the desired fractions combined and lyopholised to afford the title compound (9.8 mg, 4%) as a pale pink solid.

LCMS (Method 3, 2 min) 92% @ Rt=0.83 min, MS (ESIpos): m/z=357.10 (M+H)$^+$.

LCMS (MS18, 7 min) 92% @ Rt=2.60 min, MS (ESIpos): m/z=357.45 (M+H)$^+$.

$^1$H NMR (500 MHz, DMSO-d6) δ=1.43 (d, J=6.9 Hz, 3H), 2.23 (s, 3H), 2.46 (s, 2H), 2.93 (t, J=4.7 Hz, 4H), 5.85 (q, J=6.9 Hz, 1H), 7.56 (d, J=8.5 Hz, 1H), 7.95 (dd, J=8.5, 2.0 Hz, 1H), 8.00 (d, J=2.1 Hz, 1H), 11.17 (s, 1H)-2 missing piperazine ring proton signals covered by solvent peak.

Example 278

5-[4-(2-Hydroxypropan-2-yl)-3-(trifluoromethyl)phenyl]-3,6-dihydro-2H-1,3,4-oxadiazin-2-one

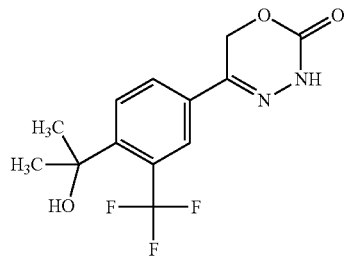 [SMILES: CC(C)(O)c1ccc(C2=NNC(=O)OC2)cc1C(F)(F)F]

To a solution of 5-[4-acetyl-3-(trifluoromethyl)phenyl]-3,6-dihydro-2H-1,3,4-oxadiazin-2-one (100 mg, 0.35 mmol, Intermediate 70) in 15 mL of tetrahydrofuran was added methylmagnesium bromide, 0.12 mL (3.5 mmol, 3 mol/L in diethyl ether) at 0° C. The resulting mixture was stirred at 0° C. for 1 hours under nitrogen atmosphere. Upon completion of the reaction, ice water was added and the resulting mixture was extracted with ethyl acetate. The combined organic layers were washed with brine and dried over anhydrous sodium sulfate. The solvent was removed in vacuo, the residue was purified by Prep-HPLC [Column: XBridge, RP18 OBD 19*150 mm; Mobile Phase A: Water (0.1% NH$_4$HCO$_3$), Mobile Phase B: ACN; Flow rate: 20 mL/min; Gradient: 25% B to 40% B in 8 min, hold 1.5 min; 254 & 220 nm R$_t$: 6.28 min] to give 35.4 mg (33%) of the title compound as a white solid.

MS (ESIpos):m/z=303 (M+H)*.

$^1$H-NMR (400 MHz, DMSO-d$_6$): δ [ppm]=11.16 (s, 1H), 8.05 (d, 1H), 7.87 (dd, 1H), 7.80 (d, 1H), 5.41 (s, 2H), 5.23 (s, 1H), 1.55 (s, 6H).

Example 279

(6S)-5-[4-(3,3-Difluoroazetidin-1-yl)-3-(trifluoromethyl)phenyl]-6-methyl-3,6-dihydro-2H-1,3,4-oxadiazin-2-one

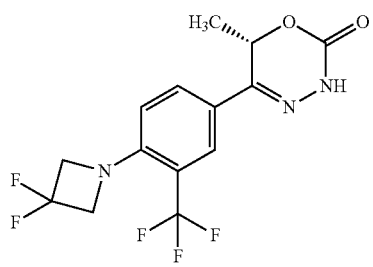 [SMILES: C[C@@H]1OC(=O)NN=C1c1ccc(N2CC(F)(F)C2)c(C(F)(F)F)c1]

A suspension of (6S)-5-[4-chloro-3-(trifluoromethyl)phenyl]-6-methyl-3,6-dihydro-2H-1,3,4-oxadiazin-2-one (100 mg, 0.34 mmol, Intermediate 74), 3,3-difluoroazetidine hydrochloride (60.3 mg, 0.47 mmol), potassium phosphate (197 mg, 0.93 mmol), tris(dibenzylideneacetone)dipalladium(0) (14.2 mg, 0.02 mmol) and 2-(dicyclohexylphosphino)-2',4',6'-tri-i-propyl-1,1'-biphenyl/XPhos (29.6 mg, 0.06 mmol) in 1,4-dioxane (1.5 mL) was degassed via nitrogen-filled balloon and heated at 100° C. for 20 hours. After this time, the reaction mixture was allowed to cool to RT and partitioned between IPA/DCM (1:4 v:v) and water, with the organic layer isolated via phase separation cartridge, and concentrated in vacuo. The residual material was purified by Biotage Isolera™ chromatography (silica gel, eluting with EtOAc/heptane (0:1 to 1:1 to 1:0), with the desired fractions combined and concentrated in vacuo to afford 70 mg (54% yield) of the title compound as a pale yellow solid.

LCMS (Method 3.2 min) 99% @ Rt=1.17 min, MS (ESIpos): m/z=390.95 (M+MeCN+H)$^+$.

LCMS (Method 3.7 min) 92% @ Rt=4.02 min, MS (ESIpos): m/z=390.95 (M+MeCN+H)$^+$.

$^1$H NMR (500 MHz, DMSO-d6) δ=1.40 (d, J=6.9 Hz, 3H), 4.51 (t, J=12.3 Hz, 4H), 5.83 (q, J=6.9 Hz, 1H), 6.80 (d, J=8.8 Hz, 1H), 7.85 (dd, J=8.8, 2.1 Hz, 1H), 7.91 (d, J=2.0 Hz, 1H), 11.03 (s, 1H).

Example 280

(6S)-5-[4-(3-Hydroxy-3-methylazetidin-1-yl)-3-(trifluoromethyl)phenyl]-6-methyl-3,6-dihydro-2H-1,3,4-oxadiazin-2-one

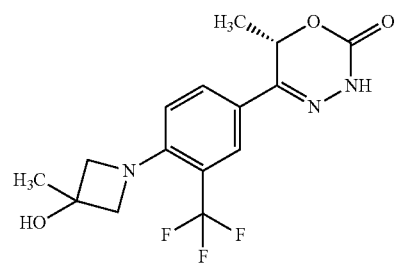 [SMILES: C[C@@H]1OC(=O)NN=C1c1ccc(N2CC(C)(O)C2)c(C(F)(F)F)c1]

The title compound was synthesized analogously to Example 280 from Intermediate 74 and 3-hydroxy-3-methylazetidine.

LCMS (Method 3, 2 min) 97% @ Rt=1.04 min, MS (ESIpos): m/z=334.00 (M+H)$^+$.

LCMS (Method 3, 7 min) 100% @ Rt=3.52 min, MS (ESIpos): m/z=334.00 (M+H)$^+$.

$^1$H NMR (500 MHz, DMSO-d6) δ=1.40 (d, J=6.9 Hz, 3H), 1.45 (s, 3H), 3.91 (d, J=8.2 Hz, 2H), 3.96 (d, J=8.2 Hz, 2H), 5.62 (s, 1H), 5.78 (q, J=6.9 Hz, 1H), 6.63 (d, J=8.9 Hz, 1H), 7.76 (dd, J=8.9, 2.1 Hz, 1H), 7.83 (d, J=2.1 Hz, 1H), 10.95 (s, 1H).

Example 281

5-{4-[(2-methoxybutyl)amino]-3-(trifluoromethyl)phenyl}-3,6-dihydro-2H-1,3,4-oxadiazin-2-one

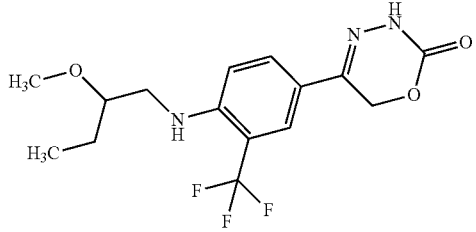 [SMILES: CCC(CNc1ccc(C2=NNC(=O)OC2)cc1C(F)(F)F)OC]

The title compound was prepared analogously to Example 226 from Intermediate 66.

LC-MS (Method 1): $R_t$=1.17 min; MS (ESIpos): m/z=346 [M+H]$^+$

Example 282

5-[4-{[3-(1H-imidazol-1-yl)propyl]amino}-3-(trifluoromethyl)phenyl]-3,6-dihydro-2H-1,3,4-oxadiazin-2-one

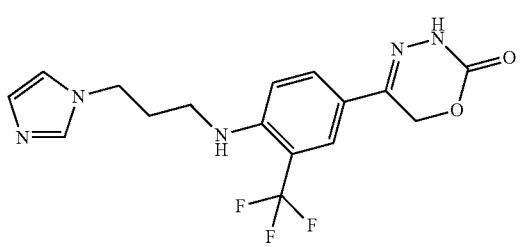 [SMILES: O=C1NN=C(c2ccc(NCCCn3ccnc3)c(C(F)(F)F)c2)CO1]

The title compound was prepared analogously to Example 226 from Intermediate 66.

LC-MS (Method 1): $R_t$=0.51 min; MS (ESIpos): m/z=368 [M+H]$^+$

Example 283

5-{4-[(2-hydroxy-2-methylpropyl)(methyl)amino]-3-(trifluoromethyl)phenyl}-3,6-dihydro-2H-1,3,4-oxadiazin-2-one

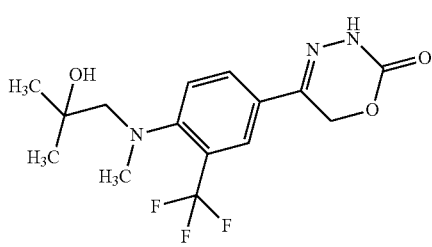 [SMILES: CN(CC(C)(C)O)c1ccc(C2=NNC(=O)OC2)cc1C(F)(F)F]

The title compound was prepared analogously to Example 226 from Intermediate 66.

LC-MS (Method 1): $R_t$=1.00 min; MS (ESIpos): m/z=346 [M+H]$^+$

Example 284

5-[4-(2-oxa-7-azaspiro[4.4]nonan-7-yl)-3-(trifluoromethyl)phenyl]-3,6-dihydro-2H-1,3,4-oxadiazin-2-one

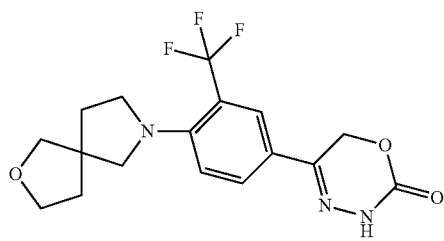 [SMILES: O=C1NN=C(c2ccc(N3CCC4(CCOC4)C3)c(C(F)(F)F)c2)CO1]

The title compound was prepared analogously to Example 226 from Intermediate 66.

LC-MS (Method 1): $R_t$=1.08 min; MS (ESIpos): m/z=370 [M+H]$^+$

Example 285

5-{4-[(1-hydroxypentan-2-yl)amino]-3-(trifluoromethyl)phenyl}-3,6-dihydro-2H-1,3,4-oxadiazin-2-one

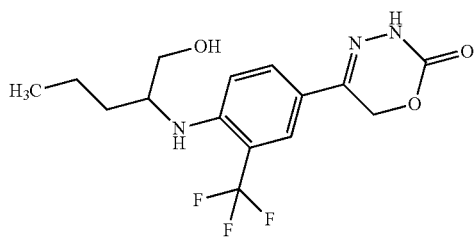 [SMILES: CCCC(CO)Nc1ccc(C2=NNC(=O)OC2)cc1C(F)(F)F]

The title compound was prepared analogously to Example 226 from Intermediate 66.

LC-MS (Method 1): $R_t$=1.04 min; MS (ESIpos): m/z=346 [M+H]$^+$

Example 286

5-[4-{[(1-methyl-1H-pyrazol-3-yl)methyl]amino}-3-(trifluoromethyl)phenyl]-3,6-dihydro-2H-1,3,4-oxadiazin-2-one

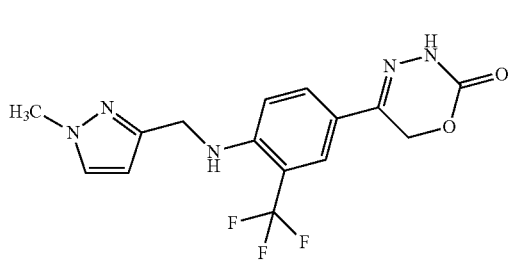 [SMILES: Cn1ccc(CNc2ccc(C3=NNC(=O)OC3)cc2C(F)(F)F)n1]

The title compound was prepared analogously to Example 226 from Intermediate 66.
LC-MS (Method 1): $R_t$=0.93 min; MS (ESIpos): m/z=354 [M+H]$^+$ Example 287

1-[4-(2-oxo-3,6-dihydro-2H-1,3,4-oxadiazin-5-yl)-2-(trifluoromethyl)phenyl]azetidine-3-carboxamide

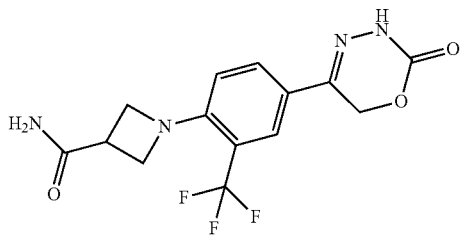 [SMILES: NC(=O)C1CN(c2ccc(C3=NNC(=O)OC3)cc2C(F)(F)F)C1]

The title compound was prepared analogously to Example 226 from Intermediate 66.
LC-MS (Method 1): $R_t$=0.74 min; MS (ESIpos): m/z=343 [M+H]$^+$ Example 288

5-[4-{[(pyridin-3-yl)methyl]amino}-3-(trifluoromethyl)phenyl]-3,6-dihydro-2H-1,3,4-oxadiazin-2-one

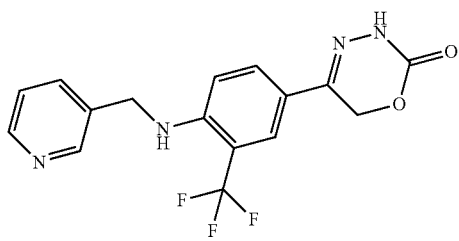 [SMILES: O=C1NN=C(c2ccc(NCc3cccnc3)c(C(F)(F)F)c2)CO1]

The title compound was prepared analogously to Example 226 from Intermediate 66.
LC-MS (Method 1): $R_t$=0.61 min; MS (ESIpos): m/z=351 [M+H]$^+$ Example 289

5-{4-[(4-hydroxycyclohexyl)(methyl)amino]-3-(trifluoromethyl)phenyl}-3,6-dihydro-2H-1,3,4-oxadiazin-2-one

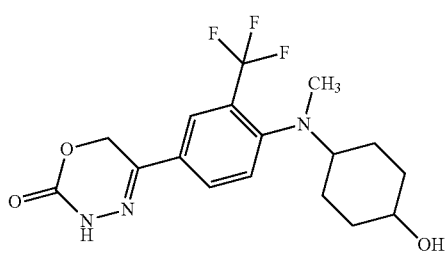 [SMILES: CN(c1ccc(C2=NNC(=O)OC2)cc1C(F)(F)F)C1CCC(O)CC1]

The title compound was prepared analogously to Example 226 from Intermediate 66.
LC-MS (Method 1): $R_t$=1.00 min; MS (ESIpos): m/z=372 [M+H]$^+$ Example 290

5-[4-{[(5-oxopyrrolidin-2-yl)methyl]amino}-3-(trifluoromethyl)phenyl]-3,6-dihydro-2H-1,3,4-oxadiazin-2-one

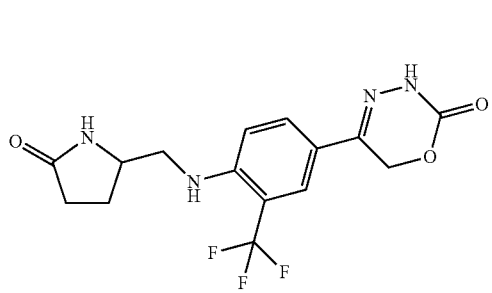 [SMILES: O=C1CCC(CNc2ccc(C3=NNC(=O)OC3)cc2C(F)(F)F)N1]

The title compound was prepared analogously to Example 226 from Intermediate 66.
LC-MS (Method 1): $R_t$=0.76 min; MS (ESIpos): m/z=357 [M+H]$^+$ Example 291

5-[4-{[2-(1H-imidazol-5-yl)ethyl]amino}-3-(trifluoromethyl)phenyl]-3,6-dihydro-2H-1,3,4-oxadiazin-2-one

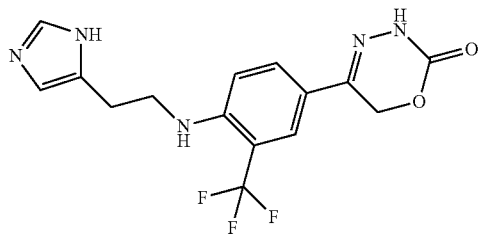 [SMILES: O=C1NN=C(c2ccc(NCCc3cnc[nH]3)c(C(F)(F)F)c2)CO1]

The title compound was prepared analogously to Example 226 from Intermediate 66.
LC-MS (Method 1): $R_t$=0.49 min; MS (ESIpos): m/z=354 [M+H]$^+$ Example 292

5-[4-{[(2R,3R)-1,3-dihydroxybutan-2-yl]amino}-3-(trifluoromethyl)phenyl]-3,6-dihydro-2H-1,3,4-oxadiazin-2-one

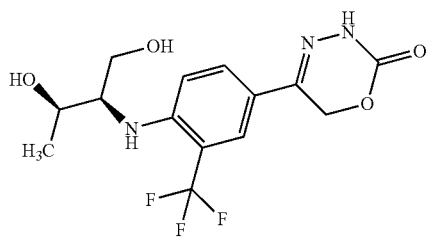 [SMILES: C[C@@H](O)[C@@H](CO)Nc1ccc(C2=NNC(=O)OC2)cc1C(F)(F)F]

Example 293

5-[4-{[(2R)-1-hydroxy-4-methylpentan-2-yl]amino}-3-(trifluoromethyl)phenyl]-3,6-dihydro-2H-1,3,4-oxadiazin-2-one

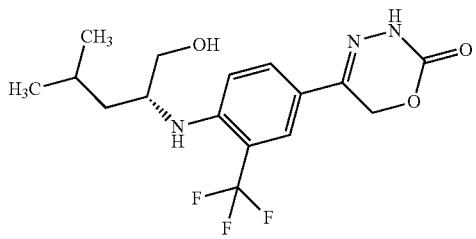 [SMILES: CC(C)C[C@H](CO)Nc1ccc(C2=NNC(=O)OC2)cc1C(F)(F)F]

The title compound was prepared analogously to Example 226 from Intermediate 66.
LC-MS (Method 1): R$_t$=0.76 min; MS (ESIpos): m/z=348 [M+H]$^+$

Example 294

5-[4-{[(oxan-4-yl)methyl]amino}-3-(trifluoromethyl)phenyl]-3,6-dihydro-2H-1,3,4-oxadiazin-2-one

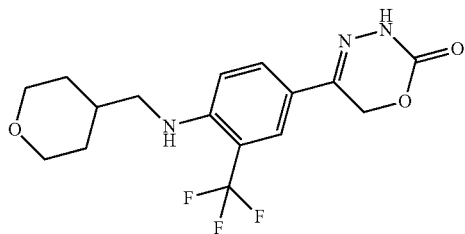 [SMILES: O=C1NN=C(c2ccc(NCC3CCOCC3)c(C(F)(F)F)c2)CO1]

The title compound was prepared analogously to Example 226 from Intermediate 66.
LC-MS (Method 1): R$_t$=1.11 min; MS (ESIpos): m/z=360 [M+H]$^+$

Example 295

5-[4-{[(1-methyl-1H-imidazol-2-yl)methyl]amino}-3-(trifluoromethyl)phenyl]-3,6-dihydro-2H-1,3,4-oxadiazin-2-one

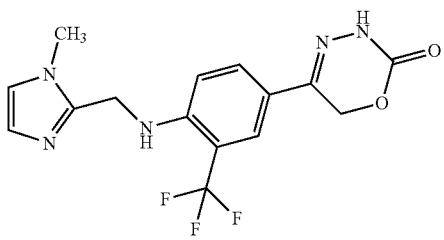 [SMILES: Cn1ccnc1CNc1ccc(C2=NNC(=O)OC2)cc1C(F)(F)F]

The title compound was prepared analogously to Example 226 from Intermediate 66.
LC-MS (Method 1): R$_t$=1.02 min; MS (ESIpos): m/z=358 [M+H]$^+$

Example 296

5-{4-[(dicyclopropylmethyl)amino]-3-(trifluoromethyl)phenyl}-3,6-dihydro-2H-1,3,4-oxadiazin-2-one

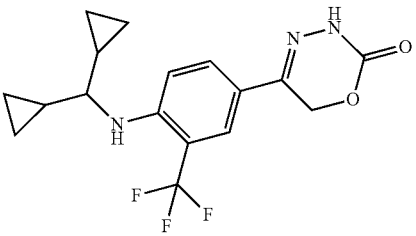 [SMILES: O=C1NN=C(c2ccc(NC(C3CC3)C3CC3)c(C(F)(F)F)c2)CO1]

The title compound was prepared analogously to Example 226 from Intermediate 66.
LC-MS (Method 1): R$_t$=0.45 min; MS (ESIpos): m/z=354 [M+H]$^+$

Example 297

5-[4-{[2-(1H-1,2,3-triazol-1-yl)ethyl]amino}-3-(trifluoromethyl)phenyl]-3,6-dihydro-2H-1,3,4-oxadiazin-2-one

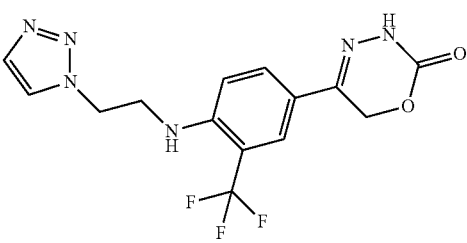 [SMILES: O=C1NN=C(c2ccc(NCCn3ccnn3)c(C(F)(F)F)c2)CO1]

The title compound was prepared analogously to Example 226 from Intermediate 66.
LC-MS (Method 1): R$_t$=1.32 min; MS (ESIpos): m/z=354 [M+H]$^+$

Example 298

5-[4-{[(4-methyloxan-4-yl)methyl]amino}-3-(trifluoromethyl)phenyl]-3,6-dihydro-2H-1,3,4-oxadiazin-2-one

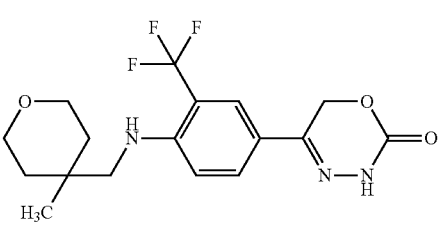 [SMILES: CC1(CNc2ccc(C3=NNC(=O)OC3)cc2C(F)(F)F)CCOCC1]

The title compound was prepared analogously to Example 226 from Intermediate 66.
LC-MS (Method 1): R$_t$=0.78 min; MS (ESIpos): m/z=355 [M+H]$^+$

Example 299

5-[4-{[(pyrimidin-5-yl)methyl]amino}-3-(trifluoromethyl)phenyl]-3,6-dihydro-2H-1,3,4-oxadiazin-2-one

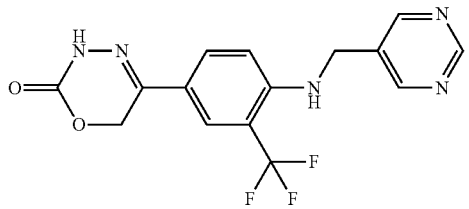 [SMILES: O=C1NN=C(c2ccc(NCc3cncnc3)c(C(F)(F)F)c2)CO1]

The title compound was prepared analogously to Example 226 from Intermediate 66.
LC-MS (Method 1): $R_t$=0.80 min; MS (ESIpos): m/z=352 [M+H]$^+$

Example 300

5-[4-{[(1-methyl-1H-pyrazol-4-yl)methyl]amino}-3-(trifluoromethyl)phenyl]-3,6-dihydro-2H-1,3,4-oxadiazin-2-one

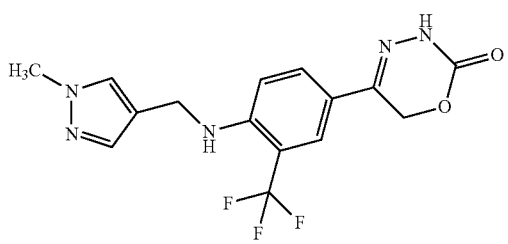 [SMILES: Cn1cc(CNc2ccc(C3=NNC(=O)OC3)cc2C(F)(F)F)cn1]

The title compound was prepared analogously to Example 226 from Intermediate 66.
LC-MS (Method 1): $R_t$=0.89 min; MS (ESIpos): m/z=354 [M+H]$^+$

Example 301

5-{4-[(1-methylazepan-4-yl)amino]-3-(trifluoromethyl)phenyl}-3,6-dihydro-2H-1,3,4-oxadiazin-2-one

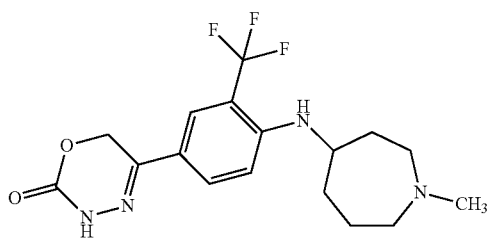 [SMILES: CN1CCCC(Nc2ccc(C3=NNC(=O)OC3)cc2C(F)(F)F)CC1]

The title compound was prepared analogously to Example 226 from Intermediate 66.
LC-MS (Method 1): $R_t$=1.11 min; MS (ESIpos): m/z=372 [M+H]$^+$

Example 302

5-[4-(4,6-dimethyl-1,4-diazepan-1-yl)-3-(trifluoromethyl)phenyl]-3,6-dihydro-2H-1,3,4-oxadiazin-2-one

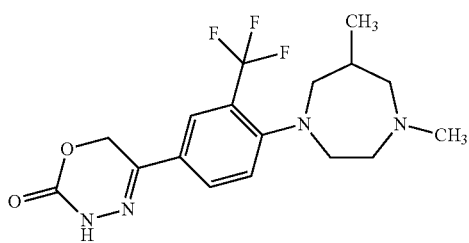 [SMILES: CC1CN(C)CCN(c2ccc(C3=NNC(=O)OC3)cc2C(F)(F)F)C1]

The title compound was prepared analogously to Example 226 from Intermediate 66.
LC-MS (Method 1): $R_t$=0.53 min; MS (ESIpos): m/z=371 [M+H]$^+$ The title compound was prepared analogously to Example 226 from Intermediate 66.
LC-MS (Method 1): $R_t$=0.55 min; MS (ESIpos): m/z=371 [M+H]$^+$

Example 303

N-methyl-N$^3$-[4-(2-oxo-3,6-dihydro-2H-1,3,4-oxadiazin-5-yl)-2-(trifluoromethyl)phenyl]-beta-alaninamide

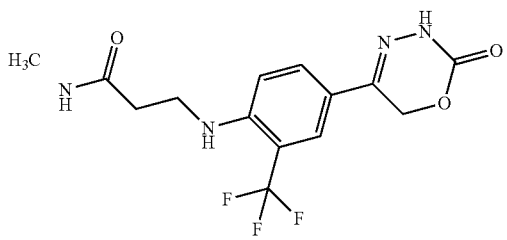

The title compound was prepared analogously to Example 226 from Intermediate 66.
LC-MS (Method 1): $R_t$=0.76 min: MS (ESIpos): m/z=345 [M+H]$^+$

Example 304

N-methyl-1-[4-(2-oxo-3,6-dihydro-2H-1,3,4-oxadiazin-5-yl)-2-(trifluoromethyl)phenyl]prolinamide

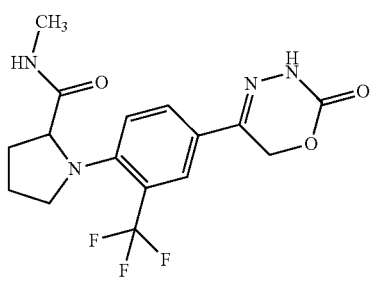 [SMILES: CNC(=O)C1CCCN1c1ccc(C2=NNC(=O)OC2)cc1C(F)(F)F]

Example 305

5-[4-{[(1-methyl-5-oxopyrrolidin-3-yl)methyl]amino}-3-(trifluoromethyl)phenyl]-3,6-dihydro-2H-1,3,4-oxadiazin-2-one

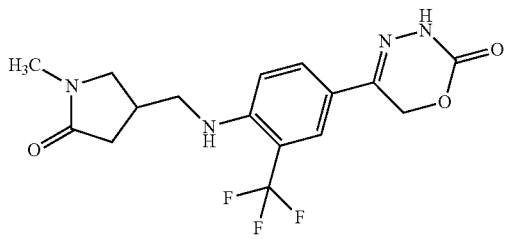 [SMILES: CN1CC(CNc2ccc(C3=NNC(=O)OC3)cc2C(F)(F)F)CC1=O]

The title compound was prepared analogously to Example 226 from Intermediate 66.
LC-MS (Method 1): $R_t$=0.81 min; MS (ESIpos): m/z=371 [M+H]$^+$

Example 306 ethyl-N$^2$-[4-(2-oxo-3,6-dihydro-2H-1,3,4-oxadiazin-5-yl)-2-(trifluoromethyl)phenyl]glycinamide

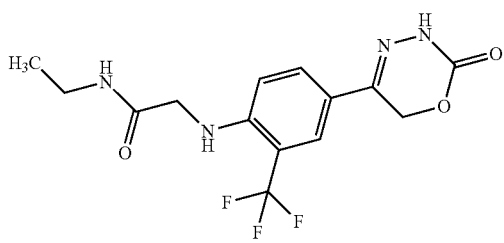 [SMILES: CCNC(=O)CNc1ccc(C2=NNC(=O)OC2)cc1C(F)(F)F]

The title compound was prepared analogously to Example 226 from Intermediate 66.
LC-MS (Method 1): $R_t$=0.81 min; MS (ESIpos): m/z=345 [M+H]$^+$

Example 307

N,N-dimethyl-N$^2$-[4-(2-oxo-3,6-dihydro-2H-1,3,4-oxadiazin-5-yl)-2-(trifluoromethyl)phenyl]glycinamide

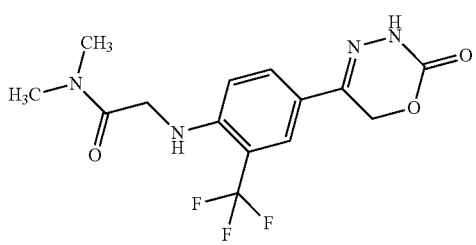 [SMILES: CN(C)C(=O)CNc1ccc(C2=NNC(=O)OC2)cc1C(F)(F)F]

LC-MS (Method 1): $R_t$=0.88 min; MS (ESIpos): m/z=345 [M+H]$^+$

Example 308

5-[4-{[(pyridazin-3-yl)methyl]amino}-3-(trifluoromethyl)phenyl]-3,6-dihydro-2H-1,3,4-oxadiazin-2-one

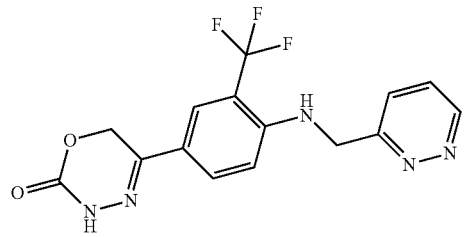 [SMILES: O=C1NN=C(c2ccc(NCc3cccnn3)c(C(F)(F)F)c2)CO1]

The title compound was prepared analogously to Example 226 from Intermediate 66.
LC-MS (Method 1): $R_t$=0.79 min; MS (ESIpos): m/z=352 [M+H]$^+$

Example 309

5-{4-[(1-methylpiperidin-4-yl)amino]-3-(trifluoromethyl)phenyl}-3,6-dihydro-2H-1,3,4-oxadiazin-2-one

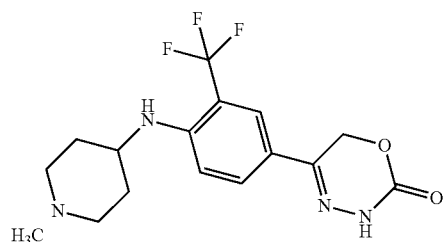

The title compound was prepared analogously to Example 226 from Intermediate 66.
LC-MS (Method 1): $R_t$=0.48 min; MS (ESIpos): m/z=357 [M+H]$^+$

Example 310

5-{4-[3-(dimethylamino)pyrrolidin-1-yl]-3-(trifluoromethyl)phenyl}-3,6-dihydro-2H-1,3,4-oxadiazin-2-one

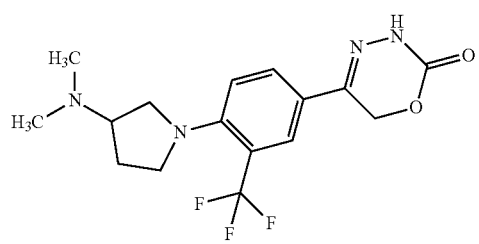 [SMILES: CN(C)C1CCN(c2ccc(C3=NNC(=O)OC3)cc2C(F)(F)F)C1]

The title compound was prepared analogously to Example 226 from Intermediate 66.
LC-MS (Method 1): R$_t$=0.50 min; MS (ESIpos): m/z=357 [M+H]$^+$ Example 311

5-{4-[(2-methylpiperidin-4-yl)amino]-3-(trifluoromethyl)phenyl}-3,6-dihydro-2H-1,3,4-oxadiazin-2-one

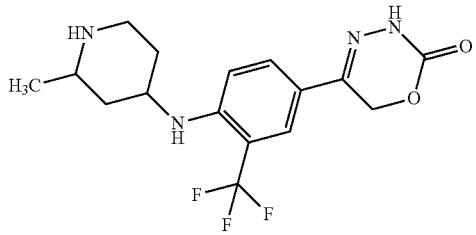 [SMILES: CC1CC(Nc2ccc(C3=NNC(=O)OC3)cc2C(F)(F)F)CCN1]

The title compound was prepared analogously to Example 226 from Intermediate 66.
LC-MS (Method 1): R$_t$=0.52 min; MS (ESIpos): m/z=357 [M+H]$^+$ Example 312

5-[4-{[3-(4H-1,2,4-triazol-4-yl)propyl]amino}-3-(trifluoromethyl)phenyl]-3,6-dihydro-2H-1,3,4-oxadiazin-2-one

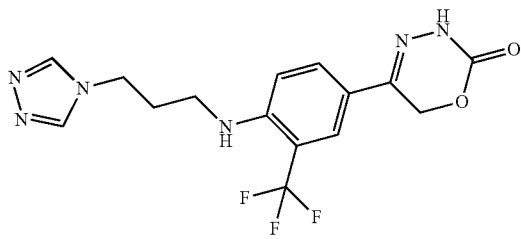 [SMILES: O=C1NN=C(c2ccc(NCCCn3cnnc3)c(C(F)(F)F)c2)CO1]

The title compound was prepared analogously to Example 226 from Intermediate 66.
LC-MS (Method 1): R$_t$=0.71 min; MS (ESIpos): m/z=369 [M+H]$^+$ Example 313

5-[4-{[2-(2-oxoimidazolidin-1-yl)ethyl]amino}-3-(trifluoromethyl)phenyl]-3,6-dihydro-2H-1,3,4-oxadiazin-2-one

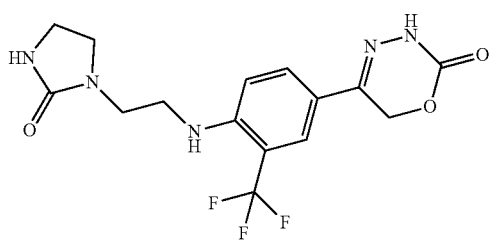 [SMILES: O=C1NN=C(c2ccc(NCCN3CCNC3=O)c(C(F)(F)F)c2)CO1]

The title compound was prepared analogously to Example 226 from Intermediate 66.
LC-MS (Method 1): R$_t$=0.77 min; MS (ESIpos): m/z=372 [M+H]$^+$ Example 314

3-{ethyl[4-(2-oxo-3,6-dihydro-2H-1,3,4-oxadiazin-5-yl)-2-(trifluoromethyl)phenyl]amino}propanenitrile

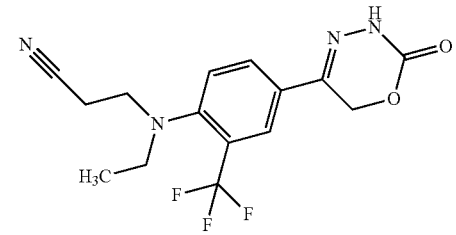 [SMILES: CCN(CCC#N)c1ccc(C2=NNC(=O)OC2)cc1C(F)(F)F]

The title compound was prepared analogously to Example 226 from Intermediate 66.
LC-MS (Method 1): R$_t$=1.15 min; MS (ESIpos): m/z=341 [M+H]$^+$ Example 315

5-[4-{[(1-ethylpyrrolidin-2-yl)methyl]amino}-3-(trifluoromethyl)phenyl]-3,6-dihydro-2H-1,3,4-oxadiazin-2-one

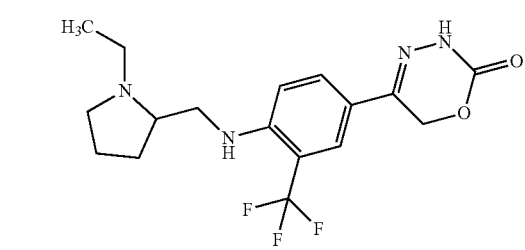 [SMILES: CCN1CCCC1CNc1ccc(C2=NNC(=O)OC2)cc1C(F)(F)F]

The title compound was prepared analogously to Example 226 from Intermediate 66.
LC-MS (Method 1): R$_t$=0.50 min; MS (ESIpos): m/z=371 [M+H]$^+$ Example 316

N-{2-[4-(2-oxo-3,6-dihydro-2H-1,3,4-oxadiazin-5-yl)-2-(trifluoromethyl)anilino]ethyl}acetamide

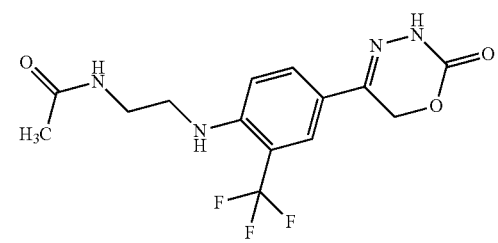 [SMILES: CC(=O)NCCNc1ccc(C2=NNC(=O)OC2)cc1C(F)(F)F]

The title compound was prepared analogously to Example 226 from Intermediate 66.
LC-MS (Method 1): $R_t$=0.75 min; MS (ESIpos): m/z=345 [M+H]⁺

Example 317

5-[4-{[2-(piperidin-1-yl)ethyl]amino}-3-(trifluoromethyl)phenyl]-3,6-dihydro-2H-1,3,4-oxadiazin-2-one

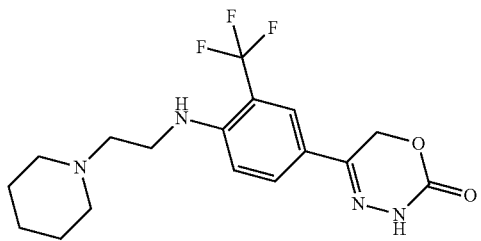 [SMILES: O=C1NN=C(c2ccc(NCCN3CCCCC3)c(C(F)(F)F)c2)CO1]

The title compound was prepared analogously to Example 226 from Intermediate 66.
LC-MS (Method 1): $R_t$=0.51 min; MS (ESIpos): m/z=371 [M+H]⁺

Example 318

5-[4-{[2-(1-methylpyrrolidin-2-yl)ethyl]amino}-3-(trifluoromethyl)phenyl]-3,6-dihydro-2H-1,3,4-oxadiazin-2-one

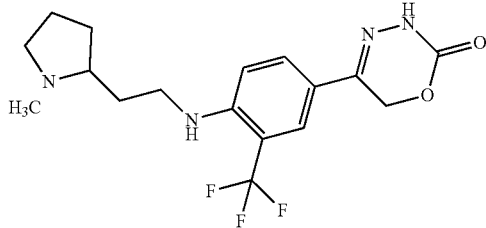

The title compound was prepared analogously to Example 226 from Intermediate 66.
LC-MS (Method 1): $R_t$=0.52 min; MS (ESIpos): m/z=371 [M+H]⁺

Example 319

5-{4-[(3-hydroxy-3-methylbutyl)amino]-3-(trifluoromethyl)phenyl}-3,6-dihydro-2H-1,3,4-oxadiazin-2-one

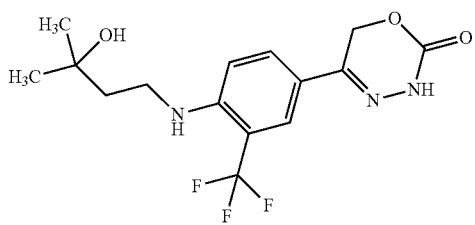 [SMILES: CC(C)(O)CCNc1ccc(C2=NNC(=O)OC2)cc1C(F)(F)F]

The title compound was prepared analogously to Example 132 from Intermediate 66.
LC-MS (Method 1): $R_t$=0.99 min; MS (ESIpos): m/z=346 [M+H]⁺
¹H-NMR (400 MHz, DMSO-d6) δ[ppm]: 1.157 (16.00), 1.663 (0.83), 1.681 (1.79), 1.698 (0.85), 2.518 (0.61), 3.273 (0.44), 3.290 (1.02), 3.302 (1.01), 3.320 (0.55), 4.668 (3.46), 5.293 (7.07), 6.407 (0.73), 6.832 (0.98), 6.855 (1.03), 7.723 (1.11), 7.728 (1.73), 7.735 (0.96), 7.757 (0.70), 7.762 (0.56), 10.870 (2.45).

Example 320

5-[4-{[4-aminocyclohexyl]amino}-3-(trifluoromethyl)phenyl]-3,6-dihydro-2H-1,3,4-oxadiazin-2-one (mixture of stereoisomers)

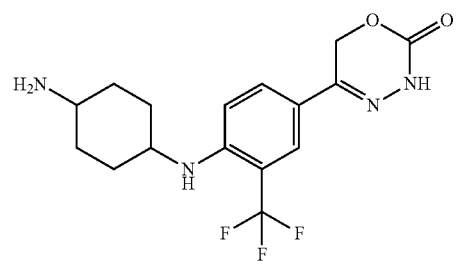 [SMILES: NC1CCC(Nc2ccc(C3=NNC(=O)OC3)cc2C(F)(F)F)CC1]

The title compound was prepared analogously to Example 132 from Intermediate 66.
LC-MS (Method 2): $R_t$=0.96 min; MS (ESIpos): m/z=357 [M+H]⁺
¹H-NMR (400 MHz, DMSO-d6) δ[ppm]: 1.311 (0.95), 1.338 (1.33), 1.566 (1.33), 1.575 (1.72), 1.587 (2.17), 1.597 (2.32), 1.611 (1.90), 1.621 (1.94), 1.630 (1.54), 1.748 (1.66), 1.759 (1.27), 1.768 (1.26), 1.777 (1.14), 1.880 (0.48), 1.907 (0.51), 2.518 (2.24), 2.523 (1.56), 2.539 (0.82), 2.836 (0.86), 3.324 (1.17), 3.627 (0.62), 4.882 (0.98), 4.903 (0.97), 5.293 (4.48), 5.300 (16.00), 6.953 (1.71), 6.975 (1.87), 7.718 (0.92), 7.727 (0.59), 7.741 (6.05), 7.761 (1.52), 10.894 (0.40).

Example 321

5-{4-[(2-amino-2-methylpropyl)amino]-3-(trifluoromethyl)phenyl}-3,6-dihydro-2H-1,3,4-oxadiazin-2-one

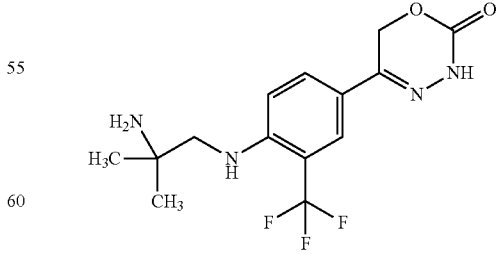

The title compound was prepared analogously to Example 132 from Intermediate 66.
LC-MS (Method 2): $R_t$=0.96 min; MS (ESIpos): m/z=331 [M+H]⁺

¹H-NMR (400 MHz, DMSO-d6) δ[ppm]: 1.092 (16.00), 1.621 (0.70), 2.518 (1.01), 2.523 (0.65), 2.971 (1.78), 2.983 (1.77), 5.299 (7.03), 5.857 (0.60), 6.867 (0.81), 6.891 (0.86), 7.737 (2.42), 7.754 (0.74), 10.880 (1.18).

Example 322

5-[4-{[3-aminocyclohexyl]amino}-3-(trifluoromethyl)phenyl]-3,6-dihydro-2H-1,3,4-oxadiazin-2-one (mixture of stereoisomers)

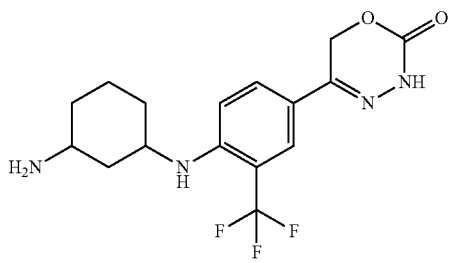 [SMILES: NC1CCCC(Nc2ccc(C3=NNC(=O)OC3)cc2C(F)(F)F)C1]

The title compound was prepared analogously to Example 132 from Intermediate 66.

LC-MS (Method 1): R$_t$=0.72 min; MS (ESIpos): m/z=357 [M+H]$^+$

¹H-NMR (400 MHz, DMSO-d6) δ[ppm]: 1.147 (0.69), 1.170 (0.75), 1.195 (0.50), 1.239 (0.68), 1.261 (1.15), 1.292 (1.73), 1.314 (1.43), 1.337 (1.03), 1.357 (1.07), 1.382 (0.92), 1.404 (0.64), 1.457 (0.43), 1.543 (0.46), 1.570 (0.51), 1.650 (1.16), 1.659 (1.16), 1.682 (1.98), 1.698 (2.56), 1.722 (2.08), 1.895 (1.24), 1.926 (1.16), 2.518 (2.84), 2.522 (1.75), 2.888 (0.85), 2.994 (0.41), 3.642 (0.72), 4.852 (0.43), 4.871 (0.42), 5.289 (16.00), 5.300 (5.89), 6.897 (1.75), 6.920 (1.84), 6.956 (0.72), 6.979 (0.78), 7.713 (7.13), 7.732 (2.73), 7.738 (2.60), 7.748 (0.88), 7.770 (0.58), 10.877 (0.75).

Example 323

5-[4-{[2-(dimethylamino)ethyl]amino}-3-(trifluoromethyl)phenyl]-3,6-dihydro-2H-1,3,4-oxadiazin-2-one

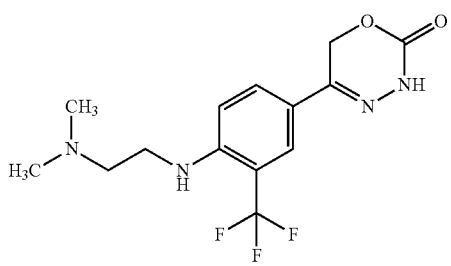

The title compound was prepared analogously to Example 132 from Intermediate 66.

LC-MS (Method 1): R$_t$=0.58 min; MS (ESIpos): m/z=331 [M+H]$^+$

¹H-NMR (400 MHz, DMSO-d6) δ[ppm]: 2.186 (16.00), 2.467 (0.79), 2.483 (2.15), 2.518 (0.97), 2.522 (0.61), 3.252 (0.87), 3.264 (0.85), 5.302 (5.87), 5.779 (0.49), 6.877 (0.75), 6.899 (0.78), 7.740 (0.81), 7.744 (1.20), 7.756 (0.61), 7.778 (0.50), 7.784 (0.41), 10.894 (1.17).

Example 324

5-[4-{[2-(dimethylamino)ethyl](methyl)amino}-3-(trifluoromethyl)phenyl]-3,6-dihydro-2H-1,3,4-oxadiazin-2-one

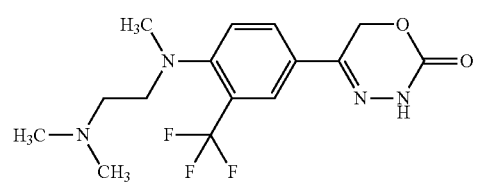 [SMILES: CN(C)CCN(C)c1ccc(C2=NNC(=O)OC2)cc1C(F)(F)F]

The title compound was prepared analogously to Example 132 from Intermediate 66.

LC-MS (Method 2): R$_t$=1.06 min; MS (ESIpos): m/z=345 [M+H]$^+$

¹H-NMR (400 MHz, DMSO-d6) δ[ppm]: 2.083 (16.00), 2.285 (0.78), 2.304 (0.89), 2.308 (0.61), 2.322 (0.99), 2.518 (0.86), 2.523 (0.55), 2.720 (5.24), 3.062 (0.75), 3.081 (0.82), 3.098 (0.69), 5.383 (5.03), 7.549 (0.60), 7.569 (0.66), 7.892 (0.42), 7.897 (0.61), 7.918 (2.09), 11.100 (0.79).

Example 325

5-[4-(2-methyl-1,3-benzothiazol-5-yl)-3-(trifluoromethyl)phenyl]-3,6-dihydro-2H-1,3,4-oxadiazin-2-one

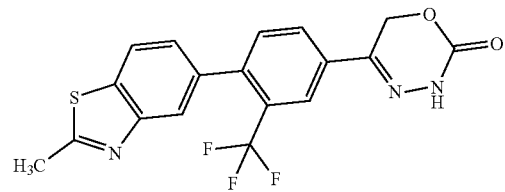 [SMILES: Cc1nc2cc(-c3ccc(C4=NNC(=O)OC4)cc3C(F)(F)F)ccc2s1]

The title compound was prepared analogously to Example 3 from Intermediate 64.

LC-MS (Method 2): R$_t$=1.19 min; MS (ESIpos): m/z=392 [M+H]$^+$

¹H-NMR (400 MHz, DMSO-d6) δ[ppm]: 1.154 (1.24), 1.171 (2.57), 1.189 (1.26), 1.987 (4.28), 2.518 (1.06), 2.523 (0.71), 2.831 (16.00), 4.017 (0.97), 4.034 (0.97), 5.489 (10.98), 7.341 (1.21), 7.344 (1.21), 7.361 (1.26), 7.364 (1.26), 7.582 (1.81), 7.603 (1.95), 7.848 (2.36), 8.029 (1.22), 8.033 (1.26), 8.049 (1.08), 8.053 (1.18), 8.112 (2.79), 8.135 (4.89), 11.257 (4.10).

Example 326

5-[4-(2-methyl-1H-benzimidazol-5-yl)-3-(trifluoromethyl)phenyl]-3,6-dihydro-2H-1,3,4-oxadiazin-2-one

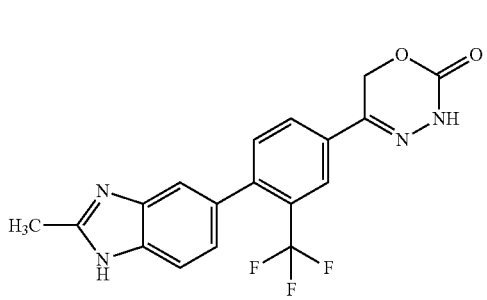 [SMILES: Cc1nc2cc(-c3ccc(C4=NNC(=O)OC4)cc3C(F)(F)F)ccc2[nH]1]

The title compound was prepared analogously to Example 3 from Intermediate 64.

LC-MS (Method 2): $R_t$=0.87 min; MS (ESIpos): m/z=375 [M+H]$^+$ $^1$H-NMR (400 MHz, DMSO-d6) δ[ppm]: 2.074 (3.86), 2.518 (2.91), 2.523 (1.64), 5.478 (16.00), 7.042 (1.26), 7.062 (2.20), 7.083 (1.18), 7.346 (2.05), 7.430 (2.27), 7.450 (2.16), 7.471 (1.90), 7.524 (1.62), 7.540 (3.42), 7.560 (2.98), 7.988 (2.21), 8.008 (2.00), 8.101 (4.18), 11.231 (4.23), 11.235 (3.86), 12.311 (1.82), 12.342 (1.57).

Example 327

5-[4-(3-methyl-1H-indazol-6-yl)-3-(trifluoromethyl)phenyl]-3,6-dihydro-2H-1,3,4-oxadiazin-2-one

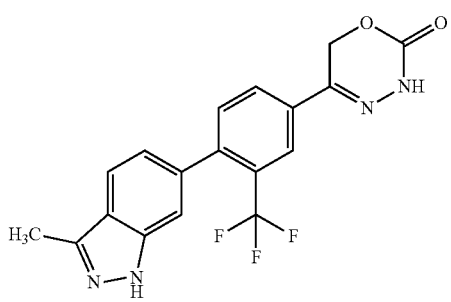 [SMILES: Cc1n[nH]c2cc(-c3ccc(C4=NNC(=O)OC4)cc3C(F)(F)F)ccc12]

The title compound was prepared analogously to Example 3 from Intermediate 64.

LC-MS (Method 2): $R_t$=1.04 min; MS (ESIpos): m/z=375 [M+H]$^+$ $^1$H-NMR (400 MHz, DMSO-d6) δ[ppm]: 2.524 (16.00), 5.486 (11.79), 5.758 (0.87), 7.007 (1.57), 7.028 (1.65), 7.371 (3.17), 7.557 (2.09), 7.578 (2.25), 7.754 (2.38), 7.774 (2.27), 8.011 (1.48), 8.015 (1.50), 8.032 (1.32), 8.035 (1.39), 8.120 (2.90), 8.123 (2.68), 11.251 (4.44), 12.748 (3.12).

Example 328

5-[4-(1,2,3,6-tetrahydropyridin-4-yl)-3-(trifluoromethyl)phenyl]-3,6-dihydro-2H-1,3,4-oxadiazin-2-one

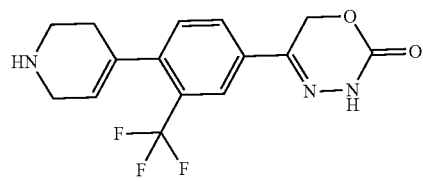 [SMILES: O=C1NN=C(c2ccc(C3=CCNCC3)c(C(F)(F)F)c2)CO1]

The title compound was prepared analogously to Example 3 from Intermediate 64.

LC-MS (Method 2): $R_t$=0.89 min; MS (ESIpos): m/z=326 [M+H]$^+$ $^1$H-NMR (400 MHz, DMSO-d6) δ[ppm]: 2.074 (0.93), 2.162 (1.73), 2.518 (2.42), 2.522 (1.40), 2.539 (0.52), 2.890 (2.15), 3.362 (1.06), 3.537 (0.43), 5.418 (16.00), 5.601 (1.78), 7.409 (1.05), 7.429 (1.21), 7.916 (1.72), 7.936 (1.59), 7.982 (2.87), 11.188 (0.95).

Example 329

5-[3-(difluoromethyl)-4-(2,5-dihydrofuran-3-yl)phenyl]-3,6-dihydro-2H-1,3,4-oxadiazin-2-one

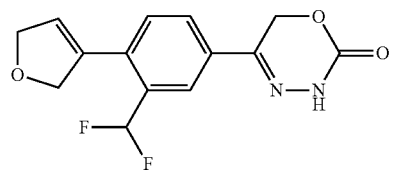 [SMILES: O=C1NN=C(c2ccc(C3=CCOC3)c(C(F)F)c2)CO1]

The title compound was prepared in analogy to Example 198 from Intermediate 77.

MS(ESIpos): m/z=293 (M–H)+.

Example 330

5-[4-(2-aminopyrimidin-5-yl)-3-fluorophenyl]-3,6-dihydro-2H-1,3,4-oxadiazin-2-one

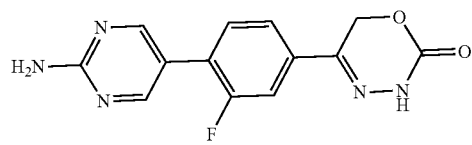 [SMILES: Nc1ncc(-c2ccc(C3=NNC(=O)OC3)cc2F)cn1]

The title compound was synthesized analogously to Example 3 from Intermediate 65.

LC-MS (Method 1): $R_t$=0.75 min; MS (ESIpos): m/z=288 [M+H]$^+$

Experimental Section—Biological Assays

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

Assay 1
Cell Proliferation Measurement

The antiproliferative activity of the compounds of the general formula (I) was examined in vitro in human cancer cells. For this purpose, the appropriate number of cells (Hela: 800; SK-MEL-3: 1000; A549: 800) were plated in 384-well plates with appropriate growth medium ((A549: DMEM/Ham's F12 (Biochrom; #FG 4815 with stabile Glutamine), FCS 10% final (Biochrom; #S 0415); Hela: DMEM/Ham's F12 (Biochrom; #FG 4815 with stabile Glutamine), FCS 10% final (Biochrom; #S 0415); SK-MEL-3: McCoy's 5A (Biochrom; #F 1015), FCS 10% final (Biochrom; #S 0415), L-Alanyl-L-Glutamine final: 2 mM, (Biochrom; #K 0302)) and incubated at 37° C. overnight. After 24 h, cells on one plate (0 h plate) were treated with 30 µl/cavity of CTG solution (Promega Cell Titer Glo (catalogue #G755B and G756B)) and incubated at room temperature for 10 min, and luminescence was measured by means of a VICTOR V (Perkin Elmer), in order to determine cell viability on commencement of treatment. The cells on the test plate were treated with the compounds of the general formula (I) as and incubated at 37° C. for 72 h. The compounds were added to the cells by means of an HP D300 digital dispenser in a 10-step 2.5-fold dilution series generally starting at a maximum final drug concentration of 100 nM. As control, the cells were treated with vehicle (DMSO at 0.3% final concentration). After 72 h, the cells were treated with 30 µl/cavity of CTG solution (Promega Cell Titer Glo (catalogue #G755B and G756B)) and incubated at room temperature for 10 min. and luminescence was measured by means of a VICTOR V (Perkin Elmer), in order to determine cell viability at the end of treatment. The percentage effect on cell growth and the $IC_{50}$ derived therefrom were determined for each test substance using the values from the 0 h plate (=maximum inhibition) and the DMSO control (=minimum inhibition). The $IC_{50}$ values were calculated using a 4-parameter fit.

TABLE 2

Anti-proliferation $IC_{50}$ values of several examples in vitro in different cell lines

| Example (Intermediate, where indicated) | HeLa $IC_{50}$ [nM] (Cervical cancer) | SK-MEL-3 $IC_{50}$ [nM] (melanoma) | IGR37 $IC_{50}$ [nM] (melanoma) |
|---|---|---|---|
| 1 | 2 | 3 | |
| 3 | 3 | 7 | |
| 4 | 7 | 16 | |
| 5 | 3 | 5 | |
| 6 | 5 | 9 | |
| 7 | 5 | 13 | |
| 8 | 6 | 18 | 16 |
| 9 | 15 | 33 | |
| 10 | 15 | 43 | |
| 11 | 19 | 49 | |
| 13 | 27 | 82 | |
| 15 | 8 | 16 | |
| 17 | 7 | 17 | |
| 18 | 18 | 74 | |
| 20 | 15 | 41 | |
| 21 | 15 | >67 | |
| 23 | 45 | >100 | |
| 24 | 55 | >100 | |
| 25-1 | 2 | 3 | |
| 25-2 | 3 | 5 | |
| 26 | 9 | 29 | |
| 27 | 2 | 6 | |
| 29 | 46 | >100 | |
| 30 | 1 | 4 | |
| 31 | 4 | 11 | 14 |
| 32 | 5 | 7 | |
| 33 | 6 | 10 | |
| 34 | 3 | 765 | |
| 36 | 23 | 39 | |
| 37 | 37 | 12 | |
| 38 | 83 | >100 | |
| 39 | 4 | 6 | |
| 40 | 5 | 7 | |
| 41 | 10 | 21 | |
| 42 | 55 | 64 | |
| 43 | 34 | 48 | |
| 44 | 14 | 9 | |
| 45 | 3 | 4 | |
| 47 | 2 | 2 | |
| 48 | 8 | 16 | |
| 49 | 6 | 13 | |
| 50 | 81 | 19800 | |
| 51 | 30 | 49 | |
| 53 | 36 | 13000 | |
| 54 | 1 | 3 | |
| 55 | 7 | 14 | |
| 56 | 5 | 10 | |
| 58 | 40 | 64 | |
| 59 | 18 | 38 | |
| 60 | 13 | 20 | |
| 61 | 10 | 16 | |
| 62 | 6 | 14 | |
| 63 | 1 | 3 | |
| 64 | 17 | 41 | |
| 65 | 2 | 3 | |
| 66 | 2 | 3 | |
| 67 | 3 | 5 | |
| 68 | 4 | 6 | |
| 69 | 1 | 1 | |
| 70 | 15 | 29 | |
| 71 | 20 | 38 | |
| 72 | 2 | 5 | |
| 74 | 11 | 23 | |
| 76 | 6 | 13 | 13 |
| 77 | 8 | 16 | |
| 78 | 10 | 21 | |
| 79 | 12 | 25 | |
| 80 | 2 | 6 | |
| 81 | 4 | 9 | |
| 82 | 4 | 9 | |
| 83 | 3 | 6 | |
| 84 | 19 | 48 | |
| 85 | 7 | 13 | |
| 86 | 6 | 25 | |
| 87 | 10 | 32 | |
| 88 | 2 | 6 | |

TABLE 2-continued

Anti-proliferation IC$_{50}$ values of several examples in vitro in different cell lines

| Example (Intermediate, where indicated) | HeLa IC$_{50}$ [nM] (Cervical cancer) | SK-MEL-3 IC$_{50}$ [nM] (melanoma) | IGR37 IC$_{50}$ [nM] (melanoma) |
|---|---|---|---|
| 89 | 2 | 5 | |
| 90 | 16 | 30 | |
| 91 | 14 | 17 | |
| 92 | 2 | 4 | 4 |
| 93 | 7 | 13 | |
| 94 | 16 | 36 | |
| 96 | 18 | 40 | |
| 97 | 5 | 8 | |
| 98 | 5 | 8 | |
| 99 | 5 | 11 | |
| 100 | 5 | 9 | |
| 101 | 2 | 4 | |
| 102 | 23 | 40 | |
| 103 | 3 | 6 | |
| 105 | 8 | 15 | |
| 106 | 9 | 16 | |
| 107 | 6 | 12 | |
| 108 | 6 | 13 | |
| 109 | 4 | 9 | |
| 110 | 8 | 14 | |
| 111 | 2 | 4 | |
| 112 | 6 | 10 | |
| 113 | 2 | 6 | |
| 114 | 4 | 7 | |
| 115 | 4 | 7 | |
| 116 | 16 | 35 | |
| 117 | 5 | 9 | |
| 118 | 3 | 6 | |
| 119 | 5 | 7 | |
| 120 | 0.3 | 1 | |
| 121 | 5 | 10 | 12 |
| 126 | 1 | 1 | 2 |
| 131 | 2 | 6 | |
| 132 | 16 | 38 | |
| 133 | 32 | 51 | |
| 134 | 12 | 26 | |
| 135 | 1 | 3 | 3 |
| 136 | 0.3 | 1 | |
| 137 | 1 | 3 | |
| 138 | 7 | 19 | |
| 139 | 14 | 29 | 40 |
| 140 | 1 | 1 | |
| 141 | 2 | 3 | |
| 142 | 3 | 4 | |
| 143 | 15 | 30 | |
| 144 | 6 | 13 | |
| 145 | 27 | 47 | |
| 146 | 1 | 2 | 2 |
| 147 | 22 | 39 | |
| 148 | 53 | >100 | |
| 149 | 2 | 4 | |
| 150 | 2 | 5 | |
| 151 | 5 | 5 | |
| 152 | 21 | 56 | |
| 153 | 4 | 7 | |
| 154 | 2 | 4 | |
| 155 | 9 | 17 | |
| 156 | 55 | 68 | |
| 157 | 44 | 71 | |
| 158 | 22 | 40 | |
| 159 | 11 | 22 | |
| 160 | 27 | 47 | |
| 161 | 6 | 10 | 12 |
| 162 | 4 | 7 | |
| 163 | 8 | 14 | |
| 164 | 6 | 8 | |
| 165 | 1 | 1 | 1 |
| 166 | 1 | 1 | 1 |
| 167 | 4 | 6 | |
| 168 | 14 | 25 | |
| 169 | 20 | 32 | |
| 170 | 27 | 40 | |
| 171 | 18 | 31 | |
| 172 | 37 | 48 | |
| 173 | 15 | 27 | |
| 174 | 1 | 1 | 1 |
| 175 | 6 | 3 | |
| 176 | 2 | 4 | |
| 177 | 12 | 17 | |
| 178 | 13 | 19 | |
| 179 | 8 | 15 | |
| 180 | 36 | 48 | |
| 181 | 3 | 6 | |
| 182 | 39 | 54 | |
| 183 | 15 | 22 | |
| 184 | 5 | 6 | |
| 185 | 4 | 6 | |
| 187 | 23 | 40 | |
| 188 | 22 | 38 | |
| 189 | 6 | 12 | |
| 190 | 0.2 | 0.4 | 0.4 |
| 191 | 0.4 | 1 | 1 |
| 192 | 2 | 6 | 7 |
| 193 | 5 | 9 | |
| 195 | 2 | 5 | |
| 196 | 15 | 31 | 33 |
| 197 | 5 | 10 | |
| 198 | 6 | 14 | |
| 199 | 2 | 5 | |
| 200 | 10 | 22 | |
| 201 | 3 | 9 | |
| 202 | 5 | 12 | |
| 203 | 1 | 2 | |
| 204 | 1 | 2 | |
| 205 | 4 | 5 | |
| 206 | 0.5 | 1 | |
| 207 | 9 | 14 | |
| 208 | 5 | 7 | |
| 209 | 7 | 7 | |
| 210 | 6 | 8 | |
| 211 | 2 | 2 | |
| 212 | 1 | 2 | |
| 213 | 14 | 21 | |
| 214 | 1 | 2 | |
| 215 | 2 | 3 | |
| 216 | 6 | 7 | |
| 217 | 14 | 16 | |
| 218 | 3 | 4 | |
| 219 | 8 | 13 | |
| 220 | 6 | 14 | |
| 221 | 1 | 2 | |
| 222 | 1 | 1 | |
| 223 | 6 | 9 | |
| 224 | 2 | 3 | |
| 225 | 3 | 5 | |
| 226 | 1 | 2 | 2 |
| 227 | 1 | | |
| 228 | 7 | | |
| 229 | 1 | | |
| 230 | 7 | | |
| 231 | 2 | | |
| 232 | 2 | 5 | 4 |
| 233 | 8 | | |
| 234 | 2 | | |
| 235 | 4 | | |
| 236 | 4 | | |
| 237 | 0.4 | | |
| 238 | 7 | | |
| 239 | 0.3 | 1 | 1 |
| 240 | 3 | 12 | 10 |
| 241 | 6 | | |
| 242 | 2 | | |
| 243 | 6 | | |
| 244 | 3 | | |

TABLE 2-continued

Anti-proliferation IC$_{50}$ values of several examples in vitro in different cell lines

| Example (Intermediate, where indicated) | HeLa IC$_{50}$ [nM] (Cervical cancer) | SK-MEL-3 IC$_{50}$ [nM] (melanoma) | IGR37 IC$_{50}$ [nM] (melanoma) |
|---|---|---|---|
| 245 | 3 | | |
| 246 | 12 | | |
| 247 | 10 | | |
| 248 | 6 | | |
| 249 | 1 | | |
| 250 | 2 | | |
| 251 | 2 | 5 | 4 |
| 252 | 1 | | |
| 253 | 1 | 40 | 5 |
| 254 | 2 | | |
| 255 | 5 | | |
| 256 | 37 | 63 | |
| 257 | 6 | 9 | |
| 258 | 3 | 6 | |
| 259 | 1 | 3 | |
| 260 | 1 | 3 | |
| 261 | 38 | >100 | |
| 262 | 2 | 5 | |
| 263 | 9 | 32 | |
| 264 | 2 | 2 | |
| 265 | 2 | 5 | 7 |
| 266 | 19 | 35 | 65 |
| 267 | 2 | 5 | 7 |
| 268 | 1 | 3 | |
| 269 | 6 | 17 | 24 |
| 270 | 9 | 15 | |
| 271 | 1 | 3 | |
| 272 | 1 | 1 | |
| 273 | 1 | 1 | |
| 274 | 19 | 31 | |
| 275 | 5 | 7 | |
| 276 | 27 | 49 | 50 |
| 277 | 0.3 | 1 | 1 |
| 278 | 58 | 80 | |
| 279 | 1 | 2 | 2 |
| 280 | 0.1 | 0.4 | 0.4 |
| Intermediate 64 | 29 | 53 | |
| Intermediate 66 | 56 | >100 | |
| Intermediate 72 | 78 | 260 | |
| Intermediate 73 | 58 | >100 | |
| Intermediate 74 | 6 | 11 | |
| Intermediate 75 | 22 | 45 | |
| Intermediate 76 | 40 | 75 | |
| Intermediate 77 | 40 | 65 | |
| Intermediate 78 | 8 | 20 | |
| Intermediate 67 | >100 | >100 | |
| 12 | 20 | 58 | |
| 14 | 49 | 64 | |
| 22 | 26 | 51 | |
| 28 | 14 | 28 | |
| 35 | 39 | 25 | |
| 46 | 21 | 34 | |
| 52 | 48 | >100 | |
| 73 | 25 | 46 | |
| 75 | 22 | 44 | |
| 95 | 33 | >100 | |
| 104 | 37 | 17 | |
| 127 | >100 | >100 | |
| 128 | >100 | >100 | |
| 129 | >100 | >100 | |
| 130 | >100 | 25600 | |
| 186 | 61 | 71 | |
| 281 | 12 | | |
| 282 | 13 | | |
| 283 | 13 | | |
| 284 | 14 | | |
| 285 | 14 | | |
| 286 | 23 | | |
| 287 | 23 | | |
| 288 | 26 | | |
| 289 | 26 | | |
| 290 | 32 | | |
| 291 | 35 | | |
| 292 | 43 | | |
| 293 | 43 | | |
| 294 | 45 | | |
| 295 | 47 | | |
| 296 | 59 | | |
| 297 | 59 | | |
| 298 | 62 | | |
| 299 | 69 | | |
| 300 | 90 | | |
| 301 | >100 | | |
| 302 | >100 | | |
| 303 | >100 | | |
| 304 | >100 | | |
| 305 | >100 | | |
| 306 | >100 | | |
| 307 | >100 | | |
| 308 | >100 | | |
| 309 | >100 | | |
| 310 | >100 | | |
| 311 | >100 | | |
| 312 | >100 | | |
| 313 | >100 | | |
| 314 | >100 | | |
| 315 | >100 | | |
| 316 | >100 | | |
| 317 | >100 | | |
| 318 | >100 | | |
| 319 | 61 | >100 | |
| 320 | >100 | >100 | |
| 321 | >100 | 54 | |
| 322 | >100 | >100 | |
| 323 | >84 | >100 | |
| 324 | >100 | >100 | |
| 325 | >100 | >100 | |
| 326 | >100 | >100 | |
| 327 | >100 | >100 | |
| 328 | 47 | >100 | |
| 329 | 41 | 64 | |
| 330 | >100 | >100 | |

Thus one aspect of the invention is the use of the compounds of formula (I) for the treatment of cervical cancer.

Another aspect of the invention is the use of the compounds of formula (I) for the treatment of skin cancer, especially melanoma.

Yet another aspect of the invention is the use of compounds of formula (I), for the treatment of skin cancer, especially melanoma, and cervical cancer.

Another aspect are compounds of formula (I) which effectively inhibit tumor cell proliferation (e.g. in HeLa cells) with IC$_{50}$ values of <100 nM.

TABLE 3-1

Anti-proliferation IC$_{50}$ values of several examples in vitro in different cell lines

| Cell line | | Example 31 | 92 | 139 | 146 | 267 | 269 | 277 |
|---|---|---|---|---|---|---|---|---|
| | | IC$_{50}$ [nM] | | | | | | |
| Breast | Hs 578T | >100 | 31 | >100 | 28 | 34 | 66 | >100 |
| Erythro-leukemia | HEL 92.1.7 | 47 | 9 | >100 | 13 | 26 | 44 | >100 |
| Glioblastoma | DK-MG | 39 | 17 | 61 | 12 | 18 | 49 | >100 |

TABLE 3-1-continued

Anti-proliferation IC$_{50}$ values of several examples in vitro in different cell lines

| Cell line | | 31 | 92 | 139 | 146 IC$_{50}$ [nM] | 267 | 269 | 277 |
|---|---|---|---|---|---|---|---|---|
| | | | | | Example | | | |
| Glioblastoma | DBTRG-05-MG | 56 | 18 | >100 | 14 | 35 | 50 | >100 |
| Melanoma | CHL-1 | 28 | 11 | 58 | 8 | 16 | 47 | >100 |
| Melanoma | A-2058 | 51 | 18 | >100 | 16 | 40 | 61 | >100 |
| Ovarian teratocarcinoma | PA-1 | 39 | 17 | >100 | 12 | 44 | 49 | >100 |

TABLE 3-2

Anti-proliferation IC$_{50}$ values of several examples in vitro in different cell lines

| Cell line | | 1 | 3 | 4 | 7 IC$_{50}$ [nM] | 8 | 135 |
|---|---|---|---|---|---|---|---|
| | | | | | Example | | |
| Astrocytoma | H4 | 30 | 25 | 47 | 44 | 50 | |
| Breast | Hs 578T | | 29 | | | | |
| Erythroleukemia | HEL 92.1.7 | 20 | 25 | | | | |
| Glioblastoma | DK-MG | | 21 | | | | |
| Lung | NCI-H1734 | 19 | 13 | 40 | 26 | 42 | |
| Melanoma | IGR-1 | 89 | 99 | | | | >100 |
| Melanoma | CHL-1 | | 9 | | | | |
| Melanoma | HMCB | 19 | 26 | | | | 13 |
| Melanoma | COLO741 | | | | | | 1 |
| Melanoma | C32 | | | | | | 15 |
| Melanoma | A-2058 | | | | | | 24 |
| Ovarian teratocarcinoma | PA-1 | | 22 | | | | |

Assay 2
Cell Proliferation Measurement

The antiproliferative activity of the compounds of the general formula (I) was examined in vitro in human cancer cells. For this purpose, 500 cells, including HeLa cells, A2058 cells, DU145 cells, HMCB cells, IGR37 cells, NCIH1734 cells, OSRC2 cells, or 750 cells, including CAL51 cells, COL0741 cells, DBTRG05MG cells, DKMG cells, G292CLONEA141B1 cells, GB1 cells, HEL cells, HEL9217 cells, JHUEM1 cells, L3.3 cells, LI7 cells, TE4 cells, or 1000 cells, including 8505C cells, HUT78 cells, NCIH1563 cells, NCIH2122 cells, NCIH2172 cells, RVH421 cells, SKMEL3 cells, or 1500 cells, including C32 cells, HS578T cells, JHOM1 cells, NCIH196 cells, OVKATE cells, were plated in 384-well plates with appropriate growth medium and incubated at 37° C. overnight. After 24 h, the cells on the test plate were treated with the compounds of the general formula (I) as and incubated at 37° C. for 72 h. The compounds were added to the cells by means of an HP D300 digital dispenser in a 10 (or more)-step dilution series. As control, the cells were treated with vehicle (DMSO at 0.3% final concentration). After 72 h, the cells were treated with 20 μl/well of 50% CTG solution in PBS (Promega Cell Titer Glo (catalogue #G755B and G756B)) and incubated at room temperature for 10 min, and luminescence was measured by means of a VICTOR V (Perkin Elmer), in order to determine cell viability at the end of treatment. The percentage effect on cell growth and the IC$_{50}$ derived therefrom were determined for each test substance using the values from untreated wells (=percent viability). The IC$_{50}$ values were calculated using a 4-parameter fit.

TABLE 4

Anti-proliferation IC$_{50}$ values of several examples in vitro in different cell lines

| Example | Cell line | 135 | 146 IC$_{50}$ [nM] | 265 |
|---|---|---|---|---|
| | | | Example Number | |
| Breast, ductal carcinoma | HS578T | 33 | 20 | 116 |
| Breast NS | CAL51 | | 37 | |
| Cervical | HeLa | 2 | 2 | 5 |
| Glioma_astrocytoma | DKMG | 22 | 13 | 59 |
| Lung adenocarcinoma | NCIH1563 | 18 | | 46 |
| Lung adenocarcinoma | NCIH2122 | | 3 | |
| Lung non small cell carcinoma | H2172 | 38 | 37 | 101 |
| Lung small cell carcinoma | H196 | 150 | 32 | 355 |
| Melanoma | A2058 | 38 | 25 | 96 |
| Melanoma | C32 | 58 | 52 | 132 |
| Melanoma | RVH421 | 140 | 47 | 262 |
| Melanoma | SKMEL3 | 5 | 3 | 10 |
| Oesophagus squamous cell carcinoma | TE4 | 15 | | 41 |
| Ovary adenocarcinoma | JHOM1 | | 8 | |
| Pancreas NS | L3.3 | 82 | 15 | 312 |
| Prostate NS | DU145 | | 14 | |

Thus one aspect of the invention is the use of the compounds of formula (I) for the treatment of brain cancer (especially glioma, more specifically glioblastoma, astrocytoma), breast cancer (especially ductal carcinoma and adenocarcinoma), cervical cancer, AML (especially erythroleucemia), lung cancer (especially NSCLC adenocarcinoma and SCLC), skin cancer (especially melanoma), oesophagus cancer (especially squamous cell carcinoma), ovarian cancer, (especially teratocarcinoma, adenocarcinoma), pancreas cancer and prostatic cancer.

Assay 3
In Vivo Xenotransplantation Models

The anti-tumor activities of Compounds of examples 135 and 146 were examined in murine xenotransplantation models of human cancer. For this purpose, mice were implanted subcutaneously with tumor cells. At a mean tumor size of 20-40 mm² animals were randomized into treatment and control groups (at least n=10 animals/group) and treatment started with vehicle only or respective Compound (formulation: 90% PEG400/10% Ethanol; application route: per os ("p.o."), orally). The oral application volume was 10 ml/kg. In the case of twice daily treatments, the time interval between two applications per day was 6-7 h. The tumor size and the body weight were determined at least weekly. The tumor area was detected by means of an electronic caliper [length (mm)×width (mm)]. The experiment was ended when the study reached the pre-determined ethical endpoint based on German and European animal welfare regulations. In vivo anti-tumor efficacy is presented as T/C ratio at study end (Treatment/Control; mean tumor weight of treatment group/mean tumor weight of control group) in Table 8. A compound having a T/C below 0.5 is defined as active (i.e., effective). Statistical analysis was assessed using SigmaStat software. A one-way analysis of variance was performed and differences to the control were compared by a pair-wise comparison procedure (Dunn's method).

Compounds of examples 135 and 146 showed potent anti-tumor efficacy in different xenograft models of human tumors upon monotherapy treatment. Specifically, Compound example 135 and/or example 146 were effective in reduction of tumor area in cervical cancer, ovarian teratocarcinoma, AML and melanoma.

TABLE 5

Anti-tumor activity of Compound of example 135, compound of example 146 and compound of example 265 in different human cancer xenograft models in mice

| Xenograft Model | Cell line isolated from patient with | Example | Dose and schedule | T/C |
|---|---|---|---|---|
| IGR-37 | Melanoma | 146 | 10 mg/kg 2QD p.o. | 0.05* |
| IGR-37 | Melanoma | 135 | 10 mg/kg 2QD p.o. | 0.06* |
| HEL92.1.7 | AML | 146 | 40 mg/kg 2QD p.o. | 0.08* |
| HeLa | Cervical cancer | 146 | 5 mg/kg 2QD p.o. | 0.08* |
| A2058 | Melanoma | 146 | 10 mg/kg 2QD p.o. | 0.23* |
| PA-1 | Ovarian teratocarcioma | 146 | 20 mg/kg 2QD p.o. | 0.49* |
| PA-1 | Ovarian teratocarcioma | 135 | 5 mg/kg 2QD p.o. | 0.63 |
| IGR-37 | Melanoma | 265 | 10 mg/kg 2QD p.o. | 0.27* |

*P < 0.05 treatment vs control at study end
T/C = ratio of mean final tumor weight of treatment group versus mean final tumor weight of control group
The abbreviation 2QD means twice per day, p.o. means per os or-oral.

Assay 4
Method for PDE3A Enzyme Inhibition

The commercially available 3H-cAMP Scintillation Proximity Assay (SPA, Perkin Elmer) system was used for enzyme inhibition studies. For the determination of the in vitro effect of example compounds on the PDE3A reactions 2 µl of the respective example compound solution in DMSO (serial dilutions) were placed in wells of microtiter plates (Isoplate-96/200W; Perkin Elmer). 50 µl of a dilution of PDE3A cell extract from Sf9 cells overexpressing human full length PDE3A (SB Drug Discovery, UK) in buffer A (50 mM Tris/HCl pH 7.5, 8.3 mM $MgCl_2$, 1.7 mM EDTA, 0.2% BSA) was added. The dilution of the PDE3A cell extract was chosen such that the reaction kinetics was linear and less than 70% of the substrate was consumed (typical dilution 1:5000). The reaction was started by addition of 50 µl (0.025 µCi) of 1:2000 in buffer A w/o BSA diluted substrate [8-3H]adenosine 3', 5'-cyclic phosphate (1 µCi/µl; Perkin Elmer). After incubation at room temperature for 60 min, the reaction was stopped by addition of 25 µl of a suspension containing 18 mg/ml yttrium scintillation proximity beads (Perkin Elmer) in water. The microtiter plates were sealed and measured in a Microbeta scintillation counter (PerkinElmer Wallac). $IC_{50}$ values were determined from sigmoidal curves by plotting percentage PDE3A activity vs log compound concentration.

Assay 5
PDE3B Enzyme Inhibition

The commercially available 3H-cAMP Scintillation Proximity Assay (SPA, Perkin Elmer) system was used for enzyme inhibition studies. For the determination of the in vitro effect of example compounds on the PDE3B reactions 2 µl of the respective example compound solution in DMSO (serial dilutions) were placed in wells of microtiter plates (Isoplate-96/200W; Perkin Elmer). 50 µl of a dilution of PDE3B cell extract from Sf9 cells overexpressing human full length PDE3B (SB Drug Discovery, UK) in buffer A (50 mM Tris/HCl pH 7.5, 8.3 mM $MgCl_2$, 1.7 mM EDTA, 0.2% BSA) was added. The dilution of the PDE3B cell extract was chosen such that the reaction kinetics was linear and less than 70% of the substrate was consumed (typical dilution 1:6000). The reaction was started by addition of 50 µl (0.025 µCi) of 1:2000 in buffer A w/o BSA diluted substrate [8-3H]adenosine 3', 5'-cyclic phosphate (1 µCi/µl; Perkin Elmer). After incubation at room temperature for 60 min, the reaction was stopped by addition of 25 µl of a suspension containing 18 mg/ml yttrium scintillation proximity beads (Perkin Elmer) in water. The microtiter plates were sealed and measured in a Microbeta scintillation counter (PerkinElmer Wallac). IC50 values were determined from sigmoidal curves by plotting percentage PDE3B activity vs log compound concentration.

One aspect of the invention are compounds of formula (I) which effectively inhibit tumor cell proliferation with $IC_{50}$ values of <100 nM in e.g. HeLa cells while $IC_{50}$ values for enzymatic PDE3A or PDE3B inhibition are often >2.5 times higher than $IC_{50}$ values for tumor cell proliferation.

Another aspect of the invention are compounds of formula (I) which effectively inhibit tumor cell proliferation with $IC_{50}$ values of <100 nM in e.g. HeLa cells while $IC_{50}$ values for enzymatic PDE3A or PDE3B inhibition are often >10 times higher than $IC_{50}$ values for tumor cell proliferation.

One aspect of the invention are compounds of formula (I) which effectively inhibit tumor cell proliferation with $IC_{50}$ values of <100 nM in e.g. HeLa cells while $IC_5n$ values for enzymatic PDE3A or PDE3B inhibition are often >30 times higher than $IC_{50}$ values for tumor cell proliferation.

TABLE 6

Inhibition of PDE3A and PDE3B

| Example/Intermediate | PDE3A $IC_{50}$ [nM] | PDE3B $IC_{50}$ [nM] |
|---|---|---|
| 1 | 275 | 173 |
| 3 | 285 | 197 |
| 4 | 203 | 154 |
| 5 | 139 | 97 |
| 6 | 100 | 110 |
| 7 | 220 | 170 |
| 8 | 210 | 243 |
| 9 | 440 | 240 |
| 10 | 220 | 230 |
| 11 | 84 | 65 |
| 13 | 110 | 44 |
| 15 | 110 | 110 |
| 17 | 25 | 17 |
| 18 | 450 | 220 |
| 20 | 200 | 100 |
| 21 | 175 | 185 |
| 23 | 380 | 270 |
| 24 | 180 | 110 |
| 25-1 | 44 | 22 |
| 25-2 | 17 | 15 |
| 26 | 700 | 270 |
| 27 | 75 | 110 |
| 29 | 300 | 160 |
| 30 | 99 | 79 |
| 31 | 310 | 603 |
| 32 | 67 | 110 |
| 33 | 65 | 80 |
| 34 | 100 | 100 |
| 36 | 280 | 320 |
| 37 | 150 | 130 |
| 38 | 210 | 260 |
| 39 | 72 | 75 |
| 40 | 42 | 39 |
| 41 | 31 | 31 |
| 42 | 170 | 250 |
| 43 | 96 | 85 |

TABLE 6-continued

Inhibition of PDE3A and PDE3B

| Example/Intermediate | PDE3A IC$_{50}$ [nM] | PDE3B IC$_{50}$ [nM] |
| --- | --- | --- |
| 44 | 190 | 200 |
| 45 | 43 | 34 |
| 47 | 53 | 33 |
| 48 | 240 | 240 |
| 49 | 230 | 190 |
| 50 | 260 | 210 |
| 51 | >1000 | >1000 |
| 53 | 580 | 390 |
| 54 | 100 | 89 |
| 55 | 280 | 250 |
| 56 | 180 | 80 |
| 58 | 310 | 570 |
| 59 | 150 | 250 |
| 60 | 270 | 510 |
| 61 | 230 | 320 |
| 62 | 85 | 180 |
| 63 | 31 | 33 |
| 64 | 221 | 193 |
| 65 | 25 | 30 |
| 66 | 65 | 95 |
| 67 | 47 | 63 |
| 68 | 81 | 152 |
| 69 | 31 | 47 |
| 70 | 75 | 170 |
| 71 | >1000 | >1000 |
| 72 | 74 | 180 |
| 74 | 42 | 100 |
| 76 | 225 | 250 |
| 77 | 33 | 83 |
| 78 | 29 | 48 |
| 79 | 29 | 71 |
| 80 | 34 | 87 |
| 81 | 130 | 270 |
| 82 | 200 | 320 |
| 83 | 100 | 250 |
| 84 | 150 | 320 |
| 85 | 33 | 78 |
| 86 | 84 | 210 |
| 87 | 81 | 230 |
| 88 | 110 | 250 |
| 89 | 110 | 140 |
| 90 | 43 | 100 |
| 91 | 68 | 85 |
| 92 | 68 | 130 |
| 93 | 50 | 100 |
| 94 | 91 | 280 |
| 96 | 50 | 110 |
| 97 | 65 | 130 |
| 98 | 100 | 120 |
| 99 | 88 | 100 |
| 100 | 48 | 66 |
| 101 | 28 | 39 |
| 102 | 170 | 280 |
| 103 | 66 | 140 |
| 105 | 48 | 100 |
| 106 | 120 | 240 |
| 107 | 150 | 160 |
| 108 | 26 | 22 |
| 109 | 46 | 32 |
| 110 | 100 | 140 |
| 111 | 72 | 81 |
| 112 | 170 | 230 |
| 113 | 210 | 215 |
| 114 | 92 | 100 |
| 115 | 92 | 100 |
| 116 | 79 | 76 |
| 117 | 77 | 95 |
| 118 | 60 | 64 |
| 119 | 36 | 13 |
| 120 | 6 | 4 |
| 121 | 150 | 299 |
| 126 | 12 | 8 |
| 131 | 32 | 42 |
| 132 | 260 | 450 |
| 133 | >1000 | >1000 |
| 134 | 270 | 580 |
| 135 | 87 | 50 |
| 136 | 32 | 27 |
| 137 | 52 | 88 |
| 138 | 150 | 200 |
| 139 | 140 | 310 |
| 140 | 58 | 80 |
| 141 | 13 | 27 |
| 142 | 25 | 47 |
| 143 | 38 | 83 |
| 144 | 55 | 100 |
| 145 | 240 | 410 |
| 146 | 40 | 80 |
| 147 | 140 | 310 |
| 148 | 190 | 210 |
| 149 | 163 | 132 |
| 150 | 240 | 250 |
| 151 | 69 | 159 |
| 152 | 63 | 76 |
| 153 | 15 | 26 |
| 154 | 70 | 120 |
| 155 | 92 | 110 |
| 156 | 440 | 650 |
| 157 | >1000 | >1000 |
| 158 | 500 | 720 |
| 159 | >1000 | >1000 |
| 160 | >1000 | >1000 |
| 161 | 66 | 49 |
| 162 | 210 | 120 |
| 163 | 35 | 51 |
| 164 | 300 | 200 |
| 165 | 77 | 66 |
| 166 | 69 | 42 |
| 167 | 34 | 66 |
| 168 | 170 | 220 |
| 169 | 180 | 240 |
| 170 | 190 | 180 |
| 171 | 150 | 210 |
| 172 | 290 | 520 |
| 173 | 58 | 58 |
| 174 | 27 | 16 |
| 175 | 26 | 24 |
| 176 | 37 | 35 |
| 177 | 160 | 130 |
| 178 | 140 | 130 |
| 179 | 140 | 110 |
| 180 | 250 | 250 |
| 181 | 74 | 77 |
| 182 | 220 | 260 |
| 183 | 200 | 170 |
| 184 | 66 | 57 |
| 185 | 49 | 48 |
| 187 | 81 | 100 |
| 188 | 90 | 100 |
| 189 | 190 | 200 |
| 190 | 38 | 25 |
| 191 | 48 | 57 |
| 192 | 320 | 120 |
| 193 | 195 | 215 |
| 195 | 58 | 77 |
| 196 | 810 | 790 |
| 197 | 650 | 803 |
| 198 | 170 | 130 |
| 199 | 210 | 200 |
| 200 | 34 | 66 |
| 201 | 86 | 77 |
| 202 | 76 | 63 |
| 203 | 37 | 88 |
| 204 | 80 | 110 |
| 205 | 53 | 123 |
| 206 | 15 | 20 |
| 207 | 74 | 180 |
| 208 | 110 | 140 |
| 209 | 275 | 533 |
| 210 | 140 | 363 |
| 211 | 29 | 54 |
| 212 | 26 | 24 |

TABLE 6-continued

Inhibition of PDE3A and PDE3B

| Example/Intermediate | PDE3A IC$_{50}$ [nM] | PDE3B IC$_{50}$ [nM] |
| --- | --- | --- |
| 213 | 68 | 71 |
| 214 | 59 | 73 |
| 215 | 66 | 100 |
| 216 | 103 | 167 |
| 217 | 65 | 210 |
| 218 | 35 | 89 |
| 219 | 58 | 97 |
| 220 | 90 | 131 |
| 221 | 28 | 56 |
| 222 | 76 | 120 |
| 223 | 140 | 100 |
| 224 | 165 | 200 |
| 225 | 45 | 220 |
| 226 | 128 | 187 |
| 227 | 13 | 9 |
| 228 | 400 | 920 |
| 229 | 82 | 67 |
| 230 | 58 | 100 |
| 231 | 100 | 110 |
| 232 | 145 | 145 |
| 233 | 86 | 250 |
| 234 | 78 | 73 |
| 235 | 170 | 180 |
| 236 | 45 | 54 |
| 237 | 120 | 140 |
| 238 | 88 | 300 |
| 239 | 27 | 26 |
| 240 | 180 | 260 |
| 241 | 66 | 130 |
| 242 | 92 | 130 |
| 243 | 48 | 100 |
| 244 | 120 | 150 |
| 245 | 75 | 100 |
| 246 | 95 | 210 |
| 247 | 65 | 180 |
| 248 | 61 | 140 |
| 249 | 100 | 110 |
| 250 | 120 | 120 |
| 251 | 61 | 97 |
| 252 | 110 | 86 |
| 253 | 190 | 155 |
| 254 | 45 | 31 |
| 255 | 100 | 76 |
| 256 | 240 | 480 |
| 257 | 75 | 120 |
| 258 | 41 | 130 |
| 259 | 34 | 110 |
| 260 | 48 | 170 |
| 261 | 550 | 600 |
| 262 | 18 | 20 |
| 263 | 50 | 46 |
| 264 | 75 | 112 |
| 265 | 657 | 383 |
| 266 | >1000 | 930 |
| 267 | 145 | 185 |
| 268 | 138 | 110 |
| 269 | 695 | 790 |
| 270 | 55 | 170 |
| 271 | 27 | 25 |
| 272 | 19 | 10 |
| 273 | 44 | 53 |
| 274 | 300 | 400 |
| 275 | 29 | 64 |
| 276 | 79 | 240 |
| 277 | 100 | 87 |
| 278 | >1000 | >1000 |
| 279 | 20 | 23 |
| 280 | 11 | 9 |
| Intermediate 64 | 610 | 490 |
| Intermediate 66 | >1000 | >1000 |
| Intermediate 72 | 320 | 400 |
| Intermediate 73 | 720 | >1000 |
| Intermediate 74 | 34 | 100 |
| Intermediate 75 | 240 | 710 |
| Intermediate 76 | 375 | 130 |
| Intermediate 77 | 150 | 330 |
| Intermediate 78 | 140 | 180 |
| Intermediate 67 | 6 | 7 |
| 12 | 31 | 30 |
| 14 | 63 | 71 |
| 22 | 52 | 33 |
| 28 | 31 | 40 |
| 35 | 79 | 75 |
| 46 | 27 | 17 |
| 52 | 65 | 30 |
| 73 | 18 | 41 |
| 75 | 31 | 78 |
| 95 | 37 | 79 |
| 104 | 35 | 58 |
| 127 | 78 | 31 |
| 128 | 280 | 270 |
| 129 | 970 | 770 |
| 130 | 200 | 160 |
| 319 | 70 | 180 |
| 320 | 76 | 220 |
| 321 | 290 | 500 |
| 322 | 580 | 780 |
| 323 | >280 | >910 |
| 324 | >1000 | >1000 |
| 325 | 56 | 150 |
| 326 | 17 | 30 |
| 327 | 11 | 16 |
| 328 | 74 | 91 |
| 329 | 100 | 93 |

Assay 6

Method for Human Cryo Hepatocytes:

Investigation of In Vitro Metabolic Stability in Cryopreserved Human Hepatocytes (Including Calculation of Hepatic In Vivo Blood Clearance (CL) and Maximal Oral Bioavailability (Fmax))

Cryopreserved Hepatocytes (e.g. purchased from Celsis InVitroTechnologies) were briefly thawed, washed with 45 mL pre-warmed in in vitro GRO HT medium and centrifuged for 5 min at 50×g. The cell pellet was resuspended in 5 ml of Krebs-Henseleit Butter (KHB). Cell viability was determined by trypan blue exclusion.

For the metabolic stability assay liver cells were distributed in WME containing 5% FCS to glass vials at a density of 1.0×106 vital cells/ml. The test compound was added to a final concentration of 1 µM. During incubation, the hepatocyte suspensions were continuously shaken at 580 rpm and aliquots were taken at 2, 8, 16, 30, 45 and 90 min, to which equal volumes of cold methanol were immediately added. Samples were frozen at −20° C. over night, after subsequently centrifuged for 15 minutes at 3000 rpm and the supernatant was analyzed with an Agilent 1290 HPLC-system with LCMS/MS detection.

The half-life of a test compound was determined from the concentration-time plot. From the half-life the intrinsic clearances were calculated. Together with the additional parameters liver blood flow, amount of liver cells in vivo and in vitro. The hepatic in vivo blood clearance (CL) and the maximal oral bioavailability (Fmax) was calculated. The hepatic in vivo blood clearance (CLblood) and the maximal oral bioavailability (Fmax) was calculated using the following formulae: CL'intrinsic [ml/(min*kg)]=kel [1/min]/((cellno/volume of incubation [ml])*fu,inc)*(cellno/liver weight [g])*(specific liver weight [g liver/kg body weight]); CLblood well-stirred [L/(h*kg)]=(QH [L/(h*kg)]*fu, blood*CL'intrinsic [L/(h*kg)])/(QH [L/(h*kg)]+fu, blood*CL'intrinsic [L/(h*kg)]); Fmax=1-CLblood/QH and using the following parameter values: Liver blood flow-1.32

L/h/kg human; specific liver weight-21 g/kg body weight; liver cells in vivo-1.1×10$^8$ cells/g liver, liver cells in vitro-1.0×10$^6$/ml; fu,inc and fu,blood is taken as 1.

TABLE 7

Results of human cryo hepatocytes test

| Example | Fmax [%] | Clblood [L/h/kg] |
|---|---|---|
| 1 | 82 | 0.24 |
| 3 | 70 | 0.39 |
| 4 | 100 | <0.01 |
| 7 | 75 | 0.33 |
| 9 | 85 | 0.19 |
| 31 | 52 | 0.64 |
| 71 | 86 | 0.19 |
| 76 | 80 | 0.27 |
| 111 | 76 | 0.32 |
| 121 | 90 | 0.13 |
| 135 | 26 | 0.98 |
| 140 | 61 | 0.51 |
| 146 | 60 | 0.53 |
| 161 | 59 | 0.55 |
| 162 | 53 | 0.62 |
| 165 | 33 | 0.88 |
| 190 | 32 | 0.90 |
| 195 | 100 | <0.01 |
| 198 | 67 | 0.44 |
| 199 | 29 | 0.94 |
| 203 | 54 | 0.61 |
| 224 | 74 | 0.35 |
| 256 | 95 | 0.07 |
| 260 | 35 | 0.86 |
| 265 | 61 | 0.51 |
| 267 | 80 | 0.27 |
| 268 | 78 | 0.30 |
| 269 | 69 | 0.41 |
| 270 | 100 | <0.01 |
| 281 | 35 | 0.85 |

Assay 7
In Vivo Pharmacokinetics in Non-Rodents (e.g. Dogs)

For in vivo pharmacokinetic experiments test compounds were administered to non-rodents (e.g. female Beagle dogs) intravenously (i.v.) at doses of 0.1 to 1 mg/kg and intragastrally (i.g.) at doses of 0.3 to 3 mg/kg formulated as solutions using solubilizers such as e.g. PEG400 in well-tolerated amounts and are usually given as short term infusion (15 min).

Blood samples were taken e.g. at 2 min, 8 min, 15 min, 30 min, 45 min, 1 h, 2 h, 4 h, 6 h, 8 h and 24 h after dosing from the vena saphena. Depending on the expected half-life additional samples were taken at later time points (e.g. 48 h, 72 h).

For pharmacokinetics after intragastral administration test compounds were given intragastrally to fasted non-rodents (e.g. dogs). Blood samples were taken e.g. at 5 min, 15 min, 30 min, 45 min, 1 h, 2 h, 4 h, 6 h, 8 h and 24 h after dosing. Depending on the expected half-life additional samples were taken at later time points (e.g. 48 h, 72 h). Blood was collected into Lithium-Heparin tubes (Monovetten@, Sarstedt) and centrifuged for 15 min at 3000 rpm. A small aliquot (e.g. 100 µL) from the supernatant (plasma) was taken and precipitated by addition of an aliquot ice cold acetonitrile (e.g. of 400 µL) and frozen at −20° C. over night. Samples were subsequently thawed and centrifuged at 3000 rpm, 4° C. for 20 minutes. Aliquots of the supernatants were taken for analytical testing using an Agilent HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (abbreviation: CLp;) in L/kg/h) with Cp/Cb being the ratio of concentrations in plasma and blood.

PK parameters calculated from concentration time profiles after i.q.: Cmax: Maximal plasma concentration (in mg/L); Cmaxnorm: Cmax divided by the administered dose (in kg/L); Tmax: Time point at which Cmax was observed (in h). Parameters calculated from both, i.v. and i.g. concentration-time profiles: AUCnorm: Area under the concentration-time curve from t=0 h to infinity (extrapolated) divided by the administered dose (in kg*h/L); AUC(0-tlast) norm: Area under the concentration-time curve from t=0 h to the last time point for which plasma concentrations could be measured divided by the administered dose (in kg*h/L); t1/2: terminal half-life (in h); F: oral bioavailability: AUCnorm after intragastral administration divided by AUCnorm after intravenous administration (in %).

TABLE 8

Results of in vivo pharmacokinetic test

| Example | CLblood dog [L/h/kg] |
|---|---|
| 3 | 2.39 |
| 31 | 0.49 |
| 135 | 0.49 |
| 146 | 2.84 |

Assay 8
In Vivo Pharmacokinetics in Rodents (e.g. Mice)

The housing and handling of animals was performed in strict compliance with the European and German Guidelines for Laboratory Animal Welfare. Animals received food and water ad libitum. For the quantification of circulating compounds in plasma, a certain dose (1-100 mg/kg) was orally administered to female NMRInu/nu mice at the age of 6-8 weeks in a solubilized form (n=3 mice per time point).

Blood was collected into Lithium-Heparin tubes (Monovetten@, Sarstedt) and centrifuged for 15 min at 3000 rpm. A small aliquot (e.g. 100 µL) from the supernatant (plasma) was taken and precipitated by addition of an aliquot ice cold acetonitrile (e.g. of 400 µL) and frozen at −20° C. over night. Samples were subsequently thawed and centrifuged at 3000 rpm, 4° C. for 20 minutes. Aliquots of the supernatants were taken for analytical testing using an Agilent HPLC-system with LCMS/MS detection. PK parameters were calculated by non-compartmental analysis using a PK calculation software.

Assay 9
Validation of PDE3A Modulator-Induced PDE3A Protein Interactions Using Immunoprecipitation and Immunoblotting HeLa cells were transfected with ORF overexpression constructs expressing V5-tagged SLFN12, or V5-tagged GFP. ORF expression constructs were obtained from the TRC (clone IDs: TRCN0000468231, TRCN0000476272, ccsbBroad304_99997). At 72 hours post transfection, cells were treated with 10 µM DNMDP or trequinsin for 4 hours followed by lysis using the ModRipa lysis buffer and immunoprecipitation of PDE3A. For each condition, 2 mg total protein lysate was incubated with 1 µg of anti-PDE3A antibody at 4° C. overnight, after which 7.5 µl each of Protein A- and Protein G-Dynabeads (Life Technologies 10001D and 10003D) were added and incubated for another 1 hour. Beads were washed and bound proteins were eluted with 30 µl of LDS PAGE gel loading buffer. Input (~60 µg total protein lysate) and IP products were resolved on 4-12% Tris-Glycine PAGE gels and immunoblotted with an anti-V5 antibody (Life Technologies R96205, 1:5000), the Bethyl anti-PDE3A antibody (1:1000), and secondary antibodies from LiCOR Biosciences (Cat. #926-32210 and 926068021, each at 1:10,000). Blots were washed and imaged using a LiCOR Odyssey infrared imager.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The invention claimed is:

1. A compound having the structure of general formula (II):

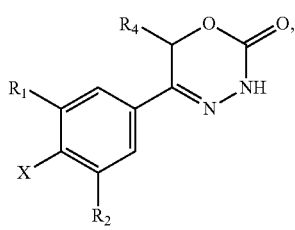

in which
R$^1$ is selected from CF$_3$ and a fluorine atom;
R$^2$ is a hydrogen atom;
R$^4$ is selected from a hydrogen atom, and a C$_1$-C$_3$-alkyl group;
and X is a fluorine atom, a chlorine atom, a bromine atom or an iodine atom, or a group selected from (C$_1$-C$_4$-alkylsulfonyl)oxy, (C$_1$-C$_4$-fluoroalkylsulfonyl)oxy and (phenylsulfonyl)oxy being optionally substituted with one, two, three, four or five substituents, each of them independently selected from halogen, nitro, cyano, C1-C4-alkyl and C1-C4-alkoxy.

2. A method comprising:
the step A of allowing the compound of general formula (II)
to react under transition metal catalysed coupling conditions with an organoboron compound in the presence of a base and a palladium catalyst and, optionally, an additional ligand;

wherein the compound of formula (II) has the structure:

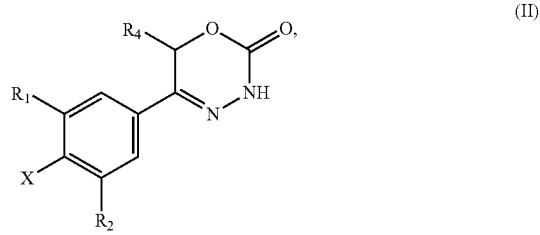

where
R$^1$ is selected from a hydrogen atom, a halogen atom, a cyano group, a C$_1$-C$_3$-alkyl group, a C$_1$-C$_3$-haloalkyl group, and a C$_1$-C$_3$-haloalkoxy group;
R$^2$ is selected from a hydrogen atom and a halogen atom;
R$^4$ is selected from a hydrogen atom, and a C$_1$-C$_3$-alkyl group;
X is a fluorine atom, a chlorine atom, a bromine atom or an iodine atom, or a group selected from (C$_1$-C$_4$-alkylsulfonyl)oxy, (C$_1$-C$_4$-fluoroalkylsulfonyl)oxy and (phenylsulfonyl)oxy being optionally substituted with one, two, three, four or five substituents, each of them independently selected from halogen, nitro, cyano, C$_1$-C$_4$-alkyl and C$_1$-C$_4$-alkoxy;
with the prerequisite that and if X is a chlorine atom, a bromine atom or an iodine atom then R$^1$ and R$^2$ is not chlorine, bromine or iodine; and
the organoboron compound is selected from
a boronic acid of formula (Ma)

 (IIIa), a boronic ester of formula

 (IIIb), and a tetrafluoroborate salt of formula

 (IIIc), whereby
R$^x$ is a C$_1$-C$_6$-alkyl group which is optionally substituted with one or two substituents and each substituent is independently selected from a hydroxy group, a C$_1$-C$_4$-alkoxy group, and a 3- to 7-membered heterocycloalkyl group,
a C$_2$-C$_6$-alkenyl group which is optionally substituted with an C$_1$-C$_4$-alkoxy group,
a C$_5$-C$_9$-cycloalkenyl group, which is optionally substituted with a hydroxy group,
a 3- to 9-membered heterocycloalkyl group, comprising one, two or three heteroatoms which are independently selected from —O—, —S—, —S(O)—, S(O)$_2$, and —NR$^9$—,
and said heterocycloalkyl group optionally further comprising a bridging group selected from —O—, —NR$^9$—, —CH$_2$—, —CH$_2$—CH$_2$—, —O—CH$_2$—, —CH$_2$—O—, —NR$^9$—CH$_2$—, and —CH$_2$—NR$^9$—;
and said heterocycloalkyl group is optionally substituted with one, two or three substituents and each substituent is independently selected from a halogen atom;
a oxo(=O) group;
a cyano group;
a hydroxy group;

a $C_1$-$C_3$-alkyl group which is optionally further substituted with a hydroxy group;
a $C_1$-$C_3$-haloalkyl group;
a $C_1$-$C_3$-alkoxy group;
a $C_1$-$C_3$-haloalkoxy group;
a $C(O)NR^5R^6$ group and
a $NR^5R^6$ group,
a 5- to 9-membered heterocycloalkyl group which is partially unsaturated and optionally substituted with one, two or three substituents and each substituent is independently selected from an oxo group (=O), a $C_1$-$C_3$-alkyl group a —$C(O)R^5R^6$ group and a halogen atom,
an aryl group which is optionally substituted with one, two, three or four substituents and each substituent is independently selected from a halogen atom, a hydroxy group, a cyano group, a $C_1$-$C_3$-alkyl group, a $C_1$-$C_3$-haloalkyl group, a $C_1$-$C_3$-alkoxy group, a $C_1$-$C_3$-haloalkoxy group, and a $NR^5R^6$ group,
a mono- or bicyclic heteroaryl group which is optionally substituted with one, two or three substituents and each substituent is independently selected from a halogen atom, a $C_1$-$C_3$-alkyl group, a cyano group, a $C_1$-$C_3$-haloalkyl group, a $C_1$-$C_3$-alkoxy group, a hydroxy group, and a $NR^5R^6$ group, with the proviso that said monocyclic heteroaryl group is not a pyridin-4-yl group; and
$R^y$ is $C_1$-$C_6$-alkyl, or the two residues $R^y$ together are a $C_2$-$C_6$-alkylene group; and
the palladium catalyst is selected from: dichlorobis(triphenylphosphine)palladium, tetrakistriphenylphosphinepalladium(0), palladium(II) acetate/triscyclohexylphosphine, tris(dibenzylideneacetone)dipalladium, bis(diphenylphosphineferrocenyl)palladium(II) chloride, 1,3-bi s(2,6-diisopropylphenyl)imidazol-2-ylidene(1,4-naphthoquinone)palladium dimer, allyl (chloro)(1,3-dimesityl-1,3-dihydro-2H-imidazol-2-ylidene)palladium, palladium(II) acetate/dicyclohexyl (2',4',6'-triisopropyl-biphenyl-2-yl)phosphine, [1,1-bis (diphenylphosphino)ferrocene]palladium(II) chloride monodichloromethane adduct, [1,1'-Bis(diphenylphosphino)ferrocene]dichloropalladium(II), chloro(2-dicyclohexylphosphino-2',4',6'-triisopropyl-1,1'-biphenyl) [2-(2'-amino-1,1'-biphenyl)]palladium(II),
palladium (II) acetate and (2-dicyclohexylphosphino-2', 4',6'-triisopropyl-1,1'-biphenyl)[2-(2'-amino-1,1'-biphenyl)] palladium(II);
in order to form a compound of general formula (I):

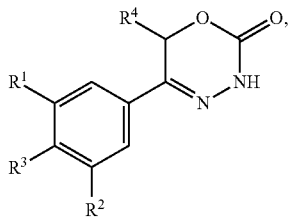

formula (I)

wherein $R^3$ is $R^x$.

3. The method according to claim 2, wherein
for the compound: 1e is trifluoromethyl and $R^2$ is a hydrogen atom,
and
Suzuki coupling conditions are used and the palladium catalyst is chloro(2-dicyclohexylphosphino-2',4',6'-triisopropyl-1,1'-biphenyl)[2-(2'-amino-1,1'-biphenyl)] palladium(II), and the ligand is 2-(dicyclohexylphosphino)-2',4',6'-triisopropylbiphenyl.

4. A method comprising:

the step B of allowing an intermediate compound of general formula (II) to react with an amine selected from $HNR^7R^8$ and a cyclic amine featuring one N—H as a ring atom, wherein $R^7/R^8$ are independently selected from a hydrogen atom, with the proviso that $R^7=R^8$=hydrogen is excluded, a $C_1$-$C_6$-alkyl group, which is optionally substituted with one, two, three or four substituents and said substituent is independently selected from a halogen atom, a cyano group, a hydroxy group, a $C(O)NR^5R^6$ group, a $NR^5R^6$ group, a $C_1$-$C_3$-alkoxy group, a $C_3$-$C_7$-cycloalkyl group which is optionally substituted with one or two substituents and said substituents are independently selected from a $C_1$-$C_3$-alkylgroup, an oxo (=O) group, a hydroxy group, and a $C_1$-$C_3$-hydroxyalkyl group;

a 3- to 7-membered heterocycloalkyl group which itself is optionally substituted with a $C_1$-$C_3$-alkyl group or an oxo (=O) group, a heteroaryl group, which itself is optionally substituted with a $C_1$-$C_3$-alkyl group;

a —$C_1$-$C_5$-alkylene-O—$C_1$-$C_5$-alkyl group, a —$C_1$-$C_5$-alkylene-S—$C_1$-$C_5$-alkyl group, a —$C_1$-$C_5$-alkylene-$NR^5$—$C_1$-$C_5$-alkyl group, a $C_3$-$C_6$-cycloalkyl group which is optionally substituted with a hydroxy group, and a 3- to 6-membered heterocycloalkyl group which is optionally substituted with one or two substituents, said substituent independently selected from $C_1$-$C_3$-alkyl group and a hydroxy group, a 3- to 9-membered heterocycloalkane containing one N—H as a ring atom is to be understood as a cyclic amine corresponding to a 3- to 9-membered heterocycloalkyl group as defined for $R^3$ supra, with the proviso it contains one N—H as a ring atom, a partially unsaturated 3- to 9-membered heterocycloalkane containing one N—H as a ring atom is to be understood as a cyclic amine corresponding to a partially unsaturated 3- to 9-membered heterocycloalkyl group, as defined for $R^3$ supra, with the proviso it contains one N—H as a ring atom, and a heteroarene containing one N—H as a ring atom is to be understood as a cyclic amine corresponding to a heteroaryl group as defined for $R^3$ supra, with the proviso it contains one N—H as a ring atom; and said cyclic amine being selected from a 3- to 9-membered heterocycloalkane, a partially unsaturated 3- to 9-membered heterocyloalkane, and a heteroarene, containing one N—H as a ring atom, respectively, and the compound of formula (II) has the structure:

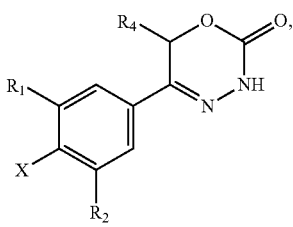

(II)

where
R$^1$ is selected from a hydrogen atom, a halogen atom, a cyano group, a C$_1$-C$_3$-alkyl group, a C$_1$-C$_3$-haloalkyl group, and a C$_1$-C$_3$-haloalkoxy group;
R$^2$ is selected from a hydrogen atom and a halogen atom;
R$^4$ is selected from a hydrogen atom, and a C$_1$-C$_3$-alkyl group;
X is F or C$_1$, with the proviso that if X is C$_1$, R$^1$ or R$^2$ cannot be F; and at least one of R$^1$ and R$^2$ exerts an electron withdrawing effect;
or a stereoisomer, a tautomer, an N-oxide, a hydrate, a solvate, or a salt thereof, or a mixture of same; and
optionally in the presence of a base, and optionally the presence of an inert solvent, and at temperature ranging from RT to 160° C., in order to form a compound of general formula (I):

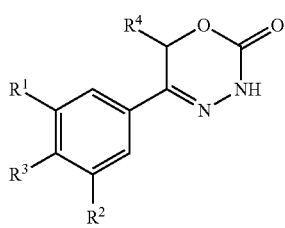

formula (I)

wherein R$^3$ is selected from —NR$^7$R$^8$, an N-linked 3- to 9-membered heterocycloalkyl group, an N-linked, partially unsaturated 3- to 9-membered heterocyloalkyl group, and an N-linked heteroaryl group.

5. The method according to claim 4 wherein
for the compound of formula (II): R$^1$ is trifluoromethyl and R$^2$ is a hydrogen atom, and
two residues R$^y$ together are —C(CH$_3$)$_2$—C(CH$_3$)$_2$— to form a pinacol ester, the base is potassium carbonate or potassium acetate.

6. A method comprising:
the step C of allowing an intermediate compound of general formula (II) to react with
an amine, optionally as a free base or as a salt, in the presence of a base, and a palladium catalyst optionally with a ligand in an inert solvent, and at a temperature ranging from 60° C. to 160° C.;
wherein the amine is selected from HNR$^7$R$^8$ and cyclic amine featuring one N—H as a ring atom, said cyclic amine being selected from a 3- to 9-membered heterocycloalkane, a partially unsaturated 3- to 9-membered heterocyloalkane, and a heteroarene, containing one N—H as a ring atom, respectively, in which
R$^7$/R$^8$ are independently selected from
a hydrogen atom, with the proviso that R$^7$=R$^g$=hydrogen is excluded,
a C$_1$-C$_6$-alkyl group,
which is optionally substituted with one, two, three or four substituents and said substituent is independently selected from
a halogen atom, a cyano group, a hydroxy group, a C(O)NR$^5$R$^6$ group, a NR$^5$R$^6$ group, a C$_1$-C$_3$-alkoxy group,
a C$_3$-C$_7$-cycloalkyl group which is optionally substituted with one or two substituents and said substituents are independently selected from a C$_1$-C$_3$-alkylgroup, a oxo (═O) group, a hydroxy group, and a C$_1$-C$_3$-hydroxyalkyl group;
a 3- to 7-membered heterocycloalkyl group which itself is optionally substituted with a C$_1$-C$_3$-alkyl group or an oxo (═O) group,
a heteroaryl group, which itself is optionally substituted with a C$_1$-C$_3$-alkyl group;
a —C$_1$-C$_5$-alkylene-O—C$_1$-C$_5$-alkyl group,
a —C$_1$-C$_5$-alkylene-S—C$_1$-C$_5$-alkyl group,
a —C$_1$-C$_5$-alkylene—NR$^5$—C$_1$-C$_5$-alkyl group,
a C$_3$-C$_6$-cycloalkyl group which is optionally substituted with a hydroxy group, and
a 3- to 6-membered heterocycloalkyl group which is optionally substituted with one or two substituents, said substituent independently selected from C$_1$-C$_3$-alkyl group and a hydroxy group,
a 3- to 9-membered heterocycloalkane containing one N—H as a ring atom is to be understood as a cyclic amine corresponding to a 3- to 9-membered heterocycloalkyl group as defined for R$^3$ supra, with the proviso it contains one N—H as a ring atom,
a partially unsaturated 3- to 9-membered heterocycloalkane containing one N—H as a ring atom is to be understood as a cyclic amine corresponding to a partially unsaturated 3- to 9-membered heterocycloalkyl group, as defined for R$^3$ supra, with the proviso it contains one N—H as a ring atom, and
a heteroarene containing one N—H as a ring atom is to be understood as a cyclic amine corresponding to a heteroaryl group as defined for R$^3$ supra, with the proviso it contains one N—H as a ring atom; and
the compound of formula (II) has the structure:

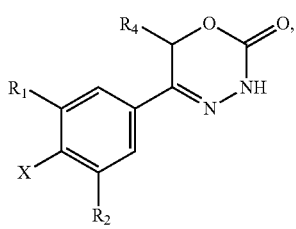

(II)

where
R$^1$ is selected from a hydrogen atom, a halogen atom, a cyano group, a C$_1$-C$_3$-alkyl group, a C$_1$-C$_3$-haloalkyl group, and a C$_1$-C$_3$-haloalkoxy group;
R$^2$ is selected from a hydrogen atom and a fluorine atom;
R$^4$ is selected from a hydrogen atom, and a C$_1$-C$_3$-alkyl group;

X is a fluorine atom, a chlorine atom, a bromine atom or an iodine atom, or a group selected from ($C_1$-$C_4$-alkylsulfonyl)oxy, ($C_1$-$C_4$-fluoroalkylsulfonyl)oxy and (phenylsulfonyl)oxy being optionally substituted with one, two, three, four or five substituents, each of them independently selected from halogen, nitro, cyano, $C_1$-$C_4$-alkyl and $C_1$-$C_4$-alkoxy;

with the prerequisite that and if X is a chlorine atom, a bromine atom or an iodine atom then $R^1$ and $R^2$ is not chlorine, bromine or iodine;

in order to form a compound of general formula (I):

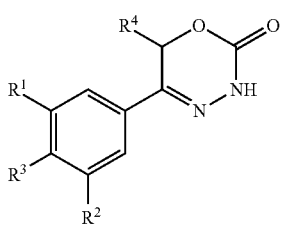

formula (I)

wherein $R^3$ is selected from —$NR^7R^8$, N-linked 3- to 9-membered heterocycloalkyl group, an N-linked, partially unsaturated 3- to 9-membered heterocyloalkyl group, and an N-linked heteroaryl group.

7. The method according to claim 2, wherein
for the compound (II): 1e is trifluoromethyl and $R^2$ is a hydrogen atom, and
the palladium catalyst is tris(dibenzylideneacetone)dipalladium(0) and the ligand is 2-(dicyclohexylphosphino)-2',4',6'-triisopropyl-1,1'-biphenyl or 2,2'-bis(diphenylphosphino)-1,1'-binaphthalene.

8. The compound according to claim 1, wherein $R^4$ is selected from a hydrogen atom and a methyl group.

9. The compound according to claim 1, wherein the compound is selected from:
5-(3,4-Difluorophenyl)-3,6-dihydro-2H-1,3,4-oxadiazin-2-one;
5-[4-Chloro-3-(trifluoromethyl)phenyl]hydro-2H-1,3,4-oxadiazin-2-one;
5-(4-Chloro-3-fluorophenyl)-3,6-dihydro-2H-1,3,4-oxadiazin-2-one;
5-[4-Fluoro-3-(trifluoromethyl)phenyl]-3,6-dihydro-2H-1,3,4-oxadiazin-2-one;
(rac)-5-[4-Chloro-3 4trifluoromethyl)phenyl]ethyl-3,6-dihydro-2H-1,3,4-oxadiazin-2-one;
(6 S)-5-[4-Chloro-3-(trifluoromethyl)phenyl]ethyl-3,6-dihydro-2H-1,3,4-oxadiazin-2-one;
(6S)-5-(-[(4-Fluoro-3-(trifluoromethyl)phenyl)-)]methyl-3,6-dihydro-2H-1,3,4-oxadiazin-2-one; and
5-[4-Bromo-3-(trifluoromethyl)phenyl]hydro-2H-1,3,4-oxadiazin-2-one.

10. The method according to claim 2, wherein $R_x$ is a methyl group which is optionally substituted with a 3 to 7 membered heterocycloalkyl group.

11. The method according to claim 2, wherein the two residues $R_y$ together are —$C(CH_3)_2$—$C(CH_3)_2$.

* * * * *